(12) United States Patent
Bartlett et al.

(10) Patent No.: US 9,951,065 B2
(45) Date of Patent: Apr. 24, 2018

(54) BENZIMIDAZOLE AND IMADAZOPYRIDINE CARBOXIMIDAMIDE COMPOUNDS

(71) Applicant: Gilead Sciences, Inc., Foster City, CA (US)

(72) Inventors: Mark J. Bartlett, Castro Valley, CA (US); Julian Andrew Codelli, Seattle, WA (US); Britton Kenneth Corkey, Redwood City, CA (US); Jennifer Leigh Cosman, Foster City, CA (US); Kristyna Elbel, South San Francisco, CA (US); Jennifer Alissa Loyer-Drew, Seattle, WA (US); David Sperandio, Palo Alto, CA (US); Joshua Van Veldhuizen, Seattle, WA (US); Hai Yang, San Mateo, CA (US); Suet Chung Yeung, Redmond, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/153,527

(22) Filed: May 12, 2016

(65) Prior Publication Data
US 2016/0333009 A1   Nov. 17, 2016

Related U.S. Application Data

(60) Provisional application No. 62/162,531, filed on May 15, 2015.

(51) Int. Cl.
| | |
|---|---|
| *C07D 235/06* | (2006.01) |
| *C07D 235/24* | (2006.01) |
| *C07D 295/125* | (2006.01) |
| *C07D 401/12* | (2006.01) |
| *C07D 471/04* | (2006.01) |
| *A61K 45/06* | (2006.01) |
| *C07D 235/08* | (2006.01) |
| *A61K 31/4184* | (2006.01) |
| *A61K 31/5377* | (2006.01) |
| *A61K 31/454* | (2006.01) |
| *A61K 31/437* | (2006.01) |
| *A61K 31/506* | (2006.01) |
| *A61K 31/497* | (2006.01) |
| *A61K 31/55* | (2006.01) |
| *A61K 31/541* | (2006.01) |
| *A61K 31/439* | (2006.01) |
| *C07D 405/12* | (2006.01) |
| *C07D 405/14* | (2006.01) |
| *C07D 471/08* | (2006.01) |

(Continued)

(52) U.S. Cl.
CPC ........ *C07D 471/04* (2013.01); *A61K 31/4184* (2013.01); *A61K 31/437* (2013.01); *A61K 31/438* (2013.01); *A61K 31/439* (2013.01); *A61K 31/444* (2013.01); *A61K 31/4439* (2013.01); *A61K 31/454* (2013.01); *A61K 31/4545* (2013.01); *A61K 31/4725* (2013.01); *A61K 31/496* (2013.01); *A61K 31/497* (2013.01); *A61K 31/506* (2013.01); *A61K 31/538* (2013.01); *A61K 31/5377* (2013.01); *A61K 31/5386* (2013.01); *A61K 31/541* (2013.01); *A61K 31/55* (2013.01); *A61K 31/553* (2013.01); *A61K 45/06* (2013.01); *C07D 235/06* (2013.01); *C07D 235/08* (2013.01); *C07D 235/12* (2013.01); *C07D 235/14* (2013.01); *C07D 235/16* (2013.01); *C07D 235/24* (2013.01); *C07D 235/28* (2013.01); *C07D 235/30* (2013.01); *C07D 295/125* (2013.01); *C07D 401/04* (2013.01); *C07D 401/12* (2013.01); *C07D 403/12* (2013.01); *C07D 405/12* (2013.01); *C07D 405/14* (2013.01); *C07D 409/12* (2013.01); *C07D 413/12* (2013.01); *C07D 471/08* (2013.01); *C07D 487/04* (2013.01)

(58) Field of Classification Search
CPC ............... C07D 235/06; C07D 235/24; C07D 295/125; C07D 401/12; C07D 471/04
See application file for complete search history.

(56) References Cited

U.S. PATENT DOCUMENTS 5,643,935 A * 7/1997 Dykstra ............. A61K 31/4184
514/256

FOREIGN PATENT DOCUMENTS

WO    WO-2014159248 A1    10/2014
WO    WO-2015002918 A1    1/2015

OTHER PUBLICATIONS

Golub et al., Science, vol. 286, Oct. 15, 1999, pp. 531-537.*

(Continued)

*Primary Examiner* — Laura L. Stockton

(57) ABSTRACT

The present disclosure provides indoleamine 2,3-dioxygenase 1 (IDO1) inhibitors of Formula I:

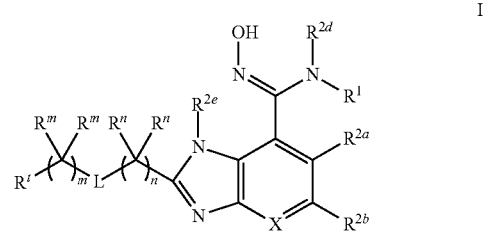

or pharmaceutically acceptable salts thereof, in which X, L, n, m, $R^1$, $R^{2a}$, $R^{2b}$, $R^n$, $R^m$, and $R^t$ are as defined herein, as well as pharmaceutical compositions that include a compound of Formula I, or pharmaceutically acceptable salts thereof, and methods of using the same to treat conditions mediated by IDO1.

23 Claims, No Drawings

(51) Int. Cl.
| | | |
|---|---|---|
| A61K 31/553 | (2006.01) | |
| C07D 235/30 | (2006.01) | |
| C07D 235/14 | (2006.01) | |
| C07D 401/04 | (2006.01) | |
| C07D 235/12 | (2006.01) | |
| A61K 31/444 | (2006.01) | |
| A61K 31/4545 | (2006.01) | |
| A61K 31/538 | (2006.01) | |
| A61K 31/5386 | (2006.01) | |
| A61K 31/438 | (2006.01) | |
| C07D 403/12 | (2006.01) | |
| A61K 31/4439 | (2006.01) | |
| C07D 413/12 | (2006.01) | |
| A61K 31/496 | (2006.01) | |
| C07D 487/04 | (2006.01) | |
| A61K 31/4725 | (2006.01) | |
| C07D 235/28 | (2006.01) | |
| C07D 235/16 | (2006.01) | |
| C07D 409/12 | (2006.01) | |

(56) References Cited

OTHER PUBLICATIONS

Beatty et al., (2013) "Phase 1 Study of the Safety, Pharmacokinetics, and Pharmacodynamics of the Oral Inhibitor of Indoleamine 2,3-dioxygenase (IDO1) INCB024360 in Patients With Advanced Malignancies," Poster Presented at the 2013 Annual Meeting of the American Society of Clinical Oncology Chicago, IL, USA, May 31-Jun. 4, 2013.
Beatty et al., (2017) First-in-Human Phase 1 Study of the Oral Inhibitor of Indoleamine 2,3-dioxygenase-1 Epacadostat (INCB024360) in Patients With Advanced Malignancies, Clinical Cancer Research [online access], DOI: 10.1158/1078-0432. CCR-16-2272. Published Jan. 2017, <http://clincancerres. aacrjournals.org/content/early/2017/01/04/1078-0432.CCR-16-2272.full-text.pdf>.
Brandacher et al. (2006) "Prognostic Value of Indoleamine 2,3-Dyoxygenase Expression in Colorectal Cancer: Effect on Tumor-infiltrating T Cells" *Clinical Cancer Research*, 12(4) 1144-1151.
Byakwaga et al., (2014) "The Kynurenine Pathway of Tryptophan Catabolism, CD4+ T-Cell Recovery, and Mortality Among HIV-Infected Ugandans Initiating Antiretroviral Therapy," *The Journal of Infectious Diseases*; 210:383-91.
Corm et al. (2009) "Indoleamine 2,3-Dioxygenase Activity of Acute Myeloid Leukemia Cells Can Be Measured from Patients' Sera by HPLC and is Inducible by IFN-γ" *Leukemia Research*, 33:490-494.
Dounay et al., (2015) "Challenges and Opportunities in the Discovery of New Therapeutics Targeting the Kynurenine Pathway," *J. Med. Chem.*, Just Accepted Manuscript, DOI: 10.1021/acs. jmedchem.5b00461, Published online Jul. 24, 2015, <http://pubs. acs.org>.
Feder-Mengus et al. (2008) "High Expression of Indoleamine 2,3-dioxygenase Gene in Prostate Cancer" *European Journal of Cancer* 44, 2266-2275.
Ferdinande et al. (2012) "Clinicopathological Significance of Indoleamine 2,3-Dioxygenase Expression in Colorectal Cancer" *British Journal of Cancer*, 106:141-147.
Gangadhar, et al., (2016) "Epacadostat Plus Pembrolizumab in Patients With Advanced Melanoma and Select Solid Tumors: Updated Phase 1 Results From ECHO-202/KEYNOTE-037," Poster Presented at the European Society for Medical Oncology Congress 2016 Copenhagen, Denmark, Oct. 7-11, 2016.
Gao et al. (2009) "The Paradoxical Patterns of Expression of Indoleamine 2,3-Dioxygenase in Colon Cancer" *Journal of the Translational Medicine*, 7:71.

Gibney et al., (2014) "Preliminary Results From a Phase 1/2 Study of INCB024360 Combined With Ipilimumab in Patients With Melanoma," Poster Presented at the American Society of Clinical Oncology Chicago, IL, May 30-Jun. 3, 2014.
Gibney et al., (2015) "Updated Results From a Phase 1/2 Study of Epacadostat (INCB024360) in Combination With Ipilimumab in Patients With Metastatic Melanoma," Poster Presented at the 18th ECCO—40th ESMO European Cancer Congress Vienna, Austria, Sep. 25-29, 2015.
Godin-Ethier et al., (2011) "Indoleamine 2,3-Dioxygenase Expression in Human Cancers: Clinical and Immunologic Perspectives," *Clin Cancer Res* [online access], doi: 10.1158/1078-0432.CCR-11-1331, Published Online Nov. 8, 2011, <http://clincancerres. aacrjournals.org/content/17/22/6985.long>.
Inaba et al. (2009) "Role of the Immunosuppressive Enzyme Indoleamine 2,3-dioxygenase in the Progression of Ovarian Carcinoma" *Gynecologic Oncology*, 115:185-192.
Inaba et al. (2010) "Indoleamine 2,3-Dioxygenase Expression Predicts Impaired Survival of Invasive Cervical Cancer Patients Treated with Radical Hysterectomy" *Gynecologic Oncology*, 117:423-428.
Ino et al. (2006) "Indoleamine 2,3-Dioxygenase is a Novel Prognostic Indicator for Endometrial Cancer" *British Journal of Cancer*, 95, 1555-1561.
International Search Report-Written Opinion dated Aug. 3, 2016 for PCT/US2016/032152.
Koblish et al., (2010) "Hydroxyamidine Inhibitors of Indoleamine-2,3-dioxygenase Potently Suppress Systemic Tryptophan Catabolism and the Growth of IDO-Expressing Tumors," *Mol Cancer Ther*; 9:489-498.
Kolbish et al., (2015) "Novel Immunotherapeutic Activity of JAK and PI3Kδ Inhibitors in a Model of Pancreatic Cancer," Poster Presented at the American Association for Cancer Research Annual Meeting 2015, Philadelphia, PA, USA.
Liu et al., (2010) "Selective Inhibition of IDO1 Effectively Regulates Mediators of Antitumor Immunity," *Blood*, vol. 115, No. 17; 3520-3530.
Moretti et al. (2014) "Indoleamine 2,3-Dyoxygenase 1 (IDO1) is Upregulated in Thyroid Carcinoma and Drives the Development of an Immunosuppressant Tumor Microenvironment" *The Journal of Clinical Endocrinology and Metabolism*, doi: 10.1210/jc.2013-3351.
Munn et al. (2004) "Expression of Indoleamine 2,3-Dioxygenase by Plasmacytoid Dendritic Cells in Tumor-draining Lymph Nodes" *The Journal of Clinical Investigation*;, Downloaded on Mar. 20, 2014, www.jci.org/articles/view/21583.
Munn et al., (2013) "Indoleamine 2,3 Dioxygenase and Metabolic Control of Immune Responses," *Trends in Immunology*, vol. 34, No. 3, 137-143.
Munn, (2012) "Blocking IDO Activity to Enhance Anti-tumor Immunity," *Frontiers in Bioscience* E4,734-745.
Newton et al., (2012) "Pharmacodynamic Assessment of INCB024360, an Inhibitor of Indoleamine 2,3-dioxygenase 1 (IDO1), in Advanced Cancer Patients," Abstract for 2012 ASCO Annual Meeting.
Ninomiya et al. (2010) "Indoleamine 2,3-Dioxygenase in Tumor Tissue Indicates Prognosis in Patients with Diffuse Large B-Cell Lymphoma Treated with R-CHOP" *Ann Hematol*; 90:409-416.
Okamoto et al. (2005) "Indoleamine 2,3-Dioxygenase Serves as a Marker of Poor Prognosis in Gene Expression Profiles of Serous Ovarian Cancer Cells", *Clinical Cancer Research*, 11:6030-6039.
Platten et al., (2012) "Tryptophan Catabolism in Cancer: Beyond IDO and Tryptophan Depletion," *Clin Cancer Res* [online access], doi:10.1158/0008-5472.CAN-12-0569, Published Online Oct. 22, 2012, <http://cancerres.aacrjournals.org/content/72/21/5435.long>.
Platten et al., (2015) "Cancer Immunotherapy by Targeting IDO1/ TDO and Their Downstream Effectors," *Frontiers in Immunology* | vol. 5 | Article 673 | 1-7.
Prendergast et al., (2011) "Indoleamine 2,3-dioxygenase as a Modifier of Pathogenic Inflammation in Cancer and other Inflammation-Associated Diseases," *Current Medicinal Chemistry*, 18, 2257-2262.

(56) References Cited

OTHER PUBLICATIONS

Suzuki et al. (2012) "Serum Indoleamine 2,3-Dioxygenase Activity Predicts Prognosis of Pulmonary Tuberculosis" *Clinical and Vaccine Immunology*, 436-442.

Sznurkowski et al. (2011) "Expression of Indoleamine 2,3-Dioxygenase Predicts Shorter Survival in Patients with Vulvar Squamous Cell Carcinoma (vSCC) Not Influencing on the Recruitment of FOXP3-expressing Regulatory T Cells in Cancer Nests" *Gynecologic Oncology*, 122:307-312.

Urakawa et al. (2009) "Prognostic Value of Indoleamine 2,3-dioxygenase Expression in High Grade Osteosarcoma", *Clin Exp Metastasis*, 26:1005-1012.

Yoshikawa et al. (2009) "Serum Concentration of L-Kynurenine Predicts the Clinical Outcome of Patients with Diffuse Large B-Cell Lymphoma Treated with R-CHOP" *European Journal of Haematology*, 84:304-309.

Yue et al., (2009) "Discovery of Potent Competitive Inhibitors of Indoleamine 2,3-Dioxygenase with in Vivo Pharmacodynamic Activity and Efficacy in a Mouse Melanoma Model," *J. Med. Chem.*, 52, 7364-7367.

Yue et al., (2009) "Supporting Information for Discovery of Potent Competitive Inhibitors of Indoleamine 2,3-Dioxygenase with in Vivo Pharmacodynamic Activity and Efficacy in a Mouse Melanoma Model," *J. Med. Chem.*, 52, 7364-7367.

Yue et al., (2017) "INCB24360 (Epacadostat), a Highly Potent and Selective Indoleamine-2,3-dioxygenase 1 (IDO1) Inhibitor for Immunooncology," *ACS Med. Chem. Lett., Article ASAP* [online access], DOI: 10.1021/acsmedchemlett.6b00391. Published online Mar. 6, 2017, <htttb://pubs.acs.org/doi/abs/10.1021/acsmedchemlett.6b00391>.

Koblish et al. (2011), "Selective IDO1 Inhibition: Pharmacodynamic and Antitumor Activity of INCB24360." Presented at the 26th Annual SITC meeting Nov. 4-6, 2011.

Office Action for Taiwan Patent Application No. 105115008 dated May 9, 2017.

Office Action for Taiwan Patent Application No. 105115008 dated May 9, 2017—English Translation.

* cited by examiner

BENZIMIDAZOLE AND IMADAZOPYRIDINE CARBOXIMIDAMIDE COMPOUNDS

This application claims priority of U.S. Provisional Patent Application No. 62/162,531, filed May 15, 2015.

FIELD

The present disclosure relates generally to inhibitors of indoleamine 2,3-dioxygenase 1 (IDO1) activity and methods of use and manufacture thereof.

BACKGROUND

Catabolism of the essential amino acid tryptophan by the inducible heme-containing enzyme indoleamine 2,3-dioxygenase 1 (IDO1) is a central pathway maintaining the immunosuppressive microenvironment in many cancers. IDO1 catalyzes the degradation of tryptophan to kynurenine, and its effects on immune suppression are due to decreased tryptophan availability and the generation of tryptophan metabolites resulting in multipronged negative effects on cytotoxic T lymphocytes, as well as expansion of immunosuppressive regulatory T cells. IDO1 is elevated in multiple cancers, is induced by chemotherapy, targeted therapy, or immunotherapy. IDO1 expression in the tumor microenvironment is correlated with poor prognosis in a variety of cancers. IDO1 inhibitors are positioned to potentiate the efficacy of multiple oncology therapeutics including immunotherapies, targeted agents, and chemotherapies. Indeed, epacadostat (INCB24360), a potent and selective IDO1 inhibitor, entered clinical trials and is demonstrating activity in combination with ipilimumab (anti-CTLA4) in melanoma.

In addition to the above, IDO1 has been shown to play a role in chronic infections, HIV and AIDS, autoimmune diseases or disorders (e.g., rheumatoid arthritis), and immunologic tolerance, prevention of fetal rejection in utero. Inhibition of IDO1 may also be an important treatment strategy for patients with neurological or neuropsychiatric diseases or disorders, such as depression.

A need remains for additional therapeutic agents useful to treat proliferative disorders or diseases that are mediated by IDO1.

SUMMARY

The present disclosure provides compounds that function as inhibitors of IDO1. The disclosure also provides compositions, including pharmaceutical compositions, kits that include the compounds, and methods of using and making the compounds. The compounds provided herein are useful in treating diseases, disorders, or conditions that are mediated by IDO1. The disclosure also provides compounds for use in therapy. The disclosure further provides compounds for use in a method of treating a disease, disorder, or condition that is mediated by IDO1. Moreover, the disclosure provides uses of the compounds in the manufacture of a medicament for the treatment of a disease, disorder or condition that is mediated by IDO1.

In one aspect, provided is a compound having the structure of Formula I:

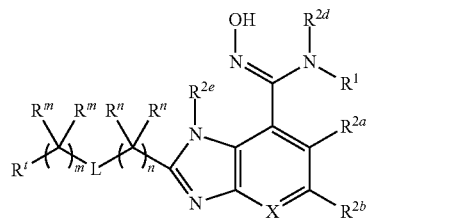

wherein $R^1$ is mono or bicyclic aryl or heteroaryl, wherein each mono or bicyclic aryl or heteroaryl is optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl, wherein two of the optional substituents can join to form an additional partially saturated heterocyclic ring; and wherein each $C_{1-6}$ alkoxy, $C_{1-6}$ alkyl, $C_{2-6}$ alkenyl, $C_{2-6}$ alkynyl, and $C_{3-6}$ cycloalkyl is optionally substituted with one, two, or three substituents independently selected from hydroxyl, halo, —CN, —N($R^{20}$)($R^{22}$) and $C_{3-6}$ cycloalkyl;

X is N or $CR^{2c}$;

$R^{2a}$, $R^{2b}$ and $R^{2c}$ are independently hydrogen, hydroxyl, halo, CN, $C_{1-6}$ haloalkyl, $C_{1-6}$ haloalkoxy, $C_{1-6}$ alkoxy, or $C_{1-6}$ alkyl;

$R^{2d}$ and $R^{2e}$ are independently hydrogen, $C_{1-6}$ haloalkyl, $C_{1-6}$ haloalkoxy, or $C_{1-6}$ alkyl;

n and m are independently 0, 1, 2, or 3;

each $R^n$ and $R^m$ are independently hydrogen, hydroxyl, halo, $C_{1-6}$ alkoxy, $C_{1-6}$ alkyl, $C_{3-6}$ cycloalkyl, aryl, heterocyclyl, or heteroaryl; or two $R^n$ or $R^m$ join to form a $C_{3-6}$ cycloalkyl; and wherein each $C_{1-6}$ alkoxy, $C_{1-6}$ alkyl, $C_{3-6}$ cycloalkyl aryl, heterocyclyl, or heteroaryl is optionally substituted with one, two, or three substituents independently selected from hydroxyl, halo, —CN, —N($R^{20}$)($R^{22}$), $C_{2-6}$ alkenyl, $C_{2-6}$ alkynyl, $C_{1-6}$ haloalkyl, $C_{1-6}$ haloalkoxy, $C_{1-6}$ alkoxy, $C_{1-6}$ alkyl, and $C_{3-6}$ cycloalkyl;

L is a bond, —$NR^3$—, —C(O)—$NR^3$—, —$NR^3$—C(O)—, —$NR^3SO_2$—, —$NR^3SO_2$—$NR^3$—, —$SO_2NR^3$—, —O—, —S—, or $S(O)_t$—, where t is 0, 1 or 2;

each $R^3$ is independently hydrogen, $C_{1-6}$ alkyl, $C_{3-6}$ cycloalkyl, aryl, heterocyclyl, or heteroaryl; and $R^t$ is hydrogen, $C_{1-6}$ alkyl, $C_{1-6}$ alkoxy, —C(O)$R^{20}$, —C(O)O$R^{20}$, —NC(O)O$R^{20}$, —N($R^{20}$)($R^{22}$), —C(O)N($R^{20}$)($R^{22}$), —$SO_2R^{20}$, —N($R^{20}$)$SO_2$($R^{21}$) N($R^{21}$)($R^{22}$), —$SO_2$N($R^{20}$)($R^{22}$), $C_{3-15}$ cycloalkyl, aryl, heteroaryl, or heterocyclyl, provided that when $R^t$ is $C_{1-6}$ alkoxy, —NC(O)O$R^{20}$, —N($R^{20}$)($R^{22}$), —N($R^{20}$)$SO_2$($R^{21}$) or —$SO_2$N($R^{20}$)($R^{22}$), and m is 0, then L is a bond;

wherein said $C_{1-6}$ alkyl, $C_{1-6}$ alkoxy, $C_{3-15}$ cycloalkyl, aryl, heterocyclyl, or heteroaryl is optionally substituted with one, two, or three substituents independently selected from hydroxyl, halo, —$NO_2$, $C_{1-6}$ haloalkyl, $C_{1-6}$ haloalkoxy, —C(O)$R^{20}$, —N($R^{20}$)($R^{22}$), —$SO_2R^{20}$, —N($R^{20}$)$SO_2$($R^{21}$), —N($R^{20}$)$SO_2$—N($R^{21}$)($R^{22}$), —$SO_2$N($R^{20}$)($R^{22}$), $C_{3-6}$ cycloalkyl, —CN, $C_{1-6}$ alkoxy, $C_{1-6}$ alkyl, and heterocyclyl; and wherein said heterocyclyl is optionally substituted with one or two oxo;

wherein said $C_{3-6}$ cycloalkyl, $C_{1-6}$ alkyl or $C_{1-6}$ alkoxy is optionally substituted with one, two, or three substituents independently selected from hydroxyl, halo, —$NO_2$, $C_{1-6}$ haloalkyl, $C_{1-6}$ haloalkoxy, $C_{1-6}$ alkoxy, —$N(R^{20})(R^{22})$, —$SO_2R^{20}$, —$N(R^{20})SO_2(R^{22})$, —$N(R^{20})SO_2$—$N(R^{21})(R^{22})$—, and —$SO_2N(R^{20})(R^{22})$; and said $C_{1-6}$ alkyl is optionally substituted with aryl;

$R^{20}$, $R^{21}$, and $R^{22}$ are independently selected from hydrogen, $C_{1-6}$ alkyl, $C_{1-6}$ haloalkyl, $C_{3-6}$ cycloalkyl, aryl, heterocyclyl, and heteroaryl;

wherein said aryl, heterocyclyl, or heteroaryl is optionally substituted with one, two, or three halogen;

or a pharmaceutically acceptable salt, isomer, or mixture thereof.

Some embodiments provide a method of using the compounds of Formula I, or additional Formula(s) described throughout, in the treatment of a disease or condition in a mammal, particularly a human, that is amenable to treatment by an IDO1 inhibitor.

In certain embodiments, the disclosure provides pharmaceutical compositions comprising a therapeutically effective amount of a compound of the disclosure (e.g. a compound of Formula I or additional Formulas described throughout), and at least one pharmaceutically acceptable excipient.

The inventions of this disclosure are described throughout. In addition, specific embodiments of the invention are as disclosed herein.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the e extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched, or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)$NR^yR^z$ and an "N-amido" group which refers to the group —$NR^yC(=O)R^z$, wherein $R^y$ and $R^z$ are independently selected from the group consisting of hydrogen, alkyl, aryl, haloalkyl, or heteroaryl; each of which may be optionally substituted.

"Amino" refers to the group —$NR^yR^z$ wherein $R^y$ and $R^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (Le, the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo, "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" refers to an unsaturated non-aromatic cyclic alkyl group, with one or more ring heteroatoms independently selected from nitrogen, oxygen and sulfur. As used herein, "heterocyclyl" or "heterocyclic ring" refers to rings that are saturated or partially saturated unless otherwise indicated, e.g., in some embodiments "heterocyclyl" or "heterocyclic ring" refers to rings that are partially saturated where specified. The term "heterocyclyl" or "heterocyclic ring" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl.

"Hydroxy" or "hydroxyl" refers to the group —OH.

"Oxo" refers to the group (=O) or (O).

"Sulfonyl" refers to the group —$S(O)_2R$, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium) $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of IDO1 activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of IDO1" or variants thereof refers to a decrease in activity in IDO1 as a direct or indirect response to the presence of a compound of the present application relative to the activity IDO1 in the absence of the compound of the present application. "Inhibition of IDO1" refers to a decrease in IDO1 activity as a direct or indirect response to the presence of a compound described herein relative to the activity of IDO1 in the absence of the compound described herein. In some embodiments, the inhibition of IDO1 activity may be compared in the same subject prior to treatment, or other subjects not receiving the treatment.

Compounds

Provided herein are compounds that function as inhibitors of IDO1. In one aspect, provided is a compound having structure of Formula I:

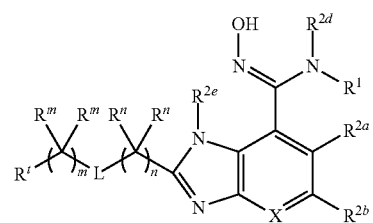

wherein
  $R^1$ is mono or bicyclic aryl or heteroaryl, wherein each mono or bicyclic aryl or heteroaryl is optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl, wherein two of the optional substituents can join to form an additional partially saturated heterocyclic ring; and
    wherein each $C_{1-6}$ alkoxy, $C_{1-6}$ alkyl, $C_{2-6}$ alkenyl, $C_{2-6}$ alkynyl, and $C_{3-6}$ cycloalkyl is optionally substituted with one, two, or three substituents independently selected from hydroxyl, halo, —CN, —N($R^{20}$)($R^{22}$) and $C_{3-6}$ cycloalkyl;
  X is N or $CR^{2c}$;
  $R^{2a}$, $R^{2b}$, and $R^{2c}$ are independently hydrogen, hydroxyl, halo, CN, $C_{1-6}$ haloalkyl, $C_{1-6}$ haloalkoxy, $C_{1-6}$ alkoxy, or $C_{1-6}$ alkyl;
  $R^{2d}$ and $R^{2e}$ are independently hydrogen, $C_{1-6}$ haloalkyl, $C_{1-6}$ haloalkoxy, or $C_{1-6}$ alkyl;
  n and m are independently 0, 1, 2, or 3;
  each $R^n$ and $R^m$ are independently hydrogen, hydroxyl, halo, $C_{1-6}$ alkoxy, $C_{1-6}$ alkyl, $C_{3-6}$ cycloalkyl, aryl, heterocyclyl, or heteroaryl; or two $R^n$ or $R^m$ join to form a $C_{3-6}$ cycloalkyl; and
    wherein each $C_{1-6}$ alkoxy, $C_{1-6}$ alkyl, $C_{3-6}$ cycloalkyl aryl, heterocyclyl, or heteroaryl is optionally substituted with one, two, or three substituents independently selected from hydroxyl, halo, —CN, —N($R^{20}$)($R^{22}$), $C_{2-6}$ alkenyl, $C_{2-6}$ alkynyl, $C_{1-6}$ haloalkyl, $C_{1-6}$ haloalkoxy, $C_{1-6}$ alkoxy, $C_{1-6}$ alkyl, and $C_{3-6}$ cycloalkyl;

L is a bond, —NR³—, —C(O)—NR³—, —NR³—C(O)—, —NR³SO₂—, —NR³SO₂—NR³—, —SO₂NR³—, —O—, —S—, or S(O)$_t$—, where t is 0, 1 or 2;

each R³ is independently hydrogen, $C_{1-6}$ alkyl, $C_{3-6}$ cycloalkyl, aryl, heterocyclyl, or heteroaryl; and R$^t$ is hydrogen, $C_{1-6}$ alkyl, $C_{1-6}$ alkoxy, —C(O)R²⁰, —C(O)OR²⁰, —NC(O)OR²⁰, —N(R²⁰)(R²²), —C(O)N(R²⁰)(R²²), —SO₂R²⁰, —N(R²⁰)SO₂(R²¹), —N(R²⁰)SO₂—N(R²¹)(R²²), —SO₂N(R²⁰)(R²²), $C_{3-15}$ cycloalkyl, aryl, heteroaryl, or heterocyclyl, provided that when R$^t$ is $C_{1-6}$ alkoxy, —NC(O)OR²⁰, —N(R²⁰)(R²²), —N(R²⁰)SO₂(R²¹) or —SO₂N(R²⁰)(R²²), and m is 0, then L is a bond;

wherein said $C_{1-6}$ alkyl, $C_{1-6}$ alkoxy, $C_{3-15}$ cycloalkyl, aryl, heterocyclyl, or heteroaryl is optionally substituted with one, two, or three substituents independently selected from hydroxyl, halo, —NO₂, $C_{1-6}$ haloalkyl, $C_{1-6}$ haloalkoxy, —C(O)R²⁰, —N(R²⁰)(R²²), —SO₂R²⁰, —N(R²⁰)SO₂(R²¹), —N(R²⁰)SO₂—N(R²¹)(R²²), —SO₂N(R²⁰)(R²²), $C_{3-6}$ cycloalkyl, —CN, $C_{1-6}$ alkoxy, $C_{1-6}$ alkyl, and heterocyclyl; and wherein said heterocyclyl is optionally substituted with one or two oxo;

wherein said $C_{3-6}$ cycloalkyl, $C_{1-6}$ alkyl or $C_{1-6}$ alkoxy is optionally substituted with one, two, or three substituents independently selected from hydroxyl, halo, —NO₂, $C_{1-6}$ haloalkyl, $C_{1-6}$ haloalkoxy, $C_{1-6}$ alkoxy, —N(R²⁰)(R²²), —SO₂R²⁰, —N(R²⁰)SO₂(R²²), —N(R²⁰)SO₂—N(R²¹)(R²²)—, and —SO₂N(R²⁰)(R²²); and said $C_{1-6}$ alkyl is optionally substituted with aryl;

R²⁰, R²¹, and R²² are independently selected from hydrogen, $C_{1-6}$ alkyl, $C_{1-6}$ haloalkyl, $C_{3-6}$ cycloalkyl, aryl, heterocyclyl, and heteroaryl;

wherein said aryl, heterocyclyl, or heteroaryl is optionally substituted with one, two, or three halogen;

or a pharmaceutically acceptable salt, isomer, or mixture thereof.

In some embodiments, R¹ is bicyclic aryl or heteroaryl optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl, wherein two of the optional substituents can join to form an additional partially saturated heterocyclic ring; and wherein each $C_{1-6}$ alkoxy, $C_{1-6}$ alkyl, $C_{2-6}$ alkenyl, $C_{2-6}$ alkynyl, and $C_{3-6}$ cycloalkyl is optionally substituted with one, two, or three substituents independently selected from hydroxyl, halo, —CN, —N(R²⁰)(R²²), and $C_{3-6}$ cycloalkyl.

In some embodiments, R¹ is bicyclic aryl or heteroaryl optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl.

In some embodiments, the compound is selected from the group consisting of:

N'-hydroxy-N-naphthalen-2-yl-1H-imidazo[4,5-b]pyridine-7-carboximidamide;

N'-hydroxy-N-naphthalen-1-yl-1H-imidazo[4,5-b]pyridine-7-carboximidamide;

N-(4-chloronaphthalen-1-yl)-N'-hydroxy-1H-imidazo[4,5-b]pyridine-7-carboximidamide;

N-(3-chloronaphthalen-2-yl)-N'-hydroxy-1H-imidazo[4,5-b]pyridine-7-carboximidamide;

N-(1-benzofuran-4-yl)-N'-hydroxy-1H-imidazo[4,5-b]pyridine-7-carboximidamide;

N-(1-benzofuran-6-yl)-N'-hydroxy-1H-imidazo[4,5-b]pyridine-7-carboximidamide;

N-(1-benzofuran-7-yl)-N'-hydroxy-1H-imidazo[4,5-b]pyridine-7-carboximidamide; and N-(1-benzofuran-5-yl)-N'-hydroxy-1H-imidazo[4,5-b]pyridine-7-carboximidamide.

In some embodiments, R¹ is phenyl optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl, wherein two of the optional substituents can join to form an additional partially saturated heterocyclic ring; and wherein each $C_{1-6}$ alkoxy, $C_{1-6}$ alkyl, $C_{2-6}$ alkenyl, $C_{2-6}$ alkynyl, and $C_{3-6}$ cycloalkyl is optionally substituted with one, two, or three substituents independently selected from hydroxyl, halo, —CN, —N(R²⁰)(R²²), and $C_{3-6}$ cycloalkyl.

In some embodiments, R¹ is phenyl optionally substituted with one, two, or three substituents independently selected from hydroxyl, halo, —CN, —O—CHF₂, —CF₃, —O—CF₃, $C_{1-4}$ alkoxy, $C_{1-4}$ alkyl, $C_{2-4}$ alkenyl, $C_{2-4}$ alkynyl, and $C_{3-6}$ cycloalkyl, and wherein two of the optional substituents can join to form an additional partially saturated heterocyclic ring.

In some embodiments, at least one of R$^{2a}$, R$^{2b}$, and, when present, R$^{2c}$ are not hydrogen. In some embodiments, R$^{2a}$ is not hydrogen. In some embodiments, R$^{2b}$ is not hydrogen. In some embodiments, R$^{2c}$ is not hydrogen.

In some embodiments, the compound is selected from the group consisting of:

N-(3-chloro-4-fluorophenyl)-6-fluoro-N'-hydroxy-1H-benzimidazole-4-carboximidamide;

N-(3-chloro-4-fluorophenyl)-7-fluoro-N'-hydroxy-3H-benzimidazole-4-carboximidamide;

7-chloro-N-(3-chloro-4-fluorophenyl)-N'-hydroxy-3H-benzimidazole-4-carboximidamide;

N-(3-chloro-4-fluorophenyl)-N'-hydroxy-7-(trifluoromethyl)-1H-benzimidazole-4-carboximidamide;

N-(3-chloro-4-fluorophenyl)-6,7-difluoro-N'-hydroxy-2-(2-morpholin-4-ylethylamino)-3H-benzimidazole-4-carboximidamide;

N-(3-chloro-4-fluorophenyl)-6,7-difluoro-N'-hydroxy-2-(methylaminomethyl)-1H-benzimidazole-4-carboximidamide;

N-(3-chloro-4-fluorophenyl)-6-fluoro-N'-hydroxy-7-methyl-3H-benzimidazole-4-carboximidamide;

N-(3-chloro-4-fluorophenyl)-N'-hydroxy-7-methyl-3H-benzimidazole-4-carboximidamide;

N-(3-chloro-4-fluorophenyl)-6,7-difluoro-N'-hydroxy-3H-benzimidazole-4-carboximidamide;

N-(3-chloro-4-fluorophenyl)-N'-hydroxy-7-(trifluoromethoxy)-3H-benzimidazole-4-carboximidamide; and N-(3-chloro-4-fluorophenyl)-5-fluoro-N'-hydroxy-3H-benzimidazole-4-carboximidamide.

In some embodiments, L is a bond.

In some embodiments, R$^t$ is $C_{1-6}$ alkyl optionally substituted with one, two, or three substituents independently selected from hydroxyl, halo, —NO₂, $C_{1-6}$ haloalkyl, $C_{1-6}$ haloalkoxy, $C_{3-6}$ cycloalkyl, —CN, and $C_{1-6}$ alkoxy.

In some embodiments, the compound is selected from the group consisting of:

N-(3-chloro-4-fluorophenyl)-N'-hydroxy-2-(methoxymethyl)-1H-imidazo[4,5-b]pyridine-7-carboximidamide;

N-(3-chloro-4-fluorophenyl)-N'-hydroxy-2-(2-hydroxyethyl)-1H-imidazo[4,5-b]pyridine-7-carboximidamide;

2-(chloromethyl)-N-[4-fluoro-3-(trifluoromethyl)phenyl]-N'-hydroxy-1H-imidazo[4,5-b]pyridine-7-carboximidamide;

N-[4-fluoro-3-(trifluoromethyl)phenyl]-N'-hydroxy-2-(hydroxymethyl)-1H-imidazo[4,5-b]pyridine-7-carboximidamide;
N-(3-chloro-4-fluorophenyl)-N'-hydroxy-2-(hydroxymethyl)-1H-imidazo[4,5-b]pyridine-7-carboximidamide;
N-(3-chloro-4-fluorophenyl)-N'-hydroxy-2-(1-hydroxyethyl)-1H-imidazo[4,5-b]pyridine-7-carboximidamide;
N-(3-chloro-4-fluorophenyl)-N'-hydroxy-2-(2,2,2-trifluoro-1-hydroxyethyl)-1H-imidazo[4,5-b]pyridine-7-carboximidamide;
N-(3-chloro-4-fluorophenyl)-2-[cyclopropyl(hydroxy)methyl]-N'-hydroxy-1H-imidazo[4,5-b]pyridine-7-carboximidamide;
N-(3-chloro-4-fluorophenyl)-N'-hydroxy-2-(2-hydroxypropan-2-yl)-1H-imidazo[4,5-b]pyridine-7-carboximidamide; and
2-(aminomethyl)-N-(3-chloro-4-fluorophenyl)-N'-hydroxy-1H-imidazo[4,5-b]pyridine-7-carboximidamide.

In some embodiments, $R^t$ is $C_{3-15}$ cycloalkyl, aryl, heteroaryl, or heterocyclyl, wherein said cycloalkyl, aryl, heterocyclyl, or heteroaryl is optionally substituted with one, two, or three substituents independently selected from hydroxyl, halo, —NO$_2$, $C_{1-6}$ haloalkyl, $C_{1-6}$ haloalkoxy, $C_{3-6}$ cycloalkyl, —CN, $C_{1-6}$ alkoxy and $C_{1-6}$ alkyl.

In some embodiments, the compound is selected from the group consisting of:
N-(3-chloro-4-fluorophenyl)-N'-hydroxy-2-(2-morpholin-4-ylethyl)-3H-imidazo[4,5-b]pyridine-7-carboximidamide;
N-(3-chloro-4-fluorophenyl)-N'-hydroxy-2-(pyrrolidin-1-ylmethyl)-3H-imidazo[4,5-b]pyridine-7-carboximidamide;
N-(3-chloro-4-fluorophenyl)-N'-hydroxy-2-(piperidin-1-ylmethyl)-3H-imidazo[4,5-b]pyridine-7-carboximidamide;
N-(3-chloro-4-fluorophenyl)-N'-hydroxy-2-pyridin-3-yl-1H-imidazo[4,5-b]pyridine-7-carboximidamide;
N-(3-chloro-4-fluorophenyl)-N'-hydroxy-2-(1H-pyrrol-2-yl)-1H-imidazo[4,5-b]pyridine-7-carboximidamide;
N-(3-chloro-4-fluorophenyl)-N'-hydroxy-2-[(2S)-pyrrolidin-2-yl]-1H-imidazo[4,5-b]pyridine-7-carboximidamide;
N-(3-chloro-4-fluorophenyl)-N'-hydroxy-2-(1H-pyrazol-5-yl)-1H-imidazo[4,5-b]pyridine-7-carboximidamide;
N-(3-chloro-4-fluorophenyl)-N'-hydroxy-2-(1H-imidazol-2-yl)-1H-imidazo[4,5-b]pyridine-7-carboximidamide;
N-(3-chloro-4-fluorophenyl)-2-cyclopropyl-N'-hydroxy-1H-imidazo[4,5-b]pyridine-7-carboximidamide;
N-(3-chloro-4-fluorophenyl)-N'-hydroxy-2-thiophen-2-yl-3H-imidazo[4,5-b]pyridine-7-carboximidamide;
N-(3-chloro-4-fluorophenyl)-N'-hydroxy-2-(morpholin-4-ylmethyl)-3H-imidazo[4,5-b]pyridine-7-carboximidamide;
N-(3-chloro-4-fluorophenyl)-N'-hydroxy-2-[hydroxy(phenyl)methyl]-1H-imidazo[4,5-b]pyridine-7-carboximidamide;
N-(3-chloro-4-fluorophenyl)-N'-hydroxy-2-methyl-1H-imidazo[4,5-b]pyridine-7-carboximidamide;
N-(3-chloro-4-fluorophenyl)-2-ethyl-N'-hydroxy-1H-imidazo[4,5-b]pyridine-7-carboximidamide;
N-(3-chloro-4-fluorophenyl)-N'-hydroxy-2-(2-piperidin-1-ylethyl)-1H-imidazo[4,5-b]pyridine-7-carboximidamide;
N-(3-chloro-4-fluorophenyl)-N'-hydroxy-2-(2-pyrrolidin-1-ylethyl)-1H-imidazo[4,5-b]pyridine-7-carboximidamide; and
N-(3-chloro-4-fluorophenyl)-N'-hydroxy-2-(5-methyl-1H-imidazol-2-yl)-1H-imidazo[4,5-b]pyridine-7-carboximidamide.

In some embodiments, $R^t$ is hydrogen.

In some embodiments, the compound is selected from the group consisting of:
N-(3-ethynylphenyl)-N'-hydroxy-1H-imidazo[4,5-b]pyridine-7-carboximidamide;
N-(3-ethynyl-4-fluorophenyl)-N'-hydroxy-1H-imidazo[4,5-b]pyridine-7-carboximidamide;
N-[3-(difluoromethyl)phenyl]-N'-hydroxy-1H-imidazo[4,5-b]pyridine-7-carboximidamide;
N'-hydroxy-N-[3-(trifluoromethoxy)phenyl]-1H-imidazo[4,5-b]pyridine-7-carboximidamide;
N'-hydroxy-N-phenyl-1H-imidazo[4,5-b]pyridine-7-carboximidamide;
N-(3-ethylphenyl)-N'-hydroxy-1H-imidazo[4,5-b]pyridine-7-carboximidamide;
N-[4-fluoro-3-(trifluoromethoxy)phenyl]-N'-hydroxy-1H-imidazo[4,5-b]pyridine-7-carboximidamide;
N-(4-fluoro-3-methoxyphenyl)-N'-hydroxy-1H-imidazo[4,5-b]pyridine-7-carboximidamide;
N-(5-bromo-2-fluorophenyl)-N'-hydroxy-3H-imidazo[4,5-b]pyridine-7-carboximidamide;
N-(3-bromo-5-fluorophenyl)-N'-hydroxy-1H-imidazo[4,5-b]pyridine-7-carboximidamide;
N'-hydroxy-N-[3-(trifluoromethyl)phenyl]-1H-imidazo[4,5-b]pyridine-7-carboximidamide;
N-[3-fluoro-5-(trifluoromethyl)phenyl]-N'-hydroxy-1H-imidazo[4,5-b]pyridine-7-carboximidamide;
N-(3-bromophenyl)-N'-hydroxy-3H-imidazo[4,5-b]pyridine-7-carboximidamide;
N-(3-bromo-4-fluorophenyl)-N'-hydroxy-3H-imidazo[4,5-b]pyridine-7-carboximidamide;
N-(3-chlorophenyl)-N'-hydroxy-3H-imidazo[4,5-b]pyridine-7-carboximidamide;
N-[4-fluoro-3-(trifluoromethyl)phenyl]-N'-hydroxy-3H-imidazo[4,5-b]pyridine-7-carboximidamide;
N-(4-fluoro-3-prop-1-ynylphenyl)-N'-hydroxy-3H-imidazo[4,5-b]pyridine-7-carboximidamide;
N-(3-bromo-4-chlorophenyl)-N'-hydroxy-3H-imidazo[4,5-b]pyridine-7-carboximidamide;
N-(3,4-dichlorophenyl)-N'-hydroxy-3H-imidazo[4,5-b]pyridine-7-carboximidamide;
N-(4-chlorophenyl)-N'-hydroxy-3H-imidazo[4,5-b]pyridine-7-carboximidamide;
N-(4-bromophenyl)-N'-hydroxy-3H-imidazo[4,5-b]pyridine-7-carboximidamide;
N-(4-fluorophenyl)-N'-hydroxy-3H-imidazo[4,5-b]pyridine-7-carboximidamide;
N-(3-cyano-4-fluorophenyl)-N'-hydroxy-1H-imidazo[4,5-b]pyridine-7-carboximidamide;
N'-hydroxy-N-[4-(trifluoromethyl)phenyl]-3H-imidazo[4,5-b]pyridine-7-carboximidamide;
N'-hydroxy-N-(3-methoxyphenyl)-3H-imidazo[4,5-b]pyridine-7-carboximidamide;
N-(4-fluoro-3-propan-2-ylphenyl)-N'-hydroxy-1H-imidazo[4,5-b]pyridine-7-carboximidamide;
N'-hydroxy-N-(4-methylphenyl)-3H-imidazo[4,5-b]pyridine-7-carboximidamide;
N-(3-chloro-4-fluorophenyl)-N'-hydroxy-1H-imidazo[4,5-b]pyridine-7-carboximidamide;
N-(5-chloro-2-fluorophenyl)-N'-hydroxy-1H-imidazo[4,5-b]pyridine-7-carboximidamide;
N-(5-bromo-2,4-difluorophenyl)-N'-hydroxy-1H-imidazo[4,5-b]pyridine-7-carboximidamide;
N-(5-chloro-2,4-difluorophenyl)-N'-hydroxy-1H-imidazo[4,5-b]pyridine-7-carboximidamide;
N-(2,5-dichlorophenyl)-N'-hydroxy-1H-imidazo[4,5-b]pyridine-7-carboximidamide;

N-(3,5-dichloro-4-fluorophenyl)-N'-hydroxy-1H-imidazo[4,5-b]pyridine-7-carboximidamide;
N-(3-chlor2,4-difluorophenyl)-N'-hydroxy-1H-imidazo[4,5-b]pyridine-7-carboximidamide;
N-(3-cyclopropyl-4-fluorophenyl)-N'-hydroxy-1H-imidazo[4,5-b]pyridine-7-carboximidamide;
N-(4-fluoro-3-phenylphenyl)-N'-hydroxy-1H-imidazo[4,5-b]pyridine-7-carboximidamide;
N-(3-but-1-ynyl-4-fluorophenyl)-N'-hydroxy-1H-imidazo[4,5-b]pyridine-7-carboximidamide;
N-[3-(2-cyclopropylethynyl)-4-fluorophenyl]-N'-hydroxy-1H-imidazo[4,5-b]pyridine-7-carboximidamide; and
N'-hydroxy-N-[4-(trifluoromethoxy)phenyl]-1H-imidazo[4,5-b]pyridine-7-carboximidamide.

In some embodiments, L is —NR$^3$.

In some embodiments, R$^t$ is C$_{1-6}$ optionally substituted with one, two, or three substituents independently selected from hydroxyl, halo, —NO$_2$, C$_{1-6}$ haloalkyl, C$_{1-6}$ haloalkoxy, —N(R$^{20}$)(R$^{22}$), —SO$_2$R$^{20}$, C$_{3-6}$ cycloalkyl, —CN, and C$_{1-6}$ alkoxy.

In some embodiments the compound is selected from the group consisting of:
N-(3-chloro-4-fluorophenyl)-2-[2-(dimethylamino)ethyl]-N'-hydroxy-3H-imidazo[4,5-b]pyridine-7-carboximidamide;
N-(3-chloro-4-fluorophenyl)-N'-hydroxy-2-[2-(methylamino)ethyl]-3H-imidazo[4,5-b]pyridine-7-carboximidamide;
N-(3-chloro-4-fluorophenyl)-N'-hydroxy-2-(2-((2-methoxyethyl)amino)ethyl)-1H-imidazo[4,5-b]pyridine-7-carboximidamide
N-(3-chloro-4-fluorophenyl)-2-[(2,2-dimethylpropylamino)methyl]-N'-hydroxy-1H-imidazo[4,5-b]pyridine-7-carboximidamide;
N-(3-chloro-4-fluorophenyl)-N'-hydroxy-2-[2-(2-methoxyethylamino)ethyl]-3H-imidazo[4,5-b]pyridine-7-carboximidamide;
ethyl N-[7-[(Z)—N-(3-chloro-4-fluorophenyl)-N'-hydroxycarbamimidoyl]-1H-imidazo[4,5-b]pyridin-2-yl]carbamate;
N-(3-chloro-4-fluorophenyl)-N'-hydroxy-2-(methylamino)-1H-imidazo[4,5-b]pyridine-7-carboximidamide;
N-(3-chloro-4-fluorophenyl)-N'-hydroxy-2-(2,2,2-trifluoroethylamino)-1H-imidazo[4,5-b]pyridine-7-carboximidamide;
N-(3-chloro-4-fluorophenyl)-2-(dimethylamino)-N'-hydroxy-1H-imidazo[4,5-b]pyridine-7-carboximidamide;
N-(3-chloro-4-fluorophenyl)-2-[2-(diethylamino)ethyl]-N'-hydroxy-1H-imidazo[4,5-b]pyridine-7-carboximidamide;
N-(3-chloro-4-fluorophenyl)-2-[2-(dimethylamino)-1-hydroxyethyl]-N'-hydroxy-1H-imidazo[4,5-b]pyridine-7-carboximidamide;
N-(3-chloro-4-fluorophenyl)-N'-hydroxy-2-[(2-methylpropylamino)methyl]-1H-imidazo[4,5-b]pyridine-7-carboximidamide;
N-(3-chloro-4-fluorophenyl)-N'-hydroxy-2-(methylaminomethyl)-1H-imidazo[4,5-b]pyridine-7-carboximidamide;
N-(3-chloro-4-fluorophenyl)-2-[2-[2,2-difluoroethyl(methyl)amino]ethyl]-N'-hydroxy-1H-imidazo[4,5-b]pyridine-7-carboximidamide;
N-(3-chloro-4-fluorophenyl)-N'-hydroxy-2-(propan-2-ylamino)-1H-imidazo[4,5-b]pyridine-7-carboximidamide;
N-(3-chloro-4-fluorophenyl)-2-[(2,2-difluoroethylamino)methyl]-N'-hydroxy-1H-imidazo[4,5-b]pyridine-7-carboximidamide;
N-(3-chloro-4-fluorophenyl)-N'-hydroxy-2-[[(3-hydroxy-2,2-dimethylpropyl)amino]methyl]-1H-imidazo[4,5-b]pyridine-7-carboximidamide;
N-(3-chloro-4-fluorophenyl)-N'-hydroxy-2-[(propan-2-ylamino)methyl]-3H-imidazo[4,5-b]pyridine-7-carboximidamide;
N-(3-chloro-4-fluorophenyl)-2-(ethylaminomethyl)-N'-hydroxy-3H-imidazo[4,5-b]pyridine-7-carboximidamide;
N-(3-chloro-4-fluorophenyl)-2-(ethylamino)-N'-hydroxy-1H-imidazo[4,5-b]pyridine-7-carboximidamide;
N-(3-chloro-4-fluorophenyl)-N'-hydroxy-2-[(3-methoxypropylamino)methyl]-3H-imidazo[4,5-b]pyridine-7-carboximidamide;
N-(3-chloro-4-fluorophenyl)-2-[(dimethylamino)methyl]-N'-hydroxy-3H-imidazo[4,5-b]pyridine-7-carboximidamide;
N-(3-chloro-4-fluorophenyl)-N'-hydroxy-2-[[3-methoxypropyl(methyl)amino]methyl]-1H-imidazo[4,5-b]pyridine-7-carboximidamide;
N-(3-chloro-4-fluorophenyl)-N'-hydroxy-2-[(2-methoxyethylamino)methyl]-3H-imidazo[4,5-b]pyridine-7-carboximidamide;
N-(3-chloro-4-fluorophenyl)-N'-hydroxy-2-[(2,2,2-trifluoroethylamino)methyl]-3H-imidazo[4,5-b]pyridine-7-carboximidamide;
N-(3-chloro-4-fluorophenyl)-2-[[2-(dimethylamino)ethylamino]methyl]-N'-hydroxy-3H-imidazo[4,5-b]pyridine-7-carboximidamide;
N-(3-chloro-4-fluorophenyl)-N'-hydroxy-2-[(3-hydroxypropylamino)methyl]-1H-imidazo[4,5-b]pyridine-7-carboximidamide;
N-[[7-[(Z)—N-(3-chloro-4-fluorophenyl)-N'-hydroxycarbamimidoyl]-3H-imidazo[4,5-b]pyridin-2-yl]methyl]acetamide;
N-(3-chlorophenyl)-N'-hydroxy-2-(methylamino)-1H-imidazo[4,5-b]pyridine-7-carboximidamide;
N-(3-chloro-4-fluorophenyl)-N'-hydroxy-2-[2-[2-methoxyethyl(methyl)amino]ethyl]-1H-imidazo[4,5-b]pyridine-7-carboximidamide;
N-(3-chloro-4-fluorophenyl)-2-[2-(diethylamino)ethylamino]-N'-hydroxy-1H-imidazo[4,5-b]pyridine-7-carboximidamide; and
N-(3-chlorophenyl)-2-((dimethylamino)methyl)-4,5-difluoro-N'-hydroxy-1H-benzo[d]imidazole-7-carboximidamide.

In some embodiments, L is —NR$^3$ and R$^t$ is C$_{3-15}$ cycloalkyl, aryl, heteroaryl, or heterocyclyl, wherein said cycloalkyl, aryl, heterocyclyl, or heteroaryl is optionally substituted with one, two, or three substituents independently selected from hydroxyl, halo, —NO$_2$, C$_{1-6}$ haloalkyl, C$_{1-6}$ haloalkoxy, C$_{3-6}$ cycloalkyl, —CN, and C$_{1-6}$ alkoxy.

In some embodiments, the compound is selected from the group consisting of:
N-(3-chloro-4-fluorophenyl)-2-(cyclopropylamino)-N'-hydroxy-1H-imidazo[4,5-b]pyridine-7-carboximidamide;
N-(3-chloro-4-fluorophenyl)-2-(cyclopropylmethylamino)-N'-hydroxy-1H-imidazo[4,5-b]pyridine-7-carboximidamide;
N-(3-chloro-4-fluorophenyl)-N'-hydroxy-2-(2-phenylethylamino)-1H-imidazo[4,5-b]pyridine-7-carboximidamide;
2-anilino-N-(3-chloro-4-fluorophenyl)-N'-hydroxy-1H-imidazo[4,5-b]pyridine-7-carboximidamide;
N-(3-chloro-4-fluorophenyl)-2-[(3,3-difluorocyclobutyl)amino]-N'-hydroxy-1H-imidazo[4,5-b]pyridine-7-carboximidamide;

N-(3-chloro-4-fluorophenyl)-N'-hydroxy-2-[(pyrimidin-2-ylamino)methyl]-3H-imidazo[4,5-b]pyridine-7-carboximidamide;
N-(3-chloro-4-fluorophenyl)-2-(cyclobutylamino)-N'-hydroxy-1H-imidazo[4,5-b]pyridine-7-carboximidamide;
N-(3-chloro-4-fluorophenyl)-N'-hydroxy-2-[(1,3-thiazol-2-ylmethylamino)methyl]-1H-imidazo[4,5-b]pyridine-7-carboximidamide;
N-(3-chloro-4-fluorophenyl)-2-[(cyclopropylmethylamino)methyl]-N'-hydroxy-3H-imidazo[4,5-b]pyridine-7-carboximidamide;
N-(3-chloro-4-fluorophenyl)-N'-hydroxy-2-[(pyridin-2-ylmethylamino)methyl]-3H-imidazo[4,5-b]pyridine-7-carboximidamide;
2-[(benzylamino)methyl]-N-(3-chloro-4-fluorophenyl)-N'-hydroxy-3H-imidazo[4,5-b]pyridine-7-carboximidamide;
N-(3-chloro-4-fluorophenyl)-N'-hydroxy-2-[[(2-methoxyphenyl)methylamino]methyl]-1H-imidazo[4,5-b]pyridine-7-carboximidamide;
N-(3-chloro-4-fluorophenyl)-N'-hydroxy-2-[(2-pyridin-2-ylethylamino)methyl]-3H-imidazo[4,5-b]pyridine-7-carboximidamide;
N-(3-chloro-4-fluorophenyl)-2-[(cyclopropylamino)methyl]-N'-hydroxy-3H-imidazo[4,5-b]pyridine-7-carboximidamide;
N-(3-chloro-4-fluorophenyl)-N'-hydroxy-2-[(pyridin-3-ylmethylamino)methyl]-3H-imidazo[4,5-b]pyridine-7-carboximidamide;
N-(3-chloro-4-fluorophenyl)-N'-hydroxy-2-[(oxan-2-ylmethylamino)methyl]-1H-imidazo[4,5-b]pyridine-7-carboximidamide;
2-(anilinomethyl)-N-(3-chloro-4-fluorophenyl)-N'-hydroxy-3H-imidazo[4,5-b]pyridine-7-carboximidamide;
N-(3-chloro-4-fluorophenyl)-N'-hydroxy-2-[(oxan-3-ylmethylamino)methyl]-1H-imidazo[4,5-b]pyridine-7-carboximidamide;
N-(3-chloro-4-fluorophenyl)-N'-hydroxy-2-[(pyrimidin-2-ylmethylamino)methyl]-3H-imidazo[4,5-b]pyridine-7-carboximidamide;
N-(3-chloro-4-fluorophenyl)-N'-hydroxy-2-[(3-morpholin-4-ylpropylamino)methyl]-3H-imidazo[4,5-b]pyridine-7-carboximidamide;
N-(3-chloro-4-fluorophenyl)-N'-hydroxy-2-[(oxan-4-ylamino)methyl]-1H-imidazo[4,5-b]pyridine-7-carboximidamide;
N-(3-chloro-4-fluorophenyl)-N'-hydroxy-2-[(pyridin-4-ylmethylamino)methyl]-3H-imidazo[4,5-b]pyridine-7-carboximidamide;
N-(3-chloro-4-fluorophenyl)-N'-hydroxy-2-[(pyrazin-2-ylmethylamino)methyl]-1H-imidazo[4,5-b]pyridine-7-carboximidamide;
N-(3-chloro-4-fluorophenyl)-N'-hydroxy-2-[(oxolan-3-ylmethylamino)methyl]-1H-imidazo[4,5-b]pyridine-7-carboximidamide;
N-(3-chloro-4-fluorophenyl)-N'-hydroxy-2-[(2-pyrimidin-2-ylethylamino)methyl]-3H-imidazo[4,5-b]pyridine-7-carboximidamide;
N-(3-chloro-4-fluorophenyl)-2-[2-[cyclopropylmethyl(methyl)amino]ethyl]-N'-hydroxy-1H-imidazo[4,5-b]pyridine-7-carboximidamide;
N-(3-chloro-4-fluorophenyl)-N'-hydroxy-2-(2-morpholin-4-ylethylamino)-1H-imidazo[4,5-b]pyridine-7-carboximidamide;
N-(3-chloro-4-fluorophenyl)-N'-hydroxy-2-[(1-methylpiperidin-2-yl)methylamino]-1H-imidazo[4,5-b]pyridine-7-carboximidamide; and
N-(3-chloro-4-fluorophenyl)-N'-hydroxy-2-[(1-methylpyrrolidin-3-yl)amino]-1H-imidazo[4,5-b]pyridine-7-carboximidamide.

In some embodiments, L is —$NR^3$— and $R^t$ is hydrogen.
In some embodiments, the compound is selected from the group consisting of:
2-(2-aminoethyl)-N-(3-chloro-4-fluorophenyl)-N'-hydroxy-3H-imidazo[4,5-b]pyridine-7-carboximidamide; and
2-amino-N-(3-chloro-4-fluorophenyl)-N'-hydroxy-1H-imidazo[4,5-b]pyridine-7-carboximidamide.

In some embodiments, L is $SO_2NR^3$—.
In some embodiments, the compound is selected from the group consisting of:
2-(benzenesulfonamidomethyl)-N-(3-chloro-4-fluorophenyl)-N'-hydroxy-1H-imidazo[4,5-b]pyridine-7-carboximidamide, and
N-(3-chloro-4-fluorophenyl)-N'-hydroxy-2-(methanesulfonamidomethyl)-3H-imidazo[4,5-b]pyridine-7-carboximidamide.

In some embodiments, X is —N—.
In some embodiments, X is —$CR^{2c}$—.
In some embodiments, the compound is selected from the group consisting of:
N-(3-chloro-4-fluorophenyl)-6-fluoro-N'-hydroxy-1H-benzimidazole-4-carboximidamide;
N-(3-chloro-4-fluorophenyl)-7-fluoro-N'-hydroxy-3H-benzimidazole-4-carboximidamide;
7-chloro-N-(3-chloro-4-fluorophenyl)-N'-hydroxy-3H-benzimidazole-4-carboximidamide;
N-(3-chloro-4-fluorophenyl)-N'-hydroxy-7-(trifluoromethyl)-1H-benzimidazole-4-carboximidamide;
N-(3-chloro-4-fluorophenyl)-6,7-difluoro-N'-hydroxy-2-(2-morpholin-4-ylethylamino)-3H-benzimidazole-4-carboximidamide;
N-(3-chloro-4-fluorophenyl)-6,7-difluoro-N'-hydroxy-2-(methylaminomethyl)-1H-benzimidazole-4-carboximidamide;
N-(3-chloro-4-fluorophenyl)-6-fluoro-N'-hydroxy-7-methyl-3H-benzimidazole-4-carboximidamide;
N-(3-chloro-4-fluorophenyl)-N'-hydroxy-7-methyl-3H-benzimidazole-4-carboximidamide;
N-(3-chloro-4-fluorophenyl)-6,7-difluoro-N'-hydroxy-3H-benzimidazole-4-carboximidamide;
N-(3-chloro-4-fluorophenyl)-N'-hydroxy-7-(trifluoromethoxy)-3H-benzimidazole-4-carboximidamide;
N-(3-chloro-4-fluorophenyl)-5-fluoro-N'-hydroxy-3H-benzimidazole-4-carboximidamide;
N-(3-chloro-4-fluorophenyl)-6,7-difluoro-N'-hydroxy-2-(hydroxymethyl)-3H-benzimidazole-4-carboximidamide;
N-(3-chloro-4-fluorophenyl)-6,7-difluoro-N'-hydroxy-2-morpholin-4-yl-3H-benzimidazole-4-carboximidamide;
N-(3-chlorophenyl)-6,7-difluoro-N'-hydroxy-2-(1-methylpiperidin-3-yl)-3H-benzimidazole-4-carboximidamide;
N-(3-chloro-4-fluorophenyl)-N'-hydroxy-3H-benzimidazole-4-carboximidamide;
6-chloro-N-(3-chloro-4-fluorophenyl)-N'-hydroxy-3H-benzimidazole-4-carboximidamide;
7-bromo-N-(3-chloro-4-fluorophenyl)-N'-hydroxy-3H-benzimidazole-4-carboximidamide;
N-(3-chloro-4-fluorophenyl)-6,7-difluoro-N'-hydroxy-2-[(3-methoxypropylamino)methyl]-1H-benzimidazole-4-carboximidamide;
N-(3-chloro-4-fluorophenyl)-2-[3-(dimethylamino)propyl]-6,7-difluoro-N'-hydroxy-3H-benzimidazole-4-carboximidamide;

N-(3-chloro-4-fluorophenyl)-2-[2-(dimethylamino)ethyl]-6,7-difluoro-N'-hydroxy-1H-benzimidazole-4-carboximidamide;
N-(3-chloro-4-fluorophenyl)-6,7-difluoro-N'-hydroxy-2-(methylamino)-3H-benzimidazole-4-carboximidamide;
N-(3-bromo-4-fluorophenyl)-2-[2-(dimethylamino)ethyl]-6,7-difluoro-N'-hydroxy-1H-benzimidazole-4-carboximidamide;
N-(3-bromophenyl)-2-[2-(dimethylamino)ethyl]-6,7-difluoro-N'-hydroxy-1H-benzimidazole-4-carboximidamide;
N-(3-chlorophenyl)-2-[2-(dimethylamino)ethyl]-6,7-difluoro-N'-hydroxy-1H-benzimidazole-4-carboximidamide;
N-(3-chloro-4-fluorophenyl)-2-[3-(dimethylamino)propylamino]-6,7-difluoro-N'-hydroxy-3H-benzimidazole-4-carboximidamide;
N-(3-chloro-4-fluorophenyl)-6,7-difluoro-N'-hydroxy-2-(2-methoxyethylamino)-3H-benzimidazole-4-carboximidamide;
N-(3-chloro-4-fluorophenyl)-2-[2-(dimethylamino)ethylamino]-6,7-difluoro-N'-hydroxy-3H-benzimidazole-4-carboximidamide;
N-(3-chloro-4-fluorophenyl)-2-[2-(diethylamino)ethylamino]-6,7-difluoro-N'-hydroxy-3H-benzimidazole-4-carboximidamide;
N-(3-chloro-4-fluorophenyl)-6,7-difluoro-N'-hydroxy-2-[(propan-2-ylamino)methyl]-1H-benzimidazole-4-carboximidamide;
N-(3-chloro-4-fluorophenyl)-2-[(dimethylamino)methyl]-6,7-difluoro-N'-hydroxy-1H-benzimidazole-4-carboximidamide;
N-(3-chloro-4-fluorophenyl)-2-(ethylaminomethyl)-6,7-difluoro-N'-hydroxy-1H-benzimidazole-4-carboximidamide;
N-(3-chloro-4-fluorophenyl)-2-[2-(dimethylamino)ethylamino]-7-fluoro-N'-hydroxy-3H-benzimidazole-4-carboximidamide;
N-(3-chloro-4-fluorophenyl)-6,7-difluoro-N'-hydroxy-2-[2-(methylamino)ethyl]-1H-benzimidazole-4-carboximidamide;
N-(3-chloro-4-fluorophenyl)-2-[2-(diethylamino)ethyl]-6,7-difluoro-N'-hydroxy-1H-benzimidazole-4-carboximidamide;
N-(3-chloro-4-fluorophenyl)-7-fluoro-N'-hydroxy-2-(2-methylsulfonylethylamino)-3H-benzimidazole-4-carboximidamide;
N-(3-chloro-4-fluorophenyl)-6,7-difluoro-N'-hydroxy-2-(2-methylsulfonylethylamino)-3H-benzimidazole-4-carboximidamide;
N-(3-chloro-4-fluorophenyl)-2-[(cyclopropylmethylamino)methyl]-6,7-difluoro-N'-hydroxy-1H-benzimidazole-4-carboximidamide;
N-(3-chloro-4-fluorophenyl)-7-fluoro-N'-hydroxy-2-(3-morpholin-4-ylpropylamino)-3H-benzimidazole-4-carboximidamide;
N-(3-chloro-4-fluorophenyl)-6,7-difluoro-N'-hydroxy-2-(2-pyrrolidin-1-ylethylamino)-3H-benzimidazole-4-carboximidamide;
N-(3-chloro-4-fluorophenyl)-2-[2-(4,4-difluoropiperidin-1-yl)ethylamino]-6,7-difluoro-N'-hydroxy-3H-benzimidazole-4-carboximidamide;
N-(3-chloro-4-fluorophenyl)-6,7-difluoro-N'-hydroxy-2-(1-morpholin-4-ylpropan-2-ylamino)-3H-benzimidazole-4-carboximidamide;
2-(aminomethyl)-N-(3-chloro-4-fluorophenyl)-6,7-difluoro-N'-hydroxy-1H-benzimidazole-4-carboximidamide;
2-amino-N-(3-chloro-4-fluorophenyl)-7-fluoro-N'-hydroxy-3H-benzimidazole-4-carboximidamide;
2-amino-N-(3-bromo-4-fluorophenyl)-6,7-difluoro-N'-hydroxy-3H-benzimidazole-4-carboximidamide;
2-amino-N-(3-bromophenyl)-6,7-difluoro-N'-hydroxy-3H-benzimidazole-4-carboximidamide;
2-amino-N-(3-chlorophenyl)-6,7-difluoro-N'-hydroxy-3H-benzimidazole-4-carboximidamide;
2-amino-N-(3-chloro-4-fluorophenyl)-6,7-difluoro-N'-hydroxy-3H-benzimidazole-4-carboximidamide;
2-amino-N-(3-bromophenyl)-7-fluoro-N'-hydroxy-3H-benzimidazole-4-carboximidamide;
2-amino-N-(3-bromo-4-fluorophenyl)-7-fluoro-N'-hydroxy-3H-benzimidazole-4-carboximidamide;
2-amino-N-(3-chlorophenyl)-7-fluoro-N'-hydroxy-3H-benzimidazole-4-carboximidamide;
2-amino-6,7-difluoro-N-[4-fluoro-3-(trifluoromethyl)phenyl]-N'-hydroxy-3H-benzimidazole-4-carboximidamide;
2-amino-7-fluoro-N-[4-fluoro-3-(trifluoromethyl)phenyl]-N'-hydroxy-3H-benzimidazole-4-carboximidamide;
N-(3-chlorophenyl)-4,5-difluoro-N'-hydroxy-2-(((3-methoxypropyl)amino)methyl)-1H-benzo[d]imidazole-7-carboximidamide;
N-(3-chlorophenyl)-2-(((cyclopropylmethyl)amino)methyl)-4,5-difluoro-N'-hydroxy-1H-benzo[d]imidazole-7-carboximidamide;
N-(3-chlorophenyl)-2-((dimethylamino)methyl)-4,5-difluoro-N'-hydroxy-1H-benzo[d]imidazole-7-carboximidamide;
N-(3-chlorophenyl)-4,5-difluoro-N'-hydroxy-2-((isopropylamino)methyl)-1H-benzo[d]imidazole-7-carboximidamide;
N-(3-chlorophenyl)-2-((ethylamino)methyl)-4,5-difluoro-N'-hydroxy-1H-benzo[d]imidazole-7-carboximidamide;
N-(3-chlorophenyl)-4,5-difluoro-N'-hydroxy-2-(hydroxymethyl)-1H-benzo[d]imidazole-7-carboximidamide;
N-(3-chlorophenyl)-4,5-difluoro-N'-hydroxy-2-((methylamino)methyl)-1H-benzo[d]imidazole-7-carboximidamide;
2-(aminomethyl)-N-(3-chlorophenyl)-4,5-difluoro-N'-hydroxy-1H-benzo[d]imidazole-7-carboximidamide; and
N-(3-chloro-4-fluorophenyl)-4-fluoro-N'-hydroxy-2-((2-morpholinoethyl)amino)-1H-benzo[d]imidazole-7-carboximidamide.

In some embodiments, L is C(O)—NR$^3$—.
In some embodiments, the compound is selected from the group consisting of:
ethyl N-[7-[(Z)—N-(3-chloro-4-fluorophenyl)-N'-hydroxycarbamimidoyl]-1H-imidazo[4,5-b]pyridin-2-yl]carbamate;
N-[[7-[(Z)—N-(3-chloro-4-fluorophenyl)-N'-hydroxycarbamimidoyl]-3H-imidazo[4,5-b]pyridin-2-yl]methyl]acetamide; and
propan-2-yl N-[7-[(Z)—N-(3-chloro-4-fluorophenyl)-N'-hydroxycarbamimidoyl]-1H-imidazo[4,5-b]pyridin-2-yl]carbamate.

In some embodiments, L is N, m is 1, and n is 0.
In some embodiments, L is N, m is 2, and n is 0.
In some embodiments, L is N, m is 3, and n is 0.
In one embodiment, the compound of Formula I is represented by Formula IA or IB:

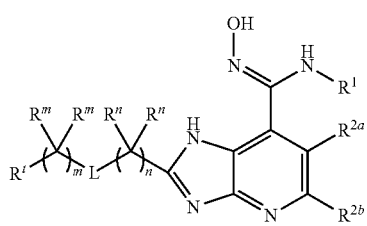
IA
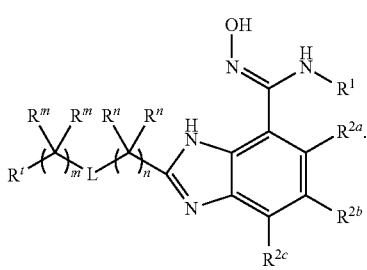
IB
In one embodiment, R¹ is selected from the group consisting of
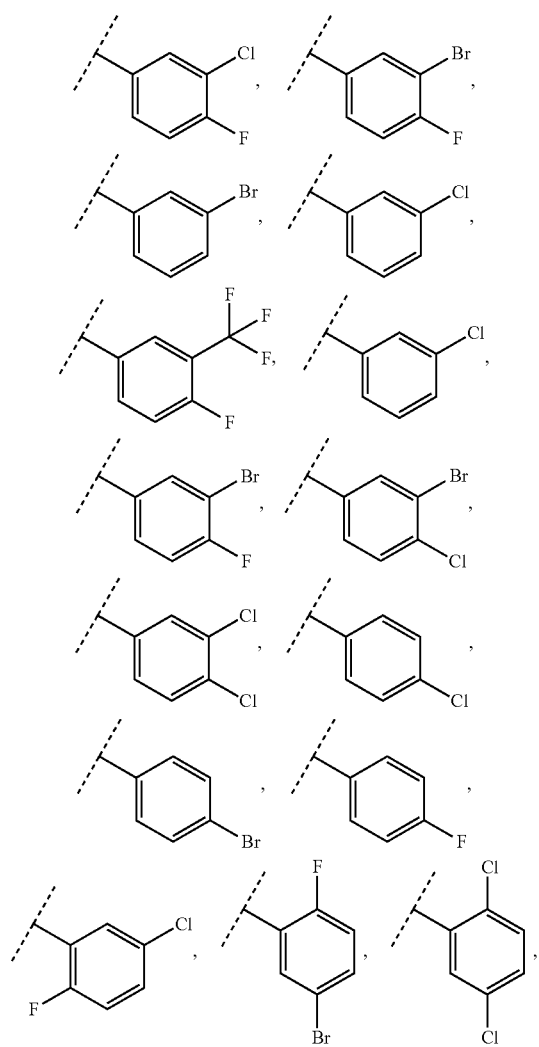
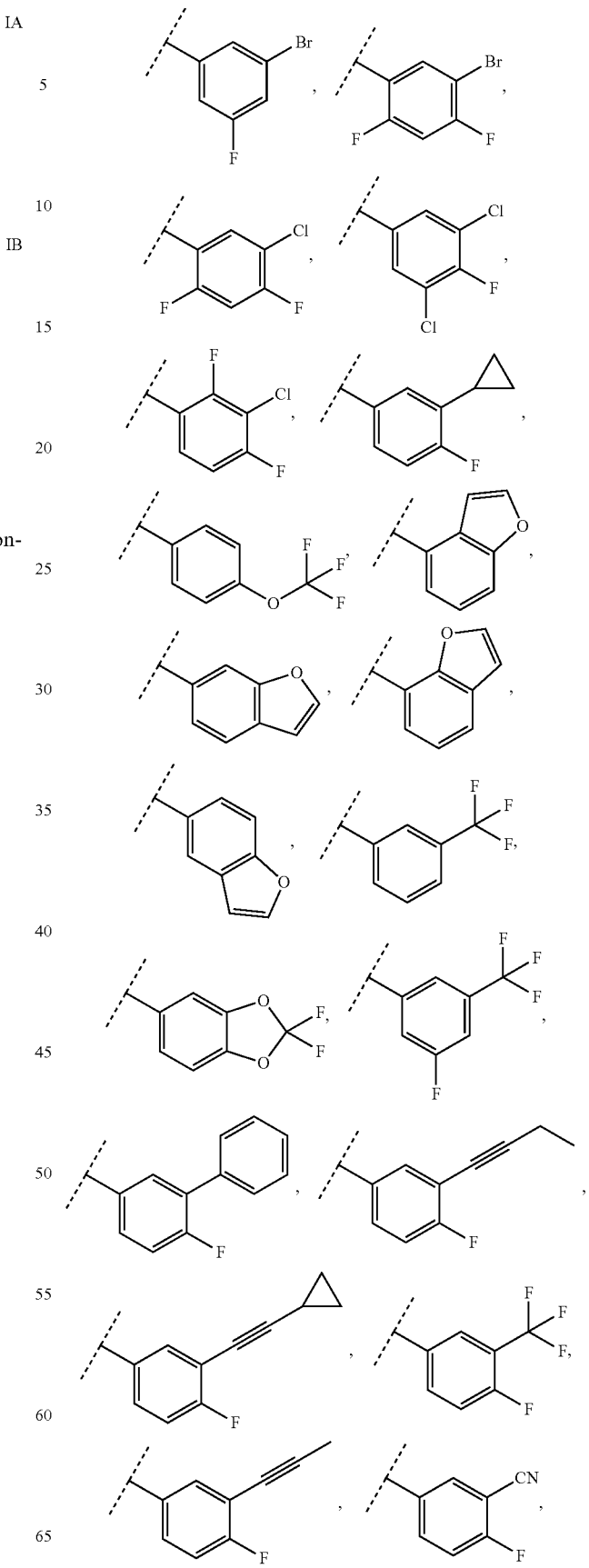

-continued
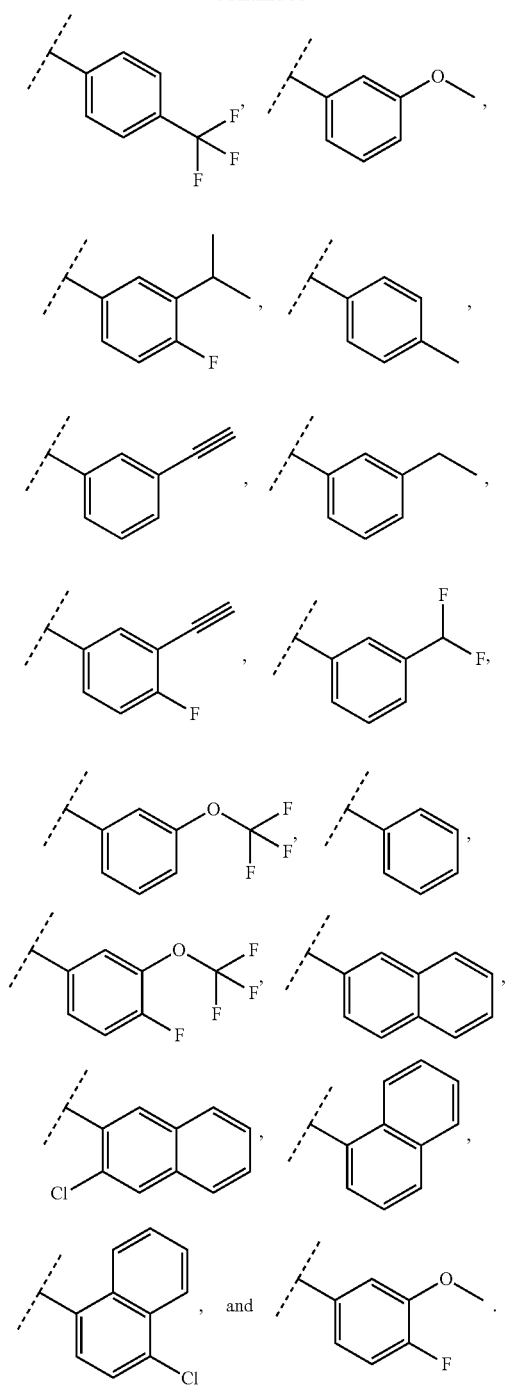
In one embodiment, $R^1$ is
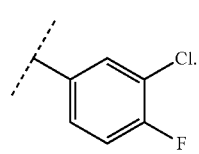
In one embodiment, the compound of Formula I is represented by Formula II:
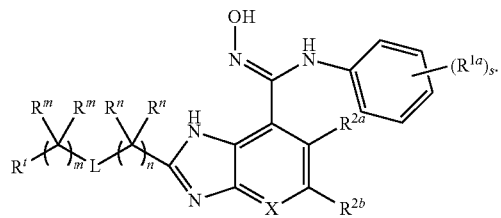
II
In one embodiment, the compound of Formula I is represented by Formula IIA or IIB:
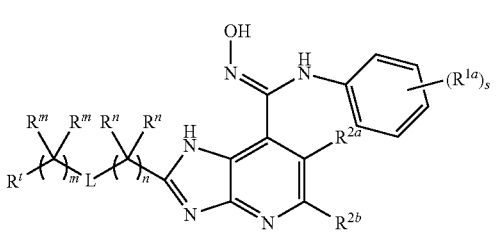
IIA
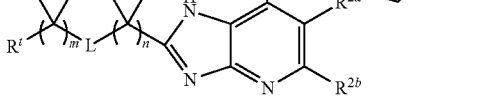
IIB
In one embodiment, the compound of Formula I is represented by Formula III:
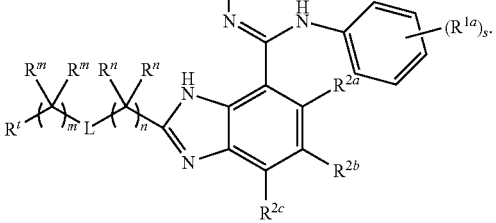
III
In one embodiment, the compound of Formula I is represented by Formula IV:
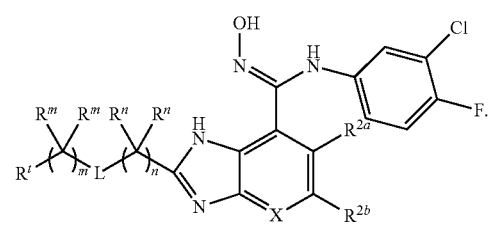
IV
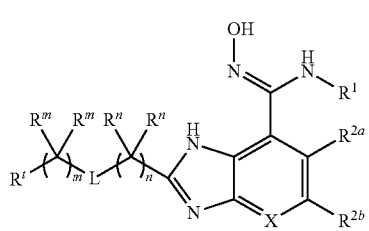

In one embodiment, the group

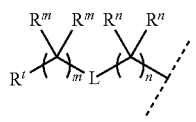

of any Formula described herein is selected from the group consisting of hydrogen, (1-methylpiperidin-2-yl)methylamino, (1-methylpyrrolidin-3-yl)amino, (2-pyrimidin-2-ylethylamino)methyl, (2S)-pyrrolidin-2-yl, (isopropyloxycarbonyl)amino, (1,3-thiazol-2-ylmethylamino)methyl, 1H-imidazol-2-yl, 1H-pyrazol-5-yl, 1H-pyrrol-2-yl, 1-hydroxyethyl, 2-(2-methoxyethylamino)ethyl, 2-(diethylamino)ethyl, 2-(diethylamino)ethylamino, 2-(dimethylamino)-1-hydroxyethyl, 2-(dimethylamino)ethyl, 2-(dimethylamino)ethylamino, [2-(dimethylamino)ethylamino]methyl, 2-(methylamino)ethyl, 2,2,2-trifluoro-1-hydroxyethyl, 2,2,2-trifluoroethylamino, (2,2,2-trifluoroethylamino)methyl, 2-[2,2-difluoroethyl(methyl)amino]ethyl, (2,2-difluoroethylamino)methyl, (2,2-dimethylpropylamino)methyl, 2-[2-methoxyethyl(methyl)amino]ethyl, 2-[cyclopropylmethyl(methyl)amino]ethyl, 2-aminoethyl, 2-hydroxyethyl, 2-hydroxypropan-2-yl, (2-methoxyethylamino)methyl, [(2-methoxyphenyl)methylamino]methyl, 2-morpholin-4-ylethyl, 2-morpholin-4-ylethylamino, 2-phenylethylamino, 2-piperidin-1-ylethyl, (2-pyridin-2-ylethylamino)methyl, 2-pyrrolidin-1-ylethyl, 3-(dimethylamino)propyl, (3,3-difluorocyclobutyl)amino, [(3-hydroxy-2,2-dimethylpropyl)amino]methyl, (3-hydroxypropylamino)methyl, [3-methoxypropyl(methyl)amino]methyl, (3-methoxypropylamino)methyl, 3-morpholin-4-ylpropylamino, (3-morpholin-4-ylpropylamino)methyl, 5-methyl-1H-imidazol-2-yl, 2-methylsulfonylethylamino, 2-(4,4-difluoropiperidin-1-yl)ethylamino, 1-morpholin-4-ylpropan-2-ylamino, 3-(dimethylamino)propylamino, 2-methoxyethylamino, 2-pyrrolidin-1-ylethylamino, 1-methylpiperidin-3-yl, aminomethyl, (dimethylamino)methyl, acetamidomethyl, amino, aminomethyl, anilino, anilinomethyl, benzenesulfonamidomethyl, (benzylamino)methyl, chloromethyl, cyclobutylamino, cyclopropyl, cyclopropyl(hydroxy)methyl, cyclopropylamino, (cyclopropylamino)methyl, cyclopropylmethylamino, (cyclopropylmethylamino)methyl, dimethylamino, ethoxy carbonyl amino, ethyl, ethylamino, ethylaminomethyl, hydroxy(phenyl)methyl, hydroxymethyl, methanesulfonamidomethyl, methoxymethyl, methyl, methylamino, methylaminomethyl, (methylpropylamino)methyl, morpholin-4-yl, morpholin-4-ylmethyl, (oxan-2-ylmethylamino)methyl, (oxan-3-ylmethylamino)methyl, (oxan-4-ylamino)methyl, (oxolan-3-ylmethylamino)methyl, piperidin-1-ylmethyl, propan-2-ylamino, (propan-2-ylamino)methyl, (pyrazin-2-ylmethylamino)methyl, pyridin-3-yl, (pyridin-3-ylmethylamino)methyl, (pyridin-4-ylmethylamino)methyl, (pyrimidin-2-ylamino)methyl, (pyrimidin-2-ylmethylamino)methyl, pyrrolidin-1-ylmethyl, and thiophen-2-yl.

In one embodiment, the group

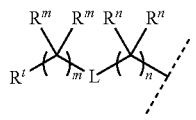

of any Formula described herein is selected from the group consisting of:

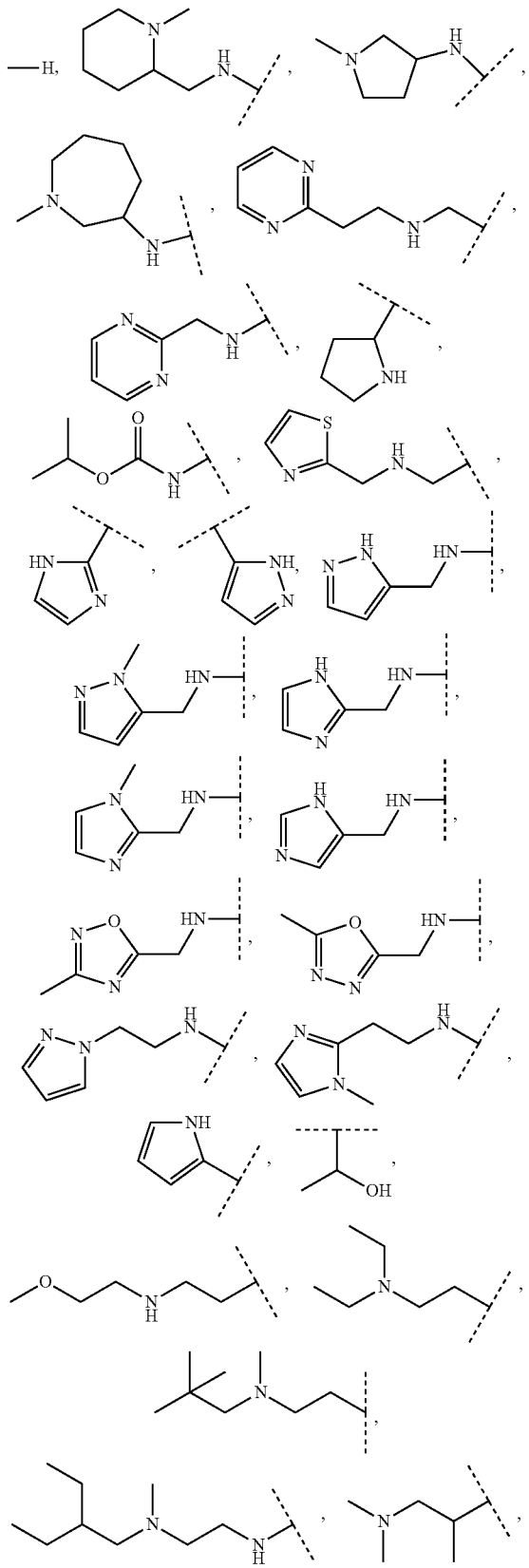

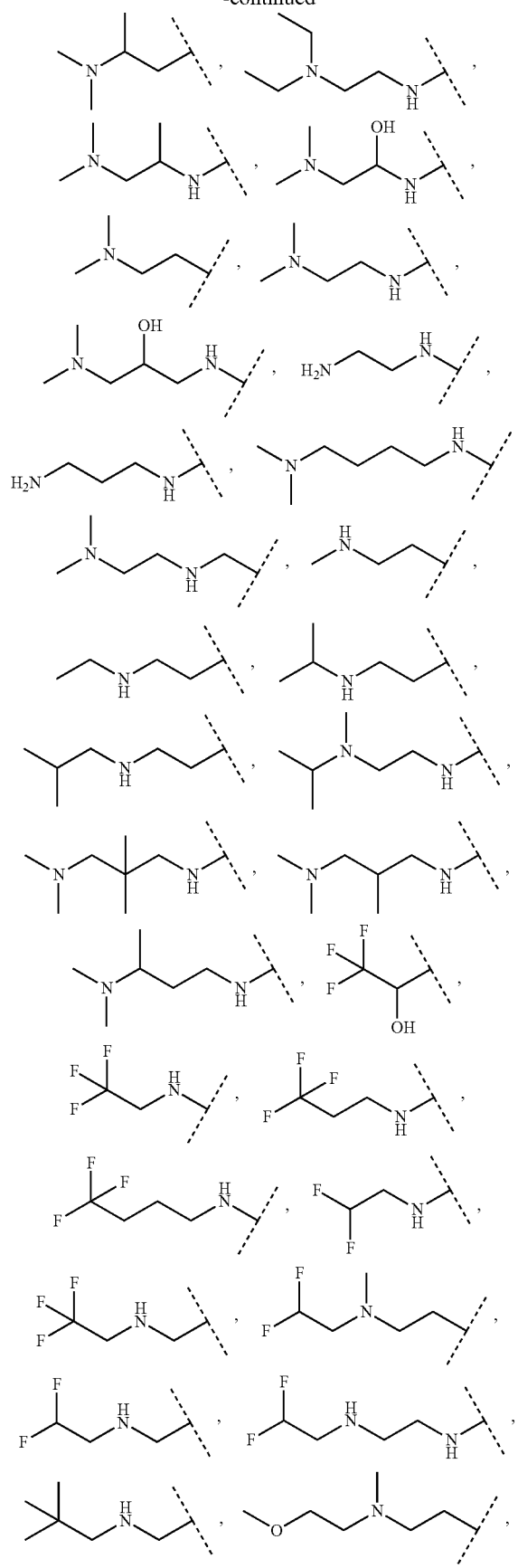
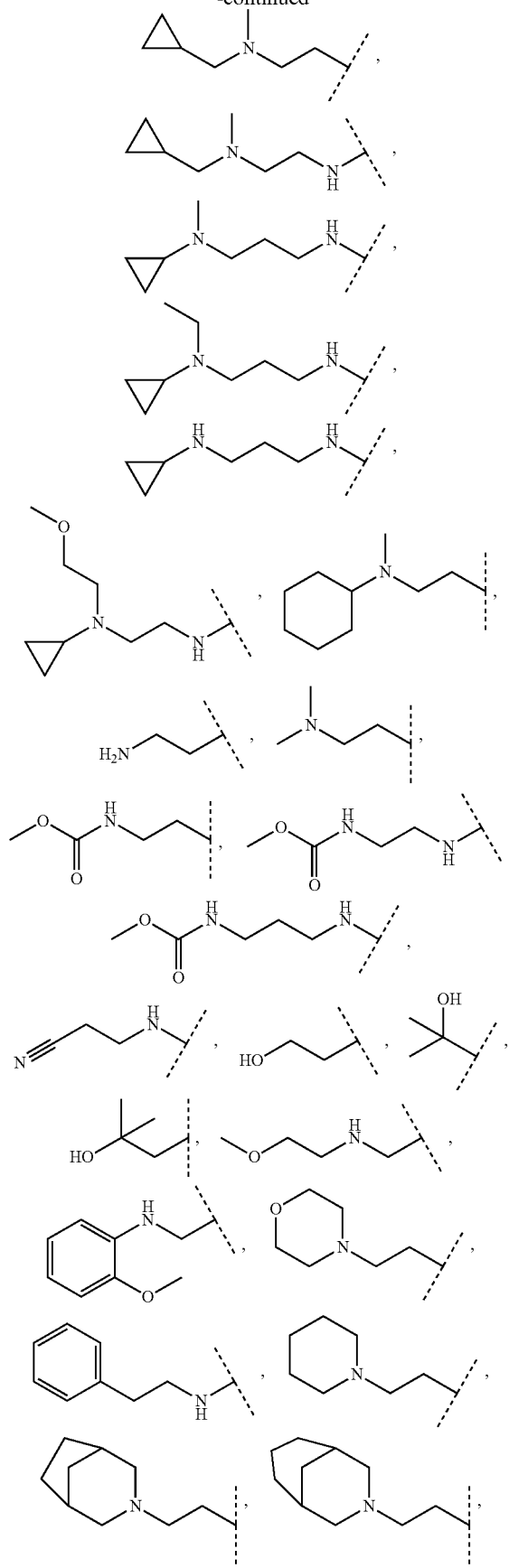

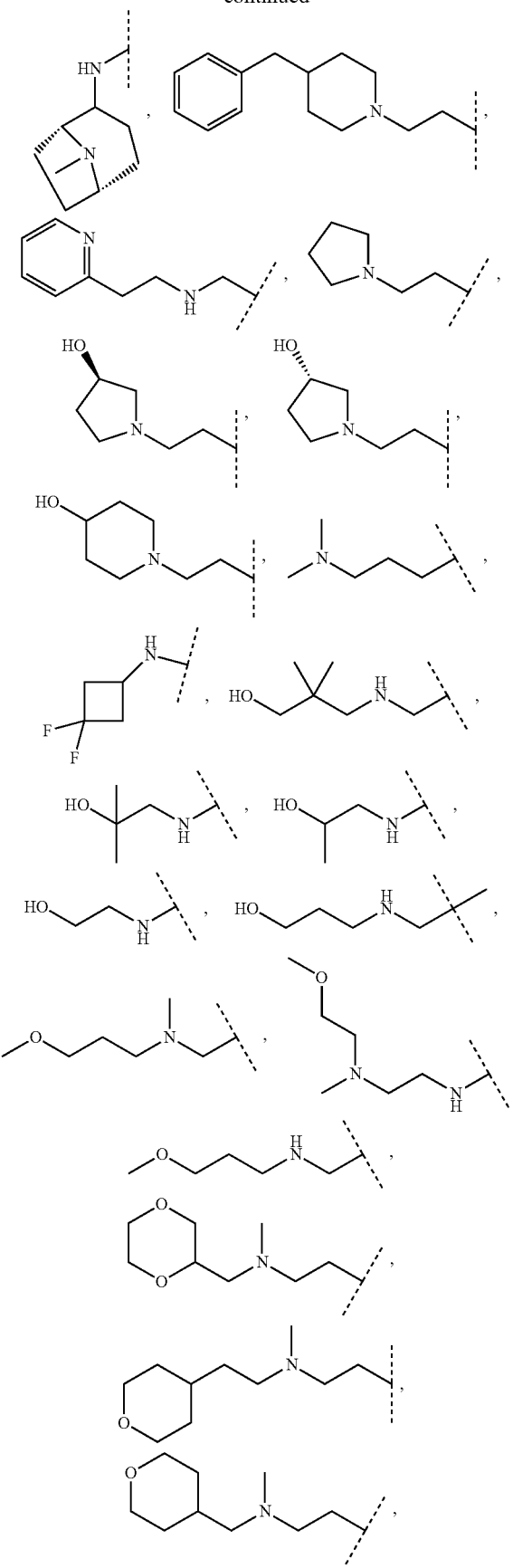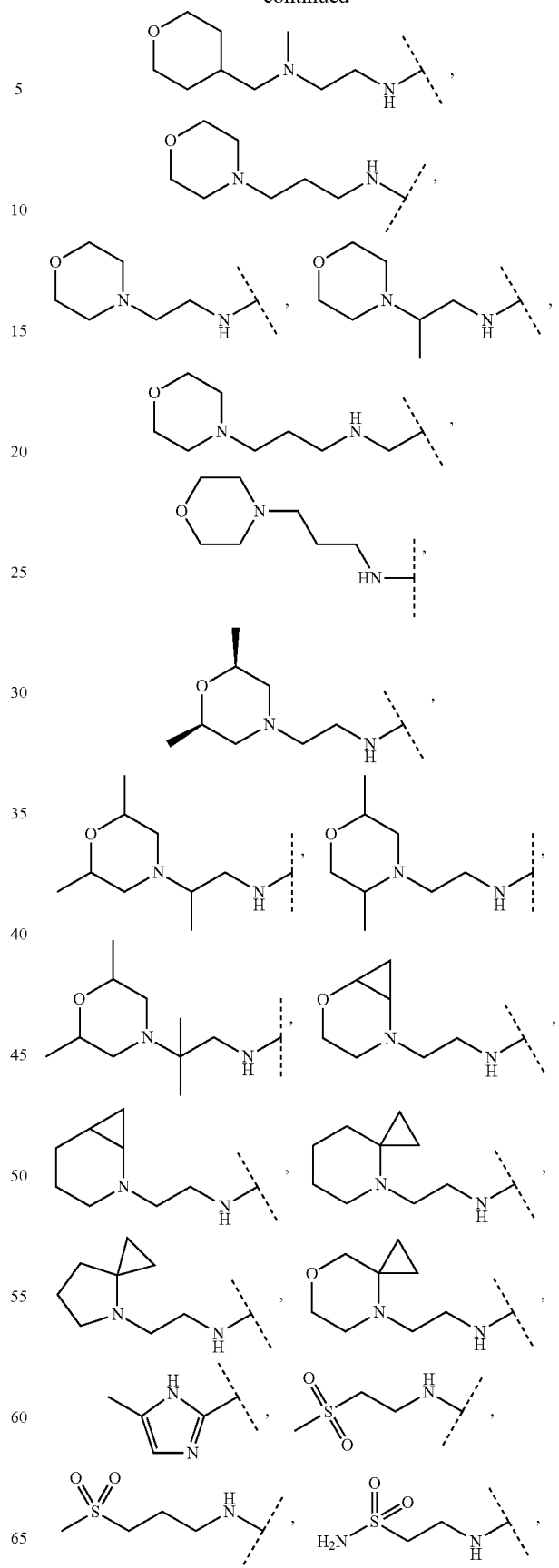

-continued
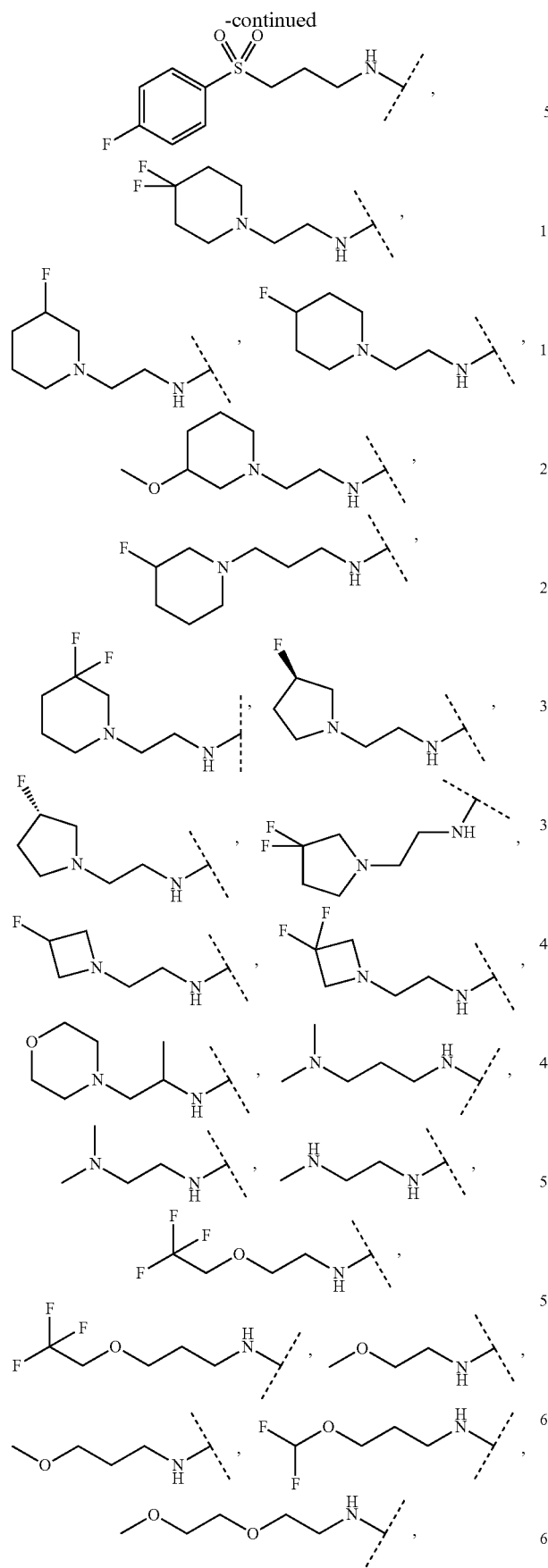
-continued
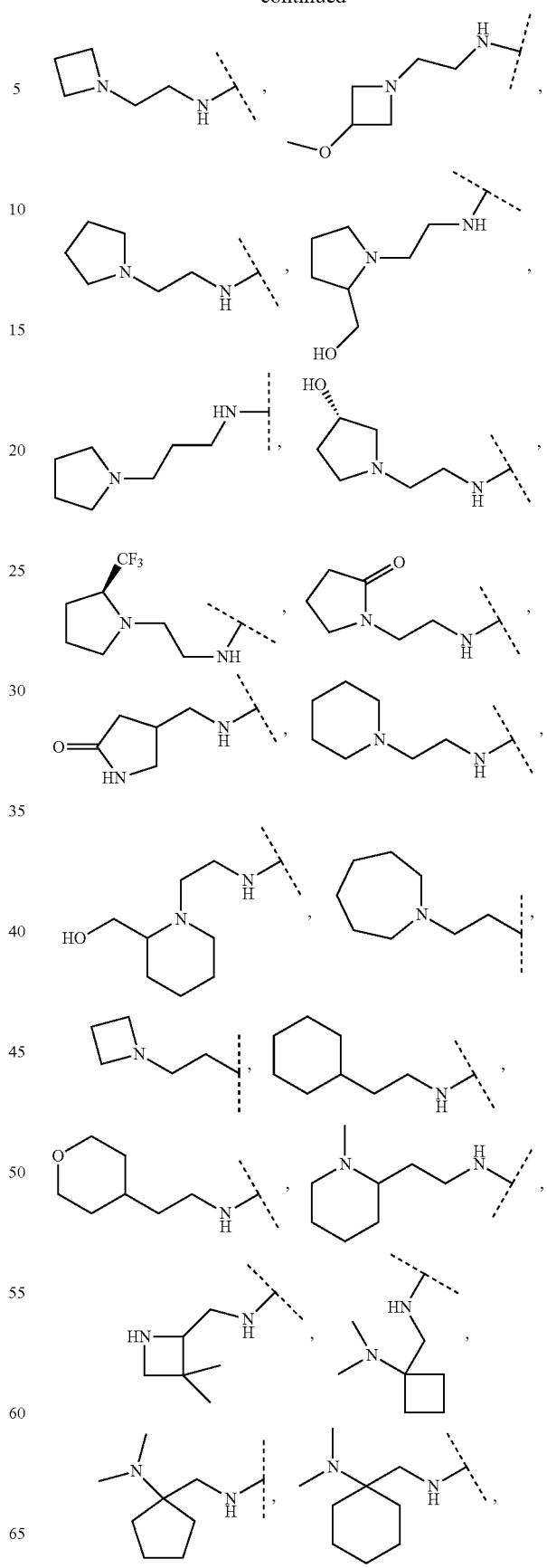

-continued
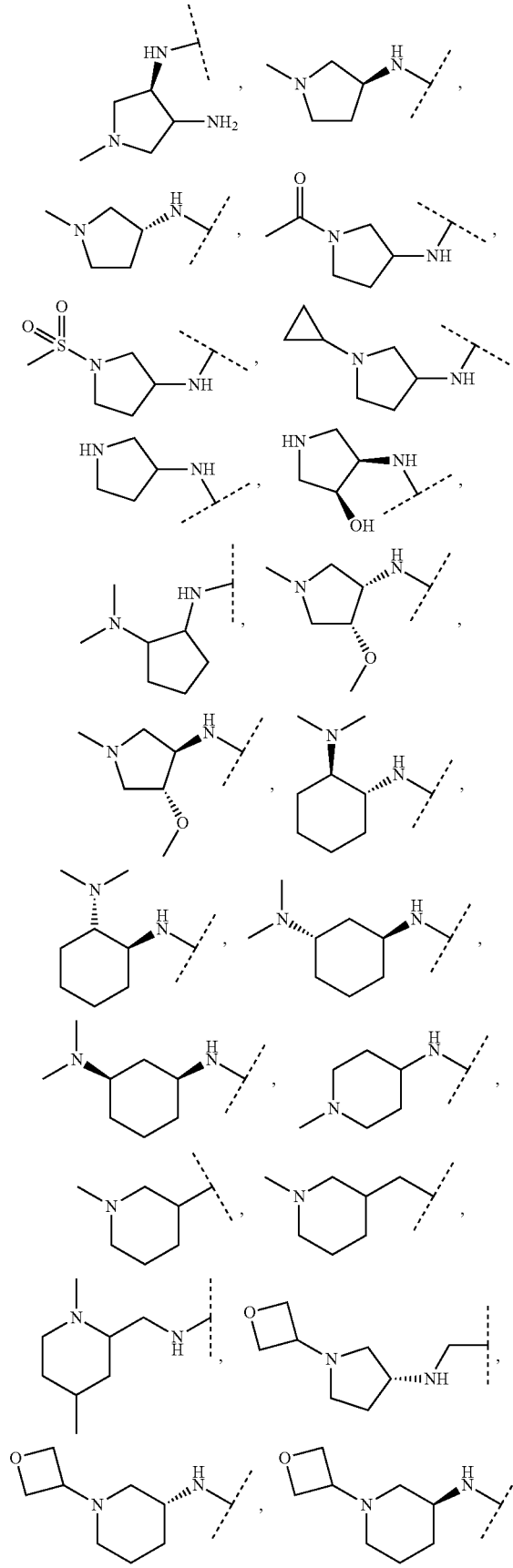
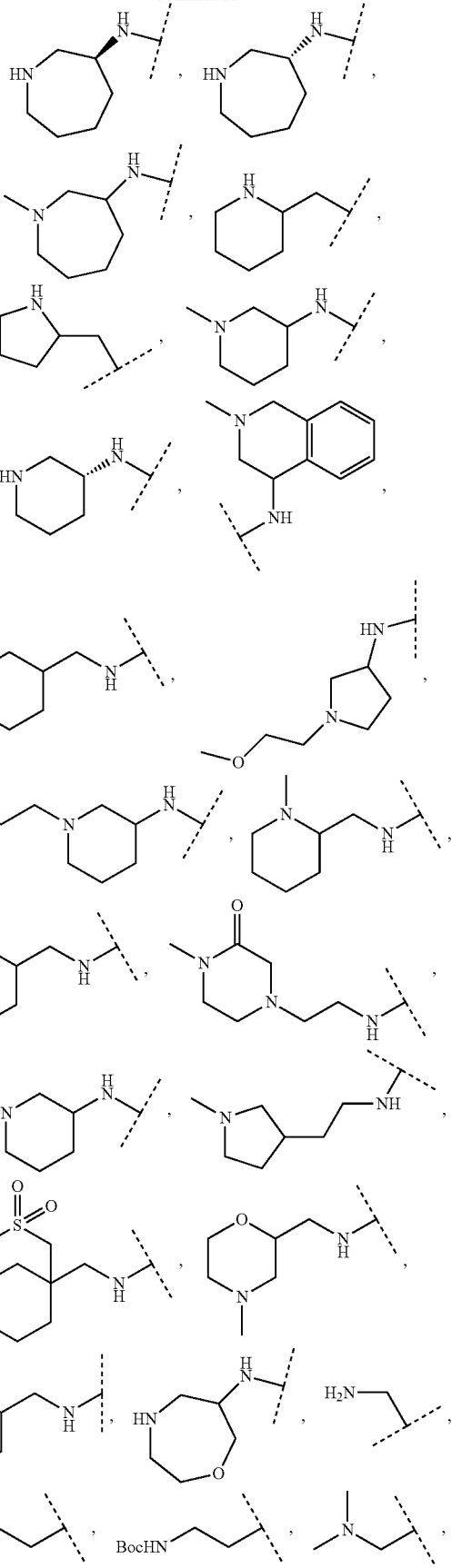

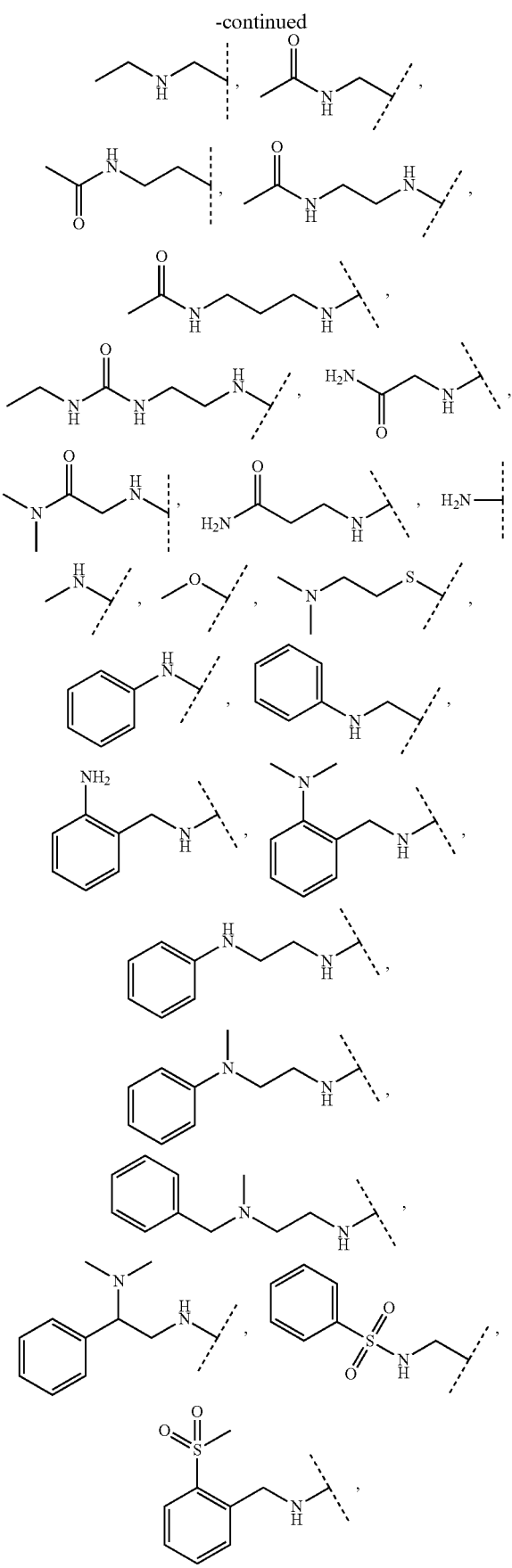
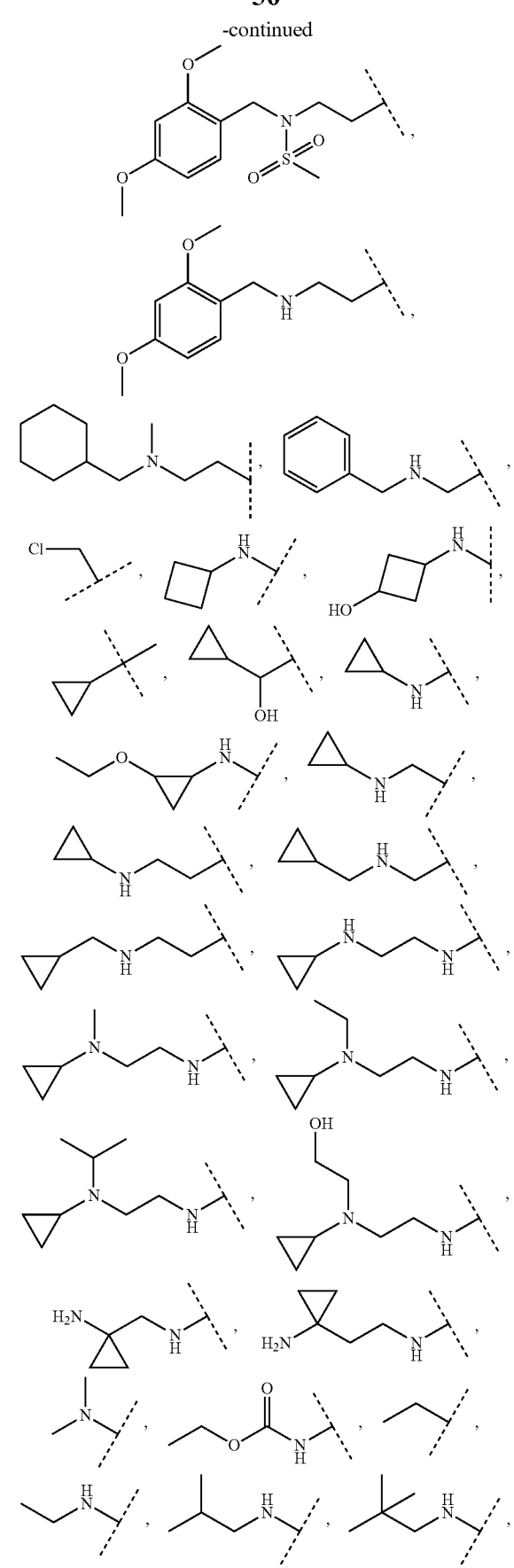

37
-continued
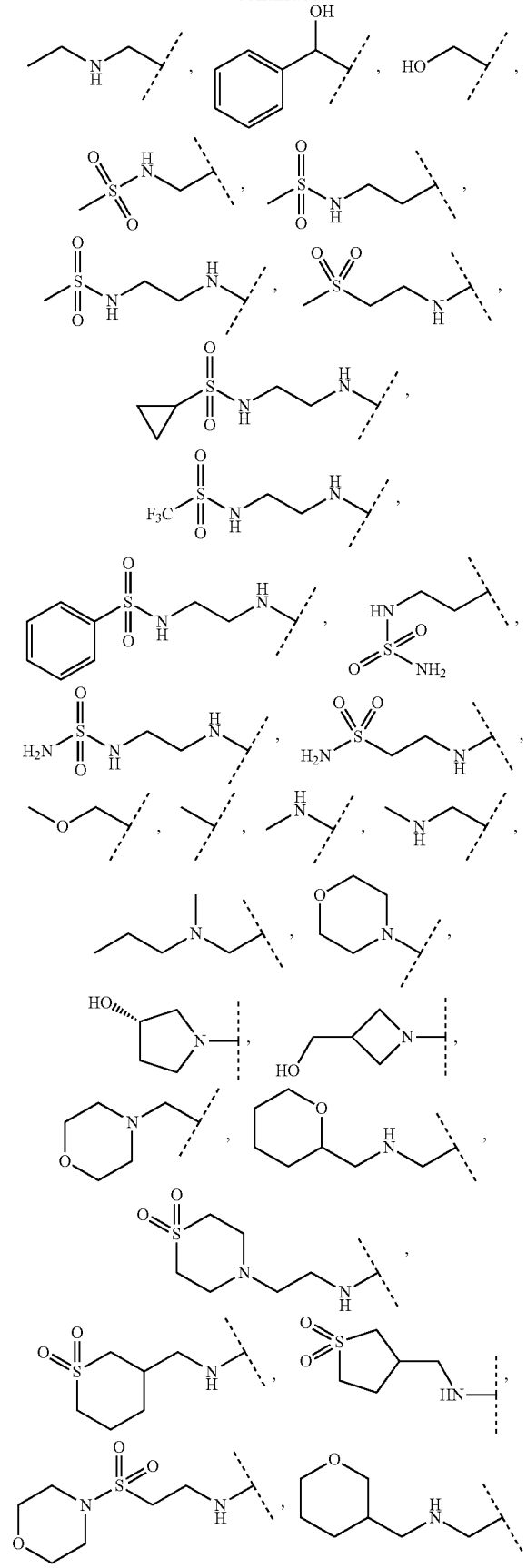
38
-continued
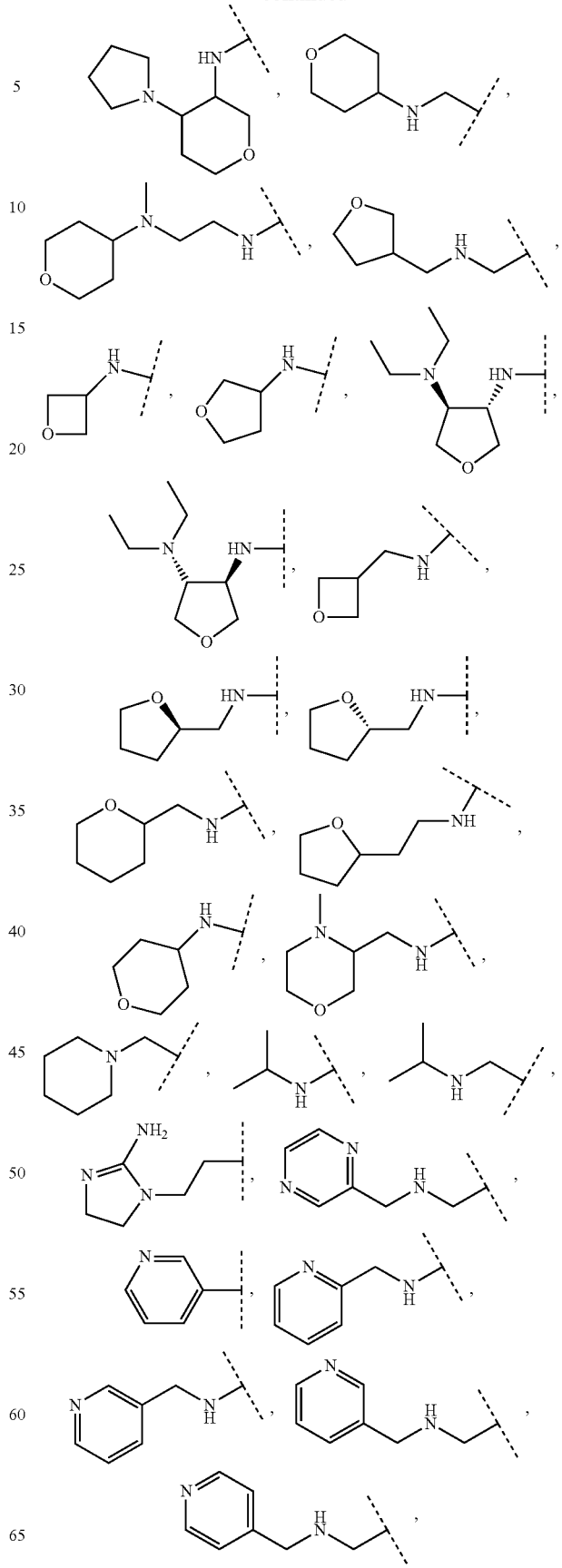

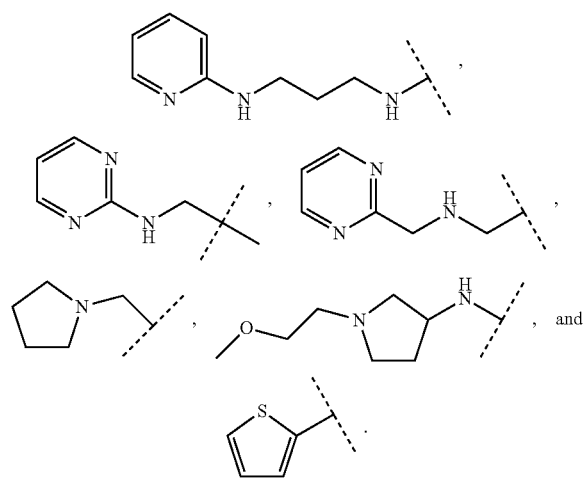
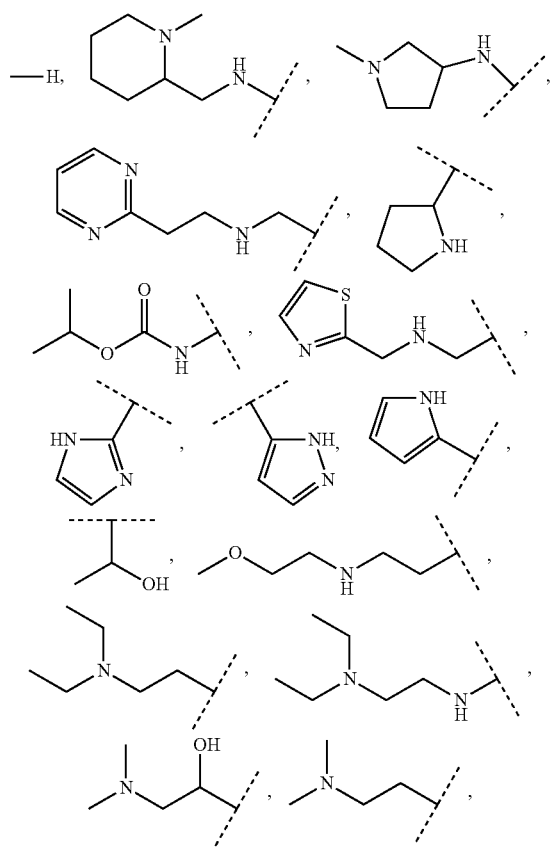
In one embodiment, the group
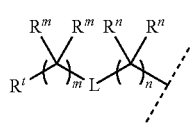
of any Formula described herein is selected from the group consisting of:
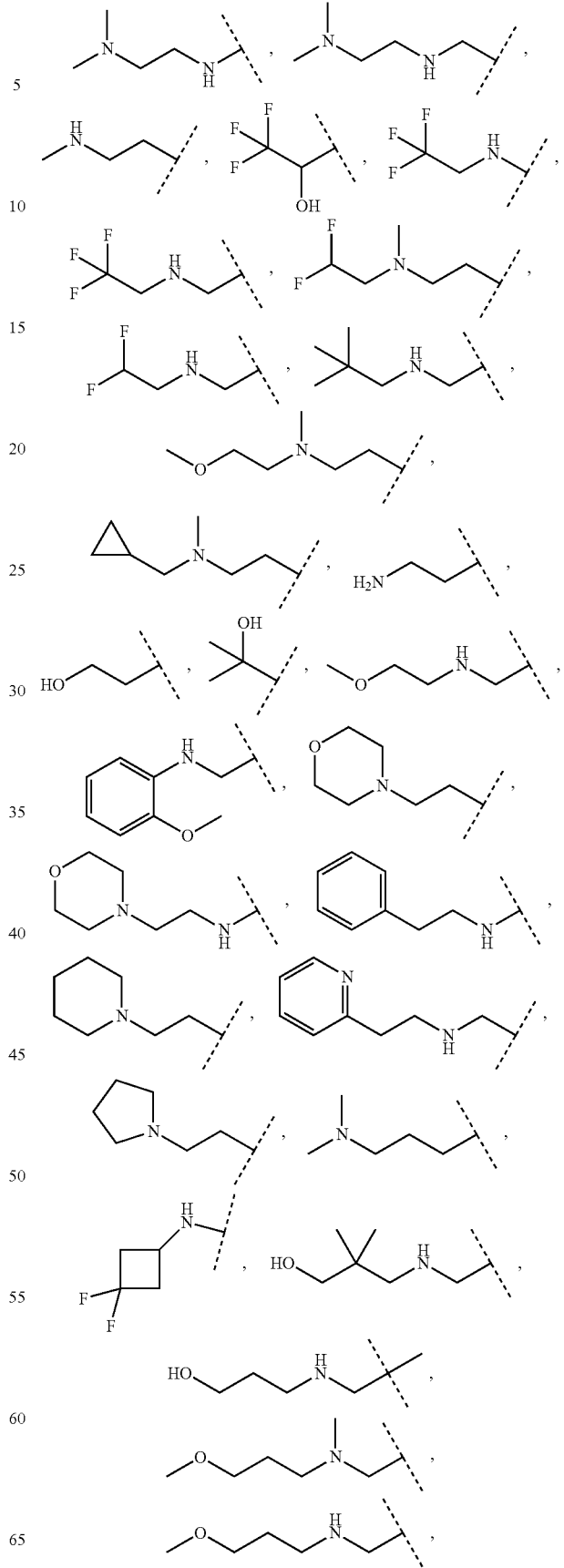

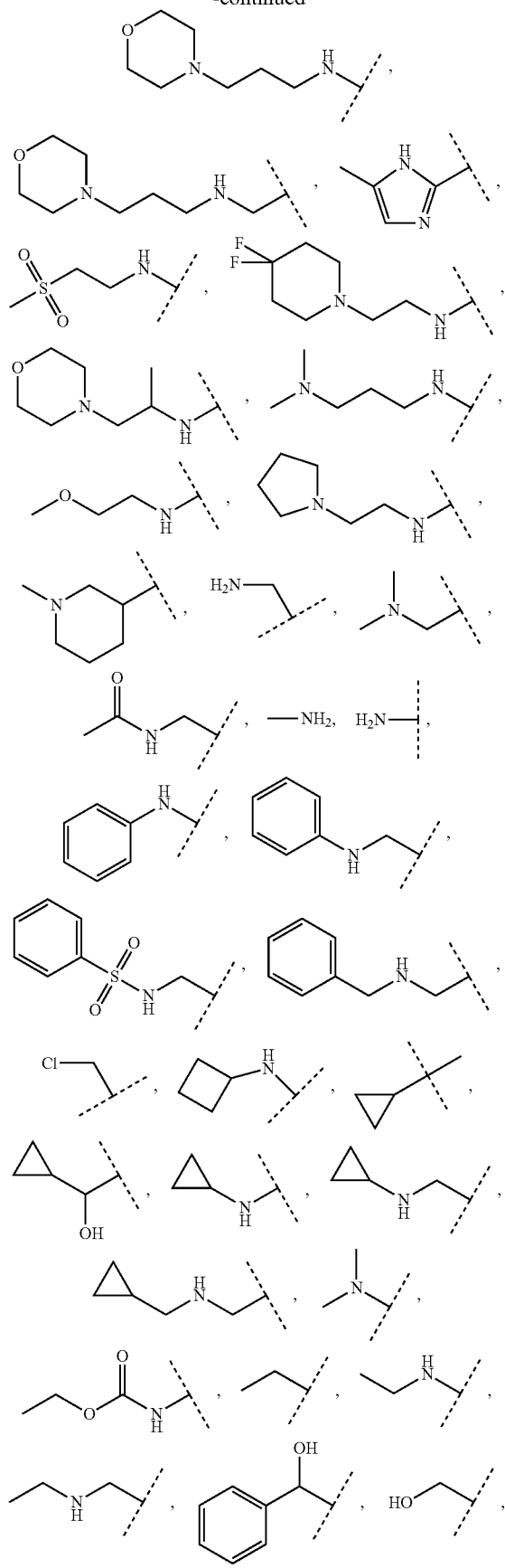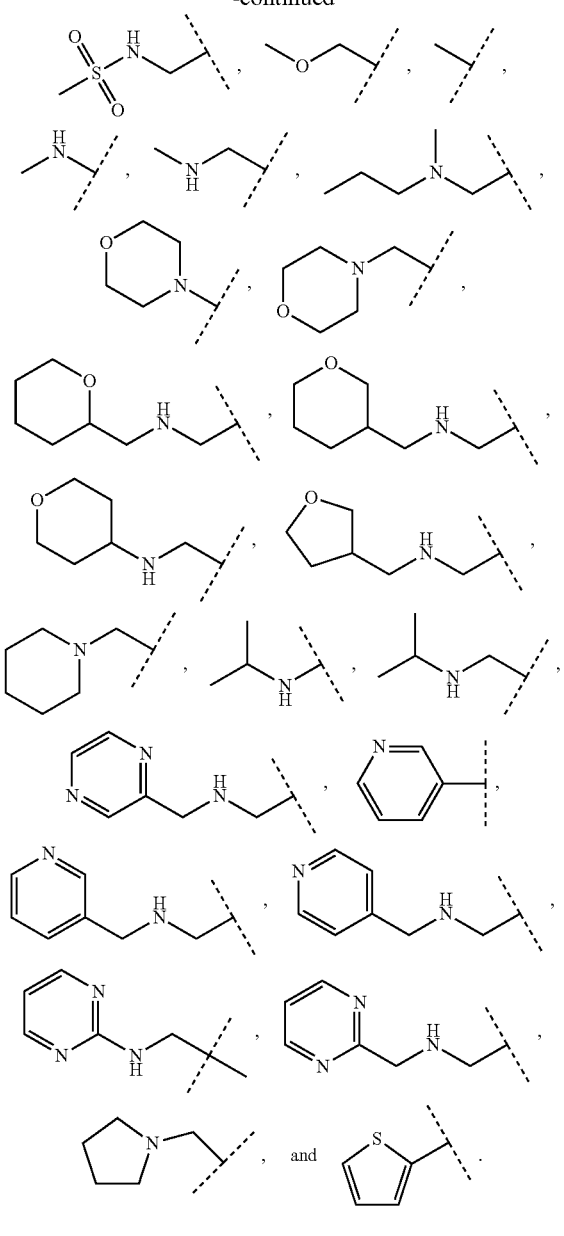
In one embodiment, the group
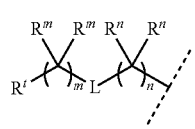
of any Formula described herein is selected from the group consisting of:

-continued
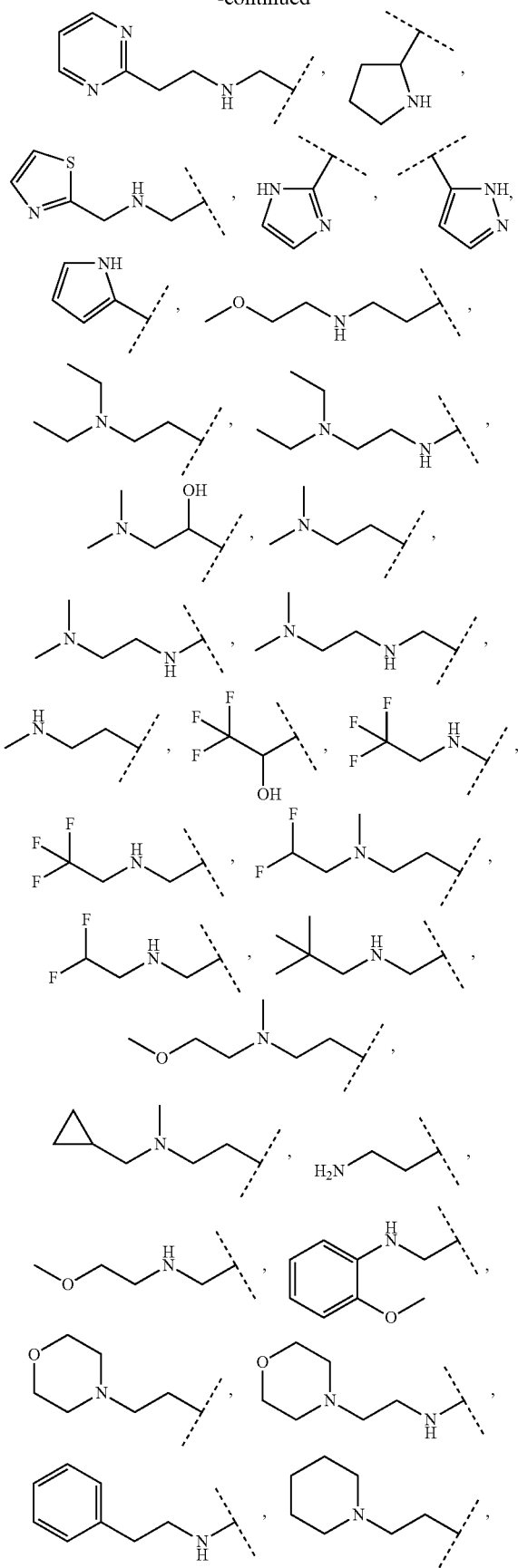
-continued
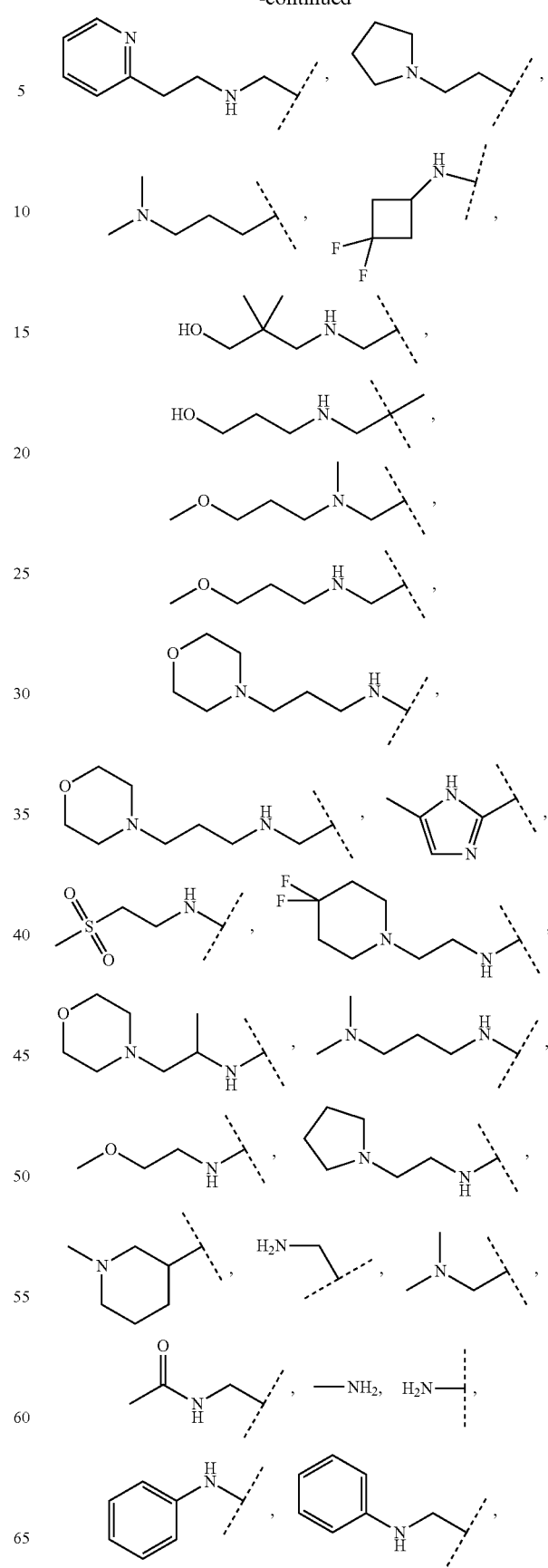

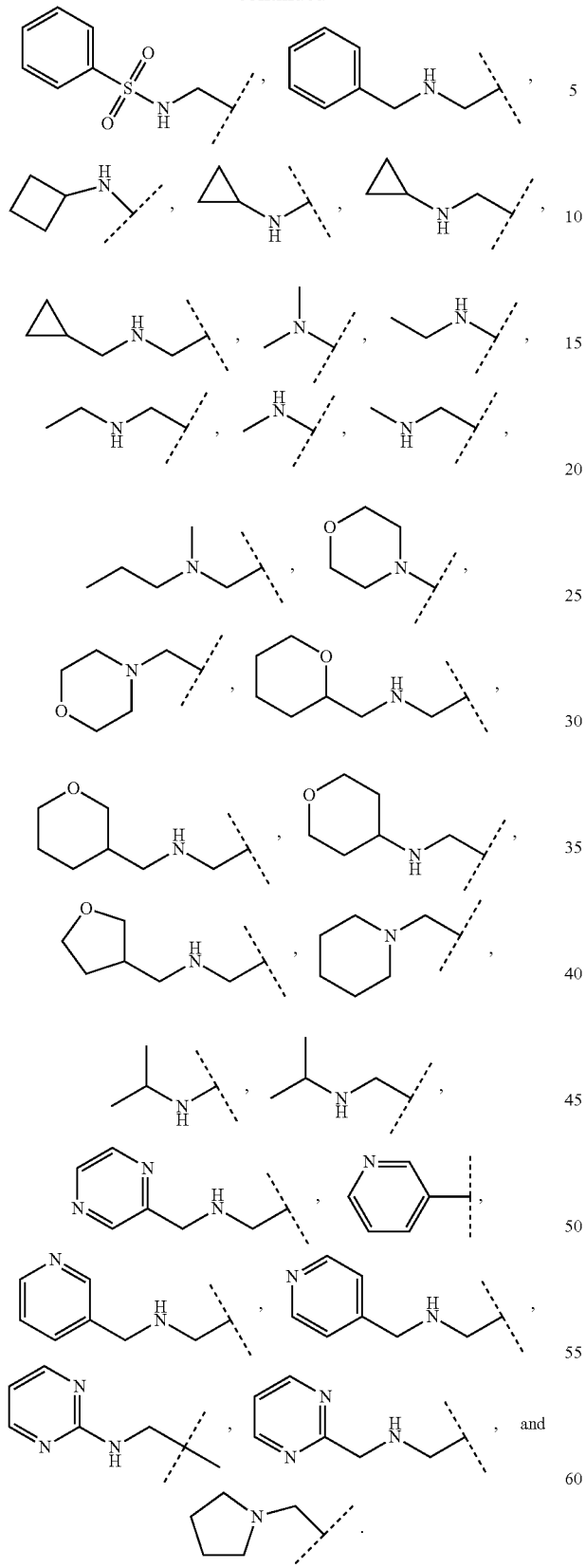

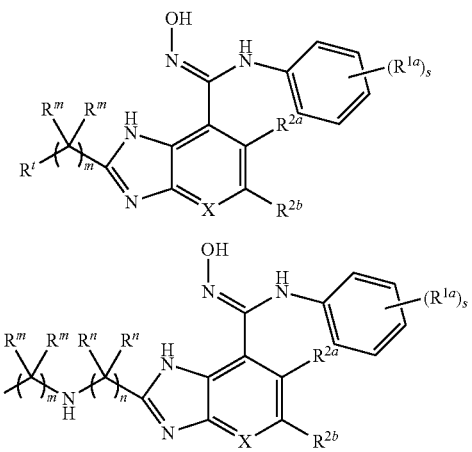

wherein $R^{2a}$, $R^{2b}$, X, $R^m$, $R^n$, m, n, and $R^t$ are as defined herein and each $R^{1a}$ is independently hydroxyl, halo, —CN, $C_{1-6}$ haloalkoxy, $C_{1-6}$ haloalkyl, $C_{1-6}$ alkoxy, $C_{1-6}$ alkyl, $C_{2-6}$ alkenyl, $C_{2-6}$ alkynyl, and $C_{3-6}$ cycloalkyl, or two of the optional substituents can join to form an additional partially saturated heterocyclic ring, and s is 0, 1, 2 or 3.

In some embodiments, each $R^{1a}$ is independently hydroxyl, halo, —CN, $C_{1-6}$ haloalkoxy, or $C_{1-6}$ haloalkyl. In some embodiments, each $R^{1a}$ is independently halo or —$CF_3$. In some embodiments, each $R^{1a}$ is independently halo. In some embodiments, s is 0. In some embodiments, s is 1. In some embodiments, s is 2. In some embodiments, s is 3.

In general, the specific compounds exemplified herein are named using ChemBioDraw Ultra. However, it is understood that other names may be used to identity compounds of the same structure. In particular, the compounds may also be named using other nomenclature systems and symbols that are commonly recognized in the art of chemistry including, for example, Chemical Abstract Service (CAS) and International Union of Pure and Applied Chemistry (IUPAC). Other compounds or radicals may be named with common names, or systematic or non-systematic names.

For example, the compound of Example 10 (shown below) may be referred to as N-(3-chloro-4-fluorophenyl)-4,5-difluoro-N'-hydroxy-1H-benzo[d]imidazole-7-carboximidamide or N-(3-chloro-4-fluorophenyl)-6,7-difluoro-N'-hydroxy-3H-benzimidazole-4-carboximidamide, where both names provide the structure below,

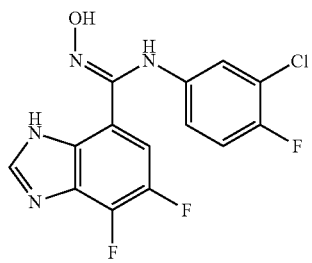 [SMILES: O/N=C(\Nc1ccc(F)c(Cl)c1)c1cc(F)c(F)c2nc[nH]c12]

Provided are also all tautomeric forms of the compounds of any Formula described herein. Tautomeric isomers are in equilibrium with one another. Regardless of which tautomer is shown, and regardless of the nature of the equilibrium In one embodiment, the compound of Formula I is represented by Formula IIA or IIB:

among tautomers, the compounds are understood by one of ordinary skill in the art to comprise both. Non-limiting examples of benzimidazole and imidazo[4,5-b]pyridine tautomers are shown below:

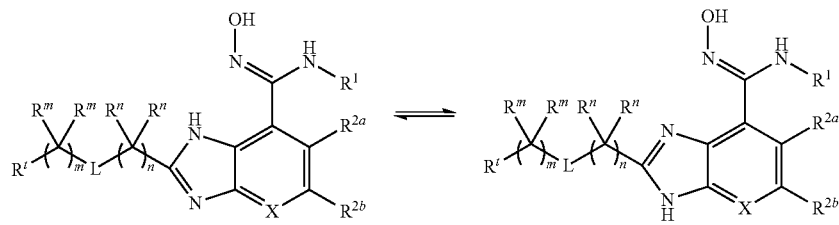

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the hydroxyamidine compounds described herein. Specifically, Z- and E-forms are included even if only one designation is named for both carbon-carbon double bonds as well as the hydroxyamidine bond.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided herein are also crystalline and amorphous forms of the compounds described herein or pharmaceutically acceptable salts, isomer, or a mixture thereof.

In certain embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of an IDO1 inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, the compounds described herein may be used to treat subjects who have or are suspected of having disease states, disorders, and conditions (also collectively referred to as "indications") responsive or believed to be responsive to the inhibition of IDO1 activity. In some embodiments, the compounds described herein may be used to inhibit the activity of an IDO1 polypeptide. In some embodiments, the compounds described herein may be used to inhibit excessive or destructive immune reactions or growth or a proliferation of a cell, such as a cancer cell, or inhibit immunosuppression.

Example indications suitable for treatment with compounds described here include, without limitation cancer, viral infection such as HIV infection, HBV infection, HCV infection, other infections (e.g., skin infections, GI infection, urinary tract infections, genito-urinary infections, and systemic infections), depression, neurodegenerative disorders such as Alzheimer's disease and Huntington's disease, trauma, age-related cataracts, organ transplantation (e.g., organ transplant rejection), and autoimmune diseases.

Examples of autoimmune diseases include, but are not limited to, asthma, collagen diseases such as rheumatoid arthritis, systemic lupus erythematosus. Sharp's syndrome, CREST syndrome (calcinosis, Raynaud's syndrome, esophageal dysmotility, sclerodactyly, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, allergic inflammation, inflammatory bowel disease, psoriasis and systemic lupus erythematosusor, malaria and Chagas disease.

In some embodiments, the compounds described herein may be used for treating cancer, viral infection, depression, a neurodegenerative disorder, trauma, age-related cataracts, organ transplant rejection, or an autoimmune disease.

In other embodiments, the disease to be treated is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), psoriasis, Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

Provided is a method for treating a subject, who has or is suspected of having a disease or condition responsive or believed to be responsive to the inhibition of IDO1 activity by administering to the subject the compound described herein or pharmaceutically acceptable salts, isomer, or a mixture thereof. Provided is also a method of inhibiting kinase activity of a IDO1 polypeptide by contacting the polypeptide with the compound described herein or pharmaceutically acceptable salts, isomer, or a mixture thereof. Provided is also a method of inhibiting a growth or a proliferation of cancer cells of hematopoietic origin comprising contacting the cancer cells with an effective amount of a compound described herein or pharmaceutically acceptable salts, isomer, or a mixture thereof.

In one embodiment, the compounds of the present application may be used in combination with one or more additional therapeutic agent that are being used and/or developed to treat cancers or inflammatory disorders. The one or more additional therapeutic agent may be a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof.

The one or more additional therapeutic agent may be an inhibitor to PI3K such as PI3Kγ, PI3Kβ, PI3Kδ, and/or PI3Kα, Janus kinase (JAK) such as JAK1, JAK2 and/or JAK3, spleen tyrosine kinase (SYK), Bruton's tyrosine kinase (BTK), bromodomain containing protein inhibitor (BRD) such as BRD4, a lysyl oxidase protein (LOX), lysyl oxidase-like protein (LOXL) such as LOXL1-5, matrix metalloprotease (MMP) such as MMP 1-10, adenosine A2B receptor (A2B), isocitrate dehydrogenase (IDH) such as IDH1, apoptosis signal-regulating kinase (ASK) such as ASK1, serine/threonine kinase TPL2, discoidin domain receptor (DDR) such as DDR1 and DDR2, histone deacetylase (HDAC), protein kinase C (PKC), or any combination thereof.

A phosphoinositide 3-kinase inhibitor (PI3K inhibitor) functions by inhibiting one or more of the phosphoinositide 3-kinase enzymes, including but not limited to PI3Kγ, PI3Kβ, PI3Kδ, and PI3Kα. Non-limiting examples of PI3K inhibitors include wortmannin, demethoxyviridin, LY294002, idelalisib, perifosine, PX-866, IPI-145, BAY 80-6946, BEZ235, RP6530, TGR 1202, INK1117, GDC-0941, BKM120, XL147 (also known as SAR245408), XL765 (also known as SAR245409), Palomid 529, GSK1059615, ZSTK474, PWT33597, IC87114, CAL263, RP6503, PI-103, GNE-477, CUDC-907 and AEZS-136. In some embodiments, the PI3K inhibitor is a PI3Kδ inhibitors, such as idelalisib, IPI-145, RP6530, and RP6503, as well as those disclosed in U.S. Pat. No. 8,569,296, and PCT publications WO. 2014/006572 and WO 2015/001491.

In some embodiments, the one or more additional therapeutic agent may be an MMP9 inhibitor, or an agent that inhibits the expression and/or activity of MMP9. A representative protein sequence for MMP9 is GenBank Accession No. NP_004985. The inhibitor can be small molecule or biologic. For instance, Gu et al., *The Journal of Neuroscience*, 25(27): 6401-6408 (2005) discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

One, two, three, or more of the therapeutic agents (e.g. a PI3K inhibitor, a JAK inhibitor, a SYK inhibitor, a BTK inhibitor, a BRD4 inhibitor, a LOXL2 inhibitor, a MMP9 inhibitor, a A2B inhibitor, an IDH inhibitor, an ASK inhibitor, a TPL2 inhibitor, a DDR1 inhibitor, a TBK inhibitor, a HDAC inhibitor, a PKC inhibitor) may be further used or combined with a chemotherapeutic agent, an immunotherapeutic agent, a radiotherapeutic agent, an anti-neoplastic agent, an anti-cancer agent, an anti-fibrotic agent, an anti-angiogenic agent, a therapeutic antibody, or any combination thereof.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives tacrolimus sirolimus azathioprine, mycophenolate; compounds (TNP-470, genistein) and growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylpednisolone, prednisone, and prenisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e., non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK(r); razoxane; rhizoxin; sizofiran; spirogermanium; tenuazonic acid; triaziquone; 2,2',2"-tricUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL(r) and docetaxel (TAXOTERE(r)); chlorambucil; gemcitabine (Gemzar(r)); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine(r)); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application. For example, gemcitabine, nab-paclitaxel, and gemcitabine/nab-paclitaxel are used with the JAK inhibitor and/or PI3Kδ inhibitor for treating hyperproliferative disorders.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston(r)); inhibitors of the enzyme aromatase, which regulates estrogen production in the adrenal glands, such as, for example, 4(5)-imidazoles, aminoglutethimide, megestrol acetate (Megace(r)), exemestane, formestane, fadrozole, vorozole (Rivisor(r)), letrozole (Femara(r)), and anastrozole (Arimidex(r).); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN(r), ENDOSTATIN(r), suramin, squalamine, tissue inhibitor of metalloproteinase-1, tissue inhibitor of metalloproternase-2, plasminogen activator inhibitor-1, plasminogen activator inhibitor-2, cartilage-derived inhibitor, paclitaxel (nab-paclitaxel), platelet factor 4, protamine sulphate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, D,L-3,4-dehydroproline, thiaproline, .alpha.-dipyridyl, beta-aminopropionitrile fumarate, 4-propyl-5-(4-pyridinyl)-2 (3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,5059,714; U.S. Pat. No. 5,120,764; U.S. Pat. No. 5,182,297; U.S. Pat. No. 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. The exemplified therapeutic antibodies may be further labeled or combined with a radioisotope particle, such as indium In 111, yttrium Y 90, iodine I-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In certain embodiments, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents treating lymphoma or leukemia include, but are not limited to, rituximab (such as Rittman), alemtuzumab (such as Campath, Mab-Campath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CC1-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds according to the invention may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Anti-HBV Combination Therapy

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents.

In certain embodiments, the present disclosure provides a method for treating an HBV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HBV infection.

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents, and a pharmaceutically acceptable carrier, diluent or excipient are provided.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

In the above embodiments, the additional therapeutic agent may be an anti-HBV agent. For example, in some embodiments, the additional therapeutic agent is selected from the group consisting of HBV combination drugs, HBV DNA polymerase inhibitors, immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, hepatitis B surface antigen (HBsAg) inhibitors, compounds targeting hepatitis B core antigen (HbcAg), cyclophilin inhibitors, HBV therapeutic vaccines, HBV prophylactic vaccines, HBV viral entry inhibitors, NTCP (Na+-taurocholate cotransporting polypeptide) inhibitors, antisense oligonucleotide targeting viral mRNA, short interfering RNAs (siRNA), miRNA gene therapy agents, endonuclease modulators, inhibitors of ribonucleotide reductase, hepatitis B virus E antigen inhibitors, recombinant scavenger receptor A (SRA) proteins, Src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), Hepatitis B virus replication inhibitors compounds such as those disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), US20130217880 (Ono pharmaceutical), and other drugs for treating HBV, and combinations thereof.

In certain embodiments, the additional therapeutic is selected from the group consisting of HBV combination drugs, HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, compounds targeting HbcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, BTK inhibitors, and hepatitis B virus replication inhibitors, and combinations thereof.

In certain embodiments a compound disclosed herein is formulated as a tablet, which may optionally contain one or more other compounds useful for treating HBV. In certain embodiments, the tablet can contain another active ingredient for treating HBV, such as HBV DNA polymerase inhibitors, immunomodulators, toll-like receptor modulators (modulators of tlr1, tlr2, tlr3, tlr4, tlr5, tlr6, tlr7, tlr8, tlr9, tlr10, tlr11, tlr12 and tlr13), modulators of tlr7, modulators of tlr8, modulators of tlr7 and tlr8, interferon alpha receptor ligands, hyaluronidase inhibitors, hepatitis B surface antigen (HBsAg) inhibitors, compounds targeting hepatitis B core antigen (HbcAg), cyclophilin inhibitors, HBV viral entry inhibitors, NTCP (Na+-taurocholate cotransporting polypeptide) inhibitors, endonuclease modulators, inhibitors of ribonucleotide reductase, hepatitis B virus E antigen inhibitors, Src kinase inhibitors, HBx inhibitors, cccDNA inhibitors, CCR2 chemokine antagonists, thymosin agonists, nucleoprotein inhibitors (HBV core or capsid protein inhibitors), stimulators of retinoic acid-inducible gene 1, stimulators of NOD2, stimulators of NOD', Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, BTK inhibitors, modulators of TIGIT, modulators of CD47, modulators of SIRP alpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, and Hepatitis B virus replication inhibitors, and combinations thereof.

In certain embodiments, such tablets are suitable for once daily dosing.

In certain embodiments, the additional therapeutic agent is selected from one or more of:

(1) Combination drugs selected from the group consisting of tenofovir disoproxil fumarate+emtricitabine (TRUVADA®); adefovir+clevudine, ABX-203+lamivudine+PEG-IFNalpha, ABX-203+adefovir+PEG-IFNalpha and GBV-015;

(2) HBV DNA polymerase inhibitors selected from the group consisting of besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009 and metacavir;

(3) Immunomodulators selected from the group consisting of rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, polymer polyethyleneimine (PEI), Gepon, VGV-1, MOR-22, BMS-936559 and IR-103;

(4) Toll-like receptor 7 modulators selected from the group consisting of GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795;

(5) Toll-like receptor 8 modulators selected from the group consisting of motolimod, resiquimod, 3M-051, 3M-052, MCT-465, IMO-4200, VTX-763, VTX-1463;

(6) Toll-like receptor 3 modulators selected from the group consisting of rintatolimod, poly-ICLC, MCT-465, MCT-475, Riboxxon, Riboxxim and ND-1.1, (7) Interferon alpha receptor ligands selected from the group consisting of interferon alpha-2b (Intron A®), pegylated interferon alpha-2a (Pegasys®), interferon alpha 1b (Hapgen®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (Inferon), Multiferon®, interferon alfa-n1 (Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, Pegi-Hep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa);

(8) Hyaluronidase inhibitors selected from the group consisting of astodrimer;

(9) Modulators of IL-10;

(10) HBsAg inhibitors selected from the group consisting of HBF-0259, PBHBV-001, PBHBV-2-15, PBHBV-2-1, REP 9AC, REP-9C and REP 9AC';

(11) Toll like receptor 9 modulators selected from CYT003;

(12) Cyclophilin inhibitors selected from the group consisting of OCB-030, SCY-635 and NVP-018;

(13) HBV Prophylactic vaccines selected from the group consisting of Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (Hansenual polymorpha yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine;

(14) HBV Therapeutic vaccines selected from the group consisting of HBsAG-HBIG complex, Bio-Hep-B, NAS-VAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, TG-1050, NU-500, HBVax, im/TriGrid/antigen vaccine, Mega-CD40L-adjuvanted vaccine, HepB-v, NO-1800, recombinant VLP-based therapeutic vaccine (HBV infection, VLP Biotech), AdTG-17909, AdTG-17910 AdTG-18202, ChronVac-B, and Lm HBV;

(15) HBV viral entry inhibitor selected from the group consisting of Myrcludex B;

(16) Antisense oligonucleotide targeting viral mRNA selected from the group consisting of ISIS-HBVRx;

(17) Short interfering RNAs (siRNA) selected from the group consisting of TKM-HBV (TKM-HepB), ALN-HBV, SR-008, ddRNAi and ARC-520;

(18) Endonuclease modulators selected from the group consisting of PGN-514;

(19) Inhibitors of ribonucleotide reductase selected from the group consisting of Trimidox;

(20) Hepatitis B virus E antigen inhibitors selected from the group consisting of wogonin;

(21) HBV antibodies targeting the surface antigens of the hepatitis B virus selected from the group consisting of GC-1102, XTL-17, XTL-19, XTL-001, KN-003 and fully human monoclonal antibody therapy (hepatitis B virus infection, Humabs BioMed);

(22) HBV antibodies including monoclonal antibodies and polyclonal antibodies selected from the group consisting of Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088);

(23) CCR2 chemokine antagonists selected from the group consisting of propagermanium;

(24) Thymosin agonists selected from the group consisting of Thymalfasin;

(25) Cytokines selected from the group consisting of recombinant IL-7, CYT-107, interleukin-2 (IL-2, Immunex); recombinant human interleukin-2 (Shenzhen Neptunus) and celmoleukin;

(26) Nucleoprotein inhibitors (HBV core or capsid protein inhibitors) selected from the group consisting of NVR-1221, NVR-3778, BAY 41-4109, morphothiadine mesilate and DVR-23;

(27) Stimulators of retinoic acid-inducible gene 1 selected from the group consisting of SB-9200, SB-40, SB-44, ORI-7246, ORI-9350, ORI-7537, ORI-9020, ORI-9198 and ORI-7170;

(28) Stimulators of NOD2 selected from the group consisting of SB-9200;

(29) Recombinant thymosin alpha-1 selected from the group consisting of NL-004 and PEGylated thymosin alpha 1;

(30) Hepatitis B virus replication inhibitors selected from the group consisting of isothiafludine, IQP-HBV, RM-5038 and Xingantie;

(31) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(32) cccDNA inhibitors selected from the group consisting of BSBI-25;

(33) PD-L1 inhibitors selected from the group consisting of MEDI-0680, RG-7446, durvalumab, KY-1003, KD-033, MSB-0010718C, TSR-042, ALN-PDL, STI-A1014 and BMS-936559;

(34) PD-1 inhibitors selected from the group consisting of nivolumab, pembrolizumab, pidilizumab, BGB-108 and mDX-400;

(35) BTK inhibitors selected from the group consisting of ACP-196, dasatinib, ibrutinib, PRN-1008, SNS-062, ONO-4059, BGB-3111, MSC-2364447, X-022, spebrutinib, TP-4207, HM-71224, KBP-7536 and AC-0025;

(36) Other drugs for treating HBV selected from the group consisting of gentiopicrin (gentiopicroside), nitazoxanide, birinapant, NOV-205 (Molixan; BAM-205), Oligotide, Mivotilate, Feron, levamisole, Ka Shu Ning, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, Jiangantai (Ganxikang), picroside, GA5 NM-HBV, DasKloster-0039, hepulantai, IMB-2613, TCM-800B, reduced glutathione and ZH-2N; and

(37) The compounds disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), and US20130217880 (Ono pharmaceutical).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, HBsAg inhibitors, compounds targeting HbcAg, cyclophilin inhibitors, HBV therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), and Hepatitis B virus replication inhibitors.

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In another specific embodiment, a compound disclosed herein, or a pharmaceutically acceptable salt thereof, is combined with an HBV DNA polymerase inhibitor, one or two additional therapeutic agents selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound disclosed herein, or a pharmaceutically acceptable salt thereof, is combined with one, two, three, four or more additional therapeutic agents selected from adefovir (Hepsera®), tenofovir disoproxil fumarate+emtricitabine (TRUVADA®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1(Humoferon®), ribavirin, interferon beta-la (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin;

In a particular embodiment, a compound disclosed herein, or a pharmaceutically acceptable salt thereof, is combined with entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®).

In a particular embodiment, a compound disclosed herein, or a pharmaceutically acceptable salt thereof, is combined with entecavir (Baraclude®), adefovir (Hepsera®), tenofovir disoproxil fumarate (Viread®), tenofovir alafenamide hemifumarate, telbivudine (Tyzeka®) or lamivudine (Epivir-HBV®).

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, HBsAg inhibitors, compounds targeting HbcAg, cyclophilin inhibitors, HBV Therapeutic vaccines, HBV prophylactic vaccines, HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), a and Hepatitis B virus replication inhibitors.

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1(Humoferon®), ribavirin, interferon beta-la (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin;

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, Arginase-1 inhibitors, PI3K inhibitors, PD-1 inhibitors, PD-L1 inhibitors and stimulators of NOD2.

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound disclosed herein, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®), one or two additional therapeutic agents selected from the group consisting of: immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of formula (I)) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of formula (I)) may be combined with the agents provided herein in any dosage amount of the compound (e.g., from 50 mg to 500 mg of compound) the same as if each combination of dosages were specifically and individually listed.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

Anti-HIV Combination Therapy

In certain embodiments, a method for treating or preventing an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, or one to three, or one to four) additional therapeutic agents.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents, and a pharmaceutically acceptable carrier, diluent or excipient are provided.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

In the above embodiments, the additional therapeutic agent may be an anti-HIV agent. For example, in some embodiments, the additional therapeutic agent is selected from the group consisting of HIV protease inhibitors, HIV non-nucleoside inhibitors of reverse transcriptase, HIV nucleoside or nucleotide inhibitors of reverse transcriptase, HIV integrase inhibitors, HIV non-catalytic site (or allosteric) integrase inhibitors, entry inhibitors (e.g., CCR5 inhibitors, gp41 inhibitors (i.e., fusion inhibitors) and CD4 attachment inhibitors), CXCR4 inhibitors, gp120 inhibitors, G6PD and NADH-oxidase inhibitors, compounds that target the HIV capsid ("capsid inhibitors"; e.g., capsid polymerization inhibitors or capsid disrupting compounds such as those disclosed in WO. 2013/006738 (Gilead Sciences), US 2013/0165489 (University of Pennsylvania), and WO. 2013/006792 (Pharma Resources), pharmacokinetic enhancers, and other drugs for treating HIV, and combinations thereof.

In further embodiments, the additional therapeutic agent is selected from one or more of:

(1) HIV protease inhibitors selected from the group consisting of amprenavir, atazanavir, fosamprenavir, indinavir, lopinavir, ritonavir, nelfmavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside or non-nucleotide inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, TMC-120, rilpivirene, BILR 355 BS, VRX 840773, lersivirine (UK-453061), RDEA806, KMO23 and MK-1439;

(3) HIV nucleoside or nucleotide inhibitors of reverse transcriptase selected from the group consisting of zidovudine, emtricitabine, didanosine, stavudine, zalcitabine, lamivudine, abacavir, abavavir sulfate, amdoxovir, elvucitabine, alovudine, MIV-210, ±-FTC, D-d4FC, emtricitabine, phosphazide, fozivudine tidoxil, apricitibine (AVX754), KP-1461, GS-9131 (Gilead Sciences) and fosalvudine tidoxil (formerly HDP 99.0003), tenofovir, tenofovir disoproxil fumarate, tenofovir alafenamide (Gilead Sciences), tenofovir alafenamide hemifumarate (Gilead Sciences), GS-9148 (Gilead Sciences), adefovir, adefovir dipivoxil, CMX-001 (Chimerix) or CMX-157 (Chimerix);

(4) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, elvitegravir, dolutegravir and GSK-744;

(5) HIV non-catalytic site, or allosteric, integrase inhibitors (NCINI) including, but not limited to, BI-224436, CX0516, CX05045, CX14442, compounds disclosed in WO. 2009/062285 (Boehringer Ingelheim), WO. 2010/130034 (Boehringer Ingelheim), WO. 2013/159064 (Gilead Sciences), WO. 2012/145728 (Gilead Sciences), WO. 2012/003497 (Gilead Sciences), WO. 2012/003498 (Gilead Sciences) each of which is incorporated by references in its entirety herein;

(6) gp41 inhibitors selected from the group consisting of enfuvirtide, sifuvirtide, albuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, cenicriviroc, PRO-140, INCB15050, PF-232798 (Pfizer), and CCR5mAb004;

(12) CD4 attachment inhibitors selected from the group consisting of ibalizumab (TMB-355) and BMS-068 (BMS-663068);

(13) pharmacokinetic enhancers selected from the group consisting of cobicistat and SPI-452; and

(14) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040), and combinations thereof.

In certain embodiments, the additional therapeutic agent is a Toll-like receptor 8 modulator selected from the group consisting of motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics).

In certain embodiments, a compound disclosed herein, or a pharmaceutically acceptable salt thereof, is combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The two, three, four or more additional therapeutic agents can be different therapeutic agents selected from the same class of therapeutic agents, or they can be selected from different classes of therapeutic agents. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In a further embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In another embodiment, a compound disclosed herein, or a pharmaceutically acceptable salt thereof, is combined with two HIV nucleoside or nucleotide inhibitor of reverse transcriptase.

In a particular embodiment, a compound disclosed herein, or a pharmaceutically acceptable salt thereof, is combined with abacavir sulfate, tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of: abacavir sulfate, tenofovir, tenofovir disoproxil fumarate, tenofovir alafenamide, and tenofovir alafenamide hemifumarate and a second additional therapeutic agent selected from the group consisting of emtricitibine and lamivudine. In a particular embodiment, a compound disclosed herein, or a pharmaceutically acceptable salt thereof, is combined with a first additional therapeutic agent selected from the group consisting of: tenofovir, tenofovir disoproxil fumarate, tenofovir alafenamide, and tenofovir alafenamide hemifumarate and a second additional therapeutic agent, wherein the second additional therapeutic agent is emtricitibine.

In certain embodiments, when a compound disclosed herein is combined with one or more additional therapeutic agents as described above, the components of the composition are administered as a simultaneous or sequential regimen. When administered sequentially, the combination may be administered in two or more administrations.

In certain embodiments, a compound disclosed herein is combined with one or more additional therapeutic agents in a unitary dosage form for simultaneous administration to a patient, for example as a solid dosage form for oral administration.

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

Kits

Provided herein are also kits that include a compound of Formula I, or a pharmaceutically acceptable salt, stereoisomer, prodrug, or solvate thereof, and suitable packaging. In one embodiment, a kit further includes instructions for use. In one aspect, a kit includes a compound of Formula I, or a pharmaceutically acceptable salt, stereoisomer, prodrug, or solvate thereof, and a label and/or instructions for use of the compounds in the treatment of the indications, including the diseases or conditions, described herein.

Provided herein are also articles of manufacture that include a compound described herein or pharmaceutically acceptable salts, isomer, or a mixture thereof in a suitable container. The container may be a vial, jar, ampoule, pre-loaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds described herein or pharmaceutically acceptable salts, isomer, or a mixture thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or pharmaceutically acceptable salts, isomer, or a mixture thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or pharmaceutically acceptable salts, isomer, or a mixture thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula I

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40

(John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds of Formula I

The compounds of Formula I may prepared by first providing the substituted imidazo[4,5-b]pyridine or benzimidazole core, and optionally further modifying the core as desired to provide the substituents disclosed herein.

Scheme 1 shows the preparation of compounds of Formula I, where m, n, L, $R^1$, $R^{2a}$, $R^{2b}$, and X are as defined herein, and $R^4$ is

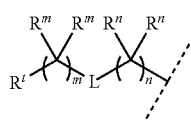

as defined herein, or a functional group that is converted thereto using standard reaction conditions and protection/deprotection steps as required.

In Scheme 1, suitably substituted 1-a and 1-b are coupled and cyclized in a suitable solvent (e.g., formic acid, ethanol, etc.) at an elevated temperature (typically about 80-100° C.) to provide the imidazo[4,5-b]pyridine or benzimidazole core 1-c. 1-c is then converted to the corresponding thioamide 1-d using Lawesson's reagent (i.e., 2,4-bis(4-methoxyphenyl)-1,3,2,4-dithiadiphosphetane-2,4-disulfide) under standard conditions. 1-e is obtained by cyclization of the thioamide 1-d using hydroxylamine. Hydrolysis of 1-e to obtain compound 1-f is achieved by reaction with a suitable base (e.g., NaOH). Alternately, 1-c is transformed to compound 1-f using phosphorous pentachloride, followed by treatment with aqueous hydroxylamine.

Scheme 2 shows the synthesis of compounds of Formula I where $R^r$ is hydrogen, and $R^1$, $R^{2a}$, $R^{2b}$, and X are as defined herein.

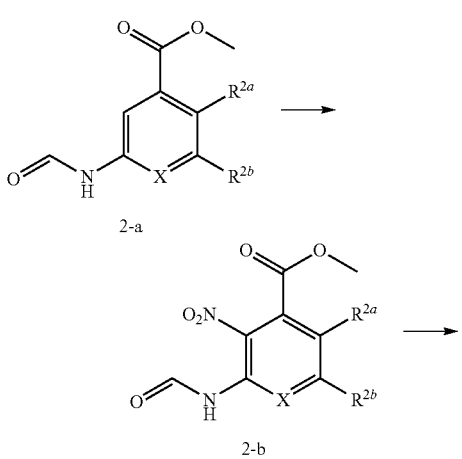

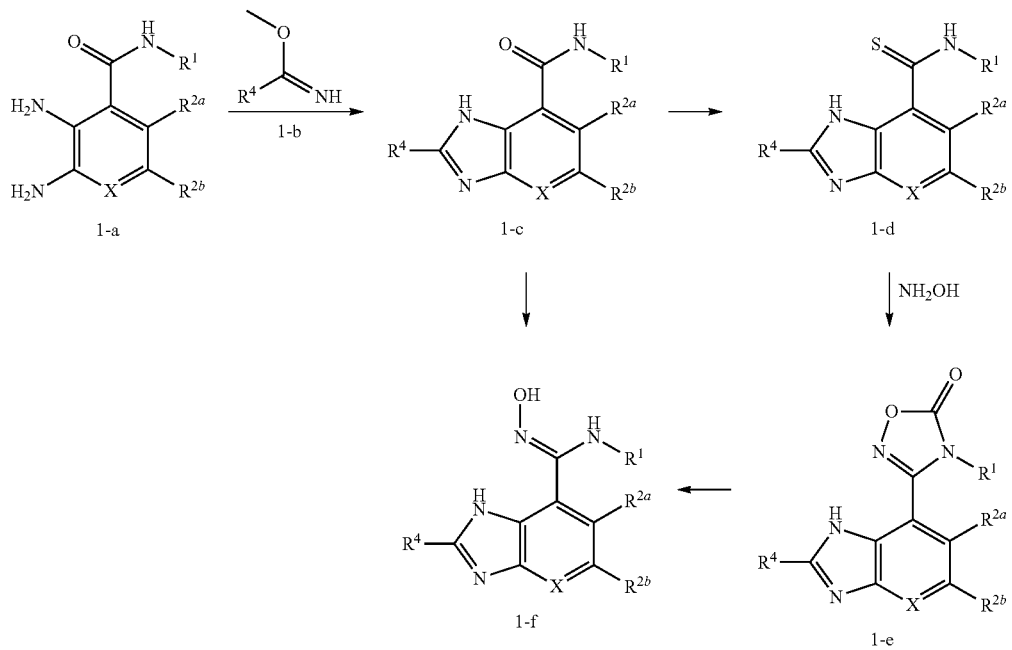

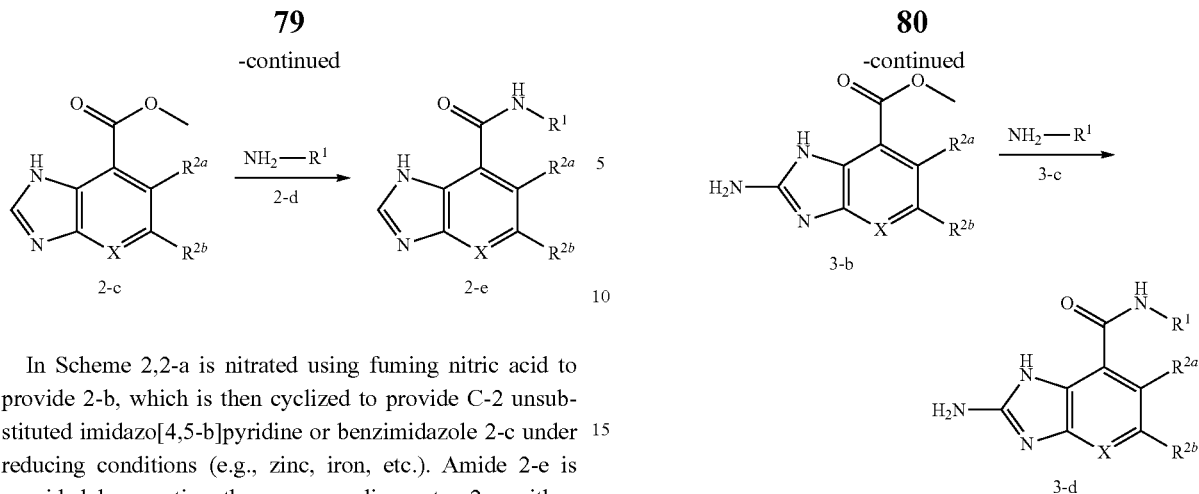

In Scheme 2, 2-a is nitrated using fuming nitric acid to provide 2-b, which is then cyclized to provide C-2 unsubstituted imidazo[4,5-b]pyridine or benzimidazole 2-c under reducing conditions (e.g., zinc, iron, etc.). Amide 2-e is provided by reacting the corresponding ester 2-c with a suitable amine 2-d under standard amide bond forming reaction conditions, and is then converted to compounds of Formula I using the methods shown above in Scheme 1.

Scheme 3 shows the synthesis of compounds of Formula I where $R^t$ is $NH_2$, and $R^1$, $R^{2a}$, $R^{2b}$, and X are as defined herein.

In Scheme 3, 3-b is obtained by reaction of 3-a with cyanogen bromide. Amide 3-d is provided by reacting the corresponding ester 3-b with a suitable amine 3-c under standard amide bond forming reaction conditions, and is then converted to compounds of Formula I using the methods shown above in Scheme 1.

In certain embodiments, the process may comprise protection and deprotection/further modification of $R^4$ (Scheme 1) to provide the desired Scheme 3

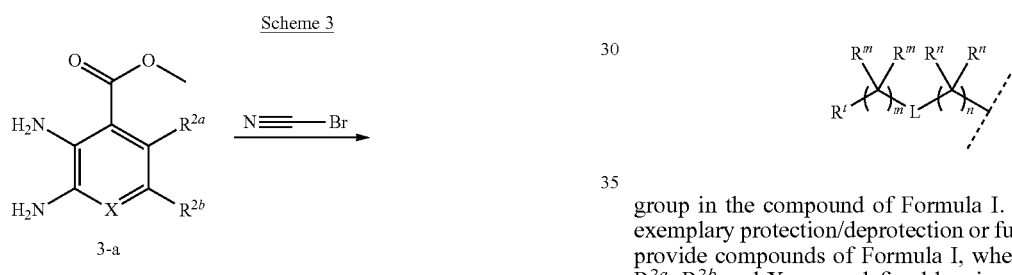

group in the compound of Formula I. Scheme 4 shows an exemplary protection/deprotection or further modification to provide compounds of Formula I, where $R^t$, $R^m$, m, L, $R^1$, $R^{2a}$, $R^{2b}$ and X are as defined herein.

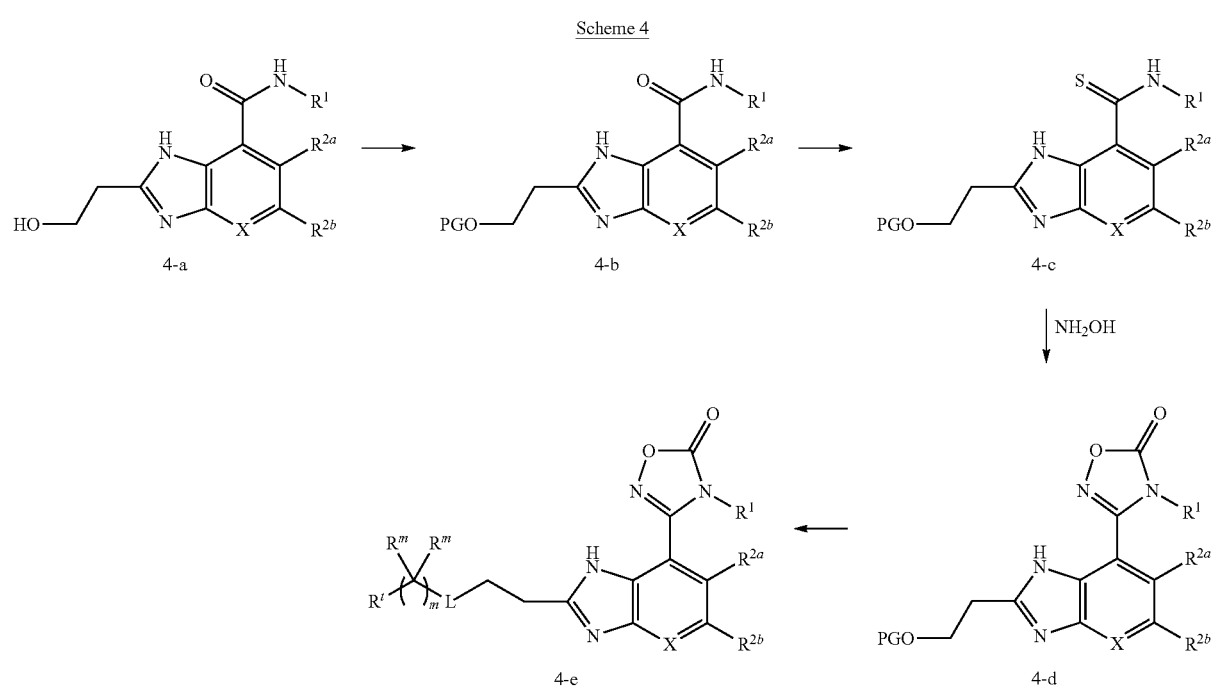

In Scheme 4, suitably substituted 4-a can be protected to provide 4-b using a suitable protecting group PG, such as a silyl ether (see, e.g., T. W. Greene and G. M. Wuts (1999) Protecting Groups in Organic Synthesis, 3rd Edition, Wiley, New York, and references cited therein). 4-b is then converted to the corresponding thioamide 4-c and cyclized using hydroxylamine as shown above in Scheme 1 to provide 4-d. 4-d can then be coverted to compound 4-e by deprotection a and optional further modification. For example, 4-d can be deprotected and converted to a suitable leaving group (e.g., a TMS-O— group) and then reacted with a suitable amine to provide compounds of formula 4-e where L is $NR^3$—. 4-e is then converted to compounds of Formula I using the methods shown above in Scheme 1.

Each of the intermediates in the above schemes may be isolated and/or purified prior to the subsequent step, or used in the next step without purification and/or isolation. It will also be appreciated that the addition of any substituent may result in the production of a number of isomeric products any or all of which may be isolated and purified using conventional techniques.

EXAMPLES

The following examples are included to demonstrate specific embodiments of the disclosure. It should be appreciated by those of skill in the art that the techniques disclosed in the examples which follow represent techniques discovered by the inventor to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

LIST OF ABBREVIATIONS AND ACRONYMS

| Abbreviation | Meaning |
| --- | --- |
| % | Percent |
| ° C. | Degree Celsius |
| A2B | Adenosine A2B receptor |
| Ac | Acetyl |
| ACN/CH$_3$CN/MeCN | Acetonitrile |
| ADME | Absorption, distribution, metabolism and excretion |
| AlMe$_3$ | Trimethylaluminum |
| APECED | Autoimmune polyendocrinopathy-candidiasis-ectodermal dystrophy |
| ASK | Apoptosis signal-regulating kinase |
| BAPN | Beta-aminoproprionitrile |
| BCNU | Carmustine |
| bicarb | Bicarbonate |
| br | Broad |
| BRD | Bromodomain containing protein inhibitor |
| BTK | Bruton's tyrosine kinase |
| BTK | Bruton's tyrosine kinase |
| CAS | Chemical Abstract Service |
| cccDNA | Covalently closed circular DNA |
| CCR | C-C chemokine receptor |
| CD | Cluster of differentiation |
| CHOP | Cyclophosphamide |
| CNS | Central nervous system |
| COPD | Chronic obstructive pulmonary disease |

-continued

| Abbreviation | Meaning |
| --- | --- |
| CREST | Calcinosis, Raynaud's syndrome, esophageal dysmotility, sclerodactyly and telangiectasia |
| CRISPR | Clustered regularly interspaced short palindromic repeats |
| CVP | Cyclophosphamide, vincristine, prednisone |
| d | Doublet |
| D | Deuterium |
| D.T. PACE | Dexamethasone, thalidomide, cisplatin, Adriamycin ®, cyclophosphamide, etoposide |
| D/d | Deuterium |
| DABAL-Me$_3$ | Bis(trimethylaluminum)-DABCO ® adduct |
| DABCO ® | 1,4-Diazabicyclo[2.2.2]octane |
| DCE | Dichloroethane |
| DCM/CH$_2$Cl$_2$ | Dichloromethane/methylene chloride |
| dd | Doublet of doublets |
| DDR | Discoidin domain receptor |
| DIPEA/DIEA | N,N-Diisopropylethylamine |
| DMF | Dimethylformamide |
| DMFO | Difluoromethylornithine |
| DMPK | Drug metabolism and pharmacokinetics |
| DMSO | Dimethylsulfoxide |
| DTIC | Dacarbazine |
| EC$_{50}$ | The half maximal effective concentration |
| EDC | 1-Ethyl-3-(3-dimethylaminopropyl)carbodiimide |
| equiv/eq | Equivalents |
| Et | Ethyl |
| Et$_3$N | Triethylamine |
| EtOAc/AcOEt | Ethylacetate |
| EtOH | Ethanol |
| F | Fahrenheit |
| Fab | Fragment antigen-binding |
| FBS | Fetal bovine serum |
| FCM | Fludarabine, cyclophosphamide, mitoxantrone |
| FCR | Fludarabine, cyclophosphamide, rituximab |
| FOLFIRI | Fluorouracil, leucovorin, and irinotecan |
| FR | Fludarabine, rituximab |
| g | Grams |
| GITR | Glucocorticoid-induced TNFR-related protein |
| Gp | Glycoprotein |
| h/hr | Hours |
| HATU | (1-[Bis(dimethylamino)methylene]-1H-1,2,3-triazolo[4,5-b]pyridinium 3-oxid hexafluorophosphate) |
| HbcAg | Hepatitis B core antigen |
| HBsAg | Hepatitis B surface antigen |
| HBV | Hepatitis B virus |
| HBx | Hepatitis B viral protein |
| HDAC | Histone deacetylase |
| hex | Hexanes |
| HOBt | Hydroxybenzotriazole |
| HPLC | High pressure liquid chromatography |
| hyperCVAD | Hyperfractionated cyclophosphamide, vincristine, doxorubicin, dexamethasone, methotrexate, cytarabine |
| Hz | Hertz |
| ICE | Iphosphamide, carboplatin, etoposide |
| ICOS | Inducible T-cell COStimulator |
| IDH | Isocitrate dehydrogenase |
| IDO1 | Indoleamine 2,3-dioxygenase 1 |
| IL | Interleukin |
| INCB24360 | Epacadostat |
| IUPAC | International Union of Pure and Applied Chemistry |
| J | Coupling constant (MHz) |
| JAK | Janus kinase |
| Kg/kg | Kilogram |
| LACA | 1-Azetidine-2-carboxylic acid |
| LCMS/LC-MS | Liquid chromatography-mass spectrometry |
| LET | Linear energy transfer |
| LOX | Lysyl oxidase protein |
| LOXL | Lysyl oxidase-like protein |
| M | Molar |
| m | multiplet |
| M+ | Mass peak |
| M + H | Mass peak plus hydrogen |
| MCP | Mitoxantrone, chlorambucil, and prednisolone |
| Me | Methyl |
| mg | Milligram |
| MHz | Megahertz |
| min/m | Minute |

| Abbreviation | Meaning |
| --- | --- |
| miRNA | MicroRNA |
| ml/mL | Milliliter |
| mM | Millimolar |
| MMF | Ester derivative mycophenolate mofetil |
| mmol | Millimole |
| MMP | Matrix metalloprotease |
| mol | Mole |
| MPA | Mycophenolate mofetil |
| MS | Mass spectroscopy |
| MS | Multiple sclerosis |
| N | Normal |
| NADH | Nicotinamide adenine dinucleotide in reduced form |
| NCINI | Non-catalytic site, or allosteric, integrase inhibitors |
| NCS | N-Chlorosuccinimide |
| ng | Nanograms |
| nM | NanoMolar |
| NMR | Nuclear magnetic resonance |
| NOD | Nucleotide-binding oligomerization domain-containing protein |
| NTCP | Na$^+$-taurocholate cotransporting polypeptide |
| PD | Programmed cell death |
| PdCl$_2$(dppf) | [1,1'-Bis(diphenylphosphino)ferrocene]dichloropalladium(II), |
| PdCl$_2$(PPh$_3$)$_2$ | Bis(triphenylphosphine)palladium(II) dichloride |
| PD-L | Programmed death-ligand |
| PEG | Polyethylene glycol |
| PEI | Polymer polyethyleneimine |
| PET | Positron emission tomography |
| Ph | Phenyl |
| PI3K | Phosphoinositide 3-kinase |
| PKC | Protein kinase C |
| prep | Preparative |
| q.s. | Quantity sufficient to achieve a stated function |
| RA | Rheumatoid arthritis |
| R-CHOP | Rituximab-CHOP (Rituximab plus CHOP) |
| R-CVP | Rituximab-CVP (Rituximab plus CVP) |
| Rf | Retention factor |
| R-FCM | Rituximab plus FCM |
| R-hyperCVAD | Rituximab-hyperCVAD |
| R-ICE | Rituximab-ICE |
| R-MCP | Rituximab-MCP |
| RPM | Revolutions per minute |
| rSIFN-co | Recombinant super compound interferon |
| RT/rt | Room temperature |
| s | Second |
| s | Singlet |
| SAHA | Vorinostat |
| sat. | Saturated |
| SEM | 2-(Trimethylsilyl)ethoxymethyl |
| SERMs | Selective estrogen receptor modulators |
| siRNA | Short interfering RNAs |
| SIRP | Signal-regulatory protein |
| SLE | Systemic lupus erythematosus |
| SPECT | Single-photon emission computed tomography |
| SRA | Scavenger receptor A |
| Src | Proto-oncogene tyrosine-protein kinase |
| sshRNAs | Short synthetic hairpin RNAs |
| STING | Sequence To and withIN Graphics |
| SYK | Spleen tyrosine kinase |
| t | Triplet |
| TALENs | Transcription activator-like effector nucleases |
| TBAF | Tetra-n-butylammonium fluoride |
| TCA | Trichloroacetic acid |
| TEA | Triethylamine |
| temp. | Temperature |
| TFA | Trifluoroacetic acid |
| THF | Tetrahydrofuran |
| TIGIT | T cell immunoreceptor with Ig and ITIM domains |
| TIM | T-cell immunoglobulin and mucin domain |
| TKM-HBV | TKM-HepB |
| Tlr | Toll-like receptor modulators |
| TNF | Tumor necrosis factor |
| TPL2 | Serine/threonine kinase |
| Vac | Vacuum |
| w/v | Weight/volume |
| w/w | Weight/weight |
| YPEG- | PEG-interferon alfa-2a |

| Abbreviation | Meaning |
| --- | --- |
| rhIFNalpha-2a | |
| YPEG-rhIFNalpha-2b | Ypeginterferon alfa-2b |
| δ | Chemical shift (ppm) |
| μg | Microgram |
| μL/μl | Microliter |
| μM | Micromolar |
| μm | Micrometer |
| μmol | Micromole |

Example 1: N-(3-Chloro-4-fluorophenyl)-N'-hydroxy-4-methyl-1H-benzo[d]imidazole-7-carboximidamide

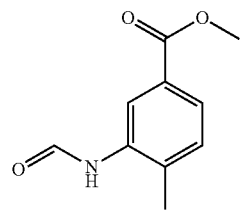

Methyl 3-formamido-4-methylbenzoate. A solution of methyl-3-amino-4-methylbenzoate (5.1 g, 31 mmol) in formic acid (42 mL) was stirred at 110° C. for 4 hr. The reaction mixture was allowed to cool to room temp. Water was added and the aqueous layer was washed three times with ethyl acetate. The combined organic layers were dried over sodium sulfate, filtered and concentrated to give the desired product. $C_{10}H_{11}NO_3$. 194.0 (M+1).

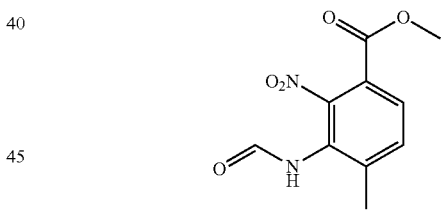

Methyl 3-formamido-4-methyl-2-nitrobenzoate. Methyl 3-formamido-4-methylbenzoate (5.3 g, 27 mmol) was added to fuming nitric acid at 0° C. portion wise over 45 min. The reaction mixture was stirred at 0° C. for an additional 1 h, and then ice was added and the mixture stirred for 1.5 h at room temperature. The precipitated solid was filtered, and washed with water. The solid was purified by silica gel to give the desired product. $C_{10}H_{10}N_2O_5$. 239.0 (M+1).

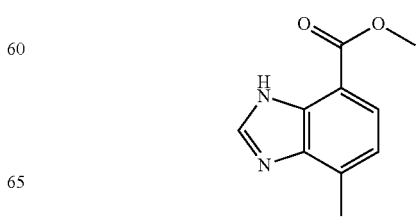

Methyl 4-methyl-1H-benzo[d]imidazole-7-carboxylate. A mixture of methyl 3-formamido-4-methyl-2-nitrobenzoate (1.0 g, 4.2 mmol) and iron (1.2 g, 21 mmol) in methanol (10 mL) and acetic acid (5 mL) was stirred at 70° C. for 3 hr. To the cooled reaction mixture was added ethyl acetate and water and the mixture was filtered and the solid was washed with ethyl acetate. The aqueous layer was washed two times with ethyl acetate. The combined organic layers were dried over sodium sulfate, filtered and concentrated to give the desired product. $C_{10}H_{10}N_2O_2$. 191.1 (M+1).

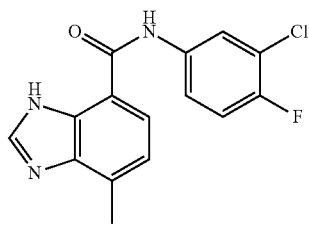 [SMILES: Cc1ccc(C(=O)Nc2ccc(F)c(Cl)c2)c2[nH]cnc12]

N-(3-chloro-4-fluorophenyl)-4-methyl-1H-benzo[d]imidazole-7-carboxamide. To a solution of the 3-chloro-4-fluoroaniline in (253 mg, 1.74 mmol) dichloroethane at 0° C. under nitrogen was added trimethylaluminum (2 M in heptane, 1.74 mL, 3.47 mmol) dropwise over 5 min. The solution was allowed to warm to room temperature and stirred for 30 min. The solution was cooled to 0° C. and to this solution was added methyl 4-methyl-1H-benzo[d]imidazole-7-carboxylate (220 mg, 1.16 mmol). The solution was stirred at 85° C. for 6 hr and, then, cooled to room temperature. To the mixture was added ethyl acetate and 10% citric acid and the resulting precipitate was filtered and dried on high vac to give the desired product. $C_{15}H_{11}ClFN_3O$. 304.4 (M+1).

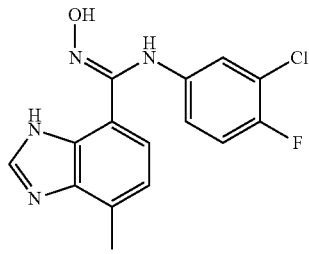 [SMILES: Cc1ccc(/C(=N/O)Nc2ccc(F)c(Cl)c2)c2[nH]cnc12]

N-(3-chloro-4-fluorophenyl)-N'-hydroxy-4-methyl-1H-benzo[d]imidazole-7-carboximidamide. A mixture of N-(3-chloro-4-fluorophenyl)-4-methyl-1H-benzo[d]imidazole-7-carboxamide (154 mg, 0.507 mmol), phosphorous pentachloride (158 mg, 0.761 mmol) in phosphoryl chloride (1.5 mL) and 1,2-dichloroethane (1.5 mL) were stirred at 80° C. for 2.5 hr. The reaction mixture was concentrated and suspended in ethanol (1.5 mL) and to this mixture was added 50% hydroxylamine in water (0.311 mL, 5.07 mmol). The reaction mixture stirred for 1 hr and was concentrated. The residue was purified by preparative HPLC to give the desired product. $C_{15}H_{12}ClFN_4O$. 319.1 (M+1).

Example 2: N-(3-Chloro-4-fluorophenyl)-N'-hydroxy-4-(trifluoromethoxy)-1H-benzo[d]imidazole-7-carboximidamide

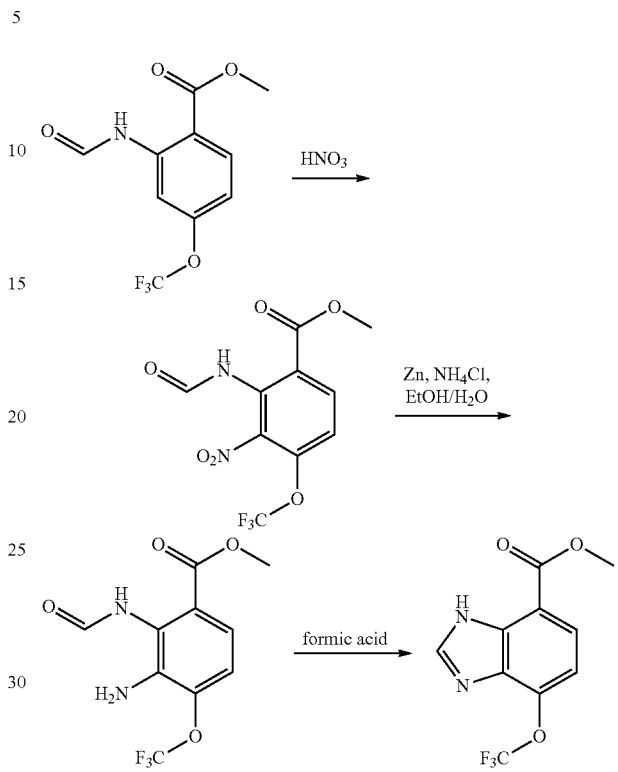

Nitric acid (18 mL) was cooled to −10° C. in a dry ice/acetone bath and methyl 2-formamido-4-(trifluoromethoxy)benzoate (1.97 g, 7.0 mol) was added and the reaction was allowed to stir for 4 hours at −10° C. The reaction was slowly quenched with water (20 mL) and extracted with EtOAc (3×10 mL). Combined organic layers were washed with brine (1×30 mL) and concentrated in vacuo to give methyl 2-formamido-3-nitro-4-(trifluoromethoxy)benzoate as a mixture of isomers.

Methyl 2-formamido-3-nitro-4-(trifluoromethoxy)benzoate (2.2 g, 7.0 mmol) was dissolved in ethanol (15 mL) and water (5 mL). Ammonium chloride (0.108 mol) was added in one portion and the reaction was allowed to stir at room temperature. Zinc powder (0.108 mol) was added portionwise over 5 minutes and the reaction was allowed to stir 5 minutes after completion of addition. The zinc was then removed by vacuum filtration and the filtrate was concentrated in vacuo. The crude was dissolved in water (20 mL) and extracted with EtOAc (4×10 mL). Combined organic layers were washed with brine (1×50 mL), dried over sodium sulfate, and concentrated in vacuo to give methyl 3-amino-2-formamido-4-(trifluoromethoxy)benzoate.

Methyl 3-amino-2-formamido-4-(trifluoromethoxy)benzoate (1.32 g, 5.0 mmol) was dissolved in formic acid (15 mL) and heated to 80° C. for 1 hour. The reaction was cooled to rt, concentrated in vacuo, and quenched with saturated sodium bicarbonate solution (10 mL). The mixture was extracted with EtOAc (4×5 mL) and combined organic layers were washed with brine (1×15 mL) and concentrated in vacuo. Crude material was purified by column chromatography to give methyl 4-(trifluoromethoxy)-1H-benzo[d]imidazole-7-carboxylate.

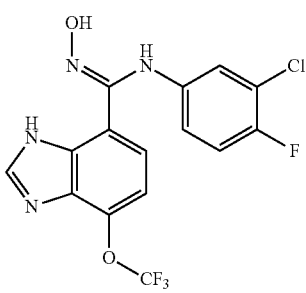 [SMILES: O/N=C(\Nc1ccc(F)c(Cl)c1)c1ccc(OC(F)(F)F)c2nc[nH]c12]

N-(3-Chloro-4-fluorophenyl)-N'-hydroxy-4-(trifluoromethoxy)-1H-benzo[d]imidazole-7-carboximidamide. Example 2 was made analogously to Example 10 using methyl 4-(trifluoromethoxy)-1H-benzo[d]imidazole-7-carboxylate in place of methyl 4,5-difluoro-1H-benzo[d]imidazole-7-carboxylate. $C_{15}H_9ClF_4N_4O_2$ 389.0/391.1 (M+1).

Example 3: N-(3-Chloro-4-fluorophenyl)-6-fluoro-N'-hydroxy-1H-benzo[d]imidazole-7-carboximidamide

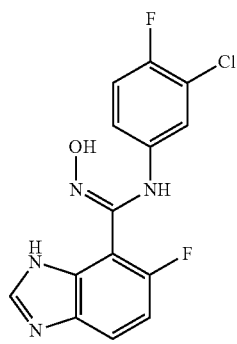 [SMILES: O/N=C(\Nc1ccc(F)c(Cl)c1)c1c(F)ccc2nc[nH]c12]

Example 3 (N-(3-chloro-4-fluorophenyl)-6-fluoro-N'-hydroxy-1H-benzo[d]imidazole-7-carboximidamide) was made analogously to Example 59 using 6-fluoro-1H-benzo[d]imidazole-7-carboxylic acid in place of 1H-imidazo[4,5-b]pyridine-7-carboxylic acid. $C_{14}H_9ClF_2N_4O$. 323.1/325.0 (M+1).

Example 4: N-(3-Chloro-4-fluorophenyl)-5-fluoro-N'-hydroxy-1H-benzo[d]imidazole-7-carboximidamide

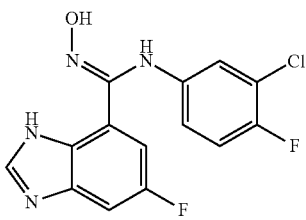 [SMILES: O/N=C(\Nc1ccc(F)c(Cl)c1)c1cc(F)cc2nc[nH]c12]

Example 4 was made analogously to Example 59 using 5-fluoro-1H-benzo[d]imidazole-7-carboxylic in place of 1H-imidazo[4,5-b]pyridine-7-carboxylic acid. $C_{14}H_9ClF_2N_4O$. 323.1 (M+1). $^1H$ NMR (400 MHz, DMSO-$d_6$) δ 11.01 (s, 1H), 8.87 (d, J=15.9 Hz, 2H), 7.60 (dd, J=8.7, 2.4 Hz, 1H), 7.20 (dd, J=10.2, 2.4 Hz, 1H), 7.02 (t, J=9.1 Hz, 1H), 6.95 (dd, J=6.6, 2.7 Hz, 1H), 6.52 (ddd, J=9.0, 4.1, 2.7 Hz, 1H).

Example 5: N-(3-Chloro-4-fluorophenyl)-4-fluoro-N'-hydroxy-1H-benzo[d]imidazole-7-carboximidamide

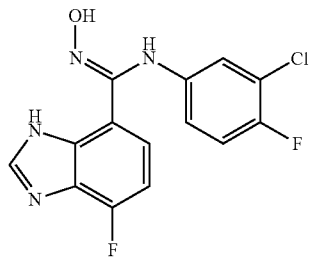 [SMILES: O/N=C(\Nc1ccc(F)c(Cl)c1)c1ccc(F)c2nc[nH]c12]

Example 5 was made analogously to Example 59 using 4-fluoro-1H-benzo[d]imidazole-7-carboxylic acid in place of 1H-imidazo[4,5-b]pyridine-7-carboxylic acid. $C_{14}H_9ClF_2N_4O$. 323.1 (M+1). $^1H$ NMR (400 MHz, DMSO-$d_6$) δ 10.75 (s, 1H), 8.75 (s, 1H), 8.27 (s, 1H), 7.16 (dd, J=8.4, 4.6 Hz, 1H), 7.09-6.94 (m, 2H), 6.90 (dd, J=6.6, 2.7 Hz, 1H), 6.47 (ddd, J=9.0, 4.0, 2.7 Hz, 1H).

Example 6: 4-Chloro-N-(3-chloro-4-fluorophenyl)-N'-hydroxy-1H-benzo[d]imidazole-7-carboximidamide

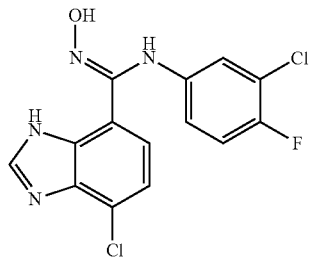 [SMILES: O/N=C(\Nc1ccc(F)c(Cl)c1)c1ccc(Cl)c2nc[nH]c12]

Example 6 was made analogously to Example 59 using 4-chloro-1H-benzo[d]imidazole-7-carboxylic acid in place of 1H-imidazo[4,5-b]pyridine-7-carboxylic acid. $C_{14}H_9Cl_2FN_4O$. 339.1 (M+1). $^1H$ NMR (400 MHz, DMSO-$d_6$) δ 10.85 (s, 1H), 8.81 (s, 1H), 8.39 (s, 1H), 7.29 (d, J=8.1 Hz, 1H), 7.18 (d, J=8.1 Hz, 1H), 7.01 (t, J=9.1 Hz, 1H), 6.93 (dd, J=6.6, 2.7 Hz, 1H), 6.47 (ddd, J=9.0, 4.0, 2.7 Hz, 1H).

Example 7: N-(3-Chloro-4-fluorophenyl)-N'-hydroxy-4-(trifluoromethyl)-1H-benzo[d]imidazole-7-carboximidamide

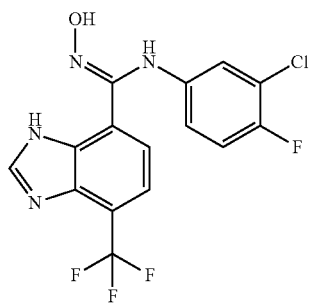 [SMILES: O/N=C(\Nc1ccc(F)c(Cl)c1)c1ccc(C(F)(F)F)c2nc[nH]c12]

Example 7 was made analogously to Example 59 using 4-(trifluoromethyl)-1H-benzo[d]imidazole-7-carboxylic acid in place of 1H-imidazo[4,5-b]pyridine-7-carboxylic acid. $C_{15}H_9ClF_4N_4O$. 373.1 (M+1). $^1$H NMR (400 MHz, DMSO-$d_6$) δ 10.97 (d, J=5.0 Hz, 1H), 8.83 (s, 1H), 8.35 (s, 1H), 7.52 (d, J=7.9 Hz, 1H), 7.30 (d, J=7.8 Hz, 1H), 7.01 (t, J=9.1 Hz, 1H), 6.93 (dd, J=6.6, 2.7 Hz, 1H), 6.46 (ddd, J=9.0, 4.1, 2.8 Hz, 1H).

Example 8: N-(3-Chloro-4-fluorophenyl)-N'-hydroxy-1H-benzo[d]imidazole-7-carboximidamide

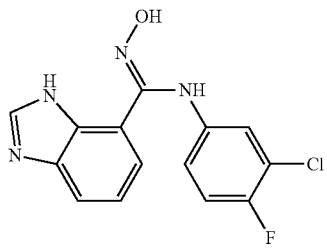 [SMILES: O/N=C(\Nc1ccc(F)c(Cl)c1)c1cccc2nc[nH]c12]

Example 8 was made analogously to Example 59 using 1H-benzo[d]imidazole-7-carboxylic acid in place of 1H-imidazo[4,5-b]pyridine-7-carboxylic acid. $C_{14}H_{10}ClFN_4O$. 305.1 (M+1).

Example 9: N-(3-Chloro-4-fluorophenyl)-6-fluoro-N'-hydroxy-7-methyl-3H-benzimidazole-4-carboximidamide

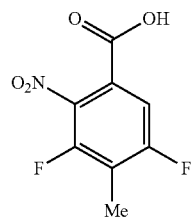 [SMILES: Cc1c(F)cc(C(=O)O)c([N+](=O)[O-])c1F]

3,5-difluoro-4-methyl-2-nitrobenzoic acid. To a solution of concentrated nitric acid (65% in water, 7.5 mL) and sulfuric acid (15 mL) at 0° C. was added 3,5-difluoro-4-methylbenzoic acid (5.0 g, 29 mmol) in portions over 1 hr. The solution was allowed to warm to room temperature and stirred for 18 hr. The reaction mixture was poured onto ice and the resulting precipitate was filtered and dried on high vac to give the desired product (6.3 g). $C_8H_5F_2NO_4$. 217.9 (M+1).

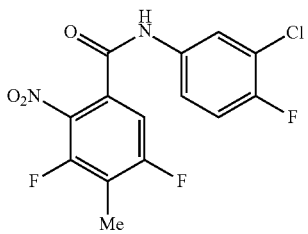 [SMILES: Cc1c(F)cc(C(=O)Nc2ccc(F)c(Cl)c2)c([N+](=O)[O-])c1F]

N-(3-chloro-4-fluorophenyl)-3,5-difluoro-4-methyl-2-nitrobenzamide. To a solution of 3-chloro-4-fluoroaniline (670 mg, 4.6 mmol), 3,5-difluoro-4-methyl-2-nitrobenzoic acid (1.0 g, 4.6 mmol), and triethylamine (1.9 mL, 14 mmol) in dichloromethane (40 mL) at 0° C. was added phosphoryl chloride (0.64 mL, 6.9 mmol). The reaction mixture was allowed to warm to room temperature and stirred for 1 hr. To the reaction mixture was added saturated sodium bicarbonate and the aqueous layer was washed three times with dichloromethane. The combined organic layers were dried over sodium sulfate, filtered, adsorbed onto silica and purified by silica gel chromatography to give the desired product (1.6 g). $C_{14}H_8ClF_3N_2O_3$. 345.0 (M+1).

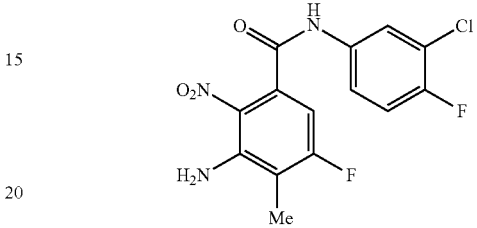

3-amino-N-(3-chloro-4-fluorophenyl)-5-fluoro-4-methyl-2-nitrobenzamide. A solution of N-(3-chloro-4-fluorophenyl)-3,5-difluoro-4-methyl-2-nitrobenzamide (674 mg, 1.96 mmol) and 28% aqueous ammonium hydroxide in ethanol (2 mL) was stirred at 80° C. for 18 hr. To this solution was added water and the resulting precipitate was filtered and dried on high vac to give the desired product (583 mg). $C_{14}H_{10}ClF_2N_3O_3$. 364.0 (M+23).

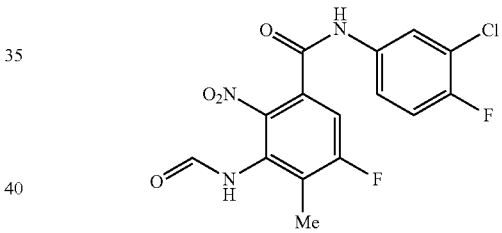

N-(3-chloro-4-fluorophenyl)-5-fluoro-3-formamido-4-methyl-2-nitrobenzamide. A mixture of acetic anhydride (0.4 mL, 4.3 mmol) in formic acid (4 mL) was stirred for 5 min. To this solution was added 3-amino-N-(3-chloro-4-fluorophenyl)-5-fluoro-4-methyl-2-nitrobenzamide (583 mg, 1.7 mmol). The reaction mixture stirred for 2 hr and was poured onto cold water and the resulting precipitate was filtered and dried on high vac to give the desired product (562 mg). $C_{15}H_{10}ClF_2N_3O_4$. 370.0 (M+1).

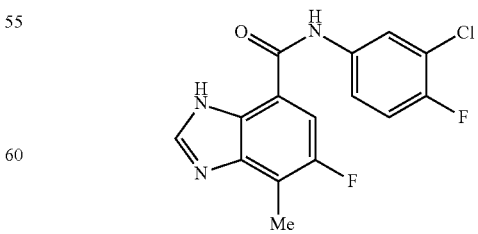

N-(3-chloro-4-fluorophenyl)-5-fluoro-4-methyl-1H-benzo[d]imidazole-7-carboxamide was made analogously to Example 1 using N-(3-chloro-4-fluorophenyl)-5-fluoro-3- formamido-4-methyl-2-nitrobenzamide in place of methyl 3-formamido-4-methyl-2-nitrobenzoate. $C_{15}H_{10}ClF_2N_3O$. 322.2 (M+1).

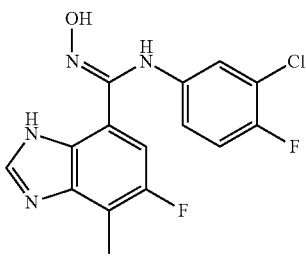 [SMILES: Cc1c(F)cc(/C(=N/O)Nc2ccc(F)c(Cl)c2)c2[nH]cnc12]

N-(3-Chloro-4-fluorophenyl)-6-fluoro-N'-hydroxy-7-methyl-3H-benzimidazole-4-carboximidamide was made analogously to Example 1 using N-(3-chloro-4-fluorophenyl)-5-fluoro-4-methyl-1H-benzo[d]imidazole-7-carboxamide in place of N-(3-chloro-4-fluorophenyl)-4-methyl-1H-benzo[d]imidazole-7-carboxamide. $C_{15}H_{11}ClF_2N_4O$. 337.0 (M+1). $^1$H NMR (400 MHz, DMSO-$d_6$) δ 10.97 (s, 1H), 8.96 (s, 1H), 8.86 (s, 1H), 7.20-7.11 (m, 1H), 7.01 (t, J=9.2 Hz, 1H), 6.97 (dd, J=6.5, 2.6 Hz, 1H), 2.44 (d, J=1.6 Hz, 3H).

Example 10: N-(3-Chloro-4-fluorophenyl)-4,5-difluoro-N'-hydroxy-1H-benzo[d]imidazole-7-carboximidamide

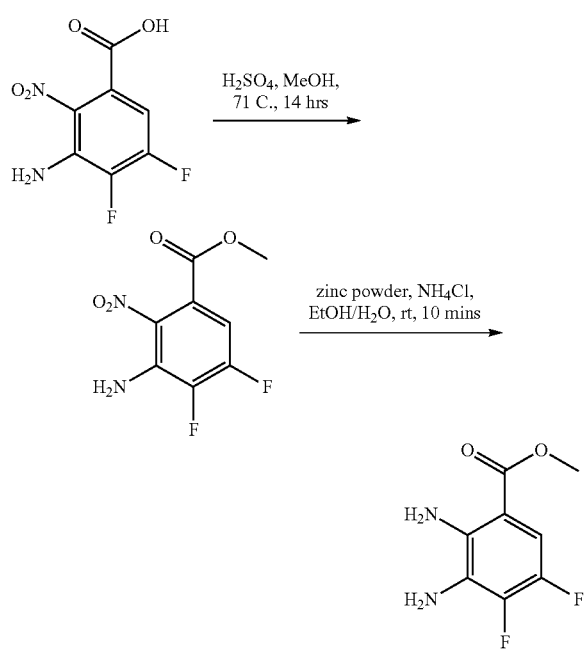

3-Amino-4,5-difluoro-2-nitrobenzoic acid (15 g, 68.8 mmol) was dissolved in methanol (200 mL) and sulfuric acid (20 mL) was added dropwise to the solution over 5 minutes. A reflux condenser was attached and the reaction was heated to 71° C. overnight. The reaction was then cooled to room temperature and concentrated in vacuo to approximately 50 mL of solvent. The reaction was neutralized to pH=7 with saturated potassium carbonate and then extracted with EtOAc (5×40 mL). Combined organic layers were washed with brine (1×60 mL) and concentrated in vacuo to give methyl 3-amino-4,5-difluoro-2-nitrobenzoate as a yellow solid which was used without further purification.

3-Amino-4,5-difluoro-2-nitrobenzoate (14.5 g, 62 mmol) was dissolved in ethanol (150 mL) and water (50 mL). Ammonium chloride (0.934 mol) was added in one portion and the reaction was allowed to stir at room temperature. Zinc powder (0.934 mol) was added portion-wise over 5 minutes and the reaction was allowed to stir 5 minutes after completion of addition. The zinc was then removed by vacuum filtration and the filtrate was concentrated in vacuo. The crude was dissolved in water (60 mL) and extracted with EtOAc (4×40 mL). Combined organic layers were washed with brine (1×50 mL), dried over sodium sulfate, and concentrated in vacuo to give methyl 2,3-diamino-4,5-difluorobenzoate as a brown powder.

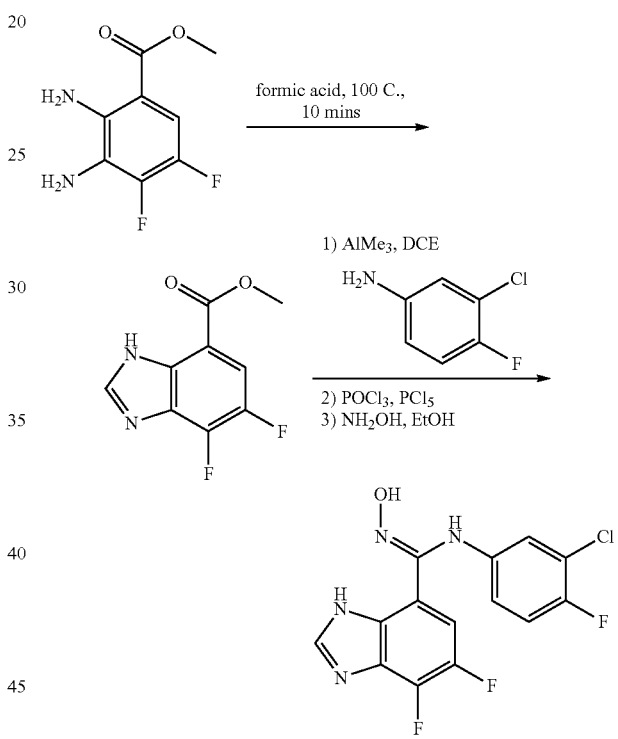

Methyl 2,3-diamino-4,5-difluorobenzoate (60 mg, 0.30 mmol) was dissolved in formic acid (2 mL) and heated to 100° C. in a sealed tube for 10 minutes. The reaction was allowed to cool to room temperature and concentrated in vacuo. The residue was dissolved in sat. sodium bicarbonate (2 mL) and extracted with EtOAc (3×3 mL). Combined organic layers were washed with water (1×5 mL) and concentrated in vacuo to give methyl 4,5-difluoro-1H-benzo[d]imidazole-7-carboxylate as a brown solid which was used without further purification.

Methyl 4,5-difluoro-1H-benzo[d]imidazole-7-carboxylate (12 mg, 0.056 mmol) was dissolved in DCE (1 mL) under an inert atmosphere. Trimethylaluminum (0.085 mL, 2.0 M in toluene) was added dropwise to the reaction followed by 3-chloro-4-fluoroaniline (0.085 mmol). The reaction was allowed to stir at rt overnight under inert atmosphere. The reaction was quenched with sat. sodium bicarb (3 mL) and extracted with EtOAc (3×2 mL). Combined organic layers were washed with water (1×4 mL) and concentrated in vacuo to give N-(3-chloro-4-fluorophenyl)-4,5-difluoro-1H-benzo[d]imidazole-7-carboxamide which was used directly in the next reaction. The crude material was dissolved in POCl$_3$ (2 mL) and PCl$_5$ (0.083 mmol) was added. The reaction was heated to 85° C. in a sealed tube for 12 hours. The reaction was allowed to cool to room temperature and concentrated in vacuo. The residue was dissolved in a pre-mixed solution of ethanol (2 mL) and hydroxylamine (0.55 mmol, 50% in water) and the reaction was allowed to stir at room temperature for 5 minutes. The reaction was concentrated in vacuo and purified by reverse-phase HPLC to afford N-(3-chloro-4-fluorophenyl)-4,5-difluoro-N'-hydroxy-1H-benzo[d]imidazole-7-carboximidamide as a white solid. C$_{14}$H$_8$ClF$_3$N$_4$O. 341.1/343.2 (M+1). $^1$H NMR (400 MHz, DMSO-d$_6$) δ 10.87 (s, 1H), 8.77 (s, 1H), 8.28 (s, 1H), 7.25 (d, J=5.5 Hz, 1H), 7.03 (t, J=9.0 Hz, 1H), 6.96 (dd, J=6.5, 2.8 Hz, 1H), 6.48 (d, J=9.1 Hz, 1H).

Example 11: 6-Chloro-N-(3-chloro-4-fluorophenyl)-N'-hydroxy-1H-benzo[d]imidazole-4-carboximidamide

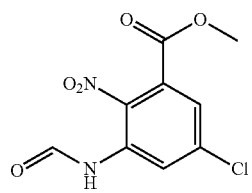 [SMILES: COC(=O)c1cc(Cl)cc(NC=O)c1[N+](=O)[O-]]

Methyl 5-chloro-3-formamido-2-nitrobenzoate was made analogously to Example 1 using methyl 3-amino-5-chloro-2-nitrobenzoate in place of methyl 3-amino-4-methylbenzoate. C$_9$H$_7$ClN$_2$O$_5$. 281.1 (M+23).

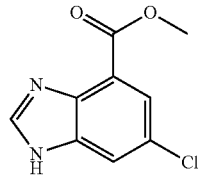

Methyl 6-chloro-1H-benzo[d]imidazole-4-carboxylate was made analogously to Example 1 using methyl 5-chloro-3-formamido-2-nitrobenzoate in place of methyl 3-formamido-4-methyl-2-nitrobenzoate. C$_9$H$_7$ClN$_2$O$_2$. 211.2 (M+1).

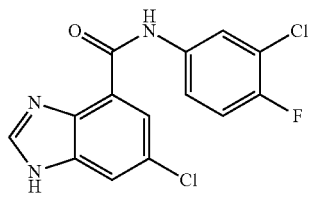 [SMILES: O=C(Nc1ccc(F)c(Cl)c1)c1cc(Cl)cc2[nH]cnc12]

6-chloro-N-(3-chloro-4-fluorophenyl)-1H-benzo[d]imidazole-4-carboxamide was made analogously to Example 1 using methyl 6-chloro-1H-benzo[d]imidazole-4-carboxylate in place of methyl 4-methyl-1H-benzo[d]imidazole-7-carboxylate. C$_{14}$H$_8$Cl$_2$FN$_3$O. 324.2 (M+1).

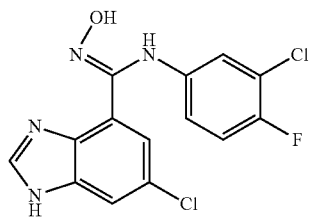 [SMILES: O/N=C(\Nc1ccc(F)c(Cl)c1)c1cc(Cl)cc2[nH]cnc12]

6-chloro-N-(3-chloro-4-fluorophenyl)-N'-hydroxy-1H-benzo[d]imidazole-4-carboximidamide was made analogously to Example 1 using 6-chloro-N-(3-chloro-4-fluorophenyl)-1H-benzo[d]imidazole-4-carboxamide in place of N-(3-chloro-4-fluorophenyl)-4-methyl-1H-benzo[d]imidazole-7-carboxamide. C$_{14}$H$_9$Cl$_2$FN$_4$O. 339.0 (M+1).

Example 12: 4-Bromo-N-(3-chloro-4-fluorophenyl)-N'-hydroxy-1H-benzo[d]imidazole-7-carboximidamide

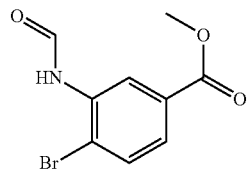

Methyl 4-bromo-3-formamidobenzoate was prepared analogously to Example 9, using methyl 3-amino-4-bromobenzoate in place of 3-amino-N-(3-chloro-4-fluorophenyl)-5-fluoro-4-methyl-2-nitrobenzamide. C$_9$H$_8$BrNO$_3$. 279.9/281.9 [M+23]

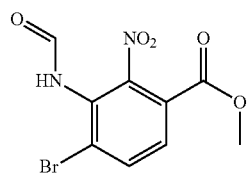 [SMILES: COC(=O)c1ccc(Br)c(NC=O)c1[N+](=O)[O-]]

Methyl 4-bromo-3-formamido-2-nitrobenzoate. To fuming nitric acid (14 mL) at −10° C. was added methyl 4-bromo-3-formamidobenzoate (5.1 g, 20 mmol), portionwise over 90 min. The mixture was stirred at 0° C. for 1 h and then poured over ice and allowed to stir and warm to rt over 1.5 h. The solid was isolated via filtration and the filter pad was washed with water. The solid was taken up in EtOAc, washed with brine, concentrated onto silica gel, and purified via column chromatography on silica gel to yield a mixture of the desired product and its regioisomer (3.5 g). C$_9$H$_7$BrN$_2$O$_5$. 324.9/326.9 [M+23]$^+$.

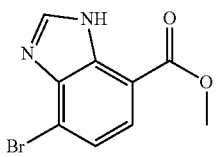

Methyl 4-bromo-1H-benzo[d]imidazole-7-carboxylate was prepared analogously to Example 1, using methyl 4-bromo-3-formamido-2-nitrobenzoate in place of methyl 3-formamido-4-methyl-2-nitrobenzoate. $C_9H_7BrN_2O_2$. 254.9/256.9 [M+1]$^+$.

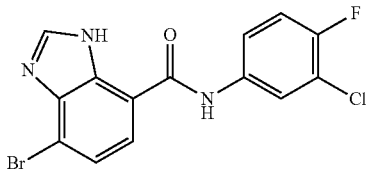 [SMILES: O=C(Nc1ccc(F)c(Cl)c1)c1ccc(Br)c2nc[nH]c12]

4-bromo-N-(3-chloro-4-fluorophenyl)-1H-benzo[d]imidazole-7-carboxamide was prepared analogously to Example 1, using methyl 4-bromo-1H-benzo[d]imidazole-7-carboxylate in place of methyl 4-methyl-1H-benzo[d]imidazole-7-carboxylate. $C_{14}H_8BrClFN_3O$. 368.0/369.9 [M+1]$^+$.

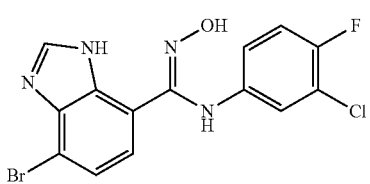 [SMILES: O/N=C(\Nc1ccc(F)c(Cl)c1)c1ccc(Br)c2nc[nH]c12]

4-bromo-N-(3-chloro-4-fluorophenyl)-N'-hydroxy-1H-benzo[d]imidazole-7-carboximidamide was prepared analogously to Example 1, using 4-bromo-N-(3-chloro-4-fluorophenyl)-1H-benzo[d]imidazole-7-carboxamide in place of N-(3-chloro-4-fluorophenyl)-4-methyl-1H-benzo[d]imidazole-7-carboxamide. $C_{14}H_9BrClFN_4O$. 382.9/384.9 [M+1]$^+$.

Example 13: 2-Amino-N-(3-chloro-4-fluorophenyl)-4,5-difluoro-N'-hydroxy-1H-benzo[d]imidazole-7-carboximidamide

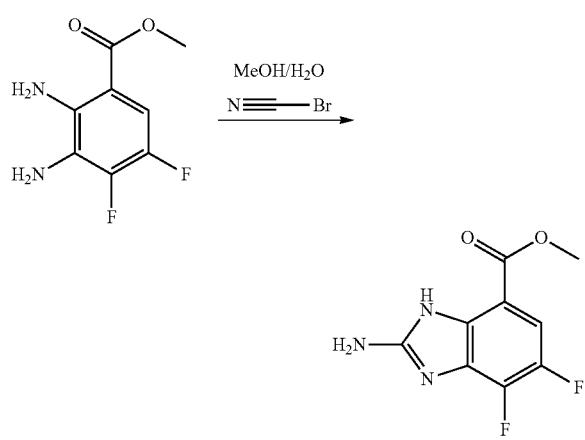

Methyl 2,3-diamino-4,5-difluorobenzoate (0.5 g, 2.0 mmol) was dissolved in methanol (7.0 mL) and water (2.50 mL). Cyanogen bromide (3.0 mmol) was added and the reaction was refluxed in a sealed tube for 45 mins. The reaction was allowed to cool to rt and diluted with water (4 mL) and EtOAc (4 mL). The water layer was isolated and neutralized to pH=8 with sat. sodium carbonate. The neutralized aqueous layer was extracted with EtOAc (3×4 mL) and combined organic layers were washed with brine (1×5 mL), dried over sodium sulfate, and concentrated in vacuo to give methyl 2-amino-4,5-difluoro-1H-benzo[d]imidazole-7-carboxylate as a brown solid.

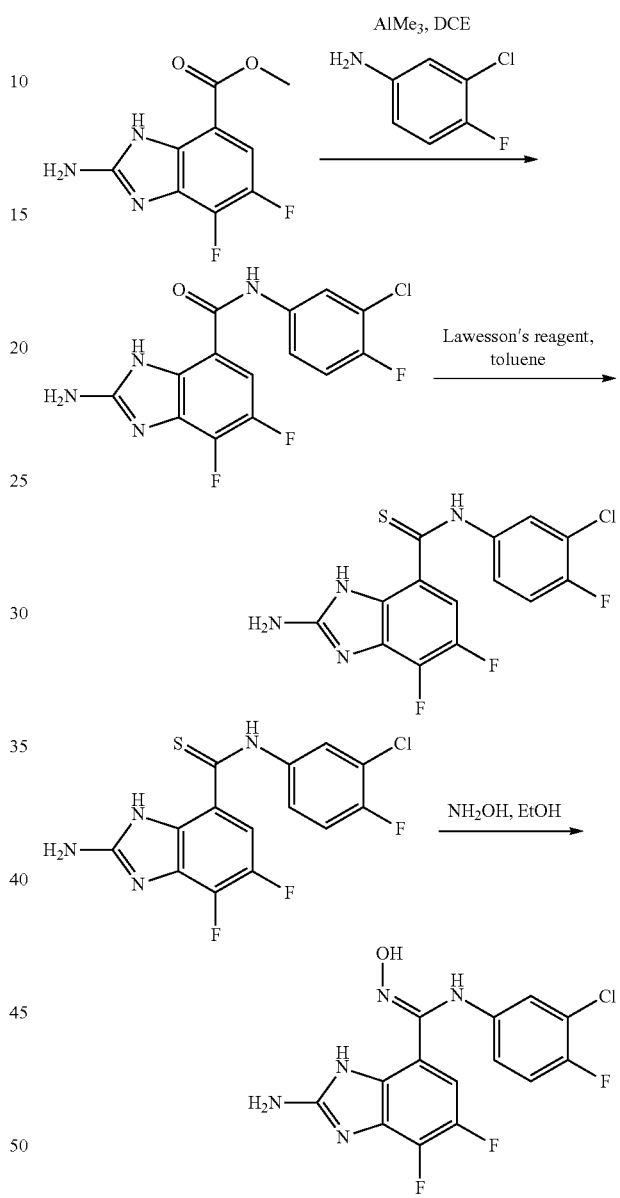

Methyl 2-amino-4,5-difluoro-1H-benzo[d]imidazole-7-carboxylate (75 mg, 0.33 mmol) was dissolved in DCE (4 mL) under inert atmosphere and cooled to 0° C. Trimethylaluminium (1.2 mL, 2M hexanes) was added dropwise followed by 3-chloro-4-fluoroaniline (1.0 mmol) and the reaction was then heated to 70° C. for 2 days. The reaction was cooled to rt and quenched with saturated bicarbonate solution. The reaction was extracted with EtOAc (3×3 mL) and combined organic layers were washed with brine (1×6 mL) and concentrated in vacuo. The crude material was dried loaded on to silica gel and purified by column chromatography (EtOAc/hex) to give 2-amino-N-(3-chloro-4-fluorophenyl)-4,5-difluoro-1H-benzo[d]imidazole-7-carboxamide as a white powder.

2-Amino-N-(3-chloro-4-fluorophenyl)-4,5-difluoro-1H-benzo[d]imidazole-7-carboxamide (20 mg, 0.0587 mmol) and Lawesson's reagent (0.176 mmol) was dissolved in toluene (2 mL) and heated to 90° C. overnight. The reaction was allowed to cool to rt and precipitates were removed by vacuum filtration and the filtrate was concentrated. The crude material was purified by column chromatography (EtOAc/hex) to give 2-amino-N-(3-chloro-4-fluorophenyl)-4,5-difluoro-1H-benzo[d]imidazole-7-carbothioamide as a yellow oil.

2-Amino-N-(3-chloro-4-fluorophenyl)-4,5-difluoro-1H-benzo[d]imidazole-7-carbothioamide (20 mg, 0.0561 mmol) was dissolved in ethanol (2 mL) and hydroxylamine (50% in aqueous solution, 0.561 mmol) was added and the reaction was allowed to stir overnight at rt. The reaction was concentrated in vacuo and purified by reverse-phase HPLC to give 2-amino-N-(3-chloro-4-fluorophenyl)-4,5-difluoro-N'-hydroxy-1H-benzo[d]imidazole-7-carboximidamide as a white solid. $C_{14}H_9ClF_3N_5O$. 356.0/357.9 (M+1). $^1$H NMR (400 MHz, Methanol-$d_4$) δ 7.27 (dd, J=5.8, 2.7 Hz, 1H), 7.15 (t, J=8.6 Hz, 1H), 7.03-6.98 (m, 2H), 6.94 (s, 1H), 6.67 (d, J=3.8 Hz, 1H).

Example 14: 2-Amino-N-(3-bromo-4-fluorophenyl)-4,5-difluoro-N'-hydroxy-1H-benzo[d]imidazole-7-carboximidamide

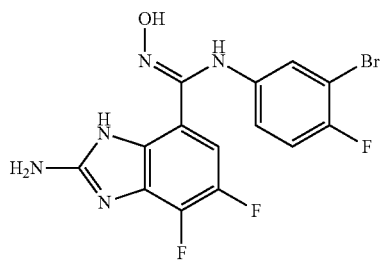

Example 14 was made analogously to Example 13 using 3-bromo-4-fluoroaniline in place of 3-chloro-4-fluoroaniline. $C_{14}H_9BrF_3N_5O$. 400.0/402.0 (M+1). $^1$H NMR (400 MHz, DMSO-$d_6$) δ 10.94 (s, 1H), 8.76 (s, 1H), 7.12 (dd, J=6.1, 2.6 Hz, 1H), 7.06 (t, J=8.8 Hz, 2H), 6.61-6.51 (m, 1H).

Example 15: 2-Amino-N-(3-bromophenyl)-4,5-difluoro-N'-hydroxy-1H-benzo[d]imidazole-7-carboximidamide

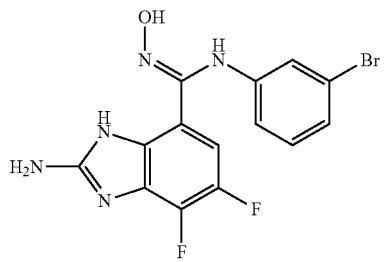

Example 15 was made analogously to Example 13 using 3-bromoaniline in place of 3-chloro-4-fluoroaniline. $C_{12}H_{10}BrF_2N_5O$. 382.0/384.1 (M+1). $^1$H NMR (400 MHz, Methanol-$d_4$) δ 7.11-6.96 (m, 4H), 6.69-6.63 (m, 1H).

Example 16: 2-Amino-N-(3-chlorophenyl)-4,5-difluoro-N'-hydroxy-1H-benzo[d]imidazole-7-carboximidamide

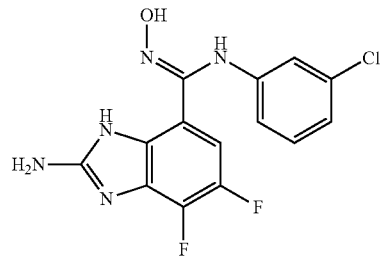 [SMILES: Nc1nc2c(F)c(F)cc(/C(=N/O)Nc3cccc(Cl)c3)c2[nH]1]

Example 16 was made analogously to Example 13 using 3-chloroaniline in place of 3-chloro-4-fluoroaniline. $C_{14}H_{10}ClF_2N_5O$. 338.0/340.1 (M+1). $^1$H NMR (400 MHz, Methanol-$d_4$) δ 8.69-8.59 (m, 2H), 8.51-8.45 (m, 1H), 8.39 (t, J=2.1 Hz, 1H), 8.21-8.15 (m, 1H).

Example 17: 2-Amino-4,5-difluoro-N-(4-fluoro-3-(trifluoromethyl)phenyl)-N'-hydroxy-1H-benzo[d]imidazole-7-carboximidamide

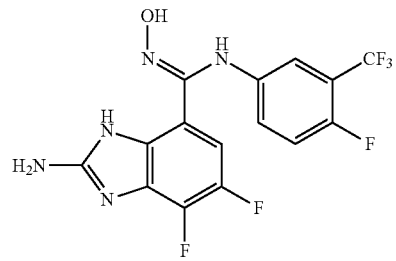 [SMILES: Nc1nc2c(F)c(F)cc(/C(=N/O)Nc3ccc(F)c(C(F)(F)F)c3)c2[nH]1]

Example 17 was made analogously to Example 13 using 4-fluoro-3-(trifluoromethyl)aniline in place of 3-chloro-4-fluoroaniline. $C_{15}H_9F_6N_5O$. 390.1 (M+1). $^1$H NMR (400 MHz, DMSO-$d_6$) δ 11.04 (s, 1H), 8.93 (s, 1H), 8.16 (s, 2H), 7.24-7.10 (m, 3H), 6.83 (dt, J=7.9, 3.5 Hz, 1H).

Example 18: 2-Amino-N-(3-bromophenyl)-4-fluoro-N'-hydroxy-1H-benzo[d]imidazole-7-carboximidamide

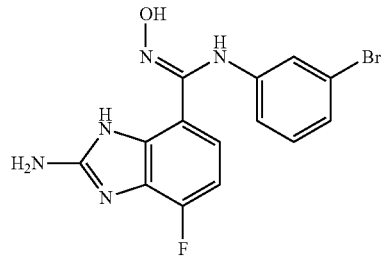

Example 18 was made analogously to Example 15 using methyl 2-amino-4-fluoro-1H-benzo[d]imidazole-7-carboxylate in place of 2-amino-4,5-difluoro-1H-benzo[d]imidazole-7-carboxylate. $C_{14}H_{11}BrFN_5O$. 364.0/366.0 (M+1). $^1$H NMR (400 MHz, Methanol-$d_4$) δ 7.16 (dd, J=8.8, 4.5 Hz, 1H), 7.09-6.92 (m, 4H), 6.65 (d, J=8.1 Hz, 1H).

Example 19: 2-Amino-N-(3-bromo-4-fluorophenyl)-4-fluoro-N'-hydroxy-1H-benzo[d]imidazole-7-carboximidamide

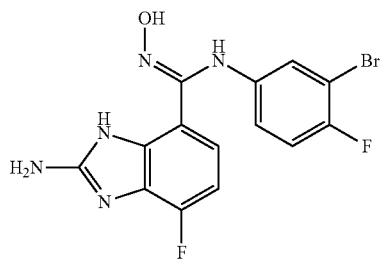

Example 19 was made analogously to Example 14 using methyl 2-amino-4-fluoro-1H-benzo[d]imidazole-7-carboxylate in place of 2-amino-4,5-difluoro-1H-benzo[d]imidazole-7-carboxylate. $C_{14}H_{10}BrF_2N_5O$. 382.0/384.0 (M+1). $^1$H NMR (400 MHz, Methanol-$d_4$) δ 7.15 (dd, J=8.8, 4.6 Hz, 1H), 7.10-6.99 (m, 2H), 6.95 (t, J=8.6 Hz, 1H), 6.69 (dt, J=8.8, 3.5 Hz, 1H).

Example 20: 2-Amino-N-(3-chlorophenyl)-4-fluoro-N'-hydroxy-1H-benzo[d]imidazole-7-carboximidamide

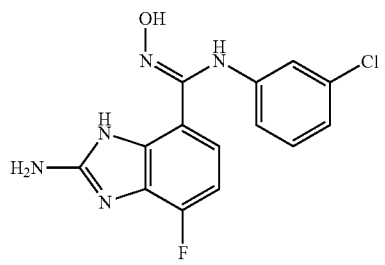 [SMILES: Nc1nc2c(F)ccc(/C(=N/O)Nc3cccc(Br)c3)c2[nH]1]

Example 20 was made analogously to Example 16 using methyl 2-amino-4-fluoro-1H-benzo[d]imidazole-7-carboxylate in place of 2-amino-4,5-difluoro-1H-benzo[d]imidazole-7-carboxylate. $C_{14}H_{11}ClFN_5O$. 320.1/322.1 (M+1). $^1$H NMR (400 MHz, Methanol-$d_4$) δ 7.16 (dd, J=8.8, 4.6 Hz, 1H), 7.10-6.99 (m, 2H), 6.89 (ddd, J=8.0, 2.0, 0.9 Hz, 1H), 6.79 (t, J=2.0 Hz, 1H), 6.64-6.58 (m, 1H).

Example 21: 2-Amino-4-fluoro-N-(4-fluoro-3-(trifluoromethyl)phenyl)-N'-hydroxy-1H-benzo[d]imidazole-7-carboximidamide

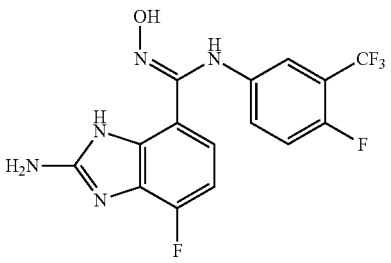

Example 21 was made analogously to Example 17 using methyl 2-amino-4-fluoro-1H-benzo[d]imidazole-7-carboxylate in place of 2-amino-4,5-difluoro-1H-benzo[d]imidazole-7-carboxylate. $C_{15}H_{10}F_5N_5O$. 372.1 (M+1). $^1$H NMR (400 MHz, DMSO-$d_6$) δ 10.95 (s, 1H), 8.93 (s, 1H), 8.32 (s, 2H), 7.24-7.05 (m, 4H), 6.83 (dd, J=8.5, 4.2 Hz, 1H).

Example 22: 2-Amino-N-(3-chloro-4-fluorophenyl)-4-fluoro-N'-hydroxy-1H-benzo[d]imidazole-7-carboximidamide

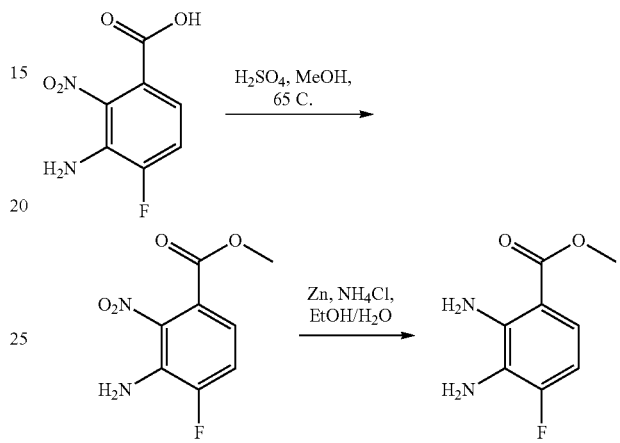

3-Amino-4-fluoro-2-nitrobenzoic acid (5 g, 25 mmol) was dissolved in methanol (120 mL) and sulfuric acid (2.5 mL) was added dropwise to the solution over 5 minutes. A reflux condenser was attached and the reaction was heated to 71° C. overnight. The reaction was then cooled to room temperature and concentrated in vacuo to approximately 50 mL of solvent. The reaction was neutralized to pH=7 with saturated potassium carbonate and then extracted with EtOAc (5×40 mL). Combined organic layers were washed with brine (1×60 mL) and concentrated in vacuo to give methyl 3-amino-4-fluoro-2-nitrobenzoate as a yellow solid which was used without further purification.

3-Amino-4-fluoro-2-nitrobenzoate (2.32 g, 11.0 mmol) was dissolved in ethanol (100 mL) and water (35 mL). Ammonium chloride (0.163 mol) was added in one portion and the reaction was allowed to stir at room temperature. Zinc powder (0.163 mol) was added portion-wise over 5 minutes and the reaction was allowed to stir 5 minutes after completion of addition. The zinc was then removed by vacuum filtration and the filtrate was concentrated in vacuo. The crude was dissolved in water (20 mL) and extracted with EtOAc (4×10 mL). Combined organic layers were washed with brine (1×50 mL), dried over sodium sulfate, and concentrated in vacuo to give methyl 2,3-diamino-4-fluorobenzoate as a brown powder.

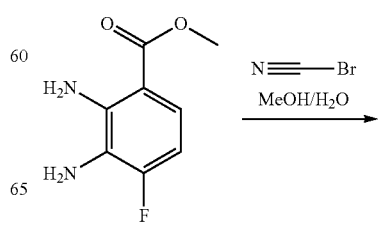

-continued

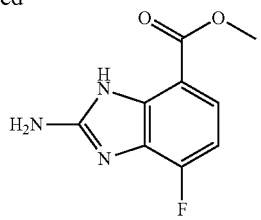

Methyl 2,3-diamino-4-fluorobenzoate (0.1 g, 0.54 mmol) was dissolved in methanol (2.0 mL) and water (1.0 mL). Cyanogen bromide (0.54 mmol) was added and the reaction was refluxed in a sealed tube for 45 mins. The reaction was allowed to cool to rt and diluted with water (4 mL) and EtOAc (4 mL). The water layer was isolated and neutralized to pH=8 with sat. sodium carbonate. The neutralized aqueous layer was extracted with EtOAc (3×4 mL) and combined organic layers were washed with brine (1×5 mL), dried over sodium sulfate, and concentrated in vacuo to give methyl 2-amino-4-fluoro-1H-benzo[d]imidazole-7-carboxylate as a brown solid.

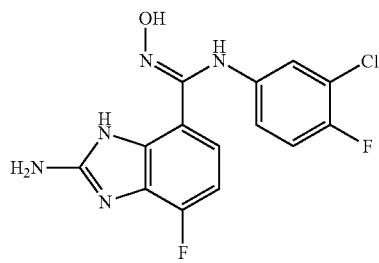 [SMILES: Nc1nc2c(F)ccc(/C(=N/O)Nc3ccc(F)c(Br)c3)c2[nH]1]

Example 22 was made analogously to Example 13 (using methyl 2-amino-4-fluoro-1H-benzo[d]imidazole-7-carboxylate in place of 2-amino-4,5-difluoro-1H-benzo[d]imidazole-7-carboxylate. $C_{14}H_{10}ClF_2N_5O$. 338.1/339.2 (M+1). $^1$H NMR (400 MHz, Methanol-$d_4$) δ 7.14 (dd, J=8.8, 4.6 Hz, 1H), 7.00 (dt, J=23.9, 9.2 Hz, 2H), 6.91 (dd, J=6.4, 2.7 Hz, 1H), 6.64 (dt, J=8.8, 3.4 Hz, 1H).

Example 23: N-(3-Chloro-4-fluorophenyl)-4,5-difluoro-N'-hydroxy-2-((2-morpholinoethyl)amino)-1H-benzo[d]imidazole-7-carboximidamide

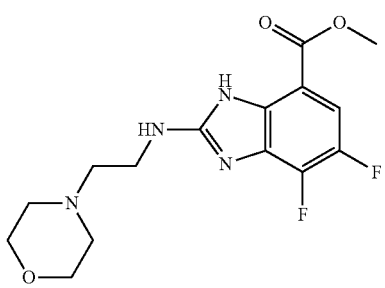 [SMILES: COC(=O)c1cc(F)c(F)c2nc(NCCN3CCOCC3)[nH]c12]

Methyl 4,5-difluoro-2-((2-morpholinoethyl)amino)-1H-benzo[d]imidazole-7-carboxylate. Dissolved methyl 2,3-diamino-4,5-difluorobenzoate (50 mg, 0.25 mmol) in THF (3 ml), to the solution was added 4-(2-isothiocyanatoethyl) morpholine (0.43 g, 0.002 mmol) and triethylamine (0.36 g, 0.003 mol). The reaction mixture was heated at 80° C. overnight, then to the reaction mixture was added 1-(3-dimethylaminopropyl)-3-ethylcarbodiimide hydrochloride (0.47 g, 0.002 mol), heated at 80° C. for 1 h. The reaction mixture was diluted with EtOAc, and washed with NaHCO$_3$ saturated solution, organic layer was evaporated and the residue was purified with Combi-Flash column chromatography to afford 84 mg desired product. $C_{15}H_{18}F_2N_4O_3$. 341.2 (M+1).

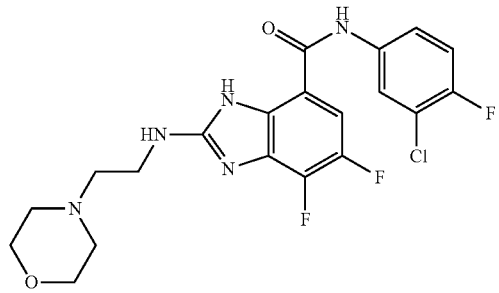 [SMILES: O=C(Nc1ccc(F)c(Cl)c1)c1cc(F)c(F)c2nc(NCCN3CCOCC3)[nH]c12]

N-(3-chloro-4-fluorophenyl)-4,5-difluoro-2-((2-morpholinoethyl)amino)-1H-benzo[d]imidazole-7-carboxamide. Dissolved 3-chloro-4-fluoroaniline (12.8 mg, 0.088 mmol) in dichloroethane (2 ml), to the solution was added trimethylamine (0.088 ml, 2M in toluene) and triethylamine (0.36 g, 0.003 mol). Then to the fraction mixture was added methyl 4,5-difluoro-2-((2-morpholinoethyl)amino)-1H-benzo[d]imidazole-7-carboxylate (20 mg, 0.06 mmol). The reaction mixture was stirred at room temperature for 2 h, then the reaction mixture was diluted with EtOAc, and washed with NaHCO$_3$ saturated solution, organic layer was evaporated and the residue was purified with Combi-Flash column chromatography to afford 27 mg desired product. $C_{20}H_{19}ClF_3N_5O_2$. 454.4 (M+1).

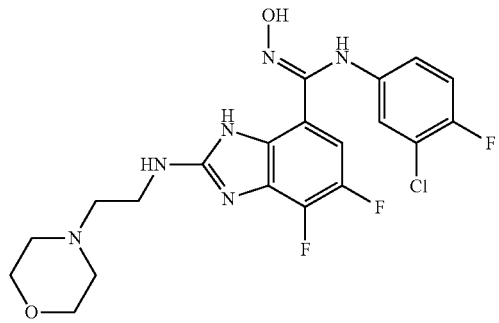 [SMILES: O/N=C(\Nc1ccc(F)c(Cl)c1)c1cc(F)c(F)c2nc(NCCN3CCOCC3)[nH]c12]

N-(3-chloro-4-fluorophenyl)-4,5-difluoro-N'-hydroxy-2-((2-morpholinoethyl)amino)-1H-benzo[d]imidazole-7-carboximidamide. Example 23 was made analogously to Example 107 using the general procedure for hydroxyamidine formation. $C_{20}H_{20}ClF_3N_6O_2$ 469.1 (M+1). 1H NMR (400 MHz, Methanol-d4) δ 7.01 6.85 (m, 3H), 6.67 (ddd, J=8.9, 4.0, 2.8 Hz, 1H), 4.00 (t, J=4.8 Hz, 4H), 3.81-3.73 (m, 2H), 3.49-3.36 (m, 6H).

Example 24: N-(3-Chlorophenyl)-4,5-difluoro-N'-hydroxy-2-(((3-methoxypropyl)amino)methyl)-1H-benzo[d]imidazole-7-carboximidamide

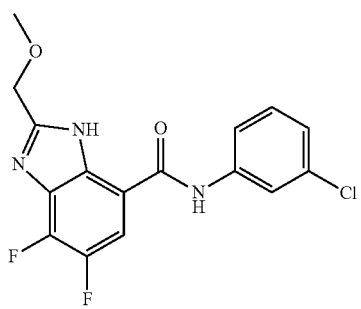 [SMILES: COCc1nc2c(F)c(F)cc(C(=O)Nc3cccc(Cl)c3)c2[nH]1]

N-(3-chlorophenyl)-4,5-difluoro-2-(methoxymethyl)-1H-benzo[d]imidazole-7-carboxamide was prepared analogously to Example 45, using 3-chloroaniline in place of 3-chloro-4-fluoroaniline. C$_{16}$H$_{12}$ClF$_2$N$_3$O$_2$. 352.1 [M+1]$^+$.

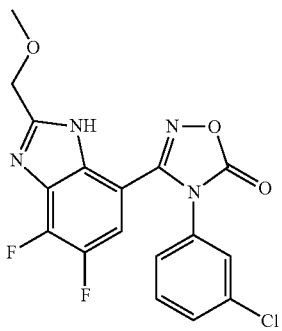 [SMILES: COCc1nc2c(F)c(F)cc(-c3noc(=O)n3-c3cccc(Cl)c3)c2[nH]1]

4-(3-chlorophenyl)-3-(4,5-difluoro-2-(methoxymethyl)-1H-benzo[d]imidazol-7-yl)-1,2,4-oxadiazol-5(4H)-one was prepared analogously to Example 45, using N-(3-chlorophenyl)-4,5-difluoro-2-(methoxymethyl)-1H-benzo[d]imidazole-7-carboxamide in place of N-(3-chloro-4-fluorophenyl)-4,5-difluoro-2-(methoxymethyl)-1H-benzo[d]imidazole-7-carboxamide. C$_{17}$H$_{11}$ClF$_2$N$_4$O$_3$. 393.0 [M+1]$^+$.

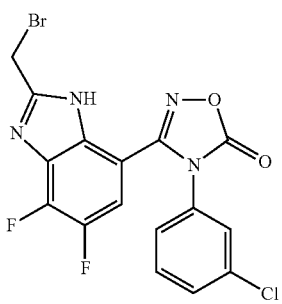

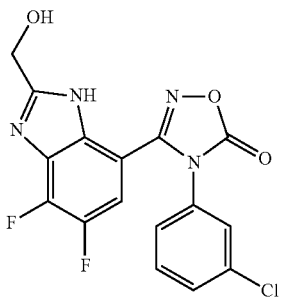

3-(2-(bromomethyl)-4,5-difluoro-1H-benzo[d]imidazol-7-yl)-4-(3-chlorophenyl)-1,2,4-oxadiazol-5 (4H)-one and 4-(3-chlorophenyl)-3-(4,5-difluoro-2-(hydroxymethyl)-1H-benzo[d]imidazol-7-yl)-1,2,4-oxadiazol-5(4H)-one were prepared analogously to Example 45, using 4-(3-chlorophenyl)-3-(4,5-difluoro-2-(methoxymethyl)-1H-benzo[d]imidazol-7-yl)-1,2,4-oxadiazol-5(4H)-one in place of 4-(3-chloro-4-fluorophenyl)-3-(4,5-difluoro-2-(methoxymethyl)-1H-benzo[d]imidazol-7-yl)-1,2,4-oxadiazol-5(4H)-one. C$_{16}$H$_8$BrClF$_2$N$_4$O$_2$. 440.9/442.9 [M+1]$^+$. C$_{16}$H$_9$ClF$_2$N$_4$O$_3$. 379.0 [M+1]$^+$.

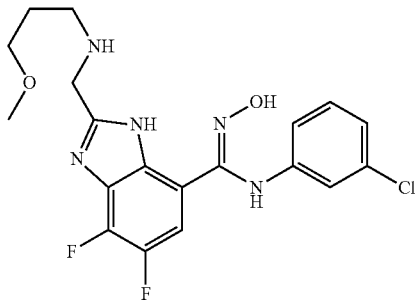 [SMILES: COCCCNCc1nc2c(F)c(F)cc(/C(=N/O)Nc3cccc(Cl)c3)c2[nH]1]

N-(3-chlorophenyl)-4,5-difluoro-N'-hydroxy-2-(((3-methoxypropyl)amino)methyl)-1H-benzo[d]imidazole-7-carboximidamide. Example 24 was prepared analogously to Example 45, using 3-(2-(bromomethyl)-4,5-difluoro-1H-benzo[d]imidazol-7-yl)-4-(3-chlorophenyl)-1,2,4-oxadiazol-5(4H)-one in place of 3-(2-(bromomethyl)-4,5-difluoro-1H-benzo[d]imidazol-7-yl)-4-(3-chloro-4-fluorophenyl)-1,2,4-oxadiazol-5(4H)-one. C$_{19}$H$_{20}$ClF$_2$N$_5$O$_2$. 424.1 [M+1]$^+$.

Example 25: N-(3-Chlorophenyl)-2-(((cyclopropylmethyl)amino)methyl)-4,5-difluoro-N'-hydroxy-1H-benzo[d]imidazole-7-carboximidamide

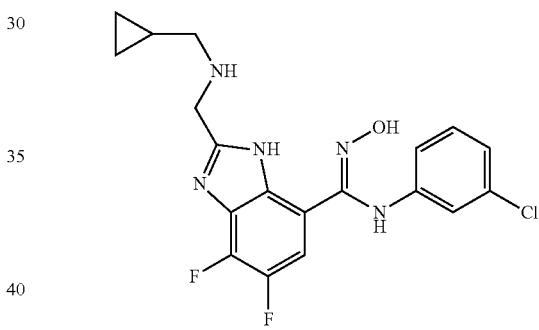

Example 25 was prepared analogously to Example 45, using 3-(2-(bromomethyl)-4,5-difluoro-1H-benzo[d]imidazol-7-yl)-4-(3-chlorophenyl)-1,2,4-oxadiazol-5(4H)-one and cyclopropylmethanamine in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. C$_{19}$H$_{18}$ClF$_2$N$_5$O. 406.1 [M+1]$^+$.

Example 26: N-(3-Chlorophenyl)-2-((dimethylamino)methyl)-4,5-difluoro-N'-hydroxy-1H-benzo[d]imidazole-7-carboximidamide

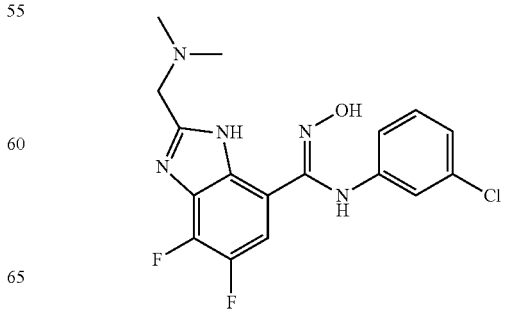

Example 26 was prepared analogously to Example 45, using 3-(2-(bromomethyl)-4,5-difluoro-1H-benzo[d]imidazol-7-yl)-4-(3-chlorophenyl)-1,2,4-oxadiazol-5(4H)-one and dimethylamine in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{17}H_{16}ClF_2N_5O$. 380.1 [M+1]$^+$. $^1$H NMR (400 MHz, DMSO-d$_6$) δ 12.93 (br s, 1H), 11.00 (br s, 1H), 10.27 (br s, 1H), 8.86 (s, 1H), 7.38-7.23 (m, 1H), 7.06-6.96 (m, 1H), 6.85 (t, J=2.1 Hz, 1H), 6.81 (d, J=7.8 Hz, 1H), 6.47 (dd, J=8.2, 1.8 Hz, 1H), 4.58 (s, 2H), 2.85 (s, 6H).

Example 27: N-(3-Chlorophenyl)-4,5-difluoro-N'-hydroxy-2-((isopropylamino)methyl)-1H-benzo[d]imidazole-7-carboximidamide

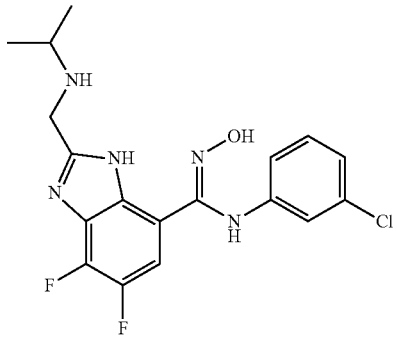 [SMILES: CC(C)NCc1nc2c(F)c(F)cc(/C(=N/O)Nc3cccc(Cl)c3)c2[nH]1]

Example 27 was prepared analogously to Example 45, using 3-(2-(bromomethyl)-4,5-difluoro-1H-benzo[d]imidazol-7-yl)-4-(3-chlorophenyl)-1,2,4-oxadiazol-5(4H)-one and isopropylamine in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{18}H_{18}ClF_2N_5O$. 394.1 [M+1]$^+$. $^1$H NMR (400 MHz, DMSO-d$_6$) δ 12.88 (br s, 1H), 11.03 (br s, 1H), 9.27 (br s, 3H), 8.85 (s, 1H), 7.31-7.20 (m, 1H), 7.04 (t, J=8.1 Hz, 1H), 6.83 (d, J=8.1 Hz, 1H), 6.80 (t, J=2.1 Hz, 1H), 6.49 (dd, J=8.3, 1.8 Hz, 1H), 4.51-4.43 (m, 2H), 3.54-3.35 (m, 1H), 1.28 (d, J=6.3 Hz, 6H).

Example 28: N-(3-Chlorophenyl)-2-((ethylamino)methyl)-4,5-difluoro-N'-hydroxy-1H-benzo[d]imidazole-7-carboximidamide

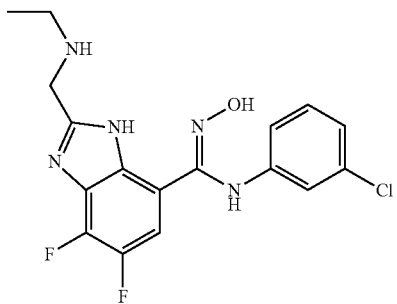 [SMILES: CCNCc1nc2c(F)c(F)cc(/C(=N/O)Nc3cccc(Cl)c3)c2[nH]1]

Example 28 was prepared analogously to Example 45, using 3-(2-(bromomethyl)-4,5-difluoro-1H-benzo[d]imidazol-7-yl)-4-(3-chlorophenyl)-1,2,4-oxadiazol-5(4H)-one and ethylamine in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{17}H_{16}ClF_2N_5O$. 380.1 [M+1]$^+$. $^1$H NMR (400 MHz, DMSO-d$_6$) δ 12.87 (br s, 1H), 11.01 (br s, 1H), 9.27 (br s, 2H), 8.85 (s, 1H), 7.30-7.21 (m, 1H), 7.03 (t, J=8.0 Hz, 1H), 6.87-6.78 (m, 2H), 6.52-6.45 (m, 1H), 4.54-4.38 (m, 2H), 3.17-2.98 (m, 2H), 1.23 (t, J=7.2 Hz, 3H).

Example 29: N-(3-Chlorophenyl)-4,5-difluoro-N'-hydroxy-2-(hydroxymethyl)-1H-benzo[d]imidazole-7-carboximidamide

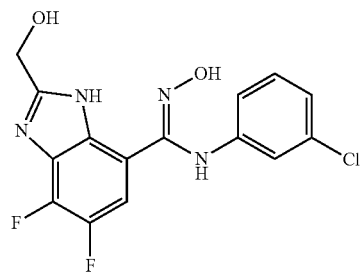 [SMILES: OCc1nc2c(F)c(F)cc(/C(=N/O)Nc3cccc(Cl)c3)c2[nH]1]

Example 29 was prepared analogously to Example 46, using 4-(3-chlorophenyl)-3-(4,5-difluoro-2-(hydroxymethyl)-1H-benzo[d]imidazol-7-yl)-1,2,4-oxadiazol-5(4H)-one in place of 4-(3-chloro-4-fluorophenyl)-3-(4,5-difluoro-2-(hydroxymethyl)-1H-benzo[d]imidazol-7-yl)-1,2,4-oxadiazol-5 (4H)-one. $C_{15}H_{11}ClF_2N_4O_2$. 353.0 [M+1]$^+$. $^1$H NMR (400 MHz, DMSO-d$_6$) δ 11.00 (br s, 1H), 8.79 (s, 1H), 7.16 (dd, J=12.0, 7.0 Hz, 1H), 7.07-7.00 (m, 1H), 6.85-6.79 (m, 2H), 6.53-6.47 (m, 1H), 4.67 (s, 2H).

Example 30: N-(3-Chlorophenyl)-4,5-difluoro-N'-hydroxy-2-((methylamino)methyl)-1H-benzo[d]imidazole-7-carboximidamide

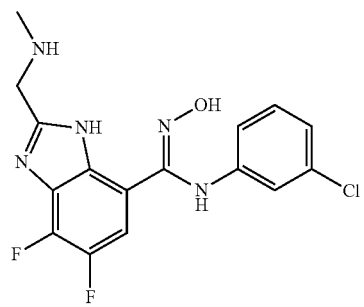 [SMILES: CNCc1nc2c(F)c(F)cc(/C(=N/O)Nc3cccc(Cl)c3)c2[nH]1]

Example 30 was prepared analogously to Example 45, using 3-(2-(bromomethyl)-4,5-difluoro-1H-benzo[d]imidazol-7-yl)-4-(3-chlorophenyl)-1,2,4-oxadiazol-5(4H)-one and methylamine in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{16}H_{14}ClF_2N_5O$. 366.0 [M+1]$^+$. $^1$H NMR (400 MHz, DMSO-d$_6$) δ 12.86 (br s, 1H), 11.00 (br s, 1H), 9.24 (br s, 2H), 8.84 (s, 1H), 7.30-7.19 (m, 1H), 7.03 (t, J=8.0 Hz, 1H), 6.88-6.75 (m, 2H), 6.53-6.45 (m, 1H), 4.45 (t, J=5.6 Hz, 2H), 2.74-2.64 (m, 3H).

Example 31: 2-(Aminomethyl)-N-(3-chlorophenyl)-4,5-difluoro-N'-hydroxy-1H-benzo[d]imidazole-7-carboximidamide

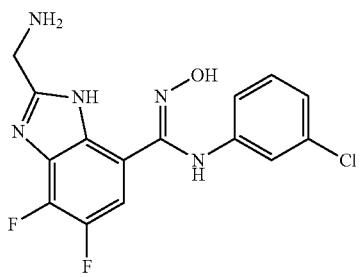

Example 31 was prepared analogously to Example 45, using 3-(2-(bromomethyl)-4,5-difluoro-1H-benzo[d]imidazol-7-yl)-4-(3-chlorophenyl)-1,2,4-oxadiazol-5(4H)-one and ammonia (0.5 M solution in dioxane) in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{15}H_{12}ClF_2N_5O$. 352.0 [M+1]$^+$. $^1$H NMR (400 MHz, DMSO-d$_6$) δ 12.77 (br s, 1H), 11.00 (br s, 1H), 8.83 (s, 1H), 8.52 (br s, 3H), 7.21 (dd, J=12.0, 6.9 Hz, 1H), 7.04 (t, J=8.1 Hz, 1H), 6.83 (dd, J=7.8, 2.0 Hz, 1H), 6.80 (t, J=2.1 Hz, 1H), 6.49 (dd, J=8.2, 2.1 Hz, 1H), 4.34 (q, J=5.4 Hz, 2H).

Example 32: N-(3-Chloro-4-fluorophenyl)-4,5-difluoro-N'-hydroxy-2-morpholino-1H-benzo-[d]imidazole-7-carboximidamide

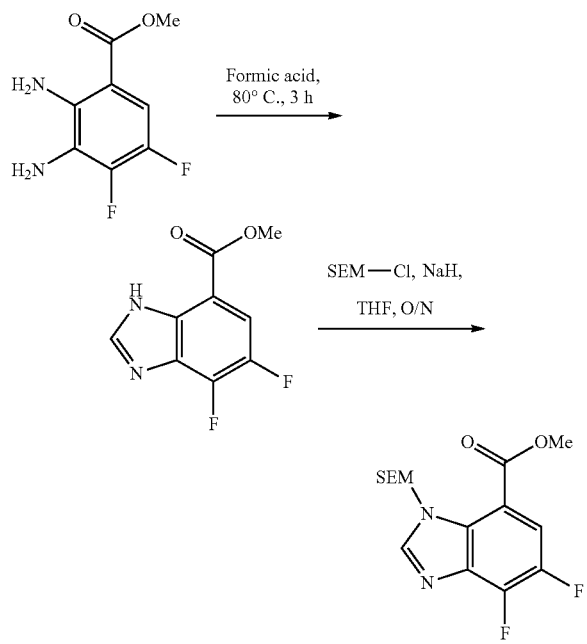

Methyl 2,3-diamino-4,5-difluorobenzoate (5.0 g, 25 mmol, 1 equiv) was dissolved in formic acid (120 mL) and stirred at 80° C. for 3 hours. Formic acid was subsequently removed in vacuo and methyl 4,5-difluoro-1H-benzo[d]imidazole-7-carboxylate was obtained as a brown solid. $C_9H_6F_2N_2O_2$, 213.0 (M+1). $^1$H NMR (400 MHz, DMSO-d$_6$) δ 8.43 (s, 1H), 7.83 (dd, J=11.5, 7.2 Hz, 1H), 3.95 (s, 3H). $^{19}$F NMR (377 MHz, DMSO-d$_6$) δ −146.16 (dd, J=21.8, 7.2 Hz, 1F), −149.09 (dd, J=21.8, 11.6 Hz, 1F).

To a suspension of methyl 4,5-difluoro-1H-benzo[d]imidazole-7-carboxylate (6.0 g, 28 mmol, 1 equiv) in THF (60 mL) was added a 60 wt % dispersion of NaH (1.7 g, 42 mmol, 1.5 equiv) in three portions. Once gas evolution ceased, the reaction mixture was cooled to 0° C. and SEM-Cl (6.0 mL, 34 mmol, 1.2 equiv) was added. The ice bath was subsequently removed and the reaction was stirred at room temperature for 3 hours before being quenched with saturated aqueous NH$_4$Cl. The reaction mixture was diluted with water and extracted three times with EtOAc. The combined organic layers were dried over MgSO$_4$, filtered and concentrated in vacuo. The crude product was purified by silica gel chromatography (0-5% MeOH/CH$_2$Cl$_2$ over 20 minutes). Methyl 4,5-difluoro-1-((2-(trimethylsilyl)ethoxy)methyl)-1H-benzo[d]imidazole-7-carboxylate was isolated as a yellow solid. $C_{15}H_{20}F_2N_2O_3Si$, 342.9 (M+1). $^1$H NMR (400 MHz, Chloroform-d) δ 8.17 (s, 1H), 7.91 (dd, J=11.5, 7.5 Hz, 1H), 5.68 (s, 2H), 4.06 (s, 3H), 3.64-3.45 (m, 2H), 0.98-0.85 (m, 2H), −0.04 (d, J=0.6 Hz, 9H). $^{19}$F NMR (377 MHz, Chloroform-d) δ −144.34 (m, 1F), −150.20 (m, 1F).

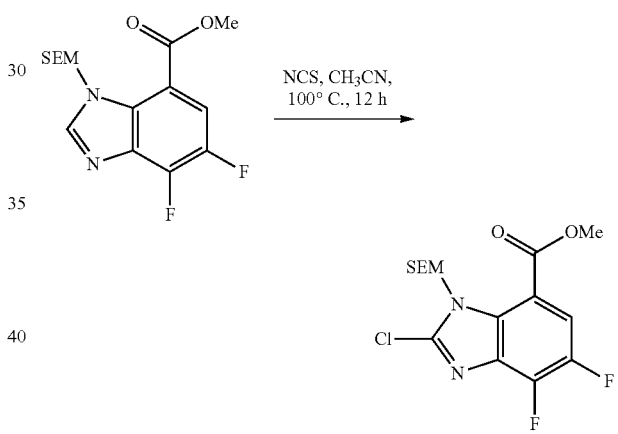

To a solution of methyl 4,5-difluoro-1-((2-(trimethylsilyl)ethoxy)methyl)-1H-benzo[d]imidazole-7-carboxylate (2.2 g, 6 mmol, 1 equiv) in acetonitrile (46.2 mL) was added NCS (1.29 g, 10 mmol, 1.5 equiv). The reaction mixture was stirred at 100° C. in a sealed vessel for 12 hours. Acetonitrile was subsequently removed in vacuo and the crude product purified by silica gel chromatography (0-5% MeOH/CH$_2$Cl$_2$ over 20 minutes). Methyl 2-chloro-4,5-difluoro-1-((2-(trimethylsilyl)ethoxy)methyl)-1H-benzo[d]imidazole-7-carboxylate was obtained as a crystalline yellow solid. $C_{15}H_{19}ClF_2N_2O_3Si$, 376.9/378.9 (M+1).

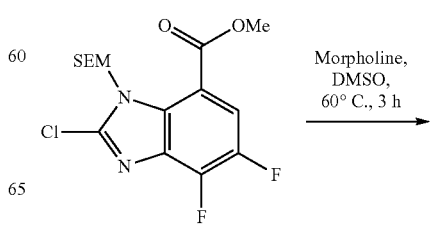

-continued

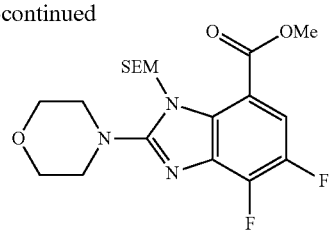

To a solution of Methyl 2-chloro-4,5-difluoro-1-((2-(trimethylsilyl)ethoxy)methyl)-1H-benzo[d]imidazole-7-carboxylate (0.29 g, 0.46 mmol, 1 equiv) in DMSO (2 mL) was added morpholine (0.14 mL, 1.6 mmol, 3.5 equiv). The reaction was stirred at 60° C. for 3 hours before being diluted with DMF/H$_2$O and purified by reverse phase HPLC (10-90% CH$_3$CN/H$_2$O over 20 mins). The TFA salt of methyl 4,5-difluoro-2-morpholino-1-((2-(trimethylsilyl)ethoxy)methyl)-1H-benzo[d]imidazole-7-carboxylate was obtained as a white solid. C$_{19}$H$_{27}$F$_2$N$_3$O$_4$Si, 428.1 (M+1).

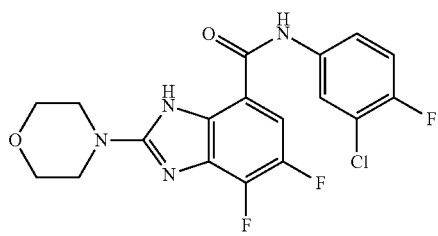 [SMILES: O=C(Nc1ccc(F)c(Cl)c1)c1cc(F)c(F)c2nc(N3CCOCC3)[nH]c12]

N-(3-Chloro-4-fluorophenyl)-4,5-difluoro-2-morpholino-1H-benzo[d]imidazole-7-carboxamide was made analogously to Example 13 using methyl 4,5-difluoro-2-morpholino-1-((2-(trimethylsilyl)ethoxy)methyl)-1H-benzo[d]imidazole-7-carboxylate and 3-chloro-4-fluoroaniline in place of methyl 2-amino-4,5-difluoro-1H-benzo[d]imidazole-7-carboxylate. C$_{18}$H$_{14}$ClF$_3$N$_4$O$_2$, 411.1/413.0 (M+1).

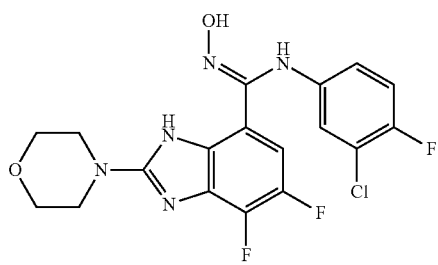 [SMILES: O/N=C(\Nc1ccc(F)c(Cl)c1)c1cc(F)c(F)c2nc(N3CCOCC3)[nH]c12]

Example 32 was made analogously to Example 59 using N-(3-chloro-4-fluorophenyl)-4,5-difluoro-2-morpholino-1H-benzo[d]imidazole-7-carboxamide in place of N-(3-chloro-4-fluorophenyl)-1H-imidazo[4,5-b]pyridine-7-carboxamide. C$_{18}$H$_{15}$ClF$_3$N$_5$O$_2$. 426.1/428.1 (M+1). $^1$H NMR (400 MHz, DMSO-d$_6$) δ 10.78 (br. s, 1H), 8.82 (s, 1H), 7.04 (t, J=9.1 Hz, 1H), 7.00 (dd, J=6.6, 2.7 Hz, 1H), 6.93 (dd, J=12.1, 6.9 Hz, 1H), 6.51 (ddd, J=9.0, 4.1, 2.7 Hz, 1H), 3.69-3.62 (m, 4H), 3.53-3.44 (m, 4H).

Example 33: N-(3-Chloro-4-fluorophenyl)-4-fluoro-N'-hydroxy-2-((2-(methylsulfonyl)ethyl)amino)-1H-benzo[d]imidazole-7-carboximidamide

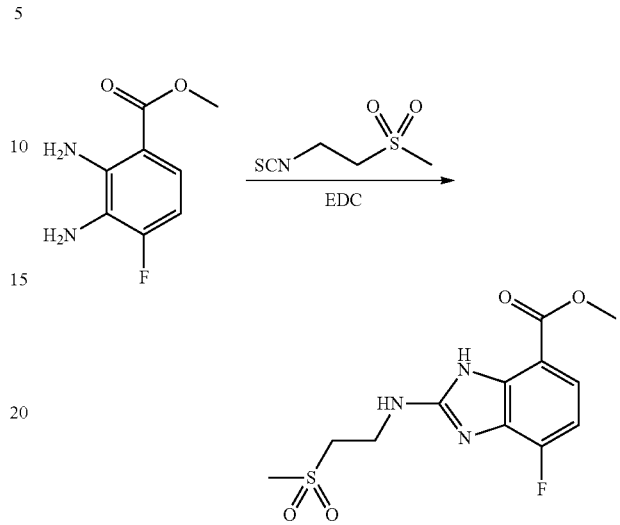

Methyl 2,3-diamino-4-fluorobenzoate (150 mg, 0.814 mmol) and 1-isothiocyanato-2-(methylsulfonyl)ethane (5.0 mmol) were dissolved in THF (4.5 mL) and triethylamine (7.0 mmol) was added and the reaction was heated to reflux overnight. 1-Ethyl-3(3-dimethylaminopropyl)carbodiimide (5.0 mmol) was added and the reaction was allowed to heat at reflux for an additional 1 hour. The reaction was allowed to cool to room temperature, quenched with water, and extracted with EtOAc (3×3 mL). The combined organic layers were washed with brine (1×4 mL), concentrated, and purified by silica gel column chromatography to give methyl 4-fluoro-2-((2-(methylsulfonyl)ethyl)amino)-1H-benzo[d]imidazole-7-carboxylate.

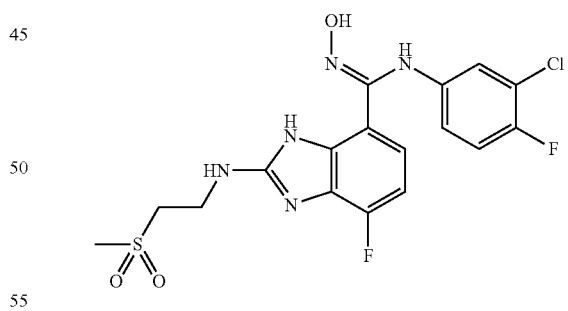

Example 33 was made analogously to Example 22 using methyl 4-fluoro-2-((2-(methylsulfonyl)ethyl)amino)-1H-benzo[d]imidazole-7-carboxylate in place of methyl 2-amino-4-fluoro-1H-benzo[d]imidazole-7-carboxylate. C$_{17}$H$_{16}$ClF$_2$N$_5$O$_3$S. 444.1/446/1 (M+1). $^1$H NMR (400 MHz, DMSO-d6) δ 10.89 (s, 1H), 8.85 (s, 1H), 7.12-6.98 (m, 3H), 6.95 (dd, J=6.5, 2.7 Hz, 1H), 6.55 (ddd, J=9.0, 4.1, 2.7 Hz, 1H), 3.89 (d, J=6.3 Hz, 2H), 3.51 (t, J=6.1 Hz, 2H), 3.08 (s, 3H).

Example 34: N-(3-Chloro-4-fluorophenyl)-4-fluoro-N'-hydroxy-2-((2-morpholinoethyl)amino)-1H-benzo[d]imidazole-7-carboximidamide

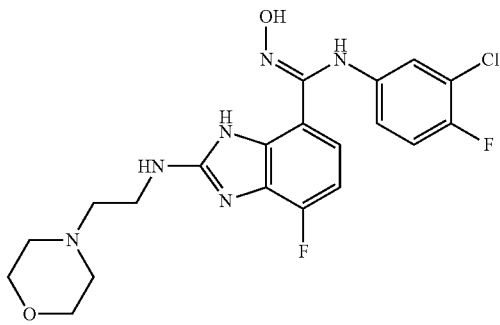 [SMILES: O/N=C(\Nc1ccc(F)c(Cl)c1)c1ccc(F)c2nc(NCCN3CCOCC3)[nH]c12]

Example 34 was made analogously to Example 33 using 4-(2-isothiocyanatoethyl)morpholine in place of 1-isothiocyanato-2-(methylsulfonyl)ethane.

Example 35: N-(3-Chloro-4-fluorophenyl)-4,5-difluoro-N'-hydroxy-2-((2-(methylsulfonyl)ethyl)amino)-1H-benzo[d]imidazole-7-carboximidamide

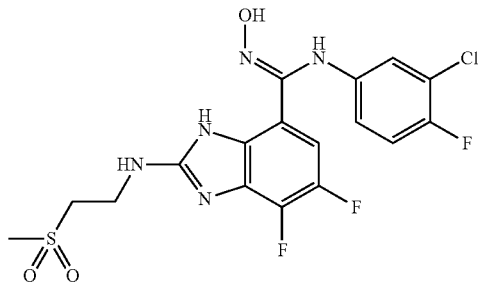 [SMILES: CS(=O)(=O)CCNc1nc2c(F)c(F)cc(/C(=N/O)Nc3ccc(F)c(Cl)c3)c2[nH]1]

Example 35 was made analogously to Example 39 using 2-(methylsulfonyl)ethanamine in place of $N^1,N^1$-dimethylpropane-1,3-diamine with an addition of triethylamine (1.2 eq) in the cyclization reaction. $C_{17}H_{15}ClF_3N_5O_3S$. 462.1/464.1 (M+1). $^1$H NMR (400 MHz, DMSO-d6) δ 10.94 (s, 1H), 8.82 (d, J=4.0 Hz, 1H), 7.65 (s, 1H), 7.10 (t, J=9.1 Hz, 1H), 7.03-6.91 (m, 2H), 6.55 (dt, J=9.0, 3.5 Hz, 1H), 3.84 (d, J=5.9 Hz, 2H), 3.48 (t, J=6.4 Hz, 2H), 3.06 (s, 3H).

Example 36: N-(3-Chloro-4-fluorophenyl)-2-((2-(4,4-difluoropiperidin-1-yl)ethyl)amino)-4,5-difluoro-N'-hydroxy-1H-benzo[d]imidazole-7-carboximidamide

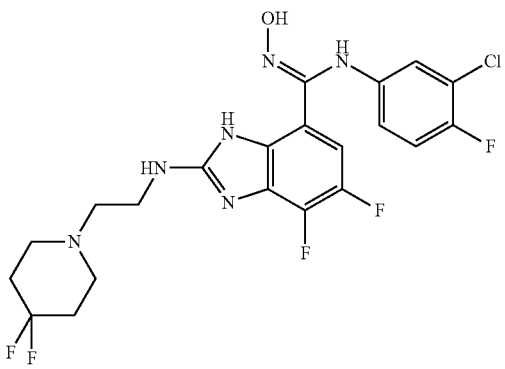 [SMILES: O/N=C(\Nc1ccc(F)c(Cl)c1)c1cc(F)c(F)c2nc(NCCN3CCC(F)(F)CC3)[nH]c12]

Example 36 was made analogously to Example 39 using 2-(4,4-difluoropiperidin-1-yl)ethanamine in place of $N^1,N^1$-dimethylpropane-1,3-diamine. $C_{21}H_{20}ClF_5N_6O$. 503.2/505/2 (M+1). $^1$H NMR (400 MHz, DMSO-d6) δ 10.81 (s, 1H), 8.71 (s, 1H), 6.94 (dd, J=6.5, 2.8 Hz, 1H), 6.87 (dd, J=12.2, 6.9 Hz, 1H), 6.76 (s, 1H), 6.59 (s, 1H), 6.53 (ddd, J=9.0, 4.1, 2.8 Hz, 1H), 3.78-3.67 (m, 2H), 3.50 (s, 4H), 3.41 (t, J=5.7 Hz, 2H), 2.34 (dt, J=13.6, 7.8 Hz, 4H).

Example 37: N-(3-Chloro-4-fluorophenyl)-4,5-difluoro-N'-hydroxy-2-((1-morpholinopropan-2-yl)amino)-1H-benzo[d]imidazole-7-carboximidamide

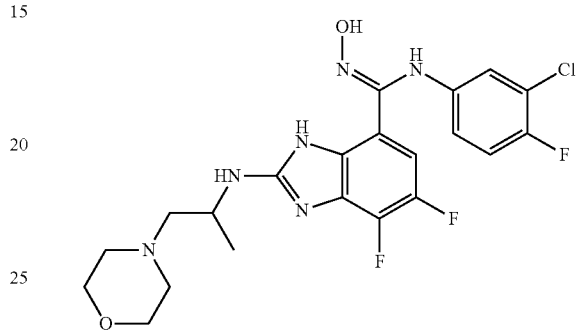

Example 37 was made analogously to Example 39 using 1-morpholinopropan-2-amine in place of $N^1,N^1$-dimethylpropane-1,3-diamine. $C_{21}H_{22}ClF_3N_6O_2$. 483.1/485.1 (M+1). $^1$H NMR (400 MHz, DMSO-d6) δ 10.82 (s, 1H), 8.69 (s, 1H), 7.14-6.97 (m, 2H), 6.93 (dd, J=6.6, 2.8 Hz, 1H), 6.87 (dd, J=12.3, 7.1 Hz, 1H), 6.58-6.49 (m, 1H), 4.41-4.26 (m, 1H), 3.85 (s, 4H), 3.49 (s, 2H), 3.32 (d, J=6.3 Hz, 4H), 1.26 (d, J=6.7 Hz, 3H).

Example 38: N-(3-Chloro-4-fluorophenyl)-4,5-difluoro-N'-hydroxy-2-(methylamino)-1H-benzo[d]imidazole-7-carboximidamide

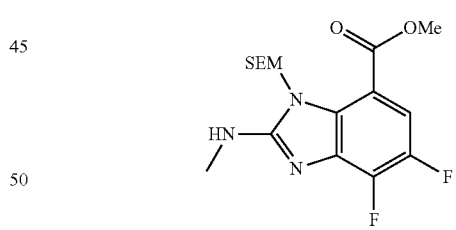

To a solution of methyl 2-chloro-4,5-difluoro-1-((2-(trimethylsilyl)ethoxy)methyl)-1H-benzo[d]imidazole-7-carboxylate (0.16 g, 0.43 mmol, 1 equiv) in DMSO (1 mL) was added a 2 M solution of methylamine in methanol (0.76 mL, 1.51 mmol, 3.5 equiv) and triethylamine (0.06 mL, 0.43 mmol, 1 equiv). The reaction was stirred at 60° C. for 2 hours before being diluted with water and extracted with EtOAc. The combined organics were dried over MgSO$_4$, filtered and concentrated in vacuo. The crude product was purified by silica gel chromatography (0-3% MeOH/CH$_2$Cl$_2$). Methyl 4,5-difluoro-2-(methylamino)-1-((2-(trimethylsilyl)ethoxy)methyl)-1H-benzo[d]imidazole-7-carboxylate was obtained as a yellow oil. $C_{16}H_{23}F_2N_3O_3Si$. 372.05 (M+1).

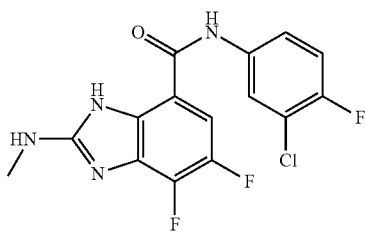 [SMILES: CNc1nc2c(F)c(F)cc(C(=O)Nc3ccc(F)c(Cl)c3)c2[nH]1]

N-(3-Chloro-4-fluorophenyl)-4,5-difluoro-2-(methylamino)-1H-benzo[d]imidazole-7-carboxamide was made analogously to Example 13 using methyl 4,5-difluoro-2-(methylamino)-1-((2-(trimethylsilyl)ethoxy)methyl)-1H-benzo[d]imidazole-7-carboxylate and 3-chloro-4-fluoroaniline in place of methyl 2-amino-4,5-difluoro-1H-benzo[d]imidazole-7-carboxylate and stirring overnight at room temperature. The crude product was purified by reverse phase HPLC (10-90% $CH_3CN/H_2O$ over 20 mins) and the TFA salt of N-(3-chloro-4-fluorophenyl)-4,5-difluoro-2-(methylamino)-1H-benzo[d]imidazole-7-carboxamide was isolated as a white solid. $C_{15}H_{10}ClF_3N_4O$. 355.06/356.98 (M+1).

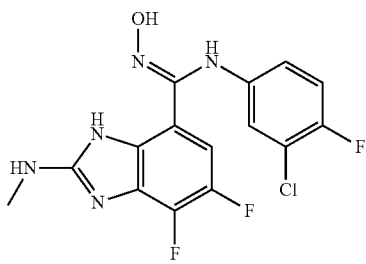 [SMILES: CNc1nc2c(F)c(F)cc(/C(=N/O)Nc3ccc(F)c(Cl)c3)c2[nH]1]

Example 38 was made analogously to Example 59 using N-(3-chloro-4-fluorophenyl)-4,5-difluoro-2-(methylamino)-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-4,5-difluoro-N'-hydroxy-2-(methylamino)-1H-benzo[d]imidazole-7-carboximidamide was isolated as a white solid. $C_{15}H_{11}ClF_3N_5O$. 370.05/371.98 (M+1). $^1$H NMR (400 MHz, DMSO-$d_6$) δ 10.94 (s, 1H), 8.79 (s, 1H), 7.08 (t, J=9.0 Hz, 1H), 7.06-7.01 (m, 1H), 6.99 (dd, J=6.6, 2.7 Hz, 1H), 6.53 (ddd, J=8.9, 4.0, 2.7 Hz, 1H), 2.98 (d, J=3.7 Hz, 3H). $^{19}$F NMR (377 MHz, DMSO-$d_6$) δ −73.7, −126.8, −147.4, −155.1 (TFA salt).

Example 39: N-(3-Chloro-4-fluorophenyl)-2-((3-(dimethylamino)propyl)amino)-4,5-difluoro-N'-hydroxy-1H-benzo[d]imidazole-7-carboximidamide

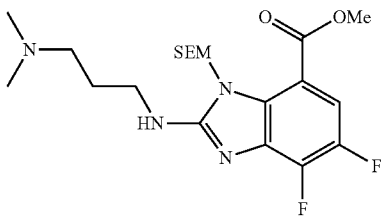 [SMILES: COC(=O)c1cc(F)c(F)c2nc(NCCCN(C)C)n(COCC[Si](C)(C)C)c12]

To a solution of methyl 2-chloro-4,5-difluoro-1-((2-(trimethylsilyl)ethoxy)methyl)-1H-benzo[d]imidazole-7-carboxylate (0.25 g, 0.66 mmol, 1 equiv) in DMSO (1.25 mL) was added N,N-dimethylpropane-1,3-diamine (0.10 mL, 0.81 mmol, 1.2 equiv). The reaction was stirred at 60° C. for 6 hours before being diluted with DMF/water and purified by reverse phase HPLC (10-90% $CH_3CN/H_2O$ over 15 mins). The TFA salt of methyl 2-((3-(dimethylamino)propyl)amino)-4,5-difluoro-1-((2-(trimethylsilyl)ethoxy)methyl)-1H-benzo[d]imidazole-7-carboxylate was obtained as a yellow oil. $C_{20}H_{32}F_2N_4O_3Si$. 443.18 (M+1).

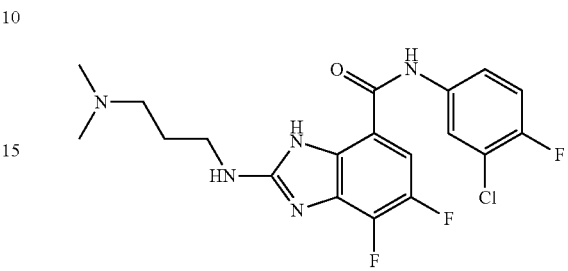

To a solution of methyl 2-((3-(dimethylamino)propyl)amino)-4,5-difluoro-1-((2-(trimethylsilyl)ethoxy)methyl)-1H-benzo[d]imidazole-7-carboxylate (TFA salt, 159 mg, 0.36 mmol, 1 equiv) and 3-chloro-4-fluoroaniline (209 mg, 1 mmol, 4 equiv) in DCE (7.5 mL) was added a 2 M solution of $AlMe_3$ in toluene (1.26 mL, 3 mmol, 7 equiv) at room temperature. The reaction was stirred overnight before quenching with 2 M aqueous NaOH and extracting with ethyl acetate. The combined organics were dried over $MgSO_4$, filtered and concentrated in vacuo. The crude product was dissolved in $CH_2Cl_2$ (2 mL) and TFA (2 mL) was added. The SEM-deprotection was stirred overnight before being concentrated in vacuo. The crude product was purified by reverse phase HPLC (10-90% $CH_3CN/H_2O$ over 15 mins). The TFA salt of N-(3-chloro-4-fluorophenyl)-2-((3-(dimethylamino)propyl)amino)-4,5-difluoro-1H-benzo[d]-imidazole-7-carboxamide was obtained as an off-white solid. $C_{19}H_{19}ClF_3N_5O$. 426.18/428.13 (M+1).

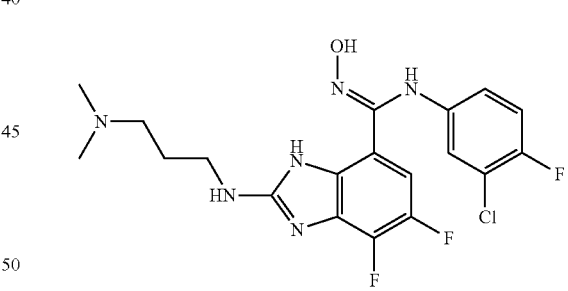

Example 39 was made analogously to Example 59 using N-(3-chloro-4-fluorophenyl)-2-((3-(dimethylamino)propyl)amino)-4,5-difluoro-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-2-((3-(dimethylamino)propyl)amino)-4,5-difluoro-N'-hydroxy-1H-benzo[d]imidazole-7-carboximidamide was isolated as a white solid. $C_{19}H_{20}ClF_3N_6O$. 441.12/443.09 (M+1). $^1$H NMR (400 MHz, DMSO-$d_6$) δ 10.85 (s, 1H), 9.72 (s, 1H), 8.74 (s, 1H), 7.09 (t, J=9.1 Hz, 1H), 7.00-6.85 (m, 2H), 6.55 (ddd, J=9.0, 4.1, 2.7 Hz, 1H), 3.42 (m, 2H), 3.10 (m, 2H), 2.80 (s, 6H), 1.93 (m, 2H). $^{19}$F NMR (377 MHz, DMSO-$d_6$) δ −73.7, −127.1, −149.4, −156.5.

Example 40: N-(3-Chloro-4-fluorophenyl)-4,5-difluoro-N'-hydroxy-2-((2-methoxyethyl)amino)-1H-benzo[d]imidazole-7-carboximidamide

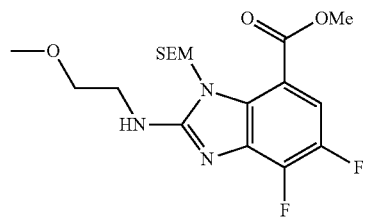 [SMILES: COCCNc1nc2c(F)c(F)cc(C(=O)OC)c2n1COCC[Si](C)(C)C]

Methyl 4,5-difluoro-2-((2-methoxyethyl)amino)-1-((2-(trimethylsilyl)ethoxy)methyl)-1H-benzo[d]imidazole-7-carboxylate was made analogously to Example 39 using 2-methoxyethanamine and triethylamine (1 equiv) in place of N,N-dimethylpropane-1,3-diamine. The TFA salt of methyl 4,5-difluoro-2-((2-methoxyethyl)amino)-1-((2-(trimethylsilyl)ethoxy)methyl)-1H-benzo[d]imidazole-7-carboxylate was isolated as a yellow oil. $C_{18}H_{27}F_2N_3O_4Si$. 416.09/417.07 (M+1).

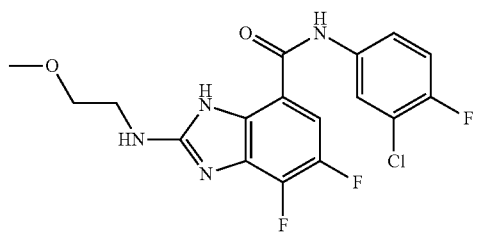 [SMILES: COCCNc1nc2c(F)c(F)cc(C(=O)Nc3ccc(F)c(Cl)c3)c2[nH]1]

N-(3-chloro-4-fluorophenyl)-4,5-difluoro-2-((2-methoxyethyl)amino)-1H-benzo[d]imidazole-7-carboxamide was made analogously to Example 39 using methyl 4,5-difluoro-2-((2-methoxyethyl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-((2-methoxyethyl)amino)-1H-benzo[d]imidazole-7-carboxamide was isolated as a white solid. $C_{17}H_{14}ClF_3N_4O_2$. 399.09/401.02 (M+1).

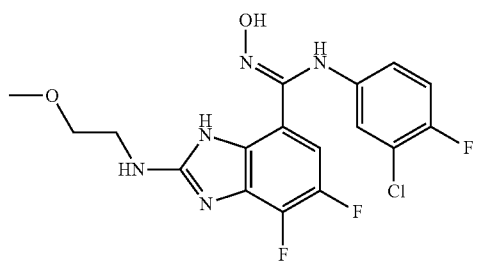 [SMILES: COCCNc1nc2c(F)c(F)cc(/C(=N/O)Nc3ccc(F)c(Cl)c3)c2[nH]1]

Example 40 was made analogously to Example 59 using N-(3-chloro-4-fluorophenyl)-4,5-difluoro-2-((2-methoxyethyl)amino)-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-4,5-difluoro-N'-hydroxy-2-((2-methoxyethyl)amino)-1H-benzo[d]imidazole-7-carboximidamide was isolated as a white solid. $C_{17}H_{15}ClF_3N_5O_2$. 414.09/416.01 (M+1). $^1$H NMR (400 MHz, DMSO-d$_6$) δ 10.98 (s, 1H), 8.79 (s, 1H), 8.11 (s, 1H), 7.09 (t, J=9.1 Hz, 1H), 7.04 (dd, J=12.1, 7.0 Hz, 1H), 6.99 (dd, J=6.6, 2.7 Hz, 1H), 6.55 (ddd, J=8.9, 4.0, 2.7 Hz, 1H), 3.56 (t, J=5.1 Hz, 2H), 3.51 (t, J=4.7 Hz, 2H), 3.29 (s, 3H). $^{19}$F NMR (377 MHz, DMSO-d$_6$) δ −75.18 (6F), −126.96 (1F), −147.44 (1F), −155.18 (1F).

Example 41: N-(3-Chloro-4-fluorophenyl)-4,5-difluoro-N'-hydroxy-2-((2-(pyrrolidin-1-yl)ethyl)amino)-1H-benzo[d]imidazole-7-carboximidamide

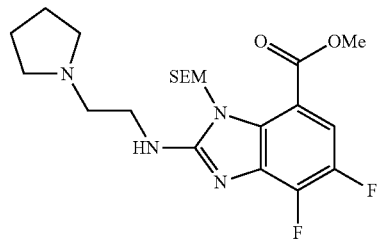 [SMILES: COC(=O)c1cc(F)c(F)c2nc(NCCN3CCCC3)n(COCC[Si](C)(C)C)c12]

Methyl 4,5-difluoro-2-((2-(pyrrolidin-1-yl)ethyl)amino)-1-((2-(trimethylsilyl)ethoxy)methyl)-1H-benzo[d]imidazole-7-carboxylate was made analogously to Example 39 using 2-(pyrrolidin-1-yl)ethanamine in place of N,N-dimethylpropane-1,3-diamine. The TFA salt of methyl 4,5-difluoro-2-((2-(pyrrolidin-1-yl)ethyl)amino)-1-((2-(trimethylsilyl)ethoxy)methyl)-1H-benzo[d]imidazole-7-carboxylate was isolated as a yellow oil. $C_{21}H_{32}F_2N_4O_3Si$. 455.21 (M+1).

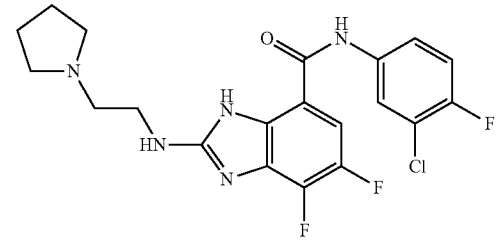 [SMILES: O=C(Nc1ccc(F)c(Cl)c1)c1cc(F)c(F)c2nc(NCCN3CCCC3)[nH]c12]

N-(3-Chloro-4-fluorophenyl)-4,5-difluoro-2-((2-(pyrrolidin-1-yl)ethyl)amino)-1H-benzo[d]imidazole-7-carboxamide was made analogously to Example 39 using methyl 4,5-difluoro-2-((2-(pyrrolidin-1-yl)ethyl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-((2-(pyrrolidin-1-yl)ethyl)amino)-1H-benzo[d]imidazole-7-carboxamide was isolated as a white solid. $C_{20}H_{19}ClF_3N_5O$. 438.21/440.12 (M+1).

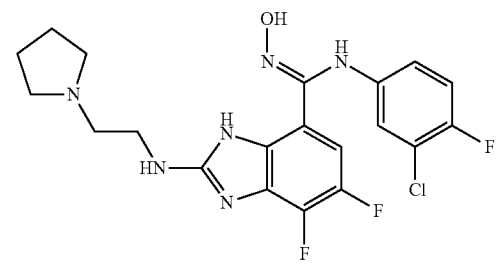 [SMILES: O/N=C(\Nc1ccc(F)c(Cl)c1)c1cc(F)c(F)c2nc(NCCN3CCCC3)[nH]c12]

Example 41 was made analogously to Example 59 using N-(3-chloro-4-fluorophenyl)-4,5-difluoro-2-((2-(pyrrolidin-1-yl)ethyl)amino)-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-4,5-difluoro-N'-hydroxy-2-((2-(pyrrolidin-1-yl)ethyl)amino)-1H-benzo[d]imidazole-7-carboximidamide was isolated as a white solid. $C_{20}H_{20}ClF_3N_6O$. 453.14/455.11 (M+1). $^1$H NMR (400 MHz, DMSO-$d_6$) δ 10.78 (s, 1H), 9.84 (s, 1H), 8.70 (s, 1H), 7.09 (t, J=9.1 Hz, 1H), 7.02 (s, 1H), 6.93 (dd, J=6.6, 2.7 Hz, 1H), 6.84 (dd, J=12.3, 6.9 Hz, 1H), 6.53 (ddd, J=9.0, 4.0, 2.7 Hz, 1H), 4.00 (dq, J=8.3, 7.1 Hz, 1H), 3.75-3.60 (m, 3H), 3.45-3.35 (m, 3H), 2.05-1.80 (m, 4H), 1.24 (td, J=7.0, 0.9 Hz, 1H). $^{19}$F NMR (377 MHz, DMSO-$d_6$) δ −74.94 (9F), −127.34 (1F), −150.32 (1F), −157.02 (1F).

Example 42: N-(3-Chloro-4-fluorophenyl)-2-((2-(diethylamino)ethyl)amino)-4,5-difluoro-N'-hydroxy-1H-benzo[d]imidazole-7-carboximidamide

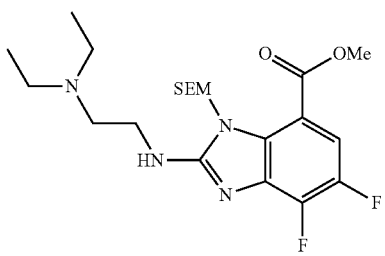 [SMILES: CCN(CC)CCNc1nc2c(F)c(F)cc(C(=O)OC)c2n1COCC[Si](C)(C)C]

Methyl 2-((2-(diethylamino)ethyl)amino)-4,5-difluoro-1-((2-(trimethylsilyl)ethoxy)methyl)-1H-benzo[d]imidazole-7-carboxylate was made analogously to Example 39 using N,N-diethylethane-1,2-diamine in place of N,N-dimethylpropane-1,3-diamine. The TFA salt of methyl 2-((2-(diethylamino)ethyl)amino)-4,5-difluoro-1-((2-(trimethylsilyl)ethoxy)methyl)-1H-benzo[d]imidazole-7-carboxylate was isolated as a yellow oil. $C_{21}H_{34}F_2N_4O_3Si$. 457.22 (M+1).

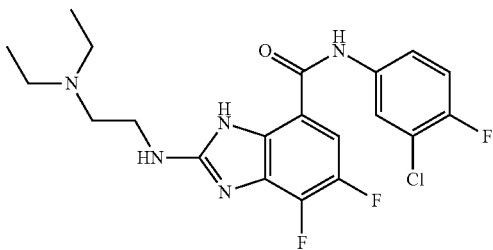 [SMILES: CCN(CC)CCNc1nc2c(F)c(F)cc(C(=O)Nc3ccc(F)c(Cl)c3)c2[nH]1]

N-(3-chloro-4-fluorophenyl)-2-((2-(diethylamino)ethyl)amino)-4,5-difluoro-1H-benzo[d]imidazole-7-carboxamide was made analogously to Example 39 using methyl 2-((2-(diethylamino)ethyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-((2-(diethylamino)ethyl)amino)-4,5-difluoro-1H-benzo[d]imidazole-7-carboxamide was isolated as a white solid. $C_{20}H_{21}ClF_3N_5O$. 440.21/442/11 (M+1).

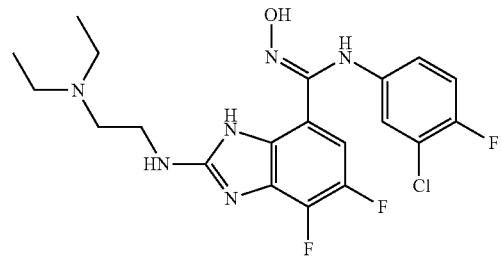 [SMILES: CCN(CC)CCNc1nc2c(F)c(F)cc(/C(=N/O)Nc3ccc(F)c(Cl)c3)c2[nH]1]

Example 42 was made analogously to Example 59 using N-(3-chloro-4-fluorophenyl)-2-((2-(diethylamino)ethyl)amino)-4,5-difluoro-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-2-((2-(diethylamino)ethyl)amino)-4,5-difluoro-N'-hydroxy-1H-benzo[d]imidazole-7-carboximidamide was isolated as a white solid. $C_{20}H_{22}ClF_3N_6O$. 455.18/457.11 (M+1). $^1$H NMR (400 MHz, DMSO-$d_6$) δ 10.77 (s, 1H), 9.73 (s, 1H), 8.70 (s, 1H), 7.08 (t, J=9.1 Hz, 1H), 6.97 (s, 1H), 6.92 (dd, J=6.5, 2.7 Hz, 1H), 6.85 (dd, J=12.2, 6.9 Hz, 1H), 6.53 (ddd, J=9.0, 4.0, 2.7 Hz, 1H), 3.68 (m, 2H), 3.31 (m, 2H), 3.26-3.13 (m, 4H), 1.20 (t, J=7.2 Hz, 6H). $^{19}$F NMR (376 MHz, DMSO-$d_6$) δ −74.9, −127.3, −150.3, −157.1.

Example 43: N-(3-Chloro-4-fluorophenyl)-2-((2-(dimethylamino)ethyl)amino)-4,5-difluoro-N'-hydroxy-1H-benzo[d]imidazole-7-carboximidamide

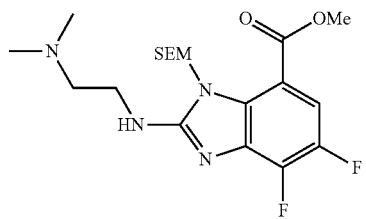 [SMILES: COC(=O)c1cc(F)c(F)c2nc(NCCN(C)C)n(COCC[Si](C)(C)C)c12]

Methyl 2-((2-(dimethylamino)ethyl)amino)-4,5-difluoro-1-((2-(trimethylsilyl)ethoxy)methyl)-1H-benzo[d]imidazole-7-carboxylate was made analogously to Example 39 using N,N-dimethylethane-1,2-diamine in place of N,N-dimethylpropane-1,3-diamine. The TFA salt of methyl 2-((2-(dimethylamino)ethyl)amino)-4,5-difluoro-1-((2-(trimethylsilyl)ethoxy)methyl)-1H-benzo[d]imidazole-7-carboxylate was isolated as a yellow oil. $C_{19}H_{30}F_2N_4O_3Si$. 429.17 (M+1).

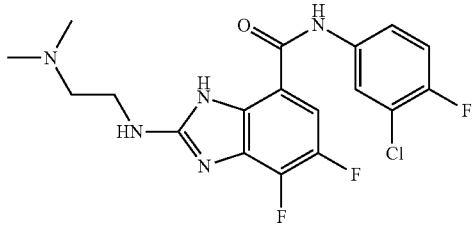 [SMILES: CN(C)CCNc1nc2c(F)c(F)cc(C(=O)Nc3ccc(F)c(Cl)c3)c2[nH]1]

N-(3-Chloro-4-fluorophenyl)-2-((2-(dimethylamino)ethyl)amino)-4,5-difluoro-1H-benzo[d]imidazole-7-carboxamide was made analogously to Example 39 using methyl 2-((2-(dimethylamino)ethyl)amino)-4,5-difluoro-1-((2-(trimethylsilyl)ethoxy)methyl)-1H-benzo[d]imidazole-7- carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-((2-(dimethylamino)ethyl)amino)-4,5-difluoro-1H-benzo[d]imidazole-7-carboxamide was isolated as a white solid. $C_{18}H_{17}ClF_3N_5O$. 412.19/414.09 (M+1).

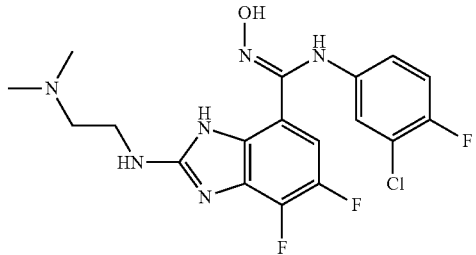 [SMILES: CN(C)CCNc1nc2c(F)c(F)cc(/C(=N/O)Nc3ccc(F)c(Cl)c3)c2[nH]1]

Example 43 was made analogously to Example 59 using N-(3-chloro-4-fluorophenyl)-2-((2-(dimethylamino)ethyl)amino)-4,5-difluoro-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-2-((2-(dimethylamino)ethyl)amino)-4,5-difluoro-N'-hydroxy-1H-benzo[d]imidazole-7-carboximidamide was isolated as a white solid. $C_{18}H_{18}ClF_3N_6O$. 427.14/429.09 (M+1). $^1$H NMR (400 MHz, DMSO-$d_6$) δ 10.78 (s, 1H), 9.74 (s, 1H), 8.71 (s, 1H), 7.09 (t, J=10.7 Hz, 1H), 7.04 (br s, 1H), 6.93 (dd, J=6.5, 2.7 Hz, 1H), 6.84 (dd, J=12.2, 7.0 Hz, 1H), 6.53 (ddd, J=9.0, 4.0, 2.7 Hz, 1H), 3.69 (q, J=5.9 Hz, 2H), 3.31 (t, J=5.8 Hz, 2H), 2.86 (s, 6H). $^{19}$F NMR (376 MHz, DMSO-$d_6$) δ −74.99 (9F), −127.32 (1F), −150.28 (1F), −156.83 (1F).

Example 44: N-(3-Chlorophenyl)-4,5-difluoro-N'-hydroxy-2-(1-methylpiperidin-3-yl)-1H-benzo[d]imidazole-7-carboximidamide

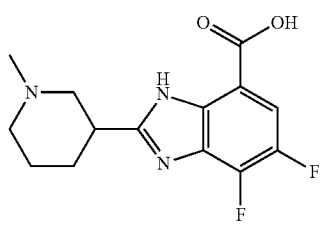 [SMILES: CN1CCCC(c2nc3c(F)c(F)cc(C(=O)O)c3[nH]2)C1]

Example 44 was made analogously to Example 53 using 1-methylpiperidine-3-carboxylic acid in place of 3-(dimethylamino)propanoic acid. The TFA salt of 4,5-difluoro-2-(1-methylpiperidin-3-yl)-1H-benzo[d]imidazole-7-carboxylic acid was isolated as a colorless oil. $C_{14}H_{15}F_2N_3O_2$. 296.14/297.12 (M+1).

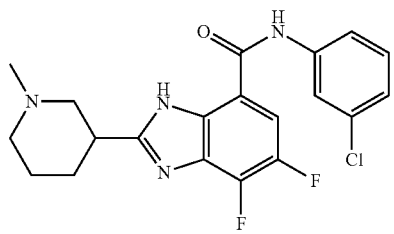 [SMILES: CN1CCCC(c2nc3c(F)c(F)cc(C(=O)Nc4cccc(Cl)c4)c3[nH]2)C1]

To a solution of 4,5-difluoro-2-(1-methylpiperidin-3-yl)-1H-benzo[d]imidazole-7-carboxylic acid (TFA salt, 63 mg, 0.19 mmol, 1 equiv), 3-chloroaniline (0.05 mL, 0.48 mmol, 2.5 equiv), and DIPEA (0.16 mL, 0.95 mmol, 5 equiv) in DMF (1 mL) was added HATU (87 mg, 0.23 mmol, 1.2 equiv) and the reaction was stirred overnight at room temperature. The crude product was purified by reverse phase HPLC (10-90% $CH_3CN/H_2O$) and the TFA salt of N-(3-chlorophenyl)-4,5-difluoro-2-(1-methylpiperidin-3-yl)-1H-benzo[d]imidazole-7-carboxamide was obtained as a white solid. $C_{20}H_{19}ClF_2N_4O$. 405.19/407.12 (M+1).

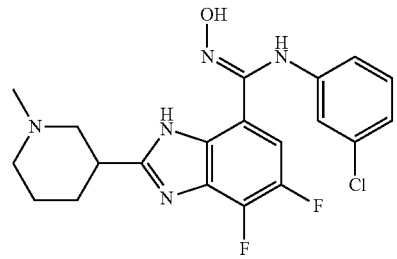 [SMILES: CN1CCCC(c2nc3c(F)c(F)cc(/C(=N/O)Nc4cccc(Cl)c4)c3[nH]2)C1]

Example 44 was made analogously to Example 59 using N-(3-chloro-4-fluorophenyl)-4,5-difluoro-2-(1-methylpiperidin-3-yl)-1H-benzo[d]imidazole-7-carboxamide in place of N-(3-chloro-4-fluorophenyl)-1H-imidazo[4,5-b]pyridine-7-carboxamide. The TFA salt of N-(3-chlorophenyl)-4,5-difluoro-N'-hydroxy-2-(1-methylpiperidin-3-yl)-1H-benzo[d]imidazole-7-carboximidamide was isolated as a white solid. $C_{20}H_{20}ClF_2N_5O$. 420.22/422.17 (M+1).

Example 45: N-(3-Chloro-4-fluorophenyl)-6,7-difluoro-N'-hydroxy-2-(((3-methoxypropyl)amino)methyl)-1H-benzo[d]imidazole-4-carboximidamide

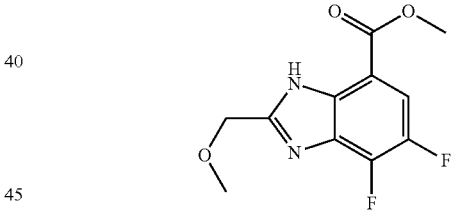

Methyl 4,5-difluoro-2-(methoxymethyl)-1H-benzo[d]imidazole-7-carboxylate. A mixture of methyl 2,3-diamino-4,5-difluorobenzoate (2.0 g, 9.9 mmol) in methoxyacetic acid (23 mL) was stirred at 120° C. for 3 hr. To the mixture was added saturated sodium bicarbonate and the aqueous layer was washed three times with ethyl acetate. The combined organic layers were dried over sodium sulfate, filtered, absorbed onto silica and purified by silica gel chromatography to give the desired product. $C_{11}H_{10}F_2N_2O_3$. 257.3 (M+1).

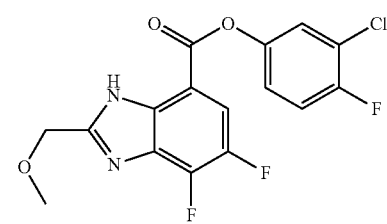 [SMILES: COCc1nc2c(F)c(F)cc(C(=O)Oc3ccc(F)c(Cl)c3)c2[nH]1]

N-(3-chloro-4-fluorophenyl)-4,5-difluoro-2-(methoxymethyl)-1H-benzo[d]imidazole-7-carboxamide. To a solution of the 3-chloro-4-fluoroaniline in (1.30 g, 8.90 mmol) in dichloroethane (60 mL) at 0° C. under nitrogen was added trimethylaluminum (2 M in heptane, 8.90 mL, 17.8 mmol) dropwise over 5 min. The solution was allowed to warm to room temperature and stirred for 30 min. The solution was cooled to 0° C. and to this solution was added methyl 4,5-difluoro-2-(methoxymethyl)-1H-benzo[d]imidazole-7-carboxylate (1.52 g, 5.93 mmol). The solution was stirred at 85° C. for 3 hr and, then, cooled to room temperature. Water and 10% citric acid were added and the resulting precipitate was filtered and dried on high vac to give the desired product. $C_{16}H_{11}ClF_3N_3O_2$. 370.1 (M+1).

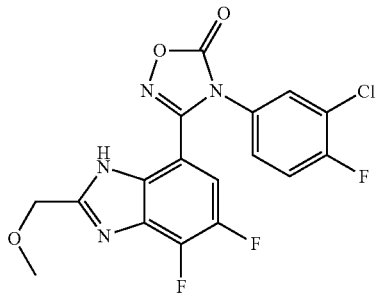 [SMILES: COCc1nc2c(F)c(F)cc(-c3noc(=O)n3-c3ccc(F)c(Cl)c3)c2[nH]1]

4-(3-chloro-4-fluorophenyl)-3-(4,5-difluoro-2-(methoxymethyl)-1H-benzo[d]imidazol-7-yl)-1,2,4-oxadiazol-5(4H)-one. A mixture of N-(3-chloro-4-fluorophenyl)-4,5-difluoro-2-(methoxymethyl)-1H-benzo[d]imidazole-7-carboxamide (1.80 g, 4.86 mmol), phosphorous pentachloride (1.52 g, 7.29 mmol) in phosphoryl chloride (14 mL) and 1,2-dichloroethane (14 mL) was stirred at 80° C. for 2.5 hr. The reaction mixture was concentrated and suspended in ethanol (14 mL) and to this mixture was added 50% hydroxylamine in water (3.0 mL, 49 mmol). The reaction mixture stirred for 1.5 hr. Water was added to the reaction mixture and the resulting precipitate was collected by filtration and dried on high vac. The dried solid and carbonyl diimidazole (1.6 g, 9.7 mmol) was suspended in ethyl acetate (50 mL) and the reaction mixture stirred for 18 hr. The resulting solution was absorbed onto silica gel and purified by silica gel chromatography to give the desired product. $C_{17}H_{10}ClF_3N_4O_3$. 411.0 (M+1).

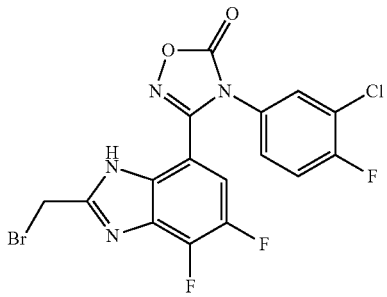

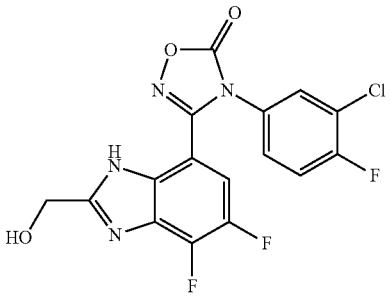

3-(2-(bromomethyl)-4,5-difluoro-1H-benzo[d]imidazol-7-yl)-4-(3-chloro-4-fluorophenyl)-1,2,4-oxadiazol-5(4H)-one and 4-(3-chloro-4-fluorophenyl)-3-(4,5-difluoro-2-(hydroxymethyl)-1H-benzo[d]imidazol-7-yl)-1,2,4-oxadiazol-5(4H)-one. To a mixture of 4-(3-chloro-4-fluorophenyl)-3-(4,5-difluoro-2-(methoxymethyl)-1H-benzo[d]imidazol-7-yl)-1,2,4-oxadiazol-5(4H)-one (937 mg, 2.28 mmol) in dichloromethane (16 mL) at 0° C. was added a solution of 1 M boron tribromide in dichloromethane (3.42 mL, 3.42 mmol). The reaction was allowed to warm to room temperature and stirred for 18 hr. The reaction mixture was diluted with dichloromethane and saturated sodium bicarbonate and the aqueous layer was washed three times with dichlormethane. The combined organic layers contained a precipitate that was filtered off to give 4-(3-chloro-4-fluorophenyl)-3-(4,5-difluoro-2-(hydroxymethyl)-1H-benzo[d]imidazol-7-yl)-1,2,4-oxadiazol-5(4H)-one (203 mg) as a white solid. The filtrate was dried over sodium sulfate, filtered, loaded onto silica gel column and purified by silica gel chromatography to give 3-(2-(bromomethyl)-4,5-difluoro-1H-benzo[d]imidazol-7-yl)-4-(3-chloro-4-fluorophenyl)-1,2,4-oxadiazol-5(4H)-one. $C_{16}H_7BrClF_3N_4O_2$. 459.0 (M+1). $C_{16}H_8ClF_3N_4O_3$. 397.1 (M+1).

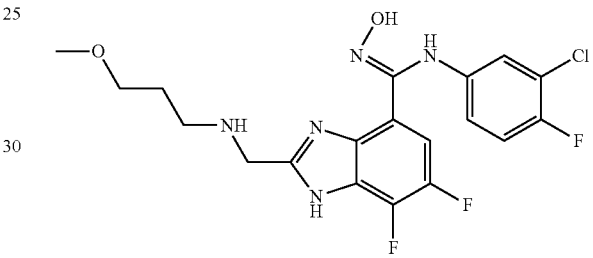

N-(3-chloro-4-fluorophenyl)-6,7-difluoro-N'-hydroxy-2-(((3-methoxypropyl)amino)methyl)-1H-benzo[d]imidazole-4-carboximidamide. A solution of 3-(2-(bromomethyl)-4,5-difluoro-1H-benzo[d]imidazol-7-yl)-4-(3-chloro-4-fluorophenyl)-1,2,4-oxadiazol-5(4H)-one (12 mg, 0.026 mmol) and 3-methoxypropylamine (0.027 mL, 0.26 mmol) in acetonitrile (1 mL) was stirred at 65° C. for 10 min. The reaction was concentrated. The residue was brought up in tetrahydrofuran (0.3 mL) and water (0.3 mL). To this solution was added 2 N sodium hydroxide (0.19 mL, 0.34 mmol) and the reaction mixture stirred for 10 min. To the mixture was added acetic acid (0.05 mL) and the solution was loaded directly onto a prep HPLC for purification to give the desired product. $C_{19}H_{19}ClF_3N_5O_2$. 442.1 (M+1).

Example 46: N-(3-Chloro-4-fluorophenyl)-4,5-difluoro-N'-hydroxy-2-(hydroxymethyl)-1H-benzo[d]imidazole-7-carboximidamide

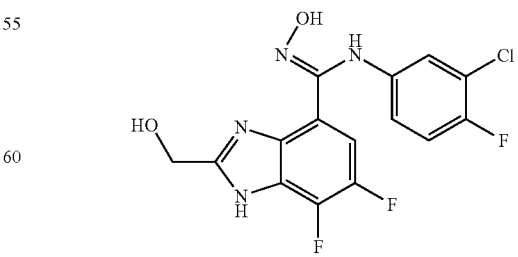

To a solution of 4-(3-chloro-4-fluorophenyl)-3-(4,5-difluoro-2-(hydroxymethyl)-1H-benzo[d]imidazol-7-yl)-1,2,4-oxadiazol-5(4H)-one (20 mg, 0.050 mmol) in tetrahydrofuran (0.4 mL) and water (0.4 mL) was added 2 N sodium hydroxide (0.38 mL, 0.76 mmol) and the reaction mixture stirred for 10 min. To the mixture was added acetic acid (0.06 mL) and the solution was loaded directly onto a prep HPLC for purification to give the desired product. $C_{15}H_{10}ClF_3N_4O_2$. 371.0 (M+1). $^1$H NMR (400 MHz, DMSO-$d_6$) δ 10.93 (s, 1H), 8.80 (s, 1H), 7.16 (dd, J=12.0, 7.0 Hz, 1H), 7.04 (t, J=9.1 Hz, 1H), 6.93 (dd, J=6.5, 2.7 Hz, 1H), 6.49 (ddd, J=9.0, 4.1, 2.7 Hz, 1H), 4.63 (s, 2H).

Example 47: 2-(Aminomethyl)-N-(3-chloro-4-fluorophenyl)-4,5-difluoro-N'-hydroxy-1H-benzo[d]imidazole-7-carboximidamide

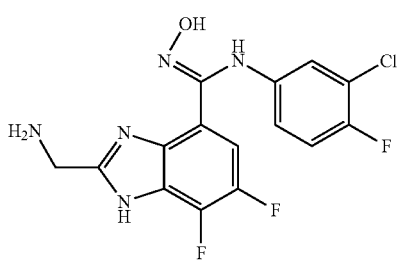 [SMILES: NCc1nc2c(/C(=N/O)Nc3ccc(F)c(Cl)c3)cc(F)c(F)c2[nH]1]

Example 47 was made analogously to Example 45 using 0.5 M ammonia in dioxane in place of 3-methoxypropylamine. $C_{15}H_{11}ClF_3N_5O$. 370.1 (M+1).

Example 48: N-(3-Chloro-4-fluorophenyl)-4,5-difluoro-N'-hydroxy-2-((methylamino)methyl)-1H-benzo[d]imidazole-7-carboximidamide

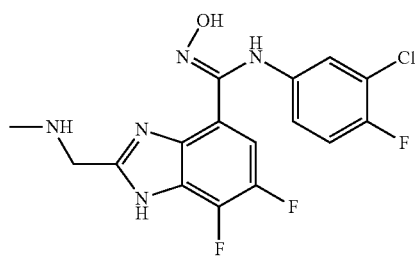 [SMILES: CNCc1nc2c(/C(=N/O)Nc3ccc(F)c(Cl)c3)cc(F)c(F)c2[nH]1]

Example 48 was made analogously to Example 45 using 2 M methylamine in tetrahydrofuran in place of 3-methoxypropylamine. $C_{16}H_{13}ClF_3N_5O$. 384.0 (M+1). $^1$H NMR (400 MHz, DMSO-$d_6$) δ 12.84 (s, 1H), 10.92 (s, 1H), 9.21 (s, 2H), 8.82 (s, 1H), 7.34-7.17 (m, 1H), 7.04 (t, J=9.1 Hz, 1H), 6.90 (dd, J=6.6, 2.7 Hz, 1H), 6.48 (dt, J=9.0, 3.5 Hz, 1H), 4.40 (t, J=5.8 Hz, 2H), 2.65 (s, 3H).

Example 49: N-(3-Chloro-4-fluorophenyl)-2-(((cyclopropylmethyl)amino)methyl)-4,5-difluoro-N'-hydroxy-1H-benzo[d]imidazole-7-carboximidamide

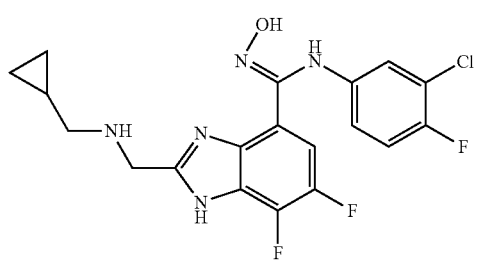 [SMILES: O/N=C(\Nc1ccc(F)c(Cl)c1)c1cc(F)c(F)c2[nH]c(CNCC3CC3)nc12]

Example 49 was made analogously to Example 45 using cyclopropylmethylamine in place of 3-methoxypropylamine. $C_{19}H_{17}ClF_3N_5O$. 424.0 (M+1).

Example 50: N-(3-Chloro-4-fluorophenyl)-2-((ethylamino)methyl)-6,7-difluoro-N'-hydroxy-1H-benzo[d]imidazole-4-carboximidamide

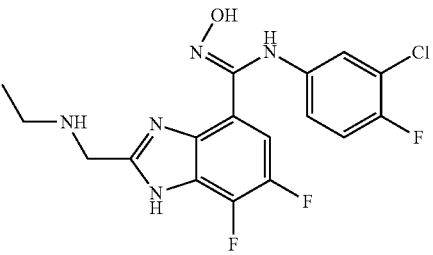 [SMILES: CCNCc1nc2c(/C(=N/O)Nc3ccc(F)c(Cl)c3)cc(F)c(F)c2[nH]1]

Example 50 was made analogously to Example 45 using 2 M ethylamine in tetrahydrofuran in place of 3-methoxypropylamine. $C_{17}H_{15}ClF_3N_5O$. 398.0 (M+1). $^1$H NMR (400 MHz, DMSO-$d_6$) δ 12.85 (s, 1H), 10.92 (s, 1H), 9.25 (s, 2H), 8.82 (s, 1H), 7.33-7.20 (m, 1H), 7.05 (t, J=9.0 Hz, 1H), 6.91 (dd, J=6.5, 2.7 Hz, 1H), 6.50 (dt, J=9.0, 3.6 Hz, 1H), 4.43 (t, J=5.9 Hz, 2H), 3.11-2.95 (m, 2H), 1.21 (t, J=7.2 Hz, 3H).

Example 51: N-(3-Chloro-4-fluorophenyl)-6,7-difluoro-N'-hydroxy-2-((isopropylamino)methyl)-1H-benzo[d]imidazole-4-carboximidamide

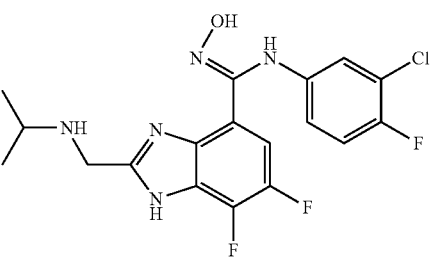 [SMILES: CC(C)NCc1nc2c(/C(=N/O)Nc3ccc(F)c(Cl)c3)cc(F)c(F)c2[nH]1]

Example 51 was made analogously to Example using isopropylamine in place of 3-methoxypropylamine. $C_{18}H_{17}ClF_3N_5O$. 412.1 (M+1). $^1$H NMR (400 MHz, DMSO-$d_6$) δ 12.85 (s, 1H), 10.94 (s, 1H), 9.25 (s, 2H), 8.82 (s, 1H), 7.33-7.20 (m, 1H), 7.06 (t, J=9.0 Hz, 1H), 6.90 (dd, J=6.5, 2.7 Hz, 1H), 6.50 (dt, J=9.1, 3.5 Hz, 1H), 4.49-4.37 (m, 2H), 3.48-3.33 (m, 1H), 1.26 (d, J=6.5 Hz, 6H).

Example 52: N-(3-Chloro-4-fluorophenyl)-2-((dimethylamino)methyl)-6,7-difluoro-N'-hydroxy-4H-benzo[d]imidazole-4-carboximidamide

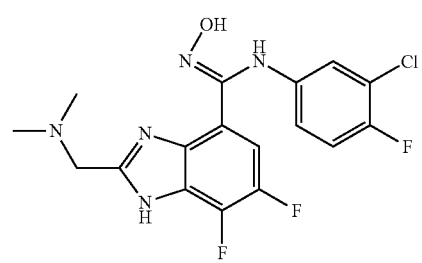 [SMILES: CN(C)Cc1nc2c(/C(=N/O)Nc3ccc(F)c(Cl)c3)cc(F)c(F)c2[nH]1]

Example 52 was made analogously to Example 45 using dimethylamine in place of 3-methoxypropylamine. $C_{17}H_{15}ClF_3N_5O$. 398.1 (M+1). $^1$H NMR (400 MHz, DMSO-d$_6$) δ12.93 (s, 1H), 10.93 (s, 1H), 10.28 (s, 1H), 8.83 (s, 1H), 7.40-7.23 (m, 1H), 7.03 (t, J=9.1 Hz, 1H), 6.95 (dd, J=6.6, 2.7 Hz, 1H), 6.49 (dt, J=9.0, 3.5 Hz, 1H), 4.56 (s, 2H), 2.83 (s, 6H).

Example 53: N-(3-Chloro-4-fluorophenyl)-2-(2-(dimethylamino)ethyl)-6,7-difluoro-N'-hydroxy-1H-benzo[d]imidazole-4-carboximidamide

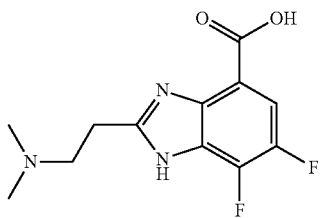 [SMILES: CN(C)CCc1nc2c(C(=O)O)cc(F)c(F)c2[nH]1]

2-(2-(dimethylamino)ethyl)-6,7-difluoro-1H-benzo[d]imidazole-4-carboxylic acid. A mixture of methyl 2,3-diamino-4,5-difluorobenzoate (2.0 g, 9.89 mmol) and 3-(dimethylamino)propanoic acid (6.08 g, 39.6 mmol) in concentrated hydrochloric acid was stirred at 120° C. overnight in a sealed screw-top flask. The reaction was concentrated under reduced pressure. Cured product was used as is in next step without purification. $C_{12}H_{13}F_2N_3O_2$. 270.10 (M+1).

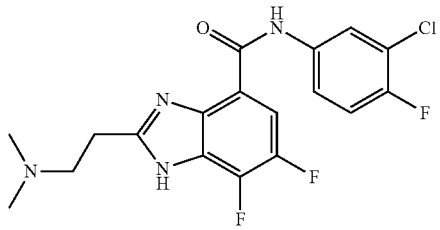 [SMILES: CN(C)CCc1nc2c(C(=O)Nc3ccc(F)c(Cl)c3)cc(F)c(F)c2[nH]1]

N-(3-chloro-4-fluorophenyl)-2-(2-(dimethylamino)ethyl)-6,7-difluoro-1H-benzo[d]imidazole-4-carboxamide. A mixture of 2-(2-(dimethylamino)ethyl)-6,7-difluoro-1H-benzo[d]imidazole-4-carboxylic acid (300 mg, 1.114 mmol), 3-chloro-4-fluoroaniline (300 mg, 1.114 mmol), bis(2-oxo-3-oxazolidinyl)phosphinic chloride (567 mg, 2.23 mmol) and diisopropylethylamine (1.94 mL, 11.1 mmol) in dichloromethane (8 mL) was stirred for 2 hr. The reaction mixture was filtered and absorbed onto silica gel and purified by silica gel chromatography to give the desired product. $C_{18}H_{16}ClF_3N_4O$.

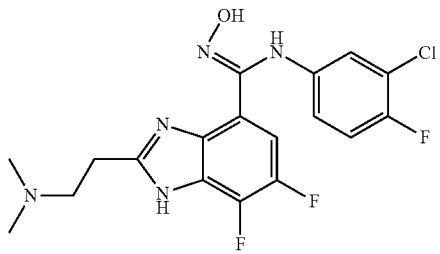 [SMILES: CN(C)CCc1nc2c(/C(=N/O)Nc3ccc(F)c(Cl)c3)cc(F)c(F)c2[nH]1]

N-(3-chloro-4-fluorophenyl)-2-(2-(dimethylamino)ethyl)-6,7-difluoro-N'-hydroxy-1H-benzo[d]imidazole-4-carboximidamide. Example 53 was made analogously to Example 95 $C_{18}H_{17}ClF_3N_5O$. 411.11 (M+1). $^1$H NMR (400 MHz, DMSO-d$_6$) δ 10.92 (s, 1H), 8.78 (s, 1H), 7.17 (dd, J=12.0, 7.0 Hz, 1H), 7.04 (t, J=9.1 Hz, 1H), 6.93 (dd, J=6.6, 2.7 Hz, 1H), 6.50 (ddd, J=9.0, 4.1, 2.7 Hz, 1H), 3.53 (t, J=7.5 Hz, 2H), 3.26 (t, J=7.6 Hz, 2H), 2.83 (s, 6H)

Example 54: N-(3-Bromo-4-fluorophenyl)-2-(2-(dimethylamino)ethyl)-6,7-difluoro-N'-hydroxy-1H-benzo[d]imidazole-4-carboximidamide

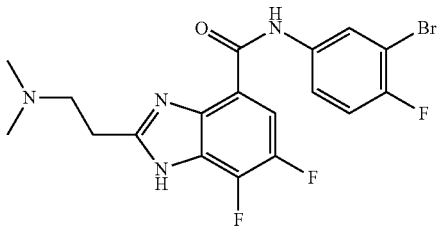 [SMILES: CN(C)CCc1nc2c(C(=O)Nc3ccc(F)c(Br)c3)cc(F)c(F)c2[nH]1]

N-(3-bromo-4-fluorophenyl)-2-(2-(dimethylamino)ethyl)-6,7-difluoro-1H-benzo[d]imidazole-4-carboxamide was made analogously to Example 53 using 3-bromo-4-fluoroaniline in place of 3-chloro-4-fluoroaniline. $C_{18}H_{16}BrF_3N_4O$. 441.1 (M+1).

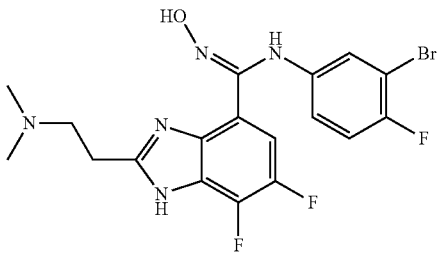 [SMILES: CN(C)CCc1nc2c(/C(=N/O)Nc3ccc(F)c(Br)c3)cc(F)c(F)c2[nH]1]

N-(3-bromo-4-fluorophenyl)-2-(2-(dimethylamino)ethyl)-6,7-difluoro-N'-hydroxy-1H-benzo[d]imidazole-4-carboximidamide. Example 54 was made analogously to Example 95. $C_{18}H_{17}BrF_3N_5O$. 456.1 (M+1). $^1$H NMR (400 MHz, DMSO-d$_6$) δ 10.89 (s, 1H), 8.76 (s, 1H), 7.17 (dd, J=11.9, 7.0 Hz, 1H), 7.07 (dd, J=6.1, 2.7 Hz, 1H), 7.00 (t, J=8.8 Hz, 1H), 6.53 (ddd, J=8.9, 4.1, 2.7 Hz, 1H), 3.53 (t, J=7.5 Hz, 2H), 3.26 (t, J=7.5 Hz, 2H), 2.83 (s, 6H).

Example 55: N-(3-Bromophenyl)-2-(2-(dimethylamino)ethyl)-6,7-difluoro-N'-hydroxy-1H-benzo[d]imidazole-4-carboximidamide

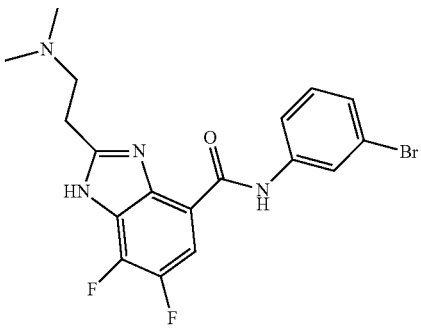 [SMILES: CN(C)CCc1nc2c(C(=O)Nc3cccc(Br)c3)cc(F)c(F)c2[nH]1]

N-(3-bromophenyl)-2-(2-(dimethylamino)ethyl)-6,7-difluoro-1H-benzo[d]imidazole-4-carboxamide was made analogously to Example 53 using 3-bromoaniline in place of 3-chloro-4-fluoroaniline. $C_{18}H_{16}BrF_3N_4O$. 423.1 (M+1).

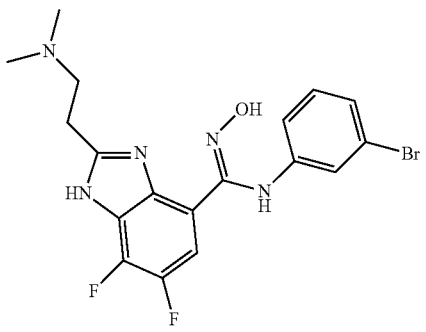 [SMILES: CN(C)CCc1nc2c(/C(=N/O)Nc3cccc(Br)c3)cc(F)c(F)c2[nH]1]

N-(3-bromophenyl)-2-(2-(dimethylamino)ethyl)-6,7-difluoro-N'-hydroxy-1H-benzo[d]imidazole-4-carboximidamide. Example 55 was made analogously to Example 95. $C_{18}H_{18}BrF_2N_5O$. 438.10. $^1H$ NMR (400 MHz, DMSO-$d_6$) δ 10.98 (s, 1H), 8.78 (s, 1H), 7.22-7.07 (m, 1H), 7.00-6.85 (m, 3H), 6.55-6.40 (m, 1H), 3.54 (t, J=7.5 Hz, 2H), 3.35-3.20 (m, 2H), 2.84 (s, 6H).

Example 56: N-(3-Chlorophenyl)-2-(2-(dimethylamino)ethyl)-6,7-difluoro-N'-hydroxy-1H-benzo[d]imidazole-4-carboximidamide

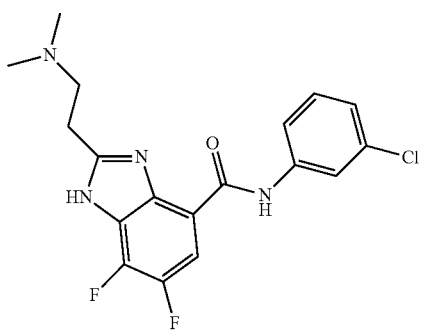 [SMILES: CN(C)CCc1nc2c(C(=O)Nc3cccc(Cl)c3)cc(F)c(F)c2[nH]1]

N-(3-chlorophenyl)-2-(2-(dimethylamino)ethyl)-6,7-difluoro-1H-benzo[d]imidazole-4-carboxamide was made analogously to Example 53 using 3-chloroaniline in place of 3-chloro-4-fluoroaniline. $C_{18}H_{17}ClF_2N_4O$. 379.11 (M+1).

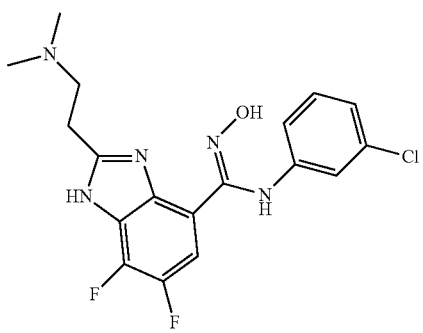 [SMILES: CN(C)CCc1nc2c(/C(=N/O)Nc3cccc(Cl)c3)cc(F)c(F)c2[nH]1]

N-(3-chlorophenyl)-2-(2-(dimethylamino)ethyl)-6,7-difluoro-N'-hydroxy-1H-benzo[d]imidazole-4-carboximidamide. Example 56 was made analogously to Example 95 $C_{18}H_{18}ClF_2N_5O$. 394.12 (M+1). $^1H$ NMR (400 MHz, DMSO-$d_6$) δ 10.94 (s, 1H), 8.78 (s, 1H), 7.14 (dd, J=12.0, 7.0 Hz, 1H), 7.00 (t, J=8.0 Hz, 1H), 6.86-6.74 (m, 2H), 6.51-6.38 (m, 1H), 3.54 (t, J=7.5 Hz, 2H), 3.27 (t, J=7.5 Hz, 2H), 2.83 (s, 6H).

Example 57: N-(3-Chloro-4-fluorophenyl)-6,7-difluoro-N'-hydroxy-2-(2-(methylamino)ethyl)-1H-benzo[d]imidazole-4-carboximidamide

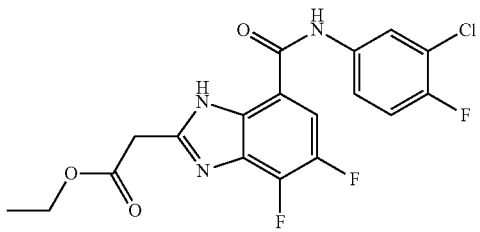 [SMILES: CCOC(=O)Cc1nc2c(F)c(F)cc(C(=O)Nc3ccc(F)c(Cl)c3)c2[nH]1]

Ethyl 2-(7-((3-chloro-4-fluorophenyl)carbamoyl)-4,5-difluoro-1H-benzo[d]imidazol-2-yl)acetate was made analogously to Example 53 using 2,3-diamino-N-(3-chloro-4-fluorophenyl)-4,5-difluorobenzamide. $C_{18}H_{13}ClF_3N_3O_3$. 412.10 (M+1).

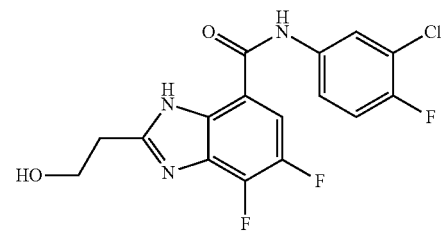 [SMILES: O=C(Nc1ccc(F)c(Cl)c1)c1cc(F)c(F)c2nc(CCO)[nH]c12]

N-(3-chloro-4-fluorophenyl)-4,5-difluoro-2-(2-hydroxyethyl)-1H-benzo[d]imidazole-7-carboxamide was made analogously to Example 183 using Ethyl 2-(7-((3-chloro-4-fluorophenyl)carbamoyl)-4,5-difluoro-1H-benzo[d]imidazol-2-yl)acetate. $C_{16}H_{11}ClF_3N_3O_2$. 370.10 (M+1).

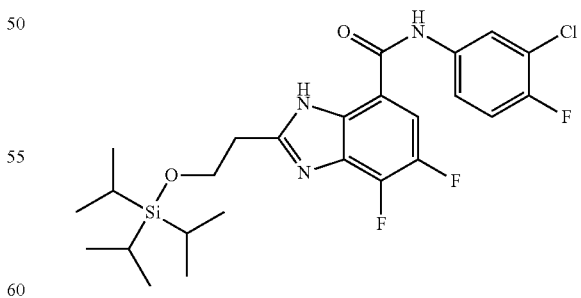

N-(3-chloro-4-fluorophenyl)-4,5-difluoro-2-(2-((triisopropylsilyl)oxy)ethyl)-1H-benzo[d]imidazole-7-carboxamide was made analogously to Example 183 using N-(3-chloro-4-fluorophenyl)-4,5-difluoro-2-(2-hydroxyethyl)-1H-benzo[d]imidazole-7-carboxamide. $C_{25}H_3ClF_3N_3O_2Si$. 526.18 (M+1).

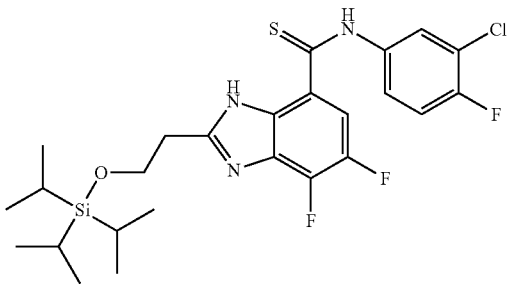 [SMILES: CC(C)[Si](OCCc1nc2c(F)c(F)cc(C(=O)Nc3ccc(F)c(Cl)c3)c2[nH]1)(C(C)C)C(C)C]

N-(3-chloro-4-fluorophenyl)-4,5-difluoro-2-(2-(((triisopropylsilyl)oxy)ethyl)-1H-benzo[d]imidazole-7-carbothioamide was made analogously to Example 183 using N-(3-chloro-4-fluorophenyl)-4,5-difluoro-2-(2-(((triisopropylsilyl)oxy)ethyl)-1H-benzo[d]imidazole-7-carboxamide. $C_{25}H_{31}ClF_3N_3OSSi$. 542.16 (M+1).

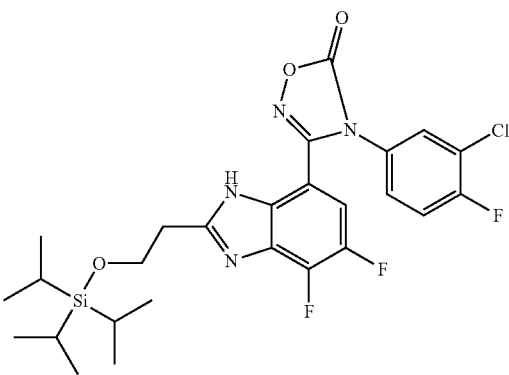 [SMILES: CC(C)[Si](OCCc1nc2c(F)c(F)cc(-c3noc(=O)n3-c3ccc(F)c(Cl)c3)c2[nH]1)(C(C)C)C(C)C]

4-(3-chloro-4-fluorophenyl)-3-(4,5-difluoro-2-(2-(((triisopropylsilyl)oxy)ethyl)-1H-benzo[d]imidazol-7-yl)-1,2,4-oxadiazol-5(4H)-one was made analogously to Example 183 using N-(3-chloro-4-fluorophenyl)-4,5-difluoro-2-(2-(((triisopropylsilyl)oxy)ethyl)-1H-benzo[d]imidazole-7-carbothioamide. $C_{26}H_{30}ClF_3N_4O_3Si$. 567.17 (M+1).

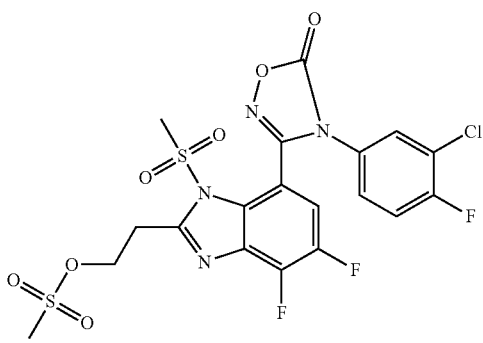 [SMILES: CS(=O)(=O)OCCc1nc2c(F)c(F)cc(-c3noc(=O)n3-c3ccc(F)c(Cl)c3)c2n1S(C)(=O)=O]

2-(7-(4-(3-chloro-4-fluorophenyl)-5-oxo-4,5-dihydro-1,2,4-oxadiazol-3-yl)-4,5-difluoro-1-(methylsulfonyl)-1H-benzo[d]imidazol-2-yl)ethyl methanesulfonate was made analogously to Example 112 using 4-(3-chloro-4-fluorophenyl)-3-(4,5-difluoro-2-(2-(((triisopropylsilyl)oxy)ethyl)-1H-benzo[d]imidazol-7-yl)-1,2,4-oxadiazol-5(4H)-one. $C_{19}H_{14}ClF_3N_4O_7S_2$. 567.00 (M+1).

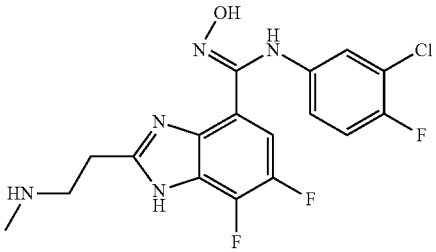 [SMILES: CNCCc1nc2c(/C(=N/O)Nc3ccc(F)c(Cl)c3)cc(F)c(F)c2[nH]1]

N-(3-chloro-4-fluorophenyl)-6,7-difluoro-N'-hydroxy-2-(2-(methylamino)ethyl)-1H-benzo[d]imidazole-4-carboximidamide. Example 57 was made analogously to Example 112 using 2-(7-(4-(3-chloro-4-fluorophenyl)-5-oxo-4,5-dihydro-1,2,4-oxadiazol-3-yl)-4,5-difluoro-1-(methylsulfonyl)-1H-benzo[d]imidazol-2-yl)ethyl methanesulfonate in place of 2-(7-(4-(3-chloro-4-fluorophenyl)-5-oxo-4,5-dihydro-1,2,4-oxadiazol-3-yl)-3-(methylsulfonyl)-3H-imidazo[4,5-b]pyridin-2-yl)ethyl methanesulfonate. $C_{16}H_{16}ClFN_6O$. 363.11 (M+1).

Example 58: N-(3-Chloro-4-fluorophenyl)-2-(2-(diethylamino)ethyl)-4,5-difluoro-N'-hydroxy-1H-benzo[d]imidazole-7-carboximidamide

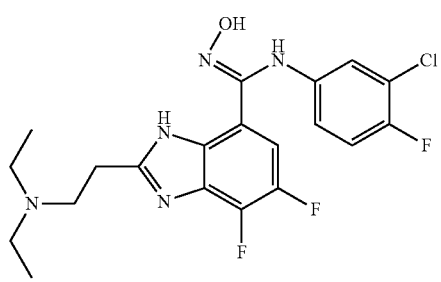 [SMILES: CCN(CC)CCc1nc2c(F)c(F)cc(/C(=N/O)Nc3ccc(F)c(Cl)c3)c2[nH]1]

Example 58 was made analogously to Example 57 using 2-(7-(4-(3-chloro-4-fluorophenyl)-5-oxo-4,5-dihydro-1,2,4-oxadiazol-3-yl)-4,5-difluoro-1-(methylsulfonyl)-1H-benzo[d]imidazol-2-yl)ethyl methanesulfonate and diethylamine in place of 24744-(3-chloro-4-fluorophenyl)-5-oxo-4,5-dihydro-1,2,4-oxadiazol-3-yl)-3-(methylsulfonyl)-3H-imidazo[4,5-b]pyridin-2-yl)ethyl methanesulfonate and methylamine. $C_{20}H_{21}ClF_3N_5O$. 440.14 $^1$H NMR (400 MHz, DMSO-d$_6$) δ 10.85 (s, 1H), 8.78 (s, 1H), 7.18 (dd, J=11.9, 6.9 Hz, 1H), 7.03 (t, J=9.0 Hz, 1H), 6.94 (dd, J=6.6, 2.7 Hz, 1H), 6.48 (ddd, J=9.0, 4.0, 2.7 Hz, 1H), 3.50 (t, J=7.6 Hz, 2H), 3.24 (t, J=7.7 Hz, 2H), 3.19 (q, J=8.3, 7.3 Hz, 4H), 1.20 (t, J=7.3 Hz, 6H).

Example 59: N-(3-Chloro-4-fluorophenyl)-N'-hydroxy-1H-imidazo[4,5-b]pyridine-7-carboximidamide

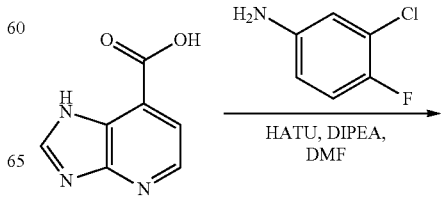

-continued

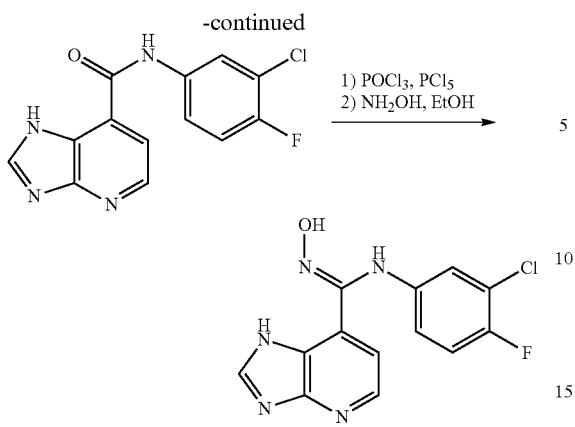

1H-imidazo[4,5-b]pyridine-7-carboxylic acid (300 mg, 2.0 mmol), 3-chloro-4-fluoroaniline (2.0 mmol), and HATU (2.4 mmol) were dissolved in DMF (5 mL) and DIPEA (6 mmol) was added. The reaction was allowed to stir at rt overnight. The reaction was quenched with saturated sodium bicarbonate solution (5 mL) and the reaction was extracted with EtOAc (3×5 mL). Combined organic layers were washed with brine (1×8 mL) and concentrated in vacuo. The crude material was purified by column chromatography (EtOAc/hex) to give N-(3-chloro-4-fluorophenyl)-1H-imidazo[4,5-b]pyridine-7-carboxamide.

N-(3-chloro-4-fluorophenyl)-1H-imidazo[4,5-b]pyridine-7-carboxamide (122 mg, 0.42 mmol) and PCl$_5$ (0.63 mmol) was dissolved in POCl$_3$ (2 mL) and heated to 85° C. for 12 hours. The reaction was cooled to rt and concentrated in vacuo. The residue was dissolved in a pre-mixed solution of hydroxylamine (50% aqueous solution, 4.0 mmol) and ethanol (2 mL) and the reaction was allowed to stir at rt for 10 minutes. The reaction was concentrated in vacuo and purified by reverse-phase HPLC to give N-(3-chloro-4-fluorophenyl)-N'-hydroxy-1H-imidazo[4,5-b]pyridine-7-carboximidamide as a white solid. $C_{13}H_9ClFN_5O$. 306.0/308.0 (M+1). $^1$H NMR (400 MHz, DMSO-d$_6$) δ 11.14 (s, 1H), 8.92 (d, J=1.9 Hz, 1H), 8.64 (s, 1H), 8.43-8.39 (m, 1H), 7.28-7.23 (m, 1H), 7.03 (t, J=9.1 Hz, 1H), 6.98-6.92 (m, 1H), 6.51 (dt, J=8.9, 3.4 Hz, 1H).

Example 60: N-(5-Chloro-2-fluorophenyl)-N'-hydroxy-1H-imidazo[4,5-b]pyridine-7-carboximidamide

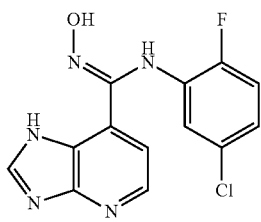 [SMILES: O/N=C(\Nc1cc(Cl)ccc1F)c1ccnc2nc[nH]c12]

Example 60 was made analogously to Example 59 using 5-chloro-2-fluoroaniline in place of 3-chloro-4-fluoroaniline. $C_{13}H_9ClFN_5O$. 306.1/308.2 (M+1). $^1$H NMR (400 MHz, Methanol-d$_4$) δ 8.88 (s, 1H), 8.46 (d, J=5.3 Hz, 1H), 7.35 (d, J=5.3 Hz, 1H), 7.01-6.95 (m, 2H), 6.92-6.85 (m, 1H).

Example 61: N-(5-Bromo-2,4-difluorophenyl)-N'-hydroxy-1H-imidazo[4,5-b]pyridine-7-carboximidamide

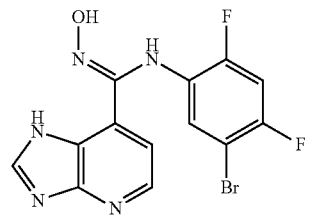 [SMILES: O/N=C(\Nc1cc(Br)c(F)cc1F)c1ccnc2nc[nH]c12]

Example 61 was made analogously to Example 59 using 5-bromo-2,4-difluoroaniline in place of 3-chloro-4-fluoroaniline. $C_{13}H_8BrF_2N_5O$. 368.0/370.0 (M+1). $^1$H NMR (400 MHz, DMSO-d$_6$) δ 11.03 (s, 1H), 8.71 (s, 1H), 8.59 (s, 1H), 8.36 (d, J=4.8 Hz, 1H), 7.34-7.21 (m, 3H).

Example 62: N-(5-Chloro-2,4-difluorophenyl)-N'-hydroxy-1H-imidazo[4,5-b]pyridine-7-carboximidamide

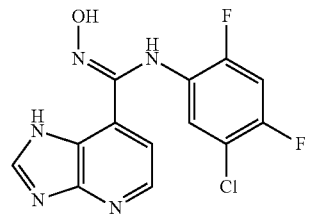 [SMILES: O/N=C(\Nc1cc(Cl)c(F)cc1F)c1ccnc2nc[nH]c12]

Example 62 was made analogously to Example 59 using 5-chloro-2,4-difluoroaniline in place of 3-chloro-4-fluoroaniline. $C_{13}H_8ClF_2N_5O$. 324.0/326.1 (M+1). $^1$H NMR (400 MHz, DMSO-d$_6$) δ 11.08 (s, 1H), 8.71 (d, J=17.2 Hz, 2H), 8.42-8.34 (m, 1H), 7.34 (dd, J=10.7, 9.3 Hz, 1H), 7.28 (d, J=5.0 Hz, 1H), 7.15 (t, J=8.2 Hz, 1H).

Example 63: N-(3,5-Dichloro-4-fluorophenyl)-N'-hydroxy-1H-imidazo[4,5-b]pyridine-7-carboximidamide

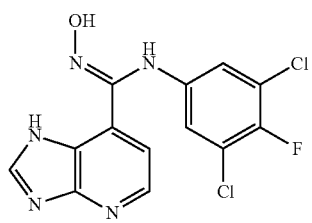 [SMILES: O/N=C(\Nc1cc(Cl)c(F)c(Cl)c1)c1ccnc2nc[nH]c12]

Example 63 was made analogously to Example 59 using 3,5-dichloro-4-fluoroaniline in place of 3-chloro-4-fluoroaniline. $C_{13}H_8Cl_2FN_5O$. 340.1/342.1 (M+1). $^1$H NMR (400 MHz, DMSO-d$_6$) δ 11.26 (s, 1H), 10.10 (s, 1H), 9.07 (d, J=1.1 Hz, 1H), 8.53 (s, 1H), 8.45-8.37 (m, 1H), 7.31 (d, J=5.2 Hz, 1H), 6.81-6.73 (m, 2H).

Example 64: N-(3-Chloro-2,4-difluorophenyl)-N'-hydroxy-1H-imidazo[4,5-b]pyridine-7-carboximidamide

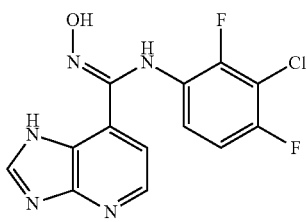 [SMILES: O/N=C(\Nc1ccc(F)c(Cl)c1F)c1ccnc2nc[nH]c12]

Example 64 was made analogously to Example 59 using 3-chloro-2,4-difluoroaniline in place of 3-chloro-4-fluoroaniline. $C_{13}H_8ClF_2N_5O$. 324.1/326.1 (M+1). $^1$H NMR (400 MHz, DMSO-$d_6$) δ 10.99 (s, OH), 8.67 (s, 1H), 8.51 (s, 1H), 8.34 (dd, J=5.0, 2.3 Hz, 1H), 7.22 (s, 1H), 7.04 (t, J=9.0 Hz, 1H), 6.84 (s, 1H).

Example 65: N-(3-Cyclopropyl-4-fluorophenyl)-N'-hydroxy-1H-imidazo[4,5-b]pyridine-7-carboximidamide

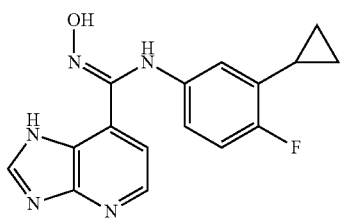 [SMILES: O/N=C(\Nc1ccc(F)c(C2CC2)c1)c1ccnc2nc[nH]c12]

Example 65 was made analogously to Example 59 using 3-cyclopropyl-4-fluoroaniline in place of 3-chloro-4-fluoroaniline. $C_{16}H_{14}FN_5O$. 312.1 (M+1).

Example 66: N'-Hydroxy-N-(4-(trifluoromethoxy)phenyl)-1H-imidazo[4,5-b]pyridine-7-carboximidamide

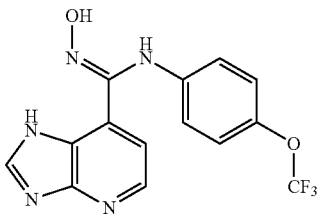 [SMILES: O/N=C(\Nc1ccc(OC(F)(F)F)cc1)c1ccnc2nc[nH]c12]

Example 66 was made analogously to Example 59 using 4-(trifluoromethoxy)aniline in place of 3-chloro-4-fluoroaniline. $C_{14}H_{10}F_3N_5O_2$. 338.1 (M+1).

Example 67: N-(Benzofuran-4-yl)-N'-hydroxy-1H-imidazo[4,5-b]pyridine-7-carboximidamide

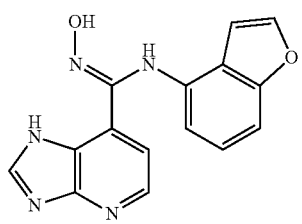 [SMILES: O/N=C(\Nc1cccc2occc12)c1ccnc2nc[nH]c12]

Example 67 was made analogously to Example 59 using benzofuran-4-amine in place of 3-chloro-4-fluoroaniline. $C_{15}H_{11}N_5O_2$. 294.1 (M+1). $^1$H NMR (400 MHz, DMSO-$d_6$) δ 11.32 (s, 1H), 8.92 (s, 1H), 8.86 (s, 1H), 8.34 (dd, J=5.2, 2.7 Hz, 1H), 7.83 (d, J=2.2 Hz, 1H), 7.16-7.09 (m, 2H), 7.06 (dd, J=2.3, 1.0 Hz, 1H), 6.95 (t, J=8.0 Hz, 1H), 6.36 (d, J=7.8 Hz, 1H).

Example 68: N-(Benzofuran-6-yl)-N'-hydroxy-1H-imidazo[4,5-b]pyridine-7-carboximidamide

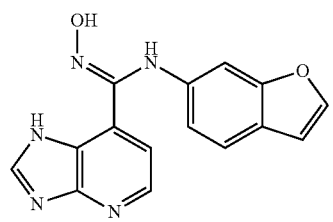 [SMILES: O/N=C(\Nc1ccc2ccoc2c1)c1ccnc2nc[nH]c12]

Example 68 was made analogously to Example 59 using benzofuran-6-amine in place of 3-chloro-4-fluoroaniline. $C_{15}H_{11}N_5O_2$. 294.1 (M+1). $^1$H NMR (400 MHz, DMSO-$d_6$) δ 11.17 (s, 1H), 8.89 (d, J=33.4 Hz, 2H), 8.40 (d, J=6.1 Hz, 1H), 7.79-7.74 (m, 1H), 7.30 (dd, J=8.6, 2.0 Hz, 1H), 7.24 (t, J=5.9 Hz, 1H), 6.90 (t, J=2.5 Hz, 1H), 6.76 (dd, J=2.2, 1.1 Hz, 1H), 6.69 (dt, J=8.4, 1.9 Hz, 1H).

Example 69: N-(Benzofuran-7-yl)-N'-hydroxy-1H-imidazo[4,5-b]pyridine-7-carboximidamide

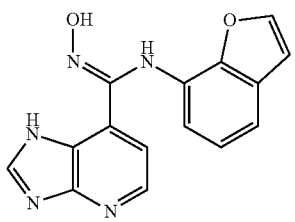 [SMILES: O/N=C(\Nc1cccc2ccoc12)c1ccnc2nc[nH]c12]

Example 69 was made analogously to Example 59 using benzofuran-7-amine in place of 3-chloro-4-fluoroaniline. $C_{15}H_{11}N_5O_2$. 294.1 (M+1).

Example 70: N-(benzofuran-5-yl)-N'-hydroxy-1H-imidazo[4,5-b]pyridine-7-carboximidamide

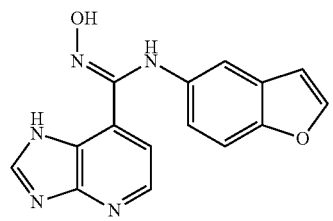 [SMILES: O/N=C(\Nc1ccc2occc2c1)c1ccnc2nc[nH]c12]

Example 70 was made analogously to Example 59 using benzofuran-5-amine in place of 3-chloro-4-fluoroaniline. $C_{15}H_{11}N_5O_2$. 294.1 (M+1).

Example 71: N-(5-Bromo-2-fluorophenyl)-N'-hydroxy-1H-imidazo[4,5-b]pyridine-7-carboximidamide

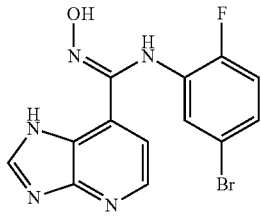 [SMILES: O/N=C(\Nc1cc(Br)ccc1F)c1ccnc2nc[nH]c12]

Example 71 was made analogously to Example 59 using acid and 5-bromo-2-fluoroaniline in place of 3-chloro-4-fluoroaniline. $C_{13}H_9BrFN_5O$. 350.1/352.1 (M+1). $^1$H NMR (400 MHz, DMSO-d$_6$) δ 11.16 (s, 1H), 10.06 (s, 1H), 8.74 (s, 1H), 8.57 (s, 1H), 8.35 (d, J=5.1H, 1H), 7.25 (s, 1H), 7.14-6.92 (m, 3H).

Example 72: N-(3-Bromo-5-fluorophenyl)-N'-hydroxy-1H-imidazo[4,5-b]pyridine-7-carboximidamide

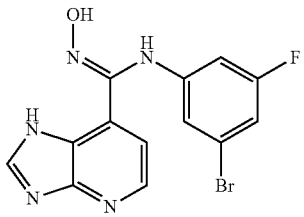 [SMILES: O/N=C(\Nc1cc(F)cc(Br)c1)c1ccnc2nc[nH]c12]

Example 72 was made analogously to Example 59 using 5-bromo-3-fluoroaniline in place of 3-chloro-4-fluoroaniline. $C_{13}H_9BrFN_5O$. 350.1/352.1 (M+1). $^1$H NMR (400 MHz, DMSO-d$_6$) δ 11.32 (s, 1H), 9.08 (s, 1H), 8.55 (s, 1H), 8.37 (d, J=5.1 Hz, 1H), 7.23 (d, J=5.1 Hz, 1H), 6.84-6.75 (m, 1H), 6.66 (t, J=1.9 Hz, 1H), 6.30 (dt, J=11.3, 2.1 Hz, 1H).

Example 73: N'-Hydroxy-N-(3-(trifluoromethyl)phenyl)-1H-imidazo[4,5-b]pyridine-7-carboximidamide

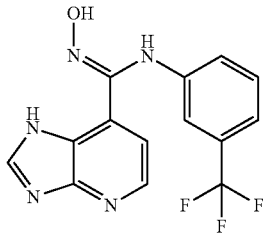 [SMILES: O/N=C(\Nc1cccc(C(F)(F)F)c1)c1ccnc2nc[nH]c12]

Example 73 was made analogously to Example 59 using 3-(trifluoromethyl)aniline in place of 3-chloro-4-fluoroaniline. $C_{14}H_{10}F_3N_5O$. 322.1 (M+1). $^1$H NMR (400 MHz, DMSO-d$_6$) δ 11.34 (s, 1H), 9.13 (s, 1H), 8.77 (s, 1H), 8.43 (d, J=5.1 Hz, 1H), 7.29 (d, J=5.1 Hz, 1H), 7.27-7.13 (m, 1H), 7.13-7.02 (m, 2H), 6.90-6.71 (m, 1H).

Example 74: N-(2,2-Difluorobenzo[d][1,3]dioxol-5-yl)-N'-hydroxy-1H-imidazo[4,5-b]pyridine-7-carboximidamide

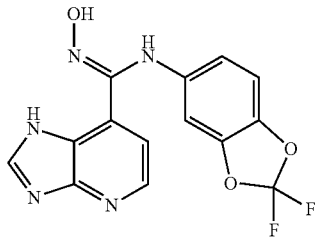 [SMILES: O/N=C(\Nc1ccc2c(c1)OC(F)(F)O2)c1ccnc2nc[nH]c12]

Example 74 was made analogously to Example 59 using 2,2-difluorobenzo[d][1,3]dioxol-5-amine in place of 3-chloro-4-fluoroaniline.

N-(2,2-difluorobenzo[d][1,3]dioxol-5-yl)-N'-hydroxy-1H-imidazo[4,5-b]pyridine-7-carboximidamide. $C_{14}H_9F_2N_5O_3$. 334.1 (M+1). $^1$H NMR (400 MHz, DMSO-d$_6$) δ 11.00 (d, J=13.0 Hz, 1H), 8.86 (s, 1H), 8.46 (s, 1H), 8.34 (d, J=5.0 Hz, 1H), 7.22 (d, J=31.8 Hz, 1H), 7.00 (d, J=8.7 Hz, 1H), 6.78 (d, J=2.2 Hz, 1H), 6.34 (dd, J=8.7, 2.3 Hz, 1H).

Example 75: N-(3-Fluoro-5-(trifluoromethyl)phenyl)-N'-hydroxy-1H-imidazo[4,5-b]pyridine-7-carboximidamide

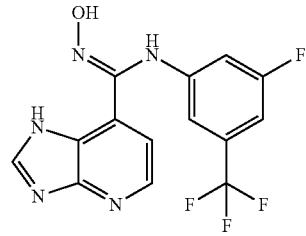 [SMILES: O/N=C(\Nc1cc(F)cc(C(F)(F)F)c1)c1ccnc2nc[nH]c12]

Example 75 was made analogously to Example 59 using 3-fluoro-5-(trifluoromethyl)aniline in place of 3-chloro-4-fluoroaniline. $C_{14}H_9F_4N_5O$. 340.1 (M+1).

Example 76: N-(2,5-Dichlorophenyl)-N'-hydroxy-1H-imidazo[4,5-b]pyridine-7-carboximidamide

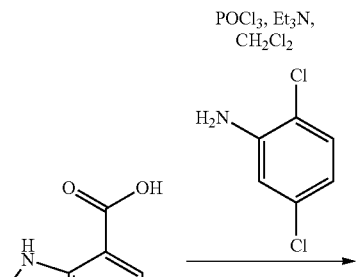

-continued

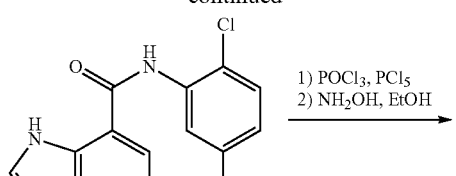

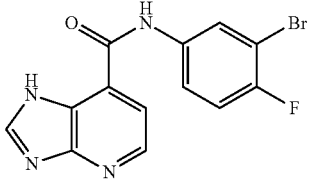

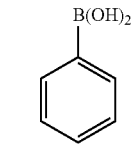

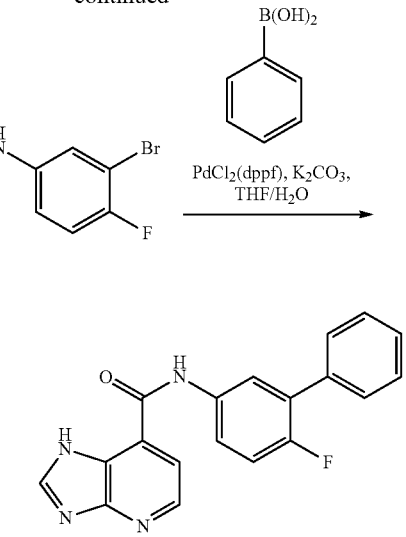

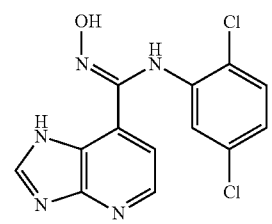


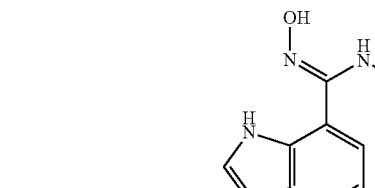

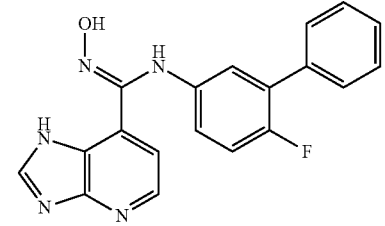

1H-imidazo[4,5-b]pyridine-7-carboxylic acid (200 mg, 1.0 mmol) and 2,5-dichloroaniline (2.0 mmol) were dissolved in DCM (3 mL) and cooled to 0° C. Triethylamine (4.0 mmol) was added dropwise followed by POCl$_3$ (2.0 mmol) and the reaction was allowed to slowly come to rt and stir for 15 mins. The reaction was quenched with saturated sodium bicarbonate solution and extracted with EtOAc (3×5 mL). Combined organic layers were washed with brine (1×7 mL) and concentrated in vacuo. The crude material was purified by column chromatography (EtOAc/hex) to give N-(2,5-dichlorophenyl)-1H-imidazo[4,5-b]pyridine-7-carboxamide.

N-(2,5-dichlorophenyl)-1H-imidazo[4,5-b]pyridine-7-carboxamide (40 mg, 0.13 mmol) was dissolved in POCl$_3$ (2 mL) and PCl$_5$ (0.195 mmol) was added. The reaction was heated to 80° C. overnight, allowed to cool to rt, and concentrated in vacuo. The crude was dissolved in a pre-mixed solution of hydroxylamine (50% in water, 1.0 mmol) and ethanol (2 mL) and allowed to stir at rt for 10 mins then concentrated in vacuo. The crude was purified by reverse-phase HPLC to give N-(2,5-dichlorophenyl)-N'-hydroxy-1H-imidazo[4,5-b]pyridine-7-carboximidamide.
C$_{13}$H$_9$Cl$_2$N$_5$O. 322.0/324.0 (M+1). $^1$H NMR (400 MHz, DMSO-d$_6$) δ 11.50 (s, 1H), 8.80 (s, 1H), 8.71 (s, 1H), 8.48-8.39 (m, 1H), 7.43-7.34 (m, 2H), 6.98 (dd, J=8.6, 2.4 Hz, 1H), 6.69 (d, J=3.2 Hz, 1H).

Example 77: N-(6-Fluoro-[1,1'-biphenyl]-3-yl)-N'-hydroxy-1H-imidazo[4,5-b]pyridine-7-carboximidamide

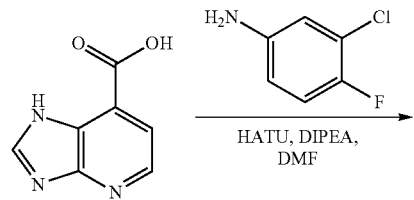

1H-imidazo[4,5-b]pyridine-7-carboxylic acid (1.5 g, 9.0 mmol), 3-bromo-4-fluoroaniline (11.0 mmol), and HATU (12.0 mmol) were dissolved in DMF (15.0 mL) and DIPEA (28.0 mmol) was added and the reaction was allowed to stir overnight at rt. The reaction was quenched with saturated sodium bicarb solution and the precipitate was isolated by vacuum filtration. The precipitate was washed with water followed by diethyl ether to give N-(3-bromo-4-fluorophenyl)-1H-imidazo[4,5-b]pyridine-7-carboxamide as a yellow powder.

N-(3-bromo-4-fluorophenyl)-1H-imidazo[4,5-b]pyridine-7-carboxamide (150 mg, 0.448 mmol) and phenyl boronic acid (2.0 mmol) was dissolved in degassed THF (2.0 mL) and water (0.50 mL). PdCl$_2$(dppf) (0.090 mmol) and K$_2$CO$_3$ (2.0 mmol) were added and the reaction was heated to 65° C. overnight. The reaction was allowed to cool to rt and quenched with saturated bicarb solution. The solution was extracted with EtOAc (3×4 mL) and combined organic layers were washed with brine (1×5 ((EtOAc/hex) to give N-(6-fluoro-[1,1'-biphenyl]-3-yl)-1H-imidazo[4,5-b]pyridine-7-carboxamide.

N-(6-fluoro-[1,1'-biphenyl]-3-yl)-1H-imidazo[4,5-b]pyridine-7-carboxamide (100 mg, 0.301 mmol) was dissolved in POCl$_3$, PCl$_5$ (2.0 mmol) was added, and the reaction was heated to 80° C. overnight. The reaction was allowed to cool to rt and concentrated in vacuo. The crude was dissolved in a pre-mixed solution of hydroxylamine (50% in water, 3.0 mmol) and ethanol (2 mL) and allowed to stir at rt for 10 mins. The reaction was purified by reverse-phase HPLC to give N-(6-fluoro-[1,1'-biphenyl]-3-yl)-N'-hydroxy-1H-imidazo[4,5-b]pyridine-7-carboximidamide. $C_{19}H_{14}FN_5O$. 348.2 (M+1).

Example 78: N-(3-(But-1-yn-1-yl)-4-fluorophenyl)-N'-hydroxy-1H-imidazo[4,5-b]pyridine-7-carboximidamide

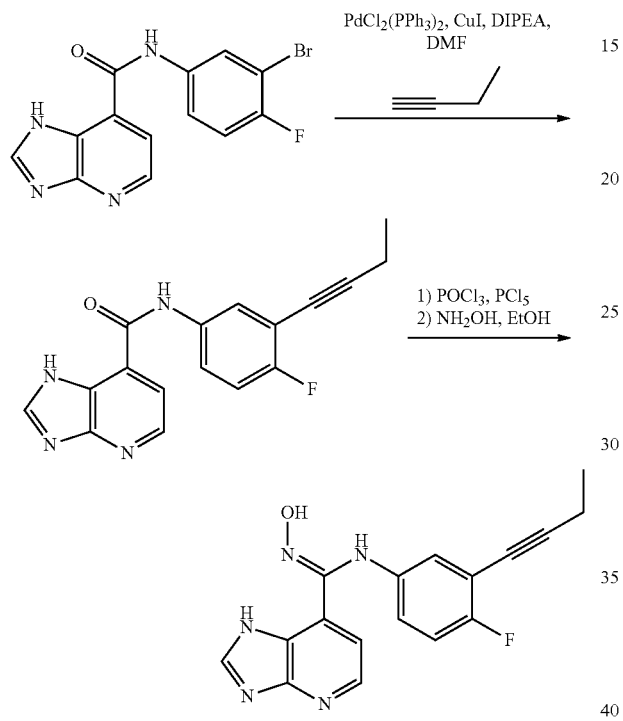

N-(3-bromo-4-fluorophenyl)-1H-imidazo[4,5-170]pyridine-7-carboxamide (100 mg, 0.298 mmol), $PdCl_2(PPh_3)_2$ (0.015 mmol), and CuI (0.0298 mmol) were dissolved in degassed DMF (0.75 mL) and DIPEA (3.0 mmol) was added. But-1-yne was bubbled through the reaction for 5 mins and then removed. The reaction was allowed to stir overnight under an atmosphere of but-1-yne. The reaction was quenched with water and extracted with EtOAc (3×3 mL). The combined organic layers were washed with brine (1×5 mL) and concentrated in vacuo. The crude was purified by column chromatography (EtOAc/hex) to give N-(3-(but-1-yn-1-yl)-4-fluorophenyl)-1H-imidazo[4,5-b]pyridine-7-carboxamide (57 mg, 62%).

N-(3-(but-1-yn-1-yl)-4-fluorophenyl)-1H-imidazo[4,5-b]pyridine-7-carboxamide (56 mg, 0.182 mmol) was dissolved in $POCl_3$ (2 mL) and $PCl_5$ (0.272 mmol) was added and the reaction was heated to 80° C. for 45 mins. The reaction was allowed to cool to rt and concentrated in vacuo. The material was dissolved in a pre-mixed solution of hydroxylamine (50% in water, 2.0 mmol) and ethanol (2 mL) and allowed to stir at rt for 10 mins. The reaction was purified by reverse-phase HPLC to give N-(3-(but-1-yn-1-yl)-4-fluorophenyl)-N'-hydroxy-1H-imidazo[4,5-b]pyridine-7-carboximidamide. $C_{17}H_{14}FN_5O$. 324.2 (M+1).

Example 79: N-(3-(Cyclopropylethynyl)-4-fluorophenyl)-N'-hydroxy-1H-imidazo[4,5-b]pyridine-7-carboximidamide

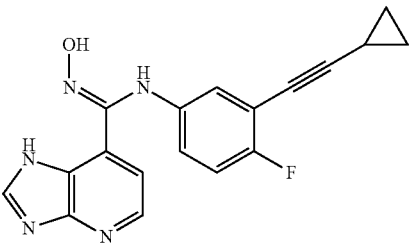 [SMILES: O/N=C(\Nc1ccc(F)c(C#CC2CC2)c1)c1ccnc2nc[nH]c12]

Example 79 was made analogously to Example 78 using ethynylcyclopropane (5 eq) in place of but-1-yne. $C_{18}H_{14}FN_5O$. 336.1 (M+1).

Example 80: N-(3-Bromophenyl)-N'-hydroxy-1H-imidazo[4,5-b]pyridine-7-carboximidamide

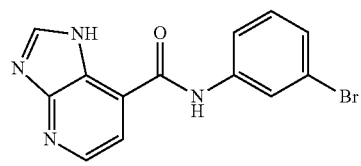 [SMILES: O=C(Nc1cccc(Br)c1)c1ccnc2nc[nH]c12]

N-(3-bromophenyl)-1H-imidazo[4,5-b]pyridine-7-carboxamide. To a solution of 1H-imidazo[4,5-b]pyridine-7-carboxylic acid (0.102 g, 0.625 mmol), 3-bromoaniline (0.07 mL, 0.625 mmol), HOBt (0.101 g, 0.750 mmol) and DIEA (0.27 mL, 1.56 mmol) in DMF (3 mL) was added EDC (0.16 mL, 0.75 mmol). The mixture stirred at room temperature for 16 h. The mixture was diluted with sat. bicarb solution and the solid was isolated via filtration. The solid was suspended in 10% citric acid solution and then isolated via filtration. The filter cake was rinsed with water and dried under vacuum to yield the desired product. $C_{13}H_9BrN_4O$. 317.0/319.0 $[M+1]^+$.

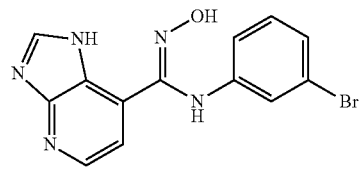 [SMILES: O/N=C(\Nc1cccc(Br)c1)c1ccnc2nc[nH]c12]

N-(3-bromophenyl)-N'-hydroxy-1H-imidazo[4,5-b]pyridine-7-carboximidamide. To a mixture of N-(3-bromophenyl)-1H-imidazo[4,5-b]pyridine-7-carboxamide (0.062 g, 0.195 mmol) and phosphoryl chloride (0.18 mL, 1.95 mmol) in DCE (2 mL) was added phosphorus pentachloride (0.061 g, 0.293 mmol). The mixture was stirred at 80° C. for 2 h. The mixture was cooled to rt and concentrated under reduced pressure. The residue was taken up in EtOH (3 mL) and hydroxylamine (0.12 mL of a 50 w/w % solution in water, 1.96 mmol) was added. The mixture stirred 2 h at rt. The mixture was concentrated and the residue was dissolved in DMSO/water and purified via preparative HPLC to yield the desired product. $C_{13}H_{10}BrN_5O$. 332.0/334.0 [M+1]$^+$. $^1$H NMR (400 MHz, DMSO-d$_6$) δ 11.25 (br s, 1H), 8.94 (br s, 1H), 8.71 (br s, 1H), 8.42 (dd, J=5.0, 2.5 Hz, 1H), 7.26 (dd, J=5.2, 2.2 Hz, 1H), 7.01-6.98 (m, 1H), 6.96-6.91 (m, 2H), 6.51 (ddd, J=4.9, 3.8, 2.2 Hz, 1H).

Example 81: N-(3-Bromo-4-fluorophenyl)-N'-hydroxy-1H-imidazo[4,5-b]pyridine-7-carboximidamide

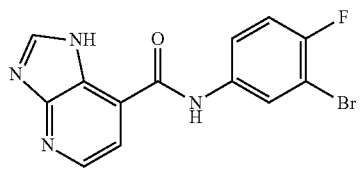

N-(3-bromo-4-fluorophenyl)-1H-imidazo[4,5-b]pyridine-7-carboxamide. To a solution of 1H-imidazo[4,5-b]pyridine-7-carboxylic acid (0.097 g, 0.595 mmol), 3-bromo-4-fluoroaniline (0.114 g, 0.597 mmol), HOBt (0.099 g, 0.729 mmol) and DIEA (0.26 mL, 1.49 mmol) in DMF (3 mL) was added EDC (0.15 mL, 0.71 mmol). The mixture stirred at room temperature for 16 h. The mixture was diluted with sat. bicarb solution and the solid was isolated via filtration. The solid was taken up in DCM/MeCN, concentrated onto silica gel, and purified via flash chromatography on silica gel to give the desired product. $C_{13}H_8BrFN_4O$. 335.0/337.0 [M+1]$^+$.

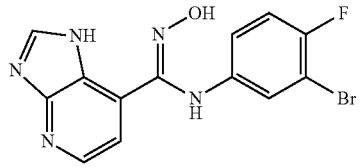

N-(3-bromo-4-fluorophenyl)-N'-hydroxy-1H-imidazo[4,5-b]pyridine-7-carboximidamide. Example 81 was synthesized analogously to Example 80, using N-(3-bromo-4-fluorophenyl)-1H-imidazo[4,5-b]pyridine-7-carboxamide in place of N-(3-bromophenyl)-1H-imidazo[4,5-b]pyridine-7-carboxamide. ($C_{13}H_9BrFN_5O$). 350.0/352.0 [M+1]$^+$. $^1$H NMR (400 MHz, DMSO-d$_6$) δ 11.18 (br s, 1H), 8.94 (br s, 1H), 8.69 (br s, 1H), 8.42 (d, J=5.1 Hz, 1H), 7.26 (d, J=5.1 Hz, 1H), 7.09 (dd, J=6.1, 2.7 Hz, 1H), 7.00 (t, J=8.8 Hz, 1H), 6.54 (ddd, J=8.9, 4.1, 2.7 Hz, 1H).

Example 82: N-(3-Chlorophenyl)-N'-hydroxy-1H-imidazo[4,5-b]pyridine-7-carboximidamide

N-(3-chlorophenyl)-1H-imidazo[4,5-b]pyridine-7-carboxamide was synthesized analogously to Example 80 using 3-chloroaniline in place of 3-bromoaniline. $C_{13}H_9ClN_4O$. 273.0 [M+1]$^+$

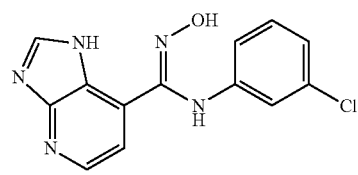 [SMILES: O/N=C(\Nc1cccc(Cl)c1)c1ccnc2nc[nH]c12]

N-(3-chlorophenyl)-N'-hydroxy-1H-imidazo[4,5-b]pyridine-7-carboximidamide. Example 82 was synthesized analogously to Example 80, using N-(3-chlorophenyl)-1H-imidazo[4,5-b]pyridine-7-carboxamide in place of N-(3-bromophenyl)-1H-imidazo[4,5-b]pyridine-7-carboxamide. $C_{13}H_{10}ClN_5O$. 288.0 [M+1]$^+$. $^1$H NMR (400 MHz, DMSO-d$_6$) δ 11.28 (br s, 1H), 8.98 (s, 1H), 8.75 (br s, 1H), 8.43 (dd, J=4.9, 1.5 Hz, 1H), 7.26 (dd, J=5.1, 1.5 Hz, 1H), 6.99 (t, J=8.1 Hz, 1H), 6.87-6.78 (m, 2H), 6.47 (ddd, J=8.3, 2.2, 0.9 Hz, 1H).

Example 83: N-(4-Fluoro-3-(trifluoromethyl)phenyl)-N'-hydroxy-1H-imidazo[4,5-b]pyridine-7-carboximidamide

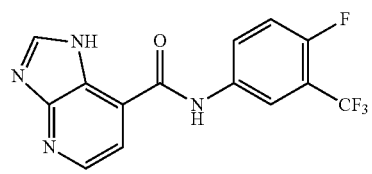 [SMILES: O=C(Nc1ccc(F)c(C(F)(F)F)c1)c1ccnc2nc[nH]c12]

N-(4-fluoro-3-(trifluoromethyl)phenyl)-1H-imidazo[4,5-b]pyridine-7-carboxamide was synthesized analogously to Example 80 using 4-fluoro-3-(trifluoromethyl)aniline in place of 3-bromoaniline. $C_{14}H_8F_4N_4O$. 325.0 [M+1]$^+$.

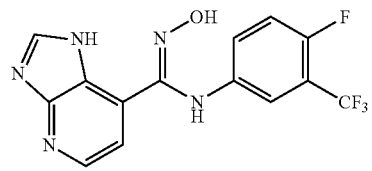 [SMILES: O/N=C(\Nc1ccc(F)c(C(F)(F)F)c1)c1ccnc2nc[nH]c12]

N-(4-fluoro-3-(trifluoromethyl)phenyl)-N'-hydroxy-1H-imidazo[4,5-b]pyridine-7-carboximidamide. Example 83 was synthesized analogously to Example 80, using N-(4-fluoro-3-(trifluoromethyl)phenyl)-1H-imidazo[4,5-b]pyridine-7-carboxamide in place of N-(3-bromophenyl)-1H-imidazo[4,5-b]pyridine-7-carboxamide. $C_{14}H_9F_4N_5O$. 340.1 [M+1]$^+$. $^1$H NMR (400 MHz, DMSO-d$_6$) δ 11.18 (br s, 1H), 9.09 (s, 1H), 8.55 (br s, 1H), 8.40 (dd, J=5.0, 1.8 Hz, 1H), 7.29 (d, J=5.0 Hz, 1H), 7.16-7.07 (m, 2H), 6.85-6.79 (m, 1H).

Example 84: N-(4-Fluoro-3-(prop-1-yn-1-yl)phenyl)-N'-hydroxy-1H-imidazo[4,5-b]pyridine-7-carboximidamide

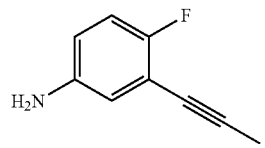

4-fluoro-3-(prop-1-yn-1-yl)aniline. A solution of 3-bromo-4-fluoroaniline (0.254 g, 1.337 mmol) and trimethyl(prop-1-yn-1-yl)silane (0.59 mL, 4.010 mmol) in DMF (1.5 mL) was degassed by bubbling $N_2$ for approx. 5 min. CuI (0.025 g, 0.134 mmol), $Pd(PPh_3)_2Cl_2$ (0.094 g, 0.134 mmol) and TBAF (4.68 mL of a 1 M solution in THF, 4.68 mmol) were added and the mixture was heated at 65° C. for 16 h. The mixture was diluted with water and extracted 3× with DCM. The combined organic layers were washed with sat. bicarb solution and brine, dried ($Na_2SO_4$), filtered and concentrated. The residue was purified via flash chromatography on silica gel to yield the desired product. $C_9H_8FN$. 150.0 $[M+1]^+$.

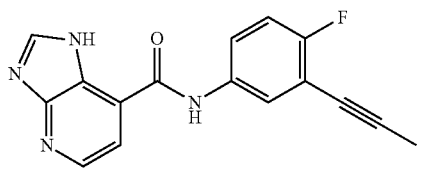 [SMILES: CC#Cc1cc(NC(=O)c2ccnc3nc[nH]c23)ccc1F]

N-(4-fluoro-3-(prop-1-yn-1-yl)phenyl)-1H-imidazo[4,5-b]pyridine-7-carboxamide. To a solution of 1H-imidazo[4,5-b]pyridine-7-carboxylic acid (0.030 g, 0.184 mmol), 4-fluoro-3-(prop-1-yn-1-yl)aniline (0.028 g, 0.134 mmol), HOBt (0.030 g, 0.221 mmol) and DIEA (0.08 mL, 0.46 mmol) in DMF (2 mL) was added EDC (0.05 mL, 0.22 mmol). The mixture stirred at room temperature for 16 h. The mixture was diluted with sat. bicarb solution and was extracted 3× with EtOAc. The combined organic layers were washed with 10% citric acid solution and brine, dried ($Na_2SO_4$), filtered, concentrated onto silica gel, and purified via flash chromatography on silica gel to yield the desired product. $C_{16}H_{11}FN_4O$. 295.1 $[M+1]^+$.

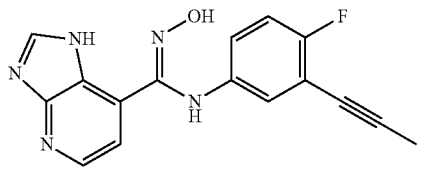 [SMILES: CC#Cc1cc(N/C(=N\O)c2ccnc3nc[nH]c23)ccc1F]

N-(4-fluoro-3-(prop-1-yn-1-yl)phenyl)-N'-hydroxy-1H-imidazo[4,5-b]pyridine-7-carboximidamide. Example 84 was synthesized analogously to Example 80, using N-(4-fluoro-3-(prop-1-yn-1-yl)phenyl)-1H-imidazo[4,5-b]pyridine-7-carboxamide in place of N-(3-bromophenyl)-1H-imidazo[4,5-b]pyridine-7-carboxamide. $C_{16}H_{12}FN_5O$. 310.1 $[M+1]^+$. $^1$H NMR (400 MHz, DMSO-$d_6$) δ 11.02 (br s, 1H), 8.75 (s, 1H), 8.60 (br s, 1H), 8.36 (d, J=4.9 Hz, 1H), 7.18 (d, J=5.0 Hz, 1H), 6.85 (t, J=9.1 Hz, 1H), 6.78 (dd, J=6.3, 2.8 Hz, 1H), 6.52 (ddd, J=8.8, 4.4, 2.9 Hz, 1H), 1.98 (s, 3H).

Example 85: N-(3-Bromo-4-chlorophenyl)-N'-hydroxy-1H-imidazo[4,5-b]pyridine-7-carboximidamide

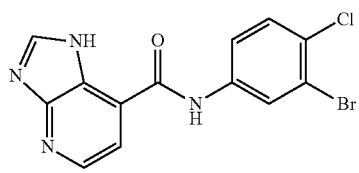

N-(3-bromo-4-chlorophenyl)-1H-imidazo[4,5-b]pyridine-7-carboxamide was synthesized analogously to Example 80, using 3-bromo-4-chloroaniline in place of 4-fluoro-3-(prop-1-yn-1-yl)aniline. $C_{13}H_8BrClN_4O$. 350.9/352.9 $[M+1]^+$.

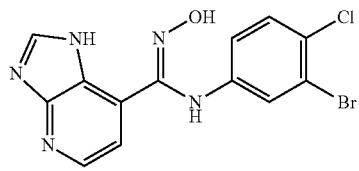 [SMILES: O/N=C(\Nc1ccc(Cl)c(Br)c1)c1ccnc2nc[nH]c12]

N-(3-bromo-4-chlorophenyl)-N'-hydroxy-1H-imidazo[4,5-b]pyridine-7-carboximidamide. Example 85 was synthesized analogously to Example 80 using N-(3-bromo-4-chlorophenyl)-1H-imidazo[4,5-b]pyridine-7-carboxamide in place of N-(3-bromophenyl)-1H-imidazo[4,5-b]pyridine-7-carboxamide. $C_{13}H_9BrClN_5O$. 366.0/368.0 $[M+1]^+$. $^1$H NMR (400 MHz, DMSO-$d_6$) δ 11.27 (br s, 1H), 9.01 (s, 1H), 8.65 (br s, 1H), 8.40 (dd, J=5.1, 1.7 Hz, 1H), 7.25 (dd, J=5.0, 1.5 Hz, 1H), 7.17 (d, J=8.7 Hz, 1H), 7.11 (dd, J=2.7, 0.8 Hz, 1H), 6.49 (dd, J=8.7, 2.6 Hz, 1H).

Example 86: N-(3,4-Dichlorophenyl)-N'-hydroxy-1H-imidazo[4,5-b]pyridine-7-carboximidamide

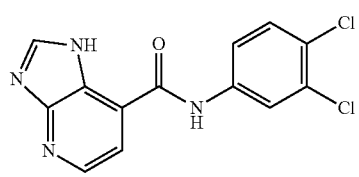 [SMILES: O=C(Nc1ccc(Cl)c(Cl)c1)c1ccnc2nc[nH]c12]

N-(3,4-dichlorophenyl)-1H-imidazo[4,5-b]pyridine-7-carboxamide. Example 86 was synthesized analogously to Example 80, using 3,4-dichloroaniline in place of 3-bromoaniline. $C_{13}H_8Cl_2N_4O$. 307.0 $[M+1]^+$.

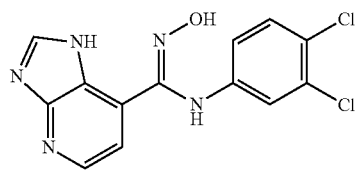 [SMILES: O/N=C(\Nc1ccc(Cl)c(Cl)c1)c1ccnc2nc[nH]c12]

N-(3,4-dichlorophenyl)-N'-hydroxy-1H-imidazo[4,5-b]pyridine-7-carboximidamide. Example 86 was synthesized analogously to Example 80, using N-(3,4-dichlorophenyl)-1H-imidazo[4,5-b]pyridine-7-carboxamide in place of N-(3-bromophenyl)-1H-imidazo[4,5-b]pyridine-7-carboxamide. $C_{13}H_9Cl_2N_5O$. 322.0 $[M+1]^+$. $^1$H NMR (400 MHz, DMSO-$d_6$) δ 11.33 (br s, 1H), 9.09 (s, 1H), 8.71 (br s, 1H), 8.44 (dd, J=5.2, 1.8 Hz, 1H), 7.29 (dd, J=5.0, 1.6 Hz, 1H), 7.21 (d, J=8.7 Hz, 1H), 7.00 (d, J=2.7 Hz, 1H), 6.49 (dd, J=8.8, 2.6 Hz, 1H).

Example 87: N-(4-Chlorophenyl)-N'-hydroxy-1H-imidazo[4,5-b]pyridine-7-carboximidamide

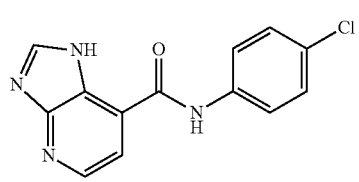 [SMILES: O=C(Nc1ccc(Cl)cc1)c1ccnc2nc[nH]c12]

N-(4-chlorophenyl)-1H-imidazo[4,5-b]pyridine-7-carboxamide. To a solution of 1H-imidazo[4,5-b]pyridine-7-carboxylic acid (0.110 g, 0.674 mmol), 4-chloroaniline (0.088 g, 0.689 mmol), HOBt (0.109 g, 0.807 mmol) and DIEA (0.30 mL, 1.72 mmol) in DMF (3 mL) was added EDC (0.18 mL, 0.809 mmol). The mixture stirred at room temperature for 16 h. The mixture was diluted with sat. bicarb solution and the solid was isolated via filtration. The solid was suspended in approx. 3 mL THF. The solid was removed via filtration and the filter cake was washed with THF. The filtrate was dried ($Na_2SO_4$), filtered and concentrated under reduced pressure to yield the desired product. $C_{13}H_9ClN_4O$. 273.0 $[M+1]^+$.

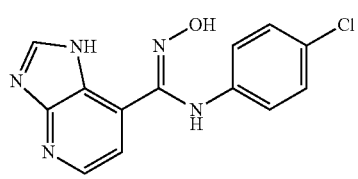 [SMILES: O/N=C(\Nc1ccc(Cl)cc1)c1ccnc2nc[nH]c12]

N-(4-chlorophenyl)-Y-hydroxy-1H-imidazo[4,5-b]pyridine-7-carboximidamide. Example 87 was synthesized analogously to Example 80, using N-(4-chlorophenyl)-1H-imidazo[4,5-b]pyridine-7-carboxamide in place of N-(3-bromophenyl)-1H-imidazo[4,5-b]pyridine-7-carboxamide. $C_{13}H_{10}ClN_5O$. 288.0 $[M+1]^+$. $^1$H NMR (400 MHz, DMSO-$d_6$) δ 11.19 (br s, 1H), 8.92 (s, 1H), 8.75 (br s, 1H), 8.41 (d, J=5.1 Hz, 1H), 7.21 (d, J=5.1 Hz, 1H), 7.07 (d, J=8.8 Hz, 2H), 6.68 (d, J=8.8 Hz, 2H).

Example 88: N-(4-Bromophenyl)-N'-hydroxy-1H-imidazo[4,5-b]pyridine-7-carboximidamide

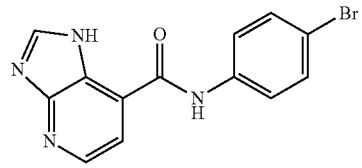 [SMILES: O=C(Nc1ccc(Br)cc1)c1ccnc2nc[nH]c12]

N-(4-bromophenyl)-1H-imidazo[4,5-b]pyridine-7-carboxamide was synthesized analogously to Example 80, using 4-bromoaniline in place of 3-bromoaniline. $C_{13}H_9BrN_4O$. 339.0/341.0 $[M+23]^+$.

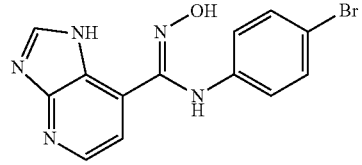 [SMILES: O/N=C(\Nc1ccc(Br)cc1)c1ccnc2nc[nH]c12]

N-(4-bromophenyl)-N'-hydroxy-1H-imidazo[4,5-b]pyridine-7-carboximidamide. Example 88 was synthesized analogously to Example 80, using N-(4-bromophenyl)-1H-imidazo[4,5-b]pyridine-7-carboxamide in place of N-(3-bromophenyl)-1H-imidazo[4,5-b]pyridine-7-carboxamide. $C_{13}H_{10}BrN_5O$. 332.0/334.0 $[M+1]^+$. $^1$H NMR (400 MHz, DMSO-$d_6$) δ 11.19 (br s, 1H), 8.89 (s, 1H), 8.72 (br s, 1H), 8.41 (d, J=5.0 Hz, 1H), 7.21 (d, J=5.3 Hz, 1H), 7.19 (d, J=8.7 Hz, 2H), 6.62 (d, J=8.8 Hz, 2H).

Example 89: N-(4-Fluorophenyl)-N'-hydroxy-1H-imidazo[4,5-b]pyridine-7-carboximidamide

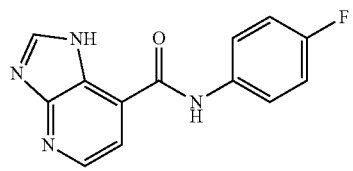 [SMILES: O=C(Nc1ccc(F)cc1)c1ccnc2nc[nH]c12]

N-(4-fluorophenyl)-1H-imidazo[4,5-b]pyridine-7-carboxamide was synthesized analogously to Example 80 using 5-fluoroaniline in place of 3-bromoaniline. $C_{13}H_9FN_4O$. 257.0 $[M+1]^+$.

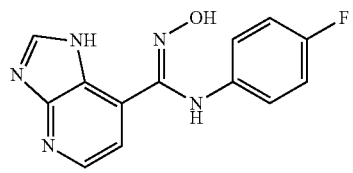 [SMILES: O/N=C(\Nc1ccc(F)cc1)c1ccnc2nc[nH]c12]

N-(4-fluorophenyl)-N'-hydroxy-1H-imidazo[4,5-b]pyridine-7-carboximidamide. Example 89 was synthesized analogously to Example 80, using N-(4-fluorophenyl)-1H-imidazo[4,5-b]pyridine-7-carboxamide in place of N-(3-bromophenyl)-1H-imidazo[4,5-b]pyridine-7-carboxamide. $C_{13}H_{10}FN_5O$. 272.1 $[M+1]^+$. $^1$H NMR (400 MHz, DMSO-$d_6$) δ 11.05 (br s, 1H), 8.80 (s, 1H), 8.72 (br s, 1H), 8.39 (dd, J=5.1, 1.3 Hz, 1H), 7.18 (d, J=5.1 Hz, 1H), 6.88 (t, J=8.8 Hz, 2H), 6.71 (dd, J=9.0, 4.8 Hz, 2H).

Example 90: N-(3-Cyano-4-fluorophenyl)-N'-hydroxy-1H-imidazo[4,5-b]pyridine-7-carboximidamide

N-(3-cyano-4-fluorophenyl)-1H-imidazo[4,5-b]pyridine-7-carboxamide was synthesized analogously to Example 80, using 3-cyano-4-fluoroaniline in place of 3-bromoaniline. $C_{14}H_8FN_5O$. 282.0 $[M+1]^+$.

N-(3-cyano-4-fluorophenyl)-N'-hydroxy-1H-imidazo[4,5-b]pyridine-7-carboximidamide. Example 90 was synthesized analogously to Example 80, using N-(3-cyano-4-fluorophenyl)-1H-imidazo[4,5-b]pyridine-7-carboxamide in place of N-(3-bromophenyl)-1H-imidazo[4,5-b]pyridine-7-carboxamide. $C_{14}H_9FN_6O$. 297.1 $[M+1]^+$.

Example 91: N'-Hydroxy-N-(4-(trifluoromethyl)phenyl)-1H-imidazo[4,5-b]pyridine-7-carboximidamide

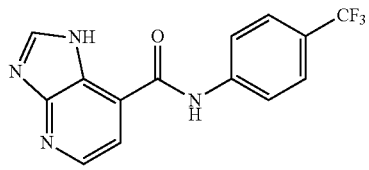 [SMILES: O=C(Nc1ccc(C(F)(F)F)cc1)c1ccnc2nc[nH]c12]

N-(4-(trifluoromethyl)phenyl)-1H-imidazo[4,5-b]pyridine-7-carboxamide was synthesized analogously to Example 84, using 4-(trifluoromethyl)aniline in place of 4-fluoro-3-(prop-1-yn-1-yl)aniline. $C_{14}H_9F_3N_4O$. 307.0 $[M+1]^+$.

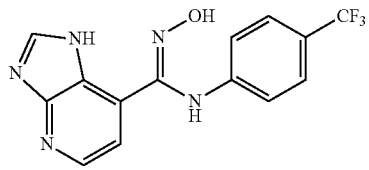 [SMILES: O/N=C(\Nc1ccc(C(F)(F)F)cc1)c1ccnc2nc[nH]c12]

N'-hydroxy-N-(4-(trifluoromethyl)phenyl)-1H-imidazo[4,5-b]pyridine-7-carboximidamide. Example 91 was synthesized analogously to Example 80 using N-(4-(trifluoromethyl)phenyl)-1H-imidazo[4,5-b]pyridine-7-carboxamide in place of N-(3-bromophenyl)-1H-imidazo[4,5-b]pyridine-7-carboxamide. $C_{14}H_{10}F_3N_5O$. 322.1 $[M+1]^+$.

Example 92: N'-Hydroxy-N-(3-methoxyphenyl)-1H-imidazo[4,5-b]pyridine-7-carboximidamide

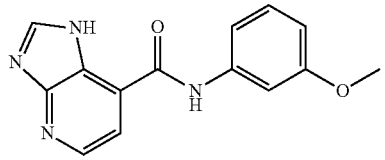 [SMILES: COc1cccc(NC(=O)c2ccnc3nc[nH]c23)c1]

N-(3-methoxyphenyl)-1H-imidazo[4,5-b]pyridine-7-carboxamide was synthesized analogously to Example 80, using 3-methoxyaniline in place of 3-bromoaniline. $C_{14}H_{12}N_4O_2$. 269.1 $[M+1]^+$.

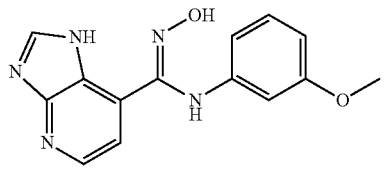 [SMILES: COc1cccc(N/C(=N\O)c2ccnc3nc[nH]c23)c1]

N'-hydroxy-N-(3-methoxyphenyl)-1H-imidazo[4,5-b]pyridine-7-carboximidamide. Example 92 was synthesized analogously to Example 80, using N-(3-methoxyphenyl)-1H-imidazo[4,5-b]pyridine-7-carboxamide in place of N-(3-bromophenyl)-1H-imidazo[4,5-b]pyridine-7-carboxamide. $C_{14}H_{13}N_5O_2$. 284.1 $[M+1]^+$.

Example 93: N-(4-Fluoro-3-isopropylphenyl)-N'-hydroxy-1H-imidazo[4,5-b]pyridine-7-carboximidamide

N-(4-fluoro-3-isopropylphenyl)-1H-imidazo[4,5-b]pyridine-7-carboxamide was synthesized analogously to Example 80, using 4-fluoro-3-isopropylaniline in place of 3-bromoaniline. $C_{16}H_{15}FN_4O$. 299.0 $[M+1]^+$.

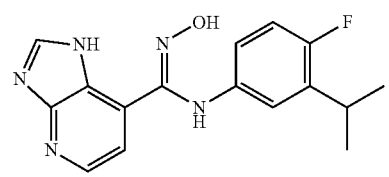 [SMILES: CC(C)c1cc(N/C(=N\O)c2ccnc3nc[nH]c23)ccc1F]

N-(4-fluoro-3-isopropylphenyl)-N'-hydroxy-1H-imidazo[4,5-b]pyridine-7-carboximidamide. Example 93 was synthesized analogously to Example 80, using N-(4-fluoro-3-isopropylphenyl)-1H-imidazo[4,5-b]pyridine-7-carboxamide in place of N-(3-bromophenyl)-1H-imidazo[4,5-b]pyridine-7-carboxamide. $C_{16}H_{16}FN_5O$. 314.1 $[M+1]^+$.

Example 94: N'-Hydroxy-N-(p-tolyl)-1H-imidazo[4,5-b]pyridine-7-carboximidamide

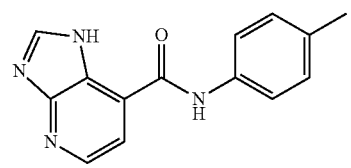 [SMILES: Cc1ccc(NC(=O)c2ccnc3nc[nH]c23)cc1]

N-(p-tolyl)-1H-imidazo[4,5-b]pyridine-7-carboxamide was synthesized analogously to Example 84, using p-toluidine in place of 4-fluoro-3-(prop-1-yn-1-yl)aniline. $C_{14}H_{12}N_4O$. 253.1 $[M+1]^+$.

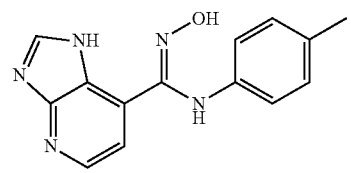 [SMILES: Cc1ccc(N/C(=N\O)c2ccnc3nc[nH]c23)cc1]

N'-hydroxy-N-(p-tolyl)-1H-imidazo[4,5-b]pyridine-7-carboximidamide. Example 94 was synthesized analogously to Example 80, using N-(p-tolyl)-1H-imidazo[4,5-b]pyridine-7-carboxamide in place of N-(3-bromophenyl)-1H-imidazo[4,5-b]pyridine-7-carboxamide. $C_{14}H_{13}N_5O$. 268.1 [M+1]+.

Example 95: N-(3-Ethynylphenyl)-Y-hydroxy-1H-imidazo[4,5-b]pyridine-7-carboximidamide

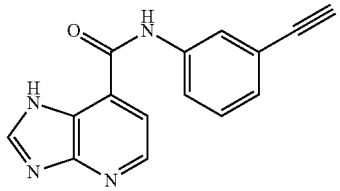 [SMILES: C#Cc1cccc(NC(=O)c2ccnc3nc[nH]c23)c1]

N-(3-ethynylphenyl)-1H-imidazo[4,5-b]pyridine-7-carboxamide. A solution of 1H-imidazo[4,5-b]pyridine-7-carboxylic acid (100 mg, 0.613 mmol), bis(2-oxo-3-oxazolidinyl)phosphinic chloride (312 mg, 1.23 mmol) and diisopropylethylamine (0.534 mL, 3.06 mmol) in dichloromethane (10 mL). was stirred for 16 hr. The reaction mixture was filtered and absorbed onto silica gel and purified by silica gel chromatography to give the desired product (140 mg). $C_{15}H_{10}N_4O$. 263.1 (M+1).

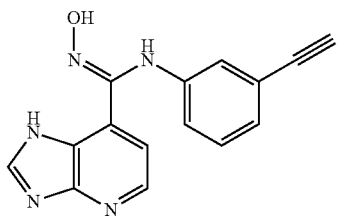 [SMILES: C#Cc1cccc(N/C(=N\O)c2ccnc3nc[nH]c23)c1]

N-(3-ethynylphenyl)-N'-hydroxy-1H-imidazo[4,5-b]pyridine-7-carboximidamide. A mixture of N-(3-ethynylphenyl)-1H-imidazo[4,5-b]pyridine-7-carboxamide (41 mg, 0.155 mmol), phosphorous pentachloride (48 mg, 0.233 mmol) in phosphoryl chloride (0.3 mL) and 1,2-dichloroethane (0.3 mL) were stirred at 80° C. for 2 hr. The reaction mixture was concentrated and suspended in ethanol (2 mL) and to this mixture was added 50% hydroxylamine in water (0.265 mL, 4.33 mmol). The reaction mixture stirred for 1 hr and was concentrated. The residue was purified by preparative HPLC to give two products (Example 95 and Example 96). N-(3-ethynylphenyl)-N'-hydroxy-1H-imidazo[4,5-b]pyridine-7-carboximidamide. $C_{15}H_{11}N_5O$. 278.07 (M+1) $^1$H NMR (400 MHz, DMSO-d$_6$) δ 11.23 (s, 1H), 8.90 (s, 1H), 8.78 (s, 1H), 8.43 (d, J=5.1 Hz, 1H), 7.24 (d, J=5.1 Hz, 1H), 7.00 (t, J=8.1 Hz, 1H), 6.93-6.85 (m, 2H), 6.59 (ddd, J=8.2, 2.3, 1.1 Hz, 1H), 4.07 (s, 1H).

Example 96: N-(3-Ethylphenyl)-N'-hydroxy-1H-imidazo[4,5-b]pyridine-7-carboximidamide

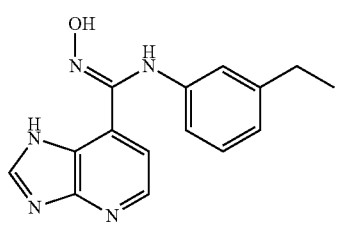 [SMILES: CCc1cccc(N/C(=N\O)c2ccnc3nc[nH]c23)c1]

N-(3-ethylphenyl)-N'-hydroxy-1H-imidazo[4,5-b]pyridine-7-carboximidamide was prepared as described in Example 95. C15H15N5O. 281.10 (M+1) $^1$H NMR (400 MHz, DMSO-d$_6$) δ 11.09 (s, 1H), 8.74 (d, J=15.8 Hz, 2H), 8.39 (d, J=5.1 Hz, 1H), 7.19 (d, J=5.1 Hz, 1H), 6.98-6.87 (m, 1H), 6.64 (ddd, J=7.5, 1.6, 0.9 Hz, 1H), 6.55-6.43 (m, 2H), 2.34 (q, J=7.6 Hz, 2H), 0.89 (t, J=7.6 Hz, 3H).

Example 97: N-(3-Ethynyl-4-fluorophenyl)-N'-hydroxy-1H-imidazo[4,5-b]pyridine-carboximidamide

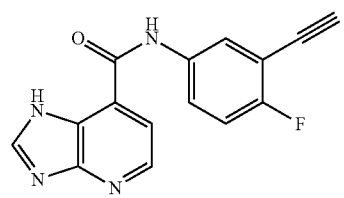 [SMILES: C#Cc1cc(NC(=O)c2ccnc3nc[nH]c23)ccc1F]

N-(3-ethynyl-4-fluorophenyl)-1H-imidazo[4,5-b]pyridine-7-carboxamide was made analogously to Example 95 using 3-ethynyl-4-fluoroaniline in place of 3-ethynylaniline. $C_{15}H_9FN_4O$. 281.00 (M+1).

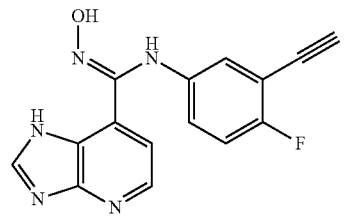 [SMILES: C#Cc1cc(N/C(=N\O)c2ccnc3nc[nH]c23)ccc1F]

N-(3-ethynyl-4-fluorophenyl)-N'-hydroxy-1H-imidazo[4,5-b]pyridine-7-carboximidamide. Example 97 was made analogously to Example 95 $C_{15}H_{10}FN_5O$. 295.09 (M+1). $^1$H NMR (400 MHz, DMSO-d$_6$) δ 11.17 (s, 1H), 8.90 (s, 1H), 8.78 (s, 1H), 8.43 (d, J=5.1 Hz, 1H), 7.26 (d, J=5.1 Hz, 1H), 6.98-6.89 (m, 2H), 6.62 (ddd, J=9.0, 4.4, 2.9 Hz, 1H), 4.39 (d, J=0.6 Hz, 1H).

Example 98: N-(3-(Difluoromethyl)phenyl)-N'-hydroxy-1H-imidazo[4,5-b]pyridine-carboximidamide

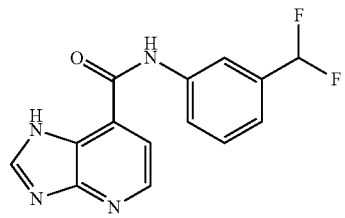 [SMILES: O=C(Nc1cccc(C(F)F)c1)c1ccnc2nc[nH]c12]

N-(3-(difluoromethyl)phenyl)-1H-imidazo[4,5-b]pyridine-7-carboxamide was made analogously to Example 95 using 3-(difluoromethyl)aniline in place of 3-ethynylaniline. C14H10F2N4O. 289.10 (M+1).

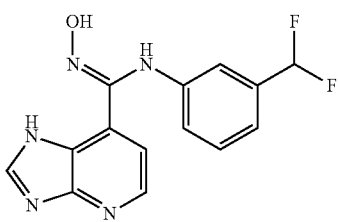 [SMILES: O/N=C(\Nc1cccc(C(F)F)c1)c1ccnc2nc[nH]c12]

N-(3-(difluoromethyl)phenyl)-N'-hydroxy-1H-imidazo[4,5-b]pyridine-7-carboximidamide. Example 98 was made analogously to Example 95 using N-(3-(difluoromethyl)phenyl)-1H-imidazo[4,5-b]pyridine-7-carboxamide. $C_{14}H_{11}F_2N_5O$. 304.10 (M+1) $^1$H NMR (400 MHz, DMSO-$d_6$) δ, 12.51 (s, 1H), 11.17 (s, 1H), 8.92 (d, J=25.4 Hz, 1H), 8.41 (s, 1H), 8.33 (d, J=5.0 Hz, 1H), 7.41-7.23 (m, 1H), 7.19-7.02 (m, 1H), 7.02-6.80 (m, 2H), 6.73 (d, J=8.2 Hz, 1H).

Example 99: N'-Hydroxy-N-(3-(trifluoromethoxy)phenyl)-1H-imidazo[4,5-b]pyridine-7-carboximidamide

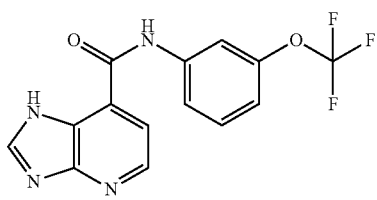 [SMILES: O=C(Nc1cccc(OC(F)(F)F)c1)c1ccnc2nc[nH]c12]

N-(3-(trifluoromethoxy)phenyl)-1H-imidazo[4,5-b]pyridine-7-carboxamide was made analogously to Example 95 using 3-(trifluoromethoxy)aniline in place of 3-ethynylaniline. $C_{14}H_9F_3N_4O_2$. 323.07 (M+1)

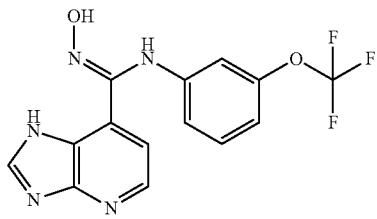 [SMILES: O/N=C(\Nc1cccc(OC(F)(F)F)c1)c1ccnc2nc[nH]c12]

N'-hydroxy-N-(3-(trifluoromethoxy)phenyl)-1H-imidazo[4,5-b]pyridine-7-carboximidamide. Example 99 was made analogously to Example 95 using N-(3-(trifluoromethoxy)phenyl)-1H-imidazo[4,5-b]pyridine-7-carboxamide. $C_{14}H_{10}F_3N_5O_2$. 338.10 (M+1). $^1$H NMR (400 MHz, DMSO-$d_6$) δ 9.54 (s, 1H), 9.22 (s, 1H), 8.58 (d, J=5.3 Hz, 1H), 7.40 (d, J=5.3 Hz, 1H), 7.12 (td, J=8.1, 0.5 Hz, 1H), 6.74 (ddt, J=8.2, 2.1, 1.0 Hz, 1H), 6.69-6.61 (m, 3H).

Example 100: N-Hydroxy-N-phenyl-1H-imidazo[4,5-b]pyridine-7-carboximidamide

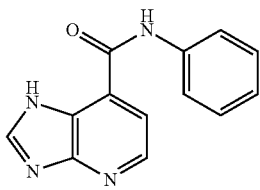 [SMILES: O=C(Nc1ccccc1)c1ccnc2nc[nH]c12]

N-phenyl-1H-imidazo[4,5-b]pyridine-7-carboxamide was made analogously to Example 95 using aniline in place of 3-ethynylaniline. C13H10N4O. 239.10 (M+1).

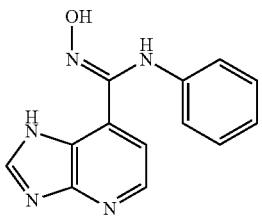 [SMILES: O/N=C(\Nc1ccccc1)c1ccnc2nc[nH]c12]

N'-hydroxy-N-phenyl-1H-imidazo[4,5-b]pyridine-7-carboximidamide. Example 100 was made analogously to Example 95 using N-phenyl-1H-imidazo[4,5-b]pyridine-7-carboxamide. $C_{13}H_{11}N_5O$. 254.10 $^1$H NMR (400 MHz, DMSO-$d_6$) δ 12.51 (s, 1H), 11.01 (s, 1H), 8.63 (s, 1H), 8.40 (d, J=1.1 Hz, 1H), 8.34-8.26 (m, 1H), 7.08-6.99 (m, 2H), 6.95 (dd, J=8.5, 7.3 Hz, 1H), 6.82-6.76 (m, 1H), 6.73-6.58 (m, 2H).

Example 101: N-(4-Fluoro-3-(trifluoromethoxy)phenyl)-N'-hydroxy-1H-imidazo[4,5-b]pyridine-7-carboximidamide

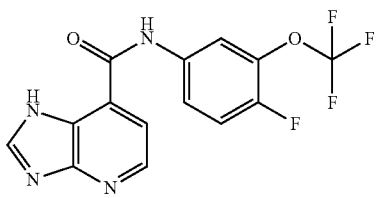 [SMILES: O=C(Nc1ccc(F)c(OC(F)(F)F)c1)c1ccnc2nc[nH]c12]

N-(4-fluoro-3-(trifluoromethoxy)phenyl)-1H-imidazo[4,5-b]pyridine-7-carboxamide was made analogously to Example 95 using 4-fluoro-3-(trifluoromethoxy)aniline in place of 3-ethynylaniline. $C_{14}H_8F_4N_4O_2$. 341.06 (M+1).

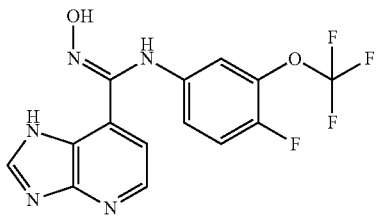 [SMILES: O/N=C(\Nc1ccc(F)c(OC(F)(F)F)c1)c1ccnc2nc[nH]c12]

N-(4-fluoro-3-(trifluoromethoxy)phenyl)-N'-hydroxy-1H-imidazo[4,5-b]pyridine-7-carboximidamide. Example 101 was made analogously to Example 95 using N-(4-fluoro-3-(trifluoromethoxy)phenyl)-1H-imidazo[4,5-b]pyridine-7-carboxamide. $C_{14}H_9F_4N_5O_2$. 355.07 (M+1). $^1$H NMR (400 MHz, DMSO-$d_6$) δ 11.26 (s, 1H), 9.10 (s, 1H), 8.77 (s, 1H), 8.45 (d, J=5.1 Hz, 1H), 7.30 (d, J=5.1 Hz, 1H), 7.24-7.10 (m, 1H), 6.76-6.70 (m, 2H).

Example 102: N-Hydroxy-N-(naphthalen-2-yl)-1H-imidazo[4,5-b]pyridine-7-carboximidamide

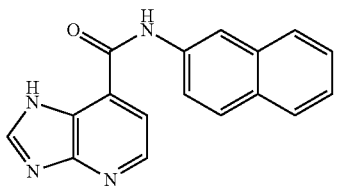 [SMILES: O=C(Nc1ccc2ccccc2c1)c1ccnc2nc[nH]c12]

N-(naphthalen-2-yl)-1H-imidazo[4,5-b]pyridine-7-carboxamide was made analogously to Example 95 using naphthalen-2-amine in place of 3-ethynylaniline. $C_{17}H_{12}N_4O$. 289.10 (M+1).

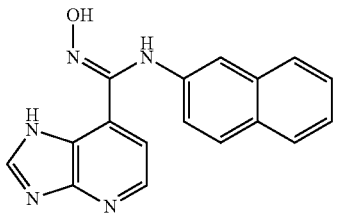 [SMILES: O/N=C(\Nc1ccc2ccccc2c1)c1ccnc2nc[nH]c12]

N-Hydroxy-N-(naphthalen-2-yl)-1H-imidazo[4,5-b]pyridine-7-carboximidamide (Example 102) and N-(3-chloronaphthalen-2-yl)-N'-hydroxy-1H-imidazo[4,5-b]pyridine-7-carboximidamide (Example 103) were made analogously to Example 95 using N-(naphthalen-2-yl)-1H-imidazo[4,5-b]pyridine-7-carboxamide give two products (N'-hydroxy-N-(naphthalen-2-yl)-1H-imidazo[4,5-b]pyridine-7-carboximidamide and N-(3-chloronaphthalen-2-yl)-N'-hydroxy-1H-imidazo[4,5-b]pyridine-7-carboximidamide). $C_{17}H_{13}N_5O$. 304.11 (M+1) and C17H12ClN5O. 338.11 (M+1).

Example 103: N-(3-Chloronaphthalen-2-yl)-N'-hydroxy-1H-imidazo[4,5-b]pyridine-7-carboximidamide

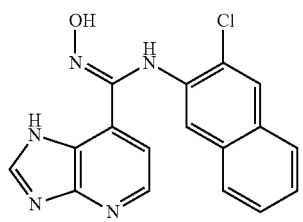 [SMILES: O/N=C(\Nc1cc2ccccc2cc1Cl)c1ccnc2nc[nH]c12]

N-(3-Chloronaphthalen-2-yl)-N'-hydroxy-1H-imidazo[4,5-b]pyridine-7-carboximidamide was prepared according to Example 102. $C_{17}H_{12}ClN_5O$. 338.11 (M+1).

Example 104: N'-hydroxy-N-(naphthalen-1-yl)-1H-imidazo[4,5-b]pyridine-7-carboximidamide

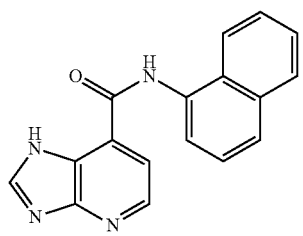 [SMILES: O=C(Nc1cccc2ccccc12)c1ccnc2nc[nH]c12]

N-(naphthalen-1-yl)-1H-imidazo[4,5-b]pyridine-7-carboxamide was made analogously to Example 95 using naphthalen-1-amine in place of 3-ethynylaniline. $C_{17}H_{12}N_4O$. 289.10 (M+1).

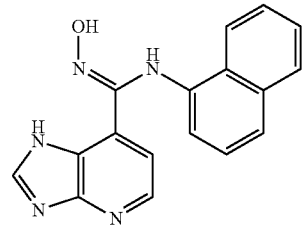 [SMILES: O/N=C(\Nc1cccc2ccccc12)c1ccnc2nc[nH]c12]

N'-hydroxy-N-(naphthalen-1-yl)-1H-imidazo[4,5-b]pyridine-7-carboximidamide (Example 104) and N-(4-chloronaphthalen-1-yl)-N'-hydroxy-1H-imidazo[4,5-b]pyridine-7-carboximidamide (Example 105) were made analogously to Example 95 using N-(naphthalen-1-yl)-1H-imidazo[4,5-b]pyridine-7-carboxamide give two products (N'-hydroxy-N-(naphthalen-1-yl)-1H-imidazo[4,5-b]pyridine-7-carboximidamide and N-(4-chloronaphthalen-1-yl)-N'-hydroxy-1H-imidazo[4,5-b]pyridine-7-carboximidamide). $C_{17}H_{13}N_5O$. 304.11 (M+1)

Example 105: N-(4-Chloronaphthalen-1-yl)-N'-hydroxy-1H-imidazo[4,5-b]pyridine-7-carboximidamide

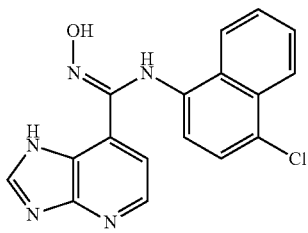 [SMILES: O/N=C(\Nc1ccc(Cl)c2ccccc12)c1ccnc2nc[nH]c12]

N-(4-Chloronaphthalen-1-yl)-N'-hydroxy-1H-imidazo[4,5-b]pyridine-7-carboximidamide. Example 105 was made analogously to Example 104. $C_{17}H_{12}ClN_5O$. 338.11 (M+1).

Example 106: N-(4-Fluoro-3-methoxyphenyl)-N'-hydroxy-1H-imidazo[4,5-b]pyridine-7-carboximidamide

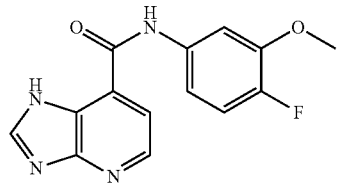 [SMILES: COc1cc(NC(=O)c2ccnc3nc[nH]c23)ccc1F]

N-(4-fluoro-3-methoxyphenyl)-1H-imidazo[4,5-b]pyridine-7-carboxamide was made analogously to Example 95 using 4-fluoro-3-methoxyaniline in place of 3-ethynylaniline. $C_{14}H_{11}FN_4O_2$. 286.09 (M+1).

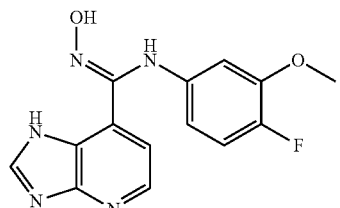

N-(4-fluoro-3-methoxyphenyl)-N'-hydroxy-1H-imidazo[4,5-b]pyridine-7-carboximidamide. Example 106 was made analogously to Example 95 using 4-fluoro-3-methoxyphenyl)-1H-imidazo[4,5-b]pyridine-7-carboxamide. $C_{14}H_{12}FN_5O_2$. 302.10 (M+1).

Example 107: N-(3-Chloro-4-fluorophenyl)-N'-hydroxy-2-methyl-1H-imidazo[4,5-b]pyridine-7-carboximidamide

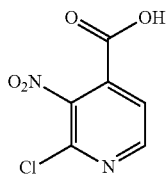 [SMILES: O=C(O)c1ccnc(Cl)c1[N+](=O)[O-]]

2-Chloro-3-nitroisonicotinic acid. To a solution of 2-chloro-4-methyl-3-nitropyridine (5.0 g, 29 mmol) in sulfuric acid (40 mL) was added potassium dichromate (11.3 g, 38.5 mmol) in portions over 20 min. The reaction was stirred at 60° C. overnight and poured onto ice. The water was washed with ethyl acetate three times and the combined organic layers were dried over sodium sulfate, filtered and concentrated to give the desired product. $C_6H_3ClN_2O_4$. 203.1 (M+1).

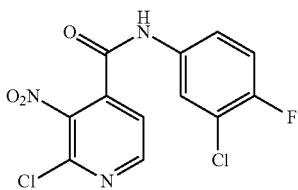 [SMILES: O=C(Nc1ccc(F)c(Cl)c1)c1ccnc(Cl)c1[N+](=O)[O-]]

2-Chloro-N-(3-chloro-4-fluorophenyl)-3-nitroisonicotinamide. To a solution of 3-chloro-4-fluoroaniline (3.84 g, 26.4 mmol), 2-chloro-3-nitroisonicotinic acid (5.34 g, 26.4 mmol) and triethylamine (11 mL, 79 mmol) in dichlormethane (100 mL) in an ice bath was added phosphoryl chloride (3.69 mL, 39.6 mmol). The ice bath was removed and the reaction stirred for 1 hr. Saturated sodium bicarbonate was added and the aqueous layer was washed three times with dichloromethane. The combined organic layers were dried over sodium sulfate, filtered and concentrated onto silica gel and purified by silica gel chromatography (0->100% ethyl acetate in dichloromethane) to give the desired product. $C_{12}H_6C_2FN_3O_3$ 330.0 (M+1).

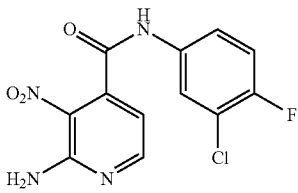 [SMILES: Nc1nccc(C(=O)Nc2ccc(F)c(Cl)c2)c1[N+](=O)[O-]]

2-Amino-N-(3-chloro-4-fluorophenyl)-3-nitroisonicotinamide. A mixture of 2-chloro-N-(3-chloro-4-fluorophenyl)-3-nitroisonicotinamide (4.78 g, 14.5 mmol) in ethanol (15 mL) and 28% ammonium hydroxide in water (14.1 mL, 101.4 mmol) was stirred in a closed vessel at 90° C. for 1.5 hr. The reaction mixture was cooled in an ice bath and the resulting precipitate filtered and washed with cold ethanol. Dried the solid on high vac to give desired product. $C_{12}H_8ClFN_4O_3$. 311.1 (M+1).

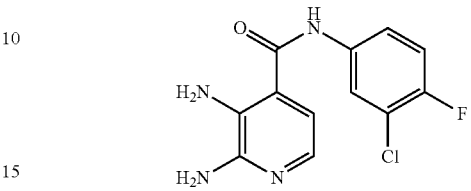

2,3-Diamino-N-(3-chloro-4-fluorophenyl)isonicotinamide. A mixture of 2-amino-N-(3-chloro-4-fluorophenyl)-3-nitroisonicotinamide (3.43 g, 11.0 mmol) and 10% Palladium on carbon (250 mg) in methanol (100 mL) was mixed in a Parr shaker at 40 psi hydrogen for 2 hr. Reaction was filtered and concentrated to give the desired product. $C_{12}H_{10}ClFN_4O$. 281.1 (M+1).

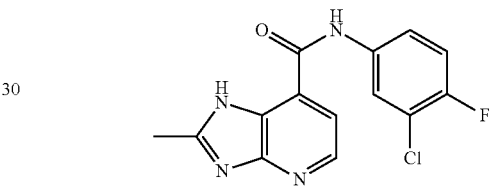

N-(3-Chloro-4-fluorophenyl)-2-methyl-1H-imidazo[4,5-b]pyridine-7-carboxamide. A mixture of 2,3-diamino-N-(3-chloro-4-fluorophenyl)isonicotinamide (1.06 g, 3.77 mmol) in acetic acid (11 mL) was stirred at 180° C. for 1 hr in a microwave. Water was added and the resulting precipitate was filtered and dried on high vac to give the desired product. $C_{14}H_{10}ClFN_4O$. 305.1 (M+1).

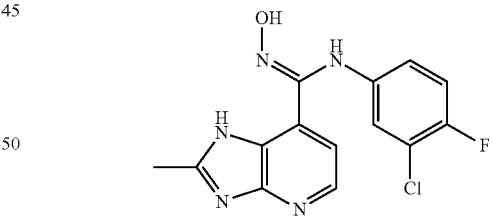

N-(3-chloro-4-fluorophenyl)-N'-hydroxy-2-methyl-1H-imidazo[4,5-b]pyridine-7-carboximidamide. A mixture of N-(3-Chloro-4-fluorophenyl)-2-methyl-1H-imidazo[4,5-b]pyridine-7-carboxamide (132 mg, 0.433 mmol), phosphorous pentachloride (135 mg, 0.650 mmol) in phosphoryl chloride (2 mL) and 1,2-dichloroethane (2 mL) were stirred at 80° C. for 2.5 hr. The reaction mixture was concentrated and suspended in ethanol (2 mL) and to this mixture was added 50% hydroxylamine in water (0.265 mL, 4.33 mmol). The reaction mixture stirred for 1 hr and was concentrated. The residue was purified by preparative HPLC to give the desired product. $C_{14}H_{11}ClFN_5O$. 320.0 (M+1).

Example 108: N-(3-Chloro-4-fluorophenyl)-2-ethyl-N'-hydroxy-1H-imidazo[4,5-b]pyridine-7-carboximidamide

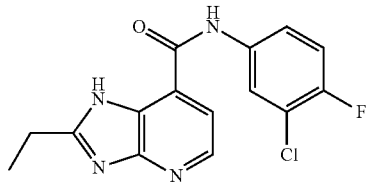 [SMILES: CCc1nc2nccc(C(=O)Nc3ccc(F)c(Cl)c3)c2[nH]1]

N-(3-chloro-4-fluorophenyl)-2-ethyl-1H-imidazo[4,5-b]pyridine-7-carboxamide was made analogously to Example 107 using propionic acid in place of acetic acid. $C_{15}H_{12}ClFN_4O$. 319.1 (M+1).

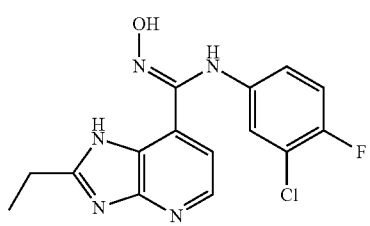 [SMILES: CCc1nc2nccc(/C(=N/O)Nc3ccc(F)c(Cl)c3)c2[nH]1]

N-(3-chloro-4-fluorophenyl)-2-ethyl-N'-hydroxy-1H-imidazo[4,5-b]pyridine-7-carboximidamide. Example 108 was made analogously to Example 107 using N-(3-chloro-4-fluorophenyl)-2-ethyl-1H-imidazo[4,5-b]pyridine-7-carboxamide in place of N-(3-Chloro-4-fluorophenyl)-2-methyl-1H-imidazo[4,5-b]pyridine-7-carboxamide. $C_{15}H_{13}ClFN_5O$. 334.1 (M+1).

Example 109: N-(3-Chloro-4-fluorophenyl)-2-cyclopropyl-N'-hydroxy-1H-imidazo[4,5-b]pyridine-7-carboximidamide

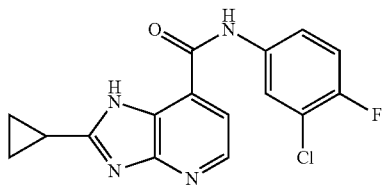 [SMILES: O=C(Nc1ccc(F)c(Cl)c1)c1ccnc2nc(C3CC3)[nH]c12]

N-(3-chloro-4-fluorophenyl)-2-cyclopropyl-1H-imidazo[4,5-b]pyridine-7-carboxamide was made analogously to Example 107 using cyclopropanecarboxylic acid in place of acetic acid. $C_{16}H_{12}ClFN_4O$. 331.1 (M+1).

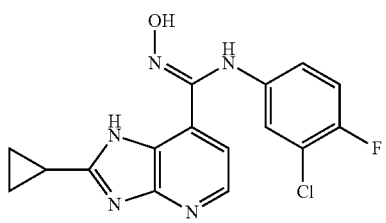 [SMILES: O/N=C(\Nc1ccc(F)c(Cl)c1)c1ccnc2nc(C3CC3)[nH]c12]

N-(3-chloro-4-fluorophenyl)-2-cyclopropyl-N'-hydroxy-1H-imidazo[4,5-b]pyridine-7-carboximidamide. Example 109 was made analogously to Example 107 using N-(3-chloro-4-fluorophenyl)-2-cyclopropyl-1H-imidazo[4,5-b]pyridine-7-carboxamide in place of N-(3-Chloro-4-fluorophenyl)-2-methyl-1H-imidazo[4,5-b]pyridine-7-carboxamide. $C_{16}H_{13}ClFN_5O$. 346.1 (M+1).

Example 110: N-(3-Chloro-4-fluorophenyl)-N'-hydroxy-2-(methoxymethyl)-1H-imidazo[4,5-b]pyridine-7-carboximidamide

N-(3-chloro-4-fluorophenyl)-2-(methoxymethyl)-1H-imidazo[4,5-b]pyridine-7-carboxamide was made analogously to Example 107 using methoxyacetic acid in place of acetic acid. $C_{15}H_{12}ClFN_4O_2$ 334.9 (M+1).

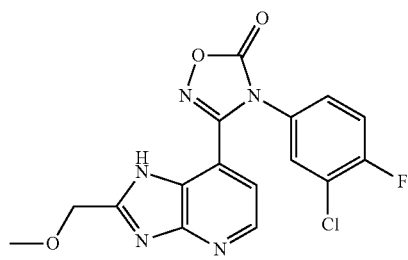 [SMILES: COCc1nc2nccc(-c3noc(=O)n3-c3ccc(F)c(Cl)c3)c2[nH]1]

4-(3-chloro-4-fluorophenyl)-3-(2-(methoxymethyl)-1H-imidazo[4,5-b]pyridin-7-yl)-1,2,4-oxadiazol-5(4H)-one. A mixture of N-(3-chloro-4-fluorophenyl)-2-(methoxymethyl)-1H-imidazo[4,5-b]pyridine-7-carboxamide (2.62 g, 7.82 mmol), phosphorous pentachloride (2.44 g, 11.7 mmol) in phosphoryl chloride (22 mL) and 1,2-dichloroethane (22 mL) were stirred at 80° C. for 2.5 hr. The reaction mixture was concentrated and suspended in ethanol (20 mL) and to this mixture was added 50% hydroxylamine in water (4.8 mL, 78 mmol). The reaction mixture stirred for 1 hr and was concentrated. Water and aqueous saturated sodium bicarbonate were added and the solid was filtered and dried on high vac. The solid was suspended in ethyl acetate (100 mL) and to this mixture was added carbonyldiimidazole (1.90 g, 11.7 mmol). The mixture was stirred for 18 hr and concentrated. The residue was purified by silica gel chromatography to give the desired product (871 mg). $C_{16}H_{11}ClFN_5O_3$. 376.3 (M+1).

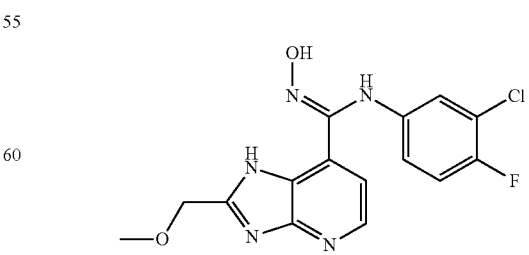

N-(3-chloro-4-fluorophenyl)-N'-hydroxy-2-(methoxymethyl)-1H-imidazo[4,5-b]pyridine-7-carboximidamide. Example 110 was made analogously to Example 95 using N-(3-chloro-4-fluorophenyl)-2-(methoxymethyl)-1H-imidazo[4,5-b]pyridine-7-carboxamide. $C_{15}H_{13}ClFN_5O_2$. 350.1 (M+1).

Example 111: 4-(3-Chloro-4-fluorophenyl)-3-(2-(hydroxymethyl)-1H-imidazo[4,5-b]pyridin-7-yl)-1,2,4-oxadiazol-5(4H)-one

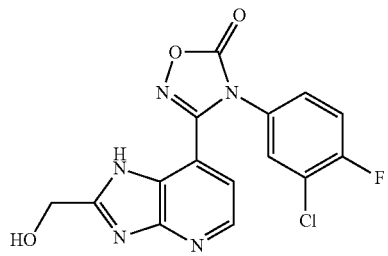 [SMILES: O=c1onc(-c2ccnc3nc(CO)[nH]c23)n1-c1ccc(F)c(Cl)c1]

To a mixture of 4-(3-chloro-4-fluorophenyl)-3-(2-(methoxymethyl)-1H-imidazo[4,5-b]pyridin-7-yl)-1,2,4-oxadiazol-5(4H)-one (400 mg, 1.07 mmol) in dichloromethane (8 mL) at 0° C. was added a solution of 1 M boron tribromide in dichloromethane (1.60 mL, 1.60 mmol). The reaction was allowed to warm to room temperature and stirred for 18 hr. The reaction mixture was diluted with dichloromethane and saturated sodium bicarbonate and the aqueous layer was washed three times with dichloromethane. The combined organic layers were dried over sodium sulfate, filtered, loaded onto silica gel column and purified by silica gel chromatography to give two product: 4-(3-chloro-4-fluorophenyl)-3-(2-(hydroxymethyl)-1H-imidazo[4,5-b]pyridin-7-yl)-1,2,4-oxadiazol-5(4H)-one (385 mg) and 3-(2-(bromomethyl)-1H-imidazo[4,5-b]pyridin-7-yl)-4-(3-chloro-4-fluorophenyl)-1,2,4-oxadiazol-5(4H)-one. $C_{15}H_9ClFN_5O_3$. 362.0 (M+1).

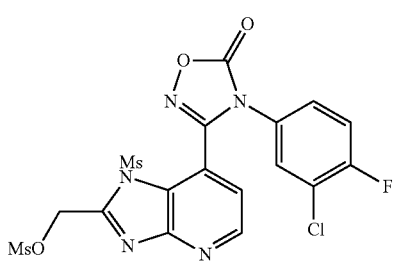

3-(2-(bromomethyl)-1H-imidazo[4,5-b]pyridin-7-yl)-4-(3-chloro-4-fluorophenyl)-1,2,4-oxadiazol-5(4H)-one. $C_{15}H_8BrClFN_5O_2$. 425.9 (M+1).

Example 112: N-(3-Chloro-4-fluorophenyl)-N'-hydroxy-2-(morpholinomethyl)-1H-imidazo[4,5-b]pyridine-7-carboximidamide (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate. To a solution of 4-(3-chloro-4-fluorophenyl)-3-(2-(hydroxymethyl)-1H-imidazo[4,5-b]pyridin-7-yl)-1,2,4-oxadiazol-5(4H)-one (510 mg, 1.41 mmol) and triethylamine (1.97 mL, 14.1 mmol) in dichlormethane (20 mL) at −78° C. was added methanesulfonyl chloride (0.548 mL, 7.05 mmol) dropwise over 10 min. The reaction mixture was warmed to 0° C. and stirred for 10 min. Water was added and the aqueous layer was washed three times with ethyl acetate. The combined organic layers were dried over sodium sulfate, filtered and concentrated. The residue was purified by silica gel chromatography to give two product: (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate (440 mg) and 4-(3-chloro-4-fluorophenyl)-3-(2-(chloromethyl)-1-(methylsulfonyl)-1H-imidazo[4,5-b]pyridin-7-yl)-1,2,4-oxadiazol-5(4H)-one. $C_{17}H_{13}ClFN_5O_7S_2$. 518.2 (M+1).

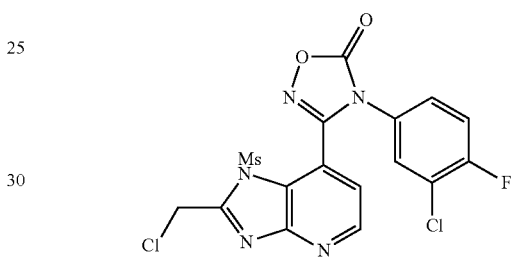

4-(3-chloro-4-fluorophenyl)-3-(2-(chloromethyl)-1-(methylsulfonyl)-1H-imidazo[4,5-b]pyridin-7-yl)-1,2,4-oxadiazol-5(4H)-one was prepared from the above reaction. $C_{16}H_{10}Cl_2FN_5O_4S$. 458.0 (M+1).

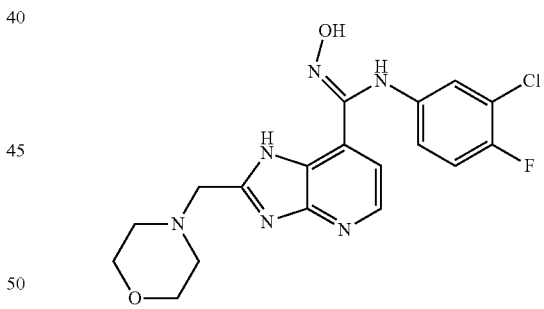

N-(3-chloro-4-fluorophenyl)-N'-hydroxy-2-(morpholinomethyl)-1H-imidazo[4,5-b]pyridine-7-carboximidamide. A solution of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate (27 mg, 0.052 mmol) and morpholine (0.10 mL, 1.1 mmol) in acetonitrile (1 mL) was stirred at 65° C. for 10 min. The reaction was concentrated. The residue was brought up in tetrahydrofuran (0.5 mL) and water (0.5 mL). To this solution was added 2 N sodium hydroxide (0.39 mL, 0.78 mmol) and the reaction mixture stirred for 10 min. To the mixture was added acetic acid (0.05 mL) and the solution was loaded directly onto a prep HPLC for purification to give the desired product. $C_{18}H_{18}ClFN_6O_2$. 405.1 (M+1).

Example 113: N-(3-Chloro-4-fluorophenyl)-2-((dimethylamino)methyl)-N'-hydroxy-1H-imidazo[4,5-b]pyridine-7-carboximidamide

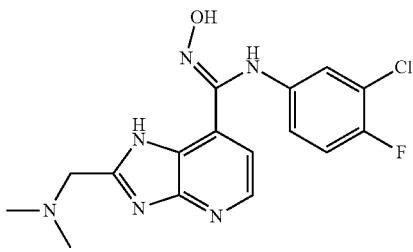 [SMILES: CN(C)Cc1nc2nccc(/C(=N/O)Nc3ccc(F)c(Cl)c3)c2[nH]1]

N-(3-chloro-4-fluorophenyl)-2-((dimethylamino)methyl)-N'-hydroxy-1H-imidazo[4,5-b]pyridine-7-carboximidamide. A solution of 4-(3-chloro-4-fluorophenyl)-3-(2-(chloromethyl)-1-(methylsulfonyl)-1H-imidazo[4,5-b]pyridin-7-yl)-1,2,4-oxadiazol-5(4H)-one (30 mg, 0.065 mmol) and dimethylamine (2 M in THF, 0.655 mL, 1.3 mmol) in acetonitrile (1 mL) was stirred at 65° C. for 3 hr min. The reaction was concentrated. The residue was brought up in tetrahydrofuran (0.5 mL) and water (0.5 mL). To this solution was added 2 N sodium hydroxide (0.39 mL, 0.78 mmol) and the reaction mixture stirred for 10 min. To the mixture was added acetic acid (0.05 mL) and the solution was loaded directly onto a prep HPLC for purification to give the desired product (12 mg). $C_{16}H_{16}ClFN_6O$. 363.1 (M+1).

Example 114: N-(3-Chloro-4-fluorophenyl)-2-((ethylamino)methyl)-N'-hydroxy-1H-imidazo[4,5-b]pyridine-7-carboximidamide

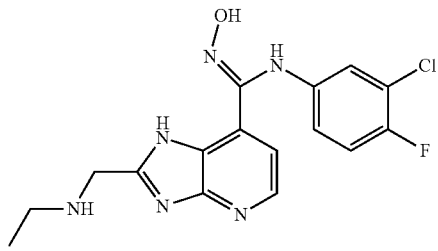 [SMILES: CCNCc1nc2nccc(/C(=N/O)Nc3ccc(F)c(Cl)c3)c2[nH]1]

N-(3-chloro-4-fluorophenyl)-2-((ethylamino)methyl)-N'-hydroxy-1H-imidazo[4,5-b]pyridine-7-carboximidamide. Example 114 was made analogously to Example 112 using 2 M ethylamine in THF in place of morpholine. $C_{16}H_{16}ClFN_6O$. 363.1 (M+1). $^1$H NMR (400 MHz, DMSO-$d_6$) δ 12.76 (s, 1H), 11.16 (s, 1H), 9.29 (s, 2H), 8.96 (s, 1H), 8.38 (d, J=5.0 Hz, 1H), 7.41-6.99 (m, 2H), 6.92 (dd, J=6.5, 2.7 Hz, 1H), 6.51 (d, J=8.7 Hz, 1H), 4.47 (s, 2H), 3.08 (s, 2H), 1.23 (t, J=7.3 Hz, 3H).

Example 115: 2-((Benzylamino)methyl)-N-(3-chloro-4-fluorophenyl)-N'-hydroxy-1H-imidazo[4,5-b]pyridine-7-carboximidamide

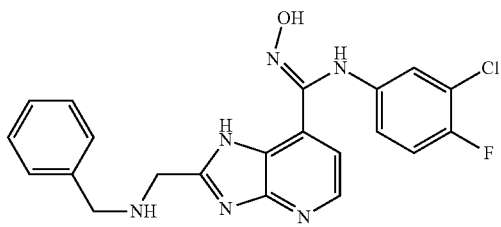

2-((benzylamino)methyl)-N-(3-chloro-4-fluorophenyl)-N'-hydroxy-1H-imidazo[4,5-b]pyridine-7-carboximidamide. Example 115 was made analogously to Example 112 using benzylamine in place of morpholine. $C_{21}H_{18}ClFN_6O$. 425.1 (M+1).

Example 116: N-(3-Chloro-4-fluorophenyl)-N'-hydroxy-2-((isopropylamino)methyl)-1H-imidazo[4,5-b]pyridine-7-carboximidamide

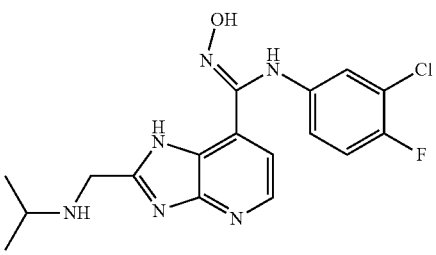 [SMILES: CC(C)NCc1nc2nccc(/C(=N/O)Nc3ccc(F)c(Cl)c3)c2[nH]1]

N-(3-chloro-4-fluorophenyl)-N'-hydroxy-2-((isopropylamino)methyl)-1H-imidazo[4,5-b]pyridine-7-carboximidamide. Example 116 was made analogously to Example 112 using isopropylamine in place of morpholine. $C_{17}H_{18}ClFN_6O$. 377.1 (M+1). $^1$H NMR (400 MHz, DMSO-$d_6$) δ 11.18 (s, 1H), 9.28 (s, 2H), 8.96 (s, 1H), 8.38 (d, J=5.0 Hz, 1H), 7.24-6.96 (m, 2H), 6.91 (dd, J=6.5, 2.7 Hz, 1H), 6.51 (s, 1H), 4.48 (s, 2H), 3.56-3.28 (m, 1H), 1.37-1.15 (m, 6H).

Example 117: N-(3-Chloro-4-fluorophenyl)-2-(((cyclopropylmethyl)amino)methyl)-N'-hydroxy-1H-imidazo[4,5-b]pyridine-7-carboximidamide

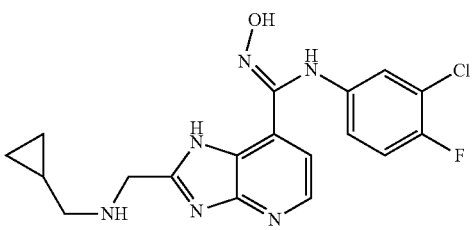 [SMILES: O/N=C(\Nc1ccc(F)c(Cl)c1)c1ccnc2nc(CNCC3CC3)[nH]c12]

N-(3-chloro-4-fluorophenyl)-2-(((cyclopropylmethyl)amino)methyl)-N'-hydroxy-1H-imidazo[4,5-b]pyridine-7-carboximidamide. Example 117 was made analogously to Example 112 using cyclopropylmethylamine in place of morpholine. $C_{18}H_{18}ClFN_6O$. 388.9 (M+1). $^1$H NMR (400 MHz, DMSO-$d_6$) δ 11.14 (s, 1H), 9.41 (s, 2H), 8.95 (s, 1H), 8.38 (d, J=5.0 Hz, 1H), 7.28-6.98 (m, 2H), 6.91 (dd, J=6.5, 2.7 Hz, 1H), 6.52 (ddd, J=9.0, 4.0, 2.8 Hz, 1H), 4.50 (s, 2H), 2.96 (s, 2H), 1.17-0.92 (m, 1H), 0.68-0.48 (m, 2H), 0.42-0.24 (m, 2H).

Example 118: N-(3-Chloro-4-fluorophenyl)-N'-hydroxy-2-(((2,2,2-trifluoroethyl)amino)methyl)-1H-imidazo[4,5-b]pyridine-7-carboximidamide

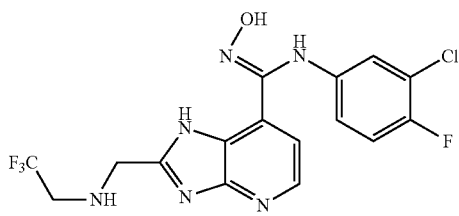 [SMILES: O/N=C(\Nc1ccc(F)c(Cl)c1)c1ccnc2nc(CNCC(F)(F)F)[nH]c12]

N-(3-chloro-4-fluorophenyl)-2-(((cyclopropylmethyl)amino)methyl)-N'-hydroxy-1H-imidazo[4,5-b]pyridine-7-carboximidamide. Example 118 was made analogously to Example 112 using 2,2,2-trifluoroethylamine in place of morpholine. $C_{16}H_{13}ClF_4N_6O$. 416.7 (M+1).

Example 119: N-(3-Chloro-4-fluorophenyl)-2-((cyclopropylamino)methyl)-N'-hydroxy-1H-imidazo[4,5-b]pyridine-7-carboximidamide

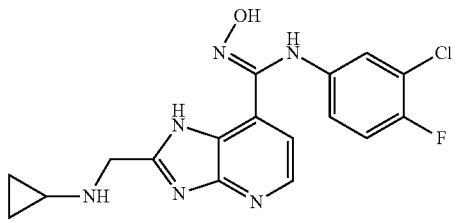 [SMILES: O/N=C(\Nc1ccc(F)c(Cl)c1)c1ccnc2nc(CNC3CC3)[nH]c12]

N-(3-chloro-4-fluorophenyl)-2-((cyclopropylamino)methyl)-N'-hydroxy-1H-imidazo[4,5-b]pyridine-7-carboximidamide. Example 119 was made analogously to Example 112 using cyclopropylamine in place of morpholine. $C_{17}H_{16}ClFN_6O$. 374.9 (M+1).

Example 120: N-(3-Chloro-4-fluorophenyl)-N'-hydroxy-2-(((3-methoxypropyl)amino)methyl)-1H-imidazo[4,5-b]pyridine-7-carboximidamide

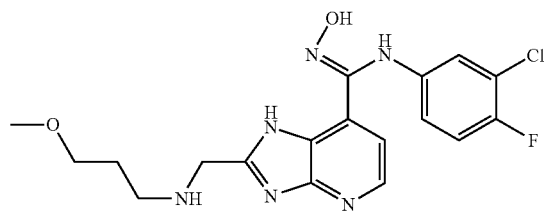 [SMILES: COCCCNCc1nc2nccc(/C(=N/O)Nc3ccc(F)c(Cl)c3)c2[nH]1]

N-(3-chloro-4-fluorophenyl)-N'-hydroxy-2-(((3-methoxypropyl)amino)methyl)-1H-imidazo[4,5-b]pyridine-7-carboximidamide. Example 120 was made analogously to Example 112 using 3-methoxypropylamine in place of morpholine. $C_{18}H_{20}ClFN_6O_2$. 407.1 (M+1).

Example 121: N-(3-Chloro-4-fluorophenyl)-N'-hydroxy-2-(((pyridin-2-ylmethyl)amino)methyl)-1H-imidazo[4,5-b]pyridine-7-carboximidamide

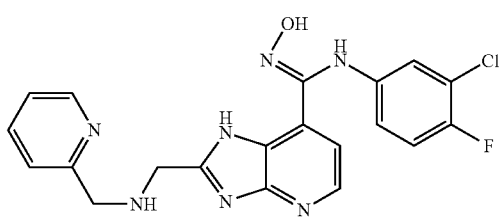 [SMILES: O/N=C(\Nc1ccc(F)c(Cl)c1)c1ccnc2nc(CNCc3ccccn3)[nH]c12]

N-(3-chloro-4-fluorophenyl)-N'-hydroxy-2-(((pyridin-2-ylmethyl)amino)methyl)-1H-imidazo[4,5-b]pyridine-7-carboximidamide. Example 121 was made analogously to Example 112 using pyridin-2-ylmethanamine in place of morpholine. $C_{20}H_{17}ClFN_7O$. 426.1 (M+1).

Example 122: N-(3-Chloro-4-fluorophenyl)-N'-hydroxy-2-(((3-methoxypropyl)(methyl)amino)methyl)-1H-imidazo[4,5-b]pyridine-7-carboximidamide

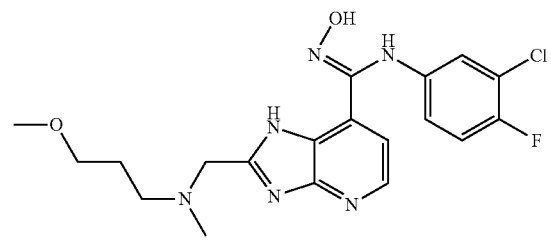 [SMILES: COCCCN(C)Cc1nc2nccc(/C(=N/O)Nc3ccc(F)c(Cl)c3)c2[nH]1]

N-(3-chloro-4-fluorophenyl)-N'-hydroxy-2-(((3-methoxypropyl)(methyl)amino)methyl)-1H-imidazo[4,5-b]pyridine-7-carboximidamide. Example 122 was made analogously to Example 112 using 3-(2-(bromomethyl)-1H-imidazo[4,5-b]pyridin-7-yl)-4-(3-chloro-4-fluorophenyl)-1,2,4-oxadiazol-5(4H)-one and 3-methoxy-N-methylpropan-1-amine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine. $C_{19}H_{22}ClFN_6O_2$. 421.2 (M+1).

Example 123: N-(3-Chloro-4-fluorophenyl)-N'-hydroxy-2-(((2-methoxybenzyl)amino)methyl)-1H-imidazo[4,5-b]pyridine-7-carboximidamide

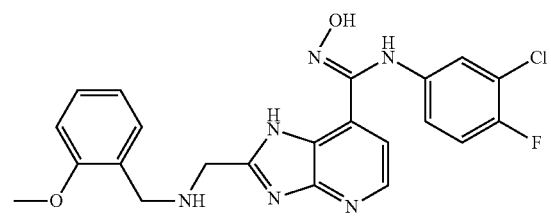 [SMILES: COc1ccccc1CNCc1nc2nccc(/C(=N/O)Nc3ccc(F)c(Cl)c3)c2[nH]1]

N-(3-chloro-4-fluorophenyl)-N'-hydroxy-2-(((2-methoxybenzyl)amino)methyl)-1H-imidazo[4,5-b]pyridine-7-carboximidamide. Example 123 was made analogously to Example 112 using 4-(3-chloro-4-fluorophenyl)-3-(2-(chloromethyl)-1-(methylsulfonyl)-1H-imidazo[4,5-b]pyridin-7-yl)-1,2,4-oxadiazol-5(4H)-one and 2-methoxybenzylamine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine. $C_{22}H_{20}ClFN_6O_2$. 455.1 (M+1).

Example 124: N-(3-Chloro-4-fluorophenyl)-N'-hydroxy-2-(((2-methoxyethyl)amino)methyl)-1H-imidazo[4,5-b]pyridine-7-carboximidamide

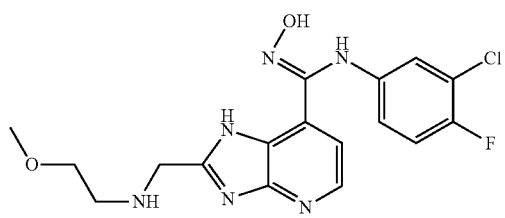 [SMILES: COCCNCc1nc2nccc(/C(=N/O)Nc3ccc(F)c(Cl)c3)c2[nH]1]

N-(3-chloro-4-fluorophenyl)-N'-hydroxy-2-(((2-methoxyethyl)amino)methyl)-1H-imidazo[4,5-b]pyridine-7-carboximidamide. Example 124 was made analogously to Example 112 using 2-methoxyethylamine in place of morpholine. $C_{17}H_{18}ClFN_6O_2$. 393.1 (M+1).

Example 125: N-(3-Chloro-4-fluorophenyl)-N'-hydroxy-2-(((2-(pyridin-2-yl)ethyl)amino)methyl)-1H-imidazo[4,5-b]pyridine-7-carboximidamide

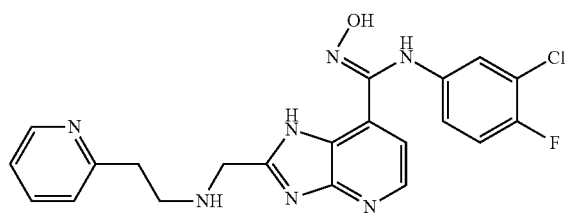 [SMILES: O/N=C(\Nc1ccc(F)c(Cl)c1)c1ccnc2nc(CNCCc3ccccn3)[nH]c12]

N-(3-chloro-4-fluorophenyl)-N'-hydroxy-2-(42-(pyridin-2-yl)ethyl)amino)methyl)-1H-imidazo[4,5-b]pyridine-7-carboximidamide. Example 125 was made analogously to Example 112 using 2-(pyridin-2-yl)ethanamine in place of morpholine. $C_{21}H_{19}ClFN_7O$. 440.1 (M+1).

Example 126: N-(3-Chloro-4-fluorophenyl)-N'-hydroxy-2-(((pyridin-3-ylmethyl)amino)methyl)-1H-imidazo[4,5-b]pyridine-7-carboximidamide

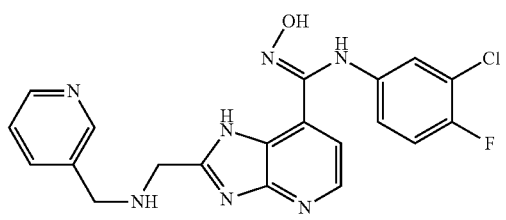 [SMILES: O/N=C(\Nc1ccc(F)c(Cl)c1)c1ccnc2nc(CNCc3cccnc3)[nH]c12]

N-(3-chloro-4-fluorophenyl)-N'-hydroxy-2-(((pyridin-3-ylmethyl)amino)methyl)-1H-imidazo[4,5-b]pyridine-7-carboximidamide. Example 126 was made analogously to Example 112 using 3-picolylamine in place of morpholine. $C_{20}H_{17}ClFN_7O$. 426.1 (M+1).

Example 127: N-(3-Chloro-4-fluorophenyl)-N'-hydroxy-2-((((tetrahydro-2H-pyran-2-yl)methyl)amino)methyl)-1H-imidazo[4,5-b]pyridine-7-carboximidamide

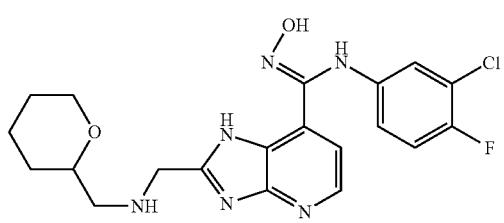 [SMILES: O/N=C(\Nc1ccc(F)c(Cl)c1)c1ccnc2nc(CNCC3CCCCO3)[nH]c12]

N-(3-chloro-4-fluorophenyl)-N'-hydroxy-2-((((tetrahydro-2H-pyran-2-yl)methyl)amino)methyl)-1H-imidazo[4,5-b]pyridine-7-carboximidamide. Example 127 was made analogously to Example 112 using 4-(3-chloro-4-fluorophenyl)-3-(2-(chloromethyl)-1-(methylsulfonyl)-1H-imidazo[4,5-b]pyridin-7-yl)-1,2,4-oxadiazol-5(4H)-one and (tetrahydro-2H-pyran-2-yl)methanamine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine. $C_{20}H_{22}ClFN_6O_2$. 433.1 (M+1).

Example 128: N-(3-Chloro-4-fluorophenyl)-N'-hydroxy-2-((phenylamino)methyl)-1H-imidazo[4,5-b]pyridine-7-carboximidamide

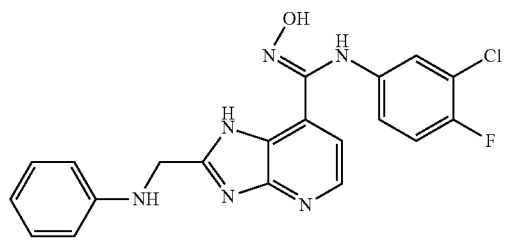 [SMILES: O/N=C(\Nc1ccc(F)c(Cl)c1)c1ccnc2nc(CNc3ccccc3)[nH]c12]

A solution of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate (14 mg, 0.027 mmol) and aniline (0.025 mL, 0.27 mmol) in acetonitrile (1 mL) was stirred at 65° C. for 18 hr. To the solution was added isopropylamine (0.1 mL) and the reaction stirred at 65° C. for 5 min. The reaction was concentrated. The residue was brought up in tetrahydrofuran (0.3 mL) and water (0.3 mL). To this solution was added 2 N sodium hydroxide (0.2 mL, 0.41 mmol) and the reaction mixture stirred for 10 min. To the mixture was added acetic acid (0.05 mL) and the solution was loaded directly onto a prep HPLC for purification to give the desired product. $C_{20}H_{16}ClFN_6O$. 411.1 (M+1).

Example 129: N-(3-Chloro-4-fluorophenyl)-N'-hydroxy-2-((((tetrahydro-2H-pyran-3-yl)methyl)amino)methyl)-1H-imidazo[4,5-b]pyridine-7-carboximidamide

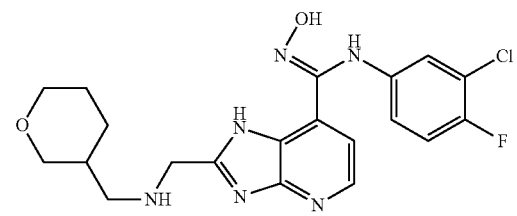 [SMILES: O/N=C(\Nc1ccc(F)c(Cl)c1)c1ccnc2nc(CNCC3CCCOC3)[nH]c12]

N-(3-chloro-4-fluorophenyl)-N'-hydroxy-2-((((tetrahydro-2H-pyran-3-yl)methyl)amino)methyl)-1H-imidazo[4,5-b]pyridine-7-carboximidamide. Example 129 was made analogously to Example 112 using (tetrahydro-2H-pyran-3-yl)methanamine in place of morpholine. $C_{20}H_{22}ClFN_6O_2$. 433.1 (M+1).

Example 130: N-(3-Chloro-4-fluorophenyl)-N'-hydroxy-2-(((pyrimidin-2-ylmethyl)amino)methyl)-1H-imidazo[4,5-b]pyridine-7-carboximidamide

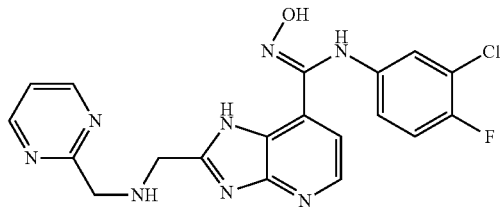 [SMILES: O/N=C(\Nc1ccc(F)c(Cl)c1)c1ccnc2nc(CNCc3ncccn3)[nH]c12]

N-(3-chloro-4-fluorophenyl)-N'-hydroxy-2-(((pyrimidin-2-ylmethyl)amino)methyl)-1H-imidazo[4,5-b]pyridine-7-carboximidamide. Example 130 was made analogously to Example 112 using pyrimidin-2-ylmethanamine in place of morpholine. $C_{19}H_{16}ClFN_8O$. 427.1 (M+1).

Example 131: N-(3-Chloro-4-fluorophenyl)-N'-hydroxy-2-(((3-morpholinopropyl)amino)methyl)-1H-imidazo[4,5-b]pyridine-7-carboximidamide

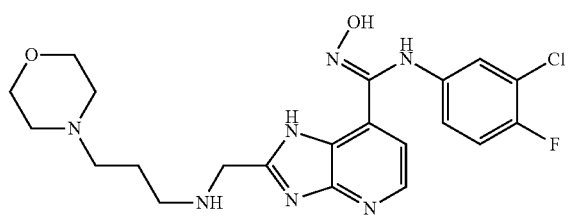 [SMILES: O/N=C(\Nc1ccc(F)c(Cl)c1)c1ccnc2nc(CNCCCN3CCOCC3)[nH]c12]

Example 131 was made analogously to Example 112 using 3-morpholinopropan-1-amine in place of morpholine. $C_{21}H_{25}ClFN_7O_2$. 462.2 (M+1).

Example 132: N-(3-Chloro-4-fluorophenyl)-N'-hydroxy-2-(((tetrahydro-2H-pyran-4-yl)amino)methyl)-1H-imidazo[4,5-b]pyridine-7-carboximidamide

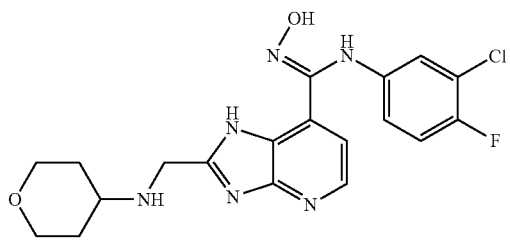 [SMILES: O/N=C(\Nc1ccc(F)c(Cl)c1)c1ccnc2nc(CNC3CCOCC3)[nH]c12]

Example 132 was made analogously to Example 112 using 4-(3-chloro-4-fluorophenyl)-3-(2-(chloromethyl)-1-(methylsulfonyl)-1H-imidazo[4,5-b]pyridin-7-yl)-1,2,4-oxadiazol-5(4H)-one and tetrahydro-2H-pyran-4-amine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine. $C_{19}H_{20}ClFN_6O_2$. 419.1 (M+1).

Example 133: N-(3-Chloro-4-fluorophenyl)-N'-hydroxy-2-(((pyridin-4-ylmethyl)amino)methyl)-1H-imidazo[4,5-b]pyridine-7-carboximidamide

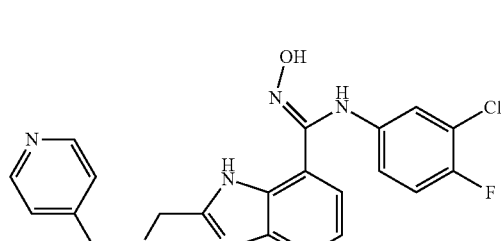

Example 133 was made analogously to Example 112 using 4-picolylamine in place of morpholine. $C_{20}H_{17}ClFN_7O$. 426.1 (M+1).

Example 134: N-(3-Chloro-4-fluorophenyl)-N'-hydroxy-2-(((pyrazin-2-ylmethyl)amino)methyl)-1H-imidazo[4,5-b]pyridine-7-carboximidamide

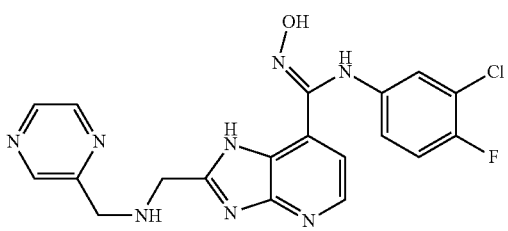 [SMILES: O/N=C(\Nc1ccc(F)c(Cl)c1)c1ccnc2nc(CNCc3cnccn3)[nH]c12]

Example 134 was made analogously to Example 112 using pyrazin-2-ylmethanamine in place of morpholine. $C_{19}H_{16}ClFN_8O$. 427.1 (M+1).

Example 135: N-(3-Chloro-4-fluorophenyl)-N'-hydroxy-2-((((tetrahydrofuran-3-yl)methyl)amino)methyl)-1H-imidazo[4,5-b]pyridine-7-carboximidamide

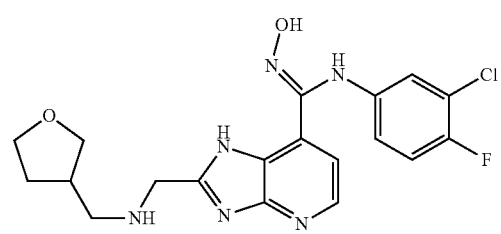 [SMILES: O/N=C(\Nc1ccc(F)c(Cl)c1)c1ccnc2nc(CNCC3CCOC3)[nH]c12]

Example 135 was made analogously to Example 112 using 4-(3-chloro-4-fluorophenyl)-3-(2-(chloromethyl)-1-(methylsulfonyl)-1H-imidazo[4,5-b]pyridin-7-yl)-1,2,4-oxadiazol-5(4H)-one and (tetrahydrofuran-3-yl)methanamine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine. $C_{19}H_{20}ClFN_6O_2$. 419.1 (M+1).

Example 136: N-(3-Chloro-4-fluorophenyl)-2-(((2-(dimethylamino)ethyl)amino)methyl)-N'-hydroxy-1H-imidazo[4,5-b]pyridine-7-carboximidamide

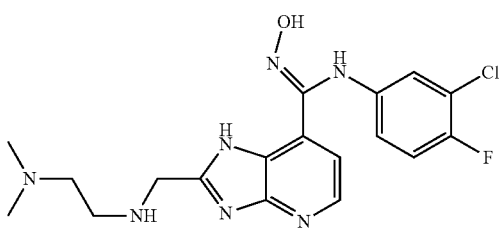 [SMILES: CN(C)CCNCc1nc2nccc(/C(=N/O)Nc3ccc(F)c(Cl)c3)c2[nH]1]

Example 136 was made analogously to Example 112 using N,N-dimethylethane-1,2-diamine in place of morpholine. $C_{18}H_{21}ClFN_7O$. 406.1 (M+1).

Example 137: N-(3-Chloro-4-fluorophenyl)-N'-hydroxy-2-(((2-(pyrimidin-2-yl)ethyl)amino)methyl)-1H-imidazo[4,5-b]pyridine-7-carboximidamide

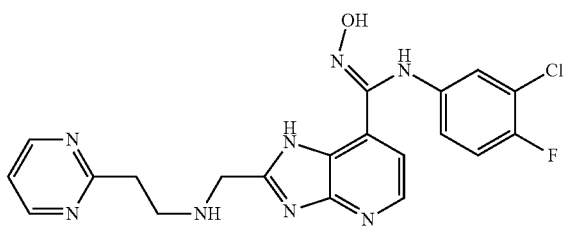 [SMILES: O/N=C(\Nc1ccc(F)c(Cl)c1)c1ccnc2nc(CNCCc3ncccn3)[nH]c12]

Example 137 was made analogously to Example 112 using 2-(pyrimidin-2-yl)ethanamine in place of morpholine. $C_{20}H_{18}ClFN_8O$. 441.1 (M+1).

Example 138: N-(3-Chloro-4-fluorophenyl)-N'-hydroxy-2-(((3-hydroxypropyl)amino)methyl)-1H-imidazo[4,5-b]pyridine-7-carboximidamide

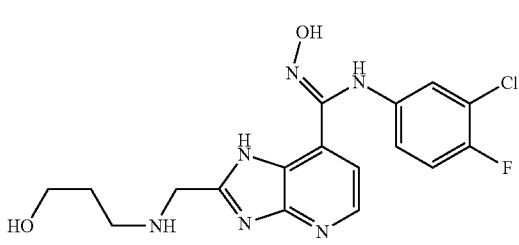 [SMILES: OCCCNCc1nc2nccc(/C(=N/O)Nc3ccc(F)c(Cl)c3)c2[nH]1]

Example 138 was made analogously to Example 112 using 3-aminopropanol in place of morpholine. $C_{17}H_{18}ClFN_6O_2$. 393.1 (M+1).

Example 139: N-(3-Chloro-4-fluorophenyl)-N'-hydroxy-2-(pyrrolidin-1-ylmethyl)-1H-imidazo[4,5-b]pyridine-7-carboximidamide

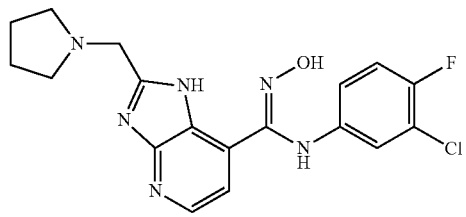 [SMILES: O/N=C(\Nc1ccc(F)c(Cl)c1)c1ccnc2nc(CN3CCCC3)[nH]c12]

Example 139 was synthesized analogously to Example 112 using pyrrolidine in place of morpholine. $C_{18}H_{18}ClFN_6O$. 389.1 [M+1]$^+$.

Example 140: N-(3-Chloro-4-fluorophenyl)-N'-hydroxy-2-(piperidin-1-ylmethyl)-1H-imidazo[4,5-b]pyridine-7-carboximidamide

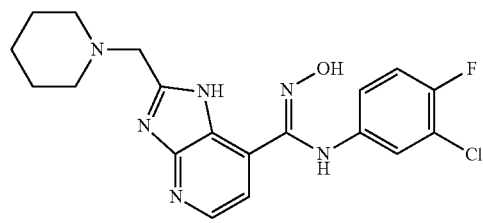 [SMILES: O/N=C(\Nc1ccc(F)c(Cl)c1)c1ccnc2nc(CN3CCCCC3)[nH]c12]

Example 140 was synthesized analogously to Example 112 using piperidine in place of morpholine. $C_{19}H_{20}ClFN_6O$. 403.1 [M+1]$^+$.

Example 141: N-(3-Chloro-4-fluorophenyl)-N'-hydroxy-2-((neopentylamino)methyl)-1H-imidazo[4,5-b]pyridine-7-carboximidamide

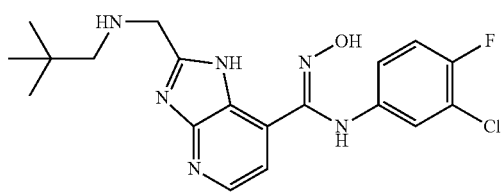 [SMILES: CC(C)(C)CNCc1nc2nccc(/C(=N/O)Nc3ccc(F)c(Cl)c3)c2[nH]1]

Example 141 was synthesized analogously to Example 112 using 3-(2-(bromomethyl)-1H-imidazo[4,5-b]pyridin-7-yl)-4-(3-chloro-4-fluorophenyl)-1,2,4-oxadiazol-5(4H)-one and 2,2-dimethylpropan-1-amine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine, respectively. $C_{19}H_{22}ClFN_6O$. 405.2 [M+1]$^+$.

Example 142: N-(3-Chloro-4-fluorophenyl)-2-(((2,2-difluoroethyl)amino)methyl)-N'-hydroxy-1H-imidazo[4,5-b]pyridine-7-carboximidamide

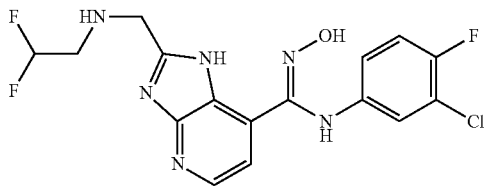 [SMILES: O/N=C(\Nc1ccc(F)c(Cl)c1)c1ccnc2nc(CNCC(F)F)[nH]c12]

Example 142 was synthesized analogously to Example 112 using 3-(2-(bromomethyl)-1H-imidazo[4,5-b]pyridin-7-yl)-4-(3-chloro-4-fluorophenyl)-1,2,4-oxadiazol-5(4H)-one and 2,2-difluoroethylamine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine, respectively. $C_{16}H_{14}ClF_3N_6O$. 399.1 [M+1]$^+$.

Example 143: N-(3-Chloro-4-fluorophenyl)-N'-hydroxy-2-(((3-hydroxy-2,2-dimethylpropyl)amino)methyl)-1H-imidazo[4,5-b]pyridine-7-carboximidamide

Example 143 was synthesized analogously to Example 112 using 3-(2-(bromomethyl)-1H-imidazo[4,5-b]pyridin-7-yl)-4-(3-chloro-4-fluorophenyl)-1,2,4-oxadiazol-5(4H)-one and 3-amino-2,2-dimethylpropan-1-ol in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine, respectively. $C_{19}H_{22}ClFN_6O_2$. 421.2 [M+1]$^+$.

Example 144: N-(3-Chloro-4-fluorophenyl)-N'-hydroxy-2-(((thiazol-2-ylmethyl)amino)methyl)-1H-imidazo[4,5-b]pyridine-7-carboximidamide

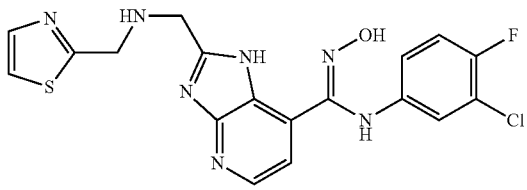 [SMILES: O/N=C(\Nc1ccc(F)c(Cl)c1)c1ccnc2nc(CNCc3nccs3)[nH]c12]

Example 144 was synthesized analogously to Example 112 using 3-(2-(bromomethyl)-1H-imidazo[4,5-b]pyridin-7-yl)-4-(3-chloro-4-fluorophenyl)-1,2,4-oxadiazol-5(4H)-one and thiazol-2-ylmethanamine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine, respectively. $C_{18}H_{15}ClFN_7OS$. 432.1 [M+1]$^+$.

Example 145: N-((7-(N-(3-Chloro-4-fluorophenyl)-N'-hydroxycarbamimidoyl)-1H-imidazo[4,5-b]pyridin-2-yl)methyl)acetamide

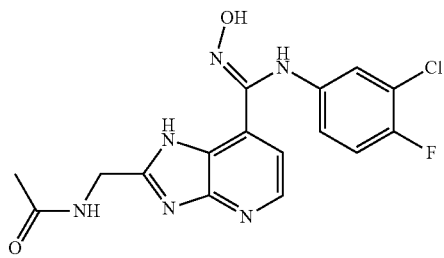 [SMILES: CC(=O)NCc1nc2nccc(/C(=N/O)Nc3ccc(F)c(Cl)c3)c2[nH]1]

A solution of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate (17 mg, 0.033 mmol) and 0.5 M ammonia in dioxane (1.44 mL, 0.722 mmol) in acetonitrile (1 mL) was stirred at 65° C. for 30 min. The reaction was concentrated. The residue was brought up in tetrahydrofuran (0.5 mL) and to this solution was added triethylamine (0.021 mL, 0.15 mmol) and acetyl chloride (0.003 mL, 0.045 mmol. The reaction stirred for 3 hr and, then, more acetyl chloride (0.003 mL, 0.045 mmol) was added. The reaction stirred for 2 hr and was concentrated. The residue was brought up in tetrahydrofuran (0.3 mL) and water (0.3 mL). To this solution was added 2 N sodium hydroxide (0.22 mL, 0.44 mmol) and the reaction mixture stirred for 10 min. To the mixture was added acetic acid (0.05 mL) and the solution was loaded directly onto a prep HPLC for purification to give the desired product. $C_{16}H_{14}ClFN_6O_2$. 377.1 (M+1).

Example 146: N-(3-Chloro-4-fluorophenyl)-N'-hydroxy-2-(thiophen-2-yl)-1H-imidazo[4,5-b]pyridine-7-carboximidamide

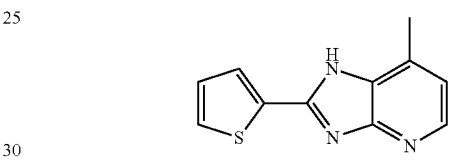

Methyl-2-(thiophen-2-yl)-1H-imidazo[4,5-b]pyridine. A solution of 4-methyl-3-nitropyridin-2-amine (400 mg, 2.61 mmol), thiophene-2-carbaldehyde (449 mg, 3.92 mmol) and sodium hydrosulfite (1.61 g, 7.84 mmol) in dimethyl sulfoxide (5 mL) and ethanol (5 mL) were stirred at 90° C. for 18 hr. The mixture was allowed to cool to room temperature and to this mixture was added water and the aqueous layer was washed three times with ethyl acetate. The combined organic layers were dried over sodium sulfate, filtered, absorbed onto silica gel and purified by silica gel chromatography to give the desired product. $C_{11}H_9N_3S$. 216.1 (M+1).

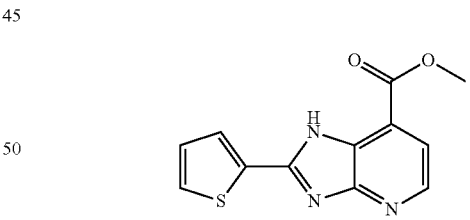

Methyl 2-(thiophen-2-yl)-1H-imidazo[4,5-b]pyridine-7-carboxylate. A solution of 7-methyl-2-(thiophen-2-yl)-1H-imidazo[4,5-b]pyridine (234 mg, 1.09 mmol) and selenium dioxide (482, 4.35 mmol) in pyridine (2.5 mL) was stirred at 120° C. for 24 hours. The reaction mixture was filtered through a pad of celite and the celite pad was washed with hot water and methanol. The filtrate was concentrated and the resulting residue was dried on high vac. The residue was brought up in methanol (10 mL) and to this solution was added thionyl chloride (0.55 mL, 7.6 mmol). The solution was stirred at 70° C. for 4 hours. The resulting mixture was concentrated to give the desired product. $C_{12}H_9N_3O_2S$. 260.1 (M+1).

N-(3-chloro-4-fluorophenyl)-2-(thiophen-2-yl)-1H-imidazo[4,5-b]pyridine-7-carboxamide. To a soln of the 3-chloro-4-fluoroaniline in (239 mg, 1.64 mmol) dichloroethane at 0° C. under nitrogen was added trimethylaluminum (2 M in heptane, 1.57, 3.15 mmol) dropwise over 5 min. The solution was allowed to warm to room temperature and stirred for 30 min. The solution was cooled to 0° C. and to this solution was added methyl 2-(thiophen-2-yl)-1H-imidazo[4,5-b]pyridine-7-carboxylate (272 mg, 1.05 mmol). The solution was stirred at 85° C. for 18 hr and, then, cooled to room temperature. Saturated sodium bicarbonate was carefully added to the solution and the aqueous layer was washed three times with dichloromethane. The aqueous layer was acidified with 10% citric acid and the resulting precipitate was filtered and dried on high vac to give the desired product. $C_{17}H_{10}ClFN_4OS$. 373.1 (M+1).

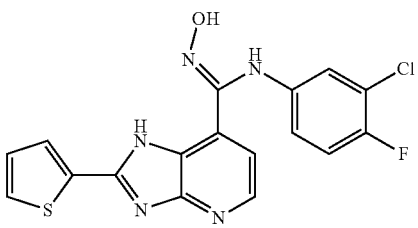 [SMILES: O/N=C(\Nc1ccc(F)c(Cl)c1)c1ccnc2nc(-c3cccs3)[nH]c12]

N-(3-chloro-4-fluorophenyl)-N'-hydroxy-2-(thiophen-2-yl)-1H-imidazo[4,5-b]pyridine-7-carboximidamide. Example 146 was made analogously to Example 107 using N-(3-chloro-4-fluorophenyl)-2-(thiophen-2-yl)-1H-imidazo[4,5-b]pyridine-7-carboxamide in place of N-(3-Chloro-4-fluorophenyl)-2-methyl-1H-imidazo[4,5-b]pyridine-7-carboxamide. $C_{17}H_{11}ClFN_5OS$. 388.1 (M+1).

Example 147: N-(3-Chloro-4-fluorophenyl)-N'-hydroxy-2-(pyridin-3-yl)-1H-imidazo[4,5-b]pyridine-7-carboximidamide

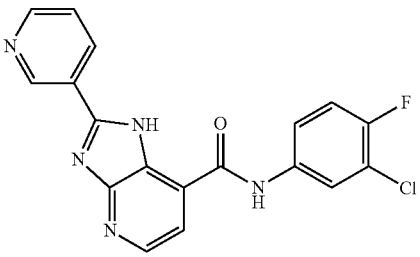 [SMILES: O=C(Nc1ccc(F)c(Cl)c1)c1ccnc2nc(-c3cccnc3)[nH]c12]

N-(3-chloro-4-fluorophenyl)-2-(pyridin-3-yl)-1H-imidazo[4,5-b]pyridine-7-carboxamide. A mixture of 2,3-diamino-N-(3-chloro-4-fluorophenyl)isonicotinamide (0.150 g, 0.534 mmol) and nicotinaldehyde (0.50 mL, 5.34 mmol) in DMSO was stirred at 100° C. under air atmosphere for 16 h. Mixture was cooled to rt and diluted with water. The aqueous layer was extracted 3× with EtOAc and the combined organic layers were washed with brine, dried (Na₂SO₄), filtered, concentrated onto silica gel, and purified via column chromatography on silica gel to yield the final product. $C_{18}H_{11}ClFN_5O$. 368.1 [M+1]⁺.

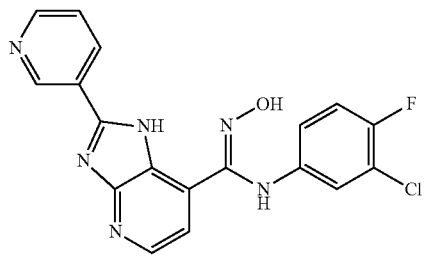 [SMILES: O/N=C(\Nc1ccc(F)c(Cl)c1)c1ccnc2nc(-c3cccnc3)[nH]c12]

Example 147 was synthesized analogously to Example 80, using N-(3-chloro-4-fluorophenyl)-2-(pyridin-3-yl)-1H-imidazo[4,5-b]pyridine-7-carboxamide in place of N-(3-bromophenyl)-1H-imidazo[4,5-b]pyridine-7-carboxamide. $C_{18}H_{12}ClFN_6O$. 383.1 [M+1]⁺.

Example 148: N-(3-Chloro-4-fluorophenyl)-N'-hydroxy-2-(1H-pyrrol-2-yl)-1H-imidazo[4,5-b]pyridine-7-carboximidamide

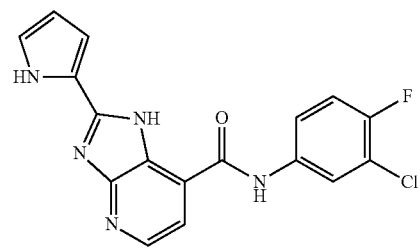 [SMILES: O=C(Nc1ccc(F)c(Cl)c1)c1ccnc2nc(-c3ccc[nH]3)[nH]c12]

N-(3-chloro-4-fluorophenyl)-2-(1H-pyrrol-2-yl)-1H-imidazo[4,5-b]pyridine-7-carboxamide was synthesized analogously to Example 147 using 1H-pyrrole-2-carbaldehyde in place of nicotinaldehyde. $C_{17}H_{11}ClFN_5O$. 356.1 [M+1]⁺.

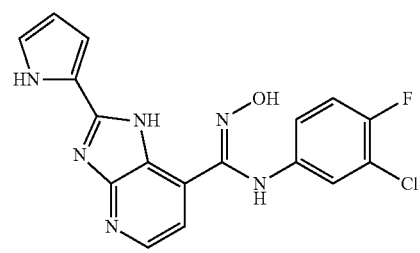 [SMILES: O/N=C(\Nc1ccc(F)c(Cl)c1)c1ccnc2nc(-c3ccc[nH]3)[nH]c12]

Example 148 was synthesized analogously to Example 80, using N-(3-chloro-4-fluorophenyl)-2-(1H-pyrrol-2-yl)-1H-imidazo[4,5-b]pyridine-7-carboxamide in place of N-(3-bromophenyl)-1H-imidazo[4,5-b]pyridine-7-carboxamide. $C_{17}H_{12}ClFN_6O$. 371.1 [M+1]⁺.

Example 149: N-(3-Chloro-4-fluorophenyl)-N'-hydroxy-2-(1H-imidazol-2-yl)-1H-imidazo[4,5-b]pyridine-7-carboximidamide

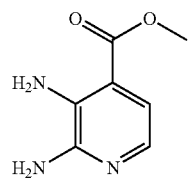

Methyl 2,3-diaminoisonicotinate. A mixture of 2,3-diaminoisonicotinic acid (2.0 g, 13 mmol) in sulfuric acid (2.5 mL) and methanol (25 mL) was stirred at 120° C. in a microwave for 1 hr. To the reaction mixture was added aqueous saturated sodium bicarbonate until basic and the aqueous layer was washed three times with ethyl acetate. The combined organic layers were dried over sodium sulfate, filtered and concentrated to give the desired product. $C_7H_9N_3O_2$. 168.1 (M+1).

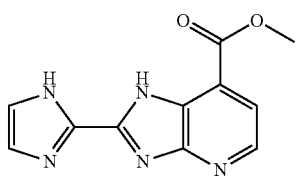 [SMILES: COC(=O)c1ccnc2nc(-c3ncc[nH]3)[nH]c12]

Methyl 2-(1H-imidazol-2-yl)-1H-imidazo[4,5-b]pyridine-7-carboxylate was made analogously to Example 147 using methyl 2,3-diaminoisonicotinate and 1H-imidazole-2-carbaldehyde. $C_{11}H_9N_5O_2$. 244.0 (M+1).

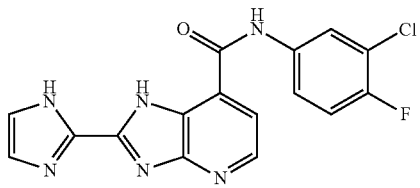 [SMILES: O=C(Nc1ccc(F)c(Cl)c1)c1ccnc2nc(-c3ncc[nH]3)[nH]c12]

N-(3-chloro-4-fluorophenyl)-2-(1H-imidazol-2-yl)-1H-imidazo[4,5-b]pyridine-7-carboxamide was made analogously to Example 146 using methyl 2-(1H-imidazol-2-yl)-1H-imidazo[4,5-b]pyridine-7-carboxylate in place of methyl 2-(thiophen-2-yl)-1H-imidazo[4,5-b]pyridine-7-carboxylate. $C_{16}H_{10}ClFN_6O$. 357.2 (M+1).

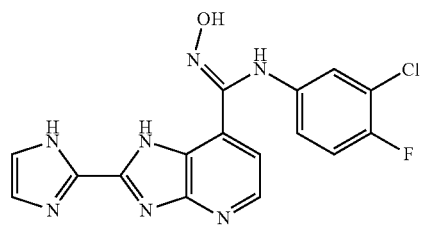 [SMILES: O/N=C(\Nc1ccc(F)c(Cl)c1)c1ccnc2nc(-c3ncc[nH]3)[nH]c12]

Example 149 was made analogously to Example 107 using N-(3-chloro-4-fluorophenyl)-2-(1H-imidazol-2-yl)-1H-imidazo[4,5-b]pyridine-7-carboxamide in place of N-(3-Chloro-4-fluorophenyl)-2-methyl-1H-imidazo[4,5-b]pyridine-7-carb oxamide. $C_{16}H_{11}ClFN_7O$. 372.1 (M+1). $^1$H NMR (400 MHz, DMSO-$d_6$) δ 11.07 (s, 1H), 8.92 (s, 1H), 8.33 (d, J=5.1 Hz, 1H), 7.44 (s, 2H), 7.18 (d, J=5.1 Hz, 1H), 7.02 (t, J=9.1 Hz, 1H), 6.96 (dd, J=6.5, 2.7 Hz, 1H), 6.56 (ddd, J=9.0, 4.1, 2.7 Hz, 1H).

Example 150: N-(3-Chloro-4-fluorophenyl)-N'-hydroxy-2-(1H-pyrazol-5-yl)-1H-imidazo[4,5-b]pyridine-7-carboximidamide

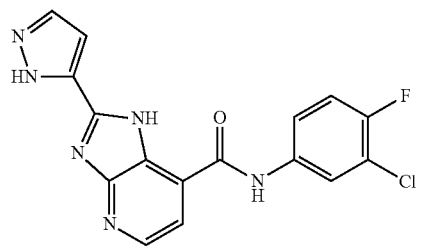 [SMILES: O=C(Nc1ccc(F)c(Cl)c1)c1ccnc2nc(-c3ccn[nH]3)[nH]c12]

N-(3-chloro-4-fluorophenyl)-2-(1H-pyrazol-5-yl)-1H-imidazo[4,5-b]pyridine-7-carboxamide was synthesized analogously to Example 147 using 1H-pyrazole-5-carbaldehyde in place of nicotinaldehyde. $C_{16}H_{10}ClFN_6O$. 357.1 [M+1]$^+$.

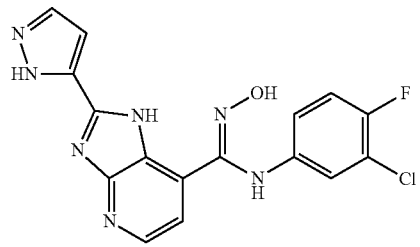 [SMILES: O/N=C(\Nc1ccc(F)c(Cl)c1)c1ccnc2nc(-c3ccn[nH]3)[nH]c12]

N-(3-chloro-4-fluorophenyl)-N'-hydroxy-2-(1H-pyrazol-5-yl)-1H-imidazo[4,5-b]pyridine-7-carboximidamide. Example 150 was synthesized analogously to Example 80, using N-(3-chloro-4-fluorophenyl)-2-(1H-pyrazol-5-yl)-1H-imidazo[4,5-b]pyridine-7-carboxamide in place of N-(3-bromophenyl)-1H-imidazo[4,5-b]pyridine-7-carboxamide. $C_{16}H_{11}ClFN_7O$. 372.1 [M+1]$^k$.

Example 151: N-(3-Chloro-4-fluorophenyl)-N'-hydroxy-2-(4-methyl-1H-imidazol-2-yl)-1H-imidazo[4,5-b]pyridine-7-carboximidamide

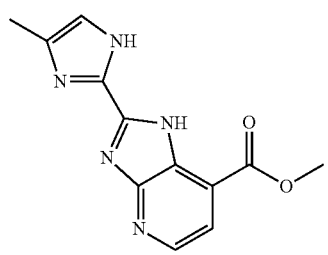

Methyl 2-(4-methyl-1H-imidazol-2-yl)-1H-imidazo[4,5-b]pyridine-7-carboxylate. A mixture of methyl 2,3-diaminoisonicotinate (0.102 g, 0.610 mmol) and 4-methyl-1H-imidazole-2-carbaldehyde (0.319 g, 2.90 mmol) in DMSO (5 mL) stirred at 100° C. under air atmosphere for 16 h. The mixture was diluted with water and the solid was isolated via filtration. The filter cake was washed with water and then cooled over dry ice and dried on the lyophilizer to give the desired product, which was taken on without purification. $C_{12}H_{11}N_5O_2$. 258.1 [M+1]$^+$.

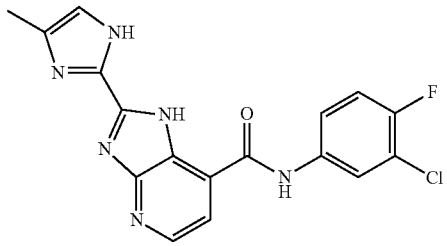 [SMILES: Cc1c[nH]c(-c2nc3nccc(C(=O)Nc4ccc(F)c(Cl)c4)c3[nH]2)n1]

N-(3-chloro-4-fluorophenyl)-2-(4-methyl-1H-imidazol-2-yl)-1H-imidazo[4,5-b]pyridine-7-carboxamide. To DABAL-Me$_3$ (0.128 g, 0.499 mmol) in THF (2 mL) was added 3-chloro-4-fluoroaniline (0.073 g, 0.499 mmol). The mixture stirred at 40° C. for 1 h. A slurry of methyl 2-(4-methyl-1H-imidazol-2-yl)-1H-imidazo[4,5-b]pyridine-7-carboxylate (0.080 g, 0.311 mmol) in THF (2.5 mL) was added and the mixture stirred at 65° C. for 16 h. The mixture was quenched by the addition of 1 N HCl (1 mL) and then was diluted with water/EtOAc. The aqueous layer was extracted 3× with EtOAc. The combined organic layers were washed with brine, dried (Na$_2$SO$_4$), filtered, concentrated onto silica gel, and purified via column chromatography on silica gel to yield the desired product. $C_{17}H_{12}ClFN_6O$. 371.1 [M+1]$^+$.

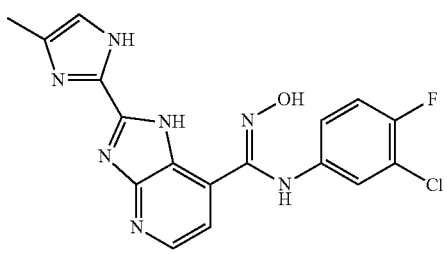 [SMILES: Cc1c[nH]c(-c2nc3nccc(/C(=N/O)Nc4ccc(F)c(Cl)c4)c3[nH]2)n1]

N-(3-chloro-4-fluorophenyl)-N'-hydroxy-2-(4-methyl-1H-imidazol-2-yl)-1H-imidazo[4,5-b]pyridine-7-carboximidamide. To a mixture of N-(3-chloro-4-fluorophenyl)-2-(4-methyl-1H-imidazol-2-yl)-1H-imidazo[4,5-b]pyridine-7-carboxamide (0.009 g, 0.024 mmol) in DCE (0.5 mL) and phosphoryl chloride (0.5 mL) was added phosphorus pentachloride (0.008 g, 0.036 mmol). The mixture stirred at 90° C. for 4 h. Additional phosphorus pentachloride (0.008 g, 0.036 mmol) was added and the mixture stirred at 90° C. for 72 h. The mixture was cooled to rt and concentrated. The residue was diluted with EtOH (3 mL) and hydroxylamine (0.05 mL of a 50 w/w % solution in water, 0.82 mmol) was added. The mixture was concentrated and the residue was diluted with DMSO/water and purified via preparative HPLC to yield the desired product. $C_{17}H_{13}ClFN_7O$. 386.0 [M+1]$^+$.

Example 152: N-(3-Chloro-4-fluorophenyl)-N'-hydroxy-2-(pyrrolidin-2-yl)-1H-imidazo[4,5-b]pyridine-7-carboximidamide

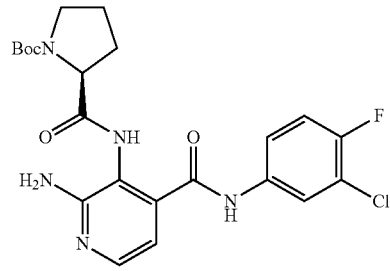 [SMILES: CC(C)(C)OC(=O)N1CCC[C@H]1C(=O)Nc1c(C(=O)Nc2ccc(F)c(Cl)c2)ccnc1N]

(S)-tert-butyl 2-((2-amino-4-((3-chloro-4-fluorophenyl)carbamoyl)pyridin-3-yl)carbamoyl)pyrrolidine-1-carboxylate. To N-Boc-L-proline (0.429 g, 1.991 mmol) in DCM (20 mL) at 0° C. was added isobutyl chloroformate (0.57 mL, 4.38 mmol) dropwise, followed by TEA (0.69 mL, 4.98 mmol). 2,3-diamino-N-(3-chloro-4-fluorophenyl)isonicotinamide (0.559 g, 1.991 mmol) was added and the mixture was allowed to warm to rt and stirred 16 h. The mixture was diluted with water and the aqueous phase was extracted 3× with EtOAc. The combined organic layers were washed with brine, dried (Na$_2$SO$_4$), filtered, concentrated onto silica gel, and purified via column chromatography on silica gel to yield the desired product. $C_{22}H_{25}ClFN_5O_4$. 478.2 [M+1]$^+$.

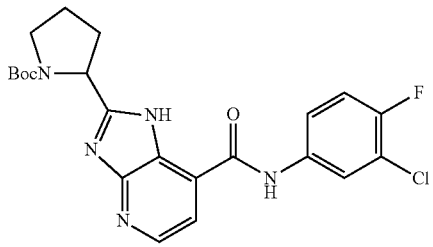 [SMILES: CC(C)(C)OC(=O)N1CCCC1c1nc2nccc(C(=O)Nc3ccc(F)c(Cl)c3)c2[nH]1]

tert-butyl 2-(7-((3-chloro-4-fluorophenyl)carbamoyl)-1H-imidazo[4,5-b]pyridin-2-yl)pyrrolidine-1-carboxylate. A solution of (S)-tert-butyl 2-((2-amino-4-((3-chloro-4-fluorophenyl)carbamoyl)pyridin-3-yl)carbamoyl)pyrrolidine-1-carboxylate (0.094 g, 0.197 mmol) in AcOH (4 mL) was heated to 65° C. for 4 h and to 80° C. for 2 h. The mixture was cooled to rt and concentrated. The residue was partitioned between sat. bicarb solution and EtOAc and the aqueous layer was extracted 3× with EtOAc. The combined organic layers were concentrated onto silica gel and purified via column chromatography on silica gel to yield the desired product. $C_{22}H_{23}ClFN_5O_3$. 460.1 [M+1]$^+$.

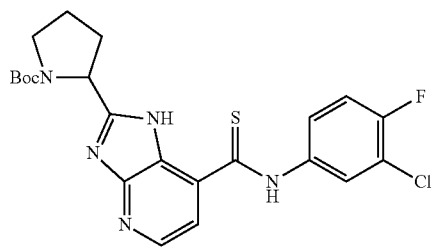

tert-butyl 2-(7-((3-chloro-4-fluorophenyl)carbamothioyl)-1H-imidazo[4,5-b]pyridin-2-yl)pyrrolidine-1-carboxylate. A mixture of tert-butyl 2-(7-((3-chloro-4-fluorophenyl)carbamoyl)-1H-imidazo[4,5-b]pyridin-2-yl)pyrrolidine-1-carboxylate (0.043 g, 0.093 mmol) and Lawesson's reagent (0.076 g, 0.187 mmol) in toluene (2 mL) was stirred at 95° C. for 16 h. The mixture was cooled to rt, concentrated onto silica gel, and purified via column chromatography on silica gel to yield the desired product. $C_{22}H_{23}ClFN_5O_2S$. 476.1 $[M+1]^+$.

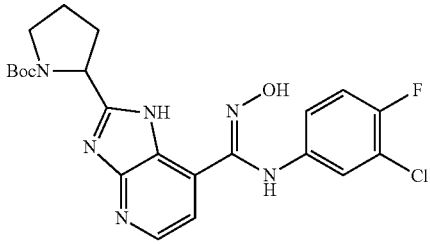 [SMILES: CC(C)(C)OC(=O)N1CCCC1c1nc2nccc(/C(=N/O)Nc3ccc(F)c(Cl)c3)c2[nH]1]

tert-butyl 2-(7-(N-(3-chloro-4-fluorophenyl)-N'-hydroxycarbamimidoyl)-1H-imidazo[4,5-b]pyridin-2-yl)pyrrolidine-1-carboxylate. To a mixture of tert-butyl 2-(7-((3-chloro-4-fluorophenyl)carbamothioyl)-1H-imidazo[4,5-b]pyridin-2-yl)pyrrolidine-1-carboxylate (0.019 g, 0.040 mmol) in MeOH (2 mL) was added hydroxylamine (0.12 mL of a 50 w/w % solution in water, 2.00 mmol). The mixture was stirred at 70° C. for 45 min. The mixture was cooled to rt and diluted with brine and EtOAc. The aqueous layer was extracted 4× with EtOAc. The combined organic layers were washed with brine, dried ($Na_2SO_4$), filtered and concentrated to yield the desired product. $C_{22}H_{24}ClFN_6O_3$. 475.2 $[M+1]^+$.

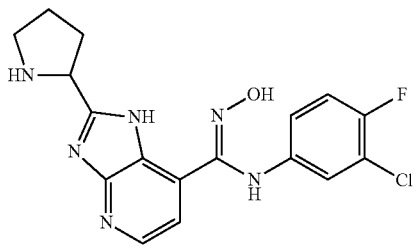 [SMILES: O/N=C(\Nc1ccc(F)c(Cl)c1)c1ccnc2nc(C3CCCN3)[nH]c12]

N-(3-chloro-4-fluorophenyl)-Y-hydroxy-2-(pyrrolidin-2-yl)-1H-imidazo[4,5-b]pyridine-7-carboximidamide. To a solution of tert-butyl 2-(7-(N-(3-chloro-4-fluorophenyl)-N'-hydroxycarbamimidoyl)-1H-imidazo[4,5-b]pyridin-2-yl)pyrrolidine-1-carboxylate (0.018 g, 0.038 mmol) in DCM (1 mL) was added TFA (1 mL). The mixture stirred at rt for 10 min and was then concentrated. The residue was dissolved in DMSO/water and purified via preparative HPLC to yield the desired product. $C_{17}H_{16}ClFN_6O$. 375.1 $[M+1]^+$.

Example 153: 2-Amino-N-(3-chloro-4-fluorophenyl)-N'-hydroxy-1H-imidazo[4,5-b]pyridine-7-carboximidamide

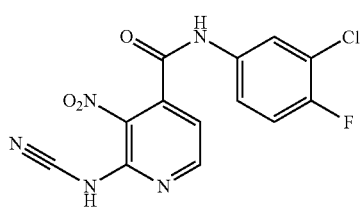 [SMILES: N#CNc1nccc(C(=O)Nc2ccc(F)c(Cl)c2)c1[N+](=O)[O-]]

N-(3-chloro-4-fluorophenyl)-2-cyanamido-3-nitroisonicotinamide. A mixture of 2-chloro-N-(3-chloro-4-fluorophenyl)-3-nitroisonicotinamide (1.02 g, 3.09 mmol), cyanamide (260 mg, 6.18 mmol), and potassium carbonate (1.28 g, 9.27 mmol) in dimethylformamide (10 mL) was stirred at 80° C. for 2 hr. The reaction mixture was absorbed onto silica gel and purified by silica gel chromatography to give the desired product (1.03 g). $C_{13}H_7ClFN_5O_3$. 336.0 (M+1).

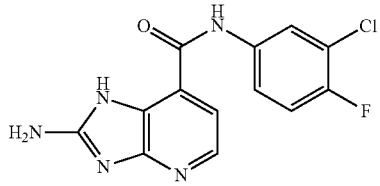 [SMILES: Nc1nc2nccc(C(=O)Nc3ccc(F)c(Cl)c3)c2[nH]1]

2-amino-N-(3-chloro-4-fluorophenyl)-1H-imidazo[4,5-b]pyridine-7-carboxamide. A mixture of N-(3-chloro-4-fluorophenyl)-2-cyanamido-3-nitroisonicotinamide (1.07 g, 3.20 mmol) and sodium hydrosulfite (1.96 g, 9.59 mmol) in ethanol (10 mL) and dimethyl sulfoxide (10 mL) was stirred at 70° C. for 24 hr. Water was added and the aqueous layer was washed three times with ethyl acetate. The combined organic layers were dried over sodium sulfate, filtered and absorbed onto silica gel and purified by silica gel chromatography to give the desired product. $C_{13}H_9ClFN_5O$. 306.1 (M+1).

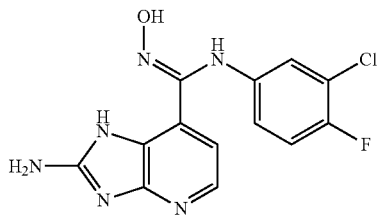 [SMILES: Nc1nc2nccc(/C(=N/O)Nc3ccc(F)c(Cl)c3)c2[nH]1]

2-Amino-N-(3-chloro-4-fluorophenyl)-N'-hydroxy-1H-imidazo[4,5-b]pyridine-7-carboximidamide. Example 153 was made analogously to Example 107 using 2-amino-N-(3-chloro-4-fluorophenyl)-1H-imidazo[4,5-b]pyridine-7-carboxamide in place of N-(3-Chloro-4-fluorophenyl)-2-methyl-1H-imidazo[4,5-b]pyridine-7-carboxamide. $C_{13}H_{10}ClFN_6O$. 321.0 (M+1). $^1$H NMR (400 MHz, DMSO-$d_6$) δ 8.84 (s, 1H), 8.15-8.10 (m, 1H), 7.94-7.89 (m, 1H), 7.10 (t, J=9.0 Hz, 1H), 7.00-6.92 (m, 1H), 6.91-6.79 (m, 1H), 6.63-6.54 (m, 1H).

Example 154: N-(3-Chloro-4-fluorophenyl)-2-(cyclopropylamino)-N'-hydroxy-1H-imidazo[4,5-b]pyridine-7-carboximidamide

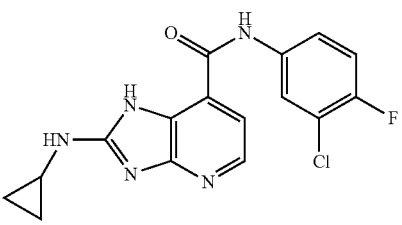 [SMILES: O=C(Nc1ccc(F)c(Cl)c1)c1ccnc2nc(NC3CC3)[nH]c12]

N-(3-chloro-4-fluorophenyl)-2-(cyclopropylamino)-1H-imidazo[4,5-b]pyridine-7-carboxamide. Dissolved 2,3-diamino-N-(3-chloro-4-fluorophenyl)isonicotinamide (0.54 g, 0.002 mol) in THF (5 ml), to the solution was added cyclopropyl isothiocyanate (0.23 g, 0.002 mmol) and triethylamine (1.95 g, 0.02 mol). The reaction mixture was heated at 80° C. overnight, then to the reaction mixture was added 1-(3-dimethylaminopropyl)-3-ethylcarbodiimide hydrochloride (0.44 g, 0.002 mol), heated at 80° C. for 1 h. The reaction mixture was diluted with EtOAc, and then water was added. Product crashed out to afford 200 mg desired product. $C_{16}H_{13}ClFN_5O$. 346.1 (M+1).

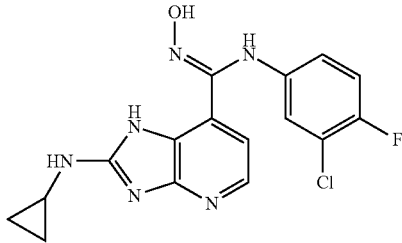 [SMILES: O/N=C(\Nc1ccc(F)c(Cl)c1)c1ccnc2nc(NC3CC3)[nH]c12]

N-(3-chloro-4-fluorophenyl)-2-(cyclopropylamino)-N'-hydroxy-1H-imidazo[4,5-b]pyridine-7-carboximidamide. Example 154 was made analogously to Example 107 using the general procedure for hydroxyamidine formation. $C_{16}H_{14}ClFN_6O$. 361.1 (M+1). 1H NMR (400 MHz, DMSO-d6) δ 11.36 (s, 1H), 8.93 (s, 1H), 8.80 (s, 1H), 8.01 (d, J=6.1 Hz, 1H), 7.13-7.00 (m, 2H), 6.97 (d, J=6.1 Hz, 1H), 6.55 (ddd, J=9.0, 4.0, 2.7 Hz, 1H), 2.81 (dq, J=6.9, 3.4 Hz, 1H), 0.83 (td, J=7.1, 5.0 Hz, 2H), 0.59 (p, J=4.7 Hz, 2H).

Example 155: N-(3-Chloro-4-fluorophenyl)-N'-hydroxy-2-(phenylamino)-1H-imidazo[4,5-b]pyridine-7-carboximidamide

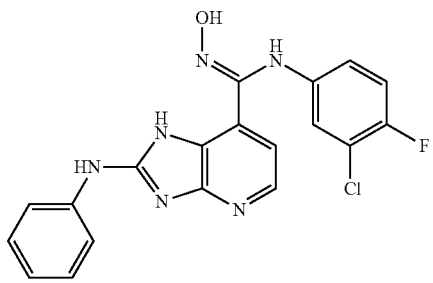 [SMILES: O/N=C(\Nc1ccc(F)c(Cl)c1)c1ccnc2nc(Nc3ccccc3)[nH]c12]

Example 155 was made analogously to Example 154 using phenyl isothiocyanate. $C_{19}H_{14}ClFN_6O$. 397.1 (M+1). 1H NMR (400 MHz, DMSO-d6) δ 11.37 (s, 1H), 10.09 (s, 1H), 8.92 (s, 1H), 8.05 (d, J=6.1 Hz, 1H), 7.66 (d, J=8.1 Hz, 2H), 7.39 (t, J=7.7 Hz, 2H), 7.14-7.04 (m, 2H), 7.02 (dt, J=5.6, 2.6 Hz, 2H), 6.60 (ddd, J=9.0, 4.0, 2.8 Hz, 1H).

Example 156: N-(3-Chloro-4-fluorophenyl)-N'-hydroxy-2-(phenethylamino)-1H-imidazo[4,5-b]pyridine-7-carboximidamide

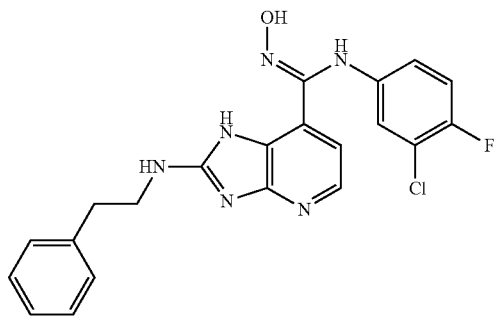 [SMILES: O/N=C(\Nc1ccc(F)c(Cl)c1)c1ccnc2nc(NCCc3ccccc3)[nH]c12]

Example 156 was made analogously to Example 154 using (2-isothiocyanatoethyl)benzene. $C_{21}H_{18}ClFN_6O$. 425.1 (M+1). 1H NMR (400 MHz, DMSO-d6) δ 11.36 (s, 1H), 8.92 (s, 1H), 7.95 (d, J=6.3 Hz, 1H), 7.37-7.16 (m, 6H), 7.13-7.05 (m, 1H), 7.02 (dd, J=6.5, 2.8 Hz, 1H), 6.96-6.85 (m, 1H), 6.57 (ddd, J=8.9, 4.0, 2.8 Hz, 1H), 3.73-3.62 (m, 2H), 2.89 (t, J=7.3 Hz, 2H).

Example 157: N-(3-Chloro-4-fluorophenyl)-N'-hydroxy-2-((2,2,2-trifluoroethyl)amino)-1H-imidazo[4, 5-b]pyridine-7-carboximidamide

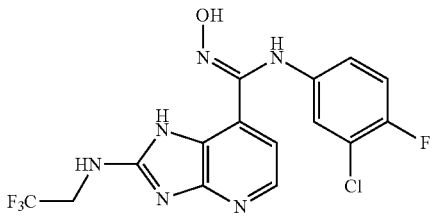 [SMILES: O/N=C(\Nc1ccc(F)c(Cl)c1)c1ccnc2nc(NCC(F)(F)F)[nH]c12]

Example 157 was made analogously to Example 154 using 1,1,1-trifluoro-2-isothiocyanatoethane. $C_{15}H_{11}ClF_4N_6O$. 403.1 (M+1). 1H NMR (400 MHz, DMSO-d6) δ 11.42 (s, 1H), 8.95 (s, 1H), 8.00 (d, J=6.2 Hz, 1H), 7.05 (ddd, J=19.0, 8.5, 4.0 Hz, 3H), 6.95 (d, J=6.5 Hz, 1H), 6.57 (dt, J=9.0, 3.3 Hz, 1H), 4.30 (s, 3H).

Example 158: N-(3-Chloro-4-fluorophenyl)-N'-hydroxy-2-(methylamino)-1H-imidazo[4,5-b]pyridine-7-carboximidamide

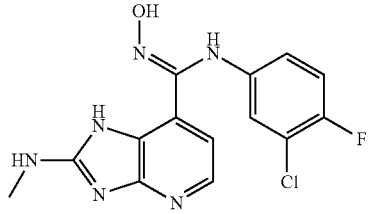 [SMILES: CNc1nc2nccc(/C(=N/O)Nc3ccc(F)c(Cl)c3)c2[nH]1]

Example 158 was made analogously to Example 154 using methyl isothiocyanate. $C_{14}H_{12}ClFN_6O$. 335.1 (M+1). 1H NMR (400 MHz, DMSO-d6) δ 12.08 (s, 1H), 11.37 (s, 1H), 8.96 (s, 1H), 7.96 (d, J=6.2 Hz, 1H), 7.08 (t, J=9.1 Hz, 1H), 7.03-6.97 (m, 1H), 6.91 (d, J=6.2 Hz, 1H), 6.56 (ddd, J=9.0, 4.0, 2.8 Hz, 1H), 3.00 (d, J=4.8 Hz, 3H).

Example 159: Isopropyl (7-(N-(3-chloro-4-fluorophenyl)-N'-hydroxycarbamimidoyl)-1H-imidazo[4, 5-b]pyridin-2-yl)carbamate

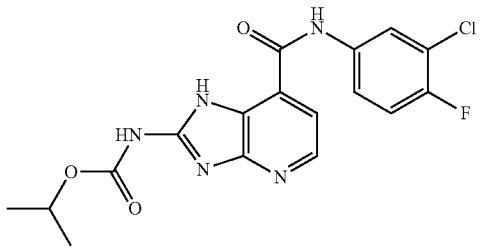 [SMILES: CC(C)OC(=O)Nc1nc2nccc(C(=O)Nc3ccc(F)c(Cl)c3)c2[nH]1]

Isopropyl (7-((3-chloro-4-fluorophenyl)carbamoyl)-1H-imidazo[4,5-b]pyridin-2-yl)carbamate. To a mixture of 2-amino-N-(3-chloro-4-fluorophenyl)-1H-imidazo[4,5-b]pyridine-7-carboxamide (30 mg, 0.098 mmol) and triethylamine (0.041 mL, 0.29 mmol) in dichloromethane at 0° C. was added solution of isopropyl chloroformate (1 M in toluene, 0.118 mL, 0.118 mmol). The reaction was allowed to warm to room temperature and stirred for 1 hr. Saturated sodium bicarbonate was added and the aqueous layer was washed three times with dichloromethane. The combined organic layers were dried over sodium sulfate, filtered and concentrated. The residue was loaded onto a silica gel column and purified by silica gel chromatography to give the desired product mixed with isopropyl 7-((3-chloro-4-fluorophenyl)carbamoyl)-2-((isopropoxycarbonyl)amino)-1H-imidazo[4,5-b]pyridine-1-carboxylate. $C_{17}H_{15}ClFN_5O_3$. 392.2 (M+1).

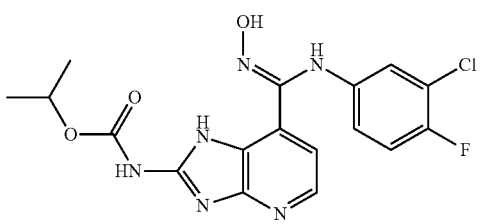 [SMILES: CC(C)OC(=O)Nc1nc2nccc(/C(=N/O)Nc3ccc(F)c(Cl)c3)c2[nH]1]

Isopropyl (7-(N-(3-chloro-4-fluorophenyl)-N'-hydroxycarbamimidoyl)-1H-imidazo[4,5-b]pyridin-2-yl)carbamate. Example 159 was made analogously to Example 107 using isopropyl (7-((3-chloro-4-fluorophenyl)carbamoyl)-1H-imidazo[4,5-b]pyridin-2-yl)carbamate in place of N-(3-Chloro-4-fluorophenyl)-2-methyl-1H-imidazo[4,5-b]pyridine-7-carboxamide. $C_{17}H_{16}ClFN_6O_3$. 407.0 (M+1). $^1$H NMR (400 MHz, DMSO-$d_6$) δ 8.83 (s, 1H), 8.18 (d, J=5.4 Hz, 1H), 7.13 (t, J=9.1 Hz, 1H), 7.02-6.91 (m, 2H), 6.67-6.57 (m, 1H), 5.00 (dq, J=6.3, 6.3 Hz, 1H), 1.31 (d, J=6.2 Hz, 6H).

Example 160: Ethyl (7-(N-(3-chloro-4-fluorophenyl)-N'-hydroxycarbamimidoyl)-1H-imidazo[4,5-b]pyridin-2-yl)carbamate

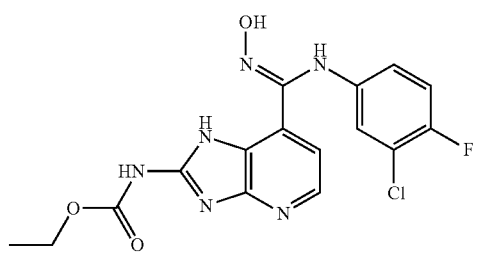 [SMILES: CCOC(=O)Nc1nc2nccc(/C(=N/O)Nc3ccc(F)c(Cl)c3)c2[nH]1]

Example 160 was made analogously to Example 154 using O-ethyl carbonisothiocyanatidate. $C_{16}H_{14}ClFN_6O_3$ 393.1 (M+1). 1H NMR (400 MHz, DMSO-d6) δ 11.54 (s, 1H), 8.83 (s, 1H), 8.20 (d, J=5.6 Hz, 1H), 7.11 (t, J=9.1 Hz, 1H), 7.03 (d, J=5.6 Hz, 1H), 6.95 (dd, J=6.5, 2.7 Hz, 1H), 6.62 (ddd, J=8.9, 4.0, 2.7 Hz, 1H), 4.26 (q, J=7.1 Hz, 2H), 1.28 (t, J=7.1 Hz, 3H).

Example 161: N-(3-Chloro-4-fluorophenyl)-2-((cyclopropylmethyl)amino)-N'-hydroxy-1H-imidazo[4,5-b]pyridine-7-carboximidamide

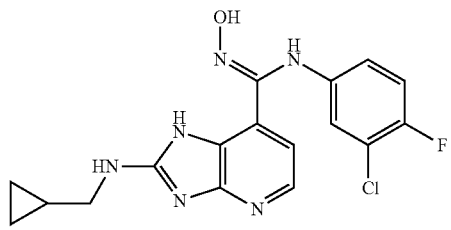 [SMILES: O/N=C(\Nc1ccc(F)c(Cl)c1)c1ccnc2nc(NCC3CC3)[nH]c12]

Example 161 was made analogously to Example 154 using cyclopropyl methyl isothiocyanate. $C_{17}H_{16}ClFN_6O$. 375.1 (M+1). 1H NMR (400 MHz, DMSO-d6) δ 11.37 (s, 1H), 8.93 (s, 1H), 7.94 (t, J=5.3 Hz, 1H), 7.50-7.25 (m, 1H), 7.14-6.97 (m, 2H), 6.91 (d, J=6.3 Hz, 1H), 6.58 (ddd, J=9.0, 4.0, 2.7 Hz, 1H), 3.31 (t, J=6.5 Hz, 2H), 1.11 (d, J=13.1 Hz, 1H), 0.57-0.40 (m, 2H), 0.33-0.19 (m, 2H).

Example 162: N-(3-Chloro-4-fluorophenyl)-2-((3,3-difluorocyclobutyl)amino)-N'-hydroxy-1H-imidazo[4,5-b]pyridine-7-carboximidamide

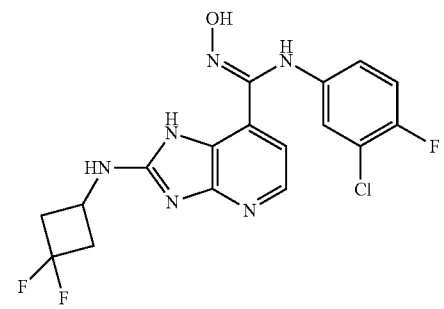 [SMILES: O/N=C(\Nc1ccc(F)c(Cl)c1)c1ccnc2nc(NC3CC(F)(F)C3)[nH]c12]

Example 162 was made analogously to Example 154 using 1,1-difluoro-3-isothiocyanatocyclobutane. $C_{17}H_{14}ClF_3N_6O$. 411.0 (M+1). 1H NMR (400 MHz, DMSO-d6) δ 11.41 (d, J=18.8 Hz, 1H), 8.97 (s, 1H), 8.69 (s, 1H), 7.99 (dd, J=7.9, 6.6 Hz, 1H), 7.09-6.97 (m, 2H), 6.94 (d, J=6.2 Hz, 1H), 6.54 (ddd, J=9.0, 4.0, 2.8 Hz, 1H), 4.28 (s, 1H), 3.03 (tt, J=14.3, 7.9 Hz, 2H), 2.77 (d, J=10.6 Hz, 2H).

Example 163: N-(3-Chloro-4-fluorophenyl)-2-(ethylamino)-N'-hydroxy-1H-imidazo[4,5-b]pyridine-7-carboximidamide

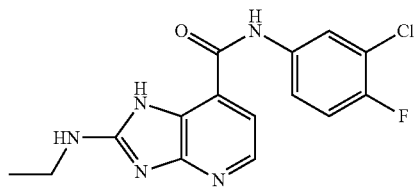 [SMILES: CCNc1nc2nccc(C(=O)Nc3ccc(F)c(Cl)c3)c2[nH]1]

N-(3-chloro-4-fluorophenyl)-2-(ethylamino)-1H-imidazo[4,5-b]pyridine-7-carboxamide was made analogously to Example 154 using ethyl isothiocyanate. $C_{15}H_{13}ClFN_5O$. 333.9 (M+1).

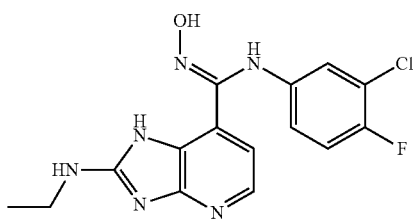 [SMILES: CCNc1nc2nccc(/C(=N/O)Nc3ccc(F)c(Cl)c3)c2[nH]1]

N-(3-chloro-4-fluorophenyl)-2-(ethylamino)-N'-hydroxy-1H-imidazo[4,5-b]pyridine-7-carboximidamide. Example 163 was made analogously to Example 107 using N-(3-chloro-4-fluorophenyl)-2-(ethylamino)-1H-imidazo[4,5-b]pyridine-7-carboxamide in place of N-(3-Chloro-4-fluorophenyl)-2-methyl-1H-imidazo[4,5-b]pyridine-7-carboxamide. $C_{15}H_{14}ClFN_6O$. 349.1 (M+1).

Example 164: N-(3-Chloro-4-fluorophenyl)-2-(cyclobutylamino)-N'-hydroxy-1H-imidazo[4,5-b]pyridine-7-carboximidamide

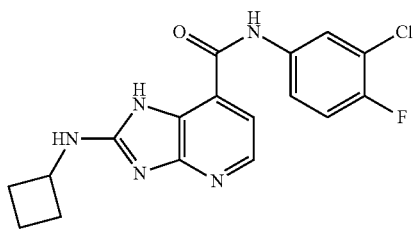 [SMILES: O=C(Nc1ccc(F)c(Cl)c1)c1ccnc2nc(NC3CCC3)[nH]c12]

N-(3-chloro-4-fluorophenyl)-2-(cyclobutylamino)-1H-imidazo[4,5-b]pyridine-7-carboxamide. Example 164 was made analogously to Example 154 using cyclobutyl isothiocyanate. $C_{17}H_{15}ClFN_5O$. 360.2 (M+1).

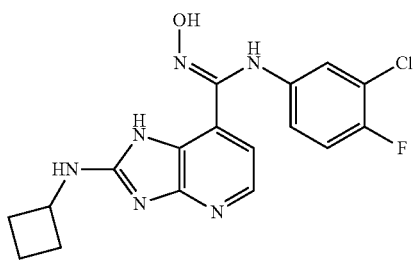 [SMILES: O/N=C(\Nc1ccc(F)c(Cl)c1)c1ccnc2nc(NC3CCC3)[nH]c12]

N-(3-chloro-4-fluorophenyl)-2-(cyclobutylamino)-N'-hydroxy-1H-imidazo[4,5-b]pyridine-7-carboximidamide. Example 164 was made analogously to Example 107 using N-(3-chloro-4-fluorophenyl)-2-(cyclobutylamino)-1H-imidazo[4,5-b]pyridine-7-carboxamide in place of N-(3-Chloro-4-fluorophenyl)-2-methyl-1H-imidazo[4,5-b]pyridine-7-carboxamide. $C_{17}H_{16}ClFN_6O$. 375.1 (M+1). $^1H$ NMR (400 MHz, DMSO-$d_6$) δ 11.40 (s, 1H), 8.98 (s, 1H), 7.96 (d, J=6.2 Hz, 1H), 7.09 (t, J=9.1 Hz, 1H), 7.05 (dd, J=6.1, 2.5 Hz, 1H), 6.92 (d, J=6.2 Hz, 1H), 6.62-6.50 (m, 1H), 4.34 (q, J=7.2 Hz, 1H), 2.39-2.24 (m, 2H), 2.15-1.98 (m, 2H), 1.82-1.58 (m, 2H).

Example 165: N-(3-Chloro-4-fluorophenyl)-N'-hydroxy-2-(isopropylamino)-1H-imidazo[4,5-b]pyridine-7-carboximidamide

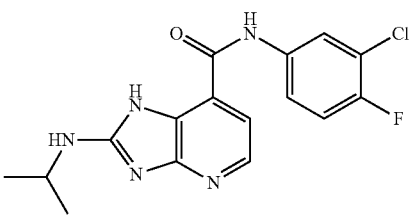 [SMILES: CC(C)Nc1nc2nccc(C(=O)Nc3ccc(F)c(Cl)c3)c2[nH]1]

N-(3-chloro-4-fluorophenyl)-2-(isopropylamino)-1H-imidazo[4,5-b]pyridine-7-carboxamide was made analogously to Example 154 using isopropyl isothiocyanate. $C_{16}H_{15}ClFN_5O$. 348.2 (M+1).

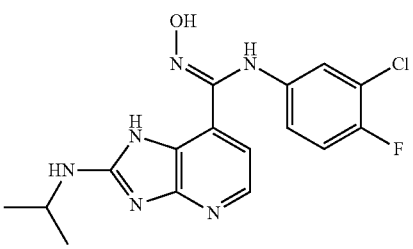 [SMILES: CC(C)Nc1nc2nccc(/C(=N/O)Nc3ccc(F)c(Cl)c3)c2[nH]1]

N-(3-chloro-4-fluorophenyl)-N'-hydroxy-2-(isopropylamino)-1H-imidazo[4,5-b]pyridine-7-carboximidamide. Example 165 was made analogously to Example 107 using N-(3-chloro-4-fluorophenyl)-2-(isopropylamino)-1H-imidazo[4,5-b]pyridine-7-carboxamide in place of N-(3-Chloro-4-fluorophenyl)-2-methyl-1H-imidazo[4,5-b]pyridine-7-carboxamide. $C_{16}H_{16}ClFN_6O$. 363.1 (M+1). $^1H$ NMR (400 MHz, DMSO-$d_6$) δ 11.42 (s, 1H), 8.97 (s, 1H), 7.96 (d, J=6.3 Hz, 1H), 7.11 (t, J=9.0 Hz, 1H), 7.05 (dd, J=6.6, 2.7 Hz, 1H), 6.92 (d, J=6.3 Hz, 1H), 6.62-6.56 (m, 1H), 4.06 (sex, J=6.5 Hz, 1H), 1.25 (d, J=6.3 Hz, 6H).

Example 166: N-(3-Chlorophenyl)-N'-hydroxy-2-(methylamino)-1H-imidazo[4,5-b]pyridine-7-carboximidamide

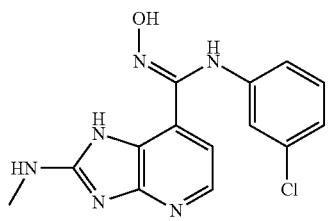 [SMILES: CNc1nc2nccc(/C(=N/O)Nc3cccc(Cl)c3)c2[nH]1]

Example 166 was made analogously to Example 158 using N-(3-chloro-4-fluorophenyl)-2-(methylamino)-1H-imidazo[4,5-b]pyridine-7-carboxamide. $C_{14}H_{13}ClN_6O$, 316.3/318.6 (M+1). $^1H$ NMR (400 MHz, DMSO-$d_6$) δ 11.42 (br. s, 1H), 8.97 (s, 1H), 7.97 (d, J=6.3 Hz, 1H), 7.06 (t, J=8.1 Hz, 1H), 6.99-6.79 (m, 2H), 6.62-6.43 (m, 1H), 3.01 (d, J=4.8 Hz, 3H).

Example 167: N-(3-Chloro-4-fluorophenyl)-2-((2-(diethylamino)ethyl)amino)-N'-hydroxy-1H-imidazo[4,5-b]pyridine-7-carboximidamide

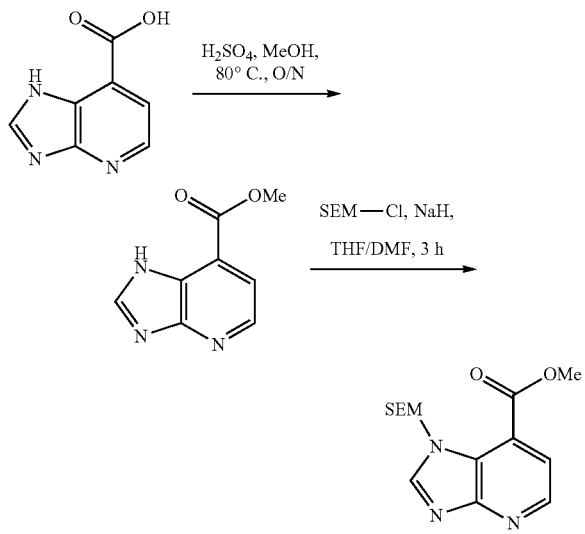

1H-Imidazo[4,5-b]pyridine-7-carboxylic acid (10 g, 61 mmol, 1 equiv) was dissolved in methanol (160 mL), H$_2$SO$_4$ (10 mL, 189 mmol, 3.08 equiv) was added, and the reaction was stirred at 80° C. for overnight. The reaction was carefully quenched by the addition of a solution of NaOMe in methanol (80 mL, 13 wt % solution, 189 mmol, 3.08 equiv) at 0° C. Methanol was subsequently removed in vacuo, the resulting solid was slurried in water and filtered. The solid was dried in a vacuum oven (65° C.) overnight. Methyl 1H-imidazo[4,5-b]pyridine-7-carboxylate was obtained as a brown solid. C$_8$H$_7$N$_3$O$_2$, 178.06 (M+1).

To a suspension of methyl 1H-imidazo[4,5-b]pyridine-7-carboxylate (7.8 g, 44 mmol, 1 equiv) in a mixture of THF/DMF (70 mL, 6:1 ratio) was added a 60 wt % dispersion of NaH (2.1 g, 53 mmol, 1.2 equiv) in three portions. Once gas evolution ceased, the reaction mixture was cooled to 0° C. and SEM-Cl (9.3 mL, 53 mmol, 1.2 equiv) was added. The ice bath was subsequently removed and the reaction was stirred at room temperature for 3 hours before being quenched with saturated aqueous NH$_4$Cl. The reaction mixture was diluted with water and extracted three times with EtOAc. The combined organic layers were dried over MgSO$_4$, filtered and concentrated in vacuo. The crude product was purified by silica gel chromatography (0-5% MeOH/CH$_2$Cl$_2$ over 20 minutes). Methyl 1-((2-(trimethylsilyl)ethoxy)methyl)-1H-imidazo[4,5-b]pyridine-7-carboxylate was isolated as a yellow solid. C$_{14}$H$_{21}$N$_3$O$_3$Si. 308.01 (M+1).

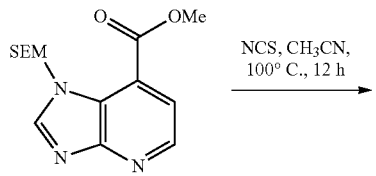

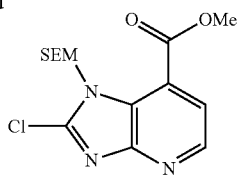

To a solution of methyl 1-((2-(trimethylsilyl)ethoxy)methyl)-1H-imidazo[4,5-b]pyridine-7-carboxylate (1.1 g, 4 mmol, 1 equiv) in acetonitrile (23.1 mL) was added NCS (0.72 g, 5 mmol, 1.5 equiv). The reaction mixture was stirred at 100° C. in a sealed vessel for 12 hours. Acetonitrile was subsequently removed in vacuo and the crude product purified by silica gel chromatography (0-5% MeOH/CH$_2$Cl$_2$ over 20 minutes). methyl 2-chloro-1-((2-(trimethylsilyl)ethoxy)methyl)-1H-imidazo[4,5-b]pyridine-7-carboxylate was obtained as a yellow solid. C$_{14}$H$_{20}$ClN$_3$O$_3$Si. 341.94/343.93 (M+1).

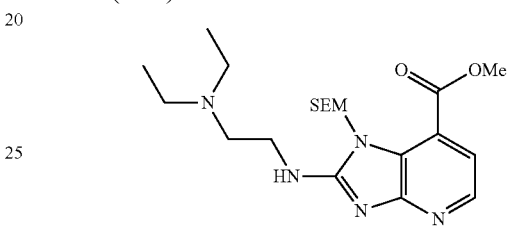

The above compound was made analogously to Example 39 using N,N-diethylethane-1,2-diamine in place of N,N-dimethylpropane-1,3-diamine and methyl 2-chloro-1-((2-(trimethylsilyl)ethoxy)methyl)-1H-imidazo[4,5-b]pyridine-7-carboxylate in place of methyl 2-chloro-4,5-difluoro-1-((2-(trimethylsilyl)ethoxy)methyl)-1H-benzo[d]imidazole-7-carboxylate. The TFA salt of methyl 2-((2-(diethylamino)ethyl)amino)-1-((2-(trimethylsilyl)ethoxy)methyl)-1H-imidazo[4,5-b]pyridine-7-carboxylate was obtained as a yellow oil. C$_{20}$H$_{35}$N$_5$O$_3$Si. 422.23 (M+1).

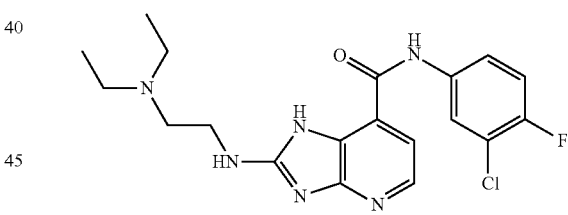

The above compound was made analogously to Example 39 using methyl 2-((2-(diethylamino)ethyl)amino)-1-((2-(trimethylsilyl) ethoxy)methyl)-1H-imidazo[4,5-b]pyridine-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-((2-(diethylamino)ethyl)amino)-1H-imidazo[4,5-b]pyridine-7-carboxamide was isolated as a white solid. C$_{19}$H$_{22}$ClFN$_6$O. 405.21/407.14 (M+1).

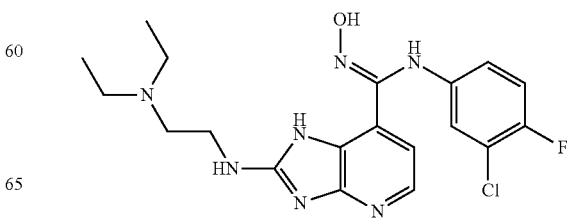

N-(3-chloro-4-fluorophenyl)-2-((2-(diethylamino)ethyl)amino)-N'-hydroxy-1H-imidazo[4,5-b]pyridine-7-carboximidamide was made analogously to Example 59 using N-(3-chloro-4-fluorophenyl)-2-((2-(diethylamino)ethyl)amino)-1H-imidazo[4,5-b]pyridine-7-carboxamide in place of N-(3-chloro-4-fluorophenyl)-1H-imidazo[4,5-b]pyridine-7-carboxamide. The TFA salt of N-(3-chloro-4-fluorophenyl)-2-((2-(diethylamino)ethyl)amino)-N'-hydroxy-1H-imidazo[4,5-b]pyridine-7-carboximidamide was isolated as a white solid. $C_{19}H_{23}ClFN_7O$. 420.16/422.13 (M+1). $^1H$ NMR (400 MHz, DMSO-$d_6$) δ 11.30 (s, 1H), 8.93 (s, 1H), 7.97 (d, J=6.2 Hz, 1H), 7.09 (t, J=9.0 Hz, 1H), 6.99 (dd, J=6.5, 2.7 Hz, 1H), 6.94 (d, J=6.0 Hz, 1H), 6.56 (ddd, J=9.0, 4.0, 2.7 Hz, 1H), 3.75 (m, 2H), 3.32 (t, J=6.1 Hz, 2H), 3.23 (q, J=7.2 Hz, 4H), 1.21 (t, J=7.2 Hz, 6H). $^{19}F$ NMR (376 MHz, DMSO-$d_6$) δ -74.40 (9F), -126.69 (1F).

Example 168: N-(3-Chloro-4-fluorophenyl)-N'-hydroxy-2-((2-morpholinoethyl)amino)-1H-imidazo[4,5-b]pyridine-7-carboximidamide

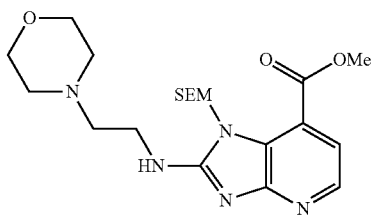 [SMILES: COC(=O)c1ccnc2nc(NCCN3CCOCC3)n(COCC[Si](C)(C)C)c12]

The above compound was made analogously to Example 39 using 2-morpholinoethanamine in place of N,N-dimethylpropane-1,3-diamine and methyl 2-chloro-1-((2-(trimethylsilyl)ethoxy)methyl)-1H-imidazo[4,5-b]pyridine-7-carboxylate in place of methyl 2-chloro-4,5-difluoro-1-((2-(trimethylsilyl)ethoxy)methyl)-1H-benzo[d]imidazole-7-carboxylate. The TFA salt of methyl 2-((2-morpholinoethyl)amino)-1-((2-(trimethylsilyl)ethoxy)methyl)-1H-imidazo[4,5-b]pyridine-7-carboxylate was isolated as a yellow oil. $C_{20}H_{33}N_5O_4Si$. 436.21 (M+1).

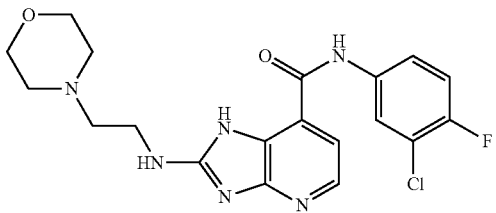 [SMILES: O=C(Nc1ccc(F)c(Cl)c1)c1ccnc2nc(NCCN3CCOCC3)[nH]c12]

The above compound was made analogously to Example 39 using methyl 2-((2-morpholinoethyl)amino)-1-((2-(trimethylsilyl)ethoxy)methyl)-1H-imidazo[4,5-b]pyridine-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-((2-morpholinoethyl)amino)-1H-imidazo[4,5-b]pyridine-7-carboxamide was isolated as a white solid. $C_{19}H_{20}ClFN_6O_2$. 419.22/421.14 (M+1).

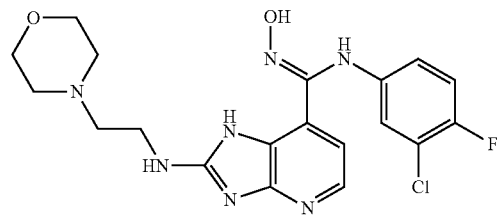 [SMILES: O/N=C(\Nc1ccc(F)c(Cl)c1)c1ccnc2nc(NCCN3CCOCC3)[nH]c12]

N-(3-Chloro-4-fluorophenyl)-N'-hydroxy-2-((2-morpholinoethyl)amino)-1H-imidazo[4,5-b]pyridine-7-carboximidamide was made analogously to Example 59 using N-(3-chloro-4-fluorophenyl)-2-((2-morpholinoethyl)amino)-1H-imidazo[4,5-b]pyridine-7-carboxamide in place of N-(3-chloro-4-fluorophenyl)-1H-imidazo[4,5-b]pyridine-7-carboxamide. The TFA salt of N-(3-chloro-4-fluorophenyl)-Y-hydroxy-2-((2-morpholinoethyl)amino)-1H-imidazo[4,5-b]pyridine-7-carboximidamide was isolated as a white solid. $C_{19}H_{21}ClFN_7O_2$. 434.16/436.14 (M+1). $^1H$ NMR (400 MHz, DMSO-$d_6$) δ 11.31 (br s, 1H), 10.11 (br s, 1H), 8.94 (s, 1H), 7.98 (d, J=6.2 Hz, 1H), 7.10 (t, J=9.1 Hz, 1H), 7.00 (dd, J=6.6, 2.7 Hz, 1H), 6.94 (d, J=6.1 Hz, 1H), 6.57 (ddd, J=9.0, 4.0, 2.8 Hz, 1H), 3.87-3.71 (m, 8H), 3.44-3.20 (m, 4H). $^{19}F$ NMR (376 MHz, DMSO-$d_6$) δ -74.51 (9F), -126.65 (1F).

Example 169: N-(3-Chloro-4-fluorophenyl)-2-(dimethylamino)-N'-hydroxy-1H-imidazo[4,5-b]pyridine-7-carboximidamide

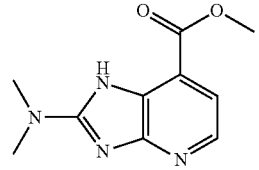

Methyl 2-(dimethylamino)-1H-imidazo[4,5-b]pyridine-7-carboxylate. Dissolved methyl 2,3-diaminoisonicotinate (0.2 g, 1 mmol) in DCM (5 mL), to the solution was added phosgeniminium chloride (0.39 g, 2 mmol) and triethylamine (0.6 g, 6 mmol). The reaction mixture was stirred at 40 degree for 3 h. Then the reaction was quenched with NaHCO$_3$ solution, diluted with EtOAc, evaporated organic solvent, the residue was purified with Combi-Flash column to afford the desired product. $C_{10}H_{12}N_4O_2$. 221.1 (M+1).

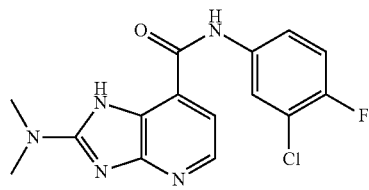 [SMILES: CN(C)c1nc2nccc(C(=O)Nc3ccc(F)c(Cl)c3)c2[nH]1]

N-(3-chloro-4-fluorophenyl)-2-(dimethylamino)-1H-benzo[d]imidazole-7-carboxamide was made analogously to Example 23 using Methyl 2-(dimethylamino)-1H-imidazo[4,5-b]pyridine-7-carboxylate. $C_{16}H_{14}ClFN_4O$. 334.2 (M+1).

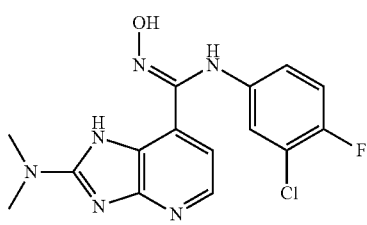 [SMILES: CN(C)c1nc2nccc(/C(=N/O)Nc3ccc(F)c(Cl)c3)c2[nH]1]

N-(3-chloro-4-fluorophenyl)-2-(dimethylamino)-N'-hydroxy-1H-imidazo[4,5-b]pyridine-7-carboximidamide. Example 169 was made analogously to Example 107 using the general procedure for hydroxyamidine formation. C$_{15}$H$_{14}$ClFN$_6$O. 349.1 (M+1). 1H NMR (400 MHz, DMSO-d6) δ 11.36 (d, J=9.1 Hz, 1H), 10.09 (s, 1H), 9.00 (s, 1H), 7.94 (d, J=6.3 Hz, 1H), 7.12-6.98 (m, 2H), 6.90 (d, J=6.3 Hz, 1H), 6.54 (ddd, J=9.0, 4.0, 2.7 Hz, 1H), 3.87 (s, 6H).

Example 170: 2-(Chloromethyl)-N-(4-fluoro-3-(trifluoromethyl)phenyl)-N'-hydroxy-3H-imidazo[4,5-b]pyridine-7-carboximidamide

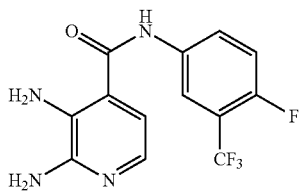

2,3-diamino-N-(4-fluoro-3-(trifluoromethyl)phenyl) isonicotinamide. To a solution of 3-fluoro-4-trifluromethyl-aniline (0.1 g, 0.65 mmol), 2,3-diaminoisonicotinic acid (0.234 g, 1 mmol) and triethylamine (0.18 mL, 1 mmol) in DMF (2 mL) was added HATU (0.186 g, 0.78 mmol). The reaction stirred for 16 hr at RT. Saturated sodium bicarbonate was added and the aqueous layer was washed three times with AcOEt. The combined organic layers were dried over sodium sulfate, filtered and concentrated onto silica gel and purified by silica gel chromatography (0->100% ethyl acetate in hexanes) to give the desired product as yellow crystals. C$_{13}$H$_{10}$F$_4$N$_4$O. 315.1 (M+1).

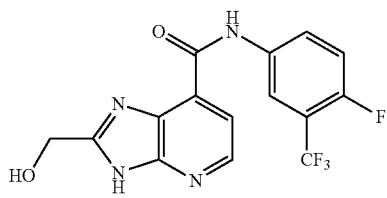 [SMILES: O=C(Nc1ccc(F)c(C(F)(F)F)c1)c1ccnc2[nH]c(CO)nc12]

N-(4-fluoro-3-(trifluoromethyl)phenyl)-2-(hydroxymethyl)-3H-imidazo[4,5-b]pyridine-7-carboxamide. 2,3-diamino-N-(4-fluoro-3-(trifluoromethyl)phenyl)isonicotinamide (0.078 g, 0.25 mmol) and 2-hydroxyacetic acid (0.378 g, 5 mmol) was heated neat in a microwave reactor to 170 C for 20 min. LiOH (0.15 g, 6 mmol) in dioxane/water (0.6/2 mL) was added and stirred for 30 min. Saturated sodium bicarbonate was added and the aqueous layer was washed three times with AcOEt. The combined organic layers were dried over sodium sulfate, filtered to give the desired product. C$_{15}$H$_{10}$F$_4$N$_4$O$_2$ 355.1 (M+1).

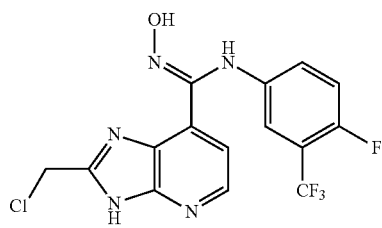 [SMILES: O/N=C(\Nc1ccc(F)c(C(F)(F)F)c1)c1ccnc2[nH]c(CCl)nc12]

2-(Chloromethyl)-N-(4-fluoro-3-(trifluoromethyl)phenyl)-N'-hydroxy-3H-imidazo[4,5-b]pyridine-7-carboximidamide. N-(4-fluoro-3-(trifluoromethyl)phenyl)-2-(hydroxymethyl)-3H-imidazo[4,5-b]pyridine-7-carboxamide (0.22 g, 0.62 mmol), POCl3 (0.6 ml, 6 mM) and PCL5 (0.26 g, 0.1 mM) was stirred in dioxane (0.6 ml) at RT for 30 min. Volatiles were removed and excess NH$_2$OH in acetonitrile (2 ml, ⅒ 50% NH$_2$OH in water/acetonitrile) was added, stirred at RT for 10 min. Volatiles were removed. Purification by preparatory HPLC (5-100% MeCN in water, 0.1% TFA) afforded the desired product. C$_{15}$H$_{10}$ClF$_4$N$_5$O. 386.1.08 (M-1).

Example 171: N-(4-Fluoro-3-(trifluoromethyl)phenyl)-N'-hydroxy-2-(hydroxymethyl)-3H-imidazo[4,5-b]pyridine-7-carboximidamide

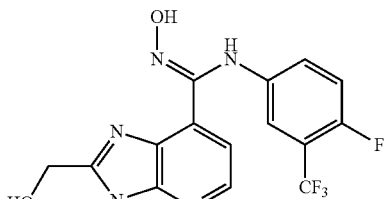

2-(Chloromethyl)-N-(4-fluoro-3-(trifluoromethyl)phenyl)-N'-hydroxy-3H-imidazo[4,5-b]pyridine-7-carboximidamide. (0.006 g, 0.17 mM), NaI (0.010 g, 0.67 mM) and NaOAc (0.010 g, 1.7 mM) were stirred in acetone (3 ml) at RT for 30 min. After filtration, volatiles were removed. Purification by preparatory HPLC (5-100% MeCN in water, 0.1% TFA) afforded the desired product. C$_{15}$H$_{11}$F$_4$N$_5$O$_2$. Exact Mass: 370.1 (M+1).

Example 172: N-(3-Chloro-4-fluorophenyl)-N'-hydroxy-2-(1-hydroxyethyl)-1H-imidazo[4,5-b]pyridine-7-carboximidamide

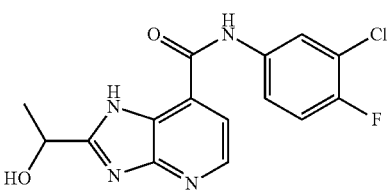 [SMILES: CC(O)c1nc2nccc(C(=O)Nc3ccc(F)c(Cl)c3)c2[nH]1]

A suspension of 2,3-diamino-N-(3-chloro-4-fluorophenyl)isonicotinamide (200 mg, 0.713 mmol) and 2-hydroxypropanoic acid (1.0 mL, 13 mmol) was sparged with argon for 1 min, then sealed and stirred at 180° C. for 1 h in a microwave reactor. The resulting mixture was cooled to room temperature and treated with 1 M lithium hydroxide (20 mL, 20 mmol), then stirred for 30 min. The resulting precipitate was filtered off and rinsed with water to afford N-(3-chloro-4-fluorophenyl)-2-(1-hydroxyethyl)-1H-imidazo[4,5-b]pyridine-7-carboxamide. $C_{15}H_{12}ClFN_4O_2$. 335.1 (M+1).

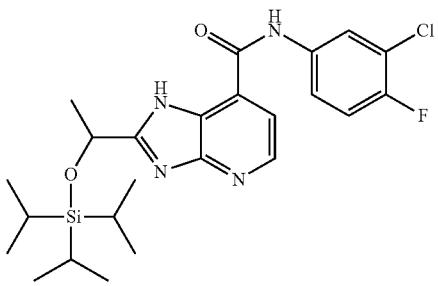 [SMILES: CC(O[Si](C(C)C)(C(C)C)C(C)C)c1nc2nccc(C(=O)Nc3ccc(F)c(Cl)c3)c2[nH]1]

N-(3-chloro-4-fluorophenyl)-2-(1-((triisopropylsilyl)oxy)ethyl)-1H-imidazo[4,5-b]pyridine-7-carboxamide was made analogously to Example 183 using N-(3-chloro-4-fluorophenyl)-2-(1-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide. $C_{24}H_{32}ClFN_4O_2Si$. 491.2 (M+1).

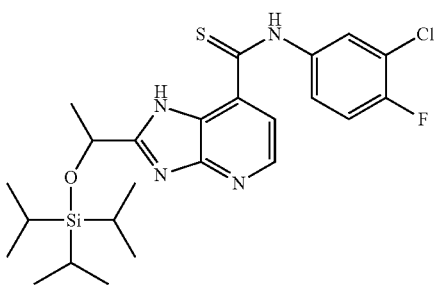 [SMILES: CC(O[Si](C(C)C)(C(C)C)C(C)C)c1nc2nccc(C(=S)Nc3ccc(F)c(Cl)c3)c2[nH]1]

N-(3-chloro-4-fluorophenyl)-2-(1-((triisopropylsilyl)oxy)ethyl)-1H-imidazo[4,5-b]pyridine-7-carbothioamide was made analogously to Example 183 using N-(3-chloro-4-fluorophenyl)-2-(1-((triisopropylsilyl)oxy)ethyl)-1H-imidazo[4,5-b]pyridine-7-carboxamide in place of N-(3-chloro-4-fluorophenyl)-2-(2-((triisopropylsilyl)oxy)ethyl)-1H-imidazo[4,5-b]pyridine-7-carboxamide. $C_{24}H_{32}ClFN_4OSSi$. 507.2 (M+1).

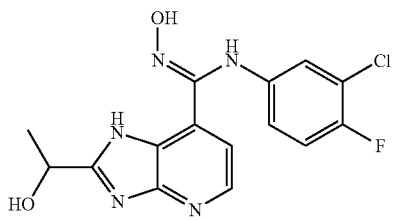 [SMILES: CC(O)c1nc2nccc(/C(=N/O)Nc3ccc(F)c(Cl)c3)c2[nH]1]

A suspension of N-(3-chloro-4-fluorophenyl)-2-(1-((triisopropylsilyl)oxy)ethyl)-1H-imidazo[4,5-b]pyridine-7-carbothioamide (30 mg, 0.059 mmol) in methanol (3 mL) was treated with hydrogen chloride (4.0 M solution in dioxane, 0.12 mL, 0.46 mmol). The resulting solution was stirred at 70° C. overnight, then cooled to room temperature, treated with an additional quantity of hydrogen chloride (4.0 M solution in dioxane, 0.12 mL, 0.46 mmol), and stirred at 70° C. for an additional 7 h. The reaction mixture was then cooled to room temperature and concentrated under reduced pressure. The resulting residue was taken up in methanol (2.4 mL), treated with hydroxylamine (50% solution in water, 0.370 mL, 6.0 mmol), and stirred at 70° C. for 2 h in a sealed vial. The mixture was then cooled to room temperature, diluted with dimethyl sulfoxide, and purified by reverse phase preparative HPLC to provide N-(3-chloro-4-fluorophenyl)-N'-hydroxy-2-(1-hydroxyethyl)-1H-imidazo[4,5-b]pyridine-7-carboximidamide. $C_{15}H_{13}ClFN_5O_2$. 350.1 (M+1).

Example 173: N-(3-Chloro-4-fluorophenyl)-N'-hydroxy-2-(hydroxy(phenyl)methyl)-1H-imidazo[4,5-b]pyridine-7-carboximidamide

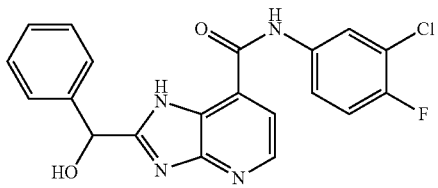 [SMILES: O=C(Nc1ccc(F)c(Cl)c1)c1ccnc2nc(C(O)c3ccccc3)[nH]c12]

A suspension of 2,3-diamino-N-(3-chloro-4-fluorophenyl)isonicotinamide (400 mg, 1.43 mmol) and 2-hydroxy-2-phenylacetic acid acid (1.74 g, 11.4 mmol) in dioxane (3.5 mL) was sparged with argon for 1 min, then sealed and stirred at 180° C. for 1 h in a microwave reactor. The resulting mixture was cooled to room temperature and treated with 1 M lithium hydroxide (14.3 mL, 14.3 mmol), then stirred for 30 min. The resulting precipitate was filtered off and rinsed with water to afford N-(3-chloro-4-fluorophenyl)-2-(hydroxy(phenyl)methyl)-1H-imidazo[4,5-b]pyridine-7-carboxamide. $C_{20}H_{14}ClFN_4O_2$. 397.1 (M+1).

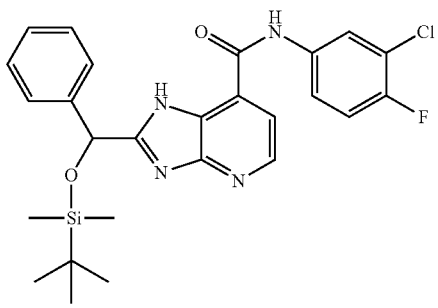

2-(((tert-butyldimethylsilyl)oxy)(phenyl)methyl)-N-(3-chloro-4-fluorophenyl)-1H-imidazo[4,5-b]pyridine-7-carboxamide was made analogously to Example 183 using N-(3-chloro-4-fluorophenyl)-2-(hydroxy(phenyl)methyl)-1H-imidazo[4,5-b]pyridine-7-carboxamide and tert-butyldimethylsilyl trifluoromethanesulfonate in place of N-(3-chloro-4-fluorophenyl)-2-(2-hydroxyethyl)-1H-imidazo[4,5-b]pyridine-7-carboxamide and triisopropylsilyl trifluoromethanesulfonate. $C_{26}H_{28}ClFN_4O_2Si$. 511.2 (M+1).

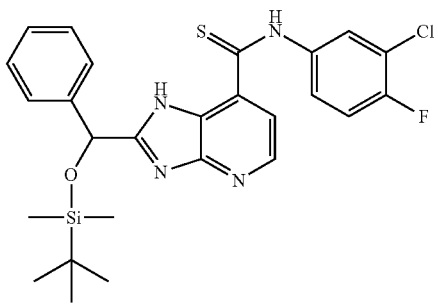 [SMILES: CC(C)(C)[Si](C)(C)OC(c1ccccc1)c1nc2nccc(C(=O)Nc3ccc(F)c(Cl)c3)c2[nH]1]

2-(((tert-butyldimethylsilyl)oxy)(phenyl)methyl)-N-(3-chloro-4-fluorophenyl)-1H-imidazo[4,5-b]pyridine-7-carbothioamide was made analogously to Example 183 using 2-(((tert-butyldimethylsilyl)oxy)(phenyl)methyl)-N-(3-chloro-4-fluorophenyl)-1H-imidazo[4,5-b]pyridine-7-carboxamide in place of N-(3-chloro-4-fluorophenyl)-2-(2-(((triisopropylsilyl)oxy)ethyl)-1H-imidazo[4,5-b]pyridine-7-carboxamide. $C_{26}H_{28}ClFN_4OSSi$. 527.1 (M+1).

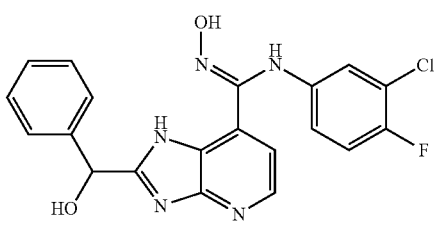 [SMILES: O/N=C(\Nc1ccc(F)c(Cl)c1)c1ccnc2nc(C(O)c3ccccc3)[nH]c12]

Example 173 was made analogously to Example 172 using 2-(((tert-butyldimethylsilyl)oxy)(phenyl)methyl)-N-(3-chloro-4-fluorophenyl)-1H-imidazo[4,5-b]pyridine-7-carbothioamide in place of N-(3-chloro-4-fluorophenyl)-2-(1-((triisopropylsilyl)oxy)ethyl)-1H-imidazo[4,5-b]pyridine-7-carbothioamide. $C_{20}H_{15}ClFN_5O_2$. 413.0 (M+1).

Example 174: N-(3-Chloro-4-fluorophenyl)-2-(cyclopropyl(hydroxy)methyl)-N'-hydroxy-1H-imidazo[4,5-b]pyridine-7-carboximidamide

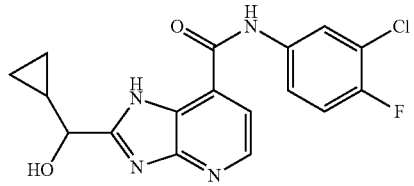 [SMILES: O=C(Nc1ccc(F)c(Cl)c1)c1ccnc2nc(C(O)C3CC3)[nH]c12]

N-(3-chloro-4-fluorophenyl)-2-(cyclopropyl(hydroxy)methyl)-1H-imidazo[4,5-b]pyridine-7-carboxamide was made analogously to Example 173 using 2-cyclopropyl-2-hydroxyacetic acid in place of 2-hydroxy-2-phenylacetic acid acid. $C_{17}H_{14}ClFN_4O_2$. 361.1 (M+1).

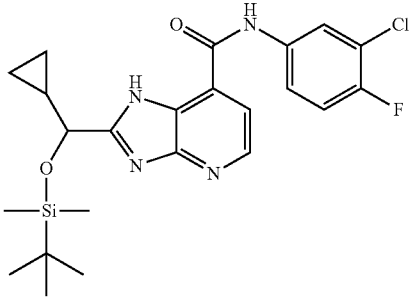 [SMILES: CC(C)(C)[Si](C)(C)OC(c1nc2nccc(C(=O)Nc3ccc(F)c(Cl)c3)c2[nH]1)C1CC1]

2-(((tert-butyldimethylsilyl)oxy)(cyclopropyl)methyl)-N-(3-chloro-4-fluorophenyl)-1H-imidazo[4,5-b]pyridine-7-carboxamide was made analogously to Example 183 using N-(3-chloro-4-fluorophenyl)-2-(cyclopropyl(hydroxy)methyl)-1H-imidazo[4,5-b]pyridine-7-carboxamide and tert-butyldimethylsilyl trifluoromethanesulfonate in place of N-(3-chloro-4-fluorophenyl)-2-(2-hydroxyethyl)-1H-imidazo[4,5-b]pyridine-7-carboxamide and triisopropylsilyl trifluoromethanesulfonate. $C_{23}H_{28}ClFN_4O_2Si$. 475.2 (M+1).

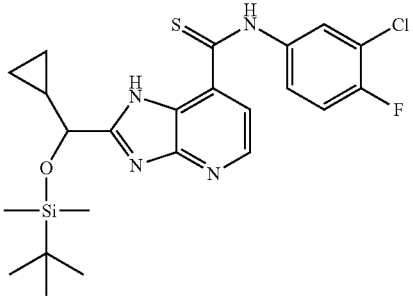 [SMILES: CC(C)(C)[Si](C)(C)OC(c1nc2nccc(C(=S)Nc3ccc(F)c(Cl)c3)c2[nH]1)C1CC1]

2-(((tert-butyldimethylsilyl)oxy)(cyclopropyl)methyl)-N-(3-chloro-4-fluorophenyl)-1H-imidazo[4,5-b]pyridine-7-carbothioamide was made analogously to Example 183 using 2-(((tert-butyldimethylsilyl)oxy)(cyclopropyl)methyl)-N-(3-chloro-4-fluorophenyl)-1H-imidazo[4,5-b]pyridine-7-carboxamide in place of N-(3-chloro-4-fluorophenyl)-2-(2-((triisopropylsilyl)oxy)ethyl)-1H-imidazo[4,5-b]pyridine-7-carboxamide. $C_{23}H_{28}ClFN_4OSSi$. 491.2 (M+1).

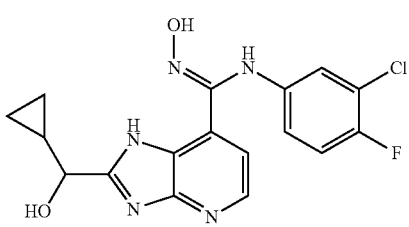 [SMILES: O/N=C(\Nc1ccc(F)c(Cl)c1)c1ccnc2nc(C(O)C3CC3)[nH]c12]

Example 175 was made analogously to Example 172 using 2-(((tert-butyldimethylsilyl)oxy)(cyclopropyl)methyl)-N-(3-chloro-4-fluorophenyl)-1H-imidazo[4,5-b]pyridine-7-carbothioamide in place of N-(3-chloro-4-fluorophenyl)-2-(1-((triisopropylsilyl)oxy)ethyl)-1H-imidazo[4,5-b]pyridine-7-carbothioamide. $C_{17}H_{15}ClFN_5O_2$. 376.1 (M+1).

Example 175: N-(3-Chloro-4-fluorophenyl)-N'-hydroxy-2-(2-hydroxypropan-2-yl)-1H-imidazo[4,5-b]pyridine-7-carboximidamide

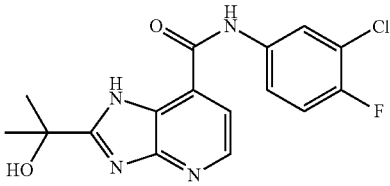 [SMILES: CC(C)(O)c1nc2nccc(C(=O)Nc3ccc(F)c(Cl)c3)c2[nH]1]

A suspension of 2,3-diamino-N-(3-chloro-4-fluorophenyl)isonicotinamide (400 mg, 1.43 mmol) and 2-hydroxy-2-methylpropanoic acid (1.19 g, 11.4 mmol) in dioxane (2 mL) was sparged with argon for 1 min, then sealed and stirred at 180° C. for 1 h in a microwave reactor. The resulting mixture was cooled to room temperature and treated with 1 M lithium hydroxide (14.3 mL, 14.3 mmol), then stirred for 30 min. The mixture was then filtered, and the resulting filtrate was acidified with 2 M hydrochloric acid to give a precipitate. The solids were filtered off and washed with water to provide N-(3-chloro-4-fluorophenyl)-2-(2-hydroxypropan-2-yl)-1H-imidazo[4,5-b]pyridine-7-carboxamide. $C_{16}H_{14}ClFN_4O_2$. 349.1 (M+1).

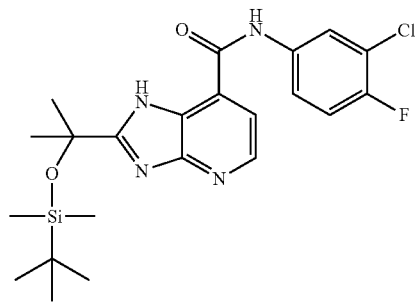 [SMILES: CC(C)(O[Si](C)(C)C(C)(C)C)c1nc2nccc(C(=O)Nc3ccc(F)c(Cl)c3)c2[nH]1]

2-(2-((tert-butyldimethylsilyl)oxy)propan-2-yl)-N-(3-chloro-4-fluorophenyl)-1H-imidazo[4,5-b]pyridine-7-carboxamide was made analogously to Example 183 using N-(3-chloro-4-fluorophenyl)-2-(2-hydroxypropan-2-yl)-1H-imidazo[4,5-b]pyridine-7-carboxamide and tert-butyldimethylsilyl trifluoromethanesulfonate in place of N-(3-chloro-4-fluorophenyl)-2-(2-hydroxyethyl)-1H-imidazo[4,5-b]pyridine-7-carboxamide and triisopropylsilyl trifluoromethanesulfonate. $C_{22}H_{28}ClFN_4O_2Si$. 463.2 (M+1).

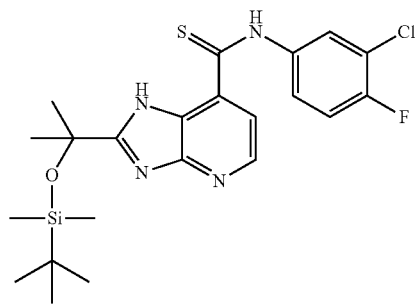 [SMILES: CC(C)(O[Si](C)(C)C(C)(C)C)c1nc2nccc(C(=S)Nc3ccc(F)c(Cl)c3)c2[nH]1]

2-(2-((tert-butyldimethylsilyl)oxy)propan-2-yl)-N-(3-chloro-4-fluorophenyl)-1H-imidazo[4,5-b]pyridine-7-carbothioamide was made analogously to Example 183 using 2-(2-((tert-butyldimethylsilyl)oxy)propan-2-yl)-N-(3-chloro-4-fluorophenyl)-1H-imidazo[4,5-b]pyridine-7-carboxamide in place of N-(3-chloro-4-fluorophenyl)-2-(2-((triisopropylsilyl)oxy)ethyl)-1H-imidazo[4,5-b]pyridine-7-carboxamide. $C_{22}H_{28}ClFN_4OSSi$. 479.1 (M+1).

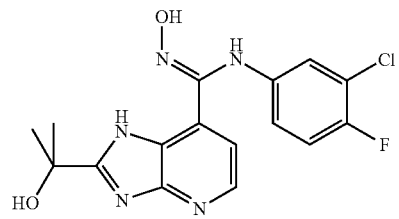 [SMILES: CC(C)(O)c1nc2nccc(/C(=N/O)Nc3ccc(F)c(Cl)c3)c2[nH]1]

Example 175 was made analogously to Example 172 using 2-(2-((tert-butyldimethylsilyl)oxy)propan-2-yl)-N-(3-chloro-4-fluorophenyl)-1H-imidazo[4,5-b]pyridine-7-carbothioamide in place of N-(3-chloro-4-fluorophenyl)-2-(1-((triisopropylsilyl)oxy)ethyl)-1H-imidazo[4,5-b]pyridine-7-carbothioamide. $C_{16}H_{15}ClFN_5O_2$. 364.1 (M+1).

Example 176: N-(3-Chloro-4-fluorophenyl)-N'-hydroxy-2-(2,2,2-trifluoro-1-hydroxyethyl)-1H-imidazo[4,5-b]pyridine-7-carboximidamide

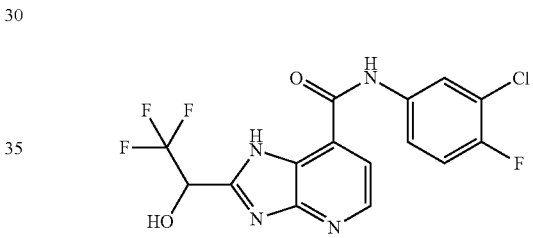

N-(3-chloro-4-fluorophenyl)-2-(2,2,2-trifluoro-1-hydroxyethyl)-1H-imidazo[4,5-b]pyridine-7-carboxamide was made analogously to Example 175 using 3,3,3-trifluoro-2-hydroxypropanoic acid in place of 2-hydroxy-2-methylpropanoic acid. $C_{15}H_9ClF_4N_4O_2$. 389.0 (M+1).

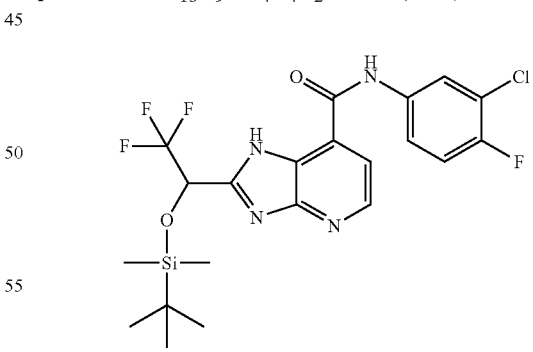

2-(1-((tert-butyldimethylsilyl)oxy)-2,2,2-trifluoroethyl)-N-(3-chloro-4-fluorophenyl)-1H-imidazo[4,5-b]pyridine-7-carboxamide was made analogously to Example 183 using N-(3-chloro-4-fluorophenyl)-2-(2,2,2-trifluoro-1-hydroxyethyl)-1H-imidazo[4,5-b]pyridine-7-carboxamide and tert-butyldimethylsilyl trifluoromethanesulfonate in place of N-(3-chloro-4-fluorophenyl)-2-(2-hydroxyethyl)-1H-imidazo[4,5-b]pyridine-7-carboxamide and triisopropylsilyl trifluoromethanesulfonate. $C_{21}H_{23}ClF_4N_4O_2Si$. 503.1 (M+1).

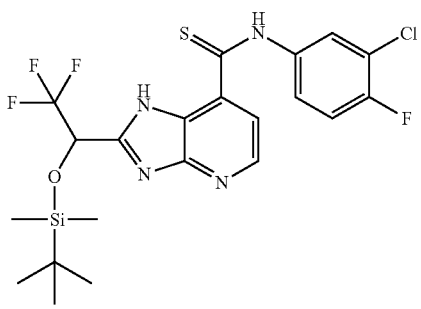 [SMILES: CC(C)(C)[Si](C)(C)OC(c1nc2nccc(C(=O)Nc3ccc(F)c(Cl)c3)c2[nH]1)C(F)(F)F]

2-(1-((tert-butyldimethylsilyl)oxy)-2,2,2-trifluoroethyl)-N-(3-chloro-4-fluorophenyl)-1H-imidazo[4,5-b]pyridine-7-carbothioamide was made analogously to Example 183 using 2-(1-((tert-butyldimethylsilyl)oxy)-2,2,2-trifluoroethyl)-N-(3-chloro-4-fluorophenyl)-1H-imidazo[4,5-b]pyridine-7-carboxamide in place of N-(3-chloro-4-fluorophenyl)-2-(2-((triisopropylsilyl)oxy)ethyl)-1H-imidazo[4,5-b]pyridine-7-carboxamide. $C_{21}H_{23}ClF_4N_4OSSi$. 519.1 (M+1).

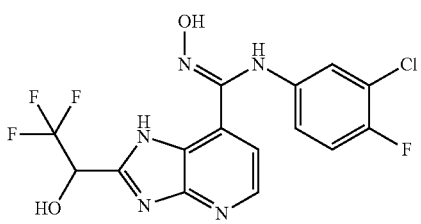 [SMILES: O/N=C(\Nc1ccc(F)c(Cl)c1)c1ccnc2nc(C(O)C(F)(F)F)[nH]c12]

Example 176 was made analogously to Example 172 using 2-(1-((tert-butyldimethylsilyl)oxy)-2,2,2-trifluoroethyl)-N-(3-chloro-4-fluorophenyl)-1H-imidazo[4,5-b]pyridine-7-carbothioamide in place of N-(3-chloro-4-fluorophenyl)-2-(1-((triisopropylsilyl)oxy)ethyl)-1H-imidazo[4,5-b]pyridine-7-carbothioamide. $C_{15}H_{10}ClF_4N_5O_2$. 404.1 (M+1).

Example 177: N-(3-Chloro-4-fluorophenyl)-N'-hydroxy-2-(hydroxymethyl)-1H-imidazo[4,5-b]pyridine-7-carboximidamide

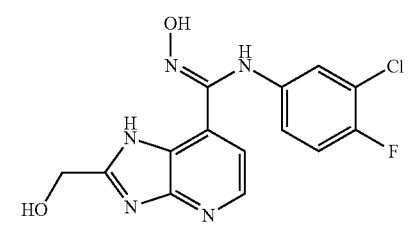

A solution of 4-(3-chloro-4-fluorophenyl)-3-(2-(hydroxymethyl)-1H-imidazo[4,5-b]pyridin-7-yl)-1,2,4-oxadiazol-5(4H)-one (20 mg, 0.055 mmol) in tetrahydrofuran (0.75 mL) was treated with water (0.75 mL) followed by 2 M sodium hydroxide (0.75 mL, 1.5 mmol). The mixture was stirred for 20 min, then acidified with acetic acid and purified by reverse phase preparative HPLC to provide the desired product. $C_{14}H_{11}ClFN_5O_2$. 336.1 (M+1).

Example 178: N-(3-Chloro-4-fluorophenyl)-N'-hydroxy-2-((methylamino)methyl)-1H-imidazo[4,5-b]pyridine-7-carboximidamide

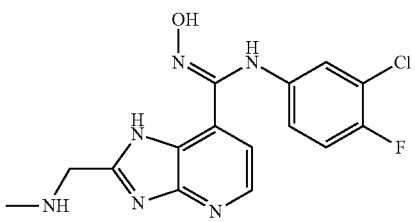 [SMILES: CNCc1nc2nccc(/C(=N/O)Nc3ccc(F)c(Cl)c3)c2[nH]1]

Example 178 was made analogously to Example 112 using methylamine (2.0 M solution in THF) in place of morpholine. $C_{15}H_{14}ClFN_6O$. 349.1 (M+1).

Example 179: 2-(Aminomethyl)-N-(3-chloro-4-fluorophenyl)-N'-hydroxy-1H-imidazo[4,5-b]pyridine-7-carboximidamide

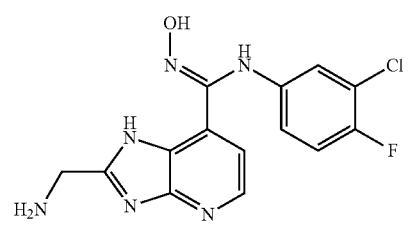 [SMILES: NCc1nc2nccc(/C(=N/O)Nc3ccc(F)c(Cl)c3)c2[nH]1]

A solution of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate (10 mg, 0.019 mmol) in acetonitrile (0.5 mL) was treated with ammonia (0.5 M solution in dioxane, 0.50 mL, 0.25 mmol) and stirred at room temperature overnight. The mixture was then concentrated under reduced pressure. The resulting residue was taken up in tetrahydrofuran (0.50 mL) and treated with water (0.50 mL) followed by 2 M sodium hydroxide (0.20 mL, 0.40 mmol). The resulting mixture was stirred at room temperature for 5 min, then acidified with acetic acid and purified by reverse phase preparative HPLC to provide the desired product. $C_{14}H_{12}ClFN_6O$. 335.1 (M+1).

Example 180: N-(3-Chloro-4-fluorophenyl)-N'-hydroxy-2-(phenylsulfonamidomethyl)-1H-imidazo[4,5-b]pyridine-7-carboximidamide

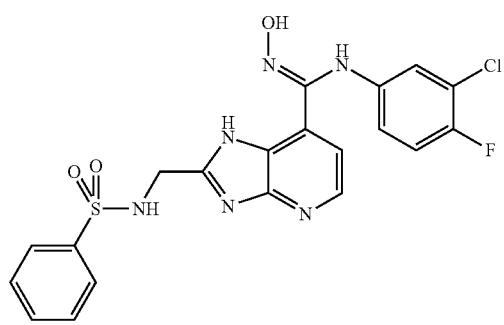 [SMILES: O=S(=O)(NCc1nc2nccc(/C(=N/O)Nc3ccc(F)c(Cl)c3)c2[nH]1)c1ccccc1]

A solution of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate (36 mg, 0.069 mmol) in acetonitrile (2 mL) was treated with ammonia (0.5 M solution in dioxane, 1.9 mL, 0.97 mmol) and stirred at room temperature overnight. The mixture was then concentrated under reduced pressure. The resulting residue was dissolved in dichloromethane (2 mL) and treated with pyridine (0.054 mL, 0.67 mmol) and divided into two batches of equal volume. One of these batches was then cooled to 0° C. and benzenesulfonyl chloride (0.78 M solution in dichloromethane, 0.130 mL, 0.100 mmol) was added dropwise with stirring. The reaction mixture was then warmed to room temperature and stirred for 10 min, then cooled to 0° C. and treated with water. The mixture was then partially concentrated under reduced pressure, then treated with tetrahydrofuran (1 mL) followed by 2 M sodium hydroxide (1 mL) and stirred for 15 min. The mixture was then acidified with acetic acid, partially concentrated under reduced pressure, diluted with dimethyl sulfoxide (1 mL), and purified by reverse phase preparative HPLC to provide the desired product. $C_{20}H_{16}ClFN_6O_3S$. 475.1 (M+1).

Example 181: N-(3-Chloro-4-fluorophenyl)-N'-hydroxy-2-(methylsulfonamidomethyl)-1H-imidazo[4,5-b]pyridine-7-carboximidamide

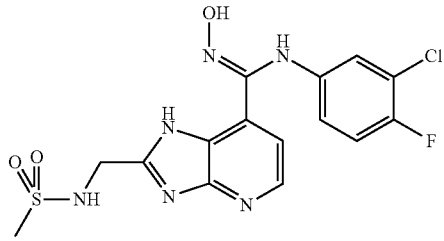 [SMILES: CS(=O)(=O)NCc1nc2nccc(/C(=N/O)Nc3ccc(F)c(Cl)c3)c2[nH]1]

Example 181 was prepared analogously to Example 180 using methanesulfonyl chloride in place of benzenesulfonyl chloride. $C_{15}H_{14}ClFN_6O_3S$. 413.0 (M+1).

Example 182: N-(3-Chloro-4-fluorophenyl)-N'-hydroxy-2-((pyrimidin-2-ylamino)methyl)-1H-imidazo[4,5-b]pyridine-7-carboximidamide

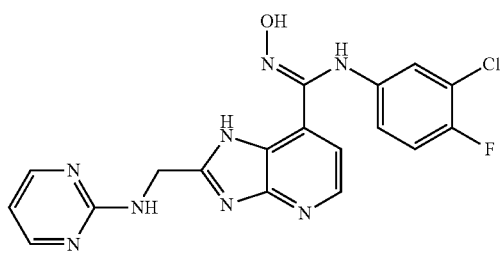 [SMILES: O/N=C(\Nc1ccc(F)c(Cl)c1)c1ccnc2nc(CNc3ncccn3)[nH]c12]

A solution of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate (59 mg, 0.114 mmol) in acetonitrile (3 mL) was treated with ammonia (0.5 M solution in dioxane, 1.9 mL, 0.97 mmol) and stirred at room temperature overnight. The solution was then divided into two batches of equal volume. One of the batches was concentrated under reduced pressure and the resulting residue taken up in DMSO (1 mL). The solution was treated with N,N-diisopropylethylamine (0.061 mL, 0.35 mmol) followed by 2-fluoropyrimidine (23 mg, 0.23 mmol) and stirred for at room temperature for 48 h. The mixture was then treated with water (1 mL) and 2 M sodium hydroxide (0.5 mL) and stirred for 15 min, then acidified acetic acid, diluted with dimethyl sulfoxide, and purified by reverse phase preparative HPLC to provide the desired product. $C_{18}H_{14}ClFN_8O$. 413.1 (M+1).

Example 183: N-(3-Chloro-4-fluorophenyl)-N'-hydroxy-2-(2-hydroxyethyl)-1H-imidazo[4,5-b]pyridine-7-carboximidamide

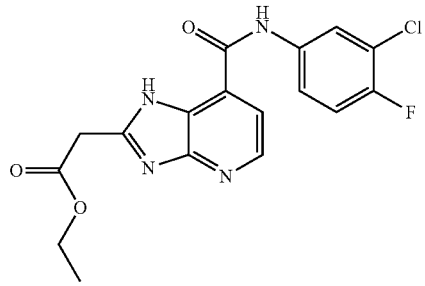 [SMILES: CCOC(=O)Cc1nc2nccc(C(=O)Nc3ccc(F)c(Cl)c3)c2[nH]1]

Ethyl 2-(7-((3-chloro-4-fluorophenyl)carbamoyl)-1H-imidazo[4,5-b]pyridin-2-yl)acetate. A suspension of 2,3-diamino-N-(3-chloro-4-fluorophenyl)isonicotinamide (10.9 g, 38.8 mmol) and ethyl 3-ethoxy-3-iminopropanoate hydrochloride (30.4 g, 155 mmol) in ethanol (100 mL) was stirred at 80° C. for 24 h. The mixture was then cooled to room temperature and an additional portion of ethyl 3-ethoxy-3-iminopropanoate hydrochloride (30.4 g, 155 mmol) was added. The suspension was stirred at 80° C. for an additional 24 h. The mixture was then cooled to room temperature and the resulting solid filtered off, rinsed with water, and dried under a stream of air to afford the desired product. $C_{17}H_{14}ClFN_4O_3$. 377.1 (M+1).

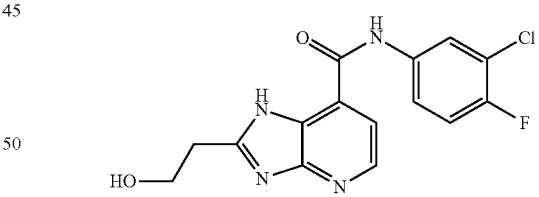

N-(3-chloro-4-fluorophenyl)-2-(2-hydroxyethyl)-1H-imidazo[4,5-b]pyridine-7-carboxamide. To a stirring suspension of ethyl 2-(7-((3-chloro-4-fluorophenyl)carbamoyl)-1H-imidazo[4,5-b]pyridin-2-yl)acetate (5.55 g, 14.7 mmol) in THF (210 mL) under a positive pressure of nitrogen was added lithium borohydride (3.21 g, 147 mmol) in five equal portions. The resulting mixture was then stirred at 40° C. for 1 h. The mixture was then cooled to 0° C. and water (83 mL) was slowly added, such that the internal temperature was kept below 15° C. After 30 min of stirring, 1M hydrochloric acid (660 mL) was slowly added, such that the internal temperature was kept below 20° C. The mixture was then heated to 40° C. and stirred for 2 h. The resulting solution was cooled to room temperature and extracted with ethyl acetate (3×500 mL). The combined organic layers were dried over sodium sulfate, filtered, and concentrated under reduced pressure to afford the desired product (2.46 g). The aqueous layer contained a yellow precipitate which was filtered off, rinsed with water, and dried under a stream of air to afford an additional quantity of desired product. $C_{15}H_{12}ClFN_4O_2$. 335.1 (M+1).

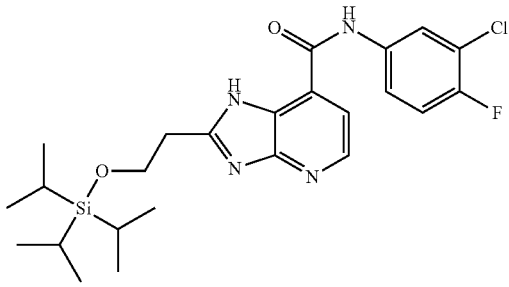 [SMILES: CC(C)[Si](OCCc1nc2nccc(C(=O)Nc3ccc(F)c(Cl)c3)c2[nH]1)(C(C)C)C(C)C]

N-(3-chloro-4-fluorophenyl)-2-(2-((triisopropylsilyl)oxy) ethyl)-1H-imidazo[4,5-b]pyridine-7-carboxamide. To a stirring suspension of N-(3-chloro-4-fluorophenyl)-2-(2-hydroxyethyl)-1H-imidazo[4,5-b]pyridine-7-carboxamide (2.46 g, 7.35 mmol) in dichloromethane (75 mL) under a nitrogen atmosphere was added 2,6-lutidine (10.2 mL, 88.2 mmol). The mixture was then cooled to 0° C. and triisopropylsilyl trifluoromethanesulfonate (11.9 mL, 44.1 mmol) was added dropwise with stirring. The mixture was then allowed to warm to room temperature and stirred for an additional 90 min. Water was added with vigorous stirring, then the organic and aqueous layers were separated and the organic layer washed four additional times with water. The organic layer was then adsorbed onto silica gel and purified by flash chromatography (0-100% EtOAc/hexanes). Product-containing fractions were combined and concentrated under reduced pressure, then triturated with acetonitrile to afford the desired product. $C_{24}H_{32}ClFN_4O_2Si$. 491.4 (M+1).

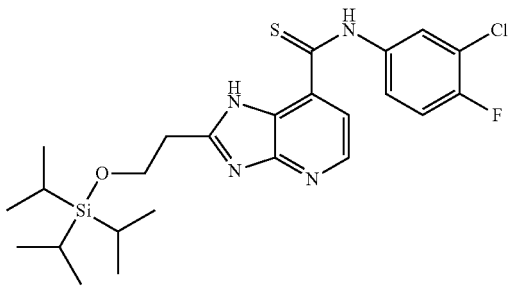

N-(3-chloro-4-fluorophenyl)-2-(2-((triisopropylsilyl)oxy) ethyl)-1H-imidazo[4,5-b]pyridine-7-carbothioamide. A suspension of N-(3-chloro-4-fluorophenyl)-2-(2-((triisopropylsilyl)oxy)ethyl)-1H-imidazo[4,5-b]pyridine-7-carboxamide (2.27 g, 4.62 mmol) and 2,4-bis(4-methoxyphenyl)-1,3,2,4-dithiadiphosphetane 2,4-disulfide (3.74 g, 9.24 mmol) in toluene (92 mL) was stirred at 95° C. for 4 h. The mixture was then cooled to room temperature and filtered, rinsing with dichloromethane. The combined filtrates were adsorbed onto silica gel and purified by flash chromatography (0-75% EtOAc/hexanes) to provide the desired product. $C_{24}H_{32}ClFN_4OSSi$. 507.2 (M+1).

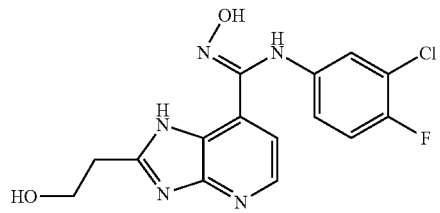 [SMILES: OCCc1nc2nccc(/C(=N/O)Nc3ccc(F)c(Cl)c3)c2[nH]1]

N-(3-chloro-4-fluorophenyl)-N'-hydroxy-2-(2-hydroxyethyl)-1H-imidazo[4,5-b]pyridine-7-carboximidamide. A solution of 4-(3-chloro-4-fluorophenyl)-3-(2-((2-((triisopropylsilyl)oxy)ethyl)-1H-imidazo[4,5-b]pyridin-7-yl)-1,2,4-oxadiazol-5(4H)-one (40 mg, 0.079 mmol) and hydrogen chloride (4.0 M solution in dioxane, 0.158 mL, 0.631 mmol) in methanol (4 mL) was stirred at 70° C. overnight in a sealed screw-top flask. The mixture was then cooled to room temperature and concentrated under reduced pressure. The resulting residue was taken up in hydroxylamine (50% solution in water, 0.259 mL, 3.991 mmol) in methanol (1.6 mL) was stirred at 70° C. in a sealed screw-top flask for 1 h. The mixture was then cooled to room temperature The mixture was acidified with acetic acid (0.300 mL, 5.24 mmol), diluted with dimethyl sulfoxide (4 mL), and purified by reverse phase preparative HPLC to provide the desired product. $C_{15}H_{13}ClFN_5O_2$. 350.10 (M+1).

Example 184: N-(3-Chloro-4-fluorophenyl)-2-(2-(dimethylamino)ethyl)-N'-hydroxy-1H-imidazo[4,5-b]pyridine-7-carboximidamide

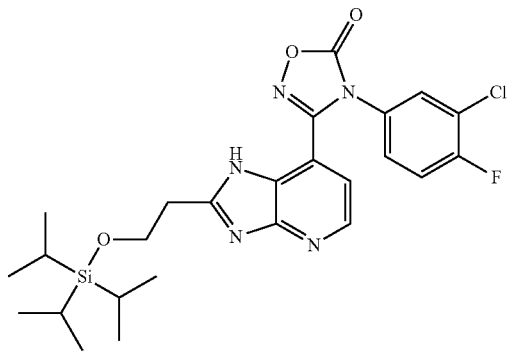 [SMILES: CC(C)[Si](OCCc1nc2nccc(-c3noc(=O)n3-c3ccc(F)c(Cl)c3)c2[nH]1)(C(C)C)C(C)C]

4-(3-chloro-4-fluorophenyl)-3-(2-(2-((triisopropylsilyl)oxy)ethyl)-1H-imidazo[4,5-b]pyridin-7-yl)-1,2,4-oxadiazol-5(4H)-one. A suspension of N-(3-chloro-4-fluorophenyl)-2-(2-((triisopropylsilyl)oxy)ethyl)-1H-imidazo[4,5-b] pyridine-7-carbothioamide (1.70 g, 3.33 mmol) and hydroxylamine (50% solution in water, 20.4 mL, 333 mmol) in methanol (135 mL) was stirred at 70° C. in a sealed screw-top flask for 1 h. The mixture was then cooled to room temperature and partially concentrated under reduced pressure to afford a white aqueous suspension. The solids were filtered off and dried under reduced pressure, then taken up in ethyl acetate (135 mL) and treated with 1,1'-carbonyldiimidazole (702 mg, 4.33 mmol). The mixture was stirred at 30° C. for 1 h, then adsorbed onto silica gel and purified by flash chromatography (0-100% EtOAc/hexanes) to provide the desired product. $C_{25}H_{31}ClFN_5O_3Si$. 532.2 (M+1).

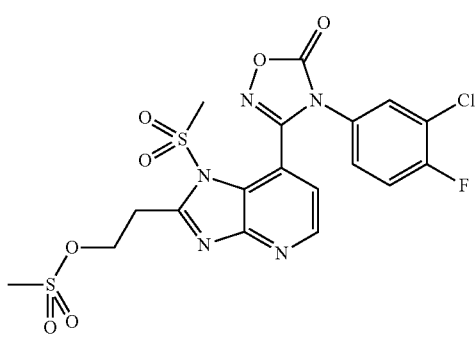 [SMILES: CS(=O)(=O)OCCc1nc2nccc(-c3noc(=O)n3-c3ccc(F)c(Cl)c3)c2n1S(C)(=O)=O]

2-(7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)ethyl methanesulfonate. A solution of 4-(3-chloro-4-fluorophenyl)-3-(2-(2-((triisopropylsilyl)oxy)ethyl)-1H-imidazo[4,5-b]pyridin-7-yl)-1,2,4-oxadiazol-5(4H)-one (1.95 g, 3.67 mmol) and hydrogen chloride (4.0 M solution in dioxane, 7.3 mL, 29 mmol) in methanol (180 mL) was stirred at 70° C. overnight in a sealed screw-top flask. The mixture was then cooled to room temperature and concentrated under reduced pressure. The resulting residue was taken up in dichloromethane (75 mL), treated with N,N-diisopropylethylamine (6.4 mL, 37 mmol), and cooled to 0° C. under a nitrogen atmosphere. Methanesulfonyl chloride (2.0 mL, 26 mmol) was added dropwise over 5 min with stirring. After 30 min, the mixture was treated with water, the layers were separated, and the organic layer was washed twice more with water. The organic phase was then concentrated under reduced pressure and purified by flash chromatography (0-65% EtOAc/hexanes) to provide the desired product (Note: the connectivity of the methanesulfonyl group on the imidazole ring was assumed to be at N(1) as indicated, though connectivity at N(3) was not rigorously ruled out). $C_{18}H_{15}ClFN_5O_7S_2$. 532.1 (M+1).

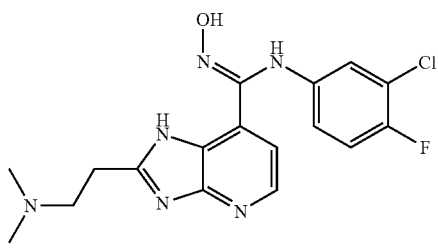 [SMILES: CN(C)CCc1nc2nccc(/C(=N/O)Nc3ccc(F)c(Cl)c3)c2[nH]1]

A solution of 2-(7-(4-(3-chloro-4-fluorophenyl)-5-oxo-4,5-dihydro-1,2,4-oxadiazol-3-yl)-1-(methylsulfonyl)-3H-imidazo[4,5-b]pyridin-2-yl)ethyl methanesulfonate (20 mg, 0.038 mmol) in acetonitrile (0.2 mL) was treated with dimethylamine (2.0 M solution in tetrahydrofuran, 0.38 mL, 0.75 mmol), and the resulting solution was stirred at room temperature for 1 h. The mixture was then concentrated under reduced pressure. The resulting residue was taken up in tetrahydrofuran (0.5 mL), treated with water (0.5 mL) followed by 2M sodium hydroxide (0.23 mL, 0.46 mmol), and stirred at room temperature for 15 min. The mixture was acidified with acetic acid (0.064 mL, 1.1 mmol), diluted with dimethyl sulfoxide (3 mL), and purified by reverse phase preparative HPLC to provide the desired product. $C_{17}H_{18}ClFN_6O$. 377.1 (M+1). $^1$H NMR (400 MHz, DMSO-$d_6$) δ 11.11 (s, 1H), 8.91 (s, 1H), 8.31 (d, J=5.1 Hz, 1H), 7.15 (d, J=5.1 Hz, 1H), 7.05 (t, J=9.1 Hz, 1H), 6.93 (dd, J=6.5, 2.7 Hz, 1H), 6.51 (ddd, J=9.0, 4.1, 2.7 Hz, 1H), 3.54 (t, J=7.3 Hz, 2H), 3.30 (t, J=7.3 Hz, 2H), 2.86 (s, 6H).

Example 185: N-(3-Chloro-4-fluorophenyl)-2-(2-(diethylamino)ethyl)-N'-hydroxy-1H-imidazo[4,5-b]pyridine-7-carboximidamide

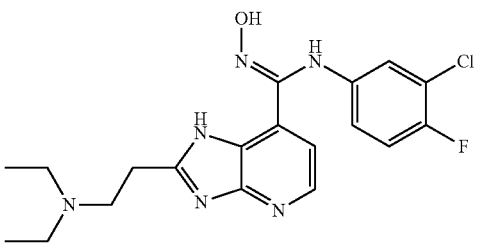 [SMILES: CCN(CC)CCc1nc2nccc(/C(=N/O)Nc3ccc(F)c(Cl)c3)c2[nH]1]

Example 185 was made analogously to Example 184 using diethylamine in place of dimethylamine. $C_{19}H_{22}ClFN_6O$. 405.1 (M+1). $^1$H NMR (400 MHz, DMSO-$d_6$) δ 11.08 (s, 1H), 8.91 (s, 1H), 8.30 (d, J=5.1 Hz, 1H), 7.16 (d, J=5.2 Hz, 1H), 7.04 (t, J=9.1 Hz, 1H), 6.93 (dd, J=6.5, 2.7 Hz, 1H), 6.50 (ddd, J=9.0, 4.1, 2.7 Hz, 1H), 3.52 (t, J=7.5 Hz, 2H), 3.28 (t, J=7.5 Hz, 2H), 3.21 (q, J=7.2 Hz, 4H), 1.22 (t, J=7.2 Hz, 6H).

Example 186: N-(3-Chloro-4-fluorophenyl)-2-(2-((cyclopropylmethyl)(methyl)amino)ethyl)-N'-hydroxy-1H-imidazo[4,5-b]pyridine-7-carboximidamide

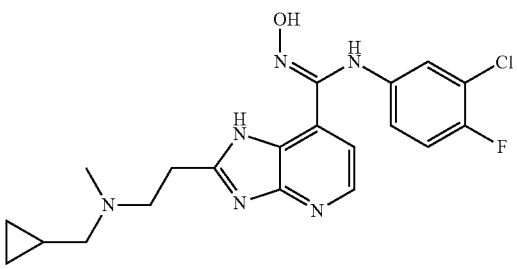 [SMILES: CN(CCc1nc2nccc(/C(=N/O)Nc3ccc(F)c(Cl)c3)c2[nH]1)CC1CC1]

Example 186 was made analogously to Example 184 using 1-cyclopropyl-N-methylmethanamine in place of dimethylamine. $C_{20}H_{22}ClFN_6O$. 417.1 (M+1). $^1$H NMR (400 MHz, DMSO-$d_6$) δ 11.08 (s, 1H), 8.90 (s, 1H), 8.31 (d, J=5.1 Hz, 1H), 7.17 (d, J=5.1 Hz, 1H), 7.04 (t, J=9.1 Hz, 1H), 6.93 (dd, J=6.5, 2.7 Hz, 1H), 6.51 (ddd, J=9.0, 4.1, 2.7 Hz, 1H), 3.59 (br s, 2H), 3.33 (t, J=7.4 Hz, 2H), 3.10 (d, J=7.3 Hz, 2H), 2.88 (s, 3H), 1.18-1.06 (m, 1H), 0.70-0.62 (m, 2H), 0.44-0.38 (m, 2H).

Example 187: N-(3-Chloro-4-fluorophenyl)-2-(2-((2,2-difluoroethyl)(methyl)amino)ethyl)-N'-hydroxy-1H-imidazo[4,5-b]pyridine-7-carboximidamide

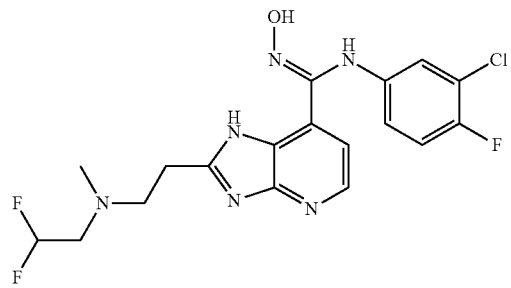 [SMILES: CN(CCc1nc2nccc(/C(=N/O)Nc3ccc(F)c(Cl)c3)c2[nH]1)CC(F)F]

A solution of 2-(7-(4-(3-chloro-4-fluorophenyl)-5-oxo-4,5-dihydro-1,2,4-oxadiazol-3-yl)-1-(methylsulfonyl)-3H-imidazo[4,5-b]pyridin-2-yl)ethyl methanesulfonate (30 mg, 0.056 mmol) in acetonitrile (0.9 mL) was treated with N,N-diisopropylethylamine (0.20 mL, 1.1 mmol) followed by 2,2-difluoro-N-methylethanamine hydrochloride (148 mg, 1.13 mmol). The resulting solution was stirred for 2 h, then treated with dimethylamine (2.0 M solution in tetrahydrofuran, 0.5 mL, 1.0 mmol). After an additional 1 h of stirring, the mixture was treated with isopropylamine (0.2 mL, 2.3 mmol) and stirred for 20 min (in order to cleave the remaining imidazolyl methanesulfonyl group). The solution was then concentrated under reduced pressure and the resulting residue taken up in tetrahydrofuran (0.75 mL). The solution was treated with water (0.75 mL) followed by 2M sodium hydroxide (0.38 mL, 0.76 mmol), and stirred at room temperature for 20 min. An additional amount of 2M sodium hydroxide (0.75 mL, 1.5 mmol) was added, and stirring resumed for 15 min. Finally, the mixture was acidified with acetic acid, partially evaporated under reduced pressure, diluted with dimethyl sulfoxide, and purified by reverse phase preparative HPLC to provide the desired product. $C_{18}H_{18}ClF_3N_6O$. 427.1 (M+1).

Example 188: N-(3-Chloro-4-fluorophenyl)-N'-hydroxy-2-(2-(methylamino)ethyl)-1H-imidazo[4,5-b]pyridine-7-carboximidamide

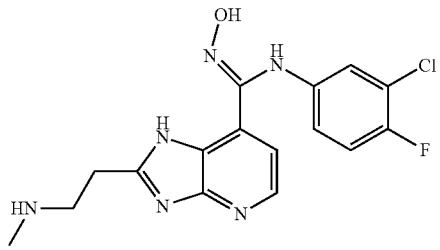 [SMILES: CNCCc1nc2nccc(/C(=N/O)Nc3ccc(F)c(Cl)c3)c2[nH]1]

A solution 2-(7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)ethyl methanesulfonate. (20 mg, 0.038 mmol) and methylamine (2.0 M solution in tetrahydrofuran, 0.376 mL, 0.752 mmol) in acetonitrile (1 mL) was stirred for 2 hr. The reaction was concentrated. The residue was brought up in tetrahydrofuran (0.5 mL) and water (0.5 mL). To this solution was added 2 N sodium hydroxide (0.22 mL, 0.43 mmol) and the reaction mixture stirred for 10 min. To the mixture was added acetic acid (0.035 mL) and the solution was loaded directly onto a prep HPLC for purification to give the desired product. $C_{16}H_{16}ClFN_6O$. 363.11 (M+1).

Example 189: 2-(2-Aminoethyl)-N-(3-chloro-4-fluorophenyl)-N'-hydroxy-1H-imidazo[4,5-b]pyridine-7-carboximidamide

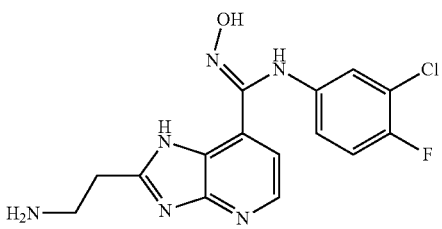 [SMILES: NCCc1nc2nccc(/C(=N/O)Nc3ccc(F)c(Cl)c3)c2[nH]1]

Example 189 was made analogously to Example 188 using ammonia (0.5 M solution in dioxane) in place of dimethylamine (2.0 M solution in tetrahydrofuran). $C_{15}H_{14}ClFN_6O$. 349.1 (M+1).

Example 190: N-(3-Chloro-4-fluorophenyl)-N'-hydroxy-2-(2-((2-methoxyethyl)amino)ethyl)-1H-imidazo[4,5-b]pyridine-7-carboximidamide

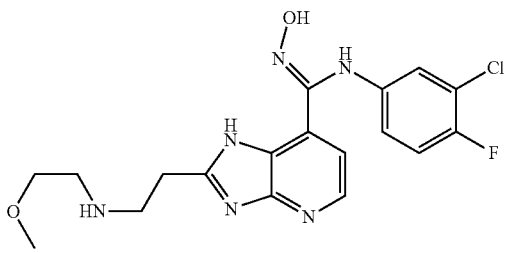 [SMILES: COCCNCCc1nc2nccc(/C(=N/O)Nc3ccc(F)c(Cl)c3)c2[nH]1]

Example 190 was made analogously to Example 188 using 2-methoxyethanamine in place of dimethylamine (2.0 M solution in tetrahydrofuran). $C_{18}H_{20}ClFN_6O_2$. 407.1 (M+1).

Example 191: N-(3-Chloro-4-fluorophenyl)-N'-hydroxy-2-(2-morpholinoethyl)-1H-imidazo[4,5-b]pyridine-7-carboximidamide

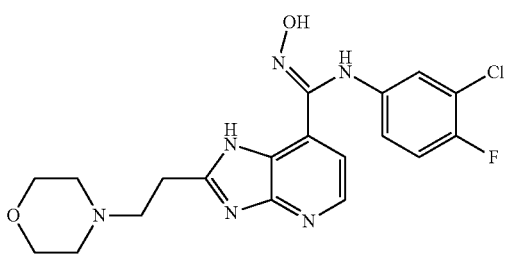 [SMILES: O/N=C(\Nc1ccc(F)c(Cl)c1)c1ccnc2nc(CCN3CCOCC3)[nH]c12]

Example 191 was made analogously to Example 188 using morpholine in place of dimethylamine (2.0 M solution in tetrahydrofuran). $C_{19}H_{20}ClFN_6O_2$. 419.13 (M+1)

Example 192: N-(3-Chloro-4-fluorophenyl)-N'-hydroxy-2-(2-(piperidin-1-yl)ethyl)-1H-imidazo[4,5-b]pyridine-7-carboximidamide

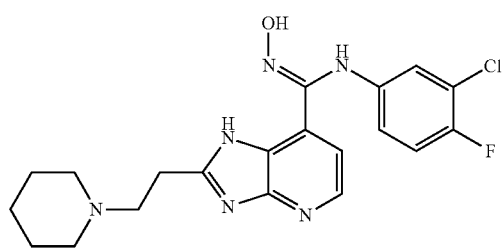 [SMILES: O/N=C(\Nc1ccc(F)c(Cl)c1)c1ccnc2nc(CCN3CCCCC3)[nH]c12]

Example 192 was made analogously to Example 184 using piperidine in place of dimethylamine. $C_{20}H_{22}ClFN_6O$. 417.1 (M+1). $^1$H NMR (400 MHz, DMSO-$d_6$) δ 11.10 (s, 1H), 8.90 (s, 1H), 8.30 (d, J=5.1 Hz, 1H), 7.16 (d, J=5.1 Hz, 1H), 7.04 (t, J=9.1 Hz, 1H), 6.93 (dd, J=6.5, 2.7 Hz, 1H), 6.52 (ddd, J=9.0, 4.1, 2.8 Hz, 1H), 3.69-2.76 (m, 8H), 1.99-1.28 (m, 6H).

Example 193: N-(3-Chloro-4-fluorophenyl)-N'-hydroxy-2-(2-(pyrrolidin-1-yl)ethyl)-1H-imidazo[4,5-b]pyridine-7-carboximidamide

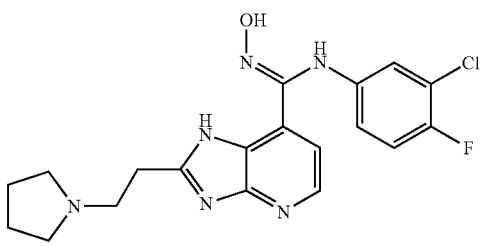 [SMILES: O/N=C(\Nc1ccc(F)c(Cl)c1)c1ccnc2nc(CCN3CCCC3)[nH]c12]

Example 193 was made analogously to Example 184 using pyrrolidine in place of dimethylamine. $C_{19}H_{20}ClFN_6O$. 403.1 (M+1). $^1H$ NMR (400 MHz, DMSO-$d_6$) δ 11.10 (s, 1H), 8.89 (s, 1H), 8.31 (d, J=5.1 Hz, 1H), 7.16 (d, J=5.1 Hz, 1H), 7.04 (t, J=9.1 Hz, 1H), 6.94 (dd, J=6.6, 2.7 Hz, 1H), 6.51 (ddd, J=9.0, 4.1, 2.7 Hz, 1H), 3.61 (t, J=7.4 Hz, 2H), 3.57-2.99 (m, 6H), 1.96 (br s, 4H).

Example 194: N-(3-Chloro-4-fluorophenyl)-N'-hydroxy-2-(2-((2-methoxyethyl)(methyl)amino)ethyl)-1H-imidazo[4,5-b]pyridine-7-carboximidamide

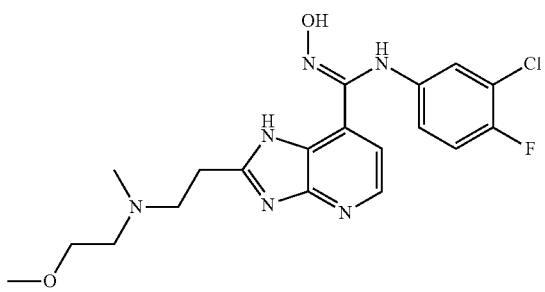 [SMILES: COCCN(C)CCc1nc2nccc(/C(=N/O)Nc3ccc(F)c(Cl)c3)c2[nH]1]

Example 194 was made analogously to Example 187 using 2-methoxy-N-methylethanamine in place of 2,2-difluoro-N-methylethanamine hydrochloride and N,N-diisopropylethylamine. $C_{19}H_{22}ClFN_6O_2$. 421.1 (M+1). $^1H$ NMR (400 MHz, DMSO-$d_6$) δ 11.09 (s, 1H), 8.89 (s, 1H), 8.30 (d, J=5.1 Hz, 1H), 7.15 (d, J=5.1 Hz, 1H), 7.04 (t, J=9.1 Hz, 1H), 6.93 (dd, J=6.5, 2.7 Hz, 1H), 6.52 (ddd, J=9.0, 4.1, 2.8 Hz, 1H), 3.70 (t, J=5.0 Hz, 2H), 3.60 (t, J=7.4 Hz, 2H), 3.40 (t, J=5.1 Hz, 2H), 3.36-3.29 (m, 5H), 2.86 (s, 3H).

Example 195: N-(3-Chloro-4-fluorophenyl)-2-(2-(dimethylamino)-1-hydroxyethyl)-N'-hydroxy-1H-imidazo[4,5-b]pyridine-7-carboximidamide

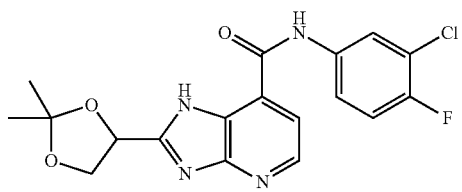 [SMILES: CC1(C)OCC(c2nc3nccc(C(=O)Nc4ccc(F)c(Cl)c4)c3[nH]2)O1]

N-(3-chloro-4-fluorophenyl)-2-(2,2-dimethyl-1,3-dioxolan-4-yl)-1H-imidazo[4,5-b]pyridine-7-carboxamide. A solution of 2,3-diamino-N-(3-chloro-4-fluorophenyl)isonicotinamide (3.00 g, 10.7 mmol) and 2,2-dimethyl-1,3-dioxolane-4-carbaldehyde (50% by weight in dichloromethane, 13.9 g, 53.4 mmol) in dimethyl sulfoxide (110 mL) was stirred vigorously under an air atmosphere at 100° C. overnight. The mixture was cooled to room temperature, diluted with water and brine solution, and extracted with dichloromethane (700 mL). The organic layer was then washed three times with water (500 mL), concentrated under reduced pressure, and adsorbed onto silica gel for purification by flash chromatography (0-70% EtOAc/hexanes) to provide the desired product. $C_{18}H_{16}ClFN_4O_3$. 391.1 (M+1).

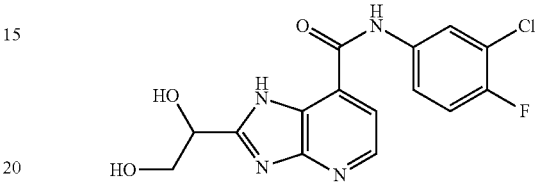

N-(3-chloro-4-fluorophenyl)-2-(1,2-dihydroxyethyl)-1H-imidazo[4,5-b]pyridine-7-carboxamide. A suspension of N-(3-chloro-4-fluorophenyl)-2-(2,2-dimethyl-1,3-dioxolan-4-yl)-1H-imidazo[4,5-b]pyridine-7-carboxamide (300 mg, 0.768 mmol) in methanol (38 mL) was treated with hydrogen chloride (4.0 M in dioxane, 1.5 mL, 6.0 mmol) and stirred at 70° C. overnight. The mixture was concentrated under reduced pressure to provide the desired product. $C_{15}H_{12}ClFN_4O_3$. 351.1 (M+1).

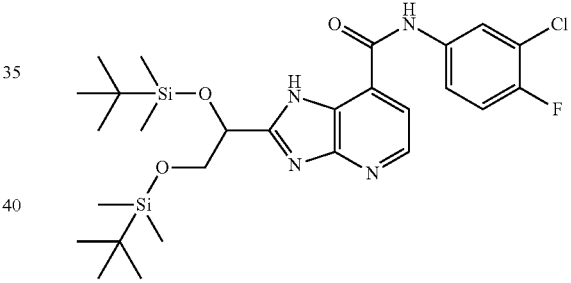

N-(3-chloro-4-fluorophenyl)-2-(2,2,3,3,8,8,9,9-octamethyl-4,7-dioxa-3,8-disiladecan-5-yl)-1H-imidazo[4,5-b]pyridine-7-carboxamide. A suspension of N-(3-chloro-4-fluorophenyl)-2-(1,2-dihydroxyethyl)-1H-imidazo[4,5-b]pyridine-7-carboxamide (727 mg, 2.07 mmol) and 2,6-lutidine (3.9 mL, 33 mmol) in dichloromethane (41 mL) was cooled to 0° C. with stirring under a nitrogen atmosphere. The mixture was then treated with tert-butyldimethylsilyl trifluoromethanesulfonate (3.8 mL, 17 mmol) dropwise and with stirring. The mixture was then warmed to room temperature and stirred for 20 min, then adsorbed onto silica gel for purification by flash chromatography (0-40% EtOAc/hexanes) to provide the desired product. $C_{27}H_{40}ClFN_4O_3Si_2$. 579.3 (M+1).

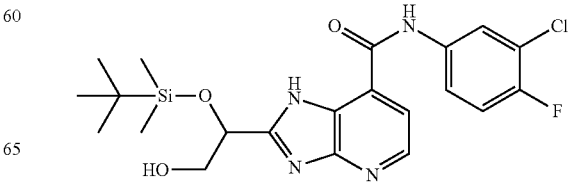

2-(1-((tert-butyldimethylsilyl)oxy)-2-hydroxyethyl)-N-(3-chloro-4-fluorophenyl)-1H-imidazo[4,5-b]pyridine-7-carboxamide. A suspension of N-(3-chloro-4-fluorophenyl)-2-(2,2,3,3,8,8,9,9-octamethyl-4,7-dioxa-3,8-disiladecan-5-yl)-1H-imidazo[4,5-b]pyridine-7-carboxamide (200 mg, 0.345 mmol) in ethanol (7 mL) was treated with pyridinium p-toluenesulfonate (781 mg, 3.11 mmol) and stirred at 80° C. for 90 min. The mixture was then cooled to room temperature, diluted with saturated aqueous sodium bicarbonate, and extracted three times with ethyl acetate. The combined organic layers were adsorbed onto silica gel for purification by flash chromatography (20-55% EtOAc/hexanes) to provide the desired product. $C_{21}H_{26}ClFN_4O_3Si$. 365.3 (M+1).

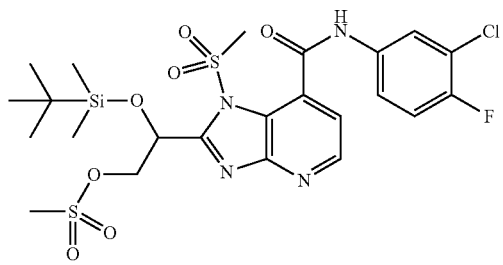 [SMILES: CC(C)(C)[Si](C)(C)OC(COS(C)(=O)=O)c1nc2nccc(C(=O)Nc3ccc(F)c(Cl)c3)c2n1S(C)(=O)=O]

2-((tert-butyldimethylsilyl)oxy)-2-(7-((3-chloro-4-fluorophenyl)carbamoyl)-1-(methylsulfonyl)-1H-imidazo[4,5-b]pyridin-2-yl)ethyl methanesulfonate. A solution of 2-(1-((tert-butyldimethylsilyl)oxy)-2-hydroxyethyl)-N-(3-chloro-4-fluorophenyl)-1H-imidazo[4,5-b]pyridine-7-carboxamide (90 mg, 0.19 mmol) and N,N-diisopropylethylamine (0.74 mL, 1.9 mmol) in dichloromethane (3.9 mL) was cooled to 0° C. with stirring under a nitrogen atmosphere. The mixture was treated with methanesulfonyl chloride (0.075 mL, 0.97 mmol) dropwise and with stirring. After 5 min, the mixture was diluted with water, then extracted three times with dichloromethane. The combined organic layers were loaded onto a silica gel cartridge for purification by flash chromatography (0-100% EtOAc/hexanes) to provide the desired product. $C_{23}H_{30}ClFN_4O_7S_2Si$. 621.2 (M+1).

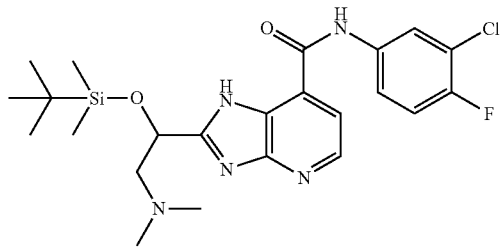 [SMILES: CN(C)CC(O[Si](C)(C)C(C)(C)C)c1nc2nccc(C(=O)Nc3ccc(F)c(Cl)c3)c2[nH]1]

2-(1-((tert-butyldimethylsilyl)oxy)-2-(dimethylamino)ethyl)-N-(3-chloro-4-fluorophenyl)-1H-imidazo[4,5-b]pyridine-7-carboxamide. A solution of 2-((tert-butyldimethylsilyl)oxy)-2-(7-((3-chloro-4-fluorophenyl)carbamoyl)-1-(methylsulfonyl)-3H-imidazo[4,5-b]pyridin-2-yl)ethyl methanesulfonate (90 mg, 0.145 mmol) in acetonitrile (2.9 mL) was treated with dimethylamine (2.0 M in tetrahydrofuran, 2.90 mL, 5.80 mmol) and stirred at 60° C. for 3 h. Additional dimethylamine (2.0 M in tetrahydrofuran, 1.0 mL, 2.0 mmol) was then added, and stirring at 60° C. resumed for 2 h. The mixture was then cooled to room temperature and concentrated under reduced pressure. Purification of the resulting residue by flash chromatography (0-30% MeOH/DCM) provided the desired product. $C_{23}H_{31}ClFN_5O_2Si$. 492.3 (M+1).

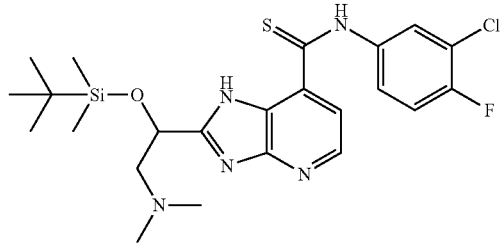 [SMILES: CN(C)CC(O[Si](C)(C)C(C)(C)C)c1nc2nccc(C(=S)Nc3ccc(F)c(Cl)c3)c2[nH]1]

2-(1-((tert-butyldimethylsilyl)oxy)-2-(dimethylamino)ethyl)-N-(3-chloro-4-fluorophenyl)-1H-imidazo[4,5-b]pyridine-7-carbothioamide was made analogously to Example 183 using 2-(1-((tert-butyldimethylsilyl)oxy)-2-(dimethylamino)ethyl)-N-(3-chloro-4-fluorophenyl)-1H-imidazo[4,5-b]pyridine-7-carboxamide in place of N-(3-chloro-4-fluorophenyl)-2-(2-((triisopropylsilyl)oxy)ethyl)-1H-imidazo[4,5-b]pyridine-7-carboxamide. $C_{23}H_{31}ClFN_5OSSi$. 508.2 (M+1).

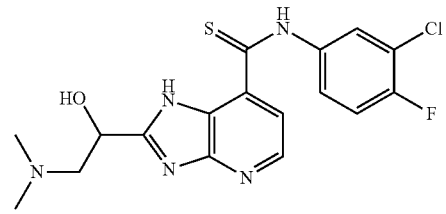 [SMILES: CN(C)CC(O)c1nc2nccc(C(=S)Nc3ccc(F)c(Cl)c3)c2[nH]1]

N-(3-chloro-4-fluorophenyl)-2-(2-(dimethylamino)-1-hydroxyethyl)-1H-imidazo[4,5-b]pyridine-7-carbothioamide. A solution of 2-(1-((tert-butyldimethylsilyl)oxy)-2-(dimethylamino)ethyl)-N-(3-chloro-4-fluorophenyl)-1H-imidazo[4,5-b]pyridine-7-carbothioamide (59 mg, 0.12 mmol) and hydrogen chloride (4.0 M solution in dioxane, 0.226 mL, 0.906 mmol) in methanol (5.8 mL) was stirred at 80° C. for 24 h. The mixture was then cooled to room temperature, diluted with dimethyl sulfoxide, and purified by reverse phase preparative HPLC to provide the desired product. $C_{17}H_{17}ClFN_5OS$. 594.2 (M+1).

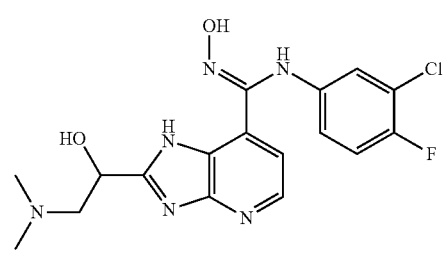 [SMILES: CN(C)CC(O)c1nc2nccc(/C(=N/O)Nc3ccc(F)c(Cl)c3)c2[nH]1]

N-(3-chloro-4-fluorophenyl)-2-(2-(dimethylamino)-1-hydroxy ethyl)-N'-hydroxy-1H-imidazo[4,5-b]pyridine-7-carboximidamide. A solution of N-(3-chloro-4-fluorophenyl)-2-(2-(dimethylamino)-1-hydroxyethyl)-1H-imidazo[4,5-b]pyridine-7-carbothioamide (5 mg, 0.013 mmol) and hydroxylamine (50% solution in water, 0.156 mL, 2.54 mmol) in methanol (1 mL) was stirred at 70° C. for 10 min. The mixture was then diluted with dimethyl sulfoxide and purified by reverse phase preparative HPLC to provide the desired product. $C_{17}H_{18}ClFN_6O_2$. 393.1 (M+1).

Example 196: N-(3-Chloro-4-fluorophenyl)-N'-hydroxy-2-((isobutylamino)methyl)-1H-imidazo[4,5-b]pyridine-7-carboximidamide

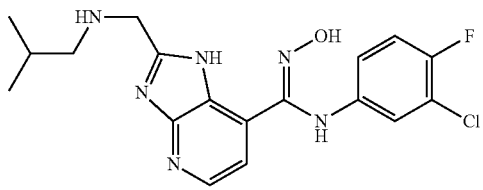 [SMILES: CC(C)CNCc1nc2nccc(/C(=N/O)Nc3ccc(F)c(Cl)c3)c2[nH]1]

Example 196 was synthesized analogously to Example 112 using 3-(2-(bromomethyl)-1H-imidazo[4,5-b]pyridin-7-yl)-4-(3-chloro-4-fluorophenyl)-1,2,4-oxadiazol-5(4H)-one and 2-methylpropan-1-amine in place of (7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)methyl methanesulfonate and morpholine, respectively. $C_{18}H_{20}ClFN_6O$. 391.1 [M+1]$^+$.

Example 197: N-(3-Chloro-4-fluorophenyl)-N'-hydroxy-3-methyl-3H-imidazo[4,5-b]pyridine-7-carboximidamide

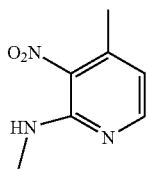

N,4-dimethyl-3-nitropyridin-2-amine. A solution of 4-methyl-3-nitro-2-chloropyridine (2.07 g, 12.0 mmol) and methylamine (40% in water, 7.2 mL, 84 mmol) in ethanol (14 mL) was stirred at 80° C. for 1.5 hr. The reaction was concentrated to give the desired product. $C_7H_9N_3O_2$. 168.0 (M+1).

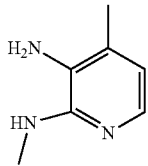

2-Methylamino-3-amino-4-methylpyridine. A mixture of N,4-dimethyl-3-nitropyridin-2-amine (2.01 g, 12.0 mmol) and 10% Paladium on Carbon (128 mg, 0.12 mmol) was mixed in a Parr Shaker at 40 psi hydrogen for 2 hr. The reaction mixture was filtered and concentrated to give the desired product. $C_7H_{11}N_3$. 138.1 (M+1).

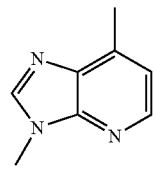

3,7-Dimethyl-3H-imidazo[4,5-b]pyridine. A solution of 2-methylamino-3-amino-4-methylpyridine (830 mg, 6.05 mmol) in trimethylorthoformate (20 mL) was stirred at 100° C. for 3 hr and concentrated. The residue was purified by silica gel chromatography to give the desired product. $C_8H_9N_3$. 148.0 (M+1).

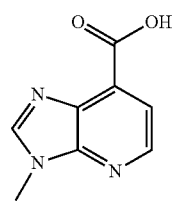

3-Methyl-3H-imidazo[4,5-b]pyridine-7-carboxylic acid. To a solution of 3,7-dimethyl-3H-imidazo[4,5-b]pyridine (726 mg, 4.93 mmol) sodium carbonate (523 mg, 4.93 mmol) in water (30 mL) at 100 C was added potassium permanganate (7.8 g, 49.2 mmol) in portions over two days. Na2CO3 and water are added to the starting material. The reaction mixture is heated until boiled, which caused a homogeneous solution. KMnO4 was added in small portions to the boiling solution. The reaction is stirred for another hour. LCMS shows low conversion. More KMnO4 was added in small batches at 100° C. for the next two days. The reaction mixture was filtered hot and the filtrate was acidified with 1 N HCl, concentrated and purified by prep HPLC to give the desired product. $C_8H_7N_3O2$. 178.0 (M+1).

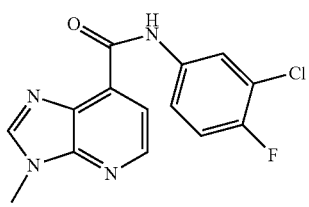 [SMILES: Cn1cnc2c(C(=O)Nc3ccc(F)c(Cl)c3)ccnc21]

N-(3-chloro-4-fluorophenyl)-3-methyl-3H-imidazo[4,5-b]pyridine-7-carboxamide. A solution of 3-methyl-3H-imidazo[4,5-b]pyridine-7-carboxylic acid (100 mg, 0.564 mmol), hydroxybenzotriazole (173 mg, 1.13 mmol), 1-ethyl-3-(3-dimethylaminopropyl)carbodiimide hydrochloride (216 mg, 1.13 mmol), and diisopropylethylamine (0.690 mL, 3.95 mmol) in dimethylformamide (2 mL) was stirred for 18 hr. To the reaction mixture was added saturated sodium bicarbonate Stirred all together overnight. Added saturated aqueous sodium bicarbonate and the resulting solid was filtered, triturated with 10% citric acid, filtered, and dried on high vac. $C_{14}H_{10}ClFN_4O$. 305.1 (M+1).

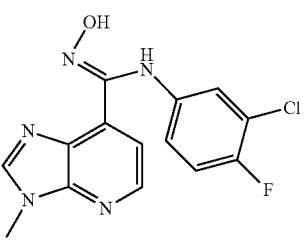 [SMILES: Cn1cnc2c(/C(=N/O)Nc3ccc(F)c(Cl)c3)ccnc21]

N-(3-chloro-4-fluorophenyl)-N'-hydroxy-3-methyl-3H-imidazo[4,5-b]pyridine-7-carboximidamide. Example 197 was made analogously to Example 107 using N-(3-chloro-4-fluorophenyl)-3-methyl-3H-imidazo[4,5-b]pyridine-7-carboxamide in place of N-(3-Chloro-4-fluorophenyl)-2-methyl-1H-imidazo[4,5-b]pyridine-7-carboxamide. $C_{14}H_{11}ClFN_5O$. 320.0 (M+1).

The following compounds were prepared according to the procedures described herein using the appropriate starting materials.

Example 198: N-(3-Chloro-4-fluorophenyl)-N'-hydroxy-2-[2-(2-methoxyethylamino)ethyl]-3H-imidazo[4,5-b]pyridine-7-carboximidamide

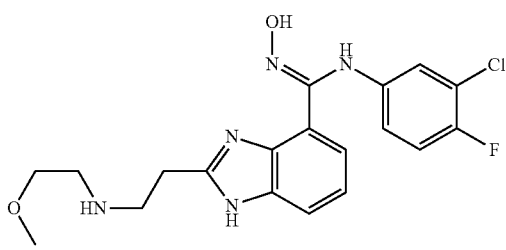 [SMILES: COCCNCCc1nc2c(/C(=N/O)Nc3ccc(F)c(Cl)c3)cccc2[nH]1]

Example 199: N-(3-Chloro-4-fluorophenyl)-2-[3-(dimethylamino)propyl]-6,7-difluoro-N'-hydroxy-3H-benzimidazole-4-carboximidamide

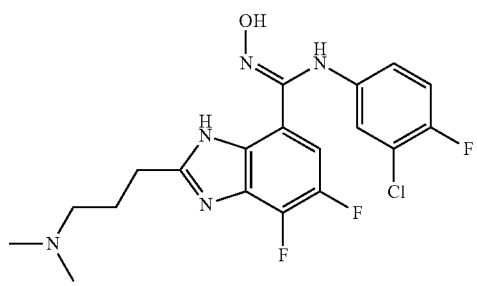 [SMILES: CN(C)CCCc1nc2c(F)c(F)cc(/C(=N/O)Nc3ccc(F)c(Cl)c3)c2[nH]1]

Example 200: N-(3-Chloro-4-fluorophenyl)-7-fluoro-N'-hydroxy-2-(3-morpholin-4-ylpropylamino)-3H-benzimidazole-4-carboximidamide

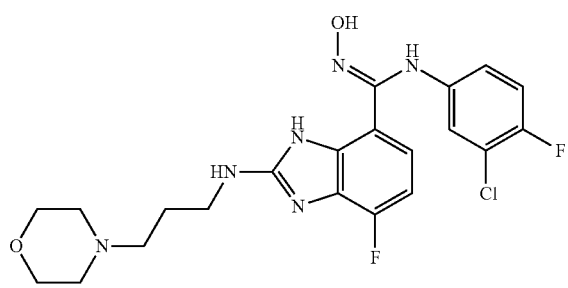 [SMILES: O/N=C(\Nc1ccc(F)c(Cl)c1)c1ccc(F)c2nc(NCCCN3CCOCC3)[nH]c12]

Example 201: N-(3-Chloro-4-fluorophenyl)-2-[2-(dimethylamino)ethylamino]-7-fluoro-N'-hydroxy-3H-benzimidazole-4-carboximidamide

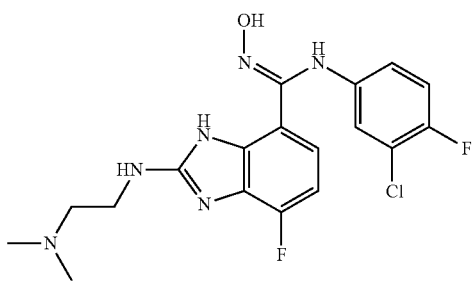 [SMILES: CN(C)CCNc1nc2c(F)ccc(/C(=N/O)Nc3ccc(F)c(Cl)c3)c2[nH]1]

Example 202: N-(3-Chloro-4-fluorophenyl)-N'-hydroxy-2-[(1-methylpiperidin-2-yl)methylamino]-1H-imidazo[4,5-b]pyridine-7-carboximidamide

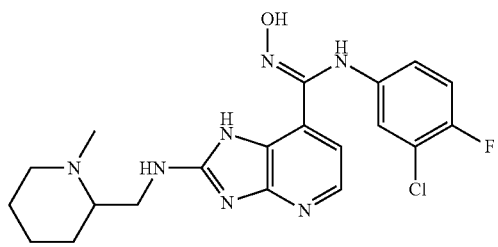 [SMILES: CN1CCCCC1CNc1nc2nccc(/C(=N/O)Nc3ccc(F)c(Cl)c3)c2[nH]1]

Example 203: N-(3-Chloro-4-fluorophenyl)-N'-hydroxy-2-[(1-methylpyrrolidin-3-yl)amino]-1H-imidazo[4,5-b]pyridine-7-carboximidamide

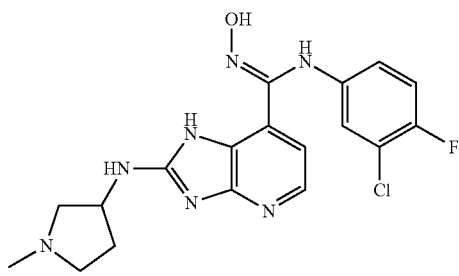 [SMILES: CN1CCC(Nc2nc3nccc(/C(=N/O)Nc4ccc(F)c(Cl)c4)c3[nH]2)C1]

Example 204: N-(3-chloro-4-fluorophenyl)-2-(2-(ethylamino)ethyl)-N'-hydroxy-3H-imidazo[4,5-b]pyridine-7-carboximidamide

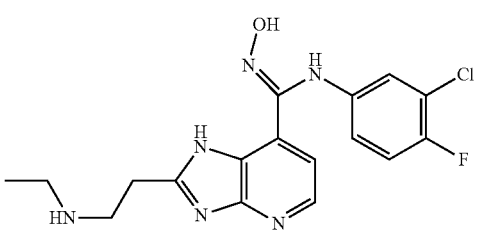 [SMILES: CCNCCc1nc2nccc(/C(=N/O)Nc3ccc(F)c(Cl)c3)c2[nH]1]

Example 204 was made analogously to Example 188 using ethylamine (2.0 M solution in tetrahydrofuran) in place of dimethylamine. $C_{17}H_{18}ClFN_6O$. 377.1 (M+1).

Example 205: N-(3-chloro-4-fluorophenyl)-N'-hydroxy-2-(2-(isopropylamino)ethyl)-3H-imidazo[4,5-b]pyridine-7-carboximidamide

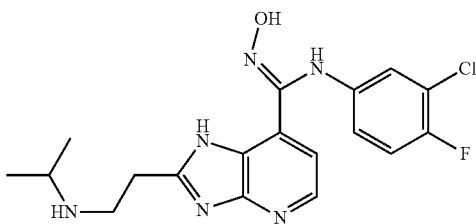 [SMILES: CC(C)NCCc1nc2nccc(/C(=N/O)Nc3ccc(F)c(Cl)c3)c2[nH]1]

Example 205 was made analogously to Example 188 using isopropylamine in place of dimethylamine. $C_{18}H_{20}ClFN_6O$. 391.1 (M+1).

Example 206: N-(3-chloro-4-fluorophenyl)-N'-hydroxy-2-(2-(isobutylamino)ethyl)-3H-imidazo[4,5-b]pyridine-7-carboximidamide

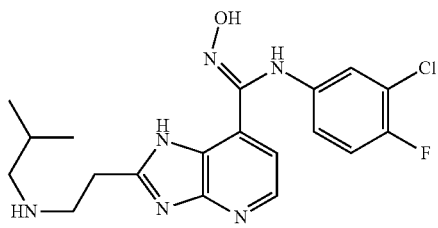 [SMILES: CC(C)CNCCc1nc2nccc(/C(=N/O)Nc3ccc(F)c(Cl)c3)c2[nH]1]

Example 206 was made analogously to Example 188 using isobutylamine in place of dimethylamine. $C_{19}H_{22}ClFN_6O$. 405.1 (M+1).

Example 207: N-(3-chloro-4-fluorophenyl)-2-(2-(cyclopropylamino)ethyl)-N'-hydroxy-3H-imidazo[4,5-b]pyridine-7-carboximidamide

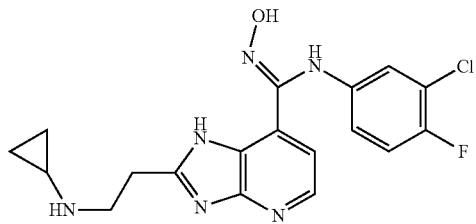 [SMILES: O/N=C(\Nc1ccc(F)c(Cl)c1)c1ccnc2nc(CCNC3CC3)[nH]c12]

Example 207 was made analogously to Example 188 using cyclopropylamine in place of dimethylamine. $C_{18}H_{18}ClFN_6O$. 389.1 (M+1).

Example 208: N-(3-chloro-4-fluorophenyl)-2-(2-((cyclopropylmethyl)amino)ethyl)-N'-hydroxy-3H-imidazo[4,5-b]pyridine-7-carboximidamide

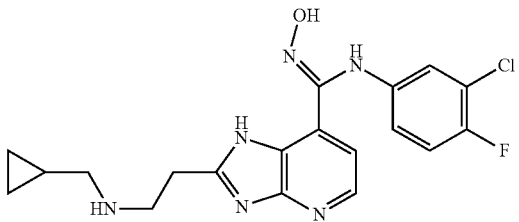 [SMILES: O/N=C(\Nc1ccc(F)c(Cl)c1)c1ccnc2nc(CCNCC3CC3)[nH]c12]

Example 208 was made analogously to Example 188 using cyclopropylmethanamine in place of dimethylamine. $C_{19}H_{20}ClFN_6O$. 403.1 (M+1).

Example 209: 2-(2-(2-amino-4,5-dihydro-1H-imidazol-1-yl)ethyl)-N-(3-chloro-4-fluorophenyl)-N'-hydroxy-1H-imidazo[4,5-b]pyridine-7-carboximidamide

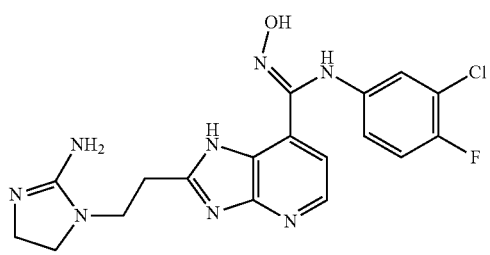 [SMILES: NC1=NCCN1CCc1nc2nccc(/C(=N/O)Nc3ccc(F)c(Cl)c3)c2[nH]1]

Example 209 was made analogously to Example 188 using 4,5-dihydro-1H-imidazol-2-amine in place of dimethylamine. $C_{18}H_{18}ClFN_8O$. 417.1 (M+1).

Example 210: N-(3-chloro-4-fluorophenyl)-4,5-difluoro-N'-hydroxy-2-(2-(methylsulfonamido)ethyl)-1H-benzo[d]imidazole-7-carboximidamide

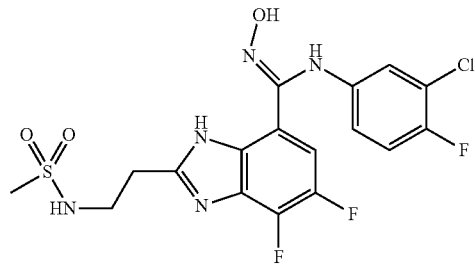 [SMILES: CS(=O)(=O)NCCc1nc2c(F)c(F)cc(/C(=N/O)Nc3ccc(F)c(Cl)c3)c2[nH]1]

Example 210 was made analogously to Example 112 using 2-(2-aminoethyl)-N-(3-chloro-4-fluorophenyl)-4,5-difluoro-N'-hydroxy-1H-benzo[d]imidazole-7-carboximidamide in place of 4-(3-chloro-4-fluorophenyl)-3-(2-(hydroxymethyl)-1H-imidazo[4,5-b]pyridin-7-yl)-1,2,4-oxadiazol-5(4H)-one. $C_{17}H_{15}ClF_3N_5O_3S$. 462.3 (M+1).

Example 211: 2-(2-aminoethyl)-N-(3-chloro-4-fluorophenyl)-4,5-difluoro-N'-hydroxy-1H-benzo[d]imidazole-7-carboximidamide

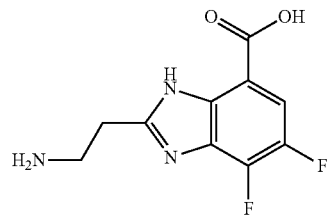 [SMILES: NCCc1nc2c(F)c(F)cc(C(=O)O)c2[nH]1]

2-(2-aminoethyl)-4,5-difluoro-1H-benzo[d]imidazole-7-carboxylic acid was made analogously to Example 53 using 3-aminopropanoic acid in place of 3-(dimethylamino)propanoic acid. $C_{10}H_9F_2N_3O_2$. 241.1 (M+1).

Example 212: N-(3-chloro-4-fluorophenyl)-N'-hydroxy-2-((2-methoxyethyl)amino)-1H-imidazo[4,5-b]pyridine-7-carboximidamide

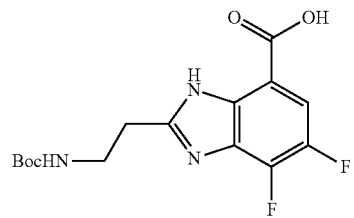 [SMILES: CC(C)(C)OC(=O)NCCc1nc2c(F)c(F)cc(C(=O)O)c2[nH]1]

To a mixture of 2-(2-aminoethyl)-4,5-difluoro-1H-benzo[d]imidazole-7-carboxylic acid (2 g, 8.29 mmol) in THF (30 mL) and sat. sodium bicarbonate solution 30 mL was added di-tertbutyldicarbonate (7.24 g, 33 mmol). Stirred for 72 h. Acidified with 4N HCl and brought the pH to 1. The reaction mixture was extracted with ethyl acetate (50 mL×3). The combined organic layers were dried over sodium sulfate, filtered and concentrated. The residue was purified by silica gel chromatography to give 2-(2-((tert-butoxycarbonyl)amino)ethyl)-4,5-difluoro-1H-benzo[d]imidazole-7-carboxylic acid. $C_{15}H_{17}F_2N_3O_4$. 342.1 (M+1).

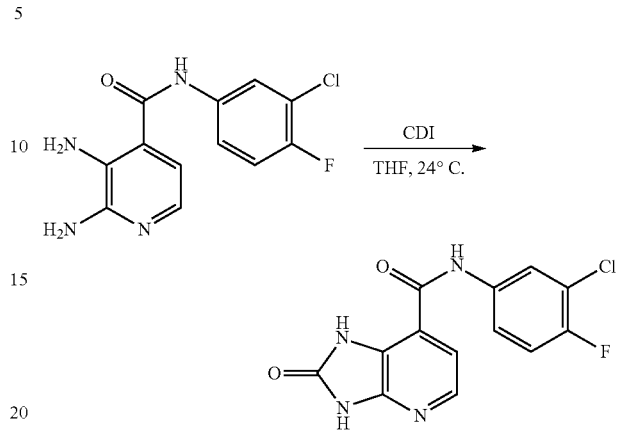

A 500 mL round bottom flask equipped with a stir bar was charged with 2,3-diamino-N-(3-chloro-4-fluorophenyl)isonicotinamide (34 g, 121.1 mmol) and 1,1'-carbonyldiimidazole (CDI) (29.5 g, 181.7 mmol) followed by THF (300 mL). The reaction mixture was stirred at room temperature for 16 hr. THF 150 mL was removed under reduced pressure. Water 250 mL was then slowly added to the reaction mixture. Reaction mixture was then stirred for 1 hour, and precipitate was isolated via vacuum filtration and washed with water (100 mL×3). The solid was dried in a vacuum oven at 40° C. overnight to afford a light red solid (34 g, 110.8 mmol) and used in the next step without further purification. $C_{13}H_8ClFN_4O_2$. 307.2 (M+1).

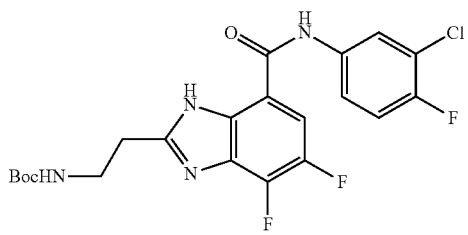 [SMILES: CC(C)(C)OC(=O)NCCc1nc2c(F)c(F)cc(C(=O)Nc3ccc(F)c(Cl)c3)c2[nH]1]

tert-butyl (2-(7-((3-chloro-4-fluorophenyl)carbamoyl)-4,5-difluoro-1H-benzo[d]imidazol-2-yl)ethyl)carbamate was made analogously to Example 53 using 2-(2-((tertbutoxycarbonyl)amino)ethyl)-4,5-difluoro-1H-benzo[d]imidazole-7-carboxy c acid in place of 2-(2-(dimethylamino)ethyl)-6,7-difluoro-1Hbenzo[d]imidazole-4-carboxylic. 469.12 (M+1). $C_{21}H_{20}ClF_3N_4O_3$. 469.12 (M+1).

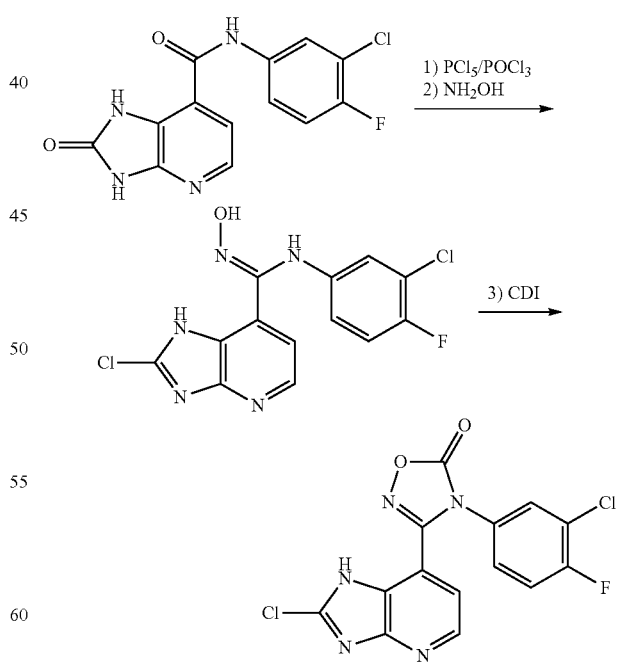

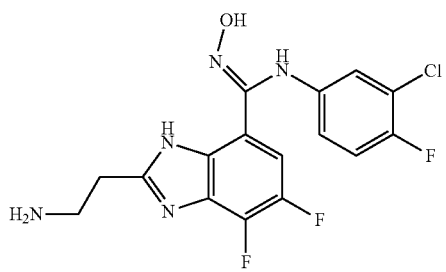 [SMILES: NCCc1nc2c(F)c(F)cc(/C(=N/O)Nc3ccc(F)c(Cl)c3)c2[nH]1]

2-(2-amino ethyl)-N-(3-chloro-4-fluorophenyl)-4,5-difluoro-N'-hydroxy-1H-benzo[d]imidazole-7-carboximidamide was made analogously to Example 53 using tert-butyl (2-(7-((3-chloro-4-fluorophenyl)carbamoyl)-4,5-difluoro-1H-benzo[d]imidazol-2-yl)ethyl)carbamate in place of N-(3-chloro-4-fluorophenyl)-2-(2-(dimethylamino)ethyl)-4,5-difluoro-1H-benzo[d]imidazole-7-carboxamide. $C_{16}H_{13}ClF_3N_5O$. 384.2 (M+1).

N-(3-chloro-4-fluorophenyl)-2-oxo-2,3-dihydro-1H-imidazo[4,5-b]pyridine-7-carboxamide (5.0 g, 16.3 mmol) was dissolved in $POCl_3$ (33 eq., 538 mmol, 82.5 mL) and $PCl_5$ (3 eq., 48.9 mmol, 10.19 g) was added. The reaction was sealed in a glass vessel and heated to 100° C. for 16 hours. The reaction was allowed to cool to room temperature and then transferred to a round bottom flask. The POCl₃ was removed under reduced pressure and the residue was taken up in 100 mL of p-dioxane. In a separate round bottom flask, NH₂OH (50% in water, 92.8 eq, 1.52 mol, 100 mL) was added to 200 mL p-dioxane and cooled to 3° C. in an ice bath with continuous stirring. The crude imidoyl chloride in p-dioxane mixture was added very slowly to the hydroxylamine mixture (over ~45 mins, dropwise) while maintaining the hydroxylamine/dioxane solution ~3° C. Once the addition was complete, the reaction was allowed to slowly come to room temperature and stirred for 20 mins. The reaction was then diluted with EtOAc (500 mL), sat. sodium bicarbonate solution (300 mL), and brine (150 mL) and allowed to stir for an additional 20 mins. The reaction was extracted and the organic layer was washed once with brine (200 mL), dried over Na₂SO₄, filtered, and concentrated to dryness to give crude 2-chloro-N-(3-chloro-4-fluorophenyl)-N'-hydroxy-1H-imidazo[4,5-b]pyridine-7-carboximidamide which was used in the next step without further purification. C₁₃H₈Cl₂FN₅O. 340.1 (M+1).

Crude 2-chloro-N-(3-chloro-4-fluorophenyl)-N'-hydroxy-1H-imidazo[4,5-b]pyridine-7-carboximidamide from previous step (5.5 g, 16.31 mmol assumed 100% yield from starting N-(3-chloro-4-fluorophenyl)-2-oxo-2,3-dihydro-1H-imidazo[4,5-b]pyridine-7-carboxamide) was dissolved in ethyl acetate (80 mL, C=0.2 M) and 1,1'-carbonyldiimidazole (CDI) (2 eq, 5.3 g, 32.6 mmol) was added. The reaction was allowed to stir at room temperature (capped but under air) for 1 hour until no SM was seen by LCMS. The reaction was then carefully diluted with water (80 mL, some gas evolution seen) and the reaction was allowed to stir for 10 mins before being poured into a separatory funnel (~15 mL of brine added to help break up emulsions) and the organic layer was extracted. The organic layer was washed once more with water (~50 mL with 10 mL brine) and the organic layer was then concentrated. The crude was wet loaded on to silica gel and purified by column chromatography (Rf 0.75 in 100% EtOAc, column run 40-100% EtOAc/hex) to give 3-(2-chloro-1H-imidazo[4,5-b]pyridin-7-yl)-4-(3-chloro-4-fluorophenyl)-1,2,4-oxadiazol-5(4H)-one as a pale yellow solid. C₁₄H₆Cl₂FN₅O₂. 365.9 (M+1).

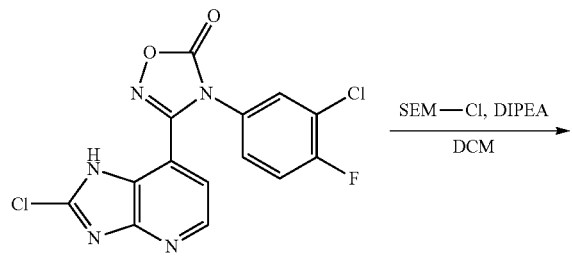

3-(2-chloro-1H-imidazo[4,5-b]pyridin-7-yl)-4-(3-chloro-4-fluorophenyl)-1,2,4-oxadiazol-5(4H)-one (804 mg, 2.2 mmol) was weighed into a round bottom flask which was then evacuated and purged twice with argon. CH₂Cl₂ (30.0 mL, C=0.075 M) was added via syringe and the reaction was cooled to 0° C. in an ice bath. Hunig's base (2.5 eq, 5.49 mmol, 0.956 mL) was added followed by SEM-Cl (2.3 eq, 5.051 mmol, 0.894 mL) (added dropwise). The reaction was allowed to stir at 0° C. for 20 mins until no starting material was seen by LCMS. The reaction was then poured into DI water (40 mL) in a separatory funnel and then shaken. The organic layer was removed and concentrated under reduced pressure. The crude was wet loaded on to a silica gel column and purified by normal phase column chromatography (20-80% EtOAc/hex, Rf=0.42 in 40% EtOAc/hex) to give 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one as a pale yellow oil which solidified upon standing.

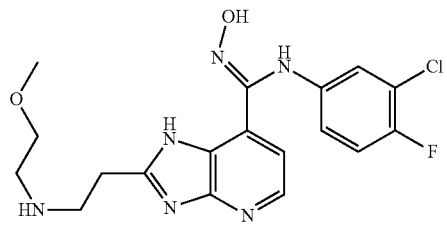 [SMILES: COCCNCCc1nc2nccc(/C(=N/O)Nc3ccc(F)c(Cl)c3)c2[nH]1]

3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one (0.015 g, 0.03 mmol) was dissolved in DMSO (0.5 ml), and 2-methoxyethanamine (4.54 mg, 0.060 mmol) was added to the solution. The reaction mixture was heated at 60° C. for 2 h. The mixture was cooled to rt and partitioned between sat. bicarb solution (1 mL) and EtOAc (2 mL) and the aqueous layer was extracted 1× with EtOAc (1 mL). The combined organic layers were washed with sat. bicarb solution (1 mL). Organic layers were then concentrated and taken up in DCM (1.6 mL) and trifluoroacetic acid (0.4 mL). The reaction mixture was stirred for 1 h and concentrated. The residue was brought up in tetrahydrofuran (0.5 mL). To this solution was added 2 N sodium hydroxide solution (0.22 mL, 0.44 mmol) and the reaction mixture stirred for 30 min. To the mixture was added acetic acid (0.10 mL), DMSO (2 mL) and water (2 mL), the solution was loaded directly onto a prep HPLC for purification to give the desired product. C₁₆H₁₆ClFN₆O₂O. 379.1 (M+1). ¹H NMR (400 MHz, DMSO-d6) δ 11.72 (s, 1H), 11.43 (s, 1H), 8.95 (s, 1H), 7.97 (d, J=6.3 Hz, 1H), 7.11 (t, J=9.0 Hz, 1H), 7.04 (dd, J=6.5, 2.7 Hz, 1H), 6.93 (d, J=6.3 Hz, 1H), 6.60 (ddd, J=9.0, 4.0, 2.8 Hz, 1H), 3.61 (t, J=5.3 Hz, 2H), 3.53 (t, J=5.1 Hz, 2H), 3.30 (s, 3H).

Example 213: tert-butyl (2-(7-(N-(3-chloro-4-fluorophenyl)-N'-hydroxycarbamimidoyl)-4,5-difluoro-1H-benzo[d]imidazol-2-yl)ethyl)carbamate

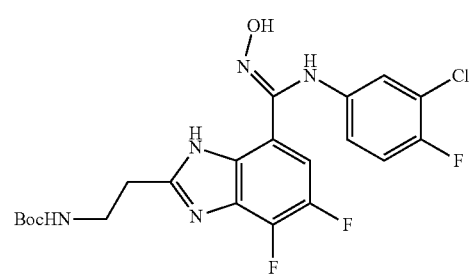 [SMILES: CC(C)(C)OC(=O)NCCc1nc2c(F)c(F)cc(/C(=N/O)Nc3ccc(F)c(Cl)c3)c2[nH]1]

Example 213 was made analogously to Example 211 using 2-(2-aminoethyl)-N-(3-chloro-4-fluorophenyl)-4,5-difluoro-N'-hydroxy-1H-benzo[d]imidazole-7-carboximidamide in place of 2-(2-aminoethyl)-4,5-difluoro-1H-benzo[d]imidazole-7-carboxylic acid. $C_{21}H_{21}ClF_3N_5O_3$. 484.4 (M+1).

Example 214: N-(3-chloro-4-fluorophenyl)-2-((2-(4,4-difluoropiperidin-1-yl)ethyl)amino)-N'-hydroxy-1H-imidazo[4,5-b]pyridine-7-carboximidamide

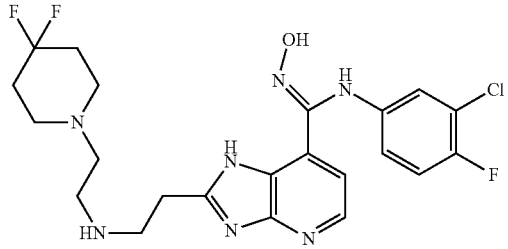 [SMILES: O/N=C(\Nc1ccc(F)c(Cl)c1)c1ccnc2nc(CCNCCN3CCC(F)(F)CC3)[nH]c12]

Example 214 was made analogously to Example 212 using 2-(4,4-difluoropiperidin-1-yl)ethanamine in place of 2-methoxyethanamine. $C_{20}H_{21}ClF_3N_7O$. 468.88 (M+1). $^1$H NMR (400 MHz, DMSO-d6) δ 8.94 (s, 1H), 7.96 (d, J=5.8 Hz, 1H), 7.09 (t, J=9.0 Hz, 1H), 6.98 (s, 1H), 6.91 (d, J=6.0 Hz, 1H), 6.55 (dt, J=8.9, 3.5 Hz, 1H), 3.33 (m, 8H), 2.33-2.18 (m, 4H).

Example 215: N-(3-chloro-4-fluorophenyl)-2-((2-(dimethylamino)ethyl)amino)-N'-hydroxy-1H-imidazo[4,5-b]pyridine-7-carboximidamide

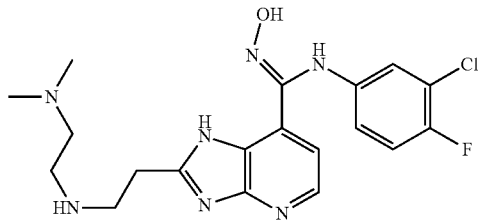 [SMILES: CN(C)CCNCCc1nc2nccc(/C(=N/O)Nc3ccc(F)c(Cl)c3)c2[nH]1]

Example 215 was made analogously to Example 212 using N1,N1-dimethylethane-1,2-diamine in place of 2-methoxyethanamine. $C_{17}H_{19}ClFN_7O$. 392.1 (M+1). $^1$H NMR (400 MHz, DMSO-d6) δ 8.93 (s, 1H), 7.94 (s, 1H), 7.08 (t, J=9.1 Hz, 1H), 6.96 (s, 1H), 6.89 (d, J=5.9 Hz, 1H), 6.54 (d, J=8.6 Hz, 1H), 3.73 (s, 2H), 3.31 (s, 2H), 2.85 (s, 6H).

Example 216: N-(3-chloro-4-fluorophenyl)-N'-hydroxy-2-((2-(methylamino)ethyl)amino)-1H-imidazo[4,5-b]pyridine-7-carboximidamide

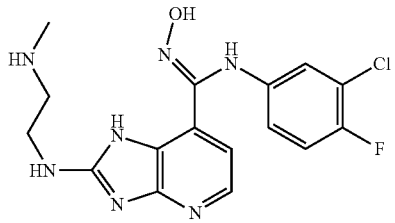 [SMILES: CNCCNc1nc2nccc(/C(=N/O)Nc3ccc(F)c(Cl)c3)c2[nH]1]

Example 216 was made analogously to Example 212 using tert-butyl (2-aminoethyl)(methyl)carbamate in place of 2-methoxyethanamine. $C_{16}H_{17}ClFN_7O$. 378.1 (M+1). $^1$H NMR (400 MHz, DMSO-d6) δ 8.94 (s, 1H), 8.57 (s, 2H), 7.95 (d, J=6.0 Hz, 1H), 7.09 (t, J=9.0 Hz, 1H), 6.97 (s, 1H), 6.90 (d, J=6.2 Hz, 1H), 6.59-6.47 (m, 1H), 3.67 (s, 2H), 3.16 (s, 2H), 2.61 (s, 3H).

Example 217: N-(3-chloro-4-fluorophenyl)-N'-hydroxy-2-((1-methylazepan-3-yl)amino)-1H-imidazo[4,5-b]pyridine-7-carboximidamide

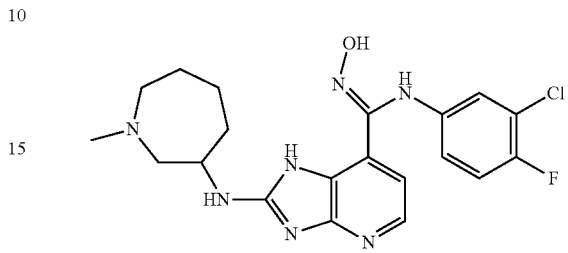

Example 217 was made analogously to Example 212 using 1-methylazepan-3-amine in place of 2-methoxyethanamine. $C_{20}H_{23}ClFN_7O$. 432.2 (M+1). $^1$H NMR (400 MHz, DMSO-d6) δ 8.92 (s, 1H), 7.96 (s, 1H), 7.09 (t, J=9.0 Hz, 1H), 6.97 (s, 1H), 6.90 (d, J=6.1 Hz, 1H), 6.55 (s, 1H), 4.25 (s, 1H), 3.6-3.3 (m, 3H), 3.18 (s, 2H), 2.87 (s, 3H), 2.13-1.41 (m, 6H).

Example 218: N-(3-chloro-4-fluorophenyl)-2-((2-(1,1-dioxidothiomorpholino)ethyl)amino)-N'-hydroxy-1H-imidazo[4,5-b]pyridine-7-carboximidamide

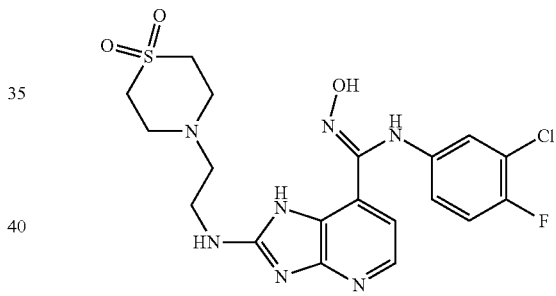

Example 218 was made analogously to Example 212 using 4-(2-aminoethyl)thiomorpholine 1,1-dioxide in place of 2-methoxyethanamine. $C_{19}H_{21}ClFN_7O_3S$. 482.1 (M+1). $^1$H NMR (400 MHz, DMSO-d6) δ 11.40 (s, 1H), 8.97 (s, 1H), 7.96 (d, J=6.4 Hz, 1H), 7.09 (t, J=9.0 Hz, 1H), 7.02 (dd, J=6.5, 2.7 Hz, 1H), 6.91 (d, J=6.2 Hz, 1H), 6.61-6.52 (m, 1H), 3.55 (d, J=5.9 Hz, 2H), 3.12 (s, 5H), 3.06 (s, 5H), 2.81 (s, 2H).

Example 219: N-(3-chloro-4-fluorophenyl)-N'-hydroxy-2-((2-((2-methoxyethyl)(methyl)amino)ethyl)amino)-1H-imidazo[4,5-b]pyridine-7-carboximidamide

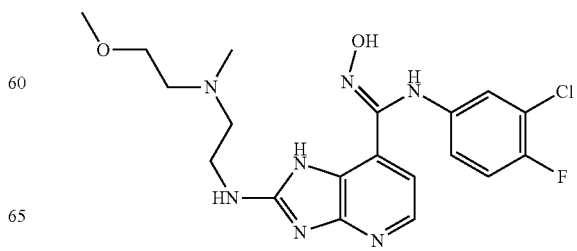

Example 219 was made analogously to Example 212 using N¹-(2-methoxyethyl)-N¹-methylethane-1,2-diamine in place of 2-methoxyethanamine. $C_{19}H_{23}ClFN_7O_2$. 427.03 (M+1). ¹H NMR (400 MHz, DMSO-d6) δ 11.36 (s, 1H), 8.96 (s, 1H), 7.97 (d, J=6.2 Hz, 1H), 7.09 (t, J=9.0 Hz, 1H), 6.98 (d, J=6.4 Hz, 1H), 6.93 (d, J=6.2 Hz, 1H), 6.55 (ddd, J=9.0, 4.0, 2.8 Hz, 1H), 3.78 (s, 2H), 3.64 (t, J=5.0 Hz, 2H), 3.37 (s, 4H), 3.24 (s, 3H), 2.86 (s, 3H).

Example 220: N-(3-chloro-4-fluorophenyl)-2-((2-((2,2-difluoroethyl)(methyl)amino)ethyl)amino)-N'-hydroxy-1H-imidazo[4,5-b]pyridine-7-carboximidamide

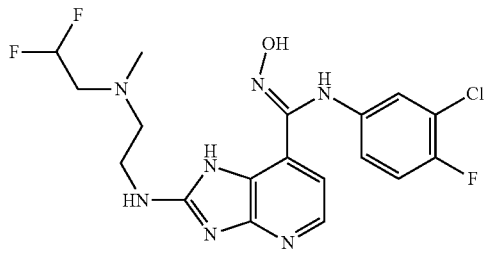 [SMILES: CN(CCNc1nc2nccc(/C(=N/O)Nc3ccc(F)c(Cl)c3)c2[nH]1)CC(F)F]

Example 220 was made analogously to Example 212 using N¹-(2,2-difluoroethyl)-M-methylethane-1,2-diamine in place of 2-methoxyethanamine. $C_{18}H_{19}ClF_3N_7O$. 442.1 (M+1). ¹H NMR (400 MHz, DMSO-d6) δ 11.40 (s, 1H), 8.96 (s, 1H), 7.96 (d, J=6.3 Hz, 1H), 7.09 (t, J=9.0 Hz, 1H), 7.01 (dd, J=6.5, 2.8 Hz, 1H), 6.92 (d, J=6.2 Hz, 1H), 6.56 (ddd, J=8.9, 3.9, 2.7 Hz, 1H), 6.25 (t, J=55.0 Hz, 1H), 3.62 (d, J=6.5 Hz, 2H), 3.18 (s, 2H), 2.97 (s, 2H), 2.57 (s, 2H).

Example 221: N-(3-chloro-4-fluorophenyl)-N'-hydroxy-2-((3-morpholinopropyl)amino)-1H-imidazo[4,5-b]pyridine-7-carboximidamide

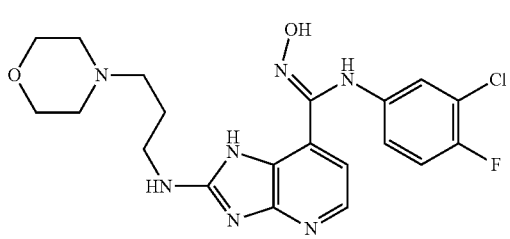 [SMILES: O/N=C(\Nc1ccc(F)c(Cl)c1)c1ccnc2nc(NCCCN3CCOCC3)[nH]c12]

Example 221 was made analogously to Example 212 using 3-morpholinylpropan-1-amine in place of 2-methoxyethanamine. $C_{20}H_{23}ClFN_7O_2$. 448.2 (M+1). ¹H NMR (400 MHz, DMSO-d6) δ 11.38 (s, 1H), 8.96 (s, 1H), 7.97 (d, J=6.2 Hz, 1H), 7.09 (t, J=9.0 Hz, 1H), 7.01 (dd, J=6.5, 2.7 Hz, 1H), 6.92 (d, J=6.2 Hz, 1H), 6.60-6.52 (m, 1H), 4.2-3.55 (m, 8H), 3.49 (d, J=6.5 Hz, 2H), 3.15 (t, J=8.0 Hz, 2H), 1.98 (d, J=8.0 Hz, 2H).

Example 222: N-(3-chloro-4-fluorophenyl)-N'-hydroxy-2-((2-(piperidin-1-yl)ethyl)amino)-1H-imidazo[4,5-b]pyridine-7-carboximidamide

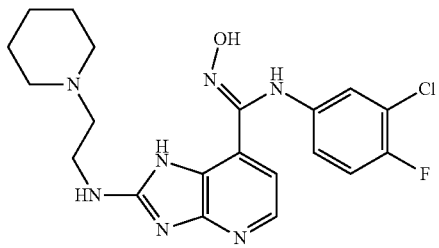 [SMILES: O/N=C(\Nc1ccc(F)c(Cl)c1)c1ccnc2nc(NCCN3CCCCC3)[nH]c12]

Example 222 was made analogously to Example 212 using 2-(piperidin-1-yl)ethanamine in place of 2-methoxyethanamine. $C_{20}H_{23}ClFN_7O$. 432.2 (M+1). ¹H NMR (400 MHz, DMSO-d6) δ 8.94 (s, 1H), 7.96 (d, J=6.2 Hz, 1H), 7.09 (t, J=9.1 Hz, 1H), 6.98 (d, J=6.3 Hz, 1H), 6.91 (d, J=6.0 Hz, 1H), 6.60-6.51 (m, 1H), 3.74 (M, 4H), 3.28 (d, J=7.0 Hz, 2H), 1.73 (s, 5H), 1.54 (s, 3H).

Example 223: N-(3-chloro-4-fluorophenyl)-2-((2-cyclohexylethyl)amino)-N'-hydroxy-1H-imidazo[4,5-b]pyridine-7-carboximidamide

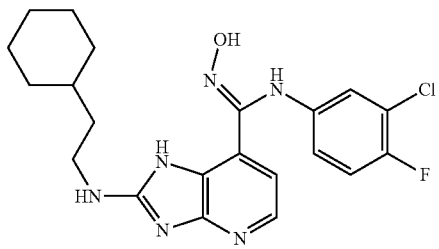 [SMILES: O/N=C(\Nc1ccc(F)c(Cl)c1)c1ccnc2nc(NCCC3CCCCC3)[nH]c12]

Example 223 was made analogously to Example 212 using 2-(3-fluoropiperidin-1-yl)ethanamine in place of 2-methoxyethanamine. $C_{21}H_{24}ClFN_6O$. 431.2 (M+1). ¹H NMR (400 MHz, DMSO-d6) δ 11.37 (s, 1H), 8.94 (s, 1H), 7.93 (s, 1H), 7.08 (t, J=9.0 Hz, 1H), 7.02 (m, 1H), 6.90 (s, 1H), 6.56 (d, J=9.0 Hz, 1H), 1.68 (m, 6H), 1.46 (d, J=7.7 Hz, 2H), 1.30 (s, 1H), 1.16 (m, 3H), 0.90 m, 3H).

Example 224: N-(3-chloro-4-fluorophenyl)-N'-hydroxy-2-((2-(tetrahydro-2H-pyran-4-yl)ethyl)amino)-1H-imidazo[4,5-b]pyridine-7-carboximidamide

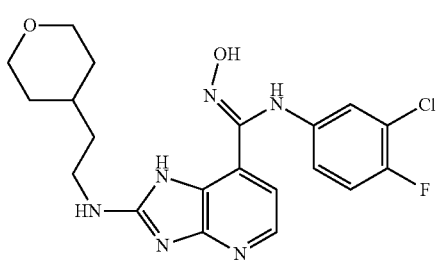 [SMILES: O/N=C(\Nc1ccc(F)c(Cl)c1)c1ccnc2nc(NCCC3CCOCC3)[nH]c12]

Example 224 was made analogously to Example 212 using 2-(tetrahydro-2H-pyran-4-yl)ethanamine in place of 2-methoxyethanamine. $C_{20}H_{22}ClFN_6O_2$. 433.2 (M+1). $^1$H NMR (400 MHz, DMSO-d6) δ 11.36 (s, 1H), 8.95 (s, 1H), 7.94 (d, J=6.2 Hz, 1H), 7.08 (t, J=9.1 Hz, 1H), 7.04-6.99 (m, 1H), 6.90 (d, J=6.1 Hz, 1H), 6.60-6.51 (m, 1H), 3.82 (dd, J=11.0, 4.2 Hz, 2H), 3.26 (d, J=12.0 Hz, 2H), 1.62-1.43 (m, 7H), 1.17 (d, J=12.6 Hz, 2H).

Example 225: N-(3-chloro-4-fluorophenyl)-2-((2,2-difluoroethyl)amino)-N'-hydroxy-1H-imidazo[4,5-b]pyridine-7-carboximidamide

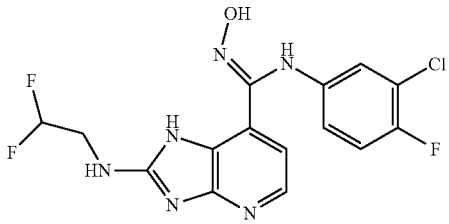 [SMILES: O/N=C(\Nc1ccc(F)c(Cl)c1)c1ccnc2nc(NCC(F)F)[nH]c12]

Example 225 was made analogously to Example 212 using 2,2-difluoroethanamine in place of 2-methoxyethanamine. $C_{15}H_{12}ClF_3N_6O$. 385.1 (M+H)+. $^1$H NMR (400 MHz, DMSO-d6) δ 11.46 (s, 1H), 8.98 (s, 1H), 7.08 (t, J=9.0 Hz, 1H), 7.03 (dd, J=6.5, 2.7 Hz, 1H), 6.93 (d, J=6.3 Hz, 1H), 6.62-6.52 (m, 1H), 6.22 (t, J=55.3 Hz, 1H), 3.87 (d, J=16.8 Hz, 2H).

Example 226: N-(3-chloro-4-fluorophenyl)-N'-hydroxy-2-(oxetan-3-ylamino)-1H-imidazo[4,5-b]pyridine-7-carboximidamide

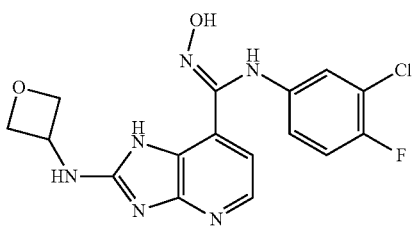 [SMILES: O/N=C(\Nc1ccc(F)c(Cl)c1)c1ccnc2nc(NC3COC3)[nH]c12]

Example 226 was made analogously to Example 212 using oxetan-3-amine in place of 2-methoxyethanamine. $C_{16}H_{14}ClFN_6O_2$. 377.1 (M+1). $^1$H NMR (400 MHz, DMSO-d6) δ 8.88 (s, 1H), 7.96 (s, 1H), 7.06 (t, J=9.1 Hz, 1H), 7.01 (d, J=5.4 Hz, 1H), 6.96 (d, J=6.5 Hz, 1H), 6.54 (ddd, J=9.0, 4.1, 2.8 Hz, 1H), 4.57 (s, 1H), 4.32 (t, J=9.8 Hz, 1H), 4.05 (s, 1H), 3.58 (s, 2H).

Example 227: N-(3-chloro-4-fluorophenyl)-N'-hydroxy-2-((tetrahydrofuran-3-yl)amino)-1H-imidazo[4,5-b]pyridine-7-carboximidamide

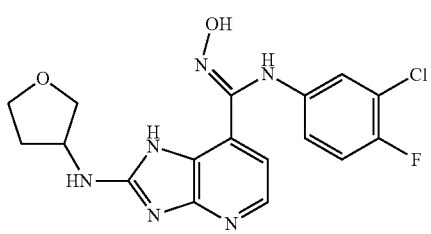 [SMILES: O/N=C(\Nc1ccc(F)c(Cl)c1)c1ccnc2nc(NC3CCOC3)[nH]c12]

Example 227 was made analogously to Example 212 using tetrahydrofuran-3-amine in place of 2-methoxyethanamine. $C_{17}H_{16}ClFN_6O_2$. 391.1 (M+1). $^1$H NMR (400 MHz, DMSO-d6) δ 11.40 (s, 1H), 8.94 (s, 1H), 8.50 (s, 1H), 7.96 (d, J=6.3 Hz, 1H), 7.09 (t, J=9.0 Hz, 1H), 7.02 (dd, J=6.5, 2.7 Hz, 1H), 6.92 (d, J=6.3 Hz, 1H), 6.57 (ddd, J=8.9, 4.0, 2.8 Hz, 1H), 4.44 (q, J=5.8, 3.7 Hz, 1H), 3.93-3.78 (m, 2H), 3.74 (td, J=8.4, 5.3 Hz, 1H), 3.69 (d, 1H), 2.30-2.18 (m, 1H), 1.90 (dd, J=14.8, 7.7 Hz, 1H).

Example 228: N-(3-chloro-4-fluorophenyl)-N'-hydroxy-2-((tetrahydro-2H-pyran-4-yl)amino)-1H-imidazo[4,5-b]pyridine-7-carboximidamide

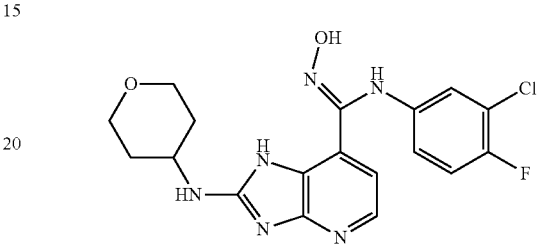

Example 228 was made analogously to Example 212 using tetrahydro-2H-pyran-4-amine in place of 2-methoxyethanamine. $C_{18}H_{18}ClFN_6O_2$. 405.1 (M+1). $^1$H NMR (400 MHz, DMSO-d6) δ 11.43 (s, 1H), 8.97 (s, 1H), 7.97 (d, J=6.3 Hz, 1H), 7.10 (t, J=9.1 Hz, 1H), 7.06 (dd, J=6.7, 2.9 Hz, 1H), 6.94 (d, J=6.3 Hz, 1H), 6.58 (dt, J=8.9, 3.4 Hz, 1H), 4.04-3.86 (m, 3H), 3.41 (td, J=11.7, 2.1 Hz, 2H), 1.87 (d, J=12.5 Hz, 2H), 1.70-1.48 (m, 2H).

Example 229: 3-((7-(N-(3-chloro-4-fluorophenyl)-N'-hydroxycarbamimidoyl)-4,5-difluoro-1H-benzo[d]imidazol-2-yl)amino)propanamide)

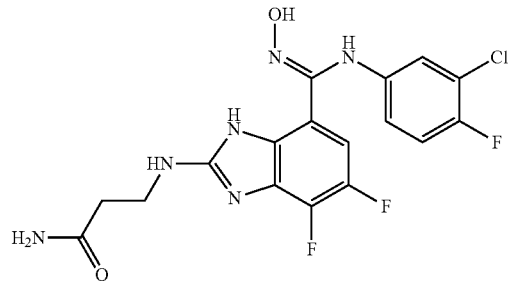 [SMILES: NC(=O)CCNc1nc2c(F)c(F)cc(/C(=N/O)Nc3ccc(F)c(Cl)c3)c2[nH]1]

A mixture of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one (0.025 g, 0.047 mmol), 3-aminopropanamide hydrochloride (0.023 g, 0.188 mmol) and DIPEA (0.05 mL, 0.282 mmol) in DMSO (0.5 mL) stirred at 60° C. for 16 h. The mixture was cooled to rt, diluted with water, and extracted 3× with EtOAc. The combined organic layers were washed with brine, dried (Na$_2$SO$_4$), filtered and concentrated. The resulting residue was brought up in DCM (0.5 mL) and TFA (0.5 mL) and stirred for 16 h. The reaction solution was concentrated. The resulting residue was brought up in THF (0.5 mL) and water (0.5 mL) and sodium hydroxide (0.76 mL of a 2 N solution, 1.5 mmol). The resulting solution was stirred for 10 min, acidified with AcOH (0.10 mL, 1.8 mmol), and purified by preparative HPLC to give the desired product (0.009 g). $C_{17}H_{14}ClF_3N_6O_2$. 427.0 (M+1).

Example 230: N-(3-chloro-4-fluorophenyl)-2-((2-((2,2-difluoroethyl)amino)ethyl)amino)-N'-hydroxy-1H-imidazo[4,5-b]pyridine-7-carboximidamide

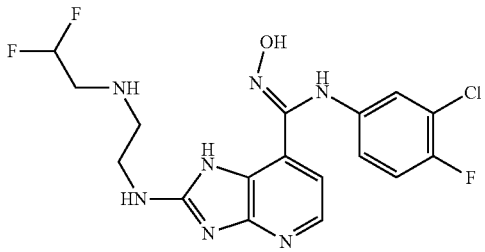 [SMILES: O/N=C(\Nc1ccc(F)c(Cl)c1)c1ccnc2nc(NCCNCC(F)F)[nH]c12]

Example 230 was made analogously to Example 229 using $N^1$-(2,2-difluoroethyl)ethane-1,2-diamine hydrochloride in place of 3-aminopropanamide hydrochloride. $C_{17}H_{17}ClF_3N_7O$. 428.1 (M+1). $^1$H NMR (400 MHz, DMSO-d6) δ 11.28 (s, 1H), 8.91 (s, 1H), 7.95 (d, J=6.1 Hz, 1H), 7.09 (t, J=9.0 Hz, 1H), 6.97 (dd, J=6.6, 2.7 Hz, 1H), 6.90 (d, J=6.1 Hz, 1H), 6.56 (ddd, J=9.0, 4.0, 2.7 Hz, 1H), 6.53-6.21 (m, 1H), 3.8-3.3 (m, 5H) 3.26 (t, J=5.9 Hz, 2H).

Example 231: N-(3-chloro-4-fluorophenyl)-2-((2-(cyclopropyl(methyl)amino)ethyl)amino)-N'-hydroxy-1H-imidazo[4,5-b]pyridine-7-carboximidamide

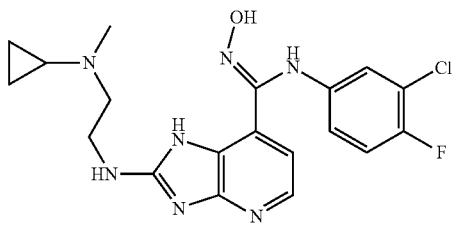 [SMILES: CN(CCNc1nc2nccc(/C(=N/O)Nc3ccc(F)c(Cl)c3)c2[nH]1)C1CC1]

Example 231 was made analogously to Example 212 using $N^1$-cyclopropyl-M-methylethane-1,2-diamine in place of 2-methoxyethanamine. $C_{19}H_{21}ClFN_7O$. 418.2 (M+1). $^1$H NMR (400 MHz, DMSO-d6) δ 11.27 (s, 1H), 8.92 (s, 1H), 7.95 (d, J=6.0 Hz, 1H), 7.83 (s, 1H), 7.08 (t, J=9.1 Hz, 1H), 6.97 (d, J=6.4 Hz, 1H), 6.91 (d, J=6.0 Hz, 1H), 6.55 (ddd, J=9.0, 4.0, 2.8 Hz, 1H), 3.76 (s, 3H), 2.90 (s, 3H), 1.02-0.66 (m, 5H).

Example 232: N-(3-chloro-4-fluorophenyl)-2-((2-(cyclopropyl(2-methoxyethyl)amino)ethyl)amino)-N'-hydroxy-1H-imidazo[4,5-b]pyridine-7-carboximidamide

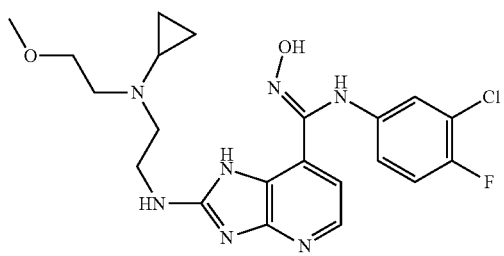 [SMILES: COCCN(CCNc1nc2nccc(/C(=N/O)Nc3ccc(F)c(Cl)c3)c2[nH]1)C1CC1]

Example 232 was made analogously to Example 212 using $N^1$-cyclopropyl-$N^1$-(2-methoxyethyl)ethane-1,2-diamine in place of 2-methoxyethanamine. $C_{21}H_{25}ClFN_7O_2$. 462.2 (M+1). $^1$H NMR (400 MHz, DMSO-d6) δ 11.32 (s, 1H), 8.93 (s, 1H), 7.96 (d, J=6.1 Hz, 1H), 7.08 (t, J=9.0 Hz, 1H), 7.02-6.89 (m, 2H), 6.56 (ddd, J=8.9, 4.0, 2.7 Hz, 1H), 3.76 (s, 4H), 3.65 (d, J=5.1 Hz, 1H), 3.37 (s, 4H), 3.26 (s, 3H), 0.79 (s, 4H).

Example 233: 2-((2-(azetidin-1-yl)ethyl)amino)-N-(3-chloro-4-fluorophenyl)-N'-hydroxy-1H-imidazo[4,5-b]pyridine-7-carboximidamide

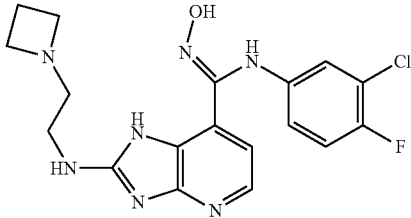 [SMILES: O/N=C(\Nc1ccc(F)c(Cl)c1)c1ccnc2nc(NCCN3CCC3)[nH]c12]

Example 233 was made analogously to Example 212 using 22-(azetidin-1-yl)ethanamine in place of 2-methoxyethanamine. $C_{18}H_{19}ClFN_7O$. 404.2 (M+1). $^1$H NMR (400 MHz, DMSO-d6) δ 11.31 (s, 1H), 9.92 (s, 1H), 8.92 (s, 1H), 7.96 (d, J=6.1 Hz, 1H), 7.08 (t, J=9.0 Hz, 1H), 6.98 (dd, J=6.6, 2.7 Hz, 1H), 6.93 (d, J=6.1 Hz, 1H), 6.55 (ddd, J=9.0, 4.0, 2.7 Hz, 1H), 4.10 (d, J=8.9 Hz, 4H), 3.38 (s, 4H), 2.32 (d, J=6.7 Hz, 2H).

Example 234: N-(3-chloro-4-fluorophenyl)-N'-hydroxy-2-((3-methoxypropyl)amino)-1H-imidazo[4,5-b]pyridine-7-carboximidamide

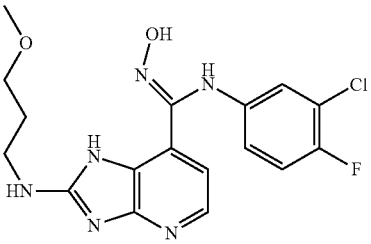 [SMILES: COCCCNc1nc2nccc(/C(=N/O)Nc3ccc(F)c(Cl)c3)c2[nH]1]

Example 234 was made analogously to Example 212 using 3-methoxypropan-1-amine in place of 2-methoxyethanamine. $C_{17}H_{18}ClFN_6O_2$. 427.03 (M+1). $^1$H NMR (400 MHz, DMSO-d6) δ 11.89 (s, 1H), 11.39 (s, 1H), 8.95 (s, 1H), 7.96 (d, J=6.2 Hz, 1H), 7.10 (t, J=9.0 Hz, 1H), 7.04 (dd, J=6.5, 2.7 Hz, 1H), 6.92 (d, J=6.2 Hz, 1H), 6.59 (ddd, J=9.0, 4.0, 2.8 Hz, 1H), 3.49 (q, J=6.6 Hz, 2H), 3.41 (t, J=6.0 Hz, 2H), 3.25 (s, 3H), 1.83 (p, J=6.5 Hz, 2H).

Example 235: N-(3-chloro-4-fluorophenyl)-N'-hydroxy-2-((2-(2-oxopyrrolidin-1-yl)ethyl)amino)-1H-imidazo[4,5-b]pyridine-7-carboximidamide

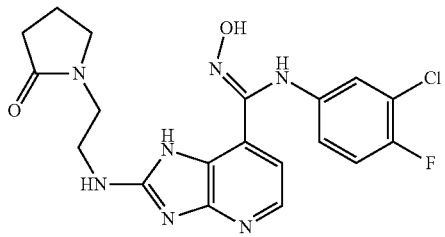 [SMILES: O=C1CCCN1CCNc1nc2nccc(/C(=N/O)Nc3ccc(F)c(Cl)c3)c2[nH]1]

Example 235 was made analogously to Example 212 using 1-(2-aminoethyl)pyrrolidin-2-one in place of 2-methoxyethanamine. $C_{19}H_{19}ClFN_7O_2$. 432.2 (M+1). $^1$H NMR (400 MHz, DMSO-d6) δ 11.99 (s, 1H), 11.43 (s, 1H), 8.97 (s, 1H), 7.98 (d, J=6.3 Hz, 1H), 7.10 (t, J=9.0 Hz, 1H), 7.04 (dd, J=6.5, 2.8 Hz, 1H), 6.96 (d, J=6.3 Hz, 1H), 6.58 (ddd, J=8.9, 4.0, 2.8 Hz, 1H), 3.59 (q, J=6.0 Hz, 2H), 3.41 (dt, J=14.1, 6.5 Hz, 4H), 2.17 (dd, J=8.7, 7.5 Hz, 2H), 2.01-1.73 (m, 2H).

Example 236: N-(3-chloro-4-fluorophenyl)-N'-hydroxy-2-((2-(morpholinosulfonyl)ethyl)amino)-1H-imidazo[4,5-b]pyridine-7-carboximidamide

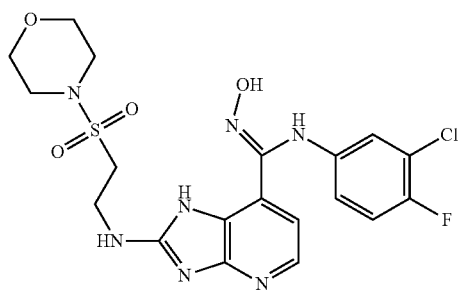 [SMILES: O=S(=O)(CCNc1nc2nccc(/C(=N/O)Nc3ccc(F)c(Cl)c3)c2[nH]1)N1CCOCC1]

Example 236 was made analogously to Example 212 using 2-(morpholinosulfonyl)ethanamine in place of 2-methoxyethanamine. $C_{19}H_{21}ClFN_7O_4S$. 498.2 (M+1). $^1$H NMR (400 MHz, DMSO-d6) δ 11.45 (s, 1H), 8.96 (s, 1H), 7.97 (d, J=6.4 Hz, 1H), 7.09 (t, J=9.0 Hz, 1H), 7.02 (dd, J=6.5, 2.7 Hz, 1H), 6.93 (d, J=6.4 Hz, 1H), 6.57 (ddd, J=9.0, 4.0, 2.8 Hz, 1H), 3.86 (q, J=6.5 Hz, 2H), 3.68-3.58 (m, 4H), 3.43 (t, J=6.7 Hz, 2H), 3.21-3.09 (m, 4H).

Example 237: N-(3-chloro-4-fluorophenyl)-2-((2-(3-fluoropiperidin-1-yl)ethyl)amino)-N'-hydroxy-1H-imidazo[4,5-b]pyridine-7-carboximidamide

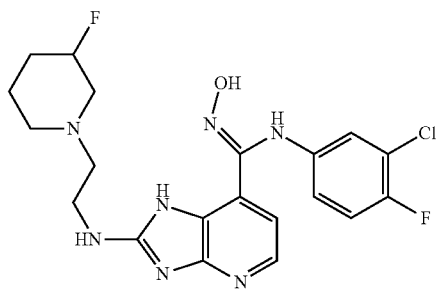 [SMILES: O/N=C(\Nc1ccc(F)c(Cl)c1)c1ccnc2nc(NCCN3CCCC(F)C3)[nH]c12]

Example 237 was made analogously to Example 212 using 2-(3-fluoropiperidin-1-yl)ethanamine TFA salt in place of 2-methoxyethanamine. $C_{20}H_{22}ClF_2N_7O$. 450.2 (M+1). $^1$H NMR (400 MHz, DMSO-d6) δ 11.33 (s, 1H), 8.95 (s, 1H), 7.99 (d, J=6.1 Hz, 1H), 7.11 (t, J=9.1 Hz, 1H), 7.01 (dd, J=6.5, 2.8 Hz, 1H), 6.94 (d, J=6.1 Hz, 1H), 6.58 (ddd, J=8.9, 4.0, 2.7 Hz, 1H), 5.09 (d, J=44.9 Hz, 1H), 3.88-3.73 (m, 2H), 3.43 (s, 2H), 3.35 (s, 2H), 3.11 (s, 2H), 2.03-1.66 (m, 4H).

Example 238: N-(3-bromo-4-fluorophenyl)-N'-hydroxy-2-((2-morpholinoethyl)amino)-1H-imidazo[4,5-b]pyridine-7-carboximidamide

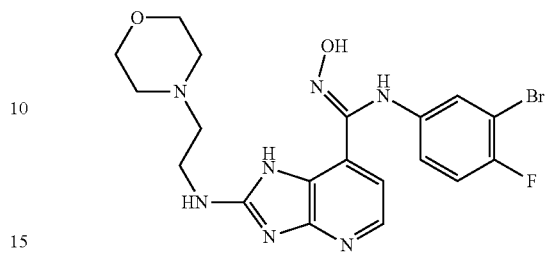

Example 238 was made analogously to Example 212 using 4-(3-bromo-4-fluorophenyl)-3-(2-chloro-3-((2-(trimethylsilyl)ethoxy)methyl)-3H-imidazo[4,5-b]pyridin-7-yl)-1,2,4-oxadiazol-5(4H)-one and 2-morpholinoethanamine in place of 3-(2-chloro-3-((2-(trimethylsilyl)ethoxy)methyl)-3H-imidazo[4,5-b]pyridin-7-yl)-4-(3-chloro-4-fluorophenyl)-1,2,4-oxadiazol-5(4H)-one and 2-methoxyethanamine, respectively. $C_{19}H_{21}BrFN_7O_2$. 478.1 (M+1). $^1$H NMR (400 MHz, DMSO-d6) δ 11.30 (s, 1H), 8.92 (s, 1H), 7.97 (d, J=6.1 Hz, 1H), 7.12 (dd, J=6.1, 2.7 Hz, 1H), 7.05 (t, J=8.7 Hz, 1H), 6.92 (d, J=6.1 Hz, 1H), 6.58 (ddd, J=8.9, 4.1, 2.7 Hz, 1H), 3.80 (m, 6H), 3.33 (s, 6H).

Example 239: N-(3-chloro-4-fluorophenyl)-N'-hydroxy-2-((2-(methyl(tetrahydro-2H-pyran-4-yl)amino)ethyl)amino)-1H-imidazo[4,5-b]pyridine-7-carboximidamide

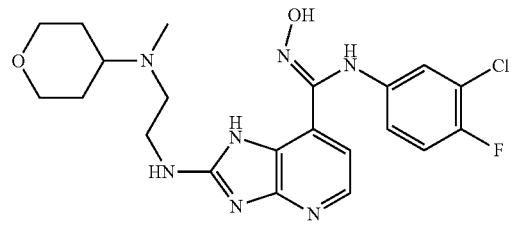 [SMILES: CN(CCNc1nc2nccc(/C(=N/O)Nc3ccc(F)c(Cl)c3)c2[nH]1)C1CCOCC1]

Example 239 was made analogously to Example 212 using $N^1$-methyl-$N^1$-(tetrahydro-2H-pyran-4-yl)ethane-1,2-diamine in place of 2-methoxyethanamine. $C_{21}H_{25}ClFN_7O_2$. 462.2 (M+1). $^1$H NMR (400 MHz, DMSO-d6) δ 8.91 (s, 1H), 7.08 (t, J=9.1 Hz, 1H), 6.95 (s, 1H), 6.90 (d, J=6.0 Hz, 1H), 6.54 (dt, J=9.0, 3.4 Hz, 1H), 3.94 (d, J=11.8 Hz, 2H), 3.31 (d, J=12.1 Hz, 3H), 2.82 (s, 3H), 1.87 (d, J=13.4 Hz, 2H), 1.65 (dd, J=12.0, 4.6 Hz, 2H).

Example 240: N-(3-chloro-4-fluorophenyl)-N'-hydroxy-2-((2-(isopropyl(methyl)amino)ethyl)amino)-1H-imidazo[4,5-b]pyridine-7-carboximidamide

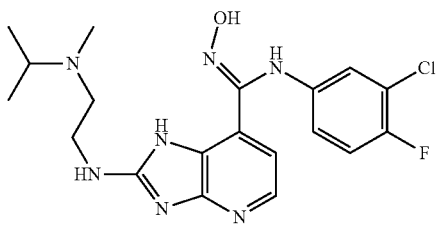 [SMILES: CC(C)N(C)CCNc1nc2nccc(/C(=N/O)Nc3ccc(F)c(Cl)c3)c2[nH]1]

Example 240 was made analogously to Example 212 using N¹-isopropyl-N¹-methylethane-1,2-diamine in place of 2-methoxyethanamine. $C_{19}H_{23}ClFN_7O$. 420.2 (M+1). ¹H NMR (400 MHz, DMSO-d6) δ 11.28 (s, 1H), 8.91 (s, 1H), 7.95 (d, J=5.9 Hz, 1H), 7.84 (s, 1H), 7.08 (t, J=9.0 Hz, 1H), 6.96 (s, 1H), 6.90 (d, J=6.0 Hz, 1H), 6.54 (dt, J=8.8, 3.5 Hz, 1H), 3.74 (s, 2H), 3.69-3.59 (m, 1H), 3.27 (s, 2H), 2.76 (s, 3H), 1.20 (d, J=6.6 Hz, 6H).

Example 241: 2-(((1-aminocyclopropyl)methyl) amino)-N-(3-chloro-4-fluorophenyl)-N'-hydroxy-1H-imidazo[4,5-b]pyridine-7-carboximidamide

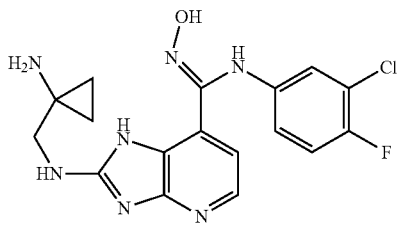 [SMILES: NC1(CNc2nc3nccc(/C(=N/O)Nc4ccc(F)c(Cl)c4)c3[nH]2)CC1]

Example 241 was made analogously to Example 212 using tert-butyl (1-(aminomethyl)cyclopropyl)carbamate in place of 2-methoxyethanamine. $C_{17}H_{17}ClFN_7O$. 390.2 (M+1). ¹H NMR (400 MHz, DMSO-d6) δ 11.34 (s, 1H), 8.92 (s, 1H), 8.34 (s, 3H), 7.95 (d, J=6.1 Hz, 1H), 7.09 (t, J=9.0 Hz, 1H), 6.98 (dd, J=6.5, 2.7 Hz, 1H), 6.91 (d, J=6.2 Hz, 1H), 6.56 (ddd, J=9.0, 4.0, 2.8 Hz, 1H), 3.68 (s, 2H), 0.92 (d, J=5.5 Hz, 4H).

Example 242: 2-((2-(1-aminocyclopropyl)ethyl) amino)-N-(3-chloro-4-fluorophenyl)-N'-hydroxy-1H-imidazo[4,5-b]pyridine-7-carboximidamide

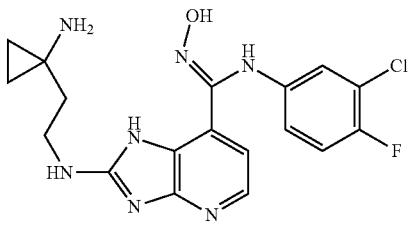 [SMILES: NC1(CCNc2nc3nccc(/C(=N/O)Nc4ccc(F)c(Cl)c4)c3[nH]2)CC1]

Example 242 was made analogously to Example 212 using tert-butyl (1-(2-aminoethyl)cyclopropyl)carbamate in place of 2-methoxyethanamine. $C_{18}H_{19}ClFN_7O$. 404.2 (M+1). ¹H NMR (400 MHz, DMSO-d6) δ 11.33 (s, 1H), 8.93 (s, 1H), 8.20 (s, 3H), 7.95 (d, J=6.2 Hz, 1H), 7.08 (t, J=9.0 Hz, 1H), 6.99 (dd, J=6.5, 2.7 Hz, 1H), 6.93 (d, J=6.1 Hz, 1H), 6.61-6.50 (m, 1H), 3.57 (t, 2H), 1.89 (t, J=7.0 Hz, 2H), 0.81 (d, J=6.9 Hz, 2H), 0.69 (d, J=5.9 Hz, 2H).

Example 243: 2-((2-(2-oxa-5-azabicyclo[4.1.0]heptan-5-yl)ethyl)amino)-N-(3-chloro-4-fluorophenyl)-N'-hydroxy-1H-imidazo[4,5-b]pyridine-7-carboximidamide

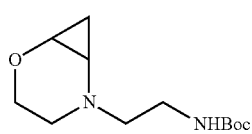 [SMILES: CC(C)(C)OC(=O)NCCN1CCOC2CC21]

tert-butyl (2-(2-oxa-5-azabicyclo[4.1.0]heptan-5-yl) ethyl)carbamate. A mixture of tert-butyl (2-bromoethyl) carbamate (0.500 g, 3.688 mmol), 2-oxa-5-azabicyclo[4.1.0] heptane hydrochloride (0.826 g, 3.688 mmol) and DIPEA (1.285 mL, 7.375 mmol) in DMSO (4 mL) was stirred at 40° C. for 16 h. The mixture was diluted with sat NaHCO₃ soln. The aqueous layer was extracted 3× with EtOAc. The combined organic layers were washed with brine, dried (Na₂SO₄), filtered and concentrated. The residue was purified via silica gel chromatography to give the desired product (0.440 g). $C_{12}H_{22}N_2O_3$. 243.1 (M+1).

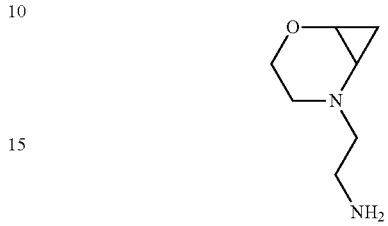

2-(2-oxa-5-azabicyclo[4.1.0]heptan-5-yl)ethanamine hydrochloride. To a solution of tert-butyl (2-(2-oxa-5-azabicyclo[4.1.0]heptan-5-yl)ethyl)carbamate (0.08 g, 0.33 mmol) in THF was added HCl (2.0 mL of a 4 M soln in dioxane, 8 mmol). The mixture stirred at rt for 16 h. The mixture was concentrated to give the desired product as the HCl salt (0.071 g). $C_7H_{16}N_2O$. 143.1 (M+1).

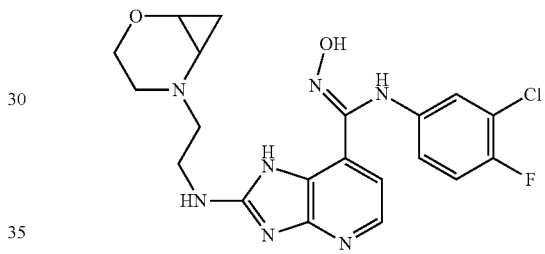

Example 243 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(2-oxa-5-azabicyclo[4.1.0] heptan-5-yl)ethanamine hydrochloride in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. $C_{20}H_{21}ClFN_7O_2$. 446.2 (M+1). ¹H NMR (400 MHz, DMSO-d6) δ 11.35 (s, 1H), 8.96 (s, 1H), 7.96 (d, J=6.2 Hz, 1H), 7.09 (t, J=9.0 Hz, 1H), 7.00 (dd, J=6.5, 2.7 Hz, 1H), 6.92 (d, J=6.2 Hz, 1H), 6.56 (dt, J=9.0, 3.4 Hz, 1H), 3.80-3.63 (m, 4H), 3.53 (t, J=11.5 Hz, 2H), 3.18 (s, 2H), 2.96-2.60 (m, 2H), 0.90 (d, J=149.8 Hz, 2H).

Example 244: 2-((2-(7-oxa-4-azaspiro[2.5]octan-4-yl)ethyl)amino)-N-(3-chloro-4-fluorophenyl)-N'-hydroxy-1H-imidazo[4,5-b]pyridine-7-carboximidamide

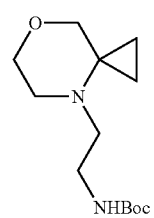

tert-butyl (2-(7-oxa-4-azaspiro[2.5]octan-4-yl)ethyl)carbamate was prepared analogously to Example 243 using 7-oxa-4-azaspiro[2.5]octane hydrochloride in place of 2-oxa-5-azabicyclo[4.1.0]heptane hydrochloride. $C_{14}H_{16}N_2O_2$. 245.1 (M+1).

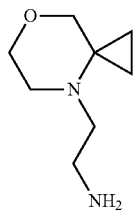

2-(7-oxa-4-azaspiro[2.5]octan-4-yl)ethanamine hydrochloride was prepared analogously to Example 243 using tert-butyl (2-(7-oxa-4-azaspiro[2.5]octan-4-yl)ethyl)carbamate in place of tert-butyl (2-(2-oxa-5-azabicyclo[4.1.0]heptan-5-yl)ethyl)carbamate. $C_8H_{16}N_2O$. 157.1 (M+1).

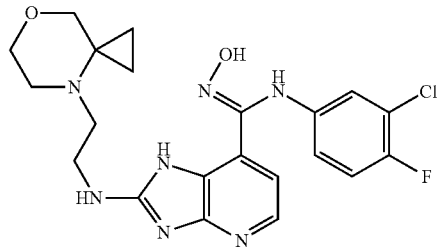 [SMILES: O/N=C(\Nc1ccc(F)c(Cl)c1)c1ccnc2nc(NCCN3CCOCC34CC4)[nH]c12]

Example 244 was made analogously to Example 229 using 2-(7-oxa-4-azaspiro[2.5]octan-4-yl)ethanamine in place of 3-aminopropanamide hydrochloride. $C_{21}H_{23}ClFN_7O_2$. 460.2 (M+1). $^1$H NMR (400 MHz, DMSO-d6) δ 11.34 (s, 1H), 8.96 (s, 1H), 7.97 (d, J=6.1 Hz, 1H), 7.09 (t, J=9.0 Hz, 1H), 6.98 (d, J=6.0 Hz, 1H), 6.93 (d, J=6.1 Hz, 1H), 6.56 (dt, J=8.8, 3.7 Hz, 1H), 4.2-3.00 (m, 10H), 1.20-0.34 (m, 4H).

Example 245: (R)-(3-chloro-4-fluorophenyl)-2-((2-(3-fluoropyrrolidin-1-yl)ethyl)amino)-N'-hydroxy-1H-imidazo[4,5-b]pyridine-7-carboximidamide

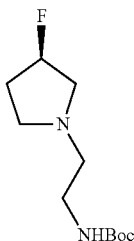 [SMILES: CC(C)(C)OC(=O)NCCN1CC[C@@H](F)C1]

(R)-tert-butyl (2-(3-fluoropyrrolidin-1-yl)ethyl)carbamate was prepared analogously to Example 242 using (R)-3-fluoropyrrolidine hydrochloride in place of 2-oxa-5-azabicyclo[4.1.0]heptane hydrochloride. $C_{11}H_{21}FN_2O_2$. 233.2 (M+1).

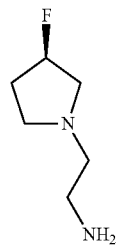

(R)-2-(3-fluoropyrrolidin-1-yl)ethanamine hydrochloride was prepared analogously to Example 242 using (R)-tert-butyl (2-(3-fluoropyrrolidin-1-yl)ethyl)carbamate in place of tert-butyl (2-(2-oxa-5-azabicyclo[4.1.0]heptan-5-yl)ethyl)carbamate. $C_6H_{13}FN_2$. 133.1 (M+1).

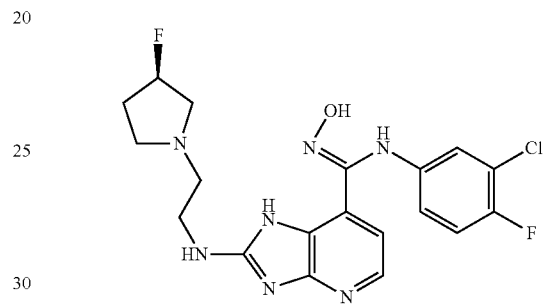

Example 245 was made analogously to Example 229 using (R)-2-(3-fluoropyrrolidin-1-yl)ethanamine hydrochloride in place of 3-aminopropanamide hydrochloride. $C_{19}H_{20}ClF_2N_7O$. 436.2 (M+1). $^1$H NMR (400 MHz, DMSO-d6) δ 11.34 (s, 1H), 8.95 (s, 1H), 7.96 (d, J=6.2 Hz, 1H), 7.09 (t, J=9.0 Hz, 1H), 6.98 (dd, J=6.3, 2.7 Hz, 1H), 6.92 (d, J=6.1 Hz, 1H), 6.55 (ddd, J=8.9, 4.0, 2.7 Hz, 1H), 5.48 (d, J=53.2 Hz, 1H), 3.90-3.35 (m, 8H), 2.43-2.09 (m, 2H).

Example 246: (S)-(3-chloro-4-fluorophenyl)-2-((2-(3-fluoropyrrolidin-1-yl)ethyl)amino)-N'-hydroxy-1H-imidazo[4,5-b]pyridine-7-carboximidamide

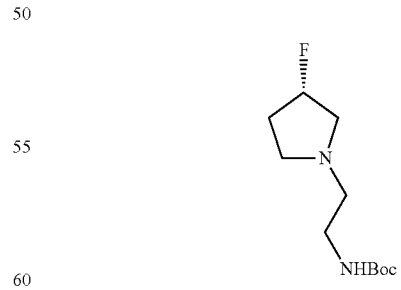

(S)-tert-butyl (2-(3-fluoropyrrolidin-1-yl)ethyl)carbamate was prepared analogously to Example 243 using (S)-3-fluoropyrrolidine hydrochloride in place of 2-oxa-5-azabicyclo[4.1.0]heptane hydrochloride. $C_{11}H_{21}FN_2O_2$. 233.2 (M+1).

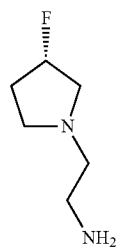

(S)-2-(3-fluoropyrrolidin-1-yl)ethanamine hydrochloride was prepared analogously to Example 242 using (S)-tert-butyl (2-(3-fluoropyrrolidin-1-yl)ethyl)carbamate in place of tert-butyl (2-(2-oxa-5-azabicyclo[4.1.0]heptan-5-yl)ethyl)carbamate. $C_6H_{13}FN_2$. 133.1 (M+1).

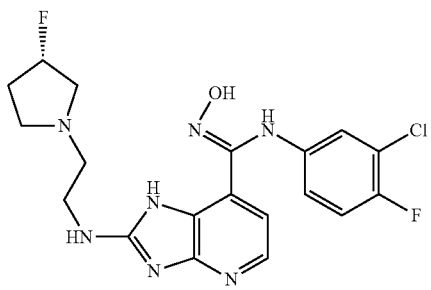 [SMILES: O/N=C(\Nc1ccc(F)c(Cl)c1)c1ccnc2nc(NCCN3CC[C@H](F)C3)[nH]c12]

Example 246 was made analogously to Example 229 using (S)-2-(3-fluoropyrrolidin-1-yl)ethanamine hydrochloride in place of 3-aminopropanamide hydrochloride. $C_{19}H_{20}ClF_2N_7O$. 436.2 (M+1) $^1$H NMR (400 MHz, DMSO-d6) δ 11.35 (s, 1H), 8.95 (s, 1H), 7.97 (d, J=6.2 Hz, 1H), 7.09 (t, J=9.0 Hz, 1H), 6.99 (dd, J=6.5, 2.7 Hz, 1H), 6.92 (d, J=6.2 Hz, 1H), 6.55 (ddd, J=9.0, 4.0, 2.8 Hz, 1H), 5.48 (d, J=53.1 Hz, 1H), 3.90-3.35 (m, 8H), 2.44-2.11 (m, 2H).

Example 247: 2-((2-(2-azabicyclo[4.1.0]heptan-2-yl)ethyl)amino)-N-(3-chloro-4-fluorophenyl)-N'-hydroxy-1H-imidazo[4,5-b]pyridine-7-carboximidamide

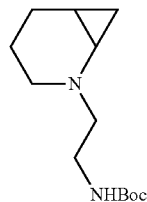 [SMILES: CC(C)(C)OC(=O)NCCN1CCCC2CC21]

tert-butyl (2-(2-azabicyclo[4.1.0]heptan-2-yl)ethyl)carbamate was prepared analogously to Example 243 using (2-azabicyclo[4.1.0]heptane in place of 2-oxa-5-azabicyclo[4.1.0]heptane hydrochloride. $C_{13}H_{24}N_2O_2$. 241.3 (M+1).

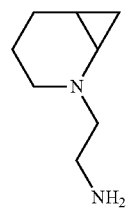

2-(2-azabicyclo[4.1.0]heptan-2-yl)ethanamine hydrochloride was prepared analogously to Example 243 using tert-butyl (2-(2-azabicyclo[4.1.0]heptan-2-yl)ethyl)carbamate in place of tert-butyl (2-(2-oxa-5-azabicyclo[4.1.0]heptan-5-yl)ethyl)carbamate. $C_8H_{16}N_2$. 141.3 (M+1).

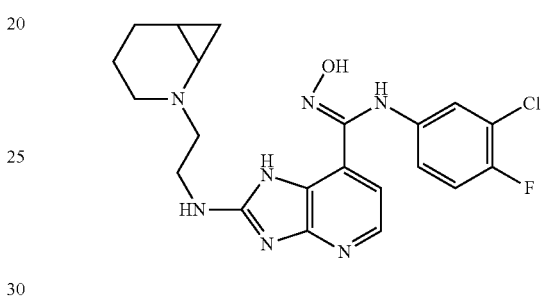

Example 247 was made analogously to Example 229 using 2-(2-azabicyclo[4.1.0]heptan-2-yl)ethanamine hydrochloride in place of 3-aminopropanamide hydrochloride. $C_{21}H_{23}ClFN_7O$. 444.2 (M+1). $^1$H NMR (400 MHz, DMSO-d6) δ 11.36 (s, 1H), 8.96 (s, 1H), 8.08 (s, 1H), 7.97 (d, J=6.2 Hz, 1H), 7.09 (t, J=9.0 Hz, 1H), 6.99 (dd, J=6.5, 2.7 Hz, 1H), 6.93 (d, J=6.2 Hz, 1H), 6.55 (ddd, J=9.0, 4.1, 2.8 Hz, 1H), 3.90-3.30 (m, 5H), 3.12 (s, 1H), 3.01 (s, 1H), 2.90 (d, J=19.4 Hz, 1H), 1.98 (d, J=10.9 Hz, 1H), 1.54 (s, 2H), 1.43-1.28 (m, 1H), 1.00-0.91 (m, 1H), 0.91-0.81 (m, 1H).

Example 248: 2-((2-(4-azaspiro[2.5]octan-4-yl)ethyl)amino)-N-(3-chloro-4-fluorophenyl)-N'-hydroxy-1H-imidazo[4,5-b]pyridine-7-carboximidamide

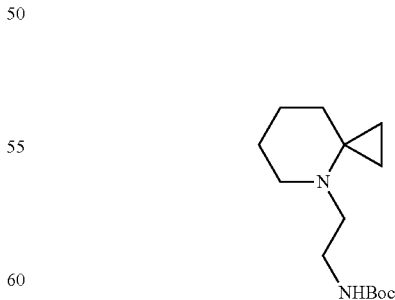

Example 248 was prepared analogously to Example 243 using 4-azaspiro[2.5]octane hydrochloride in place of 2-oxa-5-azabicyclo[4.1.0]heptane hydrochloride. $C_{14}H_{26}N_2O_2$. 255.3 (M+1).

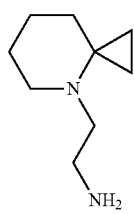 [SMILES: NCCN1CCCCC12CC2]

2-(4-azaspiro[2.5]octan-4-yl)ethanamine hydrochloride was prepared analogously to Example 243 using tert-butyl (2-(4-azaspiro[2.5]octan-4-yl)ethyl)carbamate in place of tert-butyl (2-(2-oxa-5-azabicyclo[4.1.0]heptan-5-yl)ethyl)carbamate. C$_9$H$_{18}$N$_2$. 155.3 (M+1).

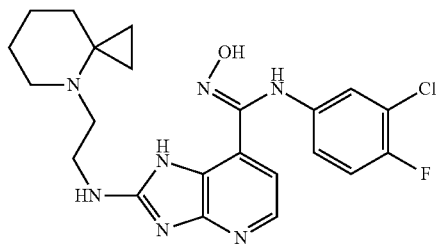 [SMILES: O/N=C(\Nc1ccc(F)c(Cl)c1)c1ccnc2nc(NCCN3CCCCC34CC4)[nH]c12]

Example 248 was made analogously to Example 229 using 2-(4-azaspiro[2.5]octan-4-yl)ethanamine hydrochloride in place of 3-aminopropanamide hydrochloride. C$_{22}$H$_{25}$ClFN$_7$O. 458.2 (M+1). $^1$H NMR (400 MHz, DMSO-d6) δ 11.31 (s, 1H), 8.95 (s, 1H), 7.97 (d, J=6.0 Hz, 1H), 7.78 (s, 1H), 7.08 (t, J=9.0 Hz, 1H), 6.96 (s, 1H), 6.92 (d, J=6.0 Hz, 1H), 6.54 (dt, J=9.0, 3.5 Hz, 1H), 3.8-3.3 (m, 8H), 1.80 (s, 2H), 1.65 (s, 2H), 1.04 (s, 2H), 0.76 (s, 2H).

Example 249: N-(3-chloro-4-fluorophenyl)-2-((2-(3-fluoroazetidin-1-yl)ethyl)amino)-N'-hydroxy-1H-imidazo[4,5-b]pyridine-7-carboximidamide

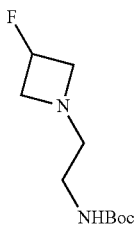

tert-butyl (2-(3-fluoroazetidin-1-yl)ethyl)carbamate was prepared analogously to Example 243 using 3-fluoroazetidine hydrochloride in place of 2-oxa-5-azabicyclo[4.1.0]heptane hydrochloride. C$_{10}$H$_{26}$FN$_2$O$_2$. 218.2 (M+1).

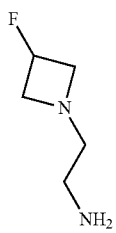

2-(3-fluoroazetidin-1-yl)ethanamine hydrochloride was prepared analogously to Example 243 using tert-butyl (2-(3-fluoroazetidin-1-yl)ethyl)carbamate in place of tert-butyl (2-(2-oxa-5-azabicyclo[4.1.0]heptan-5-yl)ethyl)carbamate. C$_9$H$_{18}$N$_2$. 119.1 (M+1).

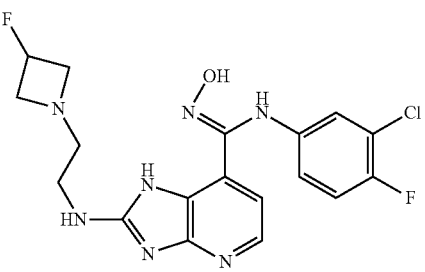 [SMILES: O/N=C(\Nc1ccc(F)c(Cl)c1)c1ccnc2nc(NCCN3CC(F)C3)[nH]c12]

Example 249 was made analogously to Example 229 using 2-(3-fluoroazetidin-1-yl)ethanamine hydrochloride in place of 3-aminopropanamide hydrochloride. C$_{18}$H$_{18}$ClF$_2$N$_7$O. 422.2 (M+1). $^1$H NMR (400 MHz, DMSO-d6) δ 11.95 (s, 1H), 11.34 (s, 1H), 8.94 (s, 1H), 7.97 (d, J=6.2 Hz, 1H), 7.08 (t, J=9.0 Hz, 1H), 6.98 (dd, J=6.4, 2.7 Hz, 1H), 6.92 (d, J=6.2 Hz, 1H), 6.55 (ddd, J=9.0, 4.1, 2.7 Hz, 1H), 5.45-5.30 (m, 1H), 4.52 (dd, J=20.6, 12.4, 5.9 Hz, 2H), 4.33 (dd, J=22.1, 12.2 Hz, 2H), 3.63 (s, 2H), 3.48 (s, 2H).

Example 250: N-(3-chloro-4-fluorophenyl)-2-((2-(3,3-difluoroazetidin-1-yl)ethyl)amino)-1\P-hydroxy-1H-imidazo[4,5-b]pyridine-7-carboximidamide

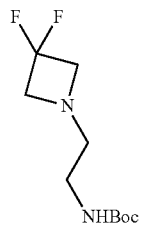

tert-butyl (2-(3,3-difluoroazetidin-1-yl)ethyl)carbamate was prepared analogously to Example 243 using 3,3-difluoroazetidine hydrochloride in place of 2-oxa-5-azabicyclo[4.1.0]heptane hydrochloride. C$_{10}$H$_{18}$F$_2$N$_2$O$_2$. 237.2 (M+1).

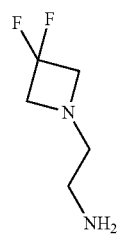

2-(3,3-difluoroazetidin-1-yl)ethanamine hydrochloride was prepared analogously to Example 243 using tert-butyl (2-(3,3-difluoroazetidin-1-yl)ethyl)carbamate in place of tert-butyl (2-(2-oxa-5-azabicyclo[4.1.0]heptan-5-yl)ethyl)carbamate. C$_5$H$_{10}$F$_2$N$_2$. 137.1 (M+1).

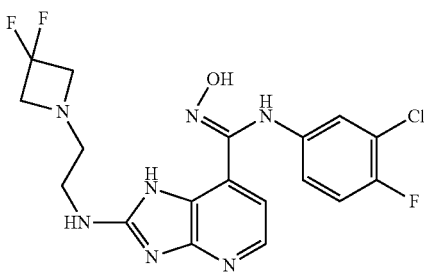 [SMILES: O/N=C(\Nc1ccc(F)c(Cl)c1)c1ccnc2nc(NCCN3CC(F)(F)C3)[nH]c12]

Example 250 was made analogously to Example 229 using 2-(3,3-difluoroazetidin-1-yl)ethanamine hydrochloride in place of 3-aminopropanamide hydrochloride. $C_{18}H_{17}ClF_3N_7O$. 440.2 (M+1). $^1$H NMR (400 MHz, DMSO-d6) δ 11.41 (s, 1H), 8.96 (s, 1H), 7.97 (d, J=6.3 Hz, 1H), 7.09 (t, J=9.0 Hz, 1H), 7.01 (dd, J=6.5, 2.7 Hz, 1H), 6.93 (d, J=6.3 Hz, 1H), 6.56 (ddd, J=9.0, 4.0, 2.8 Hz, 1H), 4.09 (s, 4H), 3.54 (s, 2H), 3.07 (s, 2H).

Example 251: 2-((2-(4-azaspiro[2.4]heptan-4-yl)ethyl)amino)-N-(3-chloro-4-fluorophenyl)-N'-hydroxy-1H-imidazo[4,5-b]pyridine-7-carboximidamide

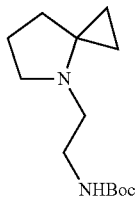 [SMILES: CC(C)(C)OC(=O)NCCN1CCCC12CC2]

tert-butyl (2-(4-azaspiro[2.4]heptan-4-yl)ethyl)carbamate was prepared analogously to Example 244 using 4-azaspiro[2.4]heptane hydrochloride in place of 2-oxa-5-azabicyclo[4.1.0]heptane hydrochloride. $C_{13}H_{24}N_2O_2$. 241.2 (M+1).

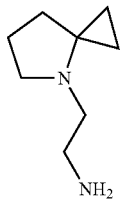

2-(4-azaspiro[2.4]heptan-4-yl)ethanamine hydrochloride was prepared analogously to Example 243 using tert-butyl (2-(4-azaspiro[2.4]heptan-4-yl)ethyl)carbamate in place of tert-butyl (2-(2-oxa-5-azabicyclo[4.1.0]heptan-5-yl)ethyl)carbamate. $C_8H_{16}N_2$. 141.1 (M+1).

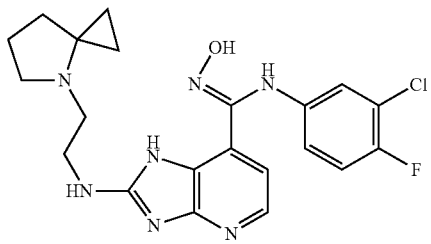 [SMILES: O/N=C(\Nc1ccc(F)c(Cl)c1)c1ccnc2nc(NCCN3CCCC34CC4)[nH]c12]

Example 251 was made analogously to Example 229 using 2-(4-azaspiro[2.4]heptan-4-yl)ethanamine hydrochloride in place of 3-aminopropanamide hydrochloride. $C_{21}H_{23}ClFN_7O$. 444.2 (M+1). $^1$H NMR (400 MHz, DMSO-d6) δ 11.33 (s, 1H), 8.95 (s, 1H), 7.97 (d, J=6.1 Hz, 1H), 7.08 (t, J=9.0 Hz, 1H), 6.98 (d, J=6.4 Hz, 1H), 6.93 (d, J=6.1 Hz, 1H), 6.55 (ddd, J=8.9, 4.0, 2.7 Hz, 1H), 3.65-3.75 (m, 4H), 3.17 (t, J=6.0 Hz, 2H), 2.17-1.92 (m, 4H), 1.22 (t, 2H), 0.84 (t, 2H).

Example 252: N-(3-chloro-4-fluorophenyl)-2-((3-(3-fluoropiperidin-1-yl)propyl)amino),N'-hydroxy-W-imidazo[4,5-b]pyridine-7-carboximidamide

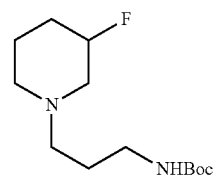 [SMILES: CC(C)(C)OC(=O)NCCCN1CCCC(F)C1]

tert-butyl (3-(3-fluoropiperidin-1-yl)propyl)carbamate was prepared analogously to Example 243 using 3-fluoropiperidine hydrochloride in place of 2-oxa-5-azabicyclo[4.1.0]heptane hydrochloride. $C_{13}H_{25}FN_2O_2$. 261.2 (M+1).

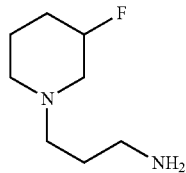

3-(3-fluoropiperidin-1-yl)propan-1-amine hydrochloride was prepared analogously to Example 243 using tert-butyl (3-(3-fluoropiperidin-1-yl)propyl)carbamate in place of tert-butyl (2-(2-oxa-5-azabicyclo[4.1.0]heptan-5-yl)ethyl)carbamate. $C_8H_{17}FN_2$. 161.1 (M+1).

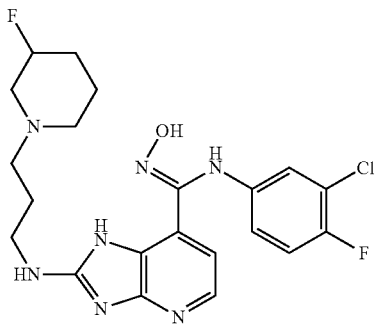 [SMILES: O/N=C(\Nc1ccc(F)c(Cl)c1)c1ccnc2nc(NCCCN3CCCC(F)C3)[nH]c12]

Example 252 was made analogously to Example 229 using 3-(3-fluoropiperidin-1-yl)propan-1-amine hydrochloride in place of 3-aminopropanamide hydrochloride. $C_{21}H_{24}ClF_2N_7O$. 464.2 (M+1). $^1$H NMR (400 MHz, DMSO-d6) δ 12.07 (s, 1H), 11.38 (s, 1H), 8.96 (s, 1H), 8.22 (d, J=58.7 Hz, 1H), 7.97 (d, J=6.2 Hz, 1H), 7.09 (t, J=9.0 Hz, 1H), 7.01 (dd, J=6.5, 2.7 Hz, 1H), 6.93 (d, J=6.2 Hz, 1H), 6.56 (ddd, J=9.0, 4.0, 2.8 Hz, 1H), 5.08 (d, J=45.5 Hz, 1H), 3.47 (d, J=6.4 Hz, 1H), 3.35 (s, 3H), 3.12 (q, J=7.4 Hz, 2H), 3.02 (s, 2H), 2.08-1.84 (m, 4H), 1.75 (d, J=14.5 Hz, 2H).

Example 253: N-(3-chloro-4-fluorophenyl)-N'-hydroxy-2-((2-(phenylamino)ethyl)amino)-1H-imidazo[4,5-b]pyridine-7-carboximidamide

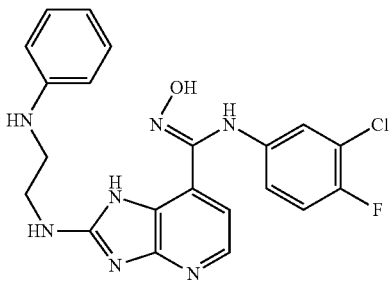 [SMILES: O/N=C(\Nc1ccc(F)c(Cl)c1)c1ccnc2nc(NCCNc3ccccc3)[nH]c12]

Example 253 was made analogously to Example 212 using N¹-phenylethane-1,2-diamine in place of 2-methoxyethanamine. C$_{21}$H$_{19}$ClFN$_7$O. 440.2 (M+1). ¹H NMR (400 MHz, DMSO-d6) δ 11.42 (s, 1H), 8.96 (s, 1H), 7.95 (d, J=6.3 Hz, 1H), 7.14-7.04 (m, 4H), 7.02 (dd, J=6.5, 2.8 Hz, 1H), 6.90 (d, J=6.3 Hz, 1H), 6.65-6.50 (m, 4H), 3.62 (d, J=6.0 Hz, 2H), 3.28 (t, J=6.3 Hz, 2H).

Example 254: N-(3-chloro-4-fluorophenyl)-N'-hydroxy-2-((2-(methyl(phenyl)amino)ethyl)amino)-1H-imidazo[4,5-b]pyridine-7-carboximidamide

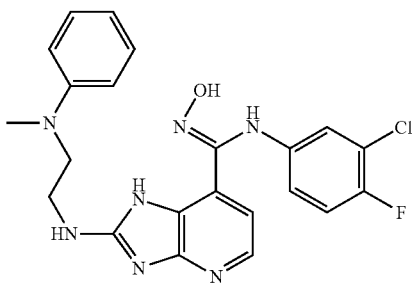 [SMILES: CN(CCNc1nc2nccc(/C(=N/O)Nc3ccc(F)c(Cl)c3)c2[nH]1)c1ccccc1]

Example 254 was made analogously to Example 212 using N¹-methyl-N¹-phenylethane-1,2-diamine in place of 2-methoxyethanamine. C$_{22}$H$_{21}$ClFN$_7$O. 454.2 (M+1). ¹H NMR (400 MHz, DMSO-d6) δ 11.95 (s, 1H), 11.42 (s, 1H), 8.97 (s, 1H), 7.95 (d, J=6.4 Hz, 1H), 7.19-7.12 (m, 2H), 7.09 (t, J=9.0 Hz, 1H), 7.03 (dd, J=6.5, 2.7 Hz, 1H), 6.92 (d, J=6.3 Hz, 1H), 6.75 (d, J=8.1 Hz, 2H), 6.61 (tt, J=7.3, 1.0 Hz, 1H), 6.56 (ddd, J=9.0, 4.0, 2.8 Hz, 1H), 3.64 (M, 4H), 2.89 (s, 3H).

Example 255: N-(3-chloro-4-fluorophenyl)-2-(((1,1-dioxidotetrahydro-2H-thiopyran-3-yl)methyl)amino)-N'-hydroxy-1H-imidazo[4,5-b]pyridine-7-carboximidamide

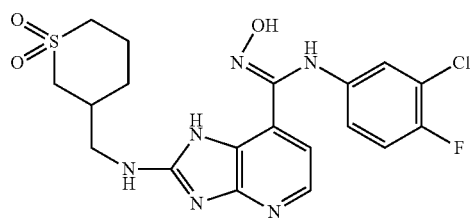 [SMILES: O=S1(=O)CCCC(CNc2nc3nccc(/C(=N/O)Nc4ccc(F)c(Cl)c4)c3[nH]2)C1]

Example 255 was made analogously to Example 212 using 3-(aminomethyl)tetrahydro-2H-thiopyran 1,1-dioxide in place of 2-methoxyethanamine. C$_{19}$H$_{20}$ClFN$_6$O$_3$S. 467.2 (M+1). ¹H NMR (400 MHz, DMSO-d6) δ 11.41 (s, 1H), 8.96 (s, 1H), 7.95 (d, J=6.3 Hz, 1H), 7.09 (t, J=9.0 Hz, 1H), 7.03 (dd, J=6.5, 2.7 Hz, 1H), 6.92 (d, J=6.3 Hz, 1H), 6.57 (ddd, J=9.0, 4.0, 2.8 Hz, 1H), 3.06 (m, 2H), 3.00-2.87 (m, 1H), 2.31 (m, 2H), 2.06 (dd, J=10.3, 3.9 Hz, 2H), 1.76 (d, J=13.6 Hz, 2H), 1.24 (q, J=12.4 Hz, 2H).

Example 256: N-(3-chloro-4-fluorophenyl)-2-((2-ethoxycyclopropyl)amino)-N'-hydroxy-1H-imidazo[4,5-b]pyridine-7-carboximidamide

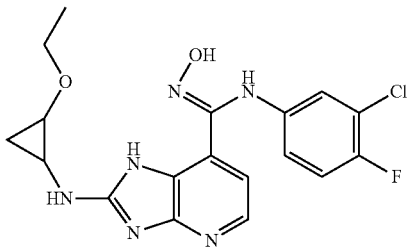 [SMILES: CCOC1CC1Nc1nc2nccc(/C(=N/O)Nc3ccc(F)c(Cl)c3)c2[nH]1]

Example 256 was made analogously to Example 212 using 2-methoxycyclopropanamine in place of 2-methoxyethanamine. C$_{18}$H$_{18}$ClFN$_6$O$_2$. 405.2 (M+1). ¹H NMR (400 MHz, DMSO-d6) δ 11.34 (s, 1H), 8.95 (s, 1H), 7.98 (d, J=6.3 Hz, 1H), 7.07 (t, J=9.1 Hz, 1H), 7.02 (d, J=5.5 Hz, 1H), 6.94 (d, J=6.2 Hz, 1H), 6.55 (ddd, J=8.9, 4.0, 2.8 Hz, 1H), 3.67-3.51 (m, 2H), 2.88 (s, 1H), 1.13 (t, J=7.0 Hz, 3H), 1.11-1.04 (m, 2H), 0.83 (s, 1H).

Example 257: N-(3-bromo-4-fluorophenyl)-N'-hydroxy-2-(methylamino)-1H-imidazo[4,5-b]pyridine-7-carboximidamide

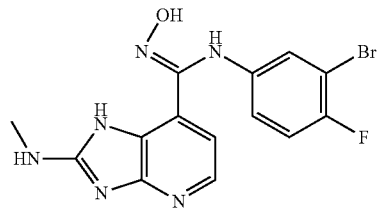 [SMILES: CNc1nc2nccc(/C(=N/O)Nc3ccc(F)c(Br)c3)c2[nH]1]

Example 257 was made analogously to Example 212 using 4-(3-bromo-4-fluorophenyl)-3-(2-chloro-1-((2-(trimethylsilyl)ethoxy)methyl)-1H-imidazo[4,5-b]pyridin-7-yl)-1,2,4-oxadiazol-5(4H)-one and methylamine (2.0 M solution in tetrahydrofuran) in place of 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-methoxyethanamine, respectively. C$_{14}$H$_{12}$BrFN$_6$O. 379.1 (M+1). ¹H NMR (400 MHz, DMSO-d6) δ 12.12 (s, 1H), 11.38 (s, 1H), 8.95 (s, 1H), 7.97 (d, J=6.2 Hz, 1H), 7.16 (dd, J=6.1, 2.7 Hz, 1H), 7.04 (t, J=8.8 Hz, 1H), 6.92 (d, J=6.2 Hz, 1H), 6.58 (ddd, J=8.9, 4.1, 2.7 Hz, 1H), 3.00 (d, J=4.7 Hz, 3H).

Example 258: 2-(2-(azepan-1-yl)ethyl)-N-(3-chloro-4-fluorophenyl)-N'-hydroxy-1H-imidazo[4,5-b]pyridine-7-carboximidamide

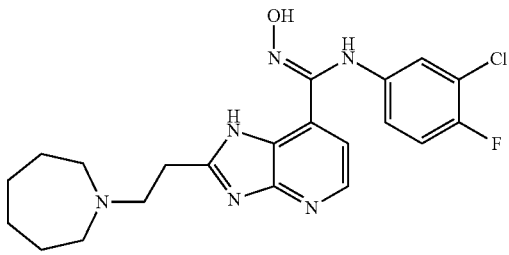 [SMILES: O/N=C(\Nc1ccc(F)c(Cl)c1)c1ccnc2nc(CCN3CCCCCC3)[nH]c12]

Example 258 was made analogously to Example 184 using hexamethyleneimine in place of dimethylamine. $C_{21}H_{24}ClFN_6O$. 431.2 (M+1). $^1$H NMR (400 MHz, DMSO-d6) δ 11.09 (s, 1H), 8.90 (s, 1H), 8.30 (d, J=5.1 Hz, 1H), 7.16 (d, J=5.1 Hz, 1H), 7.04 (t, J=9.1 Hz, 1H), 6.93 (dd, J=6.5, 2.7 Hz, 1H), 6.51 (ddd, J=9.0, 4.1, 2.8 Hz, 1H), 3.58 (t, J=7.5 Hz, 2H), 3.45-3.22 (m, 6H), 1.90-1.74 (m, 4H), 1.69-1.57 (m, 4H).

Example 259: 2-(2-(azetidin-1-yl)ethyl)-N-(3-chloro-4-fluorophenyl)-N'-hydroxy-1H-imidazo[4,5-b]-pyridine-7-carboximidamide

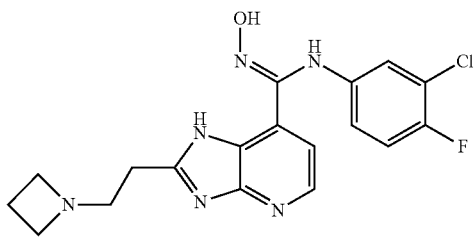 [SMILES: O/N=C(\Nc1ccc(F)c(Cl)c1)c1ccnc2nc(CCN3CCC3)[nH]c12]

Example 259 was made analogously to Example 184 using azetidine hydrochloride and N,N-diisopropylethylamine in place of dimethylamine. $C_{18}H_{18}ClFN_6O$. 389.1 (M+1).

Example 260: (R)—N-(3-chloro-4-fluorophenyl)-N'-hydroxy-2-(2-(3-hydroxypyrrolidin-1-yl)ethyl)-1H-imidazo[4,5-b]pyridine-7-carboximidamide

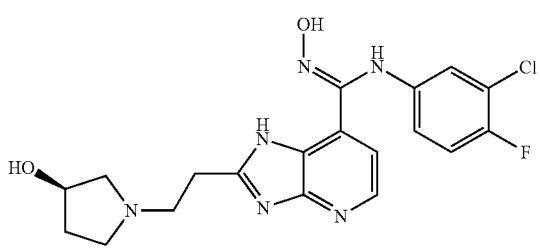 [SMILES: O/N=C(\Nc1ccc(F)c(Cl)c1)c1ccnc2nc(CCN3CC[C@@H](O)C3)[nH]c12]

Example 260 was made analogously to Example 184 using (R)-pyrrolidin-3-ol in place of dimethylamine. $C_{19}H_{20}ClFN_6O_2$. 419.1 (M+1).

Example 261: (S)—N-(3-chloro-4-fluorophenyl)-N'-hydroxy-2-(2-(3-hydroxypyrrolidin-1-yl)ethyl)-1H-imidazo[4,5-b]pyridine-7-carboximidamide

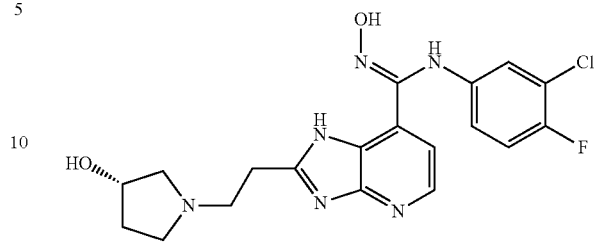

Example 261 was made analogously to Example 184 using (S)-pyrrolidin-3-ol hydrochloride and N,N-diisopropylethylamine in place of dimethylamine. $C_{19}H_{20}ClFN_6O_2$. 419.1 (M+1).

Example 262: N-(3-chloro-4-fluorophenyl)-N'-hydroxy-2-(2-(4-hydroxypiperidin-1-yl)ethyl)-1H-imidazo[4,5-b]pyridine-7-carboximidamide

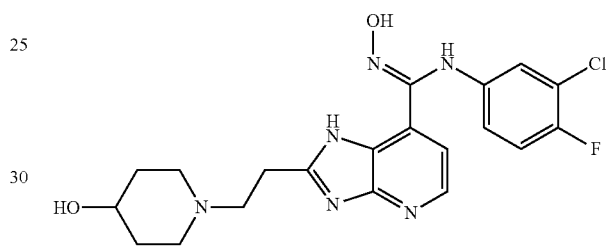

Example 262 was made analogously to Example 184 using 4-hydroxypiperidine in place of dimethylamine. $C_{20}H_{22}ClFN_6O_2$. 433.1 (M+1).

Example 263: N-(3-bromo-4-fluorophenyl)-2-(2-(dimethylamino)ethyl)-N'-hydroxy-1H-imidazo[4,5-b]pyridine-7-carboximidamide

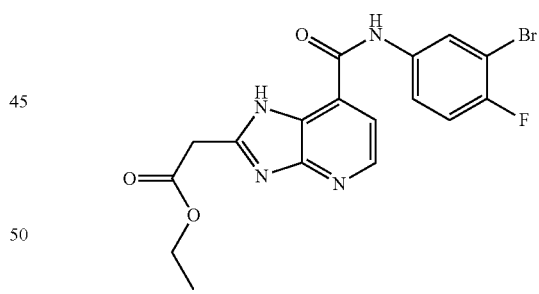

Ethyl 2-(7-((3-bromo-4-fluorophenyl)carbamoyl)-1H-imidazo[4,5-b]pyridin-2-yl)acetate was made analogously to Example 183 using 2,3-diamino-N-(3-bromo-4-fluorophenyl)isonicotinamide in place of 2,3-diamino-N-(3-chloro-4-fluorophenyl)isonicotinamide. $C_{17}H_{14}BrFN_4O_3$. 421.2, 423.1 (M+1).

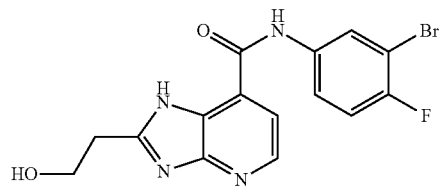 [SMILES: O=C(Nc1ccc(F)c(Br)c1)c1ccnc2nc(CCO)[nH]c12]

N-(3-bromo-4-fluorophenyl)-2-(2-hydroxyethyl)-1H-imidazo[4,5-b]pyridine-7-carboxamide was made analogously to Example 184 using ethyl 2-(7-((3-bromo-4-fluorophenyl)carbamoyl)-1H-imidazo[4,5-b]pyridin-2-yl)acetate in place of ethyl 2-(7-((3-chloro-4-fluorophenyl)carbamoyl)-1H-imidazo[4,5-b]pyridin-2-yl)acetate. $C_{15}H_{12}BrFN_4O_2$. 379.0, 381.0 (M+1).

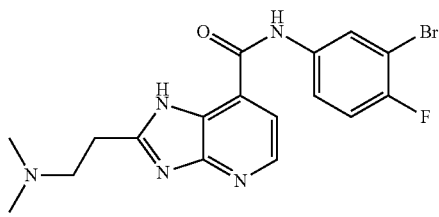 [SMILES: CN(C)CCc1nc2nccc(C(=O)Nc3ccc(F)c(Br)c3)c2[nH]1]

N-(3-bromo-4-fluorophenyl)-2-(2-(dimethylamino)ethyl)-1H-imidazo[4,5-b]pyridine-7-carboxamide was made analogously to Example 184 using N-(3-bromo-4-fluorophenyl)-2-(2-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide. $C_{17}H_{17}BrFN_5O$. 406.1, 408.1 (M+1).

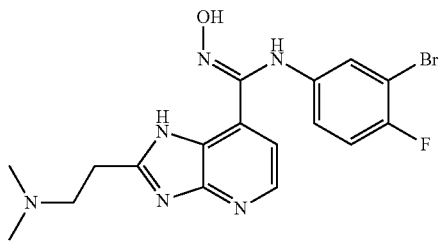 [SMILES: CN(C)CCc1nc2nccc(/C(=N/O)Nc3ccc(F)c(Br)c3)c2[nH]1]

N-(3-bromo-4-fluorophenyl)-2-(2-(dimethylamino)ethyl)-N'-hydroxy-1H-imidazo[4,5-b]pyridine-7-carboximidamide. Example XX was made analogously to Example 184 using N-(3-bromo-4-fluorophenyl)-2-(2-(dimethylamino)ethyl)-1H-imidazo[4,5-b]pyridine-7-carboxamide in place of N-(3-chloro-4-fluorophenyl)-2-(2-(dimethylamino)ethyl)-1H-imidazo[4,5-b]pyridine-7-carboxamide. $C_{17}H_{18}BrFN_6O$. 421.0, 423.0 (M+1). $^1$H NMR (400 MHz, DMSO-d6) δ 10.99 (s, 1H), 8.86 (s, 1H), 8.27 (dd, J=5.0, 0.5 Hz, 1H), 7.13 (d, J=5.1 Hz, 1H), 7.07 (dd, J=6.1, 2.7 Hz, 1H), 6.99 (t, J=8.8 Hz, 1H), 6.53 (ddd, J=9.0, 4.1, 2.8 Hz, 1H), 3.38-3.18 (m, 4H), 2.69 (s, 6H).

Example 264: N-(3-chlorophenyl)-2-(2-(dimethylamino)ethyl),N'-hydroxy-1H-imidazo[4,5-b]pyridine-7-carboximidamide

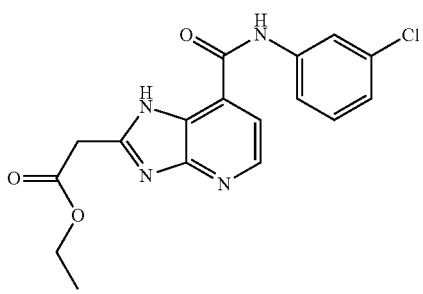 [SMILES: CCOC(=O)Cc1nc2nccc(C(=O)Nc3cccc(Cl)c3)c2[nH]1]

Ethyl 2-(7-((3-chlorophenyl)carbamoyl)-1H-imidazo[4,5-b]pyridin-2-yl)acetate was made analogously to Example 183 using 2,3-diamino-N-(3-chlorophenyl)isonicotinamide in place of 2,3-diamino-N-(3-chloro-4-fluorophenyl)isonicotinamide. $C_{17}H_{15}ClN_4O_3$. 359.3 (M+1).

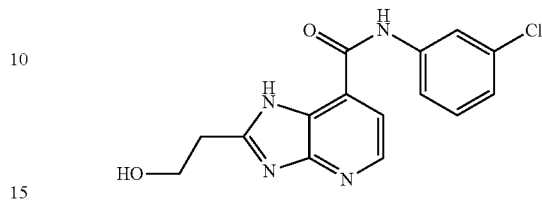

N-(3-chlorophenyl)-2-(2-hydroxyethyl)-1H-imidazo[4,5-b]pyridine-7-carboxamide was made analogously to Example 184 using ethyl 2-(7-((3-chlorophenyl)carbamoyl)-1H-imidazo[4,5-b]pyridin-2-yl)acetate in place of ethyl 2-(7-((3-chloro-4-fluorophenyl)carbamoyl)-1H-imidazo[4,5-b]pyridin-2-yl)acetate. $C_{15}H_{13}ClN_4O_2$. 317.1 (M+1).

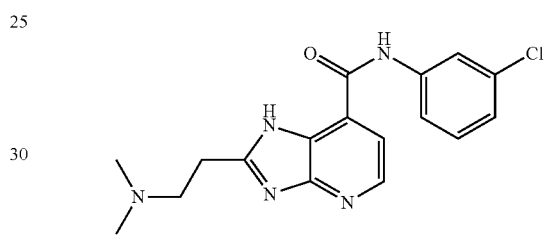

N-(3-chlorophenyl)-2-(2-(dimethylamino)ethyl)-1H-imidazo[4,5-b]pyridine-7-carboxamide was made analogously to Example 184 using N-(3-chlorophenyl)-2-(2-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide. $C_{17}H_{18}ClN_5O$. 344.3 (M+1).

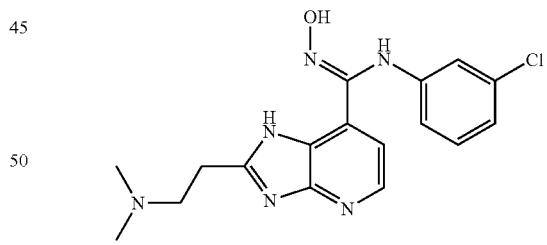

N-(3-chlorophenyl)-2-(2-(dimethylamino)ethyl)-N'-hydroxy-1H-imidazo[4,5-b]pyridine-7-carboximidamide was made analogously to Example 184 using N-(3-chlorophenyl)-2-(2-(dimethylamino)ethyl)-1H-imidazo[4,5-b]pyridine-7-carboxamide in place of N-(3-chloro-4-fluorophenyl)-2-(2-(dimethylamino)ethyl)-1H-imidazo[4,5-b]pyridine-7-carboxamide. $C_{17}H_{19}ClN_6O$. 359.1 (M+1). $^1$H NMR (400 MHz, DMSO-d6) δ 12.49 (s, 1H), 11.10 (s, 1H), 8.86 (s, 1H), 8.22 (d, J=5.2 Hz, 1H), 7.08 (d, J=5.0 Hz, 1H), 6.97 (t, J=8.0 Hz, 1H), 6.83 (t, J=2.1 Hz, 1H), 6.77 (dd, J=7.8, 1.9 Hz, 1H), 6.44 (dd, J=8.1, 2.1 Hz, 1H), 2.93 (t, J=7.3 Hz, 2H), 2.61 (t, J=7.3 Hz, 2H), 2.16 (s, 6H).

Example 265: N-(3-bromophenyl)-2-(2-(dimethylamino)ethyl)-N'-hydroxy-1H-imidazo[4,5-b]pyridine-7-carboximidamide

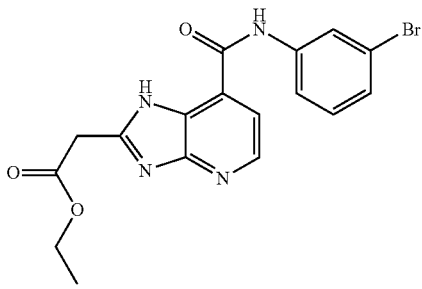 [SMILES: CCOC(=O)Cc1nc2nccc(C(=O)Nc3cccc(Br)c3)c2[nH]1]

Ethyl 2-(7-((3-bromophenyl)carbamoyl)-1H-imidazo[4,5-b]pyridin-2-yl)acetate was made analogously to Example using 2,3-diamino-N-(3-bromophenyl)isonicotinamide in place of 2,3-diamino-N-(3-chloro-4-fluorophenyl)isonicotinamide. $C_{17}H_{15}BrN_4O_3$. 403.3, 405.2 (M+1).

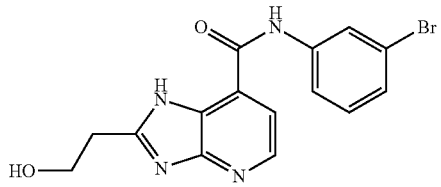 [SMILES: O=C(Nc1cccc(Br)c1)c1ccnc2nc(CCO)[nH]c12]

N-(3-bromophenyl)-2-(2-hydroxyethyl)-1H-imidazo[4,5-b]pyridine-7-carboxamide was made analogously to Example 184 using ethyl 2-(7-((3-bromophenyl)carbamoyl)-1H-imidazo[4,5-b]pyridin-2-yl)acetate in place of ethyl 2-(7-((3-chloro-4-fluorophenyl)carbamoyl)-1H-imidazo[4,5-b]pyridin-2-yl)acetate. $C_{15}H_{13}BrN_4O_2$. 361.0, 363.0 (M+1).

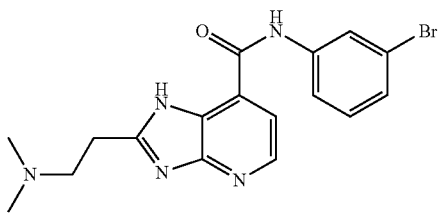 [SMILES: CN(C)CCc1nc2nccc(C(=O)Nc3cccc(Br)c3)c2[nH]1]

N-(3-bromophenyl)-2-(2-(dimethylamino)ethyl)-1H-imidazo[4,5-b]pyridine-7-carboxamide was made analogously to Example 184 using N-(3-bromophenyl)-2-(2-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide. $C_{17}H_{18}BrN_5O$. 388.2, 390.2 (M+1).

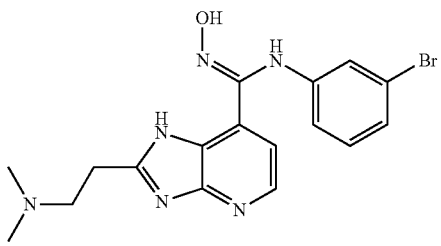 [SMILES: CN(C)CCc1nc2nccc(/C(=N/O)Nc3cccc(Br)c3)c2[nH]1]

N-(3-bromophenyl)-2-(2-(dimethylamino)ethyl)-N'-hydroxy-1H-imidazo[4,5-b]pyridine-7-carboximidamide. Example 266 was made analogously to Example 184 using N-(3-bromophenyl)-2-(2-(dimethylamino)ethyl)-1H-imidazo[4,5-b]pyridine-7-carboxamide in place of N-(3-chloro-4-fluorophenyl)-2-(2-(dimethylamino)ethyl)-1H-imidazo[4,5-b]pyridine-7-carboxamide. $C_{17}H_{19}BrN_6O$. 403.0, 405.0 (M+1). $^1$H NMR (400 MHz, DMSO-d6) δ 11.05 (s, 1H), 8.85 (s, 1H), 8.23 (dd, J=5.1, 0.5 Hz, 1H), 7.09 (d, J=5.1 Hz, 1H), 7.00-6.97 (m, 1H), 6.93-6.87 (m, 2H), 6.50-6.45 (m, 1H), 2.95 (t, J=7.3 Hz, 2H), 2.69-2.62 (m, 2H), 2.19 (s, 6H).

Example 266: N-(3-chloro-4-fluorophenyl)-N'-hydroxy-2-(2-(methylsulfonamido)ethyl)-1H-imidazo[4,5-b]pyridine-7-carboximidamide

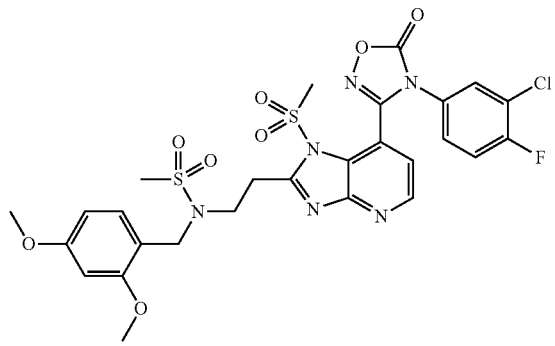 [SMILES: COc1ccc(CN(CCc2nc3nccc(-c4noc(=O)n4-c4ccc(F)c(Cl)c4)c3n2S(C)(=O)=O)S(C)(=O)=O)c(OC)c1]

N-(2-(7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)ethyl)-N-(2,4-dimethoxybenzyl)methanesulfonamide. A solution of 4-(3-chloro-4-fluorophenyl)-3-(2-(2-((2,4-dimethoxybenzyl)amino)ethyl)-1H-imidazo[4,5-b]pyridin-7-yl)-1,2,4-oxadiazol-5(4H)-one (15 mg, 0.029 mmol) and pyridine (0.046 mL, 0.57 mmol) in dichloromethane (1.0 mL) was cooled in an ice bath with stirring and treated with methanesulfonyl chloride (0.022 mL, 0.29 mmol). The reaction mixture was then allowed to warm to room temperature. After 35 min, another portion of methanesulfonyl chloride (0.022 mL, 0.29 mmol) was added, followed 15 min later by further treatment with pyridine (0.023 mL, 0.29 mmol). After another 15 min, the reaction appeared to have stalled (based on LCMS analysis), with added reagents having no effect, so N,N-diisopropylethylamine (0.10 mL, 0.57 mmol) was added, resulting in complete conversion within 15 min. The reaction mixture was concentrated under reduced pressure, and loaded directly onto a silica gel cartridge for purification by flash chromatography (0-20% methanol/dichloromethane) to afford the desired product (20 mg) $C_{27}H_{26}ClFN_6O_8S_2$. 681.0 (M+1).

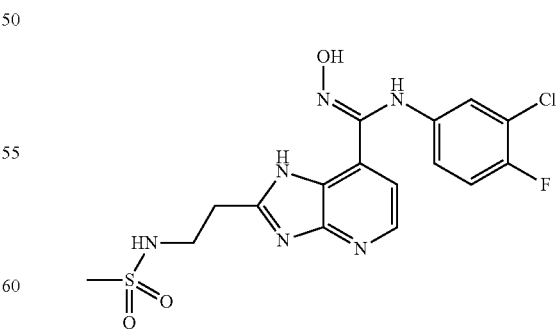

N-(3-chloro-4-fluorophenyl)-N'-hydroxy-2-(2-(methylsulfonamido)ethyl)-1H-imidazo[4,5-b]pyridine-7-carboximidamide. A solution of N-(2-(7-(4-(3-chloro-4-fluorophenyl)-5-oxo-4,5-dihydro-1,2,4-oxadiazol-3-yl)-1-(methylsulfonyl)-1H-imidazo[4,5-b]pyridin-2-yl)ethyl)-N-

(2,4-dimethoxybenzyl)methanesulfonamide (20 mg, 0.029 mmol) and triethylsilane (0.023 mL, 0.15 mmol) in dichloromethane (1 mL) was treated with trifluoroacetic acid (1 mL), and the reaction mixture was stirred overnight at room temperature. The mixture was then concentrated under reduced pressure and taken up in tetrahydrofuran (0.75 mL) and water (0.75 mL), and treated with a 2M aqueous solution of sodium hydroxide (0.75 mL, 1.5 mmol). After 15 min of stirring at room temperature, the reaction mixture was acidified with acetic acid, diluted with dimethyl sulfoxide, and purified by reverse phase preparative HPLC to provide the desired product (7 mg). $C_{16}H_{16}ClFN_6O_3S$. 427.0 (M+1).

Example 267: N-(3-chloro-4-fluorophenyl)-N'-hydroxy-2-(2-(sulfamoylamino)ethyl)-1H-imidazo[4,5-b]pyridine-7-carboximidamide

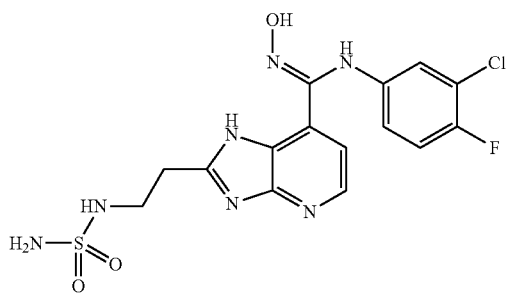 [SMILES: NS(=O)(=O)NCCc1nc2nccc(/C(=N/O)Nc3ccc(F)c(Cl)c3)c2[nH]1]

A suspension of 4-(3-chloro-4-fluorophenyl)-3-(2-(2-((2,4-dimethoxybenzyl)amino)ethyl)-1H-imidazo[4,5-b]pyridin-7-yl)-1,2,4-oxadiazol-5(4H)-one (15 mg, 0.029 mmol) and sulfamide (27 mg, 0.29 mmol) in pyridine (1 mL) was stirred at 120° C. for 20 min. The mixture was then cooled to room temperature and concentrated under reduced pressure. The resulting residue was suspended in dichloromethane (0.5 mL) and treated with triethylsilane (0.022 mL, 0.14 mmol) followed by trifluoroacetic acid (0.5 mL). After stirring at room temperature for 1 h, the reaction mixture was concentrated under reduced pressure and taken up in tetrahydrofuran (0.75 mL) and water (0.75 mL), and treated with a 2M aqueous solution of sodium hydroxide (0.75 mL, 1.5 mmol). After 15 min, another portion of 2M sodium hydroxide (1 mL, 2 mmol) was added, and the reaction was stirred for an additional 15 min. The mixture was then acidified with acetic acid, diluted with dimethyl sulfoxide, and purified by reverse phase preparative HPLC to provide the desired product (7 mg). $C_{15}H_{15}ClFN_7O_3S$. 428.0 (M+1).

Example 268: N-(3-chlorophenyl)-N'-hydroxy-2-(2-(pyrrolidin-1-yl)ethyl)-1H-imidazo[4,5-b]pyridine-7-carboximidamide

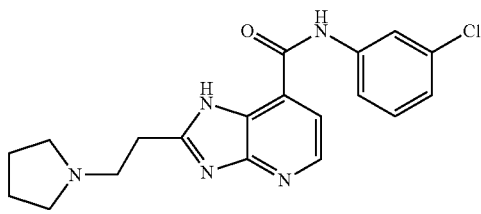 [SMILES: O=C(Nc1cccc(Cl)c1)c1ccnc2nc(CCN3CCCC3)[nH]c12]

N-(3-chlorophenyl)-2-(2-(pyrrolidin-1-yl)ethyl)-1H-imidazo[4,5-b]pyridine-7-carboxamide was made analogously to Example 184 using N-(3-chlorophenyl)-2-(2-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide and pyrrolidine in place of dimethylamine. $C_{19}H_{20}ClN_5O$. 370.1 (M+1).

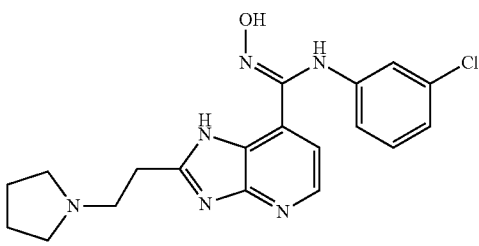 [SMILES: O/N=C(\Nc1cccc(Cl)c1)c1ccnc2nc(CCN3CCCC3)[nH]c12]

N-(3-chlorophenyl)-N'-hydroxy-2-(2-(pyrrolidin-1-yl)ethyl)-1H-imidazo[4,5-b]pyridine-7-carboximidamide was made analogously to Example using N-(3-chlorophenyl)-2-(2-(pyrrolidin-1-yl)ethyl)-1H-imidazo[4,5-b]pyridine-7-carboxamide in place of N-(3-chloro-4-fluorophenyl)-2-(2-(dimethylamino)ethyl)-1H-imidazo[4,5-b]pyridine-7-carboxamide. $C_{19}H_{21}ClN_6O$. 385.1 (M+1). $^1$H NMR (400 MHz, DMSO-d6) δ 11.08 (s, 1H), 8.90 (s, 1H), 8.26 (dd, J=5.1, 0.6 Hz, 1H), 7.11 (d, J=5.0 Hz, 1H), 6.98 (t, J=8.0 Hz, 1H), 6.84-6.76 (m, 2H), 6.46 (dd, J=8.1, 2.1 Hz, 1H), 3.50-2.84 (m, 8H), 1.87 (s, 4H).

Example 269: N-(3-bromophenyl)-N'-hydroxy-2-(2-(pyrrolidin-1-yl)ethyl)-1H-imidazo[4,5-b]pyridine-7-carboximidamide

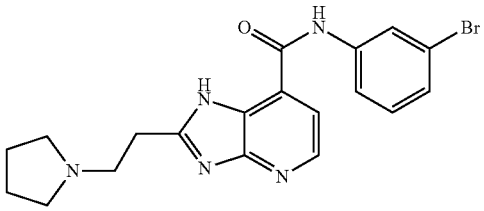 [SMILES: O=C(Nc1cccc(Br)c1)c1ccnc2nc(CCN3CCCC3)[nH]c12]

N-(3-bromophenyl)-2-(2-(pyrrolidin-1-yl)ethyl)-1H-imidazo[4,5-b]pyridine-7-carboxamide was made analogously to Example 184 using N-(3-bromophenyl)-2-(2-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide and pyrrolidine in place of dimethylamine. $C_{19}H_{20}BrN_5O$. 414.1, 416.1 (M+1).

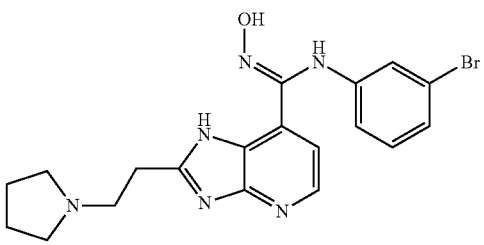 [SMILES: O/N=C(\Nc1cccc(Br)c1)c1ccnc2nc(CCN3CCCC3)[nH]c12]

N-(3-bromophenyl)-N'-hydroxy-2-(2-(pyrrolidin-1-yl)ethyl)-1H-imidazo[4,5-b]pyridine-7-carboximidamide. To a suspension of N-(3-bromophenyl)-2-(2-(pyrrolidin-1-yl)ethyl)-1H-imidazo[4,5-b]pyridine-7-carboxamide (54 mg, 0.13 mmol) in 1,2-dichloroethane (1.0 mL) and phosphorus oxychloride (1.0 mL) was added phosphorus pentachloride (33 mg, 0.16 mmol). The mixture was stirred at 90° C. for 1 h. Another portion of phosphorus pentachloride (33 mg, 0.16 mmol) was then added, and stirring resumed for an additional 45 min at 90° C. A third portion of phosphorus pentachloride (33 mg, 0.16 mmol) was then added, and stirring resumed for an additional 1 h at 90° C. The reaction mixture was then cooled to room temperature and concentrated under reduced pressure. The resulting residue was treated with hydroxylamine (50 wt. % in water, 1.0 mL, 16 mmol) in ethanol (1.0 mL) with vigorous stirring. The mixture was stirred for 15 min, then diluted with saturated aqueous sodium chloride and dichloromethane/isopropanol (2:1). The layers were then separated, and the organic phase was concentrated under reduced pressure. The resulting crude residue was suspended in 30% methanol in dichloromethane, filtered to remove salts, and loaded directly onto a silica gel cartridge for purification by flash chromatography (0-50% methanol/dichloromethane). Product-containing fractions were pooled and concentrated under reduced pressure, then taken up in 5% methanol in dichloromethane and filtered through celite to remove silica gel that may have eluted from the column with the material. The filtrate was concentrated under reduced pressure, coevaporated with methanol (3×) to remove residual dichloromethane, dissolved in methanol/water, frozen, and lyophilized to afford the product as an off-white solid (30 mg). $C_{19}H_{21}BrN_6O$. 429.1, 431.1 (M+1). $^1$H NMR (400 MHz, DMSO-d6) δ 11.07 (s, 1H), 8.90 (s, 1H), 8.27 (d, J=5.1 Hz, 1H), 7.15-7.09 (m, 1H), 7.01-6.96 (m, 1H), 6.95-6.88 (m, 2H), 6.51-6.47 (m, 1H), 3.71-2.85 (m, 8H), 1.89 (s, 4H).

Example 270: N-(2-(7-(N-(3-chloro-4-fluorophenyl)-N'-hydroxycarbamimidoyl)-1H-imidazo[4,5-b]pyridin-2-yl)ethyl)acetamide

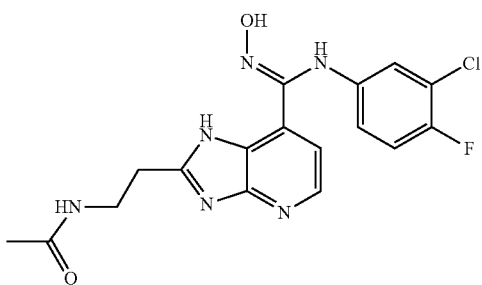 [SMILES: CC(=O)NCCc1nc2nccc(/C(=N/O)Nc3ccc(F)c(Cl)c3)c2[nH]1]

A solution of 4-(3-chloro-4-fluorophenyl)-3-(2-(2-((2,4-dimethoxybenzyl)amino)ethyl)-1H-imidazo[4,5-b]pyridin-7-yl)-1,2,4-oxadiazol-5(4H)-one (15 mg, 0.029 mmol) and 4-(dimethylamino)pyridine (1 flake) in dichloromethane (1 mL) was treated with acetic anhydride (0.027 mL, 0.29 mmol) and stirred at room temperature for 10 min. The reaction mixture was then concentrated under reduced pressure. The resulting residue was dissolved in dichloromethane (0.5 mL) and treated with triethylsilane (0.022 mL, 0.14 mmol) followed by trifluoroacetic acid (0.5 mL). The reaction solution was stirred at room temperature overnight, then concentrated under reduced pressure, taken up in tetrahydrofuran (1 mL) and water (1 mL), and treated with a 2M aqueous solution of sodium hydroxide (1 mL, 2 mmol). After stirring for 15 min, the mixture was acidified with acetic acid, diluted with dimethyl sulfoxide, and purified by reverse phase preparative HPLC to provide the desired product (9 mg). $C_{17}H_{16}ClFN_6O_2$. 391.1 (M+1).

Example 271: N-(3-chlorophenyl)-N'-hydroxy-2-(2-(piperidin-1-yl)ethyl)-1H-imidazo[4,5-b]pyridine-7-carboximidamide

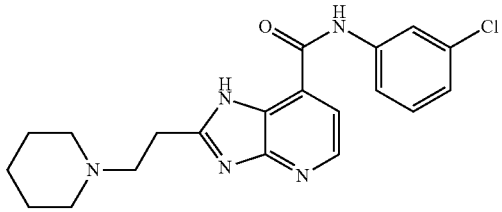

N-(3-chlorophenyl)-2-(2-(piperidin-1-yl)ethyl)-1H-imidazo[4,5-b]pyridine-7-carboxamide was made analogously to Example 184 using N-(3-chlorophenyl)-2-(2-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide and piperidine in place of dimethylamine. $C_{20}H_{22}ClN_5O$. 384.3 (M+1).

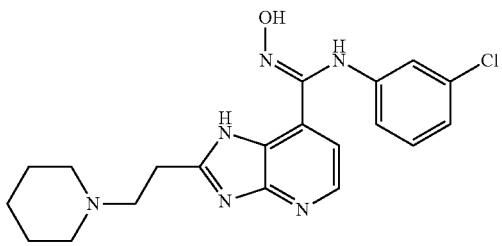 [SMILES: O/N=C(\Nc1cccc(Cl)c1)c1ccnc2nc(CCN3CCCCC3)[nH]c12]

N-(3-chlorophenyl)-N'-hydroxy-2-(2-(piperidin-1-yl)ethyl)-1H-imidazo[4,5-b]pyridine-7-carboximidamide was made analogously to Example 184 using N-(3-chlorophenyl)-2-(2-(piperidin-1-yl)ethyl)-1H-imidazo[4,5-b]pyridine-7-carboxamide in place of N-(3-chloro-4-fluorophenyl)-2-(2-(dimethylamino)ethyl)-1H-imidazo[4,5-b]pyridine-7-carboxamide. $C_{20}H_{23}ClN_6O$. 399.2 (M+1). $^1$H NMR (400 MHz, DMSO-d6) δ 11.08 (s, 1H), 8.91 (s, 1H), 8.27 (dd, J=5.0, 0.7 Hz, 1H), 7.11 (d, J=5.0 Hz, 1H), 6.98 (t, J=8.0 Hz, 1H), 6.84-6.76 (m, 2H), 6.46 (dd, J=8.2, 2.1 Hz, 1H), 3.67-2.70 (m, 8H), 1.73 (s, 4H), 1.53 (s, 2H).

Example 272: N-(3-bromophenyl)-N'-hydroxy-2-(2-(piperidin-1-yl)ethyl)-1H-imidazo[4,5-b]pyridine-7-carboximidamide

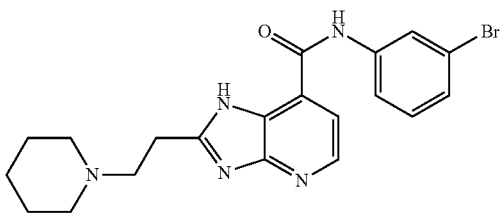 [SMILES: O=C(Nc1cccc(Br)c1)c1ccnc2nc(CCN3CCCCC3)[nH]c12]

N-(3-bromophenyl)-2-(2-(piperidin-1-yl)ethyl)-1H-imidazo[4,5-b]pyridine-7-carboxamide was made analogously to Example 184 using N-(3-bromophenyl)-2-(2-hydroxyethyl)-1H-imidazo[4,5-b]pyridine-7-carboxamide in place of N-(3-chloro-4-fluorophenyl)-2-(2-hydroxyethyl)-1H-imidazo[4,5-b]pyridine-7-carboxamide and piperidine in place of dimethylamine. C$_{20}$H$_{22}$BrN$_5$O. 428.3, 430.3 (M+1).

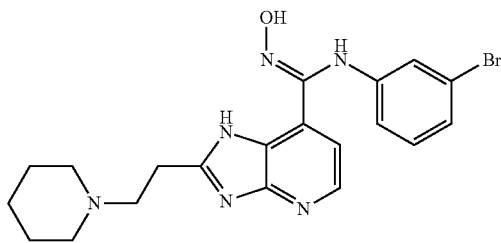 [SMILES: O/N=C(\Nc1cccc(Br)c1)c1ccnc2nc(CCN3CCCCC3)[nH]c12]

N-(3-bromophenyl)-N'-hydroxy-2-(2-(piperidin-1-yl)ethyl)-1H-imidazo[4,5-b]pyridine-7-carboximidamide was made analogously to Example 184 using N-(3-bromophenyl)-2-(2-(piperidin-1-yl)ethyl)-1H-imidazo[4,5-b]pyridine-7-carboxamide in place of N-(3-chloro-4-fluorophenyl)-2-(2-(dimethylamino)ethyl)-1H-imidazo[4,5-b]pyridine-7-carboxamide. C$_{20}$H$_{23}$BrN$_6$O. 443.1, 445.1 (M+1). $^1$H NMR (400 MHz, DMSO-d6) δ 11.07 (s, 1H), 8.90 (s, 1H), 8.27 (dd, J=5.1, 0.8 Hz, 1H), 7.12 (d, J=4.5 Hz, 1H), 6.98-6.96 (m, 1H), 6.95-6.89 (m, 2H), 6.52-6.47 (m, 1H), 3.63-2.72 (m, 8H), 1.88-1.35 (m, 6H).

Example 273: Methyl (2-(7-(N-(3-chloro-4-fluorophenyl)-N'-hydroxycarbamimidoyl)-1H-imidazo[4,5-b]pyridin-2-yl)ethyl)carbamate

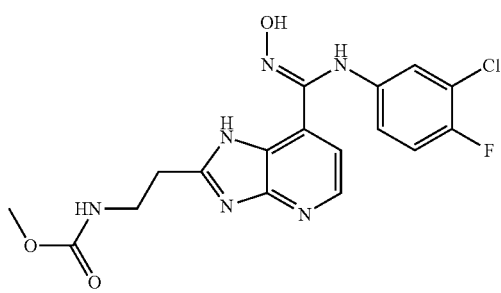 [SMILES: COC(=O)NCCc1nc2nccc(/C(=N/O)Nc3ccc(F)c(Cl)c3)c2[nH]1]

A solution of 4-(3-chloro-4-fluorophenyl)-3-(2-(2-((2,4-dimethoxybenzyl)amino)ethyl)-1H-imidazo[4,5-b]pyridin-7-yl)-1,2,4-oxadiazol-5(4H)-one (30 mg, 0.057 mmol) and N,N-diisopropylethylamine (0.20 mL, 1.2 mmol) in dichloromethane (1 mL) was treated with methyl chloroformate (0.044 mL, 0.57 mmol) dropwise and with stirring. After 1 h, another portion of methyl chloroformate (0.044 mL, 0.57 mmol) was added, and the reaction mixture was stirred for an additional 5 min. The mixture was the concentrated under reduced pressure. The resulting residue was dissolved in dichloromethane (0.5 mL) and treated with triethylsilane (0.046 mL, 0.29 mmol) followed by trifluoroacetic acid (0.5 mL). The reaction solution was stirred at room temperature overnight, then concentrated under reduced pressure, taken up in tetrahydrofuran (0.75 mL) and water (0.75 mL), and treated with a 2M aqueous solution of sodium hydroxide (1.5 mL, 3 mmol). After stirring for 5 min, the mixture was acidified with acetic acid, diluted with dimethyl sulfoxide, and purified by reverse phase preparative HPLC to provide the desired product. C$_{17}$H$_{16}$ClFN$_6$O$_3$. 407.1 (M+1).

Example 274: N-(3-chloro-4-fluorophenyl)-2-(2-((2,4-dimethoxybenzyl)amino)ethyl)-N'-hydroxy-1H-imidazo[4,5-b]pyridine-7-carboximidamide

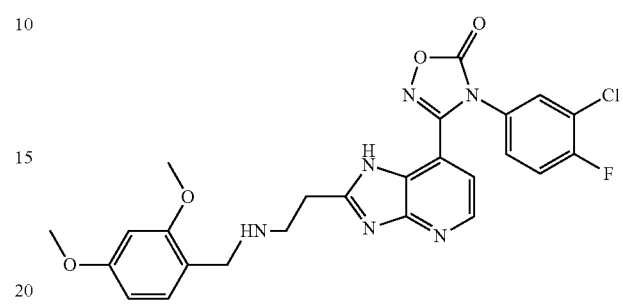

4-(3-chloro-4-fluorophenyl)-3-(2-(2-((2,4-dimethoxybenzyl)amino)ethyl)-1H-imidazo[4,5-b]pyridin-7-yl)-1,2,4-oxadiazol-5(4H)-one. A solution of 2-(7-(4-(3-chloro-4-fluorophenyl)-5-oxo-4,5-dihydro-1,2,4-oxadiazol-3-yl)-1-(methylsulfonyl)-3H-imidazo[4,5-b]pyridin-2-yl)ethyl methanesulfonate (60 mg, 0.11 mmol) in acetonitrile (2.2 mL) was treated with 2,4-dimethoxybenzylamine (0.34 mL, 2.2 mmol). The resulting solution was stirred for 2.5 h at room temperature. The reaction mixture was then concentrated under reduced pressure, and the resulting residue was taken up in dichloromethane (1 mL) and treated with trifluoroacetic acid (1 mL). The solution was stirred overnight at room temperature, then concentrated under reduced pressure. The crude material was dissolved in dichloromethane and washed with saturated aqueous potassium carbonate. The aqueous layer was extracted twice with dichloromethane, and the combined organic layers were loaded onto a silica gel cartridge for purification by flash chromatography (0-20% methanol/dichloromethane) to provide the desired product. C$_{25}$H$_{22}$ClFN$_6$O$_4$. 525.2 (M+1).

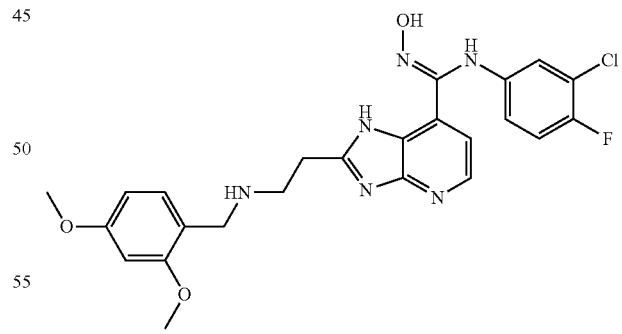

N-(3-chloro-4-fluorophenyl)-2-(2-((2,4-dimethoxybenzyl)amino)ethyl)-N'-hydroxy-1H-imidazo[4,5-b]pyridine-7-carboximidamide was made analogously to Example 177 using 4-(3-chloro-4-fluorophenyl)-3-(2-(2-((2,4-dimethoxybenzyl)amino)ethyl)-1H-imidazo[4,5-b]pyridin-7-yl)-1,2,4-oxadiazol-5(4H)-one in place of 4-(3-chloro-4-fluorophenyl)-3-(2-(hydroxymethyl)-1H-imidazo[4,5-b]pyridin-7-yl)-1,2,4-oxadiazol-5(4H)-one. C$_{24}$H$_{24}$ClFN$_6$O$_3$. 499.2 (M+1).

Example 275: 2-(2-(4-benzylpiperidin-1-yl)ethyl)-N-(3-chloro-4-fluorophenyl),N'-hydroxy-1H-imidazo[4,5-b]pyridine-7-carboximidamide

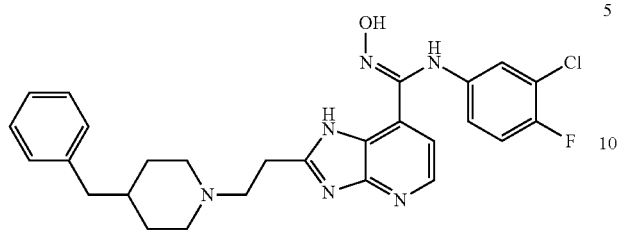

Example 275 was made analogously to Example 184 using 4-benzylpiperidine in place of dimethylamine. $C_{27}H_{28}ClFN_6O$. 507.2 (M+1). $^1$H NMR (400 MHz, DMSO-d6) δ 11.08 (s, 1H), 8.91 (s, 1H), 8.29 (d, J=5.1 Hz, 1H), 7.34-7.25 (m, 2H), 7.24-7.12 (m, 4H), 7.03 (t, J=9.1 Hz, 1H), 6.92 (dd, J=6.4, 2.7 Hz, 1H), 6.55-6.46 (m, 1H), 3.51 (s, 4H), 3.29 (t, J=7.4 Hz, 2H), 2.96 (s, 2H), 2.62-2.48 (m, 2H), 1.78 (d, J=14.5 Hz, 3H), 1.41 (s, 2H).

Example 276: 2-(2-(3-azabicyclo[3.3.1]nonan-3-yl)ethyl)-N-(3-chloro-4-fluorophenyl)-N'-hydroxy-1H-imidazo[4,5-b]pyridine-7-carboximidamide

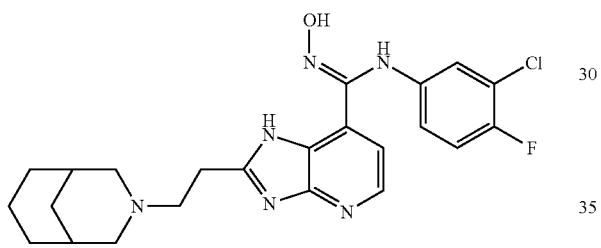

Example 276 was made analogously to Example 184 using 3-azabicyclo[3.3.1]nonane hydrochloride and N,N-diisopropylethylamine in place of dimethylamine. $C_{23}H_{26}ClFN_6O$. 457.2 (M+1). $^1$H NMR (400 MHz, DMSO-d6) δ 11.07 (s, 1H), 8.93 (s, 1H), 8.32 (dd, J=5.0, 3.2 Hz, 1H), 7.14 (dd, J=5.0, 3.0 Hz, 1H), 7.05 (td, J=9.1, 3.0 Hz, 1H), 6.93-6.88 (m, 1H), 6.50 (ddd, J=8.7, 6.2, 2.6 Hz, 1H), 3.69 (d, J=12.4 Hz, 2H), 3.54-3.47 (m, 2H), 3.41-3.34 (m, 2H), 3.25 (d, J=12.3 Hz, 2H), 2.14 (s, 3H), 1.89-1.57 (m, 7H).

Example 277: 2-(2-(3-azabicyclo[3.2.1]octan-3-yl)ethyl)-N-(3-chloro-4-fluorophenyl)-N'-hydroxy-1H-imidazo[4,5-b]pyridine-7-carboximidamide

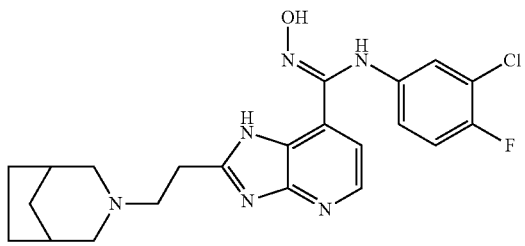 [SMILES: O/N=C(\Nc1ccc(F)c(Cl)c1)c1ccnc2nc(CCN3CC4CCC(C4)C3)[nH]c12]

Example 277 was made analogously to Example 184 using 3-azabicyclo[3.2.1]octane hydrochloride and N,N-diisopropylethylamine in place of dimethylamine. $C_{22}H_{24}ClFN_6O$. 443.2 (M+1). $^1$H NMR (400 MHz, DMSO-d6) δ 11.07 (s, 1H), 8.92 (s, 1H), 8.31 (d, J=5.1 Hz, 1H), 7.15 (d, J=5.1 Hz, 1H), 7.05 (t, J=9.0 Hz, 1H), 6.92 (dd, J=6.5, 2.6 Hz, 1H), 6.53-6.46 (m, 1H), 3.50 (t, J=6.9 Hz, 2H), 3.42 (d, J=11.7 Hz, 2H), 3.30 (t, J=7.2 Hz, 2H), 3.08 (d, J=11.6 Hz, 2H), 2.40 (s, 2H), 1.80 (s, 4H), 1.70 (d, J=11.2 Hz, 1H), 1.49 (d, J=10.0 Hz, 1H).

Example 278: N-(3-chloro-4-fluorophenyl)-N'-hydroxy-2-((1-methylpiperidin-3-yl)amino)-1H-imidazo[4,5-b]pyridine-7-carboximidamide

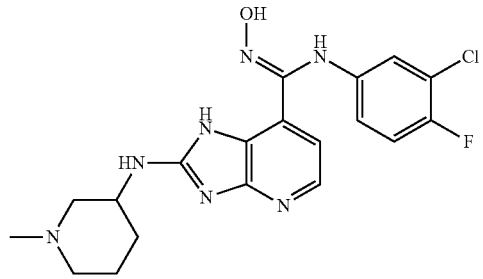 [SMILES: CN1CCCC(Nc2nc3nccc(/C(=N/O)Nc4ccc(F)c(Cl)c4)c3[nH]2)C1]

Example 278 was made analogously to Example 212 using 1-methylpiperidin-3-amine in place of 2-methoxyethanamine. $C_{19}H_{21}ClFN_7O$. 418.2 (M+1). $^1$H NMR (400 MHz, DMSO-d6) δ 11.36 (s, 1H), 9.79 (s, 1H), 8.95 (s, 1H), 7.98 (d, J=5.1 Hz, 1H), 7.10 (t, J=9.1 Hz, 1H), 7.05-6.90 (m, 2H), 6.61-6.55 (m, 1H), 4.18-4.01 (m, 1H), 2.97-2.72 (m, 6H), 2.11-1.62 (m, 4H), 1.57-1.41 (m, 1H).

Examples 279 and 280: (S)—N-(3-chloro-4-fluorophenyl)-N'-hydroxy-2-((2-(3-hydroxypyrrolidin-1-yl)ethyl)amino)-1H-imidazo[4,5-b]pyridine-7-carboximidamide and (S)—N-(3-chloro-4-fluorophenyl)-N'-hydroxy-2-(3-hydroxypyrrolidin-1-yl)-1H-imidazo[4,5-b]pyridine-7-carboximidamide

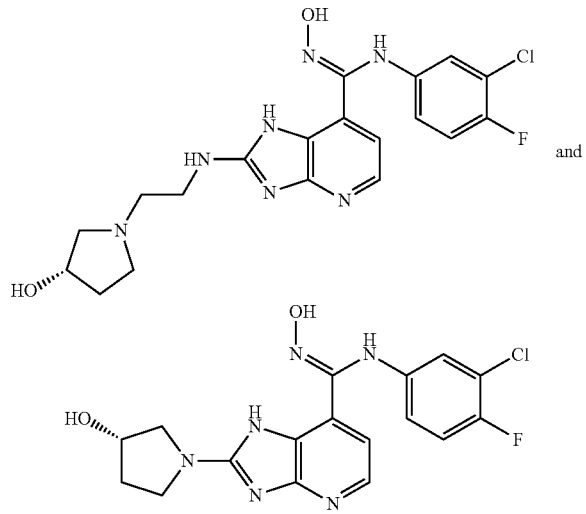

A solution of 3-(2-chloro-1-((2-(trimethyl silyl)ethoxy)methyl)-1H-imidazo[4,5-b]pyridin-7-yl)-4-(3-chloro-4-fluorophenyl)-1,2,4-oxadiazol-5(4H)-one (25 mg, 0.050 mmol) in DMSO (0.5 mL) was treated with (S)-1-(2-aminoethyl)pyrrolidin-3-ol (13 mg, 0.10 mmol). The solution was stirred at 60° C. overnight, then cooled to room temperature, diluted with ethyl acetate, and washed with saturated aqueous sodium chloride (3×). The organic layer was dried over sodium sulfate, filtered, and concentrated under reduced pressure. The resulting residue was dissolved in dichloromethane (0.5 mL) and treated with trifluoroacetic acid (0.5 mL). The solution was stirred at room temperature for 1 h, then concentrated under reduced pressure, taken up in tetrahydrofuran (0.5 mL) and water (0.5 mL) and treated with 2M aqueous sodium hydroxide (0.99 mL, 2.0 mmol). After stirring for 10 min, the mixture was acidified with acetic acid, diluted with dimethyl sulfoxide, and purified by reverse phase preparative HPLC to provide (S)—N-(3-chloro-4-fluorophenyl)-N'-hydroxy-2-((2-(3-hydroxypyrrolidin-1-yl)ethyl)amino)-1H-imidazo[4,5-b]pyridine-7-carboximidamide (10 mg) and (S)—N-(3-chloro-4-fluorophenyl)-N'-hydroxy-2-(3-hydroxypyrrolidin-1-yl)-1H-imidazo[4,5-b]pyridine-7-carboximidamide (4 mg).

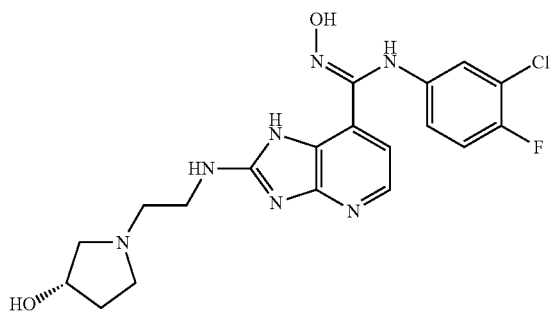 [SMILES: O/N=C(\Nc1ccc(F)c(Cl)c1)c1ccnc2nc(NCCN3CC[C@H](O)C3)[nH]c12]

(S)—N-(3-chloro-4-fluorophenyl)-N'-hydroxy-2-((2-(3-hydroxypyrrolidin-1-yl)ethyl)amino)-1H-imidazo[4,5-b]pyridine-7-carboximidamide. $C_{19}H_{21}ClFN_7O_2$. 434.2 (M+1). $^1$H NMR (400 MHz, DMSO-d6) δ 11.40 (s, 1H), 8.99 (s, 1H), 7.99 (d, J=6.2 Hz, 1H), 7.15-7.07 (m, 1H), 7.04-6.98 (m, 1H), 6.98-6.93 (m, 1H), 6.61-6.54 (m, 1H), 4.45 (s, 1H), 4.16-2.91 (m, 8H), 2.14 (s, 1H), 1.94-1.82 (m, 1H).

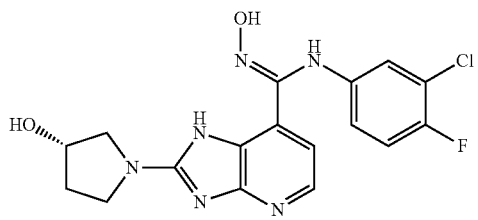 [SMILES: O/N=C(\Nc1ccc(F)c(Cl)c1)c1ccnc2nc(N3CC[C@H](O)C3)[nH]c12]

(S)—N-(3-chloro-4-fluorophenyl)-N'-hydroxy-2-(3-hydroxypyrrolidin-1-yl)-1H-imidazo[4,5-b]pyridine-7-carboximidamide. $C_{17}H_{16}ClFN_6O_2$. 391.1 (M+1). $^1$H NMR (400 MHz, DMSO-d$_6$) δ 11.38 (s, 1H), 9.03 (s, 1H), 8.02-7.94 (m, 1H), 7.11-7.03 (m, 2H), 6.91 (d, J=6.0 Hz, 1H), 6.60-6.53 (m, 1H), 4.46 (s, 1H), 3.79-3.50 (m, 4H), 2.14-2.02 (m, 1H), 1.98 (s, 1H).

Example 281: N-(3-chloro-4-fluorophenyl)-N'-hydroxy-2-((1-(2-methoxyethyl)pyrrolidin-3-yl)amino)-1H-imidazo[4,5-b]pyridine-7-carboximidamide

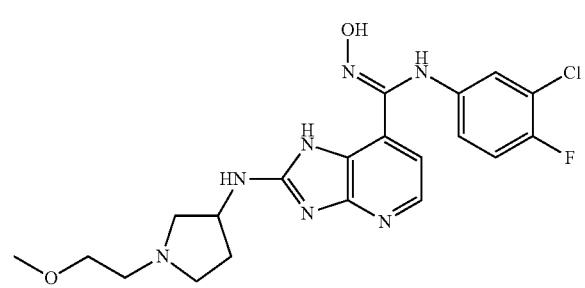 [SMILES: COCCN1CCC(Nc2nc3nccc(/C(=N/O)Nc4ccc(F)c(Cl)c4)c3[nH]2)C1]

Example 281 was made analogously to Example 212 using 1-(2-methoxyethyl)pyrrolidin-3-amine in place of 2-methoxyethanamine. $C_{20}H_{23}ClFN_7O_2$. 448.2 (M+1). $^1$H NMR (400 MHz, DMSO-d6) δ 11.32 (s, 1H), 9.98 (s, 1H), 8.95 (s, 1H), 7.99 (d, J=4.3 Hz, 1H), 7.09 (t, J=9.1 Hz, 1H), 7.04-6.92 (d, J=17.3 Hz, 3H), 6.57 (ddd, J=8.3, 5.8, 2.4 Hz, 1H), 4.70-4.49 (m, 2H), 4.00-3.09 (m, 10H), 2.08 (s, 1H), 1.97 (s, 1H).

Example 282: N-(3-chloro-4-fluorophenyl)-N'-hydroxy-2-(((4-methylmorpholin-3-yl)methyl)amino)-1H-imidazo[4,5-b]pyridine-7-carboximidamide

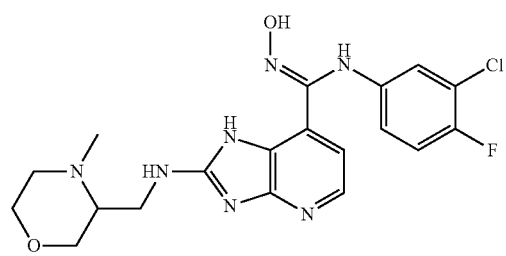 [SMILES: CN1CCOCC1CNc1nc2nccc(/C(=N/O)Nc3ccc(F)c(Cl)c3)c2[nH]1]

Example 282 was made analogously to Example 212 using (4-methylmorpholin-3-yl)methanamine in place of 2-methoxyethanamine. $C_{19}H_{21}ClFN_7O_2$. 434.2 (M+1). $^1$H NMR (400 MHz, DMSO-d6) δ 11.40 (s, 1H), 8.97 (s, 1H), 7.99 (d, J=6.3 Hz, 1H), 7.10 (t, J=9.0 Hz, 1H), 7.01 (dd, J=6.6, 2.6 Hz, 1H), 6.96 (d, J=6.2 Hz, 1H), 6.57 (ddd, J=9.0, 4.0, 2.7 Hz, 1H), 4.12-3.75 (m, 6H), 3.28-3.14 (m, 3H), 3.01 (s, 3H).

Example 283: N-(3-chloro-4-fluorophenyl)-N'-hydroxy-2-((2-(pyrrolidin-1-yl)ethyl)amino)-1H-imidazo[4,5-b]pyridine-7-carboximidamide

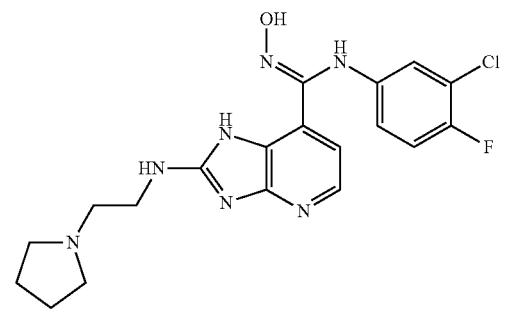 [SMILES: O/N=C(\Nc1ccc(F)c(Cl)c1)c1ccnc2nc(NCCN3CCCC3)[nH]c12]

Example 283 was made analogously to Example 212 using 2-(pyrrolidin-1-yl)ethan-1-amine in place of 2-methoxyethanamine. $C_{19}H_{21}ClFN_7O$. 418.2 (M+1). $^1$H NMR (400 MHz, DMSO-d6) δ 11.35 (s, 1H), 8.97 (s, 1H), 7.98 (d, J=6.2 Hz, 1H), 7.10 (t, J=9.0 Hz, 1H), 7.03-6.98 (m, 1H), 6.94 (d, J=6.1 Hz, 1H), 6.57 (ddd, J=9.1, 4.1, 2.8 Hz, 1H), 3.82-3.35 (m, 8H), 1.94 (s, 4H).

Example 284: N-(3-chloro-4-fluorophenyl)-N'-hydroxy-2-(((4-((methylsulfonyl)methyl)tetrahydro-2H-pyran-4-yl)methyl)amino)-1H-imidazo[4,5-b]pyridine-7-carboximidamide

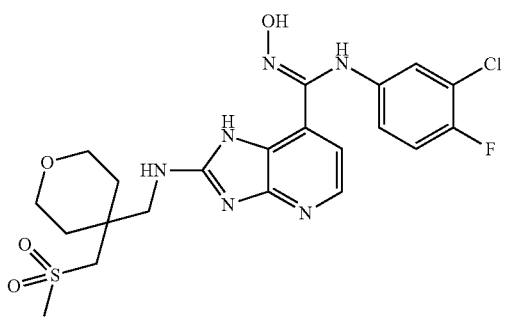 [SMILES: CS(=O)(=O)CC1(CNc2nc3nccc(/C(=N/O)Nc4ccc(F)c(Cl)c4)c3[nH]2)CCOCC1]

Example 284 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one, 2H-pyran-4-methanamine, tetrahydro-4-[(methylsulfonyl)methyl]-hydrochloride, and N,N-diisopropylethylamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate (bis-TFA salt, white solid). $C_{21}H_{24}ClFN_6O_4S$. 511.4 (M+1). $^1$H NMR (400 MHz, DMSO-$d_6$) δ 11.45 (s, 1H), 8.96 (s, 1H), 7.95 (d, J=6.4 Hz, 1H), 7.12 (t, J=9.0 Hz, 1H), 7.04 (dd, J=6.5, 2.7 Hz, 1H), 6.92 (d, J=6.4 Hz, 1H), 6.60 (ddd, J=8.9, 4.0, 2.8 Hz, 1H), 3.85 (d, J=6.6 Hz, 4H), 3.81-3.45 (m, 4H), 3.10 (s, 3H), 1.77-1.65 (m, 2H), 1.61 (dd, J=8.5, 4.6 Hz, 2H). $^{19}$F NMR (377 MHz, DMSO-$d_6$) δ -74.67 (6F), -126.62 (1F).

Example 285: N-(3-chloro-4-fluorophenyl)-N'-hydroxy-2-((2-(methylsulfonyl)benzyl)amino)-1H-imidazo[4,5-b]pyridine-7-carboximidamide

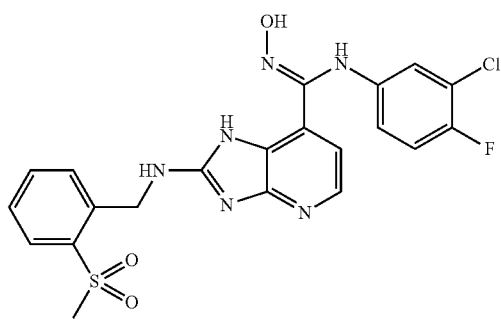 [SMILES: CS(=O)(=O)c1ccccc1CNc1nc2nccc(/C(=N/O)Nc3ccc(F)c(Cl)c3)c2[nH]1]

Example 285 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one, (2-methylsulfonylphenyl)methanamine hydrochloride, and N,N-diisopropylethylamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate (bis-TFA salt, white solid). $C_{21}H_{18}ClFN_6O_3S$. 489.4 (M+1). $^1$H NMR (400 MHz, DMSO-$d_6$) δ 11.88 (br s, 1H), 11.43 (s, 1H), 8.95 (s, 1H), 8.31 (br s, 1H), 8.03-7.91 (m, 2H), 7.75-7.67 (m, 1H), 7.66-7.56 (m, 2H), 7.09 (t, J=9.0 Hz, 1H), 7.03 (d, J=6.3 Hz, 1H), 6.93 (d, J=6.3 Hz, 1H), 6.59 (dt, J=8.9, 3.5 Hz, 1H), 5.06 (d, J=6.2 Hz, 2H), 3.39 (s, 3H). $^{19}$F NMR (376 MHz, DMSO-$d_6$) δ -74.4 (6F), -126.6 (1F).

Example 286: 2-((1-acetylpiperidin-3-yl)amino)-N-(3-chloro-4-fluorophenyl)-N'-hydroxy-1H-imidazo[4,5-b]pyridine-7-carboximidamide

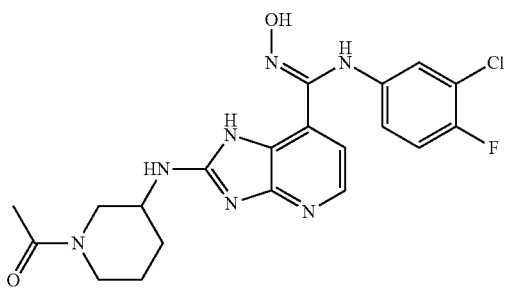 [SMILES: CC(=O)N1CCCC(Nc2nc3nccc(/C(=N/O)Nc4ccc(F)c(Cl)c4)c3[nH]2)C1]

Example 286 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 1-(3-aminopiperidin-1-yl)ethanone in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively (bis-TFA salt, off-white solid). $C_{20}H_{21}ClFN_7O_2$. 446.4 (M+1). $^1$H NMR (400 MHz, DMSO-$d_6$) δ 11.46 (s, 1H), 8.98 (s, 1H), 8.17 (br s, 1H), 7.98 (t, J=6.6 Hz, 1H), 7.11 (td, J=9.0, 4.1 Hz, 1H), 7.04 (td, J=6.7, 2.6 Hz, 1H), 6.92 (dd, J=8.6, 6.3 Hz, 1H), 6.66-6.51 (m, 1H), 4.06-3.70 (m, 3H), 3.30-3.20 (m, 3H), 2.01 (d, J=27.2 Hz, 3H), 1.98-1.95 (m, 1H) 1.80-1.60 (m, 2H), 1.59-1.41 (m, 1H). $^{19}$F NMR (376 MHz, DMSO-$d_6$) δ -74.53 (6F), -126.59 (1F).

Example 287: N-(3-chloro-4-fluorophenyl)-2-((ethylamino)methyl)-4-fluoro-N'-hydroxy-1H-benzo[d]imidazole-7-carboximidamide

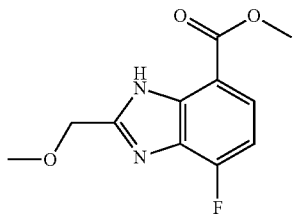

Methyl 4-fluoro-2-(methoxymethyl)-1H-benzo[d]imidazole-7-carboxylate was prepared analogously to Example 45, using methyl 2,3-diamino-4-fluorobenzoate in place of methyl 2,3-diamino-4,5-difluorobenzoate. $C_{11}H_{11}FN_2O_3$. 239.0 (M+1).

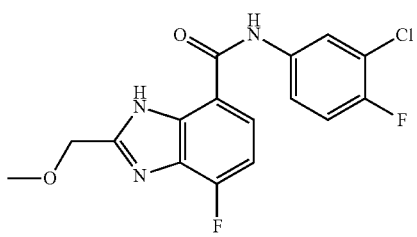 [SMILES: COCc1nc2c(F)ccc(C(=O)Nc3ccc(F)c(Cl)c3)c2[nH]1]

N-(3-chloro-4-fluorophenyl)-4-fluoro-2-(methoxymethyl)-1H-benzo[d]imidazole-7-carboxamide was prepared analogously to Example 45, using methyl 4-fluoro-2-(methoxymethyl)-1H-benzo[d]imidazole-7-carboxylate in place of methyl 4,5-difluoro-2-(methoxymethyl)-1H-benzo[d]imidazole-7-carboxylate. $C_{16}H_{12}ClF_2N_3O_2$. 352.0 (M+1).

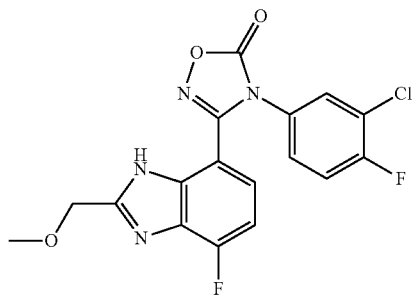 [SMILES: COCc1nc2c(F)ccc(-c3noc(=O)n3-c3ccc(F)c(Cl)c3)c2[nH]1]

4-(3-chloro-4-fluorophenyl)-3-(4-fluoro-2-(methoxymethyl)-1H-benzo[d]imidazol-7-yl)-1,2,4-oxadiazol-5(4H)-one was prepared analogously to Example 45, using N-(3-chloro-4-fluorophenyl)-4-fluoro-2-(methoxymethyl)-1H-benzo[d]imidazole-7-carboxamide in place of N-(3-chloro-4-fluorophenyl)-4,5-difluoro-2-(methoxymethyl)-1H-benzo[d]imidazole-7-carboxamide. $C_{17}H_{11}ClF_2N_4O_3$. 393.0 (M+1).

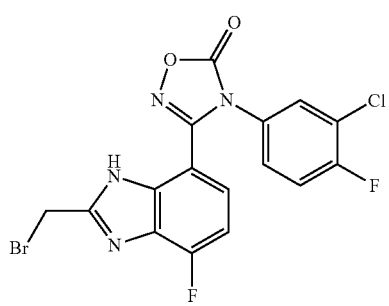 [SMILES: O=c1onc(-c2ccc(F)c3nc(CBr)[nH]c23)n1-c1ccc(F)c(Cl)c1]

3-(2-(bromomethyl)-4-fluoro-1H-benzo[d]imidazol-7-yl)-4-(3-chloro-4-fluorophenyl)-1,2,4-oxadiazol-5(4H)-one was prepared analogously to Example 45, using 4-(3-chloro-4-fluorophenyl)-3-(4-fluoro-2-(methoxymethyl)-1H-benzo[d]imidazol-7-yl)-1,2,4-oxadiazol-5(4H)-one in place of 4-(3-chloro-4-fluorophenyl)-3-(4,5-difluoro-2-(methoxymethyl)-1H-benzo[d]imidazol-7-yl)-1,2,4-oxadiazol-5(4H)-one. $C_{16}H_8BrClF_2N_4O_2$. 440.9/442.9 (M+1).

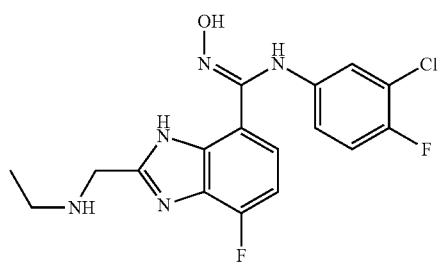 [SMILES: CCNCc1nc2c(F)ccc(/C(=N/O)Nc3ccc(F)c(Cl)c3)c2[nH]1]

N-(3-chloro-4-fluorophenyl)-2-((ethylamino)methyl)-4-fluoro-N'-hydroxy-1H-benzo[d]imidazole-7-carboximidamide. Example 287 was prepared analogously to Example 45 using 3-(2-(bromomethyl)-4-fluoro-1H-benzo[d]imidazol-7-yl)-4-(3-chloro-4-fluorophenyl)-1,2,4-oxadiazol-5(4H)-one and ethylamine (2 M in THF) in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{17}H_{16}ClF_2N_5O$. 360.1 (M+1).

Example 288: N-(3-chloro-4-fluorophenyl)-2-((dimethylamino)methyl)-4-fluoro-N'-hydroxy-1H-benzo[d]imidazole-7-carboximidamide

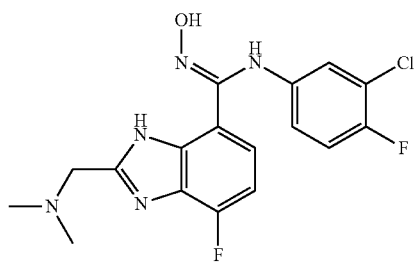 [SMILES: CN(C)Cc1nc2c(F)ccc(/C(=N/O)Nc3ccc(F)c(Cl)c3)c2[nH]1]

Example 288 was prepared analogously to Example 45 using 3-(2-(bromomethyl)-4-fluoro-1H-benzo[d]imidazol-7-yl)-4-(3-chloro-4-fluorophenyl)-1,2,4-oxadiazol-5(4H)-one and dimethylamine (2 M in THF) in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{17}H_{16}ClF_2N_5O$. 380.0 (M+1).

Example 289: N-(3-chloro-4-fluorophenyl)-4-fluoro-N'-hydroxy-2-((isopropylamino)methyl)-1H-benzo[d]imidazole-7-carboximidamide

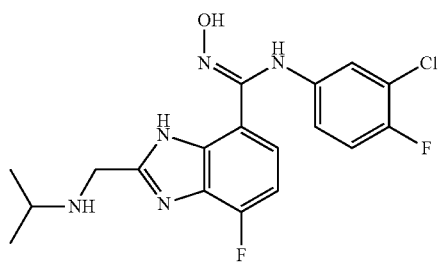 [SMILES: CC(C)NCc1nc2c(F)ccc(/C(=N/O)Nc3ccc(F)c(Cl)c3)c2[nH]1]

Example 289 was prepared analogously to Example 45 using 3-(2-(bromomethyl)-4-fluoro-1H-benzo[d]imidazol-7-yl)-4-(3-chloro-4-fluorophenyl)-1,2,4-oxadiazol-5(4H)-one and isopropylamine in place of 3-(2-(bromomethyl)-4,5-difluoro-1H-benzo[d]imidazol-7-yl)-4-(3-chloro-4-fluorophenyl)-1,2,4-oxadiazol-5 (4H)-one and 3-methoxypropylamine, respectively. $C_{18}H_{18}ClF_2N_5O$. 394.1 (M+1).

Example 290: N-(3-chloro-4-fluorophenyl)-4-fluoro-N'-hydroxy-2-((methylamino)methyl)-1H-benzo[d]imidazole-7-carboximidamide

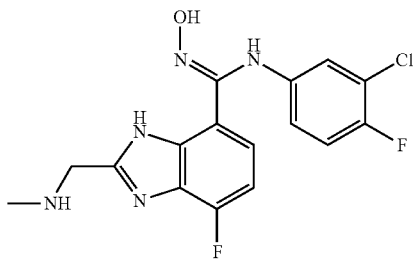 [SMILES: CNCc1nc2c(F)ccc(/C(=N/O)Nc3ccc(F)c(Cl)c3)c2[nH]1]

Example 290 was prepared analogously to Example 45 using 3-(2-(bromomethyl)-4-fluoro-1H-benzo[d]imidazol-7-yl)-4-(3-chloro-4-fluorophenyl)-1,2,4-oxadiazol-5(4H)-one and methylamine (2 M in THF) in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{16}H_{14}ClF_2N_5O$. 366.0 (M+1).

Example 291: 2-(aminomethyl)-N-(3-chloro-4-fluorophenyl)-4-fluoro-N'-hydroxy-1H-benzo[d]imidazole-7-carboximidamide

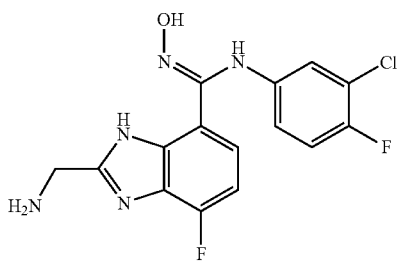 [SMILES: NCc1nc2c(F)ccc(/C(=N/O)Nc3ccc(F)c(Cl)c3)c2[nH]1]

Example 291 was prepared analogously to Example 45 using 3-(2-(bromomethyl)-4-fluoro-1H-benzo[d]imidazol-7-yl)-4-(3-chloro-4-fluorophenyl)-1,2,4-oxadiazol-5(4H)-one and ammonia (0.5 M in dioxane) in place of 3-(2-(bromomethyl)-4,5-difluoro-1H-benzo[d]imidazol-7-yl)-4-(3-chloro-4-fluorophenyl)-1,2,4-oxadiazol-5(4H)-one and 3-methoxypropylamine, respectively. $C_{15}H_{12}ClF_2N_5O$. 352.0 (M+1).

Example 292: N-(3-chloro-4-fluorophenyl)-4,5-difluoro-N'-hydroxy-2-((2-hydroxy-2-methylpropyl)amino)-1H-benzo[d]imidazole-7-carboximidamide

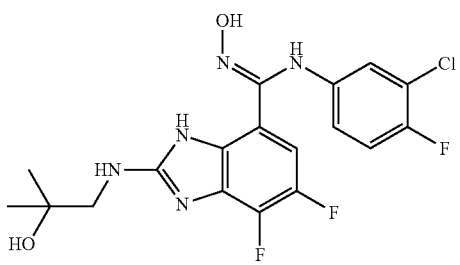 [SMILES: CC(C)(O)CNc1nc2c(F)c(F)cc(/C(=N/O)Nc3ccc(F)c(Cl)c3)c2[nH]1]

Example 292 was prepared analogously to Example 333 using 1-amino-2-methylpropan-2-ol in place of tert-butyl (2-aminoethyl)carbamate. $C_{18}H_{17}ClF_3N_5O_2$. 428.1 (M+1).

Example 293: N-(3-chloro-4-fluorophenyl)-4,5-difluoro-N'-hydroxy-2-((2-hydroxypropyl)amino)-1H-benzo[d]imidazole-7-carboximidamide

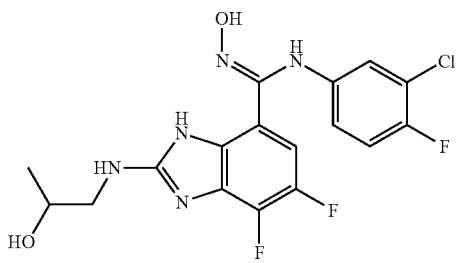 [SMILES: CC(O)CNc1nc2c(F)c(F)cc(/C(=N/O)Nc3ccc(F)c(Cl)c3)c2[nH]1]

Example 293 was prepared analogously to Example 333 using 1-aminopropan-2-ol in place of tert-butyl (2-aminoethyl)carbamate. $C_{17}H_{15}ClF_3N_5O_2$. 414.1 (M+1).

Example 294: 2-((7-(N-(3-chloro-4-fluorophenyl)-N'-hydroxycarbamimidoyl)-4,5-difluoro-1H-benzo[d]imidazol-2-yl)amino)acetamide

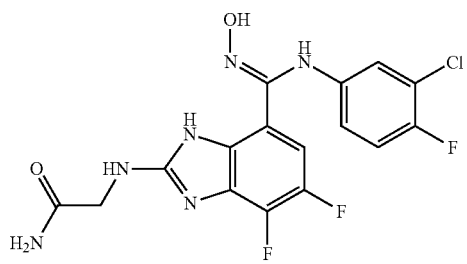 [SMILES: NC(=O)CNc1nc2c(F)c(F)cc(/C(=N/O)Nc3ccc(F)c(Cl)c3)c2[nH]1]

Example 294 was prepared analogously to Example 333 using 2-aminoacetamide in place of tert-butyl (2-aminoethyl)carbamate. $C_{16}H_{12}ClF_3N_6O_2$. 413.3 (M+1).

Example 295: N-(3-chloro-4-fluorophenyl)-4,5-difluoro-N'-hydroxy-2-((2-hydroxyethyl)amino)-1H-benzo[d]imidazole-7-carboximidamide

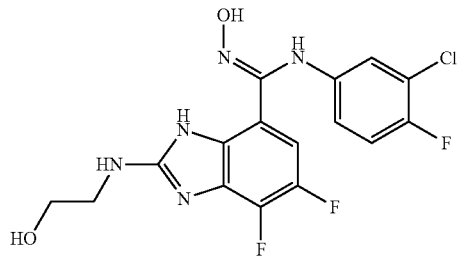 [SMILES: OCCNc1nc2c(F)c(F)cc(/C(=N/O)Nc3ccc(F)c(Cl)c3)c2[nH]1]

Example 295 was prepared analogously to Example 333 using 2-aminoethan-1-ol in place of tert-butyl (2-aminoethyl)carbamate. $C_{16}H_{13}ClF_3N_5O_2$. 400.1 (M+1).

Example 296: N-(3-chloro-4-fluorophenyl)-4,5-difluoro-N'-hydroxy-2-((3-hydroxycyclobutyl)amino)-1H-benzo[d]imidazole-7-carboximidamide

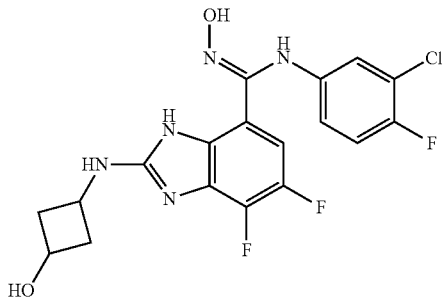 [SMILES: O/N=C(\Nc1ccc(F)c(Cl)c1)c1cc(F)c(F)c2nc(NC3CC(O)C3)[nH]c12]

Example 296 was prepared analogously to Example 333 using 3-aminocyclobutanol in place of tert-butyl (2-aminoethyl)carbamate. $C_{18}H_{15}ClF_3N_5O_2$. 426.3 (M+1).

Example 297: N-(3-chloro-4-fluorophenyl)-4,5-difluoro-N'-hydroxy-2-((3-(pyridin-2-ylamino)propyl)amino)-1H-benzo[d]imidazole-7-carboximidamide

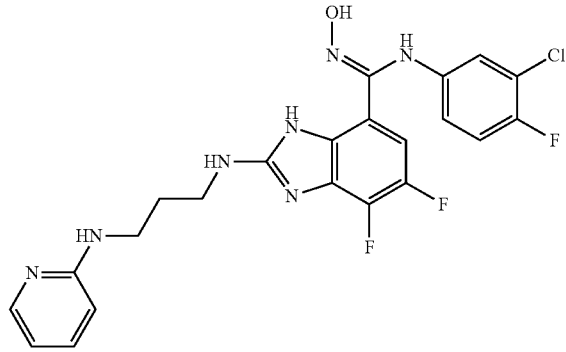 [SMILES: O/N=C(\Nc1ccc(F)c(Cl)c1)c1cc(F)c(F)c2nc(NCCCNc3ccccn3)[nH]c12]

Example 297 was prepared analogously to Example 333 using N-(3-aminopropyl)pyridine-2-amine in place of tert-butyl (2-aminoethyl)carbamate. $C_{22}H_{19}ClF_3N_7O$. 490.3 (M+1).

Example 298: N-(3-chloro-4-fluorophenyl)-4,5-difluoro-N'-hydroxy-2-((2-sulfamoylethyl)amino)-1H-benzo[d]imidazole-7-carboximidamide

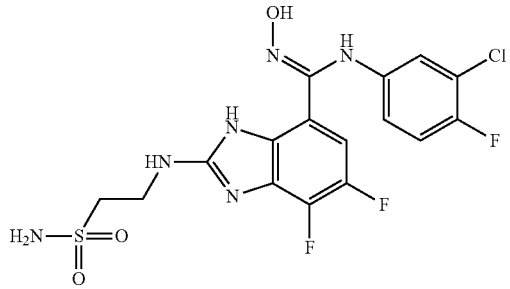 [SMILES: NS(=O)(=O)CCNc1nc2c(F)c(F)cc(/C(=N/O)Nc3ccc(F)c(Cl)c3)c2[nH]1]

Example 298 was prepared analogously to Example 333 using 2-aminoethanesulfonamide in place of tert-butyl (2-aminoethyl)carbamate. $C_{16}H_{14}ClF_3N_6O_3S$. 463.1 (M+1).

Example 299: N-(3-chloro-4-fluorophenyl)-4,5-difluoro-N'-hydroxy-2-(((1-methyl-1H-pyrazol-5-yl)methyl)amino)-1H-benzo[d]imidazole-7-carboximidamide

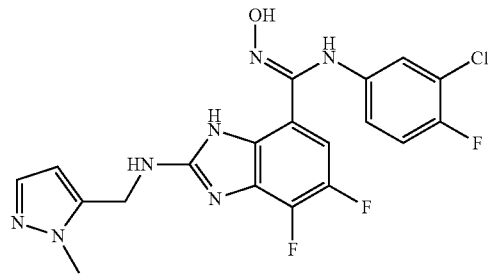 [SMILES: Cn1nccc1CNc1nc2c(F)c(F)cc(/C(=N/O)Nc3ccc(F)c(Cl)c3)c2[nH]1]

Example 299 was prepared analogously to Example 333 using (1-methyl-1H-pyrazol-5-yl)methanamine in place of tert-butyl (2-aminoethyl)carbamate. $C_{19}H_{15}ClF_3N_7O$. 450.1 (M+1).

Example 300: 2-((2-(1H-pyrazol-1-yl)ethyl)amino)-N-(3-chloro-4-fluorophenyl)-4,5-difluoro-N'-hydroxy-1H-benzo[d]imidazole-7-carboximidamide

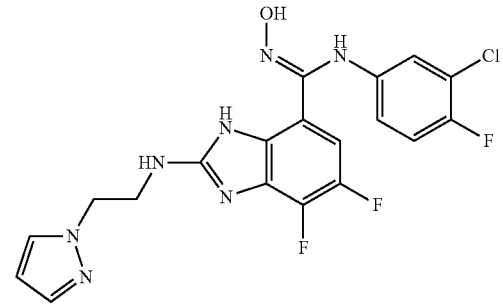 [SMILES: O/N=C(\Nc1ccc(F)c(Cl)c1)c1cc(F)c(F)c2nc(NCCn3cccn3)[nH]c12]

Example 300 was prepared analogously to Example 333 using 2-(1H-pyrazol-1-yl)ethan-1-amine in place of tert-butyl (2-aminoethyl)carbamate. $C_{19}H_{15}ClF_3N_7O$. 450.1 (M+1).

Example 301: 2-((7-(N-(3-chloro-4-fluorophenyl)-N'-hydroxycarbamimidoyl)-4,5-difluoro-1H-benzo[d]imidazol-2-yl)amino)-N,N-dimethylacetamide

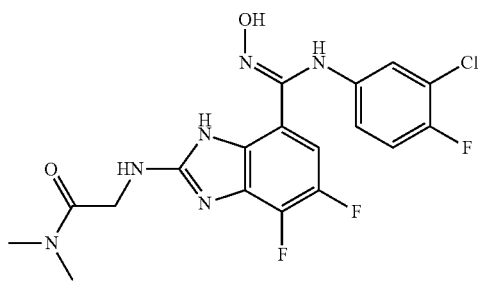 [SMILES: CN(C)C(=O)CNc1nc2c(F)c(F)cc(/C(=N/O)Nc3ccc(F)c(Cl)c3)c2[nH]1]

Example 301 was prepared analogously to Example 333 using glycine dimethylamide in place of tert-butyl (2-aminoethyl)carbamate. $C_{15}H_{16}ClF_3N_6O_2$. 441.1 (M+1).

Example 302: N-(3-chloro-4-fluorophenyl)-4,5-difluoro-N'-hydroxy-2-(2-hydroxy-2-methylpropyl)-1H-benzo[d]imidazole-7-carboximidamide

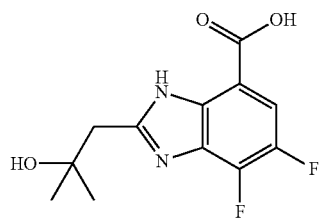 [SMILES: CC(C)(O)Cc1nc2c(F)c(F)cc(C(=O)O)c2[nH]1]

4,5-difluoro-2-(2-hydroxy-2-methylpropyl)-1H-benzo[d]imidazole-7-carboxylic acid. A mixture of 3-hydroxy-3-methylbutyric acid (1.6 mL, 15.1 mmol) and methyl 2,3-diamino-4,5-difluorobenzoate (1.529 g, 7.56 mmol) in HCl (7.5 mL of a 6 M aqueous soln) stirred at 120° C. in a sealed tube for 16 h. The mixture was cooled to rt and concentrated to remove HCl. The remaining solution was frozen and lyophilized to give the crude desired product. $C_{12}H_{12}F_2N_2O_3$. 271.1 (M+1).

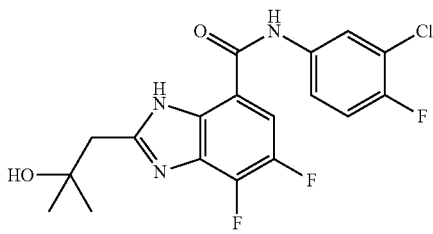 [SMILES: CC(C)(O)Cc1nc2c(F)c(F)cc(C(=O)Nc3ccc(F)c(Cl)c3)c2[nH]1]

N-(3-chloro-4-fluorophenyl)-4,5-difluoro-2-(2-hydroxy-2-methylpropyl)-1H-benzo[d]imidazole-7-carboxamide was prepared analogously to Example 80 using 4,5-difluoro-2-(2-hydroxy-2-methylpropyl)-1H-benzo[d]imidazole-7-carboxylic acid and 3-chloro-4-fluoroaniline in place of 1H imidazo[4,5-b]pyridine-7-carboxylic acid and 3-bromoaniline, respectively. $C_{18}H_{15}ClF_3N_3O_2$. 420.1 (M+23).

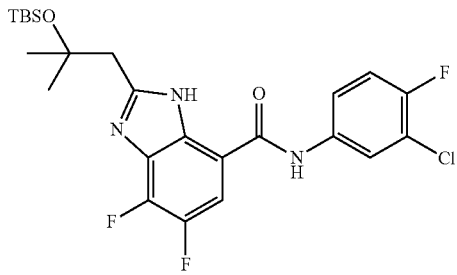 [SMILES: CC(C)(Cc1nc2c(F)c(F)cc(C(=O)Nc3ccc(F)c(Cl)c3)c2[nH]1)O[Si](C)(C)C(C)(C)C]

2-(2-((tert-butyldimethylsilyl)oxy)-2-methylpropyl)-N-(3-chloro-4-fluorophenyl)-4,5-difluoro-1H-benzo[d]imidazole-7-carboxamide. To a solution of N-(3-chloro-4-fluorophenyl)-4,5-difluoro-2-(2-hydroxy-2-methylpropyl)-1H-benzo[d]imidazole-7-carboxamide (0.145 g, 0.365 mmol) and 2,6-lutidine (0.34 mL, 2.9 mmol) in DCM (7 mL) at 0° C. was added tert-butyldimethylsilyl trifluoromethanesulfonate (0.17 mL, 0.740 mmol). The mixture warmed to rt and stirred 48 h. 2,6-Lutidine (0.34 mL, 2.9 mmol) and tert-butyldimethylsilyl trifluoromethanesulfonate (0.34 mL, 1.48 mmol) were added. After 4 h, 2,6-lutidine (0.34 mL, 2.9 mmol) and tert-butyldimethylsilyl trifluoromethanesulfonate (0.34 mL, 1.48 mmol) were added and the mixture stirred 4 h. The mixture was concentrated onto silica gel and purified via silica gel chromatography to give the desired product. $C_{24}H_{29}ClF_3N_3O_2Si$. 512.2 (M+1).

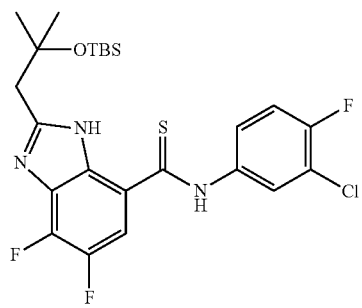 [SMILES: CC(C)(Cc1nc2c(F)c(F)cc(C(=S)Nc3ccc(F)c(Cl)c3)c2[nH]1)O[Si](C)(C)C(C)(C)C]

2-(2-((tert-butyldimethylsilyl)oxy)-2-methylpropyl)-N-(3-chloro-4-fluorophenyl)-4,5-difluoro-1H-benzo[d]imidazole-7-carbothioamide was prepared analogously to Example 13, using 2-(2-((tert-butyldimethylsilyl)oxy)-2-methylpropyl)-N-(3-chloro-4-fluorophenyl)-4,5-difluoro-1H-benzo[d]imidazole-7-carboxamide in place of 2-amino-N-(3-chloro-4-fluorophenyl)-4,5-difluoro-1H-benzo[d]imidazole-7-carboxamide. $C_{24}H_{29}ClF_3N_3OSSi$. 528.3 (M+1).

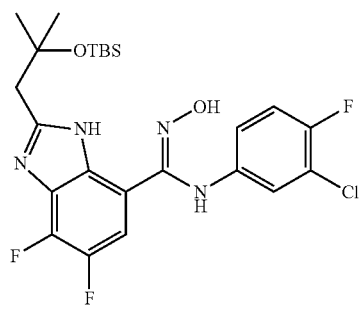 [SMILES: CC(C)(Cc1nc2c(F)c(F)cc(/C(=N/O)Nc3ccc(F)c(Cl)c3)c2[nH]1)O[Si](C)(C)C(C)(C)C]

2-(2-((tert-butyldimethylsilyl)oxy)-2-methylpropyl)-N-(3-chloro-4-fluorophenyl)-4,5-difluoro-N'-hydroxy-1H-benzo[d]imidazole-7-carboximidamide was prepared analogously to Example 13, using 2-(2-((tert-butyldimethylsilyl)oxy)-2-methylpropyl)-N-(3-chloro-4-fluorophenyl)-4,5-difluoro-1H-benzo[d]imidazole-7-carbothioamide in place of 2-amino-N-(3-chloro-4-fluorophenyl)-4,5-difluoro-1H-benzo[d]imidazole-7-carbothioamide. $C_{24}H_{30}ClF_3N_4O_2Si$. 527.3 (M+1).

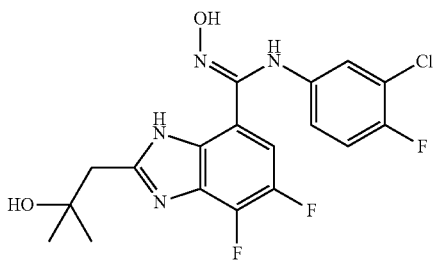 [SMILES: CC(C)(O)Cc1nc2c(F)c(F)cc(/C(=N/O)Nc3ccc(F)c(Cl)c3)c2[nH]1]

N-(3-chloro-4-fluorophenyl)-4,5-difluoro-N'-hydroxy-2-(2-hydroxy-2-methylpropyl)-1H-benzo[d]imidazole-7-carboximidamide. To a soln of 2-(2-((tert-butyldimethylsilyl)oxy)-2-methylpropyl)-N-(3-chloro-4-fluorophenyl)-4,5-difluoro-N'-hydroxy-M-benzo[d]imidazole-7-carboximidamide (0.007 g, 0.013 mmol) in THF (1 mL) at 0° C. was added HF.pyridine (0.02 mL, 0.664 mmol). Mixture warmed to rt and stirred 16 h. HF.pyridine (0.04 mL, 1.32 mmol) was added and mixture stirred an additional 24 h. The mixture was diluted with EtOAc and washed with sat $NaHCO_3$ soln. The aqueous layer was extracted with EtOAc. The combined organic layers were washed with brine and concentrated. The residue was purified by silica gel chromatography to give the desired product (0.001 g). $C_{18}H_{16}ClF_3N_4O_2$. 413.1 (M+H).

Example 303: N-(3-chloro-4-fluorophenyl)-2-((4-(dimethylamino)butyl)amino)-4,5-difluoro-N'-hydroxy-1H-benzo[d]imidazole-7-carboximidamide

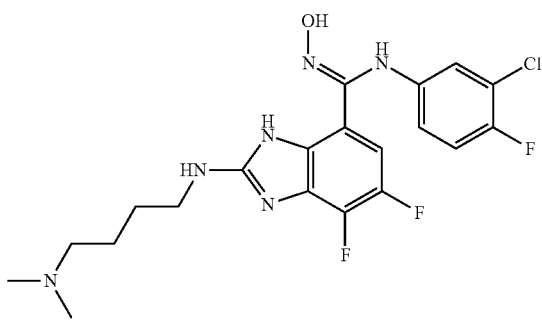 [SMILES: CN(C)CCCCNc1nc2c(F)c(F)cc(/C(=N/O)Nc3ccc(F)c(Cl)c3)c2[nH]1]

Example 303 was prepared analogously to Example 333 using 4-dimethylaminobutan-1-amine in place of tert-butyl (2-aminoethyl)carbamate. $C_{20}H_{22}ClF_3N_6O$. 455.2 (M+H).

Example 304: N-(3-chloro-4-fluorophenyl)-4,5-difluoro-N'-hydroxy-2-((piperidin-3-ylmethyl)amino)-1H-benzo[d]imidazole-7-carboximidamide

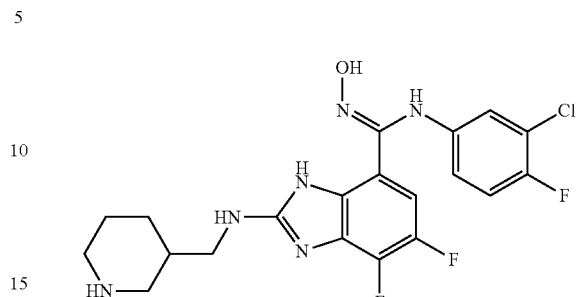

Example 304 was prepared analogously to Example 333 using 1-Boc-3-(aminomethyl)piperidine in place of tert-butyl (2-aminoethyl)carbamate. $C_{20}H_{20}ClF_3N_6O$. 453.2 (M+H).

Example 305: N-(3-chloro-4-fluorophenyl)-N'-hydroxy-2-((1-methylpiperidin-2-yl)methyl)-1H-imidazo[4,5-b]pyridine-7-carboximidamide

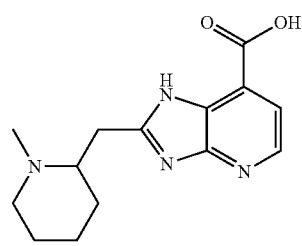 [SMILES: CN1CCCCC1Cc1nc2nccc(C(=O)O)c2[nH]1]

2-((1-methylpiperidin-2-yl)methyl)-1H-imidazo[4,5-b]pyridine-7-carboxylic acid. A suspension of 2,3-diaminoisonicotinic acid hydrochloride (200 mg, 0.106 mmol) and 2-(1-methylpiperidin-2-yl)acetic acid (498 mg, 0.317 mmol) in sulfuric acid (1.5 mL) was stirred at room temperature for 5 min and, then, was sealed in a vial and stirred at 160° C. for 3 hours. Once the mixture had cooled, water (2 mL) was added and the solution was purified by preparative HPLC to give the desired product. $C_{14}H_{18}N_4O_2$. 275.1 (M+1).

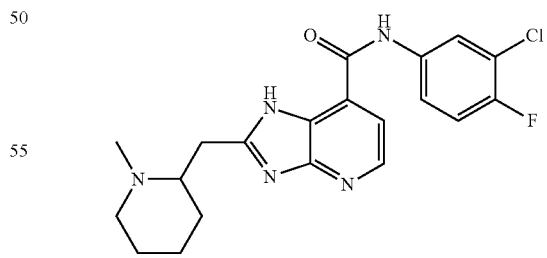

N-(3-chloro-4-fluorophenyl)-2-((1-methylpiperidin-2-yl)methyl)-1H-imidazo[4,5-b]pyridine-7-carboxamide. A solution of 2-((1-methylpiperidin-2-yl)methyl)-1H-imidazo[4,5-b]pyridine-7-carboxylic acid (75 mg, 0.273 mmol), 4-fluoro-3-chloroaniline (60 mg, 0.410 mmol), bis(2-oxo-3-oxazolidinyl)phosphinic chloride (139 mg, 0.547 mmol) and N,N-diisopropylethylamine (0.240 ml, 1.37 mmol) in dichloromethane (1.5 mL) was stirred for 3 hours. The reaction mixture was concentrated and purified by preparative HPLC. The resulting lyophilized material was mixed with saturated aqueous sodium bicarbonate (5 mL), filtered, washed with water and dried on high vacuum to give the desired product. $C_{20}H_{21}ClFN_5O$. 402.1 (M+1).

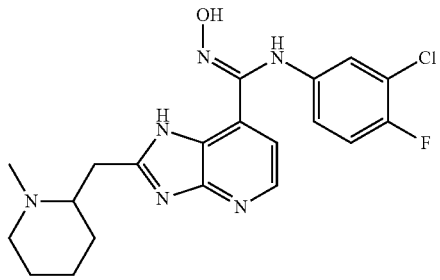 [SMILES: CN1CCCCC1Cc1nc2nccc(/C(=N/O)Nc3ccc(F)c(Cl)c3)c2[nH]1]

N-(3-chloro-4-fluorophenyl)-N'-hydroxy-2-((1-methylpiperidin-2-yl)methyl)-1H-imidazo[4,5-b]pyridine-7-carboximidamide. To a mixture of N-(3-chloro-4-fluorophenyl)-2-((1-methylpiperidin-2-yl)methyl)-1H-imidazo[4,5-b]pyridine-7-carboxamide (11 mg, 0.027 mmol) and potassium carbonate (26 mg, 0.192 mmol) in dichloromethane (0.5 ml) was added phosphorous pentachloride (11 mg, 0.055 mmol). The reaction mixture stirred for 2 hours and was concentrated. The residue was brought up in ethanol (0.5 ml) and hydroxylamine (0.07 mL, 50% in water, 1.08 mmol) and stirred for 1 hour. The reaction mixture was concentrated and purified by preparative HPLC to give the desired product. $C_{20}H_{22}ClFN_6O$. 417.1 (M+1).

Example 306: N-(3-bromophenyl)-N'-hydroxy-2-((2-morpholinoethyl)amino)-1H-imidazo[4,5-b]pyridine-7-carboximidamide

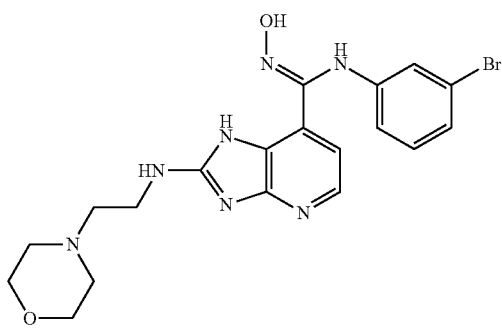 [SMILES: O/N=C(\Nc1cccc(Br)c1)c1ccnc2nc(NCCN3CCOCC3)[nH]c12]

Example 306 was prepared analogously to Example 333 using 4-(3-bromophenyl)-3-(2-chloro-1-((2-(trimethylsilyl)ethoxy)methyl)-1H-imidazo[4,5-b]pyridin-7-yl)-1,2,4-oxadiazol-5(4H)-one and 2-morpholinoethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. $C_{19}H_{22}BrN_7O_2$. 460.2/462.1 (M+H). $^1$H NMR (400 MHz, DMSO-d6) δ 11.35 (s, 1H), 8.94 (s, 1H), 7.98 (d, J=6.1 Hz, 1H), 7.09-6.95 (m, 3H), 6.93 (d, J=5.9 Hz, 1H), 6.61-6.50 (m, 1H), 3.95-3.20 (m, 12H).

Example 307: N-(3-chloro-4-fluorophenyl)-5-fluoro-N'-hydroxy-4-methoxy-1H-benzo[d]imidazole-7-carboximidamide

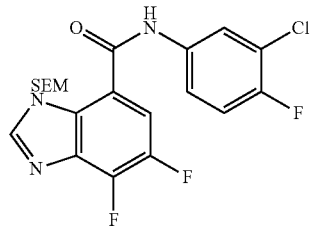 [SMILES: C[Si](C)(C)CCOCn1cnc2c(F)c(F)cc(C(=O)Nc3ccc(F)c(Cl)c3)c21]

N-(3-chloro-4-fluorophenyl)-4,5-difluoro-1-((2-(trimethylsilyl)ethoxy)methyl)-1H-benzo[d]imidazole-7-carboxamide. To a solution of N-(3-chloro-4-fluorophenyl)-4,5-difluoro-1H-benzo[d]imidazole-7-carboxamide (1.92 g, 5.89 mmol) and TEA (3.3 mL, 23.6 mmol) in DCM (60 mL) was added SEMCl (2.6 mL, 14.7 mmol). After 45 min, TEA (1.1 mL, 7.9 mmol) and SEMCl (0.9 mL, 4.9 mmol) were added. After 20 min, the mixture was diluted with EtOAc, concentrated onto silica gel, and purified via silica gel chromatography to give the desired product. $C_{20}H_{21}ClF_3N_3O_2Si$. 456.2 (M+1).

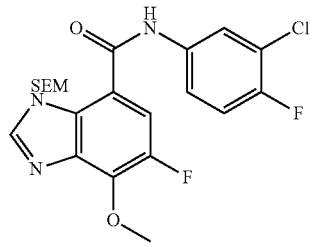 [SMILES: COc1c(F)cc(C(=O)Nc2ccc(F)c(Cl)c2)c2c1ncn2COCC[Si](C)(C)C]

N-(3-chloro-4-fluorophenyl)-5-fluoro-4-methoxy-1-((2-(trimethylsilyl)ethoxy)methyl)-1H-benzo[d]imidazole-7-carboxamide. A mixture of N-(3-chloro-4-fluorophenyl)-4,5-difluoro-1-((2-(trimethylsilyl)ethoxy)methyl)-1H-benzo[d]imidazole-7-carboxamide (0.250 g, 0.548 mmol) and sodium methoxide (0.50 mL of a 25% soln in MeOH, 2.19 mmol) in MeOH (1 mL) was stirred at 65° C. for 8 h. Mixture was cooled to rt and diluted with sat. NH$_4$Cl soln. The aqueous layer was extracted 3× with EtOAc. The combined organic layers were washed with brine, dried (Na$_2$SO$_4$), filtered and concentrated to give the desired product. $C_{21}H_{24}ClF_2N_3O_3Si$. 468.3 (M+1).

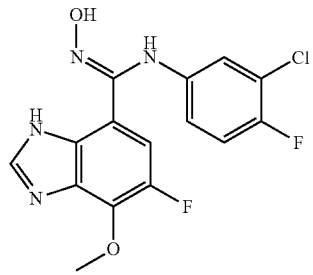 [SMILES: COc1c(F)cc(/C(=N/O)Nc2ccc(F)c(Cl)c2)c2[nH]cnc12]

N-(3-chloro-4-fluorophenyl)-5-fluoro-N'-hydroxy-4-methoxy-1H-benzo[d]imidazole-7-carboximidamide was prepared analogously to Example 305 using N-(3-chloro-4-fluorophenyl)-5-fluoro-4-methoxy-1-((2-(trimethylsilyl)ethoxy)methyl)-1H-benzo[d]imidazole-7-carboxamide in place of N-(3-chloro-4-fluorophenyl)-2-((1-methylpiperidin-2-yl)methyl)-1H-imidazo[4,5-b]pyridine-7-carboxamide. C$_{15}$H$_{11}$ClF$_2$N$_4$O$_2$. 353.1 (M+H).

Example 308: N-(3-chloro-4-fluorophenyl)-N'-hydroxy-2-((pyridin-2-ylmethyl)amino)-1H-imidazo[4,5-b]pyridine-7-carboximidamide

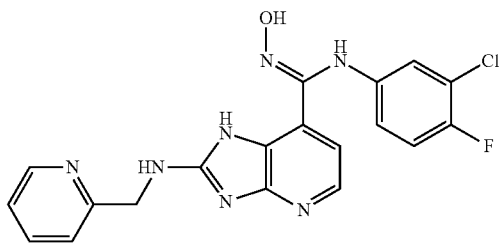 [SMILES: O/N=C(\Nc1ccc(F)c(Cl)c1)c1ccnc2nc(NCc3ccccn3)[nH]c12]

Example 308 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-picolylamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. C$_{19}$H$_{15}$ClFN$_7$O. 412.2 (M+H). $^1$H NMR (400 MHz, DMSO-d6) δ 11.48 (s, 1H), 8.99 (s, 1H), 8.59 (ddd, J=4.9, 1.8, 0.9 Hz, 1H), 7.98 (d, J=6.4 Hz, 1H), 7.84 (td, J=7.7, 1.8 Hz, 1H), 7.42 (d, J=7.9 Hz, 1H), 7.36 (ddd, J=7.4, 5.0, 1.1 Hz, 1H), 7.11 (t, J=9.0 Hz, 1H), 7.05 (dd, J=6.5, 2.7 Hz, 1H), 6.95 (d, J=6.3 Hz, 1H), 6.60 (ddd, J=9.0, 3.9, 3.0 Hz, 1H), 4.80 (d, J=5.7 Hz, 2H).

Example 309: 2-((2-(1H-pyrazol-1-yl)ethyl)amino)-N-(3-chloro-4-fluorophenyl)-N'-hydroxy-1H-imidazo[4,5-b]pyridine-7-carboximidamide

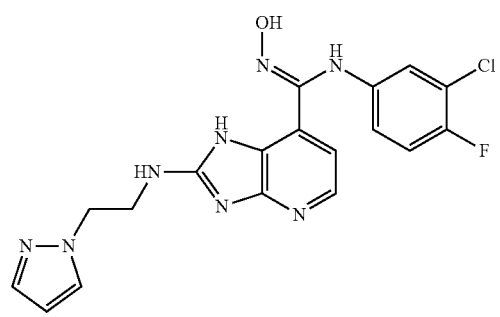 [SMILES: O/N=C(\Nc1ccc(F)c(Cl)c1)c1ccnc2nc(NCCn3cccn3)[nH]c12]

Example 309 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(1H-pyrazol-1-yl)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and ter t-butyl (2-aminoethyl)carbamate, respectively. C$_{18}$H$_{16}$ClFN$_8$O. 415.2 (M+H).

Example 310: N-(3-chloro-4-fluorophenyl)-N'-hydroxy-2-(((1-methyl-1H-pyrazol-3-yl)methyl)amino)-1H-imidazo[4,5-b]pyridine-7-carboximidamide

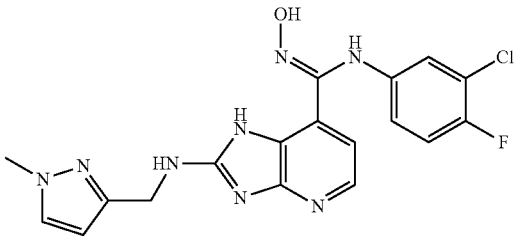 [SMILES: Cn1ccc(CNc2nc3nccc(/C(=N/O)Nc4ccc(F)c(Cl)c4)c3[nH]2)n1]

Example 310 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (1-methyl-1H-pyrazol-3-yl)methanamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. C$_{18}$H$_{16}$ClFN$_8$O. 415.2 (M+H).

Example 311: N-(3-chloro-4-fluorophenyl)-N'-hydroxy-2-((4,4,4-trifluorobutyl)amino)-1H-imidazo[4,5-b]pyridine-7-carboximidamide

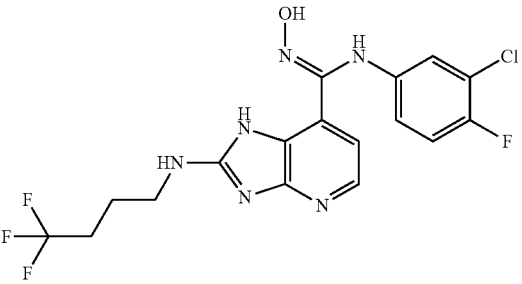 [SMILES: O/N=C(\Nc1ccc(F)c(Cl)c1)c1ccnc2nc(NCCCC(F)(F)F)[nH]c12]

Example 311 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 4,4,4-trifluorobutylamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. C$_{17}$H$_{15}$ClF$_4$N$_6$O. 431.1 (M+H).

Example 312: N-(3-chloro-4-fluorophenyl)-N'-hydroxy-2-((3,3,3-trifluoropropyl)amino)-1H-imidazo[4,5-b]pyridine-7-carboximidamide

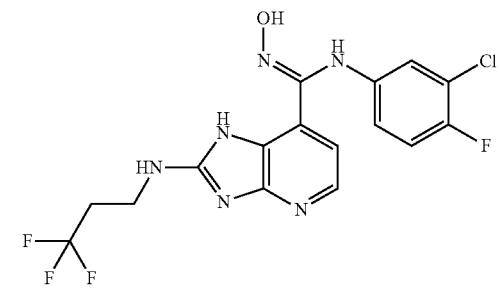 [SMILES: O/N=C(\Nc1ccc(F)c(Cl)c1)c1ccnc2nc(NCCC(F)(F)F)[nH]c12]

Example 312 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 3,3,3-trifluoropropylamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. $C_{16}H_{13}ClF_4N_6O$. 417.1 (M+H). $^1$H NMR (400 MHz, DMSO-d6) δ 11.42 (s, 1H), 8.98 (s, 1H), 7.97 (d, J=6.2 Hz, 1H), 7.10 (t, J=9.0 Hz, 1H), 7.03 (dd, J=6.3, 2.4 Hz, 1H), 6.94 (d, J=6.3 Hz, 1H), 6.58 (ddd, J=9.0, 4.0, 3.0 Hz, 1H), 3.78-3.63 (m, 2H), 2.76-2.56 (m, 2H).

Example 313: N-(3-chloro-4-fluorophenyl)-N'-hydroxy-2-((2-(2-methoxyethoxy)ethyl)amino)-1H-imidazo[4,5-b]pyridine-7-carboximidamide

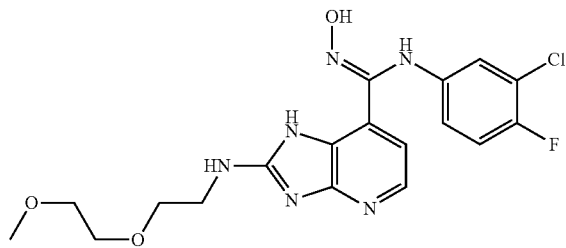 [SMILES: COCCOCCNc1nc2nccc(/C(=N/O)Nc3ccc(F)c(Cl)c3)c2[nH]1]

Example 313 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(2-methoxyethoxy)ethanamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. $C_{18}H_{20}ClFN_6O_3$. 423.2 (M+H).

Example 314: N-(3-chloro-4-fluorophenyl)-2-((3-(cyclopropyl(methyl)amino)propyl)amino)-N'-hydroxy-1H-imidazo[4,5-b]pyridine-7-carboximidamide

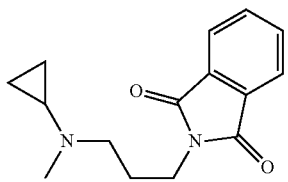 [SMILES: CN(CCCN1C(=O)c2ccccc2C1=O)C1CC1]

2-(3-(cyclopropyl(methyl)amino)propyl)isoindoline-1,3-dione. A solution of 2-(3-bromopropyl)isoindoline-1,3-dione (1.89 g, 7.03 mmol), cyclopropylmethylamine (0.59 mL, 7.03 mmol), and potassium carbonate (1.94 g, 14 mmol) in dimethylformamide (7 mL) was stirred at 40° C. for 6 hr. Water was added and the aqueous layer was washed three times with diethyl ether. The combined organic layers were washed with brine and dried over magnesium sulfate, filtered and concentrated. The residue was purified by silica gel chromatography to give the desired product (1.8 g). $C_{15}H_{18}N_2O_2$. 259.2 (M+1).

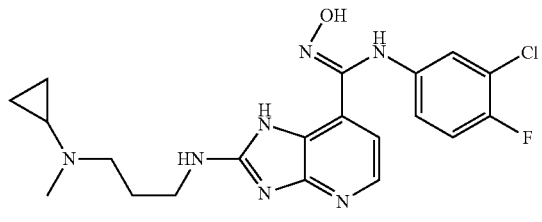 [SMILES: CN(CCCNc1nc2nccc(/C(=N/O)Nc3ccc(F)c(Cl)c3)c2[nH]1)C1CC1]

N-(3-chloro-4-fluorophenyl)-2-((3-(cyclopropyl(methyl)amino)propyl)amino)-N'-hydroxy-1H-imidazo[4,5-b]pyridine-7-carboximidamide. A solution of 2-(3-(cyclopropyl(methyl)amino)propyl)isoindoline-1,3-dione (63 mg, 0.24 mmol) and hydrazine (0.006 mL, 0.2 mmol) in ethanol (1 mL) was stirred at 80° C. for one hour. The reaction was cooled to room temperature, filtered and concentrated. To the resulting residue was added 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one (24 mg, 0.024 mmol), and dimethylsulfoxide (0.25 mL). The resulting solution was stirred at 65° C. for one hour. The reaction mixture was cooled and diluted with ethyl acetate and washed three times with saturated aqueous sodium chloride. The organic layer was dried over sodium sulfate, filtered and concentrated. The resulting residue was brought up in dichloromethane (0.5 mL) and trifluoroacetic acid (0.5 mL) and stirred for 3 hours. The reaction solution was concentrated. The resulting residue was brought up in tetrahydrofuran (0.2 mL) and methanol (0.2 mL) and to this solution was added 2 N sodium hydroxide (0.24 mL, 0.48 mmol). The resulting solution was stirred for 30 min and concentrated and purified by preparative HPLC to give the desired product (9 mg). $C_{20}H_{23}ClFN_7O$. 432.2 (M+1). $^1$H NMR (400 MHz, DMSO-d6) δ 11.34 (s, 1H), 8.95 (s, 1H), 7.96 (d, J=6.2 Hz, 1H), 7.09 (t, J=9.0 Hz, 1H), 7.00 (d, J=5.6 Hz, 1H), 6.92 (d, J=6.1 Hz, 1H), 6.61-6.53 (m, 1H), 3.54-3.42 (m, 2H), 3.30-3.19 (m, 3H), 2.92-2.77 (m, 5H), 2.05-1.92 (m, 3H), 0.96-0.78 (m, 6H).

Example 315: N-(3-chloro-4-fluorophenyl)-2-((3-(cyclopropylamino)propyl)amino)-N'-hydroxy-1H-imidazo[4,5-b]pyridine-7-carboximidamide

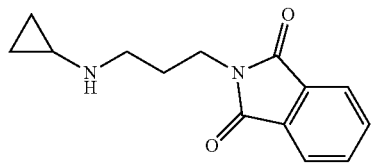 [SMILES: O=C1c2ccccc2C(=O)N1CCCNC1CC1]

2-(3-(cyclopropylamino)propyl)isoindoline-1,3-dione was prepared analogously to Example 314 using cyclopropylamine in place of cyclopropylmethylamine. $C_{14}H_{16}N_2O_2$. 245.1 (M+1).

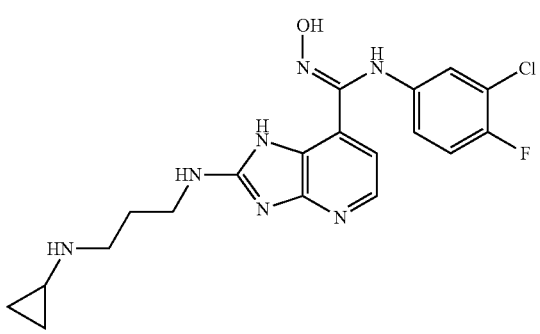 [SMILES: O/N=C(\Nc1ccc(F)c(Cl)c1)c1ccnc2nc(NCCCNC3CC3)[nH]c12]

N-(3-chloro-4-fluorophenyl)-2-((3-(cyclopropylamino)propyl)amino)-N'-hydroxy-1H-imidazo[4,5-b]pyridine-7-carboximidamide was prepared analogously to Example 314 using 2-(3-(cyclopropylamino)propyl)isoindoline-1,3-dione in place of 2-(3-(cyclopropyl(methyl)amino)propyl)isoindoline-1,3-dione. $C_{19}H_{21}ClFN_7O$. 418.2 (M+H).

Example 316: N-(3-chloro-4-fluorophenyl)-2-((3-(cyclopropyl(ethyl)amino)propyl)amino),N'-hydroxy-1H-imidazo[4,5-b]pyridine-7-carboximidamide

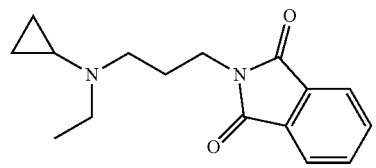 [SMILES: CCN(CCCN1C(=O)c2ccccc2C1=O)C1CC1]

2-(3-(cyclopropyl (ethyl)amino)propyl)isoindoline-1,3-dione was prepared analogously to Example 314 using N-ethylcyclopropylamine in place of cyclopropylmethylamine. $C_{16}H_{20}N_2O_2$. 273.2 (M+1).

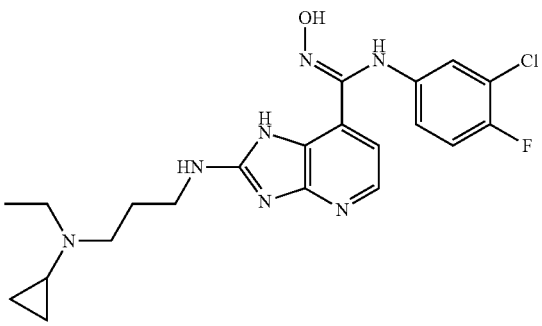 [SMILES: CCN(CCCNc1nc2nccc(/C(=N/O)Nc3ccc(F)c(Cl)c3)c2[nH]1)C1CC1]

N-(3-chloro-4-fluorophenyl)-2-((3-(cyclopropyl(ethyl)amino)propyl)amino)-N'-hydroxy-1H-imidazo[4,5-b]pyridine-7-carboximidamide was prepared analogously to Example 314 using 2-(3-(cyclopropyl(ethyl)amino)propyl)isoindoline-1,3-dione in place of 2-(3-(cyclopropyl(methyl)amino)propyl)isoindoline-1,3-dione. $C_{21}H_{25}ClFN_7O$. 446.2 (M+H). $^1$H NMR (400 MHz, DMSO-d6) δ 11.33 (s, 1H), 8.96 (s, 1H), 7.97 (d, J=6.1 Hz, 1H), 7.10 (t, J=9.0 Hz, 1H), 7.05-6.98 (m, 1H), 6.97-6.89 (m, 1H), 6.58 (dt, J=8.9, 3.5 Hz, 1H), 3.51 (s, 2H), 3.35-3.18 (m, 4H), 2.94-2.73 (m, 1H), 2.15-1.92 (m, 2H), 1.26 (t, J=7.3 Hz, 3H), 1.02-0.78 (m, 4H).

Example 317: N-(3-chloro-4-fluorophenyl)-2-((2-(4-fluoropiperidin-1-yl)ethyl)amino),N'-hydroxy-1H-imidazo[4,5-b]pyridine-7-carboximidamide

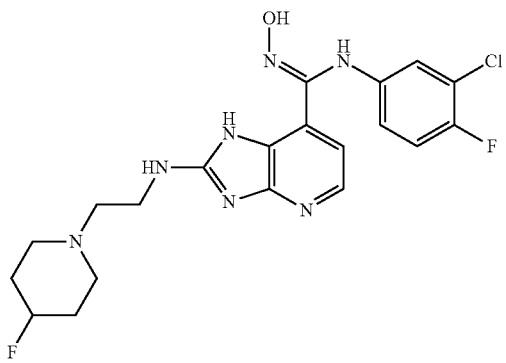 [SMILES: O/N=C(\Nc1ccc(F)c(Cl)c1)c1ccnc2nc(NCCN3CCC(F)CC3)[nH]c12]

Example 317 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(4-fluoropiperidin-1-yl)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. $C_{20}H_{22}ClF_2N_7O$. 450.2 (M+H). $^1$H NMR (400 MHz, DMSO-d6) δ 11.30 (s, 1H), 8.94 (s, 1H), 7.98 (d, J=5.6 Hz, 1H), 7.10 (t, J=9.1 Hz, 1H), 6.99 (d, J=5.7 Hz, 1H), 6.96-6.85 (m, 1H), 6.64-6.45 (m, 1H), 5.10-4.80 (m, 1H), 3.86-3.70 (m, 2H), 3.50-3.20 (m, 6H), 2.23-1.93 (m, 4H).

Example 318: N-(3-chloro-4-fluorophenyl)-N'-hydroxy-2-((2-(2,2,2-trifluoroethoxy)ethyl)amino)-1H-imidazo[4,5-b]pyridine-7-carboximidamide

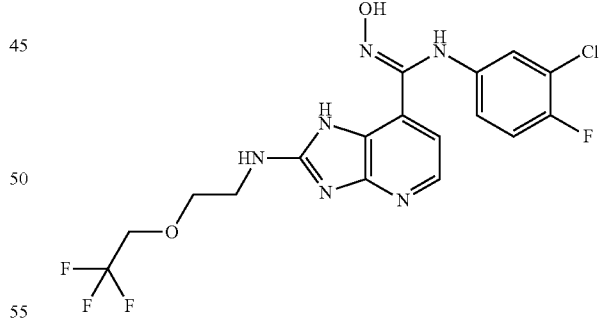

Example 318 was prepared analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(2,2,2-trifluoroethoxy)ethan-1-amine hydrochloride in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. $C_{17}H_{15}ClF_4N_6O_2$. 447.1 (M+H).

Example 319: N-(3-chloro-4-fluorophenyl)-N'-hydroxy-2-((3-(2,2,2-trifluoroethoxy)propyl)amino)-1H-imidazo[4,5-b]pyridine-7-carboximidamide

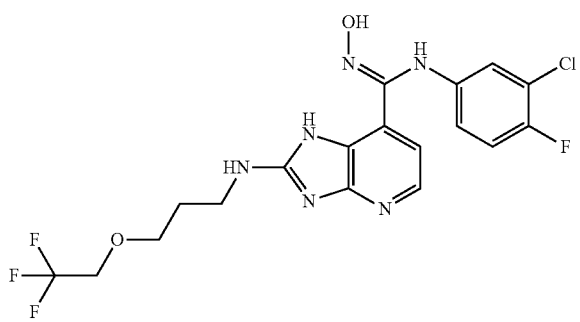 [SMILES: O/N=C(\Nc1ccc(F)c(Cl)c1)c1ccnc2nc(NCCCOCC(F)(F)F)[nH]c12]

Example 319 was prepared analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 3-(2,2,2-trifluoroethoxy)propan-1-amine hydrochloride in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. $C_{18}H_{17}ClF_4N_6O_2$. 461.2 (M+H). $^1$H NMR (400 MHz, DMSO-d6) δ 11.36 (s, 1H), 8.94 (s, 1H), 7.94 (d, J=6.2 Hz, 1H), 7.08 (t, J=9.0 Hz, 1H), 7.01 (dd, J=6.5, 2.3 Hz, 1H), 6.89 (d, J=6.3 Hz, 1H), 6.56 (ddd, J=8.9, 3.9, 2.8 Hz, 2H), 4.04 (q, J=9.5 Hz, 2H), 3.65 (t, J=6.1 Hz, 2H), 3.52-3.42 (m, 2H), 1.85 (p, J=6.9 Hz, 2H).

Example 320: N-(3-chloro-4-fluorophenyl)-N'-hydroxy-2-((2-(3-methoxypiperidin-1-yl)ethyl)amino)-1H-imidazo[4,5-b]pyridine-7-carboximidamide

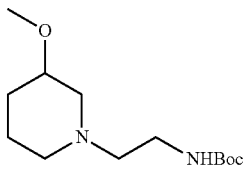 [SMILES: COC1CCCN(CCNC(=O)OC(C)(C)C)C1]

tert-Butyl (2-(3-methoxypiperidin-1-yl)ethyl)carbamate. A mixture of tert-butyl (2-bromoethyl)carbamate (0.147 g, 0.656 mmol), 3-methoxypiperidine hydrochloride (0.099 g, 0.656 mmol) and DIPEA (0.25 mL, 1.44 mmol) in DMSO (1.5 mL) was stirred at 40° C. for 16 h. The mixture was diluted with sat NaHCO$_3$ soln. The aqueous layer was extracted 3× with EtOAc. The combined organic layers were washed with brine, dried (Na$_2$SO$_4$), filtered and concentrated. The residue was purified via silica gel chromatography to give the desired product (0.047 g). $C_{13}H_{26}N_2O_3$. 259.2 (M+1).

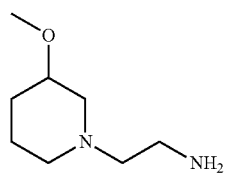

2-(3-Methoxypiperidin-1-yl)ethan-1-amine. To a solution of tert-butyl (2-(3-methoxypiperidin-1-yl)ethyl)carbamate (0.047 g, 0.182 mmol) in THF was added HCl (2.3 mL of a 4 M soln in dioxane, 9.1 mmol). The mixture stirred at rt for 16 h. The mixture was concentrated to give the desired product as the HCl salt (0.042 g). $C_8H_{18}N_2O$. 159.2 (M+1).

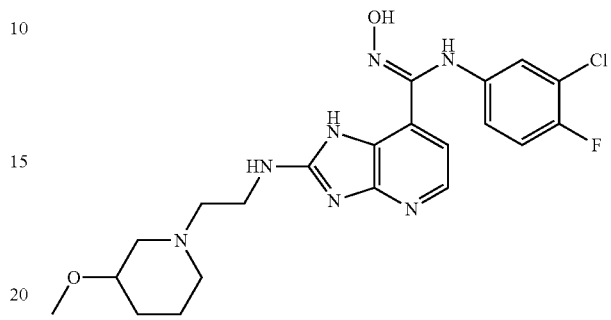

N-(3-chloro-4-fluorophenyl)-N'-hydroxy-2-((2-(3-methoxypiperidin-1-yl)ethyl)amino)-1H-imidazo[4,5-b]pyridine-7-carboximidamide was prepared analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(3-methoxypiperidin-1-yl)ethan-1-amine hydrochloride in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. $C_{21}H_{25}ClFN_7O_2$. 462.2 (M+H). $^1$H NMR (400 MHz, DMSO-d$_6$) δ 11.30 (s, 1H), 8.93 (s, 1H), 7.97 (d, J=5.6 Hz, 0H), 7.09 (t, J=9.1 Hz, 1H), 7.03-6.75 (m, 2H), 6.55 (ddd, J=9.0, 3.9, 2.7 Hz, 1H), 3.88-3.02 (m, 14H), 2.00-1.54 (m, 2H).

Example 321: N-(3-chloro-4-fluorophenyl)-2-((3-(difluoromethoxy)propyl)amino)-N'-hydroxy-1H-imidazo[4,5-b]pyridine-7-carboximidamide

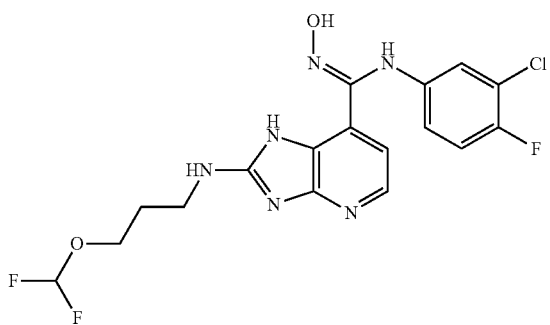 [SMILES: O/N=C(\Nc1ccc(F)c(Cl)c1)c1ccnc2nc(NCCCOC(F)F)[nH]c12]

Example 321 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 3-(difluoromethoxy)propan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. $C_{17}H_{16}ClF_3N_6O_2$. 429.1 (M+H). ¹H NMR (400 MHz, DMSO-d₆) δ 11.38 (s, 1H), 8.94 (s, 1H), 7.94 (d, J=6.2 Hz, 1H), 7.08 (t, J=9.0 Hz, 1H), 7.05-6.96 (m, 1H), 6.93-6.80 (m, 1H), 6.66 (t, J=76.1 Hz, 1H), 6.56 (ddd, J=8.8, 4.2, 2.8 Hz, 1H), 3.90 (t, J=6.2 Hz, 2H), 3.55-3.45 (m, 2H), 1.96-1.83 (m, 2H).

Example 322: (R)—N-(3-chloro-4-fluorophenyl)-N'-hydroxy-2-(((tetrahydrofuran-2-yl)methyl)amino)-1H-imidazo[4,5-b]pyridine-7-carboximidamide

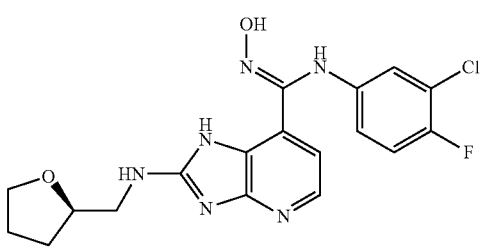 [SMILES: O/N=C(\Nc1ccc(F)c(Cl)c1)c1ccnc2nc(NC[C@H]3CCCO3)[nH]c12]

Example 322 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (R)-(−)-tetrahydrofurfurylamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)carbamate, respectively. $C_{18}H_{18}ClFN_6O_2$. 405.2 (M+1).

Example 323: (S)—N-(3-chloro-4-fluorophenyl)-N'-hydroxy-2-(((tetrahydrofuran-2-yl)methyl)amino)-1H-imidazo[4,5-b]pyridine-7-carboximidamide

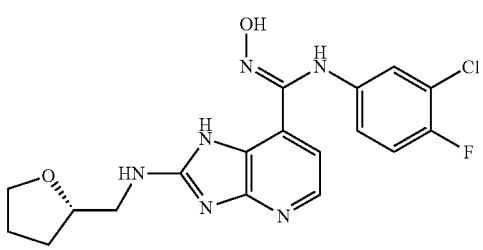 [SMILES: O/N=C(\Nc1ccc(F)c(Cl)c1)c1ccnc2nc(NC[C@@H]3CCCO3)[nH]c12]

Example 323 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (S)-(+)-tetrahydrofurfurylamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and ter t-butyl (2-aminoethyl)carbamate, respectively. $C_{18}H_{18}ClFN_6O_2$. 405.2 (M+H). ¹H NMR (400 MHz, DMSO-d₆) δ 11.45 (s, 1H), 8.97 (s, 1H), 7.98 (d, J=6.3 Hz, 1H), 7.11 (t, J=9.0 Hz, 1H), 7.04 (dd, J=6.5, 2.8 Hz, 1H), 6.93 (d, J=6.3 Hz, 1H), 6.60 (ddd, J=8.9, 4.0, 3.0 Hz, 1H), 4.09-3.98 (m, 1H), 3.80 (dt, J=8.2, 6.7 Hz, 1H), 3.68 (dt, J=8.1, 6.8 Hz, 1H), 3.63-3.52 (m, 1H), 3.51-3.38 (m, 1H), 2.03-1.76 (m, 3H), 1.66-1.49 (m, 1H).

Example 324: N-(3-chloro-4-fluorophenyl)-N'-hydroxy-2-((2-(tetrahydrofuran-2-yl)ethyl)aminol-1H-imidazo[4,5-b]pyridine-7-carboximidamide

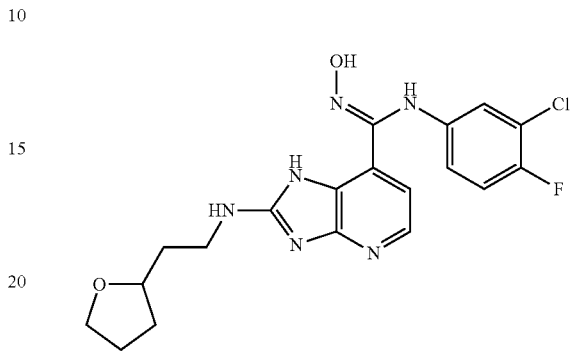

Example 324 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(oxolan-2-yl)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and ter t-butyl (2-aminoethyl)carbamate, respectively. $C_{19}H_{20}ClFN_6O_2$. 419.2 (M+H). ¹H NMR (400 MHz, DMSO-d₆) δ 11.38 (s, 1H), 8.96 (s, 1H), 7.95 (d, J=6.1 Hz, 1H), 7.10 (t, J=9.0 Hz, 1H), 7.03 (dd, J=6.5, 2.7 Hz, 1H), 6.91 (d, J=6.2 Hz, 1H), 6.58 (ddd, J=9.0, 4.1, 3.0 Hz, 1H), 3.89-3.75 (m, 2H), 3.62 (td, J=7.9, 6.4 Hz, 1H), 3.54-3.47 (m, 2H), 2.03-1.67 (m, 5H), 1.52-1.37 (m, 1H).

Example 325: N-(3-chloro-4-fluorophenyl)-N'-hydroxy-2-(piperidin-2-ylmethyl)-1H-imidazo[4,5-b]pyridine-7-carboximidamide

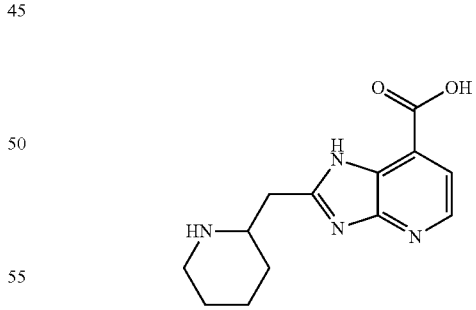

2-(piperidin-2-ylmethyl)-1H-imidazo[4,5-b]pyridine-7-carboxylic acid. A suspension of 2,3-diaminoisonicotinic acid hydrochloride (200 mg, 0.106 mmol) and 2-(piperidin-2-yl)acetic acid (453 mg, 0.317 mmol) in sulfuric acid (1.5 mL) was stirred at room temperature for 5 min and, then, was sealed in a vial and stirred at 160° C. for 3 hours. Once the mixture had cooled, water (2 mL) was added and the solution was purified by preparative HPLC to give the desired product. $C_{13}H_{16}N_4O_2$. 261.1 (M+1).

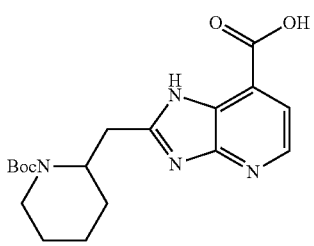 [SMILES: CC(C)(C)OC(=O)N1CCCCC1Cc1nc2nccc(C(=O)O)c2[nH]1]

2-((1-(tert-butoxycarbonyl)piperidin-2-yl)methyl)-1H-imidazo[4,5-b]pyridine-7-carboxylic acid. A solution of 2-(piperidin-2-ylmethyl)-1H-imidazo[4,5-b]pyridine-7-carboxylic acid (205 mg, 0.788 mmol), di-tert-butyl dicarbonate (189 mg, 0.866 mmol), and triethylamine (0.440 ml, 3.15 mmol) in dichloromethane (8 mL) was stirred for 3 hr and concentrated to give the desired product. $C_{18}H_{24}N_4O_4$. 361.1 (M+1).

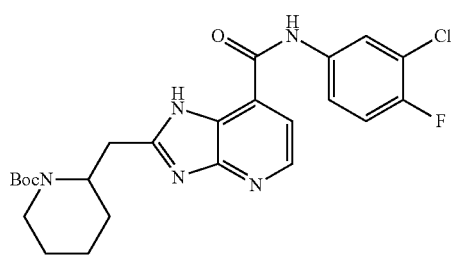 [SMILES: CC(C)(C)OC(=O)N1CCCCC1Cc1nc2nccc(C(=O)Nc3ccc(F)c(Cl)c3)c2[nH]1]

tert-butyl 2-((7-((3-chloro-4-fluorophenyl)carbamoyl)-1H-imidazo[4,5-b]pyridin-2-yl)methyl)piperidine-1-carboxylate. A solution of 2-((1-(tert-butoxycarbonyl)piperidin-2-yl)methyl)-1H-imidazo[4,5-b]pyridine-7-carboxylic acid (283 mg, 0.785 mmol), 4-fluoro-3-chloroaniline (171 mg, 1.18 mmol), 1-[bis(dimethylamino)methylene]-1H-1,2,3-triazolo[4,5-b]pyridinium 3-oxid hexafluorophosphate (388 mg, 1.02 mmol) and N,N-diisopropylethylamine (0.684 ml, 3.93 mmol) in dimethylformamide (1.5 mL) was stirred for 3 hours. The reaction mixture was concentrated and purified by preparative HPLC. The resulting lyophilized material was mixed with saturated aqueous sodium bicarbonate (5 mL), filtered, washed with water and dried on high vacuum to give the desired product. $C_{24}H_{27}ClFN_5O_3$ 488.1 (M+1).

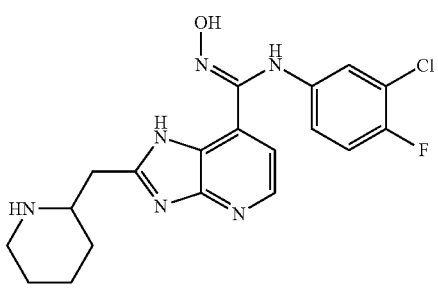 [SMILES: O/N=C(\Nc1ccc(F)c(Cl)c1)c1ccnc2nc(CC3CCCCN3)[nH]c12]

N-(3-chloro-4-fluorophenyl)-N'-hydroxy-2-(piperidin-2-ylmethyl)-1H-imidazo[4,5-b]pyridine-7-carboximidamide. To a mixture of tert-butyl 2-((7-((3-chloro-4-fluorophenyl)carbamoyl)-1H-imidazo[4,5-b]pyridin-2-yl)methyl)piperidine-1-carboxylate (100 mg, 0.205 mmol) and potassium carbonate (198 mg, 1.43 mmol) in dichloromethane (2 ml) was added phosphorous pentachloride (85 mg, 0.409 mmol). The reaction mixture stirred for 2 hours and was concentrated. The residue was brought up in ethanol (2 ml) and hydroxylamine (0.50 mL, 50% in water, 8 mmol) and stirred for 1 hour. The reaction mixture was concentrated and purified by preparative HPLC to give the desired product. $C_{19}H_{20}ClFN_6O$. 403.1 (M+1).

Example 326: N-(3-chloro-4-fluorophenyl)-2-(1-(dimethylamino)propan-2-yl)-N'-hydroxy-1H-imidazo[4,5-b]pyridine-7-carboximidamide

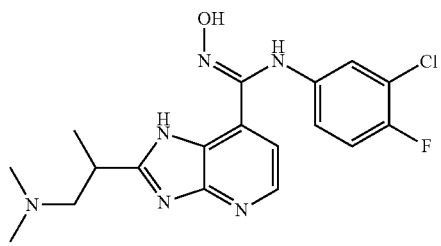 [SMILES: CC(CN(C)C)c1nc2nccc(/C(=N/O)Nc3ccc(F)c(Cl)c3)c2[nH]1]

Example 326 was prepared analogously to Example 305 using 3-(dimethylamino)-2-methylpropanoic acid in place of 2-(1-methylpiperidin-2-yl)acetic acid. $C_{18}H_{20}ClFN_6O$. 391.1 (M+1).

Example 327: N-(3-chloro-4-fluorophenyl)-N'-hydroxy-2-(2-(methylamino)propyl)-1H-imidazo[4,5-b]pyridine-7-carboximidamide

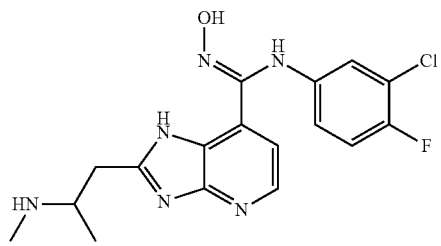 [SMILES: CNC(C)Cc1nc2nccc(/C(=N/O)Nc3ccc(F)c(Cl)c3)c2[nH]1]

Example 327 was prepared analogously to Example 325 using 3-(methylamino)butanoic acid in place of 2-(piperidin-2-yl)acetic acid. $C_{17}H_{18}ClFN_6O$. 377.1 (M+1).

Example 328: N-(3-chloro-4-fluorophenyl)-2-(2-(dimethylamino)propyl)-N'-hydroxy-1H-imidazo[4,5-b]pyridine-7-carboximidamide

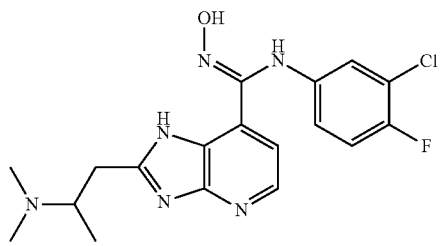 [SMILES: CC(Cc1nc2nccc(/C(=N/O)Nc3ccc(F)c(Cl)c3)c2[nH]1)N(C)C]

Example 328 was prepared analogously to Example 305 using 3-(dimethylamino)butanoic acid in place of 2-(1-methylpiperidin-2-yl)acetic acid. $C_{18}H_{20}ClFN_6O$. 391.1 (M+1).

Example 329: N-(3-chloro-4-fluorophenyl)-N'-hydroxy-2-(pyrrolidin-2-ylmethyl)-1H-imidazo[4,5-b]pyridine-7-carboximidamide

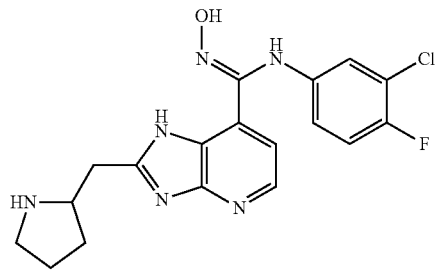 [SMILES: O/N=C(\Nc1ccc(F)c(Cl)c1)c1ccnc2nc(CC3CCCN3)[nH]c12]

Example 329 was prepared analogously to Example 325 using 2-(pyrrolidin-2-yl)acetic acid in place of 2-(piperidin-2-yl)acetic acid. $C_{18}H_{18}ClFN_6O$. 389.1 (M+1).

Example 330: N-(3-chlorophenyl)-4,5-difluoro-N'-hydroxy-2-((2-(pyrrolidin-1-yl)ethyl)amino)-1H-benzo[d]imidazole-7-carboximidamide

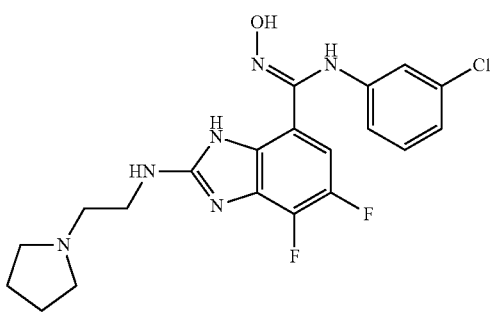 [SMILES: O/N=C(\Nc1cccc(Cl)c1)c1cc(F)c(F)c2nc(NCCN3CCCC3)[nH]c12]

Example 330 was prepared analogously to Example 39 using 2-(pyrrolidin-1-yl)ethanamine in place of N,N-dimethylpropane-1,3-diamine and 3-chloroaniline in place of 3-chloro-4-fluoroaniline. $C_{20}H_{21}ClF_2N_6O$. 435.1 (M+1). 1H NMR (400 MHz, DMSO-d6) δ 11.02-10.85 (m, 1H), 10.79 (s, 1H), 9.83-9.63 (m, 1H), 8.68 (s, 1H), 7.03 (t, J=8.0 Hz, 1H), 6.89-6.73 (m, 2H), 6.55-6.44 (m, 1H), 3.74-3.60 (m, 2H), 3.44-3.32 (m, 2H), 2.05-1.83 (m, 4H).

Example 331: N-(3-bromophenyl)-4,5-difluoro-N'-hydroxy-2-((2-(pyrrolidin-1-yl)ethyl)amino)-1H-benzo[d]imidazole-7-carboximidamide

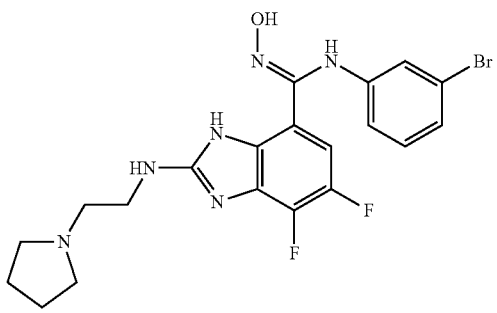 [SMILES: O/N=C(\Nc1cccc(Br)c1)c1cc(F)c(F)c2nc(NCCN3CCCC3)[nH]c12]

Example 331 was prepared analogously to Example 39 using 2-(pyrrolidin-1-yl)ethanamine in place of N,N-dimethylpropane-1,3-diamine and 3-bromoaniline in place of 3-chloro-4-fluoroaniline. $C_{20}H_{21}BrF_2N_6O$. 479.1 (M+1). NMR (400 MHz, DMSO-d6) δ 10.80 (s, 1H), 9.83-9.67 (m, 1H), 8.67 (s, 1H), 7.01-6.73 (m, 6H), 6.52 (dt, J=7.7, 1.8 Hz, 1H), 3.71-3.59 (m, 2H), 3.42-3.32 (m, 2H), 1.93 (s, 4H).

Example 332: N-(3-bromo-4-fluorophenyl)-4,5-difluoro-N'-hydroxy-2-((2-(pyrrolidin-1-yl)ethyl)amino)-1H-benzo[d]imidazole-7-carboximidamide

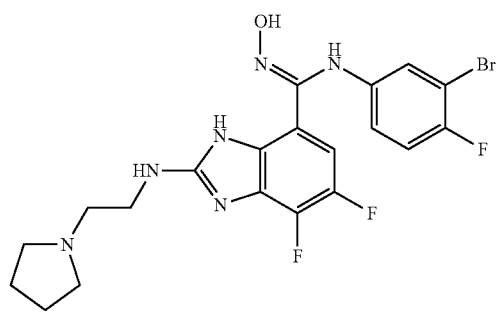 [SMILES: O/N=C(\Nc1ccc(F)c(Br)c1)c1cc(F)c(F)c2nc(NCCN3CCCC3)[nH]c12]

Example 332 was prepared analogously to Example 39 using 2-(pyrrolidin-1-yl)ethanamine in place of N,N-dimethylpropane-1,3-diamine and 3-bromo-4-fluoroaniline in place of N,N-dimethylpropane-1,3-diamine. $C_{20}H_{20}BrF_3N_6O$. 497.1 (M+1).

Example 333: 2-((2-aminoethyl)amino)-N-(3-chloro-4-fluorophenyl)-4,5-difluoro-N'-hydroxy-1H-benzo[d]imidazole-7-carboximidamide

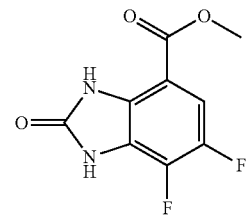 [SMILES: COC(=O)c1cc(F)c(F)c2[nH]c(=O)[nH]c12]

Methyl 6,7-difluoro-2-oxo-2,3-dihydro-1H-benzo[d]imidazole-4-carboxylate. A solution of methyl 2,3-diamino-4,5-difluorobenzoate (10 g, 50 mmol) and carbonyldiimidazole (12 g, 75 mmol) in THF (100 mL) was stirred overnight. Diethyl ether was added to the reaction mixture and the precipitate was filtered and dried on high vacuum to give the desired product. $C_9H_6F_2N_2O_3$. 229.5 (M+1).

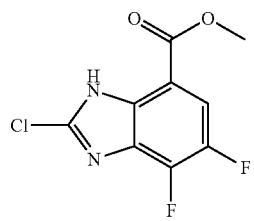 [SMILES: COC(=O)c1cc(F)c(F)c2nc(Cl)[nH]c12]

Methyl 2-chloro-4,5-difluoro-1H-benzo[d]imidazole-7-carboxylate. A mixture of methyl 6,7-difluoro-2-oxo-2,3-dihydro-1H-benzo[d]imidazole-4-carboxylate (9.98 g, 43.7 mmol) in phosphoryl chloride (80 mL) was stirred overnight at 120° C. The solution was cooled and concentrated. To the solid residue cooled in an ice bath was cautiously added a saturated aqueous sodium bicarbonate solution. The slurry was filtered and the filtrate was washed with water and dried on high vacuum to give the desired product. $C_9H_5ClF_2N_2O_2$. 247.2 (M+1).

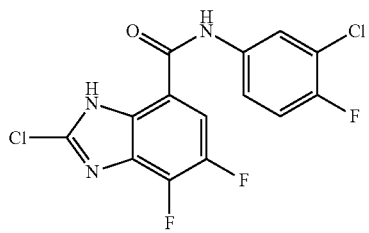 [SMILES: O=C(Nc1ccc(F)c(Cl)c1)c1cc(F)c(F)c2nc(Cl)[nH]c12]

2-chloro-N-(3-chloro-4-fluorophenyl)-4,5-difluoro-1H-benzo[d]imidazole-7-carboxamide. To a solution of the 3-chloro-4-fluoroaniline (4.43 g, 30 mmol) in dichloroethane (50 mL) at 0° C. was added a solution of trimethylaluminum (30.4 mL, 2 M in heptane, 61 mmol) dropwise over 5 min. The ice bath was removed and the mixture stirred for 30 minutes. The solution was cooled back down with and ice bath and methyl 2-chloro-4,5-difluoro-1H-benzo[d]imidazole-7-carboxylate (5 g, 20 mmol) was added to this solution as a solid. The reaction stirred at 60° C. for 6 hours. The reaction was cooled in an ice bath and to this cooled mixture was added 10% citric acid (30 mL). To this solution was added 2N sodium hydroxide and the aqueous layer was washed three times with ethyl acetate. The combined organic layers were dried over sodium sulfate, filtered and concentrated to give the desired product. $C_{14}H_6Cl_2F_3N_3O$. 360.5 (M+1).

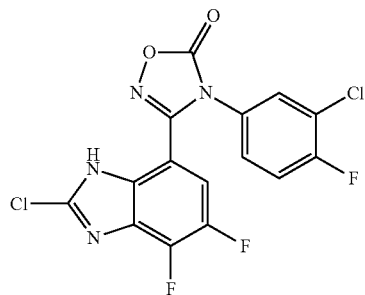 [SMILES: O=c1onc(-c2cc(F)c(F)c3nc(Cl)[nH]c23)n1-c1ccc(F)c(Cl)c1]

3-(2-chloro-4,5-difluoro-1H-benzo[d]imidazol-7-yl)-4-(3-chloro-4-fluorophenyl)-1,2,4-oxadiazol-5(4H)-one. A mixture of 2-chloro-N-(3-chloro-4-fluorophenyl)-4,5-difluoro-1H-benzo[d]imidazole-7-carboxamide (6.56 g, 18.2 mmol) and potassium carbonate (17.6 g, 127 mmol) in dichloromethane (100 mL) was stirred together for 5 min. To this mixture was added phosphorus pentachloride (7.58 g, 36 mmol) and the mixture stirred for two hours. More phosphorus penetachloride was added (7.58 g, 36 mmol) and the mixture stirred for another three hours. The reaction mixture was concentrated and placed in an ice bath. To the cooled residue was added a solution of hydroxyamine (44.5 mL, 50% in water, 728 mmol) and ethanol (100 mL) over 20 min. The ice bath was removed and the reaction stirred for 30 min. The reaction mixture was concentrated and brought up in water and washed three times with ethyl acetate. The combined organic layers were dried over sodium sulfate, filtered and concentrated to about 50 ml. To this solution was added carbonyldiimidazole (5.9 g, 36 mmol). The reaction solution stirred for 30 min and was diluted with ethyl acetate and washed twice with 1 N hydrochloric acid and once with saturated aqueous sodium chloride. The organic layer was dried over sodium sulfate, filtered, and concentrated to give the desired product. $C_{15}H_5Cl_2F_3N_4O_2$. 401.0 (M+1).

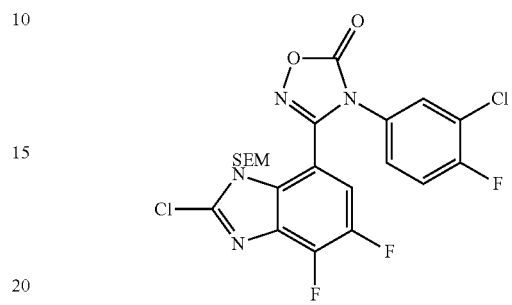

3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one. To a solution of 3-(2-chloro-4,5-difluoro-1H-benzo[d]imidazol-7-yl)-4-(3-chloro-4-fluorophenyl)-1,2,4-oxadiazol-5(4H)-one (7.3 g, 18 mmol) and triethylamine (15 mL, 109 mmol) in dichloromethane (200 mL) was added (2-(chloromethoxy)ethyl)trimethylsilanel (8 mL, 46 mmol). Reaction was stirred for 2 hr, and was adsorbed onto silica gel and purified by silica gel chromatography to give the desired product. $C_{21}H_{19}C_{12}F_3N_4O_3Si$. 554.9 (M+23).

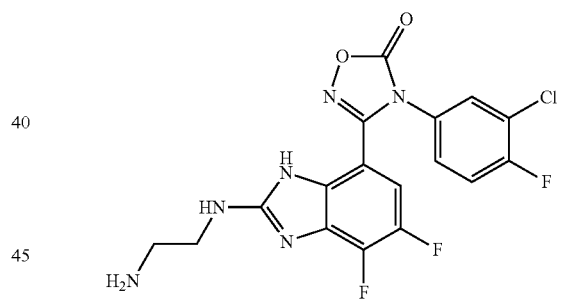

3-(2-((2-aminoethyl)amino)-4,5-difluoro-1H-benzo[d]imidazol-7-yl)-4-(3-chloro-4-fluorophenyl)-1,2,4-oxadiazol-5(4H)-one. A solution of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one (390 mg, 0.734 mmol), and tert-butyl (2-aminoethyl)carbamate (141 mg, 0.881 mmol) in dimethylsulfoxide (3.5 mL) was stirred at 65° C. overnight. The reaction mixture was cooled and diluted with ethyl acetate and washed three times with saturated aqueous sodium chloride. The organic layer was dried over sodium sulfate, filtered and concentrated. The resulting residue was brought up in dichloromethane (3 mL) and trifluoroacetic acid (3 mL) and stirred for 3 hours. The reaction solution was concentrated and brought up in saturated aqueous sodium bicarbonate and washed three times with ethyl acetate. The combined organic layers were dried over sodium sulfate, filtered and concentrated to give the desired product (312 mg). $C_{17}H_{12}ClF_3N_6O_2$. 425.2 (M+1).

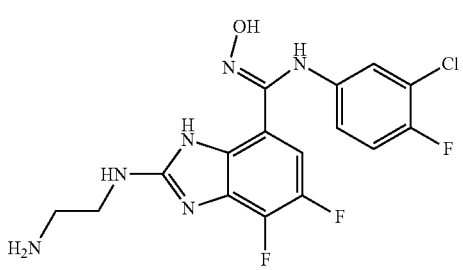 [SMILES: NCCNc1nc2c(F)c(F)cc(/C(=N/O)Nc3ccc(F)c(Cl)c3)c2[nH]1]

2-((2-aminoethyl)amino)-N-(3-chloro-4-fluorophenyl)-4,5-difluoro-N'-hydroxy-1H-benzo[d]imidazole-7-carboximidamide. A solution of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one (29 mg, 0.056 mmol), and tert-butyl (2-aminoethyl)carbamate (44 mg, 0.27 mmol) in dimethylsulfoxide (0.2 mL) was stirred at 65° C. overnight. The reaction mixture was cooled and diluted with ethyl acetate and washed three times with saturated aqueous sodium chloride. The organic layer was dried over sodium sulfate, filtered and concentrated. The resulting residue was brought up in dichloromethane (0.5 mL) and trifluoroacetic acid (0.5 mL) and stirred for 3 hours. The reaction solution was concentrated. The resulting residue was brought up in tetrahydrofuran (0.2 mL) and methanol (0.2 mL) and to this solution was added 2 N sodium hydroxide (0.27 mL, 0.54 mmol). The resulting solution was stirred for 30 min and concentrated and purified by preparative HPLC to give the desired product. $C_{16}H_{14}ClF_3N_6O$. 399.1 (M+1).

Example 334: N-(2-((7-(N-(3-chloro-4-fluorophenyl)-N'-hydroxycarbamimidoyl)-4,5-difluoro-1H-benzo[d]imidazol-2-yl)amino)ethyl)acetamide

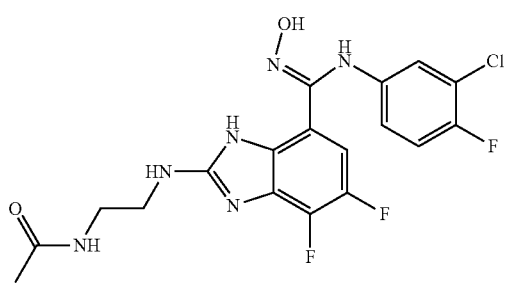 [SMILES: CC(=O)NCCNc1nc2c(F)c(F)cc(/C(=N/O)Nc3ccc(F)c(Cl)c3)c2[nH]1]

To a solution of 3-(2-((2-aminoethyl)amino)-4,5-difluoro-1H-benzo[d]imidazol-7-yl)-4-(3-chloro-4-fluorophenyl)-1,2,4-oxadiazol-5(4H)-one (29 mg, 0.068 mmol) and triethylamine (0.048 mL, 0.34 mmol) in tetrahydrofuran (0.5 mL) was added acetyl chloride (0.007 mL, 0.10 mmol). The resulting solution stirred for one hour and was concentrated. The resulting residue was brought up in tetrahydrofuran (0.4 mL) and methanol (0.4 mL) and to this solution was added 2 N sodium hydroxide (0.34 mL, 0.68 mmol). The resulting solution was stirred for one hour, concentrated and purified by preparative HPLC to give the desired product (11 mg). $C_{18}H_{16}ClF_3N_6O_2$. 441.1 (M+1).

Example 335: N-(3-chloro-4-fluorophenyl)-4,5-difluoro-N'-hydroxy-2-((2-(methylsulfonamido)ethyl)amino)-1H-benzo[d]imidazole-7-carboximidamide

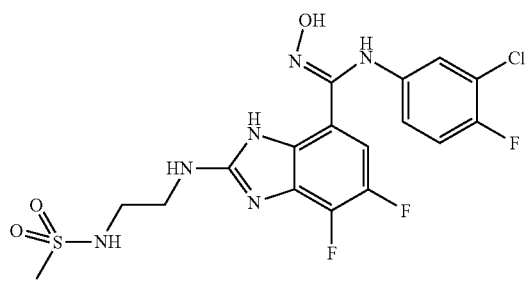 [SMILES: CS(=O)(=O)NCCNc1nc2c(F)c(F)cc(/C(=N/O)Nc3ccc(F)c(Cl)c3)c2[nH]1]

Example 335 was prepared analogously to Example 334 using methanesulfonyl chloride in place of acetyl chloride. $C_{17}H_{16}ClF_3N_6O_3S$. 477.1 (M+1).

Example 336: N-(3-chloro-4-fluorophenyl)-2-((2-(cyclopropanesulfonamido)ethyl)amino)-4,5-difluoro-N'-hydroxy-1H-benzo[d]imidazole-7-carboximidamide

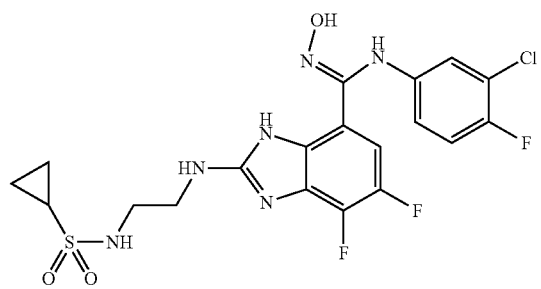 [SMILES: O=S(=O)(NCCNc1nc2c(F)c(F)cc(/C(=N/O)Nc3ccc(F)c(Cl)c3)c2[nH]1)C1CC1]

Example 336 was prepared analogously to Example 334 using cyclopropylsulfonyl chloride in place of acetyl chloride. $C_{19}H_{18}ClF_3N_6O_3S$. 503.1 (M+1).

Example 337: Methyl (2-((7-(N-(3-chloro-4-fluorophenyl)-N'-hydroxycarbamimidoyl)-4,5-difluoro-1H-benzo[d]imidazol-2-yl)amino)ethyl)carbamate

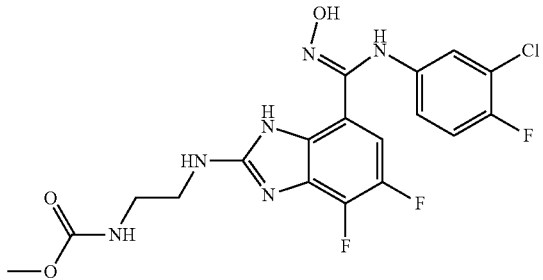 [SMILES: COC(=O)NCCNc1nc2c(F)c(F)cc(/C(=N/O)Nc3ccc(F)c(Cl)c3)c2[nH]1]

Example 337 was prepared analogously to Example 334 using methyl chloroformate in place of acetyl chloride. $C_{18}H_{16}ClF_3N_6O_3$. 457.1 (M+1).

Examples 338: N-(3-chloro-4-fluorophenyl)-4,5-difluoro-N'-hydroxy-2-((2-(sulfamoylamino)ethyl)amino)-1H-benzo[d]imidazole-7-carboximidamide

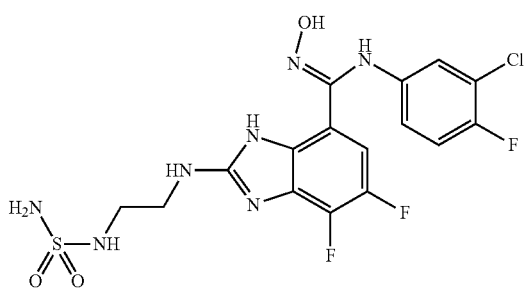 [SMILES: NS(=O)(=O)NCCNc1nc2c(F)c(F)cc(/C(=N/O)Nc3ccc(F)c(Cl)c3)c2[nH]1]

A solution of 3-(2-((2-aminoethyl)amino)-4,5-difluoro-1H-benzo[d]imidazol-7-yl)-4-(3-chloro-4-fluorophenyl)-1,2,4-oxadiazol-5(4H)-one (33 mg, 0.078 mmol) and sulfamide (75 mg, 0.78 mmol) was stirred at 110° C. for 20 min and was concentrated. The resulting residue was brought up in tetrahydrofuran (0.4 mL) and methanol (0.4 mL) and to this solution was added 2 N sodium hydroxide (0.38 mL, 0.76 mmol). The resulting solution was stirred for one hour, concentrated and purified by preparative HPLC to give the desired product. $C_{16}H_{15}ClF_3N_7O_3S$. 478.1 (M+1).

Examples 339: N-(3-chloro-4-fluorophenyl)-4,5-difluoro-N'-hydroxy-2-((2-(phenylsulfonamido)ethyl)amino)-1H-benzo[d]imidazole-7-carboximidamide

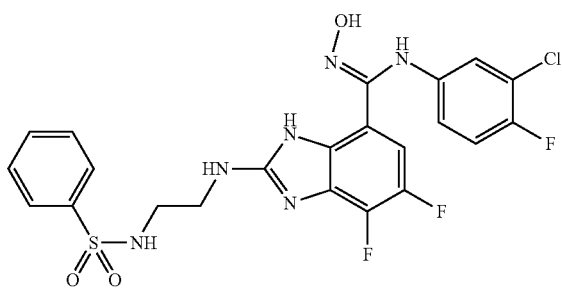 [SMILES: O=S(=O)(NCCNc1nc2c(F)c(F)cc(/C(=N/O)Nc3ccc(F)c(Cl)c3)c2[nH]1)c1ccccc1]

Example 339 was prepared analogously to Example 334 using benzenesulfonyl chloride in place of acetyl chloride. $C_{22}H_{18}ClF_3N_6O_3S$. 539.1 (M+1).

Examples 340: N-(3-chloro-4-fluorophenyl)-2-((2-cyanoethyl)amino)-4,5-difluoro-N'-hydroxy-1H-benzo[d]imidazole-7-carboximidamide

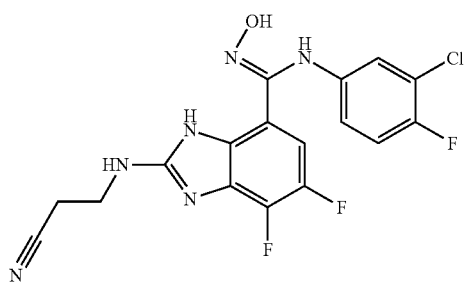 [SMILES: N#CCCNc1nc2c(F)c(F)cc(/C(=N/O)Nc3ccc(F)c(Cl)c3)c2[nH]1]

Example 340 was prepared analogously to Example 333 using 3-aminopropanenitrile in place of tert-butyl (2-aminoethyl)carbamate. $C_{17}H_{12}ClF_3N_6O$. 409.4 (M+1).

Examples 341: N-(3-chloro-4-fluorophenyl)-2-((2-(3-ethylureido)ethyl)amino)-4,5-difluoro-N'-hydroxy-1H-benzo[d]imidazole-7-carboximidamide

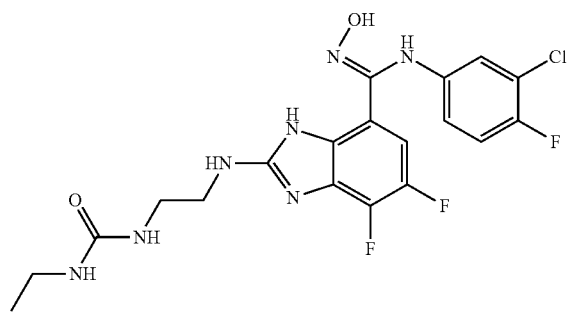 [SMILES: CCNC(=O)NCCNc1nc2c(F)c(F)cc(/C(=N/O)Nc3ccc(F)c(Cl)c3)c2[nH]1]

Example 341 was prepared analogously to Example 334 using ethyl isocyanate in place of acetyl chloride. $C_{19}H_{19}ClF_3N_7O_2$. 470.0 (M+1).

Examples 342: N-(3-chloro-4-fluorophenyl)-4,5-difluoro-N'-hydroxy-2-((pyridin-2-ylmethyl)amino)-1H-benzo[d]imidazole-7-carboximidamide

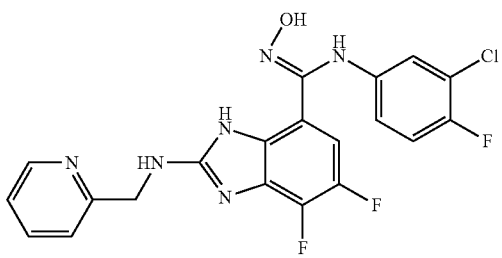 [SMILES: O/N=C(\Nc1ccc(F)c(Cl)c1)c1cc(F)c(F)c2nc(NCc3ccccn3)[nH]c12]

Example 342 was prepared analogously to Example 333 using 2-picolylamine in place of tert-butyl (2-aminoethyl)carbamate. $C_{20}H_{14}ClF_3N_6O$. 447.2 (M+1).

Examples 343: N-(3-chloro-4-fluorophenyl)-4,5-difluoro-N'-hydroxy-2-((pyridin-3-ylmethyl)amino)-1H-benzo[d]imidazole-7-carboximidamide

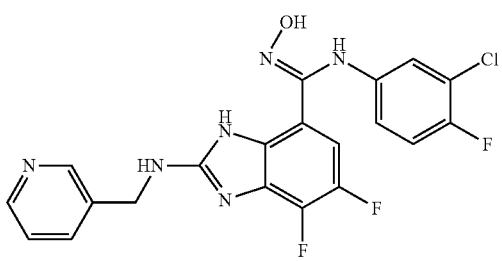 [SMILES: O/N=C(\Nc1ccc(F)c(Cl)c1)c1cc(F)c(F)c2nc(NCc3cccnc3)[nH]c12]

Example 343 was prepared analogously to Example 333 using 2-picolylamine in place of tert-butyl (2-aminoethyl)carbamate. $C_{20}H_{14}ClF_3N_6O$. 447.3 (M+1).

Example 344: N-(3-chloro-4-fluorophenyl)-4,5-difluoro-N'-hydroxy-2-((pyridin-3-ylmethyl)amino)-1H-benzo[d]imidazole-7-carboximidamide

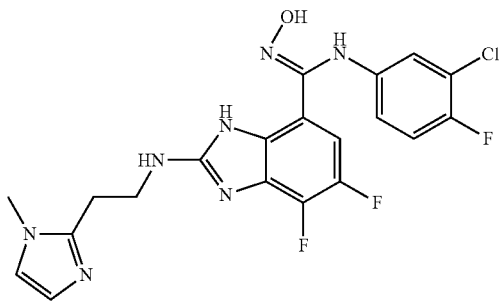 [SMILES: Cn1ccnc1CCNc1nc2c(F)c(F)cc(/C(=N/O)Nc3ccc(F)c(Cl)c3)c2[nH]1]

N-(3-chloro-4-fluorophenyl)-4,5-difluoro-N'-hydroxy-2-((pyridin-3-ylmethyl)amino)-1H-benzo[d]imidazole-7-carboximidamide. Example 344 was prepared analogously to Example 333 using 2-(1-methyl-1H-imidazol-2-yl)ethanamine in place of tert-butyl (2-aminoethyl)carbamate. $C_{20}H_{17}ClF_3N_7O$. 464.3 (M+1).

Examples 345 and 346: 2-(((1H-imidazol-2-yl)methyl)amino)-N-(3-chloro-4-fluorophenyl)-4,5-difluoro-N'-hydroxy-1H-benzo[d]imidazole-7-carboximidamide and 2-chloro-N-(3-chloro-4-fluorophenyl)-4,5-difluoro-N'-hydroxy-1H-benzo[d]imidazole-7-carboximidamide

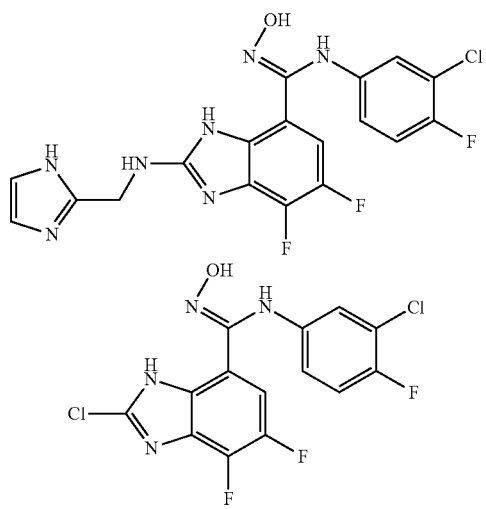

Example 345 was prepared analogously to Example 333 using (1H-imidazol-2-yl)methanamine dihydrochloride and diisopropylethylamine in place of tert-butyl (2-aminoethyl) carbamate. $C_{18}H_{13}ClF_3N_7O$. 436.3 (M+1). Unreacted 2-((2-aminoethyl)amino)-N-(3-chloro-4-fluorophenyl)-4,5-difluoro-N'-hydroxy-1H-benzo[d]imidazole-7-carboximidamide through this sequence gave Example 346 (2-chloro-N-(3-chloro-4-fluorophenyl)-4,5-difluoro-N'-hydroxy-1H-benzo[d]imidazole-7-carboximidamide). $C_{14}H_7Cl_2F_3N_4O$. 375.1 (M+1).

Example 347: 2-((2-aminobenzyl)amino)-N-(3-chloro-4-fluorophenyl)-4,5-difluoro-N'-hydroxy-1H-benzo[d]imidazole-7-carboximidamide

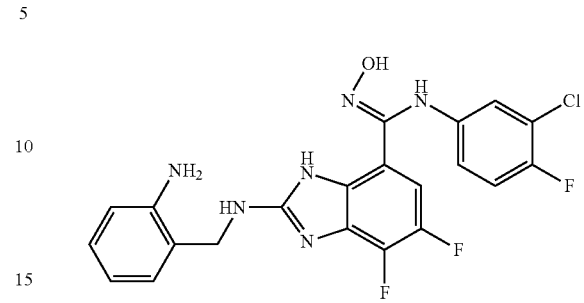

Example 347 was prepared analogously to Example 333 using 2-(aminomethyl)aniline in place of tert-butyl (2-aminoethyl)carbamate. $C_{21}H_{16}ClF_3N_6O$. 461.1 (M+1).

Example 348: N-(3-chloro-4-fluorophenyl)-2-((2-(dimethylamino)benzyl)amino)-4,5-difluoro-N'-hydroxy-1H-benzo[d]imidazole-7-carboximidamide

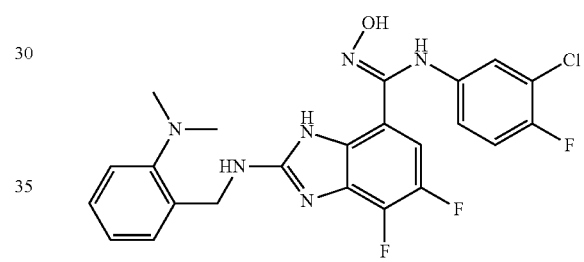

Example 348 was prepared analogously to Example 333 using 2-(aminomethyl)-N,N-dimethylaniline in place of tert-butyl (2-aminoethyl)carbamate. $C_{23}H_{20}ClF_3N_6O$. 489.2 (M+1).

Example 349: N-(3-chloro-4-fluorophenyl)-4,5-difluoro-N'-hydroxy-2-(((1-methyl-1H-imidazol-2-yl)methyl)amino)-1H-benzo[d]imidazole-7-carboximidamide

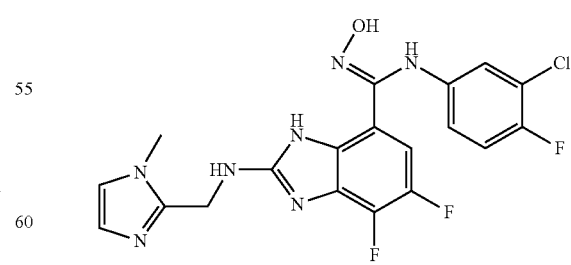

Example 349 was prepared analogously to Example 333 using (1-methyl-1H-imidazol-2-yl)methanamine in place of tert-butyl (2-aminoethyl)carbamate. $C_{19}H_{15}ClF_3N_7O$. 450.1 (M+1).

Example 350: N-(3-chloro-4-fluorophenyl)-4,5-difluoro-N'-hydroxy-2-((pyrimidin-2-ylmethyl)amino)-1H-benzo[d]imidazole-7-carboximidamide

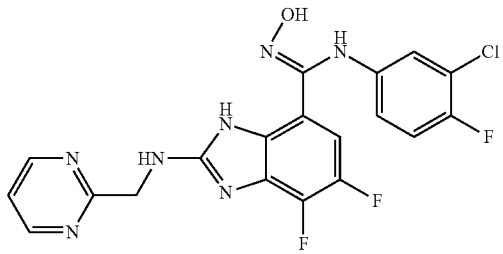

Example 350 was prepared analogously to Example 333 using pyrimidin-2-ylmethanamine hydrochloride and diisopropylethylamine in place of tert-butyl (2-aminoethyl)carbamate. $C_{19}H_{13}ClF_3N_7O$. 448.1 (M+1).

Example 351: N-(3-chloro-4-fluorophenyl)-2-((3-(dimethylamino)-2,2-dimethylpropyl)amino)-4,5-difluoro-N'-hydroxy-1H-benzo[d]imidazole-7-carboximidamide

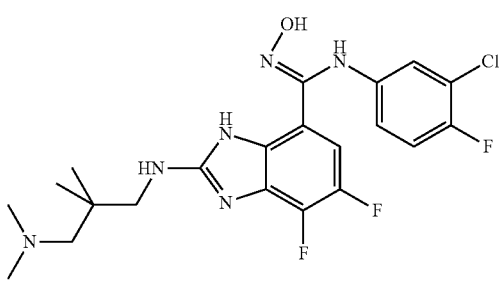 [SMILES: CN(C)CC(C)(C)CNc1nc2c(F)c(F)cc(/C(=N/O)Nc3ccc(F)c(Cl)c3)c2[nH]1]

Example 351 was prepared analogously to Example 333 using $N^1,N^1,2,2$-tetramethylpropane-1,3-diamine in place of tert-butyl (2-aminoethyl)carbamate. $C_{11}H_{24}ClF_3N_6O$. 469.2 (M+1). $^1$H NMR (400 MHz, DMSO-d6) δ 10.80 (s, 1H), 8.71 (s, 1H), 7.08 (t, J=9.1 Hz, 1H), 6.91 (dd, J=6.5, 2.7 Hz, 1H), 6.89-6.80 (m, 1H), 6.52 (ddd, J=9.0, 4.0, 2.7 Hz, 1H), 3.33 (s, 2H), 2.98 (s, 2H), 2.85 (s, 6H), 1.03 (s, 6H).

Example 352: N-(3-chloro-4-fluorophenyl)-2-((3-(dimethylamino)-2-methylpropyl)amino)-4,5-difluoro-N'-hydroxy-1H-benzo[d]imidazole-7-carboximidamide

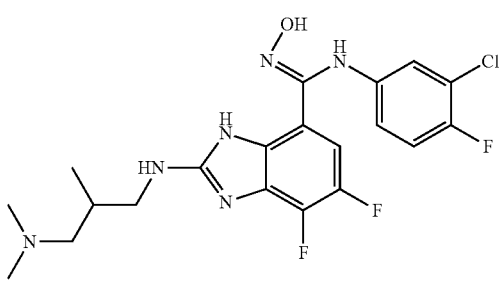 [SMILES: CC(CNc1nc2c(F)c(F)cc(/C(=N/O)Nc3ccc(F)c(Cl)c3)c2[nH]1)CN(C)C]

Example 352 was prepared analogously to Example 333 using $N^1,N^1,2$-trimethylpropane-1,3-diamine in place of tert-butyl (2-aminoethyl)carbamate. $C_{20}H_{22}ClF_3N_6O$. 455.2 (M+1). $^1$H NMR (400 MHz, DMSO-d6) δ 10.80 (s, 1H), 8.74 (s, 1H), 7.07 (t, J=9.1 Hz, 1H), 6.97-6.80 (m, 2H), 6.52 (dt, J=8.2, 3.5 Hz, 1H), 3.38-3.25 (m, 2H), 3.02-2.61 (m, 8H), 2.31-2.16 (m, 1H), 1.01-0.89 (m, 3H).

Example 353: N-(3-chloro-4-fluorophenyl)-2-((3-(dimethylamino)butyl)amino)-4,5-difluoro-N'-hydroxy-1H-benzo[d]imidazole-7-carboximidamide

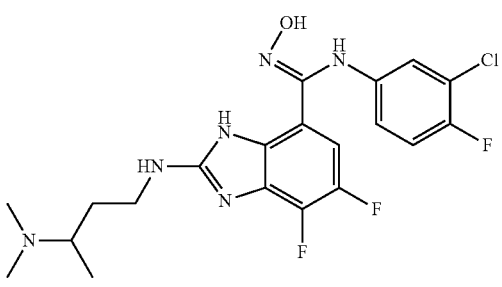 [SMILES: CC(CCNc1nc2c(F)c(F)cc(/C(=N/O)Nc3ccc(F)c(Cl)c3)c2[nH]1)N(C)C]

Example 353 was prepared analogously to Example 333 using $N^3,N^3$-dimethylbutane-1,3-diamine in place of tert-butyl (2-aminoethyl)carbamate. $C_{20}H_{22}ClF_3N_6O$. 455.2 (M+1). $^1$H NMR (400 MHz, DMSO-d6) δ 10.78 (s, 1H), 8.71 (s, 1H), 7.07 (t, J=9.1 Hz, 1H), 6.91 (dd, J=6.6, 2.7 Hz, 1H), 6.89-6.79 (m, 1H), 6.52 (dt, J=9.0, 3.4 Hz, 1H), 3.49-3.28 (m, 3H), 2.69 (d, J=4.4 Hz, 6H), 2.01 (d, J=11.7 Hz, 1H), 1.71 (dt, J=14.1, 7.5 Hz, 1H), 1.22 (d, J=6.5 Hz, 3H).

Example 354: N-(3-chloro-4-fluorophenyl)-4,5-difluoro-N'-hydroxy-2-((2-(1-methylpyrrolidin-2-yl)ethyl)amino)-1H-benzo[d]imidazole-7-carboximidamide

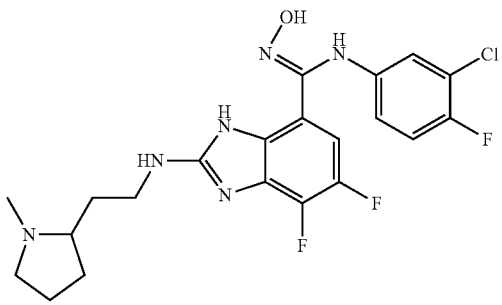 [SMILES: CN1CCCC1CCNc1nc2c(F)c(F)cc(/C(=N/O)Nc3ccc(F)c(Cl)c3)c2[nH]1]

Example 354 was prepared analogously to Example 333 using 2-(1-methylpyrrolidin-2-yl)ethanamine in place of tert-butyl (2-aminoethyl)carbamate. $C_{21}H_{22}ClF_3N_6O$. 467.2 (M+1). $^1$H NMR (400 MHz, DMSO-d6) δ 10.79 (s, 1H), 9.55 (s, 1H), 8.70 (s, 1H), 7.07 (t, J=9.1 Hz, 1H), 6.92 (dd, J=6.5, 2.7 Hz, 1H), 6.89-6.81 (m, 1H), 6.51 (ddd, J=9.0, 4.1, 2.8 Hz, 1H), 3.62-3.47 (m, 1H), 3.47-3.32 (m, 2H), 3.32-3.18 (m, 1H), 3.11-2.98 (m, 1H), 2.81 (d, J=4.6 Hz, 3H), 2.34-2.09 (m, 2H), 2.05-1.69 (m, 3H), 1.68-1.57 (m, 1H).

Example 355: N-(3-chloro-4-fluorophenyl)-4,5-difluoro-N'-hydroxy-2-((2-(1-methylpiperidin-2-yl)ethyl)amino)-1H-benzo[d]imidazole-7-carboximidamide

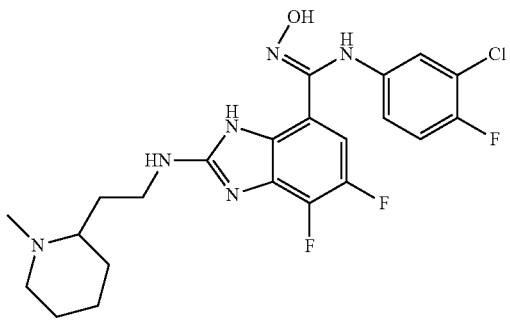 [SMILES: CN1CCCCC1CCNc1nc2c(F)c(F)cc(/C(=N/O)Nc3ccc(F)c(Cl)c3)c2[nH]1]

Example 355 was prepared analogously to Example 333 using 2-(1-methylpiperidin-2-yl)ethanamine in place of tert-butyl (2-aminoethyl)carbamate. $C_{22}H_{24}ClF_3N_6O$. 481.2 (M+1). $^1$H NMR (400 MHz, DMSO-d6) δ 10.75 (s, 1H), 9.13 (s, 1 h), 8.67 (s, 1H), 7.07 (t, J=8.9 Hz, 1H), 6.93-6.88 (m, 1H), 6.80-6.74 (m, 1H), 6.55-6.49 (m, 1H), 2.85-2.81 (m, 2H), 2.80-2.75, (m, 2H), 2.56-2.6 (m, 1H), 2.52 (s, 3H), 1.83-1.35 (m, 8H).

Example 356: N-(3-chloro-4-fluorophenyl)-4,5-difluoro-N'-hydroxy-2-(((4-methylmorpholin-2-yl)methyl)amino)-1H-benzo[d]imidazole-7-carboximidamide

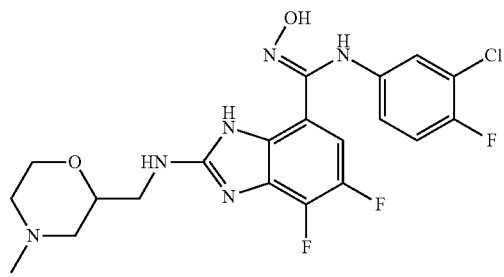 [SMILES: CN1CCOC(CNc2nc3c(F)c(F)cc(/C(=N/O)Nc4ccc(F)c(Cl)c4)c3[nH]2)C1]

Example 356 was prepared analogously to Example 333 using (4-methylmorpholin-2-yl)methanamine in place of tert-butyl (2-aminoethyl)carbamate. $C_{20}H_{20}ClF_3N_6O_2$. 469.2 (M+1). $^1$H NMR (400 MHz, DMSO-d6) δ 10.79 (s, 1H), 9.89 (s, 1H), 8.67 (s, 1H), 7.09 (t, J=9.1 Hz, 1H), 6.91 (dd, J=6.5, 2.8 Hz, 1H), 6.81 (dd, J=12.3, 6.9 Hz, 1H), 6.53 (ddd, J=8.9, 4.1, 2.7 Hz, 1H), 4.07 (d, J=12.7 Hz, 1H), 3.96-3.83 (m, 1H), 3.66 (t, J=12.4 Hz, 1H), 3.59-3.32 (m, 4H), 3.10-2.95 (m, 1H), 2.90-2.80 (m, 4H).

Example 357: N-(3-chloro-4-fluorophenyl)-N'-hydroxy-2-(((4-methylmorpholin-2-yl)methyl)amino)-1H-imidazo[4,5-b]pyridine-7-carboximidamide

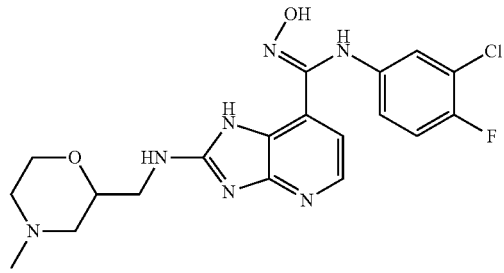 [SMILES: CN1CCOC(CNc2nc3nccc(/C(=N/O)Nc4ccc(F)c(Cl)c4)c3[nH]2)C1]

Example 357 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and (4-methylmorpholin-2-yl)methanamine in place of tert-butyl (2-aminoethyl)carbamate. $C_{19}H_{21}ClFN_7O_2$. 434.2 (M+1). $^1$H NMR (400 MHz, DMSO-d6) δ 11.38 (s, 1H), 10.18 (s, 1H), 8.93 (s, 1H), 7.96 (d, J=6.2 Hz, 1H), 7.10 (t, J=9.0 Hz, 1H), 6.99 (dd, J=6.5, 2.8 Hz, 1H), 6.91 (d, J=6.2 Hz, 1H), 6.58 (ddd, J=9.0, 4.1, 2.8 Hz, 1H), 4.07 (d, J=12.8 Hz, 1H), 3.90 (s, 1H), 3.73-3.34 (m, 5H), 3.08-2.94 (m, 1H), 2.92-2.77 (m, 4H).

Example 358: N-(3-chloro-4-fluorophenyl)-N'-hydroxy-2-(((1-methyl-1H-pyrazol-5-yl)methyl)amino)-1H-imidazo[4,5-b]pyridine-7-carboximidamide

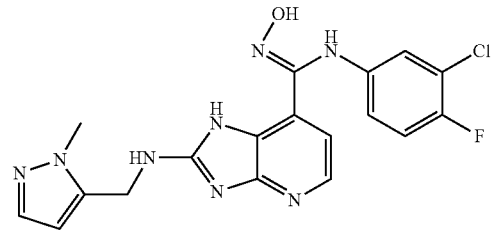 [SMILES: Cn1nccc1CNc1nc2nccc(/C(=N/O)Nc3ccc(F)c(Cl)c3)c2[nH]1]

Example 358 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and (1-methyl-1H-pyrazol-5-yl)methanamine in place of tert-butyl (2-aminoethyl)carbamate. $C_{18}H_{16}ClFN_8O$. 415.1 (M+1). $^1$H NMR (400 MHz, DMSO-d6) δ 11.45 (s, 1H), 8.98 (s, 1H), 7.97 (d, J=6.3 Hz, 1H), 7.32 (d, J=1.9 Hz, 1H), 7.08 (t, J=9.0 Hz, 1H), 7.04 (dd, J=6.5, 2.7 Hz, 1H), 6.93 (d, J=6.4 Hz, 1H), 6.61-6.53 (m, 1H), 6.18 (d, J=1.9 Hz, 1H), 4.71 (d, J=5.9 Hz, 2H), 3.83 (s, 3H).

Example 359: 2-((7-(N-(3-chloro-4-fluorophenyl)-N'-hydroxycarbamimidoyl)-1H-imidazo[4,5-b]pyridin-2-yl)amino)-N,N-dimethylacetamide

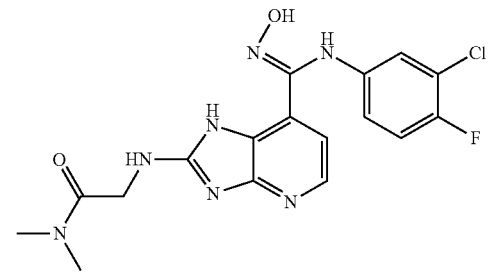 [SMILES: CN(C)C(=O)CNc1nc2nccc(/C(=N/O)Nc3ccc(F)c(Cl)c3)c2[nH]1]

Example 359 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and (4-methylmorpholin-2-yl)methanamine in place of tert-butyl (2-aminoethyl)

carbamate. $C_{17}H_{17}ClFN_7O_2$. 406.2 (M+1). $^1$H NMR (400 MHz, DMSO-d6) δ 11.43 (s, 1H), 8.95 (s, 1H), 7.98 (d, J=6.2 Hz, 1H), 7.10 (t, J=9.0 Hz, 1H), 7.02 (dd, J=6.5, 2.7 Hz, 1H), 6.92 (d, J=6.2 Hz, 1H), 6.58 (ddd, J=8.9, 3.9, 2.7 Hz, 1H), 4.30 (d, J=4.9 Hz, 2H), 2.98 (s, 3H), 2.89 (s, 3H).

Examples 360 and 361: N-(3-chloro-4-fluorophenyl)-N'-hydroxy-2-(3-(hydroxymethyl)azetidin-1-yl)-1H-imidazo[4,5-b]pyridine-7-carboximidamide and N-(3-chloro-4-fluorophenyl)-N'-hydroxy-2-((oxetan-3-ylmethyl)amino)-1H-imidazo[4,5-b]pyridine-7-carboximidamide

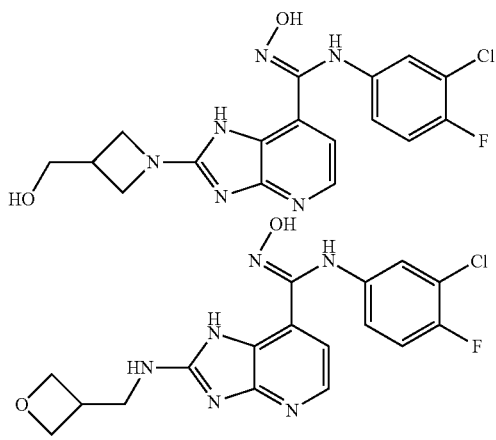

Examples 360 and 361 were prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and oxetan-3-ylmethanamine in place of tert-butyl (2-aminoethyl)carbamate. $C_{17}H_{16}ClFN_6O_2$. 391.1 (M+1). $^1$H NMR (400 MHz, DMSO-d6) δ 12.73 (s, 1H), 11.22 (s, 1H), 8.92 (s, 1H), 8.09 (s, 1H), 7.08 (t, J=9.0 Hz, 1H), 7.03 (d, J=5.4 Hz, 1H), 6.99 (dd, J=6.4, 2.7 Hz, 1H), 6.53 (ddd, J=9.0, 4.1, 2.8 Hz, 1H), 4.98 (s, 1H), 4.23 (dd, J=12.4, 4.9 Hz, 1H), 3.78 (dd, J=12.3, 8.6 Hz, 1H), 3.35-3.23 (m, 1H). $C_{17}H_{16}ClFN_6O_2$. 391.1 (M+1). $^1$H NMR (400 MHz, DMSO-d6) δ 11.16 (s, 1H), 9.44-9.28 (m, 1H), 9.09 (s, 1H), 7.97-7.85 (m, 1H), 7.09 (dd, J=6.5, 2.7 Hz, 1H), 7.04 (t, J=9.0 Hz, 1H), 6.83 (s, 1H), 6.59 (dt, J=8.9, 3.6 Hz, 1H), 4.26 (dd, J=12.3, 4.8 Hz, 1H), 3.91-3.81 (m, 1H), 3.25 (t, J=10.9 Hz, 1H).

Example 362: N-(3-chloro-4-fluorophenyl)-N'-hydroxy-2-((2-(1-methyl-1H-imidazol-2-yl)ethyl)amino)-1H-imidazo[4,5-b]pyridine-7-carboximidamide

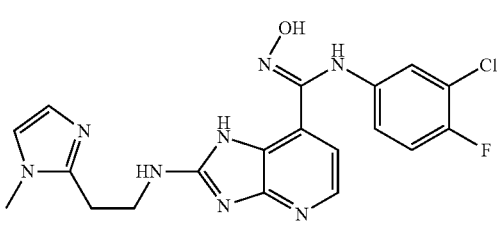 [SMILES: Cn1ccnc1CCNc1nc2nccc(/C(=N/O)Nc3ccc(F)c(Cl)c3)c2[nH]1]

Example 362 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 2-(1-methyl-1H-imidazol-2-yl)ethanamine in place of tert-butyl (2-aminoethyl)carbamate. $C_{19}H_{18}ClFN_8O$. 429.2 (M+1). $^1$H NMR (400 MHz, DMSO-d6) δ 11.36 (s, 1H), 8.96 (s, 1H), 7.97 (d, J=6.2 Hz, 1H), 7.58 (d, J=2.0 Hz, 1H), 7.54 (d, J=2.0 Hz, 1H), 7.08 (t, J=9.0 Hz, 1H), 6.99 (dd, J=6.5, 2.7 Hz, 1H), 6.94 (d, J=6.2 Hz, 1H), 6.60-6.50 (m, 1H), 3.83-3.68 (m, 5H), 3.31-3.21 (m, 2H).

Example 363: N-(3-chloro-4-fluorophenyl)-N'-hydroxy-2-((3-(pyridin-2-ylamino)propyl)amino)-1H-imidazo[4,5-b]pyridine-7-carboximidamide

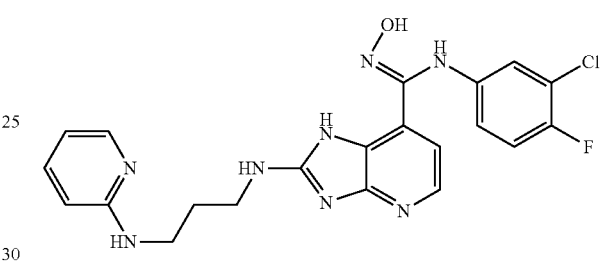

Example 363 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and $N^1$-(pyridin-2-yl)propane-1,3-diamine in place of tert-butyl (2-aminoethyl)carbamate. $C_{21}H_{20}ClFN_8O$. 455.2 (M+1). $^1$H NMR (400 MHz, DMSO-d6) δ 11.34 (s, 1H), 8.95 (s, 1H), 7.95 (d, J=6.2 Hz, 1H), 7.92 (d, J=6.2 Hz, 1H), 7.85-7.74 (m, 1H), 7.08 (t, J=9.0 Hz, 1H), 7.01 (dd, J=6.5, 2.7 Hz, 1H), 6.91 (d, J=6.2 Hz, 1H), 6.84-6.72 (m, 1H), 6.56 (dt, J=9.0, 4.0, 3.0 Hz, 1H), 3.56-3.44 (m, 2H), 3.42-3.31 (m, 2H), 1.96-1.83 (m, 2H).

Example 364: N-(3-chloro-4-fluorophenyl)-N'-hydroxy-2-(neopentylamino)-1H-imidazo[4,5-b]pyridine-7-carboximidamide

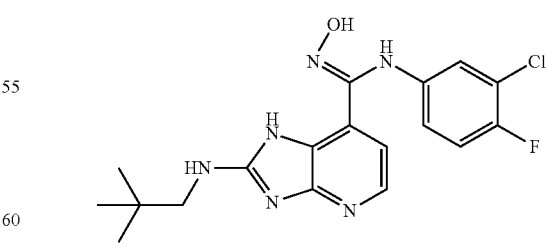

Example 364 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]

imidazol-7-yl)-4-(3-chloro-4-fluorophenyl)-1,2,4-oxadiazol-5(4H)-one and isopentylamine in place of tert-butyl (2-aminoethyl)carbamate. $C_{18}H_{20}ClFN_6O$. 391.2 (M+1). $^1$H NMR (400 MHz, DMSO-d6) δ 11.41 (s, 1H), 8.95 (s, 1H), 7.95 (d, J=6.3 Hz, 1H), 7.09 (t, J=8.9 Hz, 1H), 7.03 (dd, J=6.6, 2.7 Hz, 1H), 6.91 (d, J=6.2 Hz, 1H), 6.62-6.53 (m, 1H), 3.27 (d, J=6.3 Hz, 2H), 0.92 (s, 9H).

Example 365: N-(3-chloro-4-fluorophenyl)-N'-hydroxy-2-(isobutylamino)-1H-imidazo[4,5-b]pyridine-7-carboximidamide

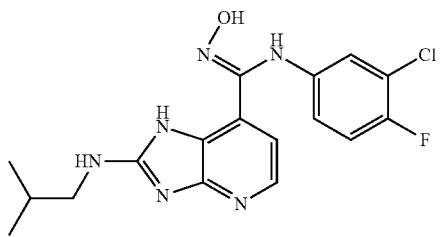 [SMILES: CC(C)CNc1nc2nccc(/C(=N/O)Nc3ccc(F)c(Cl)c3)c2[nH]1]

Example 365 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and isobutylamine in place of tert-butyl (2-aminoethyl)carbamate. $C_{17}H_{18}ClFN_6O$. 377.2 (M+1). $^1$H NMR (400 MHz, DMSO-d6) δ 11.38 (s, 1H), 8.95 (s, 1H), 7.95 (d, J=6.2 Hz, 1H), 7.08 (t, J=9.0 Hz, 1H), 7.03 (dd, J=6.6, 2.7 Hz, 1H), 6.91 (d, J=6.2 Hz, 1H), 6.61-6.51 (m, 1H), 3.29-3.18 (m, 2H), 1.95-1.78 (m, 1H), 0.90 (d, J=6.7 Hz, 6H).

Example 366: N-(3-chloro-4-fluorophenyl)-N'-hydroxy-2-(((tetrahydro-2H-pyran-2-yl)methyl)amino)-1H-imidazo[4,5-b]pyridine-7-carboximidamide

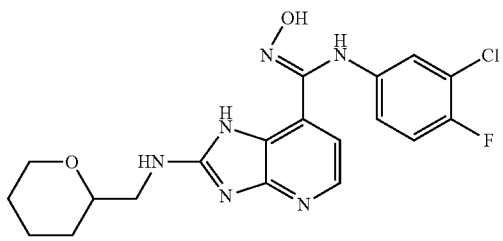 [SMILES: O/N=C(\Nc1ccc(F)c(Cl)c1)c1ccnc2nc(NCC3CCCCO3)[nH]c12]

Example 366 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and (tetrahydro-2H-pyran-2-yl)methanamine in place of tert-butyl (2-aminoethyl)carbamate. $C_{19}H_{20}ClFN_6O_2$. 419.2 (M+1). $^1$H NMR (400 MHz, DMSO-d6) δ 11.43 (s, 1H), 8.95 (s, 1H), 7.95 (d, J=6.4 Hz, 1H), 7.10 (t, J=9.0 Hz, 1H), 7.02 (dd, J=6.5, 2.7 Hz, 1H), 6.90 (d, J=6.3 Hz, 1H), 6.62-6.54 (m, 1H), 3.91 (d, J=11.2 Hz, 1H), 3.57-3.43 (m, 2H), 3.44-3.30 (m, 2H), 1.84-1.71 (m, 1H), 1.58 (d, J=12.7 Hz, 1H), 1.54-1.38 (m, 3H), 1.30-1.14 (m, 1H).

Example 367: N-(3-chloro-4-fluorophenyl)-N'-hydroxy-2-(((tetrahydrofuran-3-yl)methyl)amino)-1H-imidazo[4,5-b]pyridine-7-carboximidamide

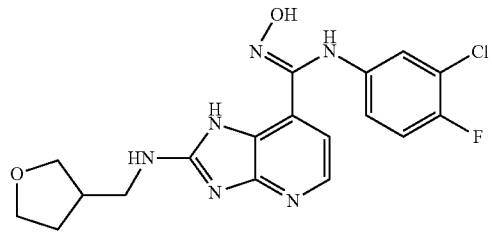 [SMILES: O/N=C(\Nc1ccc(F)c(Cl)c1)c1ccnc2nc(NCC3CCOC3)[nH]c12]

Example 367 was prepared analogously to Example 333 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and (tetrahydrofuran-3-yl)methanamine in place of tert-butyl (2-aminoethyl)carbamate. $C_{18}H_{18}ClFN_6O_2$. 405.2 (M+1). $^1$H NMR (400 MHz, DMSO-d6) δ 11.38 (s, 1H), 8.96 (s, 1H), 7.95 (d, J=6.3 Hz, 1H), 7.08 (t, J=9.0 Hz, 1H), 7.03 (dd, J=6.5, 2.7 Hz, 1H), 6.91 (d, J=6.2 Hz, 1H), 6.59-6.53 (m, 1H), 3.75 (td, J=8.1, 5.6 Hz, 1H), 3.68 (dd, J=8.6, 7.0 Hz, 1H), 3.62 (td, J=8.0, 6.7 Hz, 1H), 3.47 (dd, J=8.7, 5.1 Hz, 1H), 3.43-3.36 (m, 2H), 2.00-1.90 (m, 1H), 1.58 (dq, J=12.8, 6.4, 6.3 Hz, 1H).

Example 368: N-(3-chloro-4-fluorophenyl)-4-fluoro-N'-hydroxy-2-((2-morpholinoethyl)amino)-1H-benzo[d]imidazole-7-carboximidamide

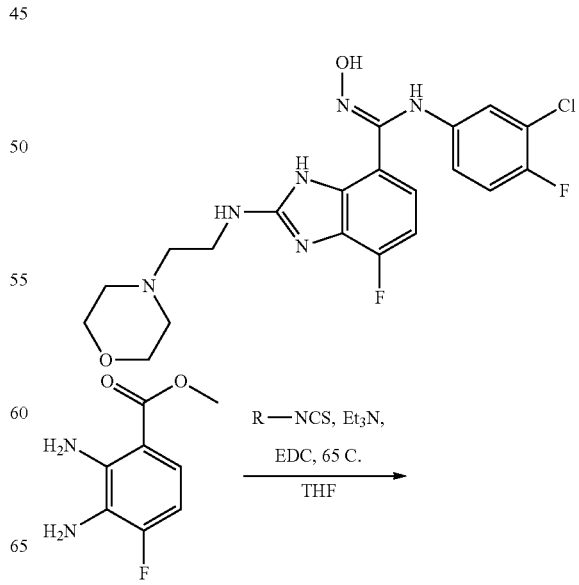

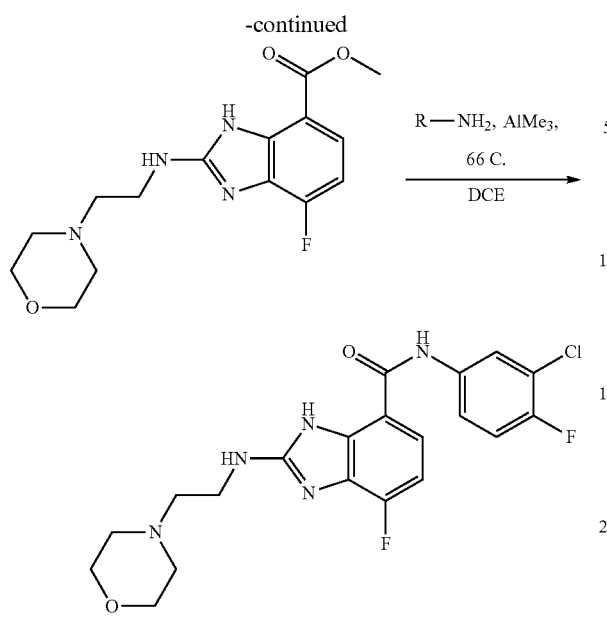

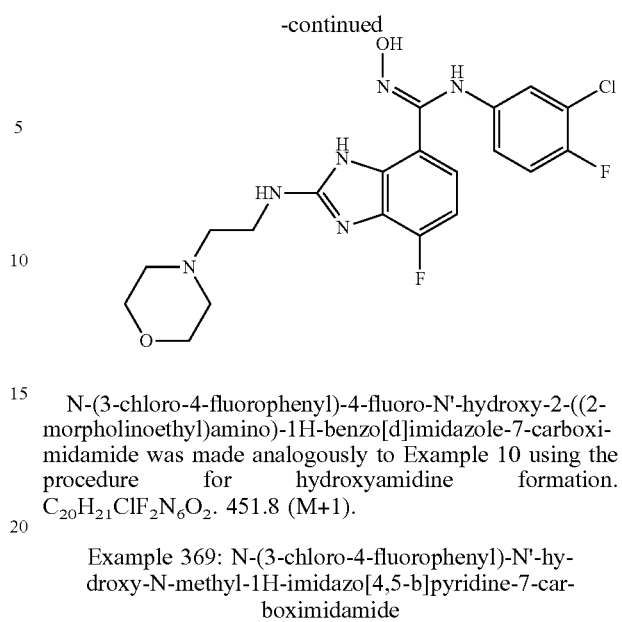

N-(3-chloro-4-fluorophenyl)-4-fluoro-N'-hydroxy-2-((2-morpholinoethyl)amino)-1H-benzo[d]imidazole-7-carboximidamide was made analogously to Example 10 using the procedure for hydroxyamidine formation. $C_{20}H_{21}ClF_2N_6O_2$. 451.8 (M+1).

Example 369: N-(3-chloro-4-fluorophenyl)-N'-hydroxy-N-methyl-1H-imidazo[4,5-b]pyridine-7-carboximidamide Methyl 2,3-diamino-4-fluorobenzoate (0.150 g, 0.814 mmol) was dissolved in THF (4.0 mL) and 4-(2-isothiocyanatoethyl)morpholine (5.0 mmol) and triethylamine (7.0 mmol) was added. The reaction was sealed in a vial and heated to 66° C. for 12 hours. 1-(3-dimethylaminopropyl)-3-ethylcarbodiimide hydrochloride (5.0 mmol) was added in one portion and the reaction was allowed to heat an additional 1 hour at 66° C. The reaction was cooled to rt and quenched with saturated sodium bicarbonate solution (4 mL). The reaction mixture was extracted with EtOAc (3×3 mL) and the combined organic layers were washed once with water, concentrated, and purified by silica gel column chromatography (0-15% MeOH/CH$_2$Cl$_2$, Rf=0.33 in 10% MeOH/CH$_2$Cl$_2$) to give methyl 4-fluoro-2-((2-morpholinoethyl)amino)-1H-benzo[d]imidazole-7-carboxylate.

Methyl 4-fluoro-2-((2-morpholinoethyl)amino)-1H-benzo[d]imidazole-7-carboxylate (0.208 g, 0.645 mmol) and 3-chloro-4-fluoroaniline (3.0 mmol) were dissolved in DCE (6.0 mL) under inert conditions. Trimethylaluminium (5.0 mmol, 2.26 mL) was added at 0 C and the reaction was then heated to 60 C overnight. The reaction was allowed to cool to rt, quenched with water (3 mL) and extracted with EtOAc (4×3 mL). The combined organic layers were washed once with water, concentrated, and purified by silica gel chromatography (Rf=0.37 10% MeOH/DCM) to give the desired product.

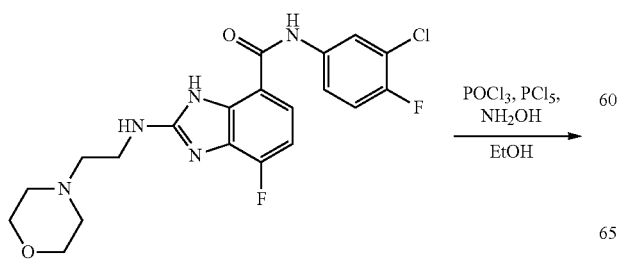

1H-imidazo[4,5-b]pyridine-7-carboxylic acid (0.20 g, 1.22 mmol) and 3-chloro-4-fluoro-N-methylaniline hydrochloride (1.02 mmol) were dissolved in DMF (3.0 mL) and HATU (1.2 mmol) and DIPEA (2.78 mmol) were added and the reaction was allowed to stir overnight at rt. The reaction was quenched with sat/sodium bicarbonate solution (3.0 mL) and the reaction was extracted with EtOAc (3 2 mL). Combined organic layers were washed with water (1×4 mL) and the crude was purified by silica gel chromatography (Rf=0.25 50% EtOAc/hex) to give N-(3-chloro-4-fluorophenyl)-N-methyl-1H-imidazo[4,5-b]pyridine-7-carboxamide.

N-(3-chloro-4-fluorophenyl)-N-methyl-1H-imidazo[4,5-b]pyridine-7-carboxamide (0.05 g, 0.164 mmol) was dissolved in toluene (3.0 mL) and Lawesson's reagent (0.656 mmol) was added. The reaction was sealed in a vial and heated overnight at 100 C. The reaction was then cooled to rt and solids were removed by vacuum filtration. The filtrate was concentrated and purified by silica gel chromatography to give N-(3-chloro-4-fluorophenyl)-N-methyl-1H-imidazo[4,5-b]pyridine-7-carbothioamide.

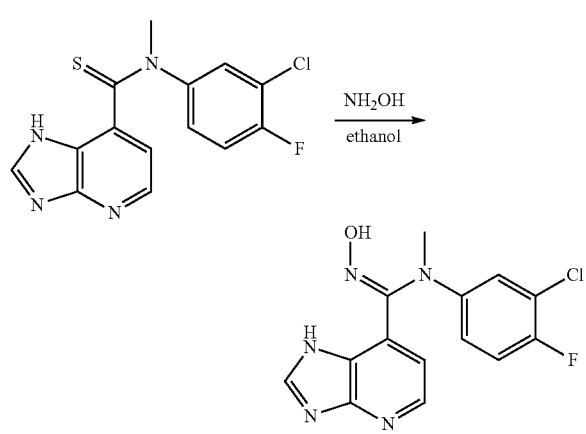

N-(3-chloro-4-fluorophenyl)-N-methyl-1H-imidazo[4,5-b]pyridine-7-carbothioamide (0.014 g, 0.0455 mmol) was dissolved in ethanol (3.0 mL) and hydroxylamine (50% solution in water) (0.455 mmol) was added and the reaction was allowed to stir at rt overnight. The reaction was concentrated to dryness then purified by RP HPLC to give N-(3-chloro-4-fluorophenyl)-N'-hydroxy-N-methyl-1H-imidazo[4,5-b]pyridine-7-carboximidamide (3.1 mg, 21%). $C_{14}H_{11}ClFN_5O$. 320.7 (M+1).

Example 370: 2-amino-N-(3-chloro-4-fluorophenyl)-5-fluoro-N'-hydroxy-1H-benzo[d]imidazole-7-carboximidamide

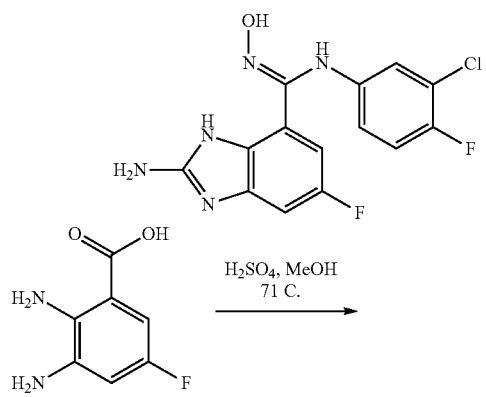

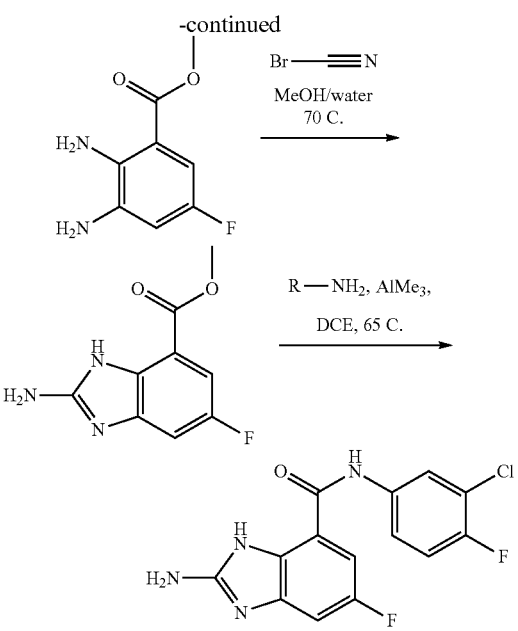

2,3-diamino-5-fluorobenzoic acid (5.0 g, 29 mmol) was dissolved in sulfuric acid (5.0 mL) and MeOH (40.0 mL) and heated to 71 C overnight. The reaction was allowed to cool to rt then concentrated to approximately half the volume. The reaction was neutralized to pH=7 with saturated sodium carbonate solution then extracted with EtOAc (5×20 mL). Combined organic layers were washed once with water and concentrated to dryness to give methyl 2,3-diamino-5-fluorobenzoate.

Methyl 2,3-diamino-5-fluorobenzoate (2.0 g, 11.0 mmol) and cyanogen bromide (11.0 mmol) were dissolved in methanol (45 mL) and water (20 mL) and heated to 70 C for 30 mins. The reaction was cooled to rt and diluted with water (5 mL) and EtOAc (20 mL). The water layer was separated and neutralized to pH=7 with saturated sodium carbonate solution then extracted with EtOAc (4×10 mL). The combined organic layers were washed once with water then concentrated to give methyl 2-amino-5-fluoro-1H-benzo[d]imidazole-7-carboxylate.

Methyl 2-amino-5-fluoro-1H-benzo[d]imidazole-7-carboxylate (0.2 g, 0.956 mmol) and 3-chloro-4-fluoroaniline (4.0 mmol) were dissolved in DCE (3.0 mL) and cooled to 0 C under an inert atmosphere. Trimethylaluminium (7.0 mmol, 3.34 mL) was added and the reaction was slowly heated to 65 C overnight. The reaction was cooled to rt, quenched with water (3 mL) and extracted with EtOAc (3×5 mL). Combined organic layers were washed once with water and purified by silica gel chromatography (Rf 100% EtOAc=0.32) to give 2-amino-N-(3-chloro-4-fluorophenyl)-5-fluoro-1H-benzo[d]imidazole-7-carboxamide.

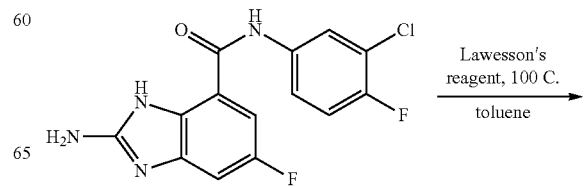

-continued

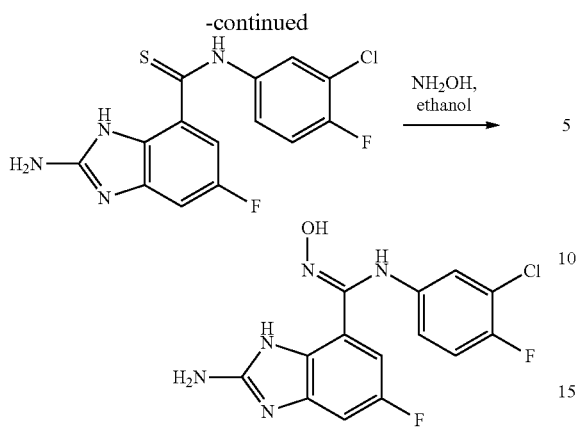

2-amino-N-(3-chloro-4-fluorophenyl)-5-fluoro-1H-benzo[d]imidazole-7-carboxamide and Lawesson's reagent (3.0 mmol) were dissolved in toluene and heated overnight at 100 C. The reaction was allowed to cool to rt and the solids were removed by filtration. The filtrate was concentrated and used directly in the next reaction with no further purification.

2-amino-N-(3-chloro-4-fluorophenyl)-5-fluoro-1H-benzo[d]imidazole-7-carbothioamide (0.267 g, 0.788 mmol) was dissolved in ethanol (3 mL) and hydroxylamine (50% solution in water) (0.5 mL) was added and the reaction was allowed to stir overnight at rt. The reaction was concentrated and purified by RP HPLC to give 2-amino-N-(3-chloro-4-fluorophenyl)-5-fluoro-N'-hydroxy-1H-benzo[d]imidazole-7-carboximidamide. $C_{14}H_{10}ClF_2N_5O$. 338.1 (M+1).

Example 371: 2-amino-N-(3-chlorophenyl)-5-fluoro-N'-hydroxy-1H-benzo[d]imidazole-7-carboximidamide

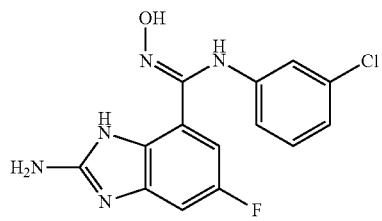 [SMILES: Nc1nc2cc(F)cc(/C(=N/O)Nc3cccc(Br)c3)c2[nH]1]

Example 371 was made analogously to Example 370 using 3-chloroaniline in place of 3-chloro-4-fluoroaniline. $C_{14}H_{11}ClFN_5O$. 320.7 (M+1). 1H NMR (400 MHz, DMSO-d6) δ 12.05 (s, 1H), 11.10 (s, 1H), 8.83 (s, 1H), 8.26 (s, 2H), 7.26 (dd, J=8.3, 2.4 Hz, 1H), 7.06 (t, J=8.3 Hz, 1H), 6.91 (dd, J=10.5, 2.4 Hz, 1H), 6.88-6.83 (m, 2H), 6.57-6.48 (m, 1H).

Example 372: 2-amino-N-(3-bromophenyl)-5-fluoro-N'-hydroxy-1H-benzo[d]imidazole-7-carboximidamide

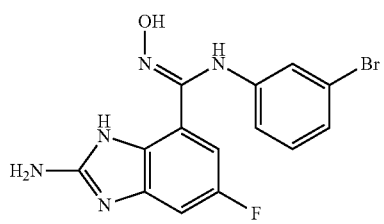

Example 372 was made analogously to Example 370 using 3-bromoaniline in place of 3-chloro-4-fluoroaniline. $C_{14}H_{11}BrFN_5O$. 365.2 (M+1). 1H NMR (400 MHz, DMSO-d6) δ 12.05 (s, 1H), 11.10 (s, 1H), 8.82 (s, 1H), 8.27 (s, 2H), 7.26 (dd, J=8.3, 2.4 Hz, 1H), 7.04-6.95 (m, 3H), 6.91 (dd, J=10.5, 2.4 Hz, 1H), 6.60-6.51 (m, 1H).

Example 373: 2-amino-N-(3-bromo-4-fluorophenyl)-5-fluoro-N'-hydroxy-1H-benzo[d]imidazole-7-carboximidamide

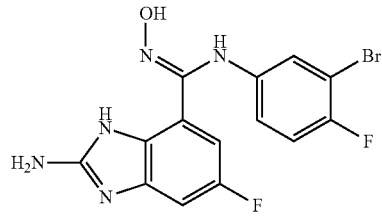 [SMILES: Nc1nc2cc(F)cc(/C(=N/O)Nc3ccc(F)c(Br)c3)c2[nH]1]

Example 373 was made analogously to Example 370 using 3-bromo-4-fluoroaniline in place of 3-chloro-4-fluoroaniline. $C_{14}H_{10}BrF_2N_5O$. 383.2 (M+1). 1H NMR (400 MHz, DMSO-d6) δ 12.11 (s, 1H), 11.03 (s, 1H), 8.79 (s, 1H), 8.36-8.23 (m, 2H), 7.26 (dd, J=8.3, 2.4 Hz, 1H), 7.13-7.04 (m, 2H), 6.92 (dd, J=10.5, 2.4 Hz, 1H), 6.60 (ddd, J=8.9, 4.2, 2.8 Hz, 1H).

Example 374: N-(3-chloro-4-fluorophenyl)-2-((2-(1,1-dioxidothiomorpholino)ethyl)amino)-4,5-difluoro-N'-hydroxy-1H-benzo[d]imidazole-7-carboximidamide

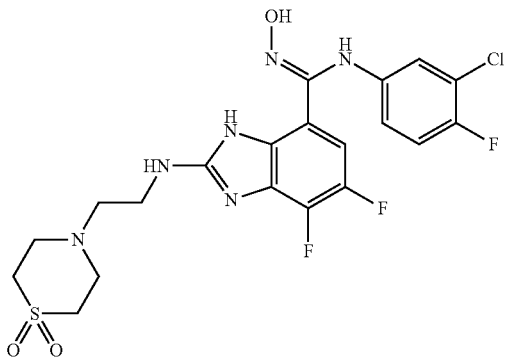 [SMILES: O=S1(=O)CCN(CCNc2nc3c(F)c(F)cc(/C(=N/O)Nc4ccc(F)c(Cl)c4)c3[nH]2)CC1]

Example 374 was made analogously to Example 32 using 4-(2-aminoethyl)thiomorpholine 1,1-dioxide. $C_{20}H_{20}ClF_3N_6O_3S$. 517.9 (M+1).

Example 375: N-(3-chloro-4-fluorophenyl)-2-((2-(diethylamino)ethyl)amino)-4-fluoro-N'-hydroxy-1H-benzo[d]imidazole-7-carboximidamide

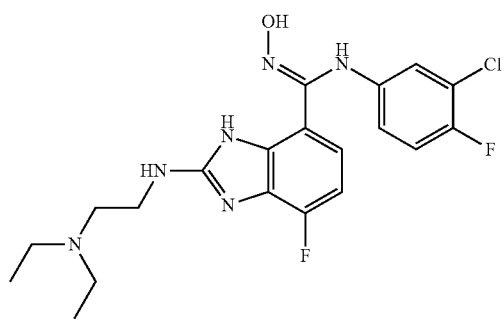

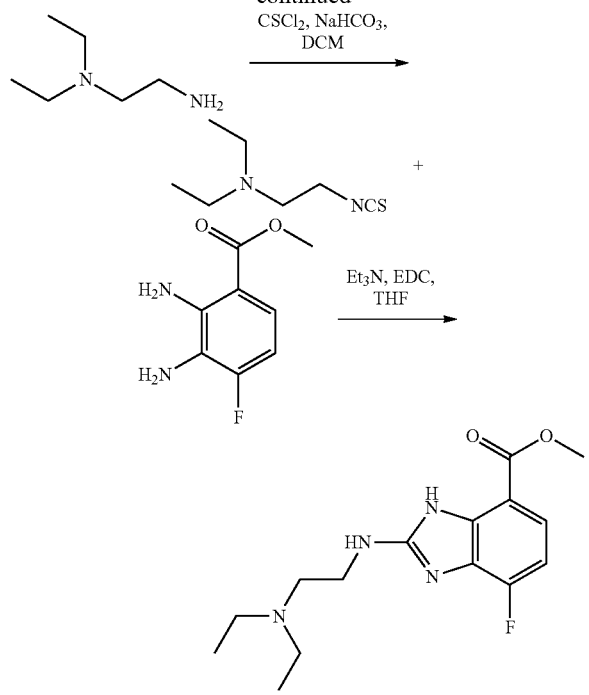

N$^1$,N$^1$-diethylethane-1,2-diamine (0.50 g, 4.0 mmol) and sodium bicarbonate (86 mmol) were dissolved in DCM (12.0 mL) under argon. Thiophosgene (17.0 mmol) was added dropwise and the reaction was allowed to stir at rt for 2 hours. DCM (10 mL) and water (10 mL) were added and the water layer was extracted with DCM (2×8 mL). Combined organic layers were washed with water (1×20 mL) and concentrated to a volume of 5 mL to give N,N-diethyl-2-isothiocyanatoethan-1-amine which was used without further purification.

N-(3-chloro-4-fluorophenyl)-2-((2-(diethylamino)ethyl)amino)-4-fluoro-N'-hydroxy-1H-benzo[d]imidazole-7-carboximidamide was made analogously to Example 23 using N,N-diethyl-2-isothiocyanatoethan-1-amine, methyl 2,3-diamino-4-fluorobenzoate, and 3-chloro-4-fluoroaniline. $C_{20}H_{22}ClF_3N_6O$. 437.9 (M+1).

Example 376: N-(3-chloro-4-fluorophenyl)-4-fluoro-N'-hydroxy-2-((2-(pyrrolidin-1-yl)ethyl)amino)-1H-benzo[d]imidazole-7-carboximidamide

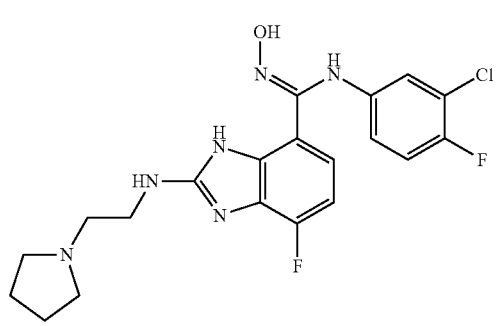 [SMILES: O/N=C(\Nc1ccc(F)c(Cl)c1)c1ccc(F)c2nc(NCCN3CCCC3)[nH]c12]

Example 376 was made analogously to Example 375 using 2-(pyrrolidin-1-yl)ethan-1-amine in place of N$^1$,N$^1$-diethylethane-1,2-diamine. $C_{20}H_{21}ClF_2N_6O$. 435.8 (M+1).

Example 377: N-(3-chloro-4-fluorophenyl)-4,5-difluoro-N'-hydroxy-2-((2-morpholinopropyl)amino)-1H-benzo[d]imidazole-7-carboximidamide

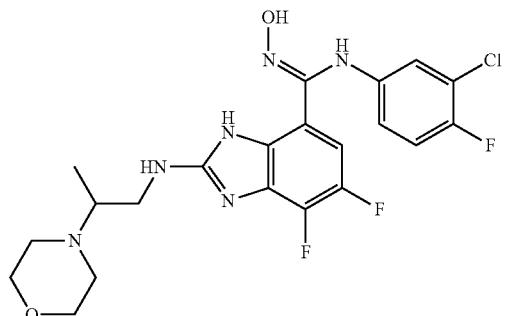

Example 377 was made analogously to Example 32 using 2-morpholinopropan-1-amine. $C_{21}H_{22}ClF_3N_6O_2$ 483.9 (M+1). 1H NMR (400 MHz, DMSO-d6) δ 10.82 (s, 1H), 8.71 (s, 1H), 7.17 (s, 1H), 7.09 (td, J=9.1, 2.4 Hz, 2H), 6.94 (dd, J=6.5, 2.7 Hz, 1H), 6.88 (dd, J=12.2, 6.9 Hz, 1H), 6.78 (d, J=6.4 Hz, 1H), 6.60 (d, J=9.1 Hz, 1H), 6.54 (ddd, J=9.0, 4.1, 2.7 Hz, 1H), 3.89 (s, 4H), 3.72 (s, 1H), 3.69-3.55 (m, 2H), 3.37 (s, 4H), 1.29 (d, J=6.6 Hz, 3H).

Example 378: N-(3-chloro-4-fluorophenyl)-2-((1-(dimethylamino)propan-2-yl)amino)-4,5-difluoro-N'-hydroxy-1H-benzo[d]imidazole-7-carboximidamide

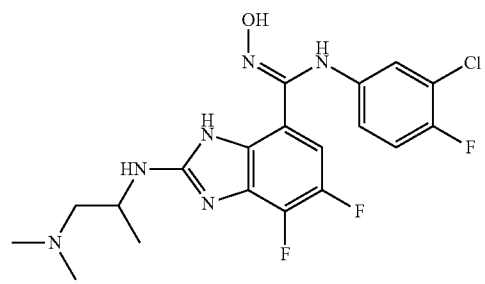 [SMILES: CC(CN(C)C)Nc1nc2c(F)c(F)cc(/C(=N/O)Nc3ccc(F)c(Cl)c3)c2[nH]1]

Example 378 was made analogously to Example 23 using N$^1$,N$^1$-dimethylpropane-1,2-diamine. $C_{19}H_{20}ClF_3N_6O$. 441.8 (M+1).

Example 379: N-(3-chloro-4-fluorophenyl)-2-((2-(dimethylamino)ethyl)amino)-5-fluoro-N'-hydroxy-1H-benzo[d]imidazole-7-carboximidamide

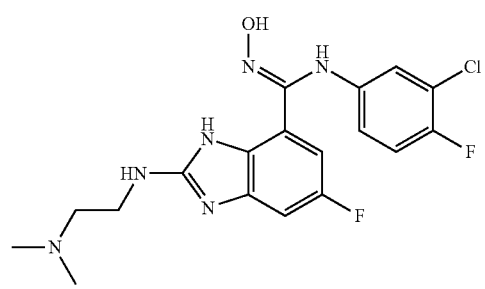 [SMILES: CN(C)CCNc1nc2cc(F)cc(/C(=N/O)Nc3ccc(F)c(Cl)c3)c2[nH]1]

Example 379 was made analogously to Example 23 using methyl 2,3-diamino-5-fluorobenzoate and 2-isothiocyanato- N,N-dimethylethan-1-amine. $C_{18}H_{19}ClF_2N_6O$. 409.8 (M+1). 1H NMR (400 MHz, Methanol-d4) δ −7.19 (dd, J=8.1, 2.4 Hz, 1H), 6.97 (t, J=8.9 Hz, 1H), 6.94-6.89 (m, 2H), 6.69 (dt, J=8.8, 3.4 Hz, 1H), 3.85 (d, J=5.8 Hz, 3H), 3.46 (dd, J=12.2, 6.4 Hz, 3H), 2.99 (s, 6H).

Example 380: N-(3-chloro-4-fluorophenyl)-5-fluoro-N'-hydroxy-2-((2-(pyrrolidin-1-yl)ethyl)amino)-1H-benzo[d]imidazole-7-carboximidamide

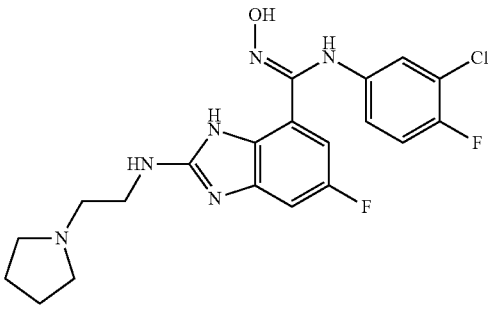 [SMILES: O/N=C(\Nc1ccc(F)c(Cl)c1)c1cc(F)cc2nc(NCCN3CCCC3)[nH]c12]

Example 380 was made analogously to Example 375 using 1-(2-isothiocyanatoethyl)pyrrolidine. $C_{20}H_{21}ClF_2N_6O$. 435.8 (M+1).

Example 381: N-(3-chloro-4-fluorophenyl)-2-((3-(dimethylamino)-2,2-dimethylpropyl)amino)-4-fluoro-N'-hydroxy-1H-benzo[d]imidazole-7-carboximidamide

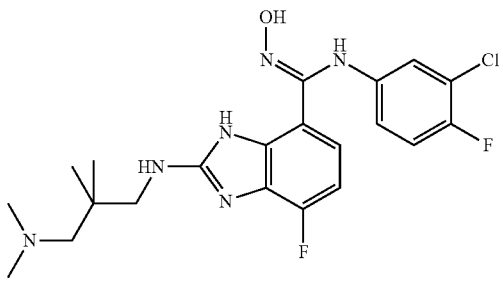 [SMILES: CN(C)CC(C)(C)CNc1nc2c(F)ccc(/C(=N/O)Nc3ccc(F)c(Cl)c3)c2[nH]1]

Example 381 was made analogously to Example 23 using methyl 2,3-diamino-4-fluorobenzoate and 3-isothiocyanato-N,N,2,2-tetramethylpropan-1-amine (made from $N^1,N^1,2,2$-tetramethylpropane-1,3-diamine). $C_{21}H_{25}ClF_2N_6O$. 451.9 (M+1).

Example 382: N-(3-bromo-4-fluorophenyl)-2-((2-(dimethylamino)ethyl)amino)-4-fluoro-N'-hydroxy-1H-benzo[d]imidazole-7-carboximidamide

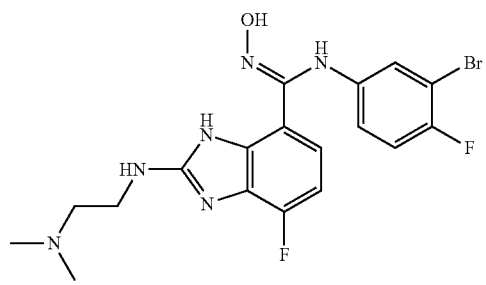 [SMILES: CN(C)CCNc1nc2c(F)ccc(/C(=N/O)Nc3ccc(F)c(Br)c3)c2[nH]1]

Example 382 was made analogously to Example 23 using methyl 2,3-diamino-4-fluorobenzoate, 2-isothiocyanato-N,N-dimethylethan-1-amine, and 3-bromo-4-fluoroaniline. $C_{18}H_{19}BrF_2N_6O$. 454.3 (M+1). 1H NMR (400 MHz, Methanol-d4) δ 7.41 (dd, J=6.0, 2.4 Hz, 1H), 7.36 (dd, J=8.7, 4.4 Hz, 1H), 7.16 (dd, J=9.9, 8.7 Hz, 1H), 7.09-7.01 (m, 2H), 3.94 (t, J=5.9 Hz, 2H), 3.52 (t, J=6.0 Hz, 2H), 3.01 (s, 6H).

Example 383: N-(3-bromophenyl)-2-((2-(dimethylamino)ethyl)amino)-4-fluoro-N'-hydroxy-1H-benzo[d]imidazole-7-carboximidamide

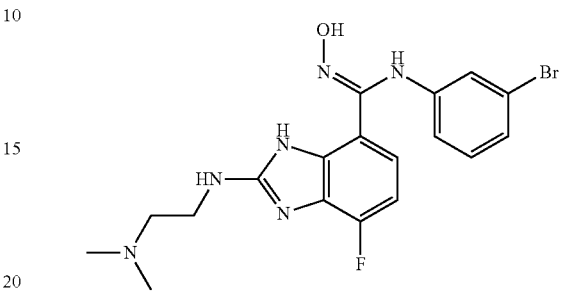

Example 383 was made analogously to Example 23 using methyl 2,3-diamino-4-fluorobenzoate, 2-isothiocyanato-N,N-dimethylethan-1-amine, and 3-bromoaniline. $C_{18}H_{20}BrFN_6O$. 436.3 (M+1). 1H NMR (400 MHz, Methanol-d4) δ −7.33 (dd, J=8.8, 4.5 Hz, 1H), 7.26 (d, J=8.4 Hz, 2H), 7.19-7.06 (m, 2H), 6.93 (d, J=8.6 Hz, 1H), 3.92 (t, J=6.0 Hz, 2H), 3.51 (t, J=6.0 Hz, 2H), 3.01 (s, 6H).

Example 384: N-(3-chlorophenyl)-2-((2-(dimethylamino)ethyl)amino)-4-fluoro-N'-hydroxy-1H-benzo[d]imidazole-7-carboximidamide

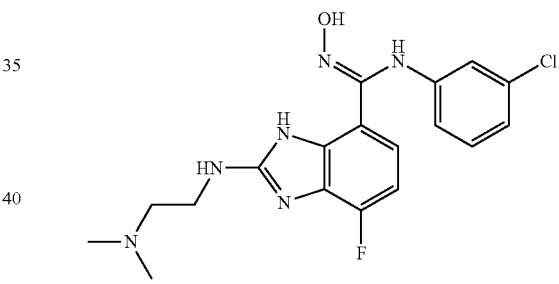

Example 384 was made analogously to Example 23 using methyl 2,3-diamino-4-fluorobenzoate, 2-isothiocyanato-N,N-dimethylethan-1-amine, and 3-chloroaniline. $C_{18}H_{20}ClFN_6O$. 391.8 (M+1). 1H NMR (400 MHz, Methanol-d4) δ −7.39 (dd, J=8.7, 4.4 Hz, 1H), 7.22-7.01 (m, 5H), 6.94 (dq, J=7.1, 2.3 Hz, 1H), 3.94 (t, J=6.0 Hz, 2H), 3.52 (t, J=6.1 Hz, 3H), 3.00 (s, 6H).

Example 385: N-(3-chlorophenyl)-2-((3-(dimethylamino)propyl)amino)-4,5-difluoro-N'-hydroxy-1H-benzo[d]imidazole-7-carboximidamide

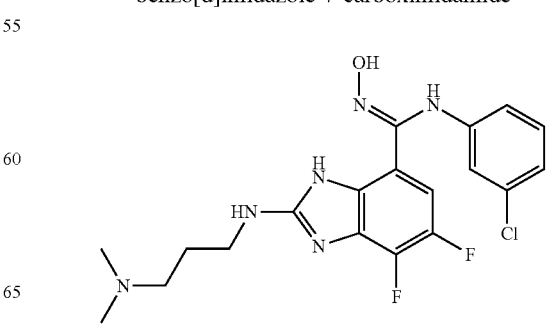

Example 385 was made analogously to Example 32 using methyl 2-chloro-4,5-difluoro-1-((2-(trimethylsilyl)ethoxy)methyl)-1H-benzo[d]imidazole-7-carboxylate, N1,N1-dimethylpropane-1,3-diamine, and 3-chloroaniline. C$_{19}$H$_{21}$ClF$_2$N$_6$O. 423.9 (M+1). 1H NMR (400 MHz, DMSO-d6) δ 10.88 (s, 1H), 9.69 (s, 1H), 8.74 (s, 1H), 7.05 (t, J=8.3 Hz, 1H), 6.95-6.78 (m, 3H), 6.52 (dt, J=8.3, 1.6 Hz, 1H), 3.42 (d, J=6.4 Hz, 2H), 3.09 (d, J=10.5 Hz, 2H), 2.80 (d, J=4.4 Hz, 6H), 1.94 (p, J=6.8 Hz, 2H).

Example 386: N-(3-bromophenyl)-2-((3-(dimethylamino)propyl)amino)-4,5-difluoro-N'-hydroxy-1H-benzo[d]imidazole-7-carboximidamide

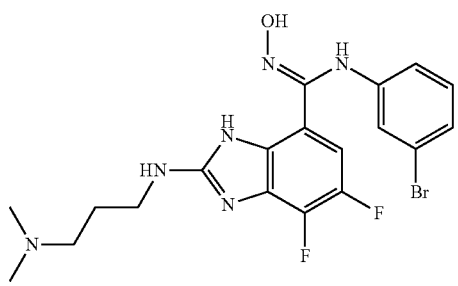 [SMILES: CN(C)CCCNc1nc2c(F)c(F)cc(/C(=N/O)Nc3cccc(Br)c3)c2[nH]1]

Example 386 was made analogously to Example 32 using methyl 2-chloro-4,5-difluoro-1-((2-(trimethylsilyl)ethoxy)methyl)-1H-benzo[d]imidazole-7-carboxylate, N1,N1-dimethylpropane-1,3-diamine, and 3-bromoaniline. C$_{19}$H$_{21}$BrF$_2$N$_6$O. 468.3 (M+1). 1H NMR (400 MHz, Methanol-d4) δ −7.37-7.27 (m, 1H), 7.10-6.99 (m, 3H), 6.69 (ddd, J=8.0, 2.2, 1.1 Hz, 1H), 3.57 (t, J=6.6 Hz, 2H), 3.28-3.21 (m, 2H), 2.93 (s, 6H), 2.18-2.08 (m, 2H).

Example 387: N-(3-bromo-4-fluorophenyl)-2-((3-(dimethylamino)propyl)amino)-4,5-difluoro-N'-hydroxy-1H-benzo[d]imidazole-7-carboximidamide

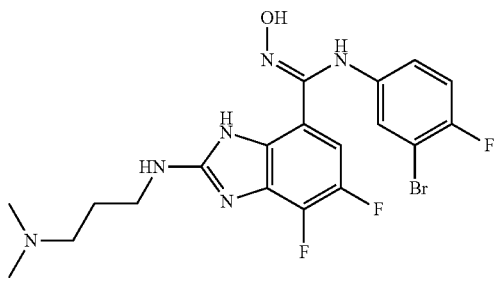 [SMILES: CN(C)CCCNc1nc2c(F)c(F)cc(/C(=N/O)Nc3ccc(F)c(Br)c3)c2[nH]1]

Example 387 was made analogously to Example 32 using methyl 2-chloro-4,5-difluoro-1-((2-(trimethylsilyl)ethoxy)methyl)-1H-benzo[d]imidazole-7-carboxylate, N1,N1-dimethylpropane-1,3-diamine, and 3-bromo-4-fluoroaniline. C$_{19}$H$_{20}$BrF$_3$N$_6$O. 486.3 (M+1). 1H NMR (400 MHz, Methanol-d4) δ 7.14-7.04 (m, 2H), 6.96 (t, J=8.6 Hz, 1H), 6.74 (ddd, J=8.9, 4.0, 2.7 Hz, 1H), 3.56 (t, J=6.6 Hz, 2H), 3.28-3.21 (m, 2H), 2.93 (s, 6H), 2.17-2.09 (m, 2H).

Example 388: N-(3-chloro-4-fluorophenyl)-2-((3-(dimethylamino)propyl)amino)-4-fluoro-N'-hydroxy-1H-benzo[d]imidazole-7-carboximidamide

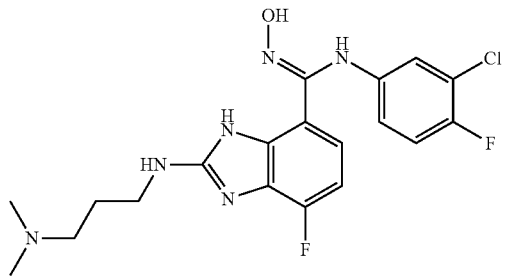 [SMILES: CN(C)CCCNc1nc2c(F)ccc(/C(=N/O)Nc3ccc(F)c(Cl)c3)c2[nH]1]

Example 388 was made analogously to Example 23 using methyl 2,3-diamino-4-fluorobenzoate and 3-isothiocyanato-N,N-dimethylpropan-1-amine. C$_{19}$H$_{21}$ClF$_2$N$_6$O. 423.8 (M+1) 1H NMR (400 MHz, Methanol-d4) δ 7.44 (dd, J=8.8, 4.3 Hz, 1H), 7.39 (dd, J=6.4, 2.3 Hz, 1H), 7.23 (dd, J=9.8, 8.8 Hz, 1H), 7.15-7.05 (m, 2H), 3.62 (t, J=6.8 Hz, 2H), 3.34-3.30 (m, 2H), 2.17 (t, J=8.0 Hz, 2H).

Example 389: N-(3-chloro-4-fluorophenyl)-2-((3-(dimethylamino)propyl)amino)-5-fluoro-N'-hydroxy-1H-benzo[d]imidazole-7-carboximidamide

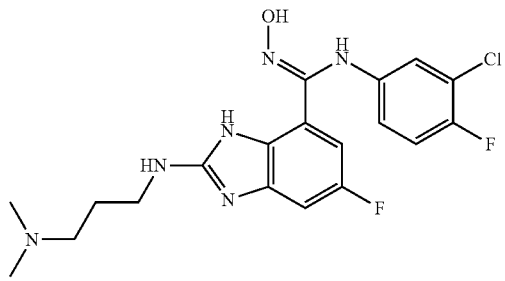 [SMILES: CN(C)CCCNc1nc2cc(F)cc(/C(=N/O)Nc3ccc(F)c(Cl)c3)c2[nH]1]

Example 389 was made analogously to Example 23 using methyl 2,3-diamino-5-fluorobenzoate, 3-isothiocyanato-N,N-dimethylpropan-1-amine, and 3-chloro-4-fluoroaniline. C$_{19}$H$_{21}$ClF$_2$N$_6$O. 423.8 (M+1).

Example 390: 2-((2-(benzyl(methyl)amino)ethyl)amino)-N-(3-chloro-4-fluorophenyl)-4,5-difluoro-N'-hydroxy-W-benzo[d]imidazole-7-carboximidamide

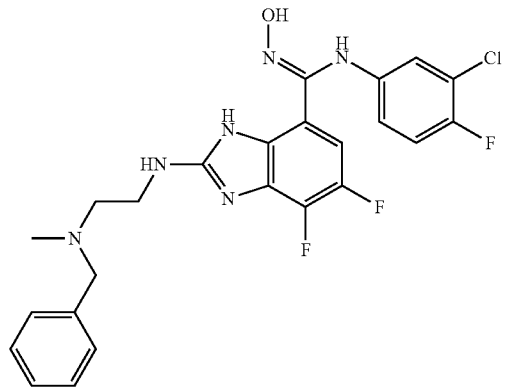 [SMILES: CN(CCNc1nc2c(F)c(F)cc(/C(=N/O)Nc3ccc(F)c(Cl)c3)c2[nH]1)Cc1ccccc1]

Example 390 was made analogously to Example 32 using N$^1$-benzyl-N$^1$-methylethane-1,2-diamine. C$_{24}$H$_{22}$ClF$_3$N$_6$O. 503.9 (M+1).

Example 391: N-(3-chloro-4-fluorophenyl)-2-(2-((cyclohexylmethyl)(methyl)amino)ethyl)-N'-hydroxy-1H-imidazo[4,5-b]pyridine-7-carboximidamide

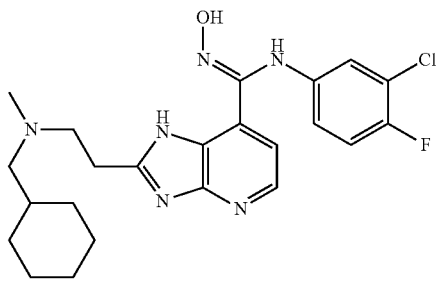 [SMILES: CN(CCc1nc2nccc(/C(=N/O)Nc3ccc(F)c(Cl)c3)c2[nH]1)CC1CCCCC1]

Example 391 was made analogously to Example 184 using N-(3-chloro-4-fluorophenyl)-2-(2-hydroxyethyl)-1H-imidazo[4,5-b]pyridine-7-carboxamide and 1-cyclohexyl-N-methylmethanamine. $C_{23}H_{28}ClFN_6O$. 459.9 (M+1).

Example 392: N-(3-chloro-4-fluorophenyl)-N'-hydroxy-2-(2-(methyl(neopentyl)amino)ethyl)-1H-imidazo[4,5-b]pyridine-7-carboximidamide

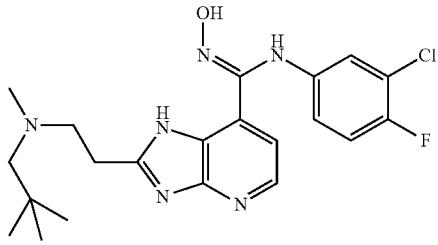 [SMILES: CN(CCc1nc2nccc(/C(=N/O)Nc3ccc(F)c(Cl)c3)c2[nH]1)CC(C)(C)C]

Example 392 was made analogously to Example 184 using N,2,2-trimethylpropan-1-amine hydrochloride. $C_{21}H_{26}ClFN_6O$. 434.1 (M+1).

Example 393: N-(3-chloro-4-fluorophenyl)-2-(2-(cyclohexyl(methyl)amino)ethyl)-N'-hydroxy-1H-imidazo[4,5-b]pyridine-7-carboximidamide

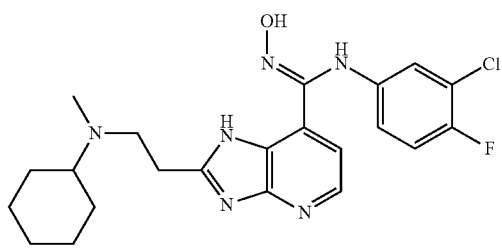 [SMILES: CN(CCc1nc2nccc(/C(=N/O)Nc3ccc(F)c(Cl)c3)c2[nH]1)C1CCCCC1]

Example 393 was made analogously to Example 184 using N-methylcyclohexanamine. $C_{22}H_{26}ClFN_6O$. 445.9 (M+1).

Example 394: N-(3-chloro-4-fluorophenyl)-4,5-difluoro-N'-hydroxy-2-((2-(methyl((tetrahydro-2H-pyran-4-yl)methyl)amino)ethyl)amino)-1H-benzo[d]imidazole-7-carboximidamide

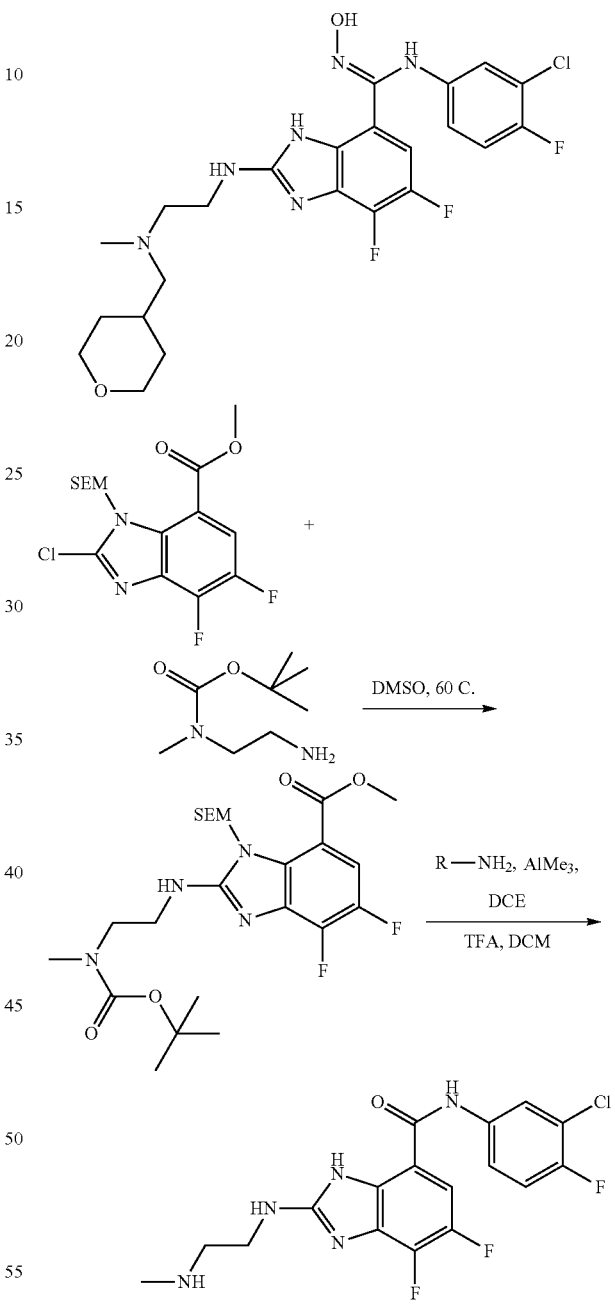

Methyl 2-chloro-4,5-difluoro-1-((2-(trimethylsilyl)ethoxy)methyl)-1H-benzo[d]imidazole-7-carboxylate (1.39 g, 4.0 mmol) and tert-butyl (2-aminoethyl)(methyl)carbamate (6.0 mmol) were dissolved in DMSO (5.0 mL) and heated overnight at 60 C. The reaction was allowed to cool to rt and quenched with water (3 mL). The reaction was extracted with EtOAc (5×3 mL) and combined organic layers were washed once with water and purified by silica gel column chromatography to give methyl 2-((2-((tertbutoxycarbonyl)(methyl)amino)ethyl)amino)-4,5-difluoro-1-((2-(trimethylsilyl)ethoxy)methyl)-1H-benzo[d]imidazole-7-carboxylate.

Methyl 2-((2-(((tert-butoxycarbonyl)(methyl)amino)ethyl)amino)-4,5-difluoro-1-((2-(trimethylsilyl)ethoxy)methyl)-1H-benzo[d]imidazole-7-carboxylate (1.14 g, 2.0 mmol) and 3-chloro-4-fluoroaniline (9.0 mmol) were dissolved in DCE (15.0 mL) under an inert atmosphere. Triemthylaluminium (9.0 mmol, 4.430 mL) was added at 0 C and the reaction was allowed to come to rt and stir overnight. The reaction was quenched with water (5 mL) and extracted with DCM (3×6 mL). Combined organic layers were washed with water (1×8 mL) and concentrated to dryness. The crude was dissolved in DCM (8 mL) and TFA (4 mL) was added and the reaction was allowed to stir at rt for 1 hour. The reaction was concentrated and purified by silica gel chromatography to give N-(3-chloro-4-fluorophenyl)-4,5-difluoro-2-((2-(methylamino)ethyl)amino)-1H-benzo[d]imidazole-7-carboxamide.

(0.053 g, 0.132 mmol) and tetrahydro-2H-pyran-4-carbaldehyde (0.126 mmol) were dissolved in DCE (2.0 mL) under inert conditions. Sodium triacetoxyborohydride (STAB) (0.176 mmol) was added and the reaction was allowed to stir for 2 hours at rt. The reaction was quenched with water (3 mL) and then extracted with DCM (3×4 mL). Combined organic layers were washed once with water, dried over $Mg_2SO_4$, filtered, and concentrated to give N-(3-chloro-4-fluorophenyl)-4,5-difluoro-2-((2-(methyl((tetrahydro-2H-pyran-4-yl)methyl)amino)ethyl)amino)-1H-benzo[d]imidazole-7-carboxamide, which was then converted to N-(3-chloro-4-fluorophenyl)-4,5-difluoro-N'-hydroxy-2-((2-(methyl((tetrahydro-2H-pyran-4-yl)methyl)amino)ethyl)amino)-1H-benzo[d]imidazole-7-carboximidamide using hydroxyamidine formation conditions described herein. $C_{23}H_{26}ClF_3N_6O_2$. 512.0 (M+1). 1H NMR (400 MHz, Methanol-d4) δ 7.45 (s, 1H), 6.95 (t, J=8.9 Hz, 1H), 6.86 (td, J=7.4, 4.9 Hz, 2H), 6.66-6.60 (m, 1H), 3.90-3.81 (m, 2H), 3.75 (t, J=5.1 Hz, 2H), 3.43 (d, J=5.9 Hz, 2H), 3.41-3.35 (m, 2H), 3.14 (d, J=7.1 Hz, 2H), 3.00 (s, 3H), 1.71 (d, J=13.0 Hz, 2H), 1.43-1.26 (m, 3H).

Example 395: N-(3-chloro-4-fluorophenyl)-4,5-difluoro-N'-hydroxy-2-((2-(methylamino)ethyl)amino)-1H-benzo[d]imidazole-7-carboximidamide

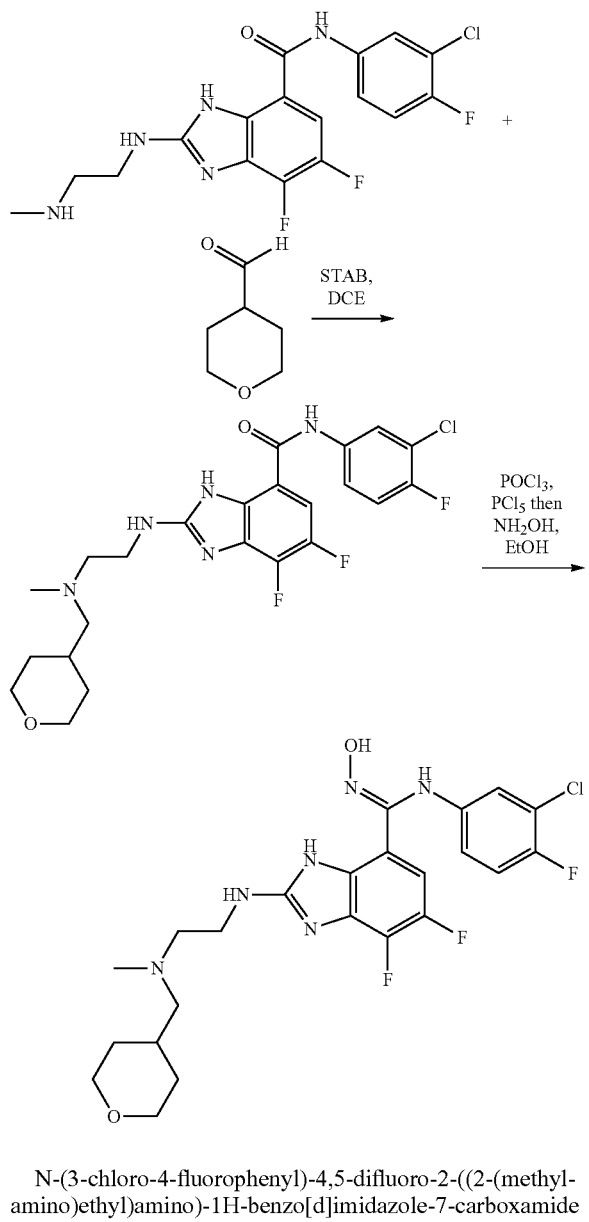

N-(3-chloro-4-fluorophenyl)-4,5-difluoro-2-((2-(methylamino)ethyl)amino)-1H-benzo[d]imidazole-7-carboxamide

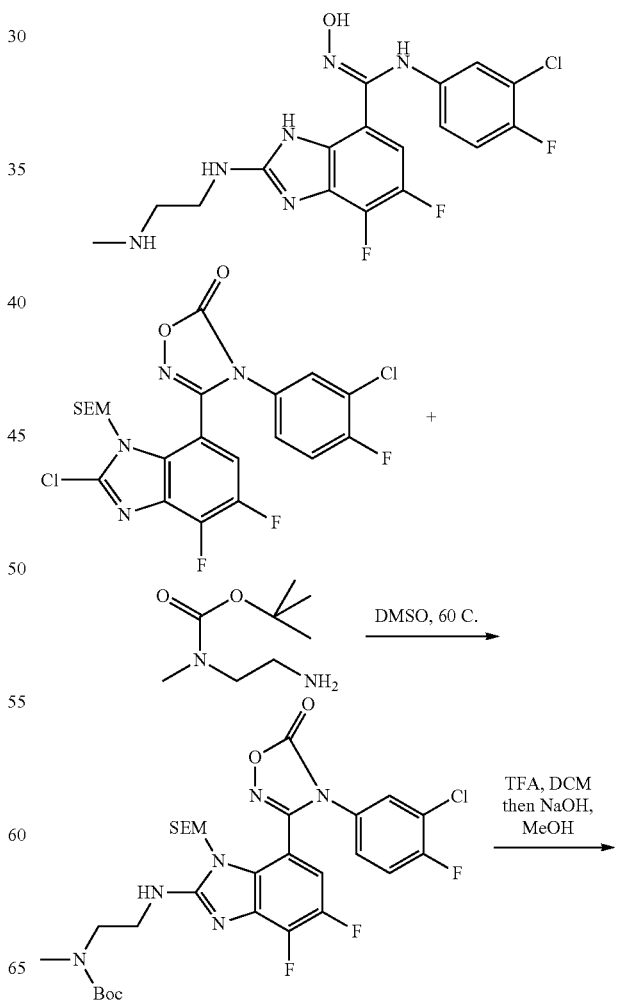

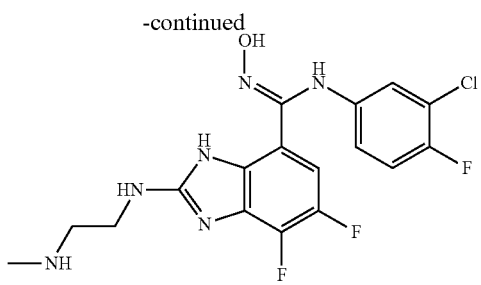

3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one (0.03 g, 0.0565 mmol) and tert-butyl (2-aminoethyl)(methyl)carbamate (0.0847 mmol) were dissolved in DMS (0.6 mL) and heated overnight at 60 C. The reaction was cooled to rt, diluted with water, and extracted with DCM (3×1 mL). Combined organic layers were washed once with water and concentrated to give tert-butyl (2-((7-(4-(3-chloro-4-fluorophenyl)-5-oxo-4,5-dihydro-1,2,4-oxadiazol-3-yl)-4,5-difluoro-1-((2-(trimethylsilyl)ethoxy)methyl)-1H-benzo[d]imidazol-2-yl)amino)ethyl)(methyl)carbamate which was used without further purification.

Tert-butyl (2-((7-(4-(3-chloro-4-fluorophenyl)-5-oxo-4,5-dihydro-1,2,4-oxadiazol-3-yl)-4,5-difluoro-1-((2-(trimethylsilyl)ethoxy)methyl)-1H-benzo[d]imidazol-2-yl)amino)ethyl)(methyl)carbamate (0.057 mmol) was dissolved in DCM (2 mL) and TFA (1.0 mL) was added and the reaction was allowed to stir at rt for 2 hours before being concentrated to dryness. The residue was then dissolved in MeOH (2.0 mL) and 1M NaOH (0.5 mL) was added and the reaction was allowed to stir at rt for 30 mins. The reaction was then concentrated and purified by RP HPLC to N-(3-chloro-4-fluorophenyl)-4,5-difluoro-N'-hydroxy-2-((2-(methylamino)ethyl)amino)-1H-benzo[d]imidazole-7-carboximidamide. $C_{17}H_{16}ClF_3N_6O$. 413.8 (M+1). 1H NMR (400 MHz, DMSO-d6) δ 10.72 (s, 1H), 8.65 (s, 1H), 8.50 (s, 2H), 6.98 (t, J=9.1 Hz, 1H), 6.85-6.80 (m, 1H), 6.76 (s, 1H), 6.42 (dt, J=8.9, 3.4 Hz, 1H), 3.52 (d, J=5.8 Hz, 2H), 3.04 (t, J=5.9 Hz, 2H), 2.50 (t, J=5.3 Hz, 3H).

Example 396: 2-(2-(benzyl(methyl)amino)ethyl)-N-(3-chloro-4-fluorophenyl)-N'-hydroxy-1H-imidazo[4,5-b]pyridine-7-carboximidamide

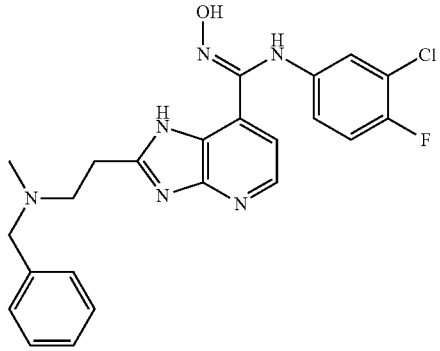 [SMILES: CN(CCc1nc2nccc(/C(=N/O)Nc3ccc(F)c(Cl)c3)c2[nH]1)Cc1ccccc1]

Example 396 was made analogously to Example 184 using N-(3-chloro-4-fluorophenyl)-2-(2-hydroxyethyl)-1H-imidazo[4,5-b]pyridine-7-carboxamide and N-methyl-1-phenylmethanamine. $C_{23}H_{22}ClFN_6O$. 454.1 (M+1). 1H NMR (400 MHz, DMSO-d6) δ 11.07 (s, 1H), 8.90 (s, 1H), 8.30 (d, J=5.0 Hz, 1H), 7.56 (dd, J=6.4, 3.3 Hz, 2H), 7.50 (dt, J=4.5, 2.9 Hz, 3H), 7.15 (d, J=5.1 Hz, 1H), 7.03 (t, J=9.1 Hz, 1H), 6.91 (dd, J=6.5, 2.7 Hz, 1H), 6.51 (ddd, J=8.9, 4.0, 2.7 Hz, 1H), 4.44 (s, 2H), 3.57 (t, J=7.5 Hz, 2H), 3.36 (t, J=7.4 Hz, 2H), 2.76 (s, 3H).

Example 397: N-(3-chloro-4-fluorophenyl)-2-((2-((2-ethylbutyl)(methyl)amino)ethyl)amino)-4,5-difluoro-N'-hydroxy-1H-benzo[d]imidazole-7-carboximidamide

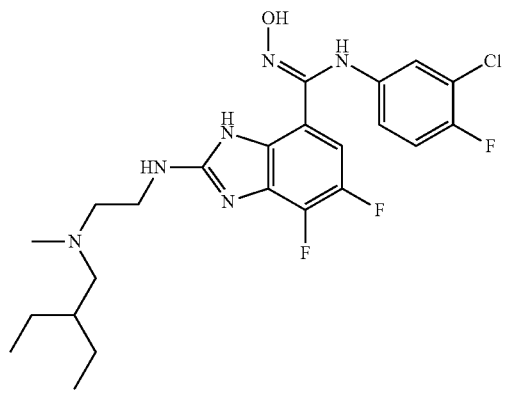 [SMILES: CCC(CC)CN(C)CCNc1nc2c(F)c(F)cc(/C(=N/O)Nc3ccc(F)c(Cl)c3)c2[nH]1]

Example 397 was made analogously to Example 395 using 2-ethylbutanal for the reductive amination. $C_{23}H_{28}ClF_3N_6O$. 498.1 (M+1).

Example 398: N-(3-chloro-4-fluorophenyl)-2-((2-((cyclopropylmethyl)(methyl)amino)ethyl)amino)-4,5-difluoro-N'-hydroxy-1H-benzo[d]imidazole-7-carboximidamide

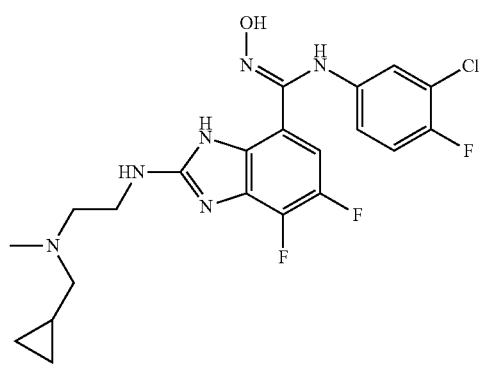 [SMILES: CN(CCNc1nc2c(F)c(F)cc(/C(=N/O)Nc3ccc(F)c(Cl)c3)c2[nH]1)CC1CC1]

Example 398 was made analogously to Example 394 using cyclopropanecarbaldehyde for the reductive amination. $C_{21}H_{22}ClF_3N_6O$. 468.1 (M+1). 1H NMR (400 MHz, Methanol-d4) δ 6.95 (t, J=8.9 Hz, 1H), 6.92-6.86 (m, 2H), 6.66 (ddd, J=8.9, 3.9, 2.8 Hz, 1H), 3.77 (t, J=5.3 Hz, 2H), 3.46 (d, J=8.4 Hz, 2H), 3.14 (d, J=7.2 Hz, 2H), 3.02 (s, 3H), 1.16 (ddd, J=7.7, 4.7, 2.9 Hz, 1H), 0.71 (dd, J=8.1, 1.5 Hz, 2H), 0.40 (dd, J=4.7, 1.3 Hz, 2H).

Example 399: N-(3-chloro-4-fluorophenyl)-N'-hydroxy-2-(2-(methyl((tetrahydro-2H-pyran-4-yl)methyl)amino)ethyl)-1H-imidazo[4,5-b]pyridine-7-carboximidamide

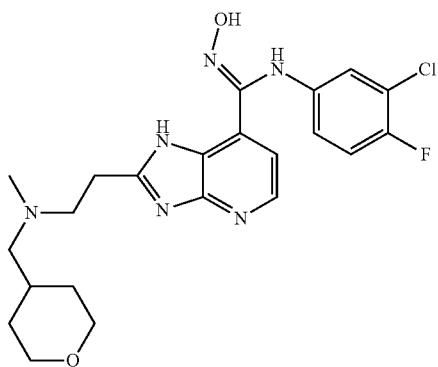 [SMILES: CN(CCc1nc2nccc(/C(=N/O)Nc3ccc(F)c(Cl)c3)c2[nH]1)CC1CCOCC1]

Example 399 was made analogously to Example 184 using N-methyl-1-(tetrahydro-2H-pyran-4-yl)methanamine. $C_{22}H_{26}ClFN_6O_2$. 461.9 (M+1).

Example 400: 2-(2-(((1,4-dioxan-2-yl)methyl)(methyl)amino)ethyl)-N-(3-chloro-4-fluorophenyl)-N'-hydroxy-1H-imidazo[4,5-b]pyridine-7-carboximidamide

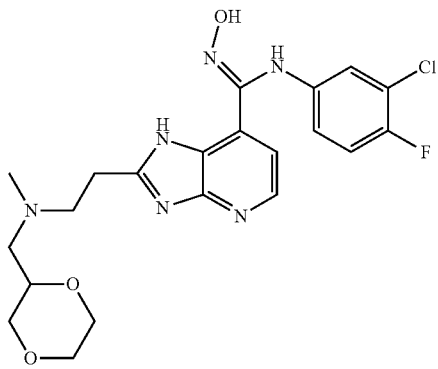 [SMILES: CN(CCc1nc2nccc(/C(=N/O)Nc3ccc(F)c(Cl)c3)c2[nH]1)CC1COCCO1]

Example 400 was made analogously to Example 184 using 1-(1,4-dioxan-2-yl)-N-methylmethanamine hydrochloride. $C_{21}H_{24}ClFN_6O_3$. 463.9 (M+1). 1H NMR (400 MHz, DMSO-d6) δ 11.09 (s, 1H), 8.89 (s, 1H), 8.31 (d, J=5.1 Hz, 1H), 7.16 (d, J=5.1 Hz, 1H), 7.05 (t, J=9.1 Hz, 1H), 6.93 (dd, J=6.5, 2.7 Hz, 1H), 6.52 (ddd, J=9.0, 4.0, 2.7 Hz, 1H), 4.10-4.01 (m, 1H), 3.83-3.20 (m, 13H), 2.89 (s, 3H).

Example 401: N-(3-chloro-4-fluorophenyl)-N'-hydroxy-2-(2-(methyl(2-(tetrahydro-2H-pyran-4-yl)ethyl)amino)ethyl)-1H-imidazo[4,5-b]pyridine-7-carboximidamide

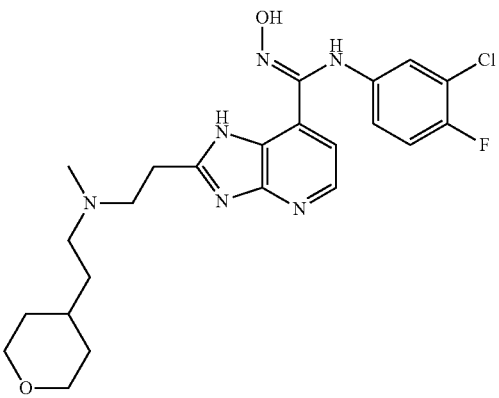 [SMILES: CN(CCc1nc2nccc(/C(=N/O)Nc3ccc(F)c(Cl)c3)c2[nH]1)CCC1CCOCC1]

Example 401 was made analogously to Example 184 using N-methyl-2-(tetrahydro-2H-pyran-4-yl)ethan-1-amine. $C_{23}H_{28}ClFN_6O_2$. 476.0 (M+1). 1H NMR (400 MHz, DMSO-d6) δ 11.07 (s, 1H), 8.91 (s, 1H), 8.30 (d, J=5.1 Hz, 1H), 7.16 (d, J=5.1 Hz, 1H), 7.04 (t, J=9.1 Hz, 1H), 6.93 (dd, J=6.5, 2.7 Hz, 1H), 6.55-6.48 (m, 1H), 3.83 (dd, J=11.2, 4.3 Hz, 2H), 3.55 (s, 1H), 3.35-3.23 (m, 4H), 3.23-3.15 (m, 2H), 2.84 (s, 3H), 1.59 (dd, J=15.6, 10.5 Hz, 6H), 1.20 (d, J=11.8 Hz, 2H).

Example 402: N-(3-chloro-4-fluorophenyl)-2-((2-(cyclopropylamino)ethyl)amino)-N'-hydroxy-1H-imidazo[4,5-b]pyridine-7-carboximidamide

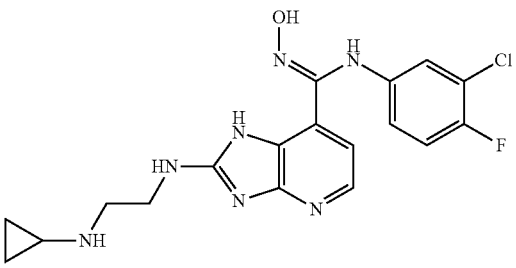 [SMILES: O/N=C(\Nc1ccc(F)c(Cl)c1)c1ccnc2nc(NCCNC3CC3)[nH]c12]

Example 402 was made analogously to Example 395 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and tert-butyl (2-aminoethyl)(cyclopropyl)carbamate. $C_{18}H_{19}ClFN_7O$. 404.8 (M+1). 1H NMR (400 MHz, DMSO-d6) δ 11.39 (s, 1H), 8.97 (s, 3H), 7.99 (d, J=6.3 Hz, 1H), 7.11 (t, J=9.1 Hz, 1H), 7.01 (dd, J=6.5, 2.7 Hz, 1H), 6.95 (d, J=6.3 Hz, 1H), 6.58 (ddd, J=9.0, 4.1, 2.8 Hz, 1H), 3.75 (s, 2H), 3.31 (s, 2H), 2.80 (s, 1H), 0.87-0.75 (m, 4H).

Example 403: N-(3-chloro-4-fluorophenyl)-2-((2-(cyclopropyl(ethyl)amino)ethyl)amino)-N'-hydroxy-1H-imidazo[4,5-b]pyridine-7-carboximidamide

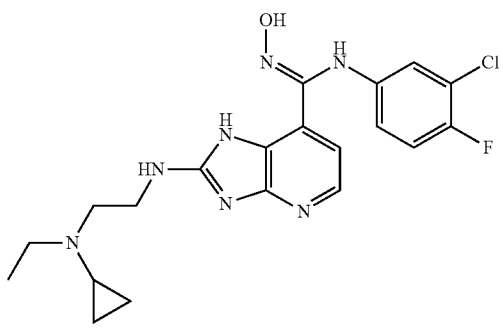 [SMILES: CCN(CCNc1nc2nccc(/C(=N/O)Nc3ccc(F)c(Cl)c3)c2[nH]1)C1CC1]

Example 403 was made analogously to Example 402 using N$^1$-cyclopropyl-N$^1$-ethylethane-1,2-diamine. C$_{20}$H$_{23}$ClFN$_7$O. 432.2 (M+1). 1H NMR (400 MHz, DMSO-d6) δ 8.95 (s, 1H), 7.97 (d, J=6.1 Hz, 1H), 7.10 (t, J=9.1 Hz, 1H), 6.99 (s, 1H), 6.93 (d, J=6.0 Hz, 1H), 6.61-6.53 (m, 1H), 3.80 (s, 2H), 3.45 (s, 2H), 3.33 (s, 2H), 2.86 (s, 1H), 1.27 (t, J=7.2 Hz, 3H), 1.00-0.78 (m, 4H).

Example 404: N-(2-((7-(N-(3-chloro-4-fluorophenyl)-N'-hydroxycarbamimidoyl)-1H-imidazo[4,5-b]pyridin-2-yl)amino)ethyl)acetamide

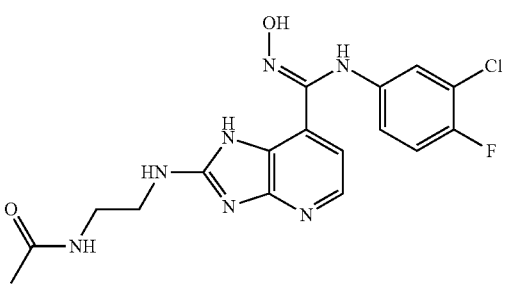 [SMILES: CC(=O)NCCNc1nc2nccc(/C(=N/O)Nc3ccc(F)c(Cl)c3)c2[nH]1]

Example 404 was made analogously to Example 402 using N-(2-aminoethyl)acetamide. C$_{17}$H$_{17}$ClFN$_7$O$_2$. 406.3 (M+1). 1H NMR (400 MHz, DMSO-d6) δ 11.42 (s, 1H), 8.97 (s, 1H), 8.03 (s, 1H), 7.97 (d, J=6.3 Hz, 1H), 7.11 (t, J=9.0 Hz, 1H), 7.04 (dd, J=6.5, 2.7 Hz, 1H), 6.92 (d, J=6.3 Hz, 1H), 6.63-6.55 (m, 1H), 3.50 (d, J=6.0 Hz, 2H), 3.30 (d, J=6.0 Hz, 2H), 1.82 (s, 3H).

Example 405: N-(3-chloro-4-fluorophenyl)-N'-hydroxy-2-((2-(methylsulfonamido)ethyl)amino)-1H-imidazo[4,5-b]pyridine-7-carboximidamide

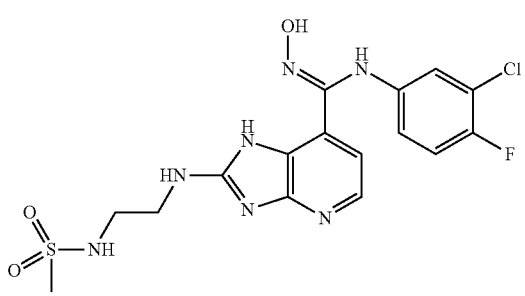 [SMILES: CS(=O)(=O)NCCNc1nc2nccc(/C(=N/O)Nc3ccc(F)c(Cl)c3)c2[nH]1]

Example 405 was made analogously to Example 402 using N-(2-aminoethyl)methanesulfonamide. C$_{16}$H$_{17}$ClFN$_7$O$_3$S. 442.1 (M+1). 1H NMR (400 MHz, DMSO-d6) δ 11.44 (s, 1H), 8.97 (s, 1H), 7.97 (d, J=6.3 Hz, 1H), 7.25 (d, J=5.8 Hz, 1H), 7.11 (t, J=9.0 Hz, 1H), 7.03 (s, 1H), 6.92 (d, J=6.4 Hz, 1H), 6.59 (dt, J=8.9, 3.4 Hz, 1H), 3.57 (d, J=6.2 Hz, 2H), 3.21 (d, J=6.1 Hz, 2H), 2.94 (s, 3H).

Example 406: N-(3-chloro-4-fluorophenyl)-2-((2-(cyclopropyl(isopropyl)amino)ethyl)amino)-N'-hydroxy-1H-imidazo[4,5-b]pyridine-7-carboximidamide

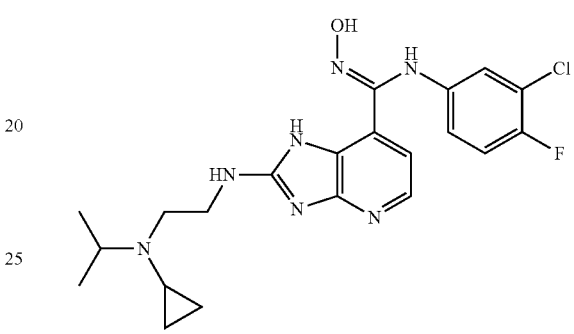

Example 406 was made analogously to Example 402 using N$^1$-cyclopropyl-N$^1$-isopropylethane-1,2-diamine. C$_{21}$H$_{25}$ClFN$_7$O. 446.4 (M+1). 1H NMR (400 MHz, DMSO-d6) δ 11.30 (s, 1H), 8.94 (s, 1H), 7.97 (s, 1H), 7.10 (t, J=9.0 Hz, 1H), 7.03-6.94 (m, 1H), 6.92 (d, J=6.0 Hz, 1H), 6.56 (d, J=8.4 Hz, 1H), 3.80 (s, 3H), 3.42 (s, 2H), 2.86 (s, 1H), 1.30 (d, J=6.7 Hz, 6H), 1.01 (s, 2H), 0.89 (s, 2H).

Example 407: N-(3-chloro-4-fluorophenyl)-2-((2-(cyclopropyl(2-hydroxyethyl)amino)ethyl)amino)-N'-hydroxy-1H-imidazo[4,5-b]pyridine-7-carboximidamide

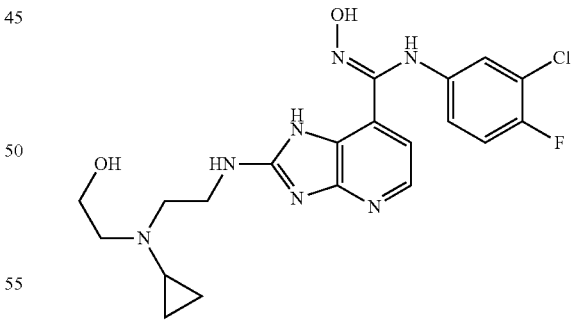

Example 407 was made analogously to Example 402 using 2-((2-aminoethyl)(cyclopropyl)amino)ethan-1-ol dihydrochloride and Hunig's base. C$_{20}$H$_{23}$ClFN$_7$O$_2$. 448.2 (M+1). 1H NMR (400 MHz, Methanol-d4) δ 7.89 (d, J=6.5 Hz, 1H), 7.05 (d, J=6.5 Hz, 1H), 7.03-6.95 (m, 2H), 6.67 (ddd, J=8.9, 4.0, 2.8 Hz, 1H), 4.06 (t, J=6.3 Hz, 2H), 4.01-3.95 (m, 2H), 3.71 (t, J=6.3 Hz, 2H), 3.59-3.52 (m, 2H), 2.98 (dt, J=7.3, 3.5 Hz, 1H), 1.19-1.12 (m, 2H), 1.07-1.01 (m, 2H).

Example 408: 2-((2-aminoethyl)amino)-N-(3-chloro-4-fluorophenyl)-N'-hydroxy-1H-imidazo[4,5-b]pyridine-7-carboximidamide

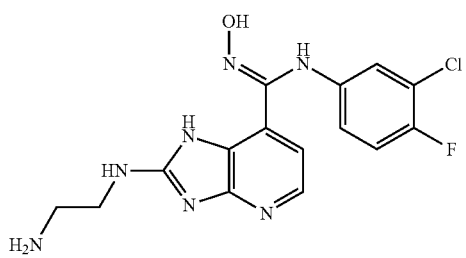 [SMILES: NCCNc1nc2nccc(/C(=N/O)Nc3ccc(F)c(Cl)c3)c2[nH]1]

Example 408 was made analogously to Example 402 using tert-butyl (2-aminoethyl)carbamate. $C_{15}H_{15}ClFN_7O$. 364.9 (M+1).

Example 409: N-(3-chloro-4-fluorophenyl)-N'-hydroxy-2-(((5-oxopyrrolidin-3-yl)methyl)amino)-1H-imidazo[4,5-b]pyridine-7-carboximidamide

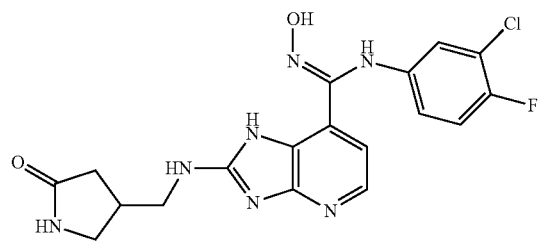 [SMILES: O=C1CC(CNc2nc3nccc(/C(=N/O)Nc4ccc(F)c(Cl)c4)c3[nH]2)CN1]

Example 409 was made analogously to Example 402 using 4-(aminomethyl)pyrrolidin-2-one. $C_{18}H_{17}ClFN_7O_2$. 418.4 (M+1).

Example 410: 2-(((1H-pyrazol-5-yl)methyl)amino)-N-(3-chloro-4-fluorophenyl)-N'-hydroxy-1H-imidazo[4,5-b]pyridine-7-carboximidamide

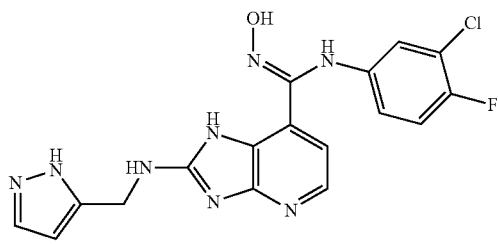 [SMILES: O/N=C(\Nc1ccc(F)c(Cl)c1)c1ccnc2nc(NCc3ccn[nH]3)[nH]c12]

Example 410 was made analogously to Example 402 using (1H-pyrazol-5-yl)methanamine. $C_{17}H_{14}ClFN_8O$. 401.1 (M+1).

Examples 411 and 412: N-(3-((7-(N-(3-chloro-4-fluorophenyl)-N'-hydroxycarbamimidoyl)-1H-imidazo[4,5-b]pyridin-2-yl)amino)propyl)acetamide and 2-((3-aminopropyl)amino)-N-(3-chloro-4-fluorophenyl)-N'-hydroxy-1H-imidazo[4,5-b]pyridine-7-carboximidamide

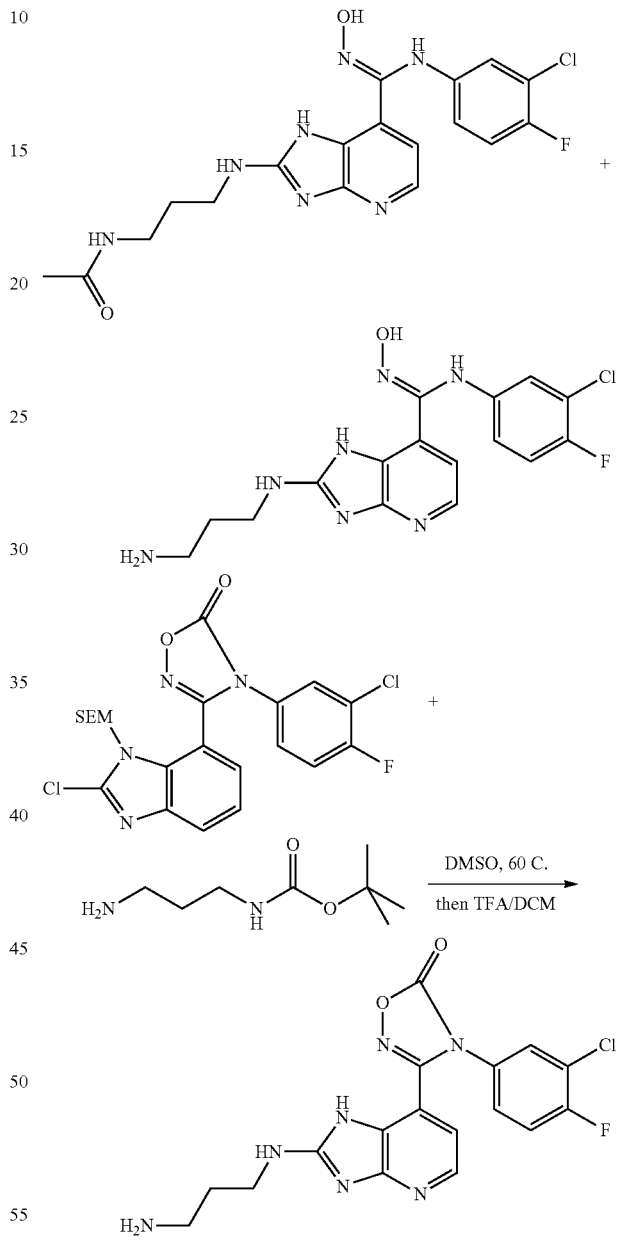

3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one (0.06 g, 0.121 mmol) and tert-butyl (3-aminopropyl)carbamate (0.181 mmol) were dissolved in DMSO (2.80 mL) and heated overnight at 60 C. The reaction was cooled to rt, diluted with water (3 mL) and extracted with EtOAc (3×2 mL). Combined organic layers were washed with water (1×5 mL) and concentrated. The crude was dissolved in DCM (2 mL) and TFA (1.0 mL) was added and the reaction was allowed to stir at rt for 2 hours before being concentrated to dryness to give 3-(2-((3-aminopropyl) amino)-1H-imidazo[4,5-b]pyridin-7-yl)-4-(3-chloro-4-fluorophenyl)-1,2,4-oxadiazol-5(4H)-one.

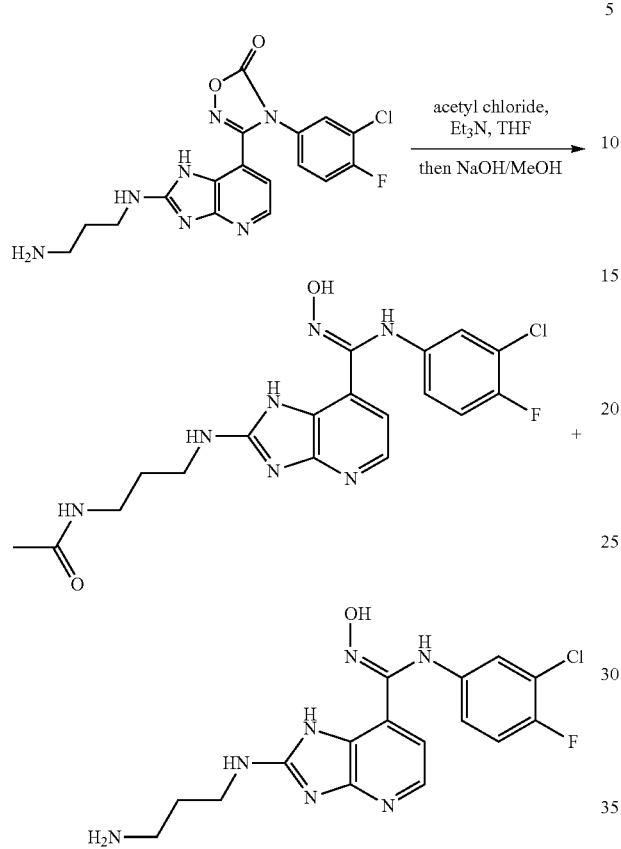

3-(2-((3-aminopropyl)amino)-1H-imidazo[4,5-b]pyridin-7-yl)-4-(3-chloro-4-fluorophenyl)-1,2,4-oxadiazol-5(4H)-one (0.015 g, 0.0317 mmol) was dissolved in THF (1.0 mL) and triethylamine (0.186 mmol) was added. Acetyl chloride (0.0557 mmol) was added slowly and the reaction was allowed to stir at rt for 1 hour before being concentrated to dryness. The residue was dissolved in THF (0.4 mL), MeOH (0.4 mL) and 1M NaOH (0.6 mL) and stirred at rt for 1 hour. The reaction was concentrated and purified by RP HPLC to give two products: N-(3-((7-(N-(3-chloro-4-fluorophenyl)-N'-hydroxycarbamimidoyl)-1H-imidazo[4,5-b]pyridin-2-yl)amino)propyl)acetamide (2.8 mg, 18%) and 2-((3-aminopropyl)amino)-N-(3-chloro-4-fluorophenyl)-N'-hydroxy-1H-imidazo[4,5-b]pyridine-7-carboximidamide.

N-(3-((7-(N-(3-chloro-4-fluorophenyl)-N'-hydroxycarbamimidoyl)-1H-imidazo[4,5-b]pyridin-2-yl)amino)propyl) acetamide: $C_{18}H_{19}ClFN_7O_2$. 420.2 (M+1). 1H NMR (400 MHz, Methanol-d4) δ 7.84 (d, J=6.5 Hz, 1H), 7.04-6.96 (m, 3H), 6.67 (ddd, J=8.9, 4.0, 2.8 Hz, 1H), 3.58 (t, J=6.7 Hz, 2H), 3.28 (d, J=6.7 Hz, 2H), 1.96 (s, 3H), 1.87 (t, J=6.7 Hz, 2H).

2-((3-aminopropyl)amino)-N-(3-chloro-4-fluorophenyl)-N'-hydroxy-1H-imidazo[4,5-b]pyridine-7-carboximidamide: $C_{16}H_{17}ClFN_7O$. 378.3 (M+1). 1H NMR (400 MHz, Methanol-d4) δ 7.85 (d, J=6.6 Hz, 1H), 7.04-6.95 (m, 3H), 6.68 (ddd, J=8.9, 3.9, 2.8 Hz, 1H), 3.68 (t, J=6.6 Hz, 2H), 3.11-3.03 (m, 2H), 2.12-2.02 (m, 2H).

Example 413: N-(3-chloro-4-fluorophenyl)-N'-hydroxy-2-((2-(sulfamoylamino)ethyl)amino)-1H-imidazo[4,5-b]pyridine-7-carboximidamide

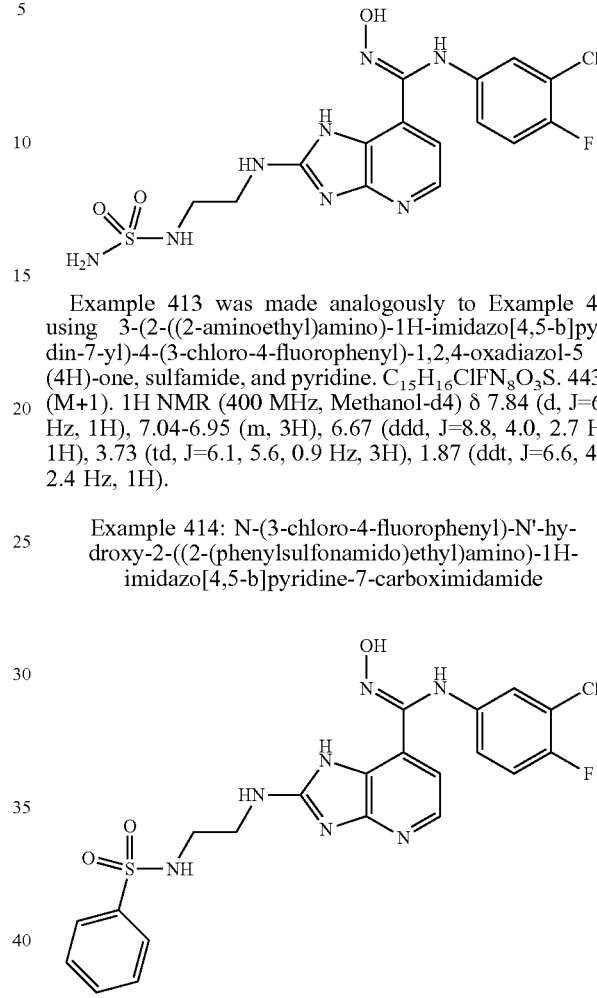

Example 413 was made analogously to Example 411 using 3-(2-((2-aminoethyl)amino)-1H-imidazo[4,5-b]pyridin-7-yl)-4-(3-chloro-4-fluorophenyl)-1,2,4-oxadiazol-5(4H)-one, sulfamide, and pyridine. $C_{15}H_{16}ClFN_8O_3S$. 443.1 (M+1). 1H NMR (400 MHz, Methanol-d4) δ 7.84 (d, J=6.5 Hz, 1H), 7.04-6.95 (m, 3H), 6.67 (ddd, J=8.8, 4.0, 2.7 Hz, 1H), 3.73 (td, J=6.1, 5.6, 0.9 Hz, 3H), 1.87 (ddt, J=6.6, 4.6, 2.4 Hz, 1H).

Example 414: N-(3-chloro-4-fluorophenyl)-N'-hydroxy-2-((2-(phenylsulfonamido)ethyl)amino)-1H-imidazo[4,5-b]pyridine-7-carboximidamide

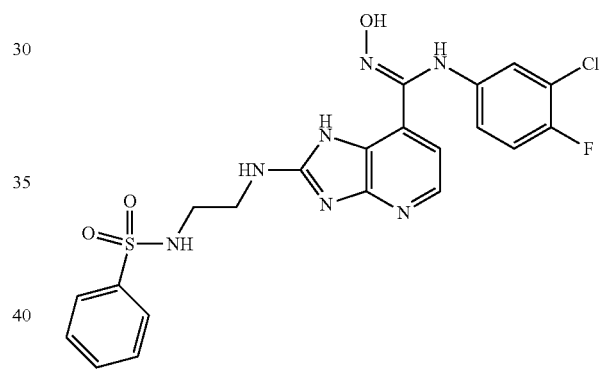

Example 414 was made analogously to Example 411 using 3-(2-((2-aminoethyl)amino)-1H-imidazo[4,5-b]pyridin-7-yl)-4-(3-chloro-4-fluorophenyl)-1,2,4-oxadiazol-5(4H)-one, benzenesulfonyl chloride, and triethylamine. $C_{21}H_{19}ClFN_7O_3S$. 504.1 (M+1).

Example 415: Methyl (2-((7-(N-(3-chloro-4-fluorophenyl)-N'-hydroxycarbamimidoyl)-1H-imidazo[4,5-b]pyridin-2-yl)amino)ethyl)carbamate

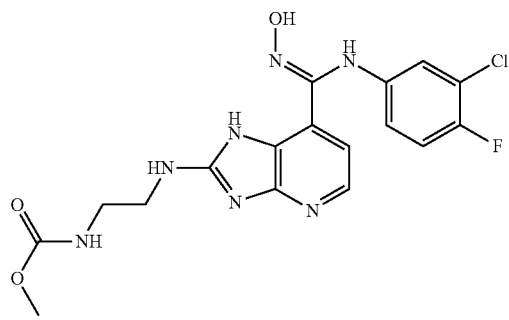 [SMILES: COC(=O)NCCNc1nc2nccc(/C(=N/O)Nc3ccc(F)c(Cl)c3)c2[nH]1]

Example 415 was made analogously to Example 411 using 3-(2-((2-aminoethyl)amino)-1H-imidazo[4,5-b]pyridin-7-yl)-4-(3-chloro-4-fluorophenyl)-1,2,4-oxadiazol-5 (4H)-one, methyl chloroformate, and triethylamine. $C_{17}H_{17}ClFN_7O_3$ 422.1 (M+1). 1H NMR (400 MHz, DMSO-d6) δ 11.43 (s, 1H), 8.96 (s, 1H), 7.97 (d, J=6.4 Hz, 1H), 7.28 (s, 1H), 7.11 (t, J=9.0 Hz, 1H), 7.04 (dd, J=6.5, 2.8 Hz, 1H), 6.93 (d, J=6.3 Hz, 1H), 6.59 (ddd, J=9.0, 4.0, 2.7 Hz, 1H), 3.53 (d, J=3.9 Hz, 5H), 3.25 (d, J=6.0 Hz, 2H).

Example 416: N-(3-chloro-4-fluorophenyl)-2-((2-(cyclopropanesulfonamido)ethyl)amino)-N'-hydroxy-1H-imidazo[4,5-b]pyridine-7-carboximidamide

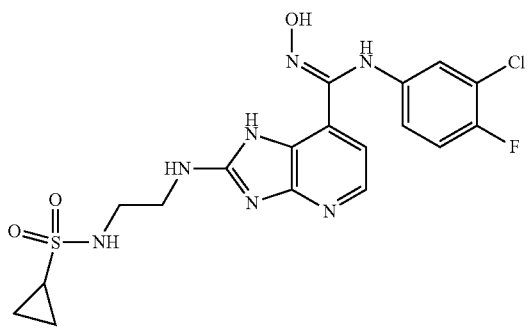 [SMILES: O=S(=O)(NCCNc1nc2nccc(/C(=N/O)Nc3ccc(F)c(Cl)c3)c2[nH]1)C1CC1]

Example 416 was made analogously to Example 411 using 3-(2-((2-aminoethyl)amino)-1H-imidazo[4,5-b]pyridin-7-yl)-4-(3-chloro-4-fluorophenyl)-1,2,4-oxadiazol-5 (4H)-one, cyclopropanesulfonyl chloride, and triethylamine. $C_{18}H_{19}ClFN_7O_3S$. 468.9 (M+1). 1H NMR (400 MHz, Methanol-d4) δ 7.84 (d, J=6.5 Hz, 1H), 7.04-6.96 (m, 3H), 6.67 (ddd, J=8.9, 3.9, 2.8 Hz, 1H), 3.70 (dd, J=6.5, 5.3 Hz, 2H), 3.42 (dd, J=6.6, 5.3 Hz, 2H), 2.56 (ddd, J=7.9, 5.5, 2.9 Hz, 1H), 1.10-0.97 (m, 4H).

Example 417: N-(3-chloro-4-fluorophenyl)-N'-hydroxy-2-((2-(((trifluoromethyl)sulfonamido)ethyl)amino)-1H-imidazo[4,5-b]pyridine-7-carboximidamide

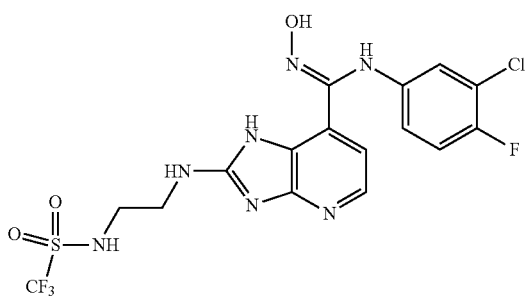 [SMILES: O=S(=O)(NCCNc1nc2nccc(/C(=N/O)Nc3ccc(F)c(Cl)c3)c2[nH]1)C(F)(F)F]

Example 417 was made analogously to Example 411 using 3-(2-((2-aminoethyl)amino)-1H-imidazo[4,5-b]pyridin-7-yl)-4-(3-chloro-4-fluorophenyl)-1,2,4-oxadiazol-5 (4H)-one, trifluoromethanesulfonyl chloride, and triethylamine. $C_{16}H_{14}ClF_4N_7O_3S$. 496.3 (M+1).

Example 418: 2-(((1H-imidazol-2-yl)methyl)amino)-N-(3-chloro-4-fluorophenyl)-N'-hydroxy-1H-imidazo[4,5-b]pyridine-7-carboximidamide

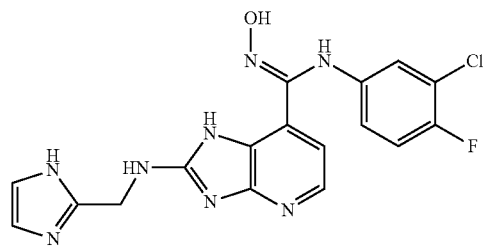 [SMILES: O/N=C(\Nc1ccc(F)c(Cl)c1)c1ccnc2nc(NCc3ncc[nH]3)[nH]c12]

Example 418 was made analogously to Example 402 using (1H-imidazol-2-yl)methanamine dihydrochloride and Hunig's base. $C_{17}H_{14}ClFN_8O$. 401.2 (M+1). 1H NMR (400 MHz, DMSO-d6) δ 8.90 (s, 1H), 7.97 (d, J=5.9 Hz, 1H), 7.60 (s, 2H), 7.10 (t, J=9.0 Hz, 1H), 6.94 (d, J=15.7 Hz, 2H), 6.60-6.53 (m, 1H), 4.92 (s, 2H).

Example 419: 2-(((1H-imidazol-5-yl)methyl)amino)-N-(3-chloro-4-fluorophenyl)-N'-hydroxy-1H-imidazo[4,5-b]pyridine-7-carboximidamide

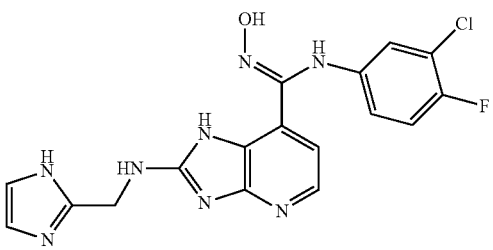 [SMILES: O/N=C(\Nc1ccc(F)c(Cl)c1)c1ccnc2nc(NCc3ncc[nH]3)[nH]c12]

Example 419 was made analogously to Example 402 using (1H-imidazol-5-yl)methanamine dihydrochloride and Hunig's base. $C_{17}H_{14}ClFN_8O$. 401.2 (M+1).

Example 420: N-(3-chloro-4-fluorophenyl)-N'-hydroxy-2-(((3-methyl-1,2,4-oxadiazol-5-yl)methyl)amino)-1H-imidazo[4,5-b]pyridine-7-carboximidamide

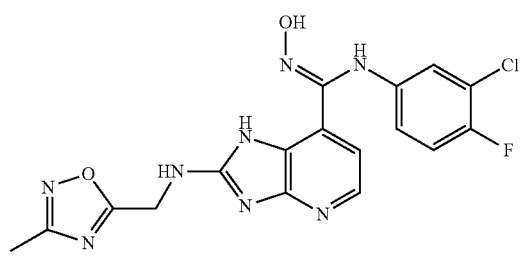 [SMILES: Cc1noc(CNc2nc3nccc(/C(=N/O)Nc4ccc(F)c(Cl)c4)c3[nH]2)n1]

Example 420 was made analogously to Example 402 using (3-methyl-1,2,4-oxadiazol-5-yl)methanamine. $C_{17}H_{14}ClFN_8O_2$. 417.2 (M+1). 1H NMR (400 MHz, DMSO-d6) δ 8.97 (s, 1H), 8.50 (d, J=12.2 Hz, 1H), 7.99 (d, J=6.4 Hz, 1H), 7.11 (d, J=9.1 Hz, 1H), 7.08-7.03 (m, 1H), 6.96 (d, J=6.4 Hz, 1H), 6.60 (ddd, J=9.0, 4.0, 2.7 Hz, 1H), 4.97 (d, J=6.0 Hz, 2H), 2.32 (s, 3H).

Example 421: N-(3-bromophenyl)-N'-hydroxy-2-(methylamino)-1H-imidazo[4,5-b]pyridine-7-carboximidamide

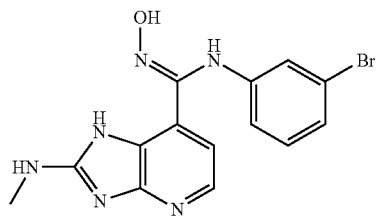 [SMILES: CNc1nc2nccc(/C(=N/O)Nc3cccc(Br)c3)c2[nH]1]

Example 421 was made analogously to Example 402 using 4-(3-bromophenyl)-3-(2-chloro-1-((2-(trimethylsilyl)ethoxy)methyl)-1H-imidazo[4,5-b]pyridin-7-yl)-1,2,4-oxadiazol-5(4H)-one and methylamine (2.0 M in MeOH). $C_{14}H_{13}BrN_6O$. 361.2 (M+1). 1H NMR (400 MHz, DMSO-d6) δ 8.97 (s, 1H), 7.97 (d, J=6.2 Hz, 1H), 7.07 (d, J=2.0 Hz, 1H), 7.02-6.92 (m, 3H), 6.57 (dt, J=7.0, 2.1 Hz, 1H), 3.02 (d, J=4.7 Hz, 3H).

Example 422: Methyl (3-((7-(N-(3-chloro-4-fluorophenyl)-N'-hydroxycarbamimidoyl)-1H-imidazo[4,5-b]pyridin-2-yl)amino)propyl)carbamate

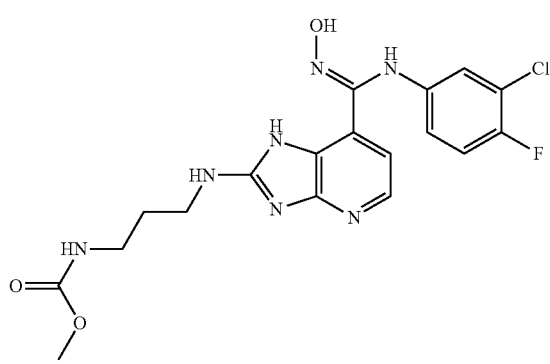 [SMILES: COC(=O)NCCCNc1nc2nccc(/C(=N/O)Nc3ccc(F)c(Cl)c3)c2[nH]1]

Example 422 was made analogously to Example 411 using 3-(2-((3-aminopropyl)amino)-1H-imidazo[4,5-b]pyridin-7-yl)-4-(3-chloro-4-fluorophenyl)-1,2,4-oxadiazol-5(4H)-one, methyl chloroformate, and triethylamine. $C_{18}H_{19}ClFN_7O_3$. 436.2 (M+1). 1H NMR (400 MHz, DMSO-d6) δ 8.94 (s, 1H), 7.96 (d, J=6.2 Hz, 1H), 7.19 (d, J=5.6 Hz, 1H), 7.10 (t, J=9.0 Hz, 1H), 7.04 (dd, J=6.6, 2.7 Hz, 1H), 6.91 (d, J=6.2 Hz, 1H), 6.59 (ddd, J=8.9, 4.0, 2.8 Hz, 1H), 3.53 (s, 3H), 3.44 (d, J=6.5 Hz, 2H), 3.07 (d, J=6.3 Hz, 2H), 1.79-1.64 (m, 2H).

Example 423: N-(3-bromophenyl)-N'-hydroxy-2-methoxy-1H-imidazo[4,5-b]pyridine-7-carboximidamide

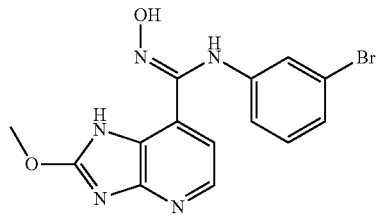 [SMILES: COc1nc2nccc(/C(=N/O)Nc3cccc(Br)c3)c2[nH]1]

Example 423 was made analogously to Example 402 using 4-(3-bromophenyl)-3-(2-chloro-1-((2-(trimethylsilyl)ethoxy)methyl)-1H-imidazo[4,5-b]pyridin-7-yl)-1,2,4-oxadiazol-5(4H)-one and sodium hydride in MeOH to generate sodium methoxide in situ. $C_{14}H_{12}BrN_5O_2$. 362.0 (M+1).

Example 424: N-(3-bromophenyl)-N'-hydroxy-2-((2-(methylsulfonyl)ethyl)amino)-1H-imidazo[4,5-b]pyridine-7-carboximidamide

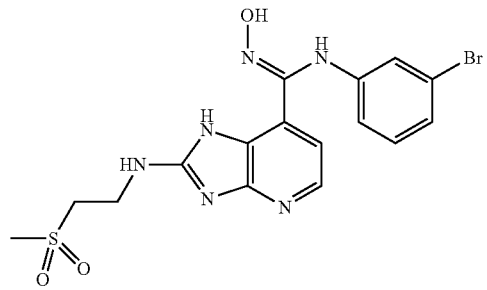 [SMILES: CS(=O)(=O)CCNc1nc2nccc(/C(=N/O)Nc3cccc(Br)c3)c2[nH]1]

Example 424 was made analogously to Example 402 using 4-(3-bromophenyl)-3-(2-chloro-1-((2-(trimethylsilyl)ethoxy)methyl)-1H-imidazo[4,5-b]pyridin-7-yl)-1,2,4-oxadiazol-5(4H)-one, 2-(methylsulfonyl)ethan-1-amine hydrochloride, and Hunig's base. $C_{16}H_{17}BrN_6O_3S$. 453.2 (M+1).

Example 425: N-(3-bromophenyl)-N'-hydroxy-2-((2-(methylsulfonamido)ethyl)amino)-1H-imidazo[4,5-b]pyridine-7-carboximidamide

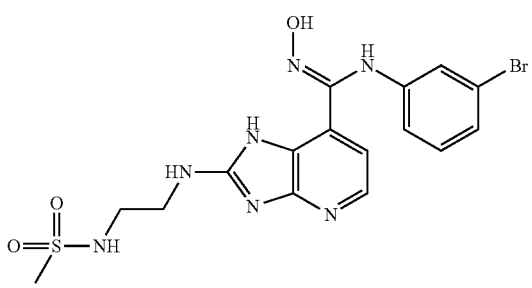 [SMILES: CS(=O)(=O)NCCNc1nc2nccc(/C(=N/O)Nc3cccc(Br)c3)c2[nH]1]

Example 425 was made analogously to Example 424 using N-(2-aminoethyl)methanesulfonamide. $C_{16}H_{18}BrN_7O_3S$. 468.2 (M+1).

Example 426: N-(3-bromophenyl)-N'-hydroxy-2-((2-sulfamoylethyl)amino)-1H-imidazo[4,5-b]pyridine-7-carboximidamide

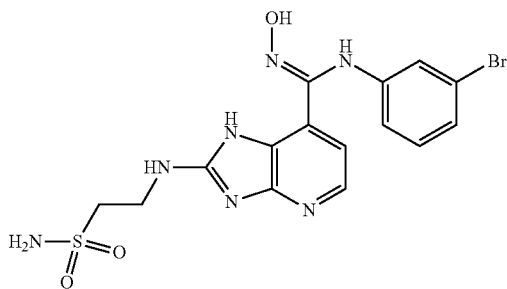 [SMILES: NS(=O)(=O)CCNc1nc2nccc(/C(=N/O)Nc3cccc(Br)c3)c2[nH]1]

Example 426 was made analogously to Example 424 using 4-(3-bromophenyl)-3-(2-chloro-1-((2-(trimethylsilyl)ethoxy)methyl)-1H-imidazo[4,5-b]pyridin-7-yl)-1,2,4-oxadiazol-5(4H)-one and 2-aminoethane-1-sulfonamide. $C_{15}H_{16}BrN_7O_3S$. 454.2 (M+1).

Example 427: N-(3-chloro-4-fluorophenyl)-N'-hydroxy-2-(((5-methyl-1,3,4-oxadiazol-2-yl)methyl)amino)-1H-imidazo[4,5-b]pyridine-7-carboximidamide

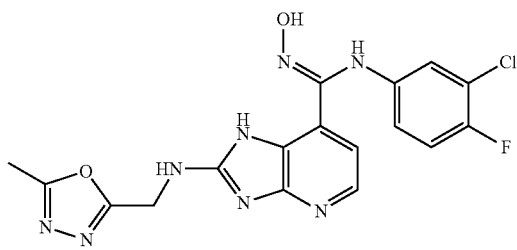 [SMILES: Cc1nnc(CNc2nc3nccc(/C(=N/O)Nc4ccc(F)c(Cl)c4)c3[nH]2)o1]

Example 427 was made analogously to Example 402 using (5-methyl-1,3,4-oxadiazol-2-yl)methanamine oxalate and Hunig's base. $C_{17}H_{14}ClFN_8O_2$. 417.2 (M+1).

Example 428: N-(3-chloro-4-fluorophenyl)-4,5-difluoro-N'-hydroxy-2-(((1-methylpiperidin-2-yl)methyl)amino)-1H-benzo[d]imidazole-7-carboximidamide

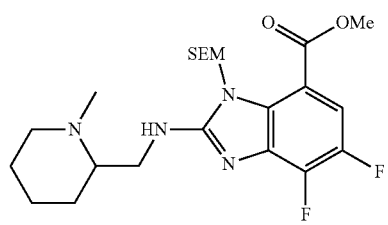 [SMILES: COC(=O)c1cc(F)c(F)c2nc(NCC3CCCCN3C)n(COCC[Si](C)(C)C)c12]

Methyl 4,5-difluoro-2-(((1-methylpiperidin-2-yl)methyl)amino)-1-((2-(trimethylsilyl)ethoxy)methyl)-1H-benzo[d]imidazole-7-carboxylate was made analogously to Example 39 using (1-methylpiperidin-2-yl)methanamine in place of N,N-dimethylpropane-1,3-diamine. The TFA salt of methyl 4,5-difluoro-2-(((1-methylpiperidin-2-yl)methyl)amino)-1-((2-(trimethylsilyl)ethoxy)methyl)-1H-benzo[d]imidazole-7-carboxylate was isolated as a yellow oil. $C_{22}H_{34}F_2N_4O_3Si$. 469.2 (M+1).

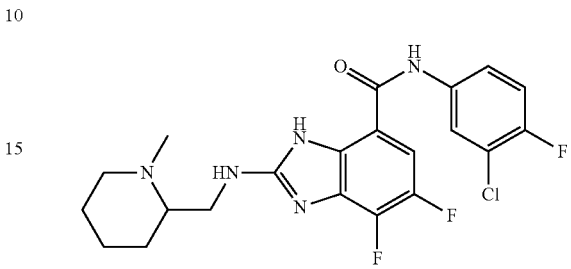

N-(3-chloro-4-fluorophenyl)-4,5-difluoro-2-(((1-methylpiperidin-2-yl)methyl)amino)-1H-benzo[d]imidazole-7-carboxamide was made analogously to Example 39 using methyl 4,5-difluoro-2-(((1-methylpiperidin-2-yl)methyl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-((1-methylpiperidin-2-yl)methyl)amino)-1H-benzo[d]imidazole-7-carboxamide was isolated as a white solid. $C_{21}H_{21}ClF_3N_5O$. 452.2/454.1 (M+1).

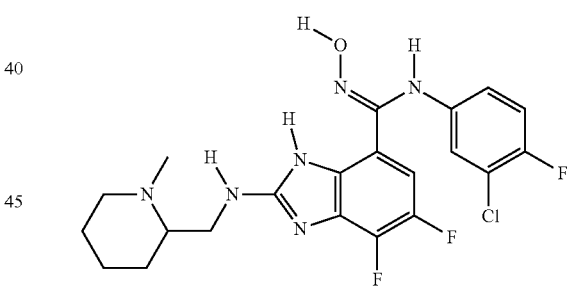

Example 428 was made analogously to Example 59 using N-(3-chloro-4-fluorophenyl)-4,5-difluoro-2-(((1-methylpiperidin-2-yl)methyl)amino)-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-4,5-difluoro-N'-hydroxy-2-(((1-methylpiperidin-2-yl)methyl)amino)-1H-benzo[d]imidazole-7-carboximidamide was isolated as an off-white solid. $C_{21}H_{22}ClF_3N_6O$. 467.2/469.1 (M+1). $^1H$ NMR (400 MHz, DMSO-d6) δ 10.78 (s, 1H), 9.25 (s, 1H), 8.69 (s, 1H), 7.10 (t, J=9.1 Hz, 1H), 7.00 (s, 1H), 6.92 (dd, J=6.5, 2.7 Hz, 1H), 6.83 (dd, J=12.2, 6.8 Hz, 1H), 6.53 (ddd, J=9.0, 4.1, 2.7 Hz, 1H), 3.79 (m, 1H), 3.68 (m, 1H), 3.41 (m, 1H), 3.24 (m, 1H), 3.04 (m, 1H), 2.97 (s, 3H), 2.83 (m, 1H), 1.94 (m, 1H), 1.85-1.70 (m, 2H), 1.65-1.40 (m, 2H). $^{19}F$ NMR (377 MHz, DMSO) δ −75.02 (9F), −127.46 (1F), −150.44 (1F), −157.01 (1F).

Example 429: N-(3-chloro-4-fluorophenyl)-4,5-difluoro-N'-hydroxy-2-(((4-methylmorpholin-3-yl)methyl)amino)-1H-benzo[d]imidazole-7-carboximidamide

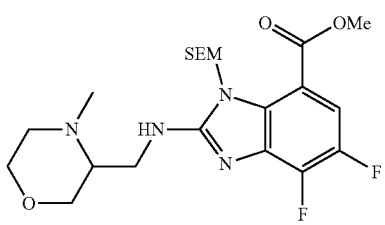 [SMILES: COC(=O)c1cc(F)c(F)c2nc(NCC3COCCN3C)n(COCC[Si](C)(C)C)c12]

Example 429 was made analogously to Example 39 using (4-methylmorpholin-3-yl)methanamine in place of N,N-dimethylpropane-1,3-diamine. The TFA salt of methyl 4,5-difluoro-2-(((4-methylmorpholin-3-yl)methyl)amino)-1-((2-(trimethylsilyl)ethoxy)methyl)-1H-benzo[d]imidazole-7-carboxylate was isolated as a yellow oil. $C_{21}H_{32}F_2N_4O_4Si$. 471.2 (M+1).

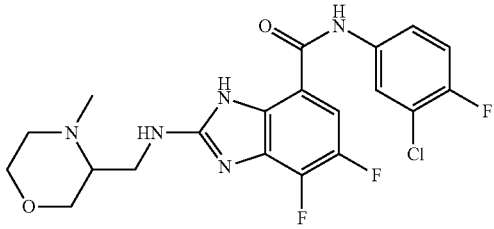 [SMILES: CN1CCOCC1CNc1nc2c(F)c(F)cc(C(=O)Nc3ccc(F)c(Cl)c3)c2[nH]1]

N-(3-chloro-4-fluorophenyl)-4,5-difluoro-2-(((4-methylmorpholin-3-yl)methyl)amino)-1H-benzo[d]imidazole-7-carboxamide was made analogously to Example 39 using methyl 4,5-difluoro-2-(((4-methylmorpholin-3-yl)methyl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-(((4-methylmorpholin-3-yl)methyl)amino)-1H-benzo[d]imidazole-7-carboxamide was isolated as a white solid. $C_{20}H_{19}ClF_3N_5O_2$. 454.2/456.1 (M+1).

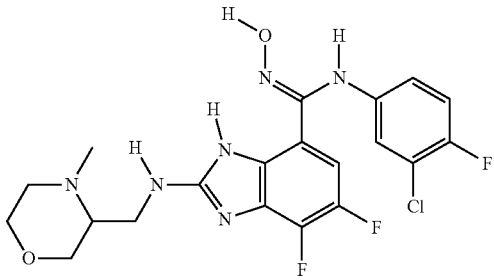 [SMILES: CN1CCOCC1CNc1nc2c(F)c(F)cc(/C(=N/O)Nc3ccc(F)c(Cl)c3)c2[nH]1]

Example 429 was made analogously to Example 59 using N-(3-chloro-4-fluorophenyl)-4,5-difluoro-2-(((4-methylmorpholin-3-yl)methyl)amino)-1H-benzo[d]imidazole-7-carboxamide in place of N-(3-chloro-4-fluorophenyl)-1H-imidazo[4,5-b]pyridine-7-carboxamide. The TFA salt of N-(3-chloro-4-fluorophenyl)-4,5-difluoro-N'-hydroxy-2-(((4-methylmorpholin-3-yl)methyl)amino)-1H-benzo[d]imidazole-7-carboximidamide was isolated as an off-white solid. $C_{20}H_{20}ClF_3N_6O_2$. 469.1/471.1 (M+1). $^1$H NMR (400 MHz, DMSO-d6) δ 10.76 (s, 1H), 8.68 (s, 1H), 7.09 (t, J=9.1 Hz, 1H), 6.92 (dd, J=6.5, 2.8 Hz, 2H), 6.83 (dd, J=12.2, 6.8 Hz, 1H), 6.53 (ddd, J=8.9, 4.0, 2.7 Hz, 1H), 4.10-3.84 (m, 4H), 3.80-3.65 (m, 2H), 3.58-3.34 (m, 2H), 3.26 (m, 1H), 3.03 (s, 3H). $^{19}$F NMR (377 MHz, DMSO-d6) δ −74.98 (9F), −127.43 (1F), −150.47 (dd, J=21.1, 12.8 Hz, 1F), −157.02 (1F).

Example 430: N-(3-bromophenyl)-2-((2-(dimethylamino)ethyl)amino)-4,5-difluoro-N'-hydroxy-1H-benzo[d]imidazole-7-carboximidamide

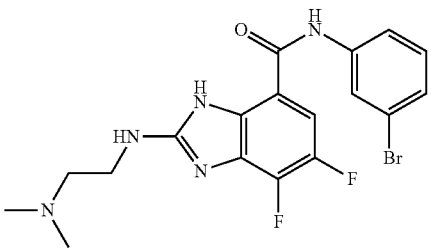 [SMILES: CN(C)CCNc1nc2c(F)c(F)cc(C(=O)Nc3cccc(Br)c3)c2[nH]1]

N-(3-bromophenyl)-2-((2-(dimethylamino)ethyl)amino)-4,5-difluoro-1H-benzo[d]imidazole-7-carboxamide was made analogously to Example 39 using methyl 2-((2-(dimethylamino)ethyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-bromophenyl)-2-((2-(dimethylamino)ethyl)amino)-4,5-difluoro-1H-benzo[d]imidazole-7-carboxamide was isolated as a white solid. $C_{18}H_{18}BrF_2N_5O$. 438.1/440.1 (M+1).

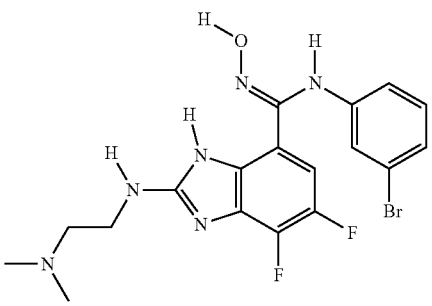 [SMILES: CN(C)CCNc1nc2c(F)c(F)cc(/C(=N/O)Nc3cccc(Br)c3)c2[nH]1]

Example 430 was made analogously to Example 59 using N-(3-bromophenyl)-2-((2-(dimethylamino)ethyl)amino)-4,5-difluoro-1H-benzo[d]imidazole-7-carboxamide in place of N-(3-chloro-4-fluorophenyl)-1H-imidazo[4,5-b]pyridine-7-carboxamide. The TFA salt of N-(3-bromophenyl)-2-((2-(dimethylamino)ethyl)amino)-4,5-difluoro-N'-hydroxy-1H-benzo[d]imidazole-7-carboximidamide was isolated as an off-white solid. $C_{18}H_{19}BrF_2N_6O$. 455.1/456.1 (M+1). $^1$H NMR (400 MHz, DMSO-d6) δ 10.80 (s, 1H), 8.68 (s, 1H), 7.04-6.93 (m, 3H), 6.89 (s, 1H), 6.81 (dd, J=12.2, 6.9 Hz, 1H), 6.54 (dt, J=7.7, 1.7 Hz, 1H), 3.70 (m, 2H), 3.32 (m, 2H), 2.86 (s, 6H). $^{19}$F NMR (377 MHz, DMSO) δ −74.85 (9F), −150.52 (1F), −157.05 (1F).

Example 431: N-(3-chlorophenyl)-2-((2-(dimethylamino)ethyl)amino)-4,5-difluoro-N'-hydroxy-1H-benzo[d]imidazole-7-carboximidamide

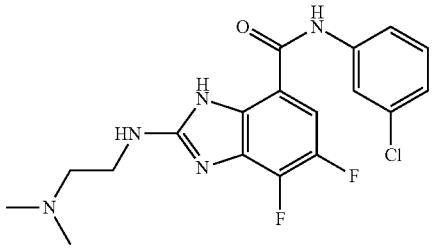 [SMILES: CN(C)CCNc1nc2c(F)c(F)cc(C(=O)Nc3cccc(Cl)c3)c2[nH]1]

N-(3-chlorophenyl)-2-((2-(dimethylamino)ethyl)amino)-4,5-difluoro-1H-benzo[d]imidazole-7-carboxamide was made analogously to Example 39 using methyl 2-((2-(dimethylamino)ethyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chlorophenyl)-2-((2-(dimethylamino)ethyl)amino)-4,5-difluoro-1H-benzo[d]imidazole-7-carboxamide was isolated as a white solid. $C_{18}H_{18}ClF_2N_5O$. 394.1/396.2 (M+1).

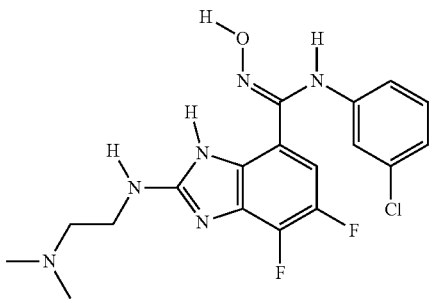 [SMILES: CN(C)CCNc1nc2c(F)c(F)cc(/C(=N/O)Nc3cccc(Cl)c3)c2[nH]1]

Example 431 was made analogously to Example 59 using N-(3-chlorophenyl)-2-((2-(dimethylamino)ethyl)amino)-4,5-difluoro-1H-benzo[d]imidazole-7-carboxamide in place of N-(3-chloro-4-fluorophenyl)-1H-imidazo[4,5-b]pyridine-7-carboxamide. The TFA salt of N-(3-chlorophenyl)-2-((2-(dimethylamino)ethyl)amino)-4,5-difluoro-N'-hydroxy-1H-benzo[d]imidazole-7-carboximidamide was isolated as an off-white solid. $C_{18}H_{19}ClF_2N_6O$. 409.1/411.1 (M+1)). $^1$H NMR (400 MHz, DMSO-d6) δ 10.79 (s, 1H), 8.68 (s, 1H), 7.05 (t, J=8.0 Hz, 1H), 6.86-6.72 (m, 3H), 6.54-6.46 (m, 1H), 3.69 (s, 3H), 3.32 (s, 4H), 2.86 (s, 6H). $^{19}$F NMR (376 MHz, DMSO-d6) δ −74.52, −150.61, −157.17.

Example 432: N-(3-bromo-4-fluorophenyl)-2-((2-(dimethylamino)ethyl)amino)-4,5-difluoro-N'-hydroxy-1H-benzo[d]imidazole-7-carboximidamide

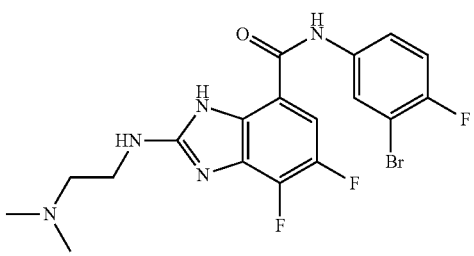 [SMILES: CN(C)CCNc1nc2c(F)c(F)cc(C(=O)Nc3ccc(F)c(Br)c3)c2[nH]1]

N-(3-bromo-4-fluorophenyl)-2-((2-(dimethylamino)ethyl)amino)-4,5-difluoro-1H-benzo[d]imidazole-7-carboxamide was made analogously to Example 39 using methyl 2-((2-(dimethylamino)ethyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate and 3-bromo-4-fluoroaniline in place of 3-chloro-4-fluoroaniline. The TFA salt of N-(3-bromo-4-fluorophenyl)-2-((2-(dimethylamino)ethyl)amino)-4,5-difluoro-1H-benzo[d]imidazole-7-carboxamide was isolated as a white solid. $C_{18}H_{17}BrF_3N_5O$. 456.1/458.1 (M+1).

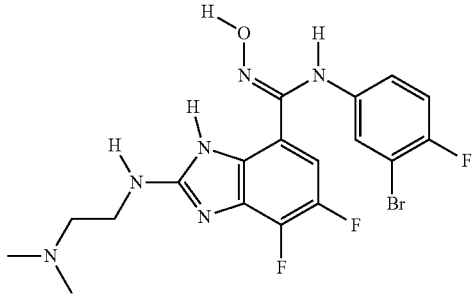 [SMILES: CN(C)CCNc1nc2c(F)c(F)cc(/C(=N/O)Nc3ccc(F)c(Br)c3)c2[nH]1]

Example 432 was made analogously to Example 59 using N-(3-bromo-4-fluorophenyl)-2-((2-(dimethylamino)ethyl)amino)-4,5-difluoro-1H-benzo[d]imidazole-7-carboxamide in place of N-(3-chloro-4-fluorophenyl)-1H-imidazo[4,5-b]pyridine-7-carboxamide. The TFA salt of N-(3-bromo-4-fluorophenyl)-2-((2-(dimethylamino)ethyl)amino)-4,5-difluoro-N'-hydroxy-1H-benzo[d]imidazole-7-carboximidamide was isolated as an off-white solid. $C_{18}H_{18}BrF_3N_6O$. 471.2/474.1 (M+1). $^1$H NMR (400 MHz, DMSO-d6) δ 10.71 (s, 1H), 8.64 (s, 1H), 7.08-7.01 (m, 2H), 6.79 (s, 2H), 6.54 (ddd, J=9.0, 4.2, 2.7 Hz, 1H), 3.66 (s, 2H), 3.30 (s, 2H), 2.84 (s, 6H).

Example 433: N-(3-chloro-4-fluorophenyl)-4,5-difluoro-2-((3-morpholinopropyl)amino)-1H-benzo[d]imidazole-7-carboxamide

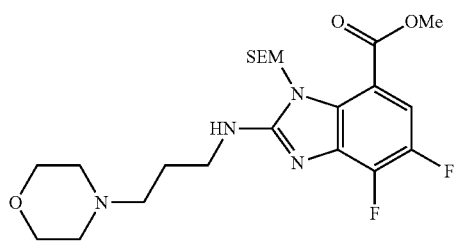 [SMILES: COC(=O)c1cc(F)c(F)c2nc(NCCCN3CCOCC3)n(COCC[Si](C)(C)C)c12]

Methyl 4,5-difluoro-2-((3-morpholinopropyl)amino)-1-((2-(trimethylsilyl)ethoxy)methyl)-1H-benzo[d]imidazole-7-carboxylate was made analogously to Example 39 using 3-morpholinopropan-1-amine in place of N,N-dimethylpropane-1,3-diamine. The TFA salt of methyl 4,5-difluoro-2-((3-morpholinopropyl)amino)-1-((2-(trimethylsilyl)ethoxy)methyl)-1H-benzo[d]imidazole-7-carboxylate was isolated as a yellow oil. $C_{22}H_{34}F_2N_4O_4Si$. 485.1 (M+1).

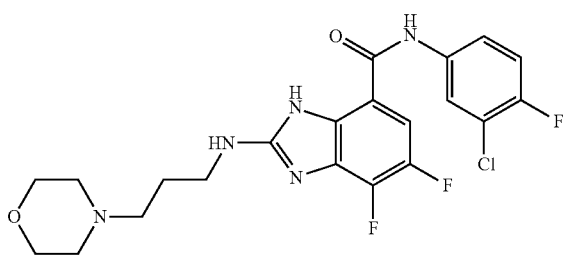 [SMILES: O=C(Nc1ccc(F)c(Cl)c1)c1cc(F)c(F)c2nc(NCCCN3CCOCC3)[nH]c12]

N-(3-chloro-4-fluorophenyl)-4,5-difluoro-2-((3-morpholinopropyl)amino)-1H-benzo[d]imidazole-7-carboxamide was made analogously to Example 39 using methyl 4,5-difluoro-2-((3-morpholinopropyl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-((3-morpholinopropyl)amino)-1H-benzo[d]imidazole-7-carboxamide was isolated as a white solid. $C_{21}H_{21}ClF_3N_5O_2$. 468.2/470.1 (M+1).

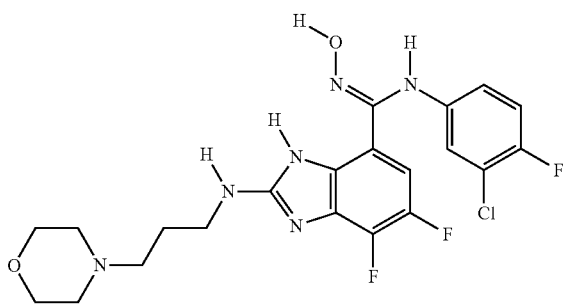 [SMILES: O/N=C(\Nc1ccc(F)c(Cl)c1)c1cc(F)c(F)c2nc(NCCCN3CCOCC3)[nH]c12]

Example 433 was made analogously to Example 432 using N-(3-chloro-4-fluorophenyl)-4,5-difluoro-2-((3-morpholinopropyl)amino)-1H-benzo[d]imidazole-7-carboxamide in place of N-(3-bromo-4-fluorophenyl)-2-((2-(dimethylamino)ethyl)amino)-4,5-difluoro-1H-benzo[d]imidazole-7-carboxamide. The TFA salt of N-(3-chloro-4-fluorophenyl)-4,5-difluoro-N'-hydroxy-2-((3-morpholinopropyl)amino)-1H-benzo[d]imidazole-7-carboximidamide was isolated as an off-white solid. $C_{21}H_{22}ClF_3N_6O_2$. 483.1/485.1 (M+1). $^1$H NMR (400 MHz, DMSO-d6) δ 10.75 (s, 1H), 8.66 (s, 1H), 7.09 (t, J=9.1 Hz, 1H), 6.92 (dd, J=6.5, 2.7 Hz, 1H), 6.82 (s, 2H), 6.54 (dq, J=9.0, 3.1 Hz, 1H), 3.82 (m, 2H), 3.42 (m, 2H), 3.27 (m, 2H), 3.17 (t, J=7.9 Hz, 2H), 1.97 (t, J=7.8 Hz, 2H).

Example 434: N-(3-chloro-4-fluorophenyl)-4,5-difluoro-N'-hydroxy-2-((3-(pyrrolidin-1-yl)propyl)amino)-1H-benzo[d]imidazole-7-carboximidamide

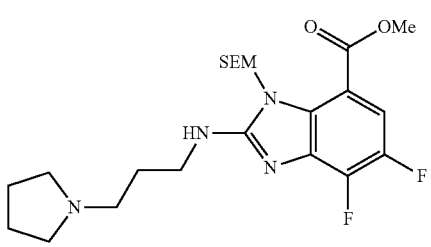 [SMILES: COC(=O)c1cc(F)c(F)c2nc(NCCCN3CCCC3)n(COCC[Si](C)(C)C)c12]

Methyl 4,5-difluoro-2-((3-(pyrrolidin-1-yl)propyl)amino)-1-((2-(trimethylsilyl)ethoxy)methyl)-1H-benzo[d]imidazole-7-carboxylate was made analogously to Example 39 using 3-(pyrrolidin-1-yl)propan-1-amine in place of N,N-dimethylpropane-1,3-diamine. The TFA salt of methyl 4,5-difluoro-2-((3-(pyrrolidin-1-yl)propyl)amino)-1-((2-(trimethylsilyl)ethoxy)methyl)-1H-benzo[d]imidazole-7-carboxylate was isolated as a yellow oil. $C_{22}H_{34}F_2N_4O_3Si$. 469.2 (M+1).

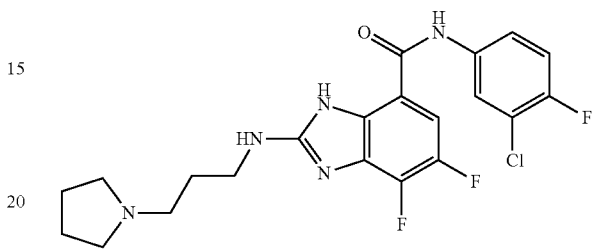

N-(3-chloro-4-fluorophenyl)-4,5-difluoro-2-((3-(pyrrolidin-1-yl)propyl)amino)-1H-benzo[d]imidazole-7-carboxamide was made analogously to Example 39 using methyl 4,5-difluoro-2-((3-(pyrrolidin-1-yl)propyl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-((3-(pyrrolidin-1-yl)propyl)amino)-1H-benzo[d]imidazole-7-carboxamide was isolated as a white solid. $C_{21}H_{21}ClF_3N_5O$. 452.0/454.1 (M+1).

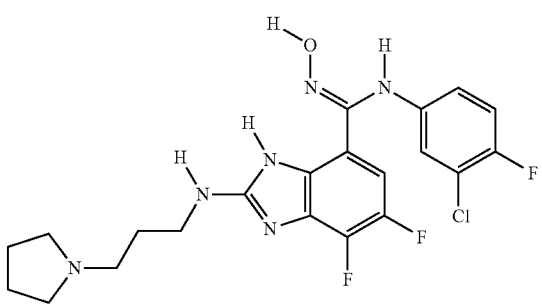 [SMILES: O/N=C(\Nc1ccc(F)c(Cl)c1)c1cc(F)c(F)c2nc(NCCCN3CCCC3)[nH]c12]

Example 434 was made analogously to Example 432 using N-(3-chloro-4-fluorophenyl)-4,5-difluoro-2-((3-(pyrrolidin-1-yl)propyl)amino)-1H-benzo[d]imidazole-7-carboxamide in place of N-(3-bromo-4-fluorophenyl)-2-((2-(dimethylamino)ethyl)amino)-4,5-difluoro-1H-benzo[d]imidazole-7-carboxamide. The TFA salt of N-(3-chloro-4-fluorophenyl)-4,5-difluoro-N'-hydroxy-2-((3-(pyrrolidin-1-yl)propyl)amino)-1H-benzo[d]imidazole-7-carboximidamide was isolated as an off-white solid. $C_{21}H_{22}ClF_3N_6O$. 467.2/469.1 (M+1). $^1$H NMR (400 MHz, DMSO-d6) δ 10.75 (s, 1H), 9.68 (s, 1H), 8.66 (s, 1H), 7.09 (t, J=9.1 Hz, 1H), 6.92 (dd, J=6.5, 2.7 Hz, 1H), 6.90-6.75 (m, 2H), 6.54 (ddd, J=9.0, 4.1, 2.8 Hz, 1H), 3.55-3.34 (m, 8H), 3.17 (m, 2H), 1.93 (m, 6H). $^{19}$F NMR (377 MHz, DMSO) δ −74.57, −127.43, −150.48, −157.56.

Example 435: 2-(((3R)-4-amino-1-methylpyrrolidin-3-yl)amino)-N-(3-chloro-4-fluorophenyl)-4,5-difluoro-N'-hydroxy-1H-benzo[d]imidazole-7-carboximidamide

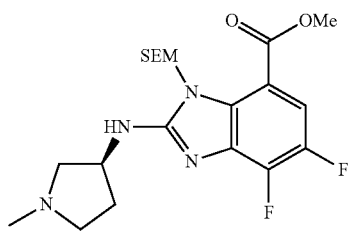 [SMILES: COC(=O)c1cc(F)c(F)c2nc(N[C@H]3CCN(C)C3)n(COCC[Si](C)(C)C)c12]

Methyl (S)-4,5-difluoro-2-((1-methylpyrrolidin-3-yl)amino)-1-((2-(trimethylsilyl)ethoxy)methyl)-1H-benzo[d]imidazole-7-carboxylate was made analogously to Example 39 using (S)-1-methylpyrrolidin-3-amine in place of N,N-dimethylpropane-1,3-diamine. The TFA salt of methyl (S)-4,5-difluoro-2-((1-methylpyrrolidin-3-yl)amino)-1-((2-(trimethylsilyl)ethoxy)methyl)-1H-benzo[d]imidazole-7-carboxylate was isolated as a yellow oil. $C_{21}H_{32}F_2N_4O_3Si$. 441.0 (M+1).

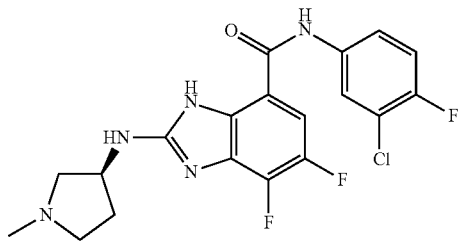 [SMILES: CN1CC[C@H](Nc2nc3c(F)c(F)cc(C(=O)Nc4ccc(F)c(Cl)c4)c3[nH]2)C1]

(S)—N-(3-chloro-4-fluorophenyl)-4,5-difluoro-2-((1-methylpyrrolidin-3-yl)amino)-1H-benzo[d]imidazole-7-carboxamide was made analogously to Example 39 using methyl (S)-4,5-difluoro-2-((1-methylpyrrolidin-3-yl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of (S)—N-(3-chloro-4-fluorophenyl)-4,5-difluoro-2-((1-methylpyrrolidin-3-yl)amino)-1H-benzo[d]imidazole-7-carboxamide was isolated as a white solid. $C_{19}H_{17}ClF_3N_5O$. 424.1/426.1 (M+1).

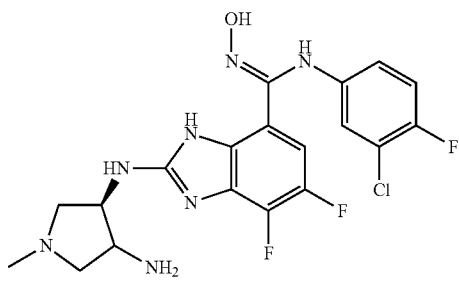 [SMILES: CN1CC(N)[C@H](Nc2nc3c(F)c(F)cc(/C(=N/O)Nc4ccc(F)c(Cl)c4)c3[nH]2)C1]

Example 435 was made analogously to Example 432 using (S)—N-(3-chloro-4-fluorophenyl)-4,5-difluoro-2-((1-methylpyrrolidin-3-yl)amino)-1H-benzo[d]imidazole-7-carboxamide in place of N-(3-bromo-4-fluorophenyl)-2-((2-(dimethylamino)ethyl)amino)-4,5-difluoro-1H-benzo[d]imidazole-7-carboxamide. The TFA salt of 2-(((3R)-4-amino-1-methylpyrrolidin-3-yl)amino)-N-(3-chloro-4-fluorophenyl)-4,5-difluoro-N'-hydroxy-1H-benzo[d]imidazole-7-carboximidamide was isolated as an off-white solid (15.8 mg, 67%). $C_{19}H_{19}ClF_3N_7O$. 454.1/456.1 (M+1). $^1$H NMR (400 MHz, DMSO-d6) δ 10.80 (s, 1H), 8.67 (s, 1H), 7.10 (t, J=9.2 Hz, 1H), 7.08 (br s, 1H), 6.92 (dd, J=6.5, 2.7 Hz, 1H), 6.83 (dd, J=12.2, 7.0 Hz, 1H), 6.54 (ddd, J=8.9, 4.0, 2.7 Hz, 1H), 6.10 (s, 2H), 4.77 (s, 1H), 4.00 (dq, J=8.3, 7.0 Hz, 1H), 3.90 (dd, J=12.5, 8.1 Hz, 1H), 3.82 (t, J=9.9 Hz, 1H), 3.67 (d, J=12.7 Hz, 1H), 3.58 (td, J=11.2, 8.1 Hz, 1H), 3.38 (s, 3H), 2.76-2.64 (m, 1H), 2.25-2.12 (m, 1H). $^{19}$F NMR (376 MHz, DMSO) δ −74.87, −127.5, −150.4, −156.9.

Example 436: N-(3-chloro-4-fluorophenyl)-2-((2-(dimethylamino)-2-phenylethyl)amino)-4,5-difluoro-N'-hydroxy-1H-benzo[d]imidazole-7-carboximidamide

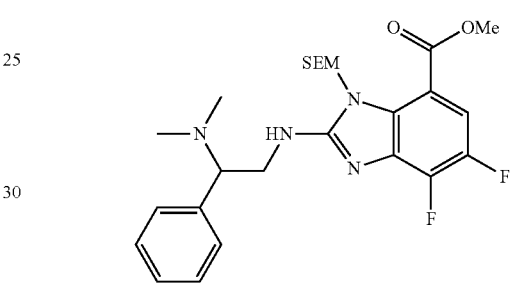

Methyl 2-((2-(dimethylamino)-2-phenylethyl)amino)-4,5-difluoro-1-((2-(trimethylsilyl)ethoxy)methyl)-1H-benzo[d]imidazole-7-carboxylate was made analogously to Example 39 using $N^1,N^1$-dimethyl-1-phenylethane-1,2-diamine in place of N,N-dimethylpropane-1,3-diamine. The TFA salt of methyl 2-((2-(dimethylamino)-2-phenylethyl)amino)-4,5-difluoro-1-((2-(trimethylsilyl)ethoxy)methyl)-1H-benzo[d]imidazole-7-carboxylate was isolated as a yellow oil. $C_{25}H_{34}F_2N_4O_3Si$. 505.1 (M+1).

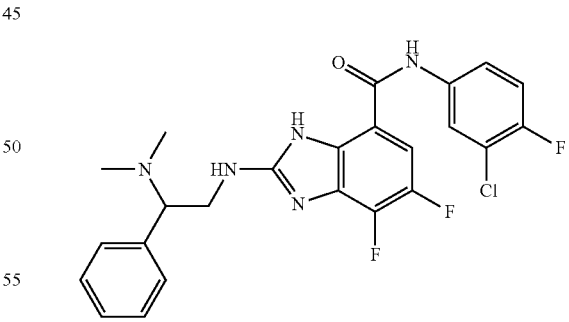

N-(3-chloro-4-fluorophenyl)-2-((2-(dimethylamino)-2-phenyl ethyl)amino)-4,5-difluoro-1H-benzo[d]imidazole-7-carboxamide was made analogously to Example 39 using methyl 2-((2-(dimethylamino)-2-phenylethyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-42-(trimethylsilyl)ethoxy)methyl)-1H-benzo[d]imidazole-7-carboxylate. The TFA salt of N-(3-chloro-4-fluorophenyl)-2-((2-(dimethylamino)-2-phenylethyl)amino)-4,5-difluoro-1H-benzo[d]imidazole-7-carboxamide was isolated as a white solid. $C_{24}H_{21}ClF_3N_5O$. 488.1/490.1 (M+1).

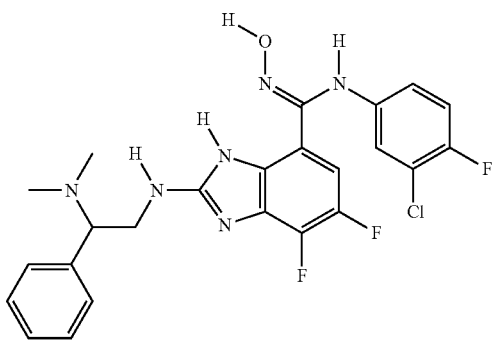 [SMILES: CN(C)C(CNc1nc2c(F)c(F)cc(/C(=N/O)Nc3ccc(F)c(Cl)c3)c2[nH]1)c1ccccc1]

Example 436 was made analogously to Example 432 using N-(3-chloro-4-fluorophenyl)-2-((2-(dimethylamino)-2-phenylethyl)amino)-4,5-difluoro-1H-benzo[d]imidazole-7-carboxamide in place of N-(3-bromo-4-fluorophenyl)-2-((2-(dimethylamino)ethyl)amino)-4,5-difluoro-1H-benzo[d]imidazole-7-carboxamide. The TFA salt of N-(3-chloro-4-fluorophenyl)-2-((2-(dimethylamino)-2-phenylethyl)amino)-4,5-difluoro-N'-hydroxy-1H-benzo[d]imidazole-7-carboximidamide was isolated as an off-white solid. $C_{24}H_{22}ClF_3N_6O$. 503.1/505.1 (M+1). $^1$H NMR (400 MHz, DMSO-d6) δ 10.75 (s, 1H), 10.68 (s, 1H), 8.66 (s, 1H), 7.62-7.55 (m, 1H), 7.53 (d, J=3.3 Hz, 3H), 7.09 (t, J=8.9 Hz, 1H), 6.89 (dd, J=6.5, 2.7 Hz, 1H), 6.85-6.74 (m, 1H), 6.67-6.58 (m, 1H), 6.54-6.46 (m, 1H), 4.69 (m, 1H), 4.26 (m, 1H), 3.97 (m, 1H), 2.75 (s, 6H). $^{19}$F NMR (377 MHz, DMSO-d6) δ −74.37 (9F), −127.54 (1F), −150.55 (1F), −156.90 (1F).

Example 437: N-(3-chloro-4-fluorophenyl)-2-(((1R,2R)-2-(dimethylamino)cyclohexyl)amino)-4,5-difluoro-N'-hydroxy-1H-benzo[d]imidazole-7-carboximidamide

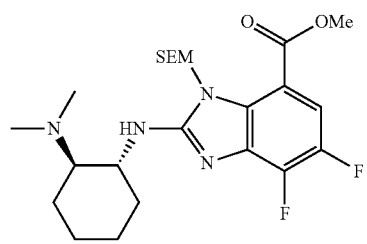 [SMILES: COC(=O)c1cc(F)c(F)c2nc(N[C@@H]3CCCC[C@H]3N(C)C)n(COCC[Si](C)(C)C)c12]

Methyl 2-(((1R,2R)-2-(dimethylamino)cyclohexyl)amino)-4,5-difluoro-1-((2-(trimethylsilyl)ethoxy)methyl)-1H-benzo[d]imidazole-7-carboxylate was made analogously to Example 39 using (1R,2R)—$N^1,N^1$-dimethylcyclohexane-1,2-diamine in place of N,N-dimethylpropane-1,3-diamine. The TFA salt of methyl 2-(41R,2R)-2-(dimethylamino)cyclohexyl)amino)-4,5-difluoro-1-((2-(trimethylsilyl)ethoxy)methyl)-1H-benzo[d]imidazole-7-carboxylate was isolated as a yellow oil. $C_{23}H_{36}F_2N_4O_3Si$. 483.2 (M+1).

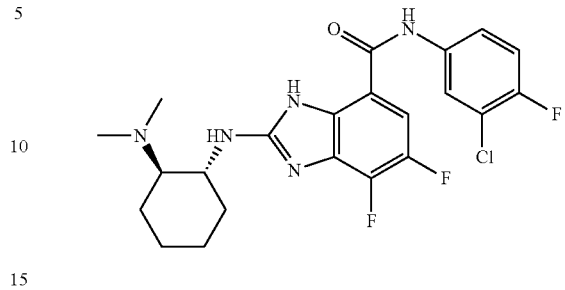

N-(3-chloro-4-fluorophenyl)-2-(((1R,2R)-2-(dimethylamino)cyclohexyl)amino)-4,5-difluoro-1H-benzo[d]imidazole-7-carboxamide was made analogously to Example 39 using methyl 2-(((1R,2R)-2-(dimethylamino)cyclohexyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-(((1R,2R)-2-(dimethylamino)cyclohexyl)amino)-4,5-difluoro-1H-benzo[d]imidazole-7-carboxamide was isolated as a white solid. $C_{22}H_{23}ClF_3N_5O$. 466.2/468.1 (M+1).

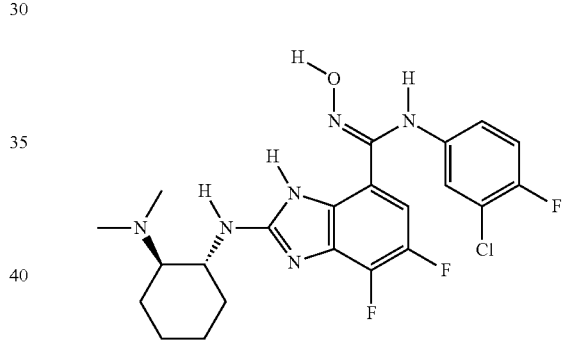

Example 437 was made analogously to Example 402 using N-(3-chloro-4-fluorophenyl)-2-(((1R,2R)-2-(dimethylamino)cyclohexyl)amino)-4,5-difluoro-1H-benzo[d]imidazole-7-carboxamide in place of N-(3-chloro-4-fluorophenyl)-2-(((1-(dimethylamino)cyclohexyl)methyl)amino)-4,5-difluoro-1H-benzo[d]imidazole-7-carboxamide. The TFA salt of N-(3-chloro-4-fluorophenyl)-2-(((1R,2R)-2-(dimethylamino)cyclohexyl)amino)-4,5-difluoro-N'-hydroxy-1H-benzo[d]imidazole-7-carboximidamide was isolated as an off-white solid. $C_{22}H_{24}ClF_3N_6O$. 481.2/483.1 (M+1). $^1$H NMR (400 MHz, DMSO-d6) δ 10.78 (s, 1H), 8.91 (s, 1H), 8.67 (s, 1H), 7.11 (t, J=9.1 Hz, 1H), 6.91 (dd, J=6.5, 2.7 Hz, 1H), 6.84 (dd, J=12.3, 7.0 Hz, 1H), 6.79 (d, J=9.7 Hz, 1H), 6.53 (ddd, J=9.0, 4.0, 2.7 Hz, 1H), 4.02 (m, 1H), 3.33 (m, 1H), 2.77 (s, 3H), 2.78 (s, 3H), 2.07 (m, 1H), 1.93 (app. d, J=9.9 Hz, 1H), 1.83 (app. d, J=11.8 Hz, 1H), 1.70 (app. d, J=9.5 Hz, 1H), 1.63-1.48 (m, 1H), 1.36 (dq, J=27.4, 13.2, 12.3 Hz, 3H). $^{19}$F NMR (377 MHz, DMSO-d6) δ −75.02 (9F), −127.56 (1F), −150.41 (1F), −156.89 (1F).

Example 438: N-(3-chloro-4-fluorophenyl)-2-(((1-(dimethylamino)cyclopentyl)methyl)amino)-4,5-difluoro-N'-hydroxy-1H-benzo[d]imidazole-7-carboximidamide

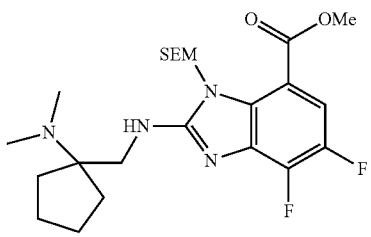 [SMILES: COC(=O)c1cc(F)c(F)c2nc(NCC3(N(C)C)CCCC3)n(COCC[Si](C)(C)C)c12]

Methyl 2-(((1-(dimethylamino)cyclopentyl)methyl)amino)-4,5-difluoro-1-((2-(trimethylsilyl)ethoxy)methyl)-1H-benzo[d]imidazole-7-carboxylate was made analogously to Example 39 using 1-(aminomethyl)-N,N-dimethylcyclopentan-1-amine in place of N,N-dimethylpropane-1,3-diamine. The TFA salt of methyl 2-(((1-(dimethylamino)cyclopentyl)methyl)amino)-4,5-difluoro-1-((2-(trimethylsilyl)ethoxy)methyl)-1H-benzo[d]imidazole-7-carboxylate was isolated as a yellow oil. $C_{23}H_{36}F_2N_4O_3Si$. 483.2 (M+1).

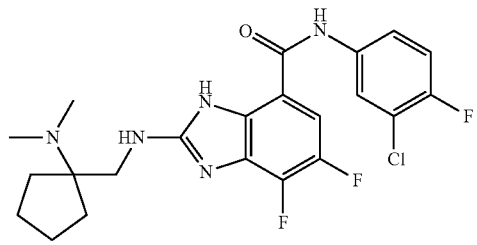 [SMILES: CN(C)C1(CNc2nc3c(F)c(F)cc(C(=O)Nc4ccc(F)c(Cl)c4)c3[nH]2)CCCC1]

N-(3-chloro-4-fluorophenyl)-2-(((1-dimethylamino)cyclopentyl)methyl)amino)-4,5-difluoro-1H-benzo[d]imidazole-7-carboxamide was made analogously to Example 39 using methyl 2-(((1-(dimethylamino)cyclopentyl)methyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-42-(trimethylsilyl)ethoxy)methyl)-1H-benzo[d]imidazole-7-carboxylate. The TFA salt of N-(3-chloro-4-fluorophenyl)-2-(((1-(dimethylamino)cyclopentyl)methyl)amino)-4,5-difluoro-1H-benzo[d]imidazole-7-carboxamide was isolated as a white solid. $C_{22}H_{23}ClF_3N_5O$. 466.2/468.1 (M+1).

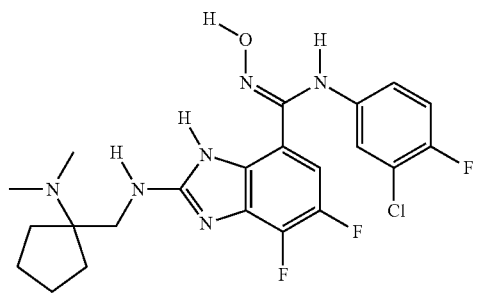 [SMILES: CN(C)C1(CNc2nc3c(F)c(F)cc(/C(=N/O)Nc4ccc(F)c(Cl)c4)c3[nH]2)CCCC1]

Example 438 was made analogously to Example 402 using N-(3-chloro-4-fluorophenyl)-2-(((1-(dimethylamino)cyclopentyl)methyl)amino)-4,5-difluoro-1H-benzo[d]imidazole-7-carboxamide in place of N-(3-chloro-4-fluorophenyl)-2-(((1-(dimethylamino)cyclohexyl)methyl)amino)-4,5-difluoro-1H-benzo[d]imidazole-7-carboxamide. The TFA salt of N-(3-chloro-4-fluorophenyl)-2-(((1-(dimethylamino)cyclopentyl)methyl)amino)-4,5-difluoro-N'-hydroxy-1H-benzo[d]imidazole-7-carboximidamide was isolated as an off-white solid. $C_{22}H_{24}ClF_3N_6O$. 481.2/483.1 (M+1). $^1$H NMR (400 MHz, DMSO-d6) δ 10.79 (s, 1H), 9.68 (s, 1H), 8.70 (s, 1H), 7.15-7.01 (m, 2H), 6.93 (dd, J=6.5, 2.7 Hz, 1H), 6.85 (dd, J=12.2, 6.9 Hz, 1H), 6.52 (ddd, J=9.0, 4.1, 2.8 Hz, 1H), 3.74 (d, J=6.6 Hz, 2H), 2.84 (s, 3H), 2.83 (s, 3H), 1.96-1.79 (m, 4H), 1.71 (t, J=5.6 Hz, 4H). $^{19}$F NMR (377 MHz, DMSO) δ −74.89 (9F), −127.51 (1F), −150.42 (1F), −157.09 (1F).

Example 439: N-(3-chloro-4-fluorophenyl)-2-(((1S,3S)-3-(dimethylamino)cyclohexyl)amino)-4,5-difluoro-N'-hydroxy-1H-benzo[d]imidazole-7-carboximidamide

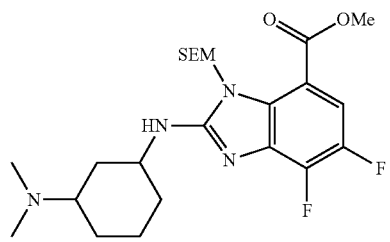 [SMILES: COC(=O)c1cc(F)c(F)c2nc(NC3CCCC(N(C)C)C3)n(COCC[Si](C)(C)C)c12]

Methyl 2-((3-(dimethylamino)cyclohexyl)amino)-4,5-difluoro-1-((2-(trimethylsilyl)ethoxy)methyl)-1H-benzo[d]imidazole-7-carboxylate was made analogously to Example 39 using $N^1,N^1$-dimethylcyclohexane-1,3-diamine in place of N,N-dimethylpropane-1,3-diamine. The TFA salt of methyl 2-((3-(dimethylamino)cyclohexyl)amino)-4,5-difluoro-1-((2-(trimethylsilyl)ethoxy)methyl)-1H-benzo[d]imidazole-7-carboxylate was isolated as a yellow oil. $C_{23}H_{36}F_2N_4O_3Si$. 483.1 (M+1).

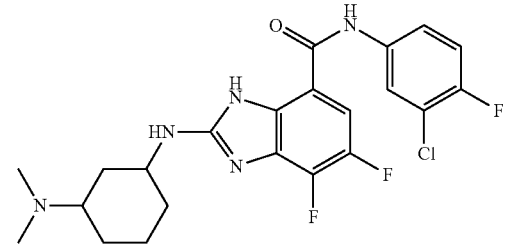 [SMILES: CN(C)C1CCCC(Nc2nc3c(F)c(F)cc(C(=O)Nc4ccc(F)c(Cl)c4)c3[nH]2)C1]

N-(3-chloro-4-fluorophenyl)-2-((3-(dimethylamino)cyclohexyl)amino)-4,5-difluoro-1H-benzo[d]imidazole-7-carboxamide was made analogously to Example 39 using methyl 2-((3-(dimethylamino)cyclohexyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-((3-(dimethylamino)cyclohexyl)amino)-4,5-difluoro-1H-benzo[d]imidazole-7-carboxamide was isolated as a white solid. $C_{22}H_{23}ClF_3N_5O$. 466.2 (M+1).

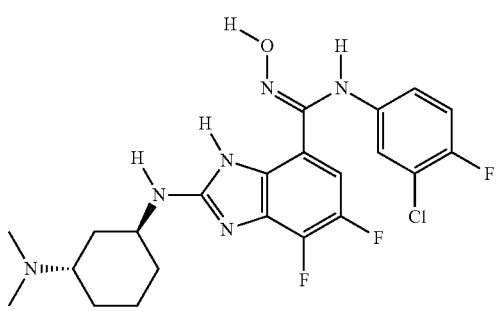 [SMILES: CN(C)[C@H]1CCC[C@H](Nc2nc3c(F)c(F)cc(/C(=N/O)Nc4ccc(F)c(Cl)c4)c3[nH]2)C1]

Example 439 was made analogously to Example 402 using N-(3-chloro-4-fluorophenyl)-2-((3-(dimethylamino)cyclohexyl)amino)-4,5-difluoro-1H-benzo[d]imidazole-7-carboxamide in place of N-(3-chloro-4-fluorophenyl)-2-(((1-(dimethylamino)cyclohexyl)methyl)amino)-4,5-difluoro-1H-benzo[d]imidazole-7-carboxamide. The two diastereomers were separated by reverse phase HPLC and the TFA salt of N-(3-chloro-4-fluorophenyl)-2-(((1S,3S)-3-(dimethylamino)cyclohexyl)amino)-4,5-difluoro-N'-hydroxy-1H-benzo[d]imidazole-7-carboximidamide was isolated as an off-white solid. ($C_{22}H_{24}ClF_3N_6O$. 481.1/483.1 (M+1). $^1$H NMR (400 MHz, DMSO-d6) δ 10.81 (s, 1H), 9.45 (s, 1H), 8.69 (s, 1H), 7.10 (t, J=9.1 Hz, 1H), 6.92 (dd, J=6.5, 2.7 Hz, 1H), 6.81 (t, J=9.8 Hz, 1H), 6.54 (ddd, J=9.0, 4.0, 2.7 Hz, 1H), 3.33 (m, 1H), 2.76 (d, J=5.0 Hz, 3H), 2.74 (d, J=4.9 Hz, 3H), 2.39 (d, J=11.9 Hz, 1H), 1.93 (dd, J=27.6, 11.7 Hz, 4H), 1.48-1.30 (m, 4H), 1.21 (d, J=13.5 Hz, 1H). $^{19}$F NMR (377 MHz, DMSO-d6) δ -74.82, -127.48, -149.43, -156.88.

Example 440: N-(3-chloro-4-fluorophenyl)-2-(((1S,3R)-3-(dimethylamino)cyclohexyl)amino)-4,5-difluoro-N'-hydroxy-1H-benzo[d]imidazole-7-carboximidamide

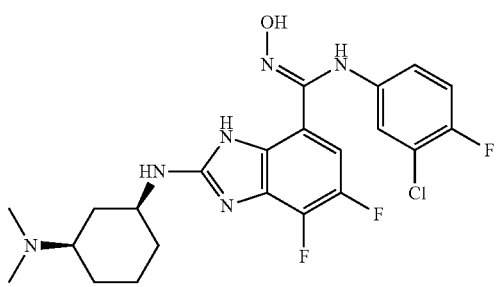 [SMILES: CN(C)[C@@H]1CCC[C@H](Nc2nc3c(F)c(F)cc(/C(=N/O)Nc4ccc(F)c(Cl)c4)c3[nH]2)C1]

The TFA salt of N-(3-chloro-4-fluorophenyl)-2-(4/S,3R)-3-(dimethylamino)cyclohexyl)amino)-4,5-difluoro-N'-hydroxy-1H-benzo[d]imidazole-7-carboximidamide was isolated from the sequence described in Example 439 as an off-white solid. $C_{22}H_{24}ClF_3N_6O$. 481.1/483.0 (M+1). $^1$H NMR (400 MHz, DMSO-d6) δ 10.77 (s, 1H), 9.27 (s, 1H), 8.65 (s, 1H), 7.11 (t, J=9.1 Hz, 1H), 7.00 (s, 1H), 6.91 (dd, J=6.5, 2.7 Hz, 1H), 6.79 (dd, J=12.0, 7.5 Hz, 1H), 6.54 (dt, J=9.1, 3.5 Hz, 1H), 5.06 (q, J=9.0 Hz, 1H), 4.21 (m, 1H), 3.29 (m, 1H), 2.77 (d, J=4.6 Hz, 3H), 2.72 (d, J=4.7 Hz, 3H), 2.29 (d, J=14.9 Hz, 1H), 1.98 (m, 1H), 1.77 (m, 3H), 1.56 (m, 3H).

Example 441: N-(3-chloro-4-fluorophenyl)-2-(((1-(dimethylamino)cyclobutyl)methyl)amino)-4,5-difluoro-N'-hydroxy-1H-benzo[d]imidazole-7-carboximidamide

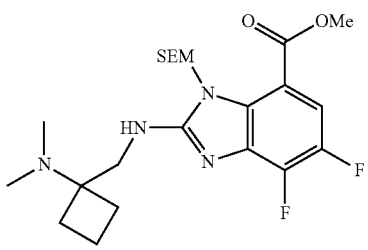 [SMILES: COC(=O)c1cc(F)c(F)c2nc(NCC3(N(C)C)CCC3)n(COCC[Si](C)(C)C)c12]

Methyl 2-(((1-(dimethylamino)cyclobutyl)methyl)amino)-4,5-difluoro-1-((2-(trimethylsilyl)ethoxy)methyl)-1H-benzo[d]imidazole-7-carboxylate was made analogously to Example 39 using 1-(aminomethyl)-N,N-dimethylcyclobutan-1-amine in place of N,N-dimethylpropane-1,3-diamine. The TFA salt of methyl 2-(((1-(dimethylamino)cyclobutyl)methyl)amino)-4,5-difluoro-1-((2-(trimethylsilyl)ethoxy)methyl)-1H-benzo[d]imidazole-7-carboxylate was isolated as a yellow oil. $C_{22}H_{34}F_2N_4O_3Si$. 469.2 (M+1).

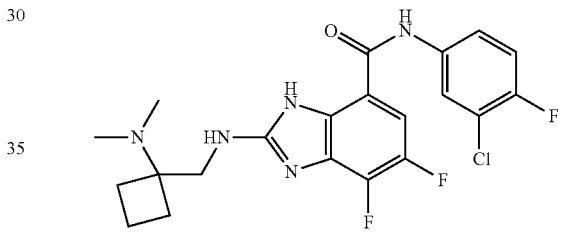

N-(3-chloro-4-fluorophenyl)-2-(41-(dimethylamino)cyclobutyl)methyl)amino)-4,5-difluoro-1H-benzo[d]imidazole-7-carboxamide was made analogously to Example 39 using methyl 2-(((1-(dimethylamino)cyclobutyl)methyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-(((1-(dimethylamino)cyclobutyl)methyl)amino)-4,5-difluoro-1H-benzo[d]imidazole-7-carboxamide was isolated as a white solid. $C_{21}H_{21}ClF_3N_5O$. 452.2/545.1 (M+1).

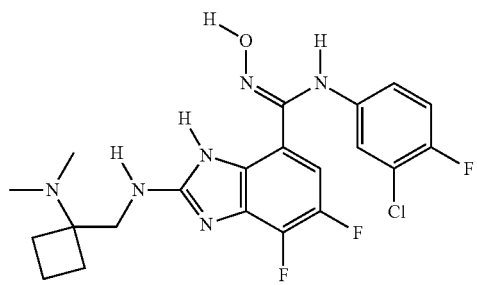 [SMILES: CN(C)C1(CNc2nc3c(F)c(F)cc(/C(=N/O)Nc4ccc(F)c(Cl)c4)c3[nH]2)CCC1]

Example 441 was made analogously to Example 402 using N-(3-chloro-4-fluorophenyl)-2-(((1-(dimethylamino)

cyclobutyl)methyl)amino)-4,5-difluoro-1H-benzo[d]imidazole-7-carboxamide in place of N-(3-chloro-4-fluorophenyl)-2-(((1-(dimethylamino)cyclohexyl)methyl)amino)-4,5-difluoro-1H-benzo[d]imidazole-7-carboxamide. The TFA salt of N-(3-chloro-4-fluorophenyl)-2-(((1-(dimethylamino)cyclobutyl)methyl)amino)-4,5-difluoro-N'-hydroxy-1H-benzo[d]imidazole-7-carboximidamide was isolated as an off-white solid. $C_{21}H_{22}ClF_3N_6O$. 467.2/469.1 (M+1). $^1$H NMR (400 MHz, DMSO-d6) δ 10.79 (s, 1H), 8.70 (s, 1H), 7.17 (t, J=6.6 Hz, 1H), 7.08 (t, J=9.1 Hz, 1H), 6.94 (dd, J=6.5, 2.7 Hz, 1H), 6.87 (dd, J=12.2, 6.9 Hz, 1H), 6.54 (ddd, J=9.0, 4.0, 2.7 Hz, 1H), 6.06 (s, 1H), 4.06 (d, J=6.6 Hz, 2H), 3.20 (s, 6H), 2.74 (dt, J=14.1, 10.0 Hz, 2H), 2.12-1.99 (m, 2H), 1.85-1.70 (m, 2H). $^{19}$F NMR (376 MHz, DMSO-d6) δ −75.09, −127.43, −150.31, −156.83.

Example 442: N-(3-chloro-4-fluorophenyl)-4,5-difluoro-N'-hydroxy-2-((1-methylpiperidin-4-yl)amino)-1H-benzo[d]imidazole-7-carboximidamide

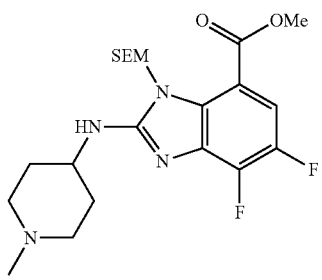 [SMILES: COC(=O)c1cc(F)c(F)c2nc(NC3CCN(C)CC3)n(COCC[Si](C)(C)C)c12]

Methyl 4,5-difluoro-2-((1-methylpiperidin-4-yl)amino)-1-((2-(trimethylsilyl)ethoxy)methyl)-1H-benzo[d]imidazole-7-carboxylate was made analogously to Example 39 using 1-methylpiperidin-4-amine in place of N,N-dimethylpropane-1,3-diamine. The TFA salt of methyl 4,5-difluoro-2-((1-methylpiperidin-4-yl)amino)-1-((2-(trimethylsilyl)ethoxy)methyl)-1H-benzo[d]imidazole-7-carboxylate was isolated as a yellow oil. $C_{21}H_{32}F_2N_4O_3Si$. 455.1 (M+1).

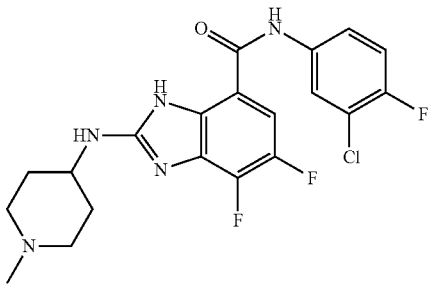 [SMILES: CN1CCC(Nc2nc3c(F)c(F)cc(C(=O)Nc4ccc(F)c(Cl)c4)c3[nH]2)CC1]

N-(3-chloro-4-fluorophenyl)-4,5-difluoro-2-((1-methylpiperidin-4-yl)amino)-1H-benzo[d]imidazole-7-carboxamide was made analogously to Example 39 using methyl 4,5-difluoro-2-((1-methylpiperidin-4-yl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-((1-methylpiperidin-4-yl)amino)-1H-benzo[d]imidazole-7-carboxamide was isolated as a white solid. $C_{20}H_{19}ClF_3N_5O$. 438.2/440.3 (M+1).

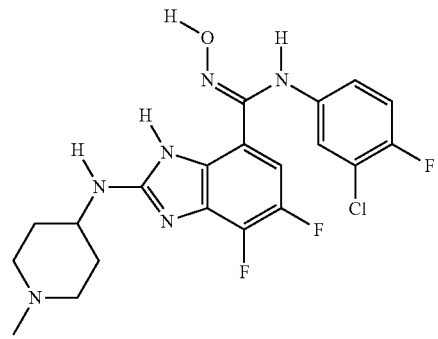 [SMILES: CN1CCC(Nc2nc3c(F)c(F)cc(/C(=N/O)Nc4ccc(F)c(Cl)c4)c3[nH]2)CC1]

Example 442 was made analogously to Example 402 using N-(3-chloro-4-fluorophenyl)-4,5-difluoro-2-((1-methylpiperidin-4-yl)amino)-1H-benzo[d]imidazole-7-carboxamide in place of N-(3-chloro-4-fluorophenyl)-2-(((1-(dimethylamino)cyclohexyl)methyl)amino)-4,5-difluoro-1H-benzo[d]imidazole-7-carboxamide. The TFA salt of N-(3-chloro-4-fluorophenyl)-4,5-difluoro-N'-hydroxy-2-((1-methylpiperidin-4-yl)amino)-1H-benzo[d]imidazole-7-carboximidamide was isolated as an off-white solid. $C_{20}H_{20}ClF_3N_6O$. 453.1/455.1 (M+1). $^1$H NMR (400 MHz, DMSO-d6) δ 10.78 (s, 1H), 9.26 (s, 1H), 8.68 (s, 1H), 7.09 (t, J=9.1 Hz, 1H), 6.92 (m, 1H), 6.82 (m, 1H), 6.53 (ddd, J=8.9, 4.1, 2.7 Hz, 1H), 4.31-4.17 (m, 1H), 3.09 (q, J=11.6 Hz, 4H), 2.80 (d, J=4.7 Hz, 3H), 2.17 (d, J=13.6 Hz, 2H), 1.64 (q, J=13.0, 11.7 Hz, 2H).

Example 443: N-(3-chloro-4-fluorophenyl)-4,5-difluoro-N'-hydroxy-2-((1-methylpiperidin-3-yl)amino)-1H-benzo[d]imidazole-7-carboximidamide

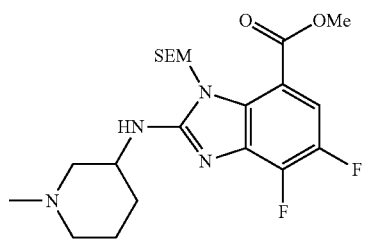 [SMILES: COC(=O)c1cc(F)c(F)c2nc(NC3CCCN(C)C3)n(COCC[Si](C)(C)C)c12]

Methyl 4,5-difluoro-2-((1-methylpiperidin-3-yl)amino)-1-((2-(trimethylsilyl)ethoxy)methyl)-1H-benzo[d]imidazole-7-carboxylate was made analogously to Example 39 using 1-methylpiperidin-3-amine in place of N,N-dimethylpropane-1,3-diamine. The TFA salt of methyl 4,5-difluoro-2-((1-methylpiperidin-3-yl)amino)-1-((2-(trimethylsilyl)ethoxy)methyl)-1H-benzo[d]imidazole-7-carboxylate was isolated as a yellow oil. $C_{21}H_{32}F_2N_4O_3Si$. 455.2 (M+1).

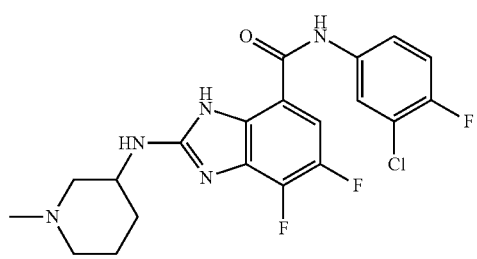 [SMILES: CN1CCCC(Nc2nc3c(F)c(F)cc(C(=O)Nc4ccc(F)c(Cl)c4)c3[nH]2)C1]

N-(3-chloro-4-fluorophenyl)-4,5-difluoro-2-((1-methyl-piperidin-3-yl)amino)-1H-benzo[d]imidazole-7-carboxamide was made analogously to Example 39 using methyl 4,5-difluoro-2-((1-methylpiperidin-3-yl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-4,5-difluoro-2-((1-methylpiperidin-3-yl)amino)-1H-benzo[d]imidazole-7-carboxamide was isolated as a white solid. $C_{20}H_{19}ClF_3N_5O$. 438.2/440.1 (M+1).

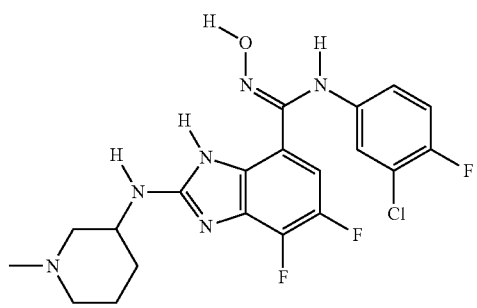 [SMILES: CN1CCCC(Nc2nc3c(F)c(F)cc(/C(=N/O)Nc4ccc(F)c(Cl)c4)c3[nH]2)C1]

Example 443 was made analogously to Example 402 using N-(3-chloro-4-fluorophenyl)-4,5-difluoro-2-((1-methylpiperidin-3-yl)amino)-1H-benzo[d]imidazole-7-carboxamide in place of N-(3-chloro-4-fluorophenyl)-2-(((1-(dimethylamino)cyclohexyl)methyl)amino)-4,5-difluoro-1H-benzo[d]imidazole-7-carboxamide. The TFA salt of N-(3-chloro-4-fluorophenyl)-4,5-difluoro-N'-hydroxy-2-((1-methylpiperidin-3-yl)amino)-1H-benzo[d]imidazole-7-carboximidamide was isolated as an off-white solid. $C_{20}H_{20}ClF_3N_6O$. 453.2/455.1 (M+1). $^1$H NMR (400 MHz, DMSO-d6) δ 10.80 (s, 1H), 9.63 (s, 1H), 8.68 (s, 1H), 7.10 (t, J=9.1 Hz, 1H), 6.92 (dd, J=6.5, 2.8 Hz, 1H), 6.82 (dd, J=12.3, 6.9 Hz, 1H), 6.54 (ddd, J=9.0, 4.1, 2.7 Hz, 1H), 4.03 (m, 1H), 3.65 (m, 1H), 3.42 (m, 1H), 2.88 (d, J=4.7 Hz, 1H), 2.83 (d, J=4.6 Hz, 3H), 2.78 (d, J=8.7 Hz, 1H), 2.06-1.65 (m, 3H), 1.53-1.38 (m, 1H). $^{19}$F NMR (377 MHz, DMSO-d6) δ −74.95 (9F), −127.50 (1F), −150.55 (1F), −156.90 (1F).

Example 444: N-(3-chloro-4-fluorophenyl)-2-(((1S,2S)-2-(dimethylamino)cyclohexyl)amino)-4,5-difluoro-N'-hydroxy-1H-benzo[d]imidazole-7-carboximidamide

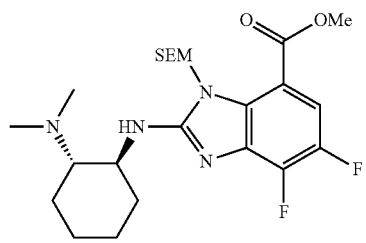 [SMILES: COC(=O)c1cc(F)c(F)c2nc(N[C@H]3CCCC[C@@H]3N(C)C)n(COCC[Si](C)(C)C)c12]

Methyl 2-(((1S,2S)-2-(dimethylamino)cyclohexyl)amino)-4,5-difluoro-1-((2-(trimethylsilyl)ethoxy)methyl)-1H-benzo[d]imidazole-7-carboxylate was made analogously to Example 39 using (1 S,2S)—$N^1,N^1$-dimethylcyclohexane-1,2-diamine in place of N,N-dimethylpropane-1,3-diamine. The TFA salt of methyl 2-(((1S,2S)-2-(dimethylamino)cyclohexyl)amino)-4,5-difluoro-1-((2-(trimethylsilyl)ethoxy)methyl)-1H-benzo[d]imidazole-7-carboxylate was isolated as a yellow oil. $C_{23}H_{36}F_2N_4O_3Si$. 483.2/484.1 (M+1).

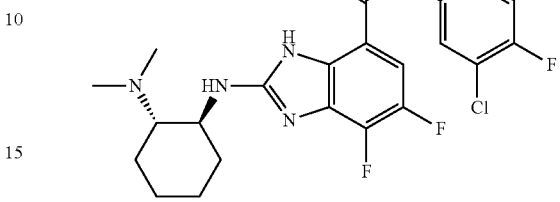

N-(3-chloro-4-fluorophenyl)-2-(((1S,2S)-2-(dimethylamino)cyclohexyl)amino)-4,5-difluoro-1H-benzo[d]imidazole-7-carboxamide was made analogously to Example 39 using methyl 2-(((1S,2S)-2-(dimethylamino)cyclohexyl)amino)-4,5-difluoro-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. The TFA salt of N-(3-chloro-4-fluorophenyl)-2-(((1S,2S)-2-(dimethylamino)cyclohexyl)amino)-4,5-difluoro-1H-benzo[d]imidazole-7-carboxamide was isolated as a white solid. $C_{22}H_{23}ClF_3N_5O$. 466.2/468.1 (M+1).

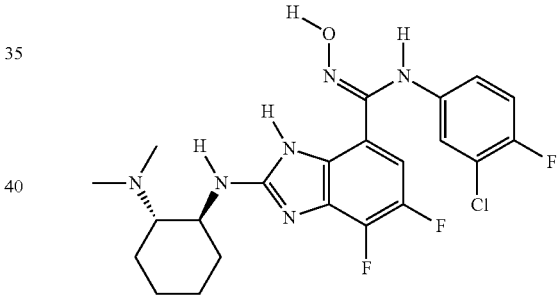

Example 444 was made analogously to Example 402 using N-(3-chloro-4-fluorophenyl)-2-(4/S,2S)-2-(dimethylamino)cyclohexyl)amino)-4,5-difluoro-1H-benzo[d]imidazole-7-carboxamide in place of N-(3-chloro-4-fluorophenyl)-2-(((1-(dimethylamino)cyclohexyl)methyl)amino)-4,5-difluoro-1H-benzo[d]imidazole-7-carboxamide. The TFA salt of N-(3-chloro-4-fluorophenyl)-2-(((1S,2S)-2-(dimethylamino)cyclohexyl)amino)-4,5-difluoro-N'-hydroxy-1H-benzo[d]imidazole-7-carboximidamide was isolated as an off-white solid. $C_{22}H_{24}ClF_3N_6O$. 481.2/483.1 (M+1). $^1$H NMR (400 MHz, DMSO-d6) δ 10.92-10.67 (m, 1H), 8.92 (s, 1H), 8.67 (s, 1H), 7.11 (t, J=9.1 Hz, 1H), 6.91 (dd, J=6.5, 2.7 Hz, 1H), 6.88-6.75 (m, 2H), 6.53 (ddd, J=9.0, 4.0, 2.7 Hz, 1H), 4.04 (m, 1H), 3.33 (td, J=11.6, 3.5 Hz, 1H), 2.77 (d, J=4.3 Hz, 6H), 2.13-2.03 (m, 1H), 1.94 (app. d, J=10.7 Hz, 1H), 1.83 (app. d, J=11.9 Hz, 1H), 1.70 (app. d, J=9.4 Hz, 1H), 1.53 (app. dd, J=13.6, 10.1 Hz, 1H), 1.37 (m, 3H). $^{19}$F NMR (376 MHz, DMSO-d6) δ −75.01 (9F), −127.56 (1F), −150.41 (1F), −156.9 (d, J=22.3 Hz, 1F).

Example 445: (S)—N-(3-chloro-4-fluorophenyl)-4,5-difluoro-N'-hydroxy-2-(piperidin-3-ylamino)-1H-benzo[d]imidazole-7-carboximidamide

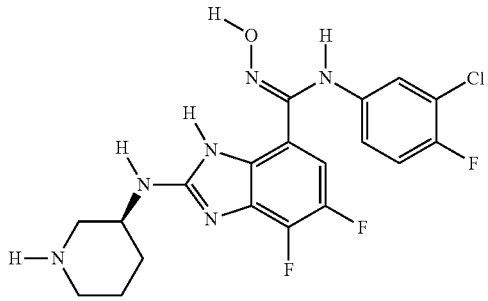 [SMILES: O/N=C(\Nc1ccc(F)c(Cl)c1)c1cc(F)c(F)c2nc(N[C@H]3CCCNC3)[nH]c12]

Example 445 was made analogously to Example 333 using tert-butyl (S)-3-aminopiperidine-1-carboxylate in place of tert-butyl (2-aminoethyl)carbamate. The TFA salt of (S)—N-(3-chloro-4-fluorophenyl)-4,5-difluoro-N'-hydroxy-2-(piperidin-3-ylamino)-1H-benzo[d]imidazole-7-carboximidamide was isolated as an off-white solid. $C_{19}H_{18}ClF_3N_6O$. 439.2/441.1 (M+1). $^1$H NMR (400 MHz, DMSO-d6) δ 10.78 (s, 1H), 8.69-8.50 (m, 3H), 7.10 (t, J=9.1 Hz, 1H), 6.91 (dd, J=6.5, 2.7 Hz, 1H), 6.86 (m, 1H), 6.79 (m, 1H), 6.55 (ddd, J=9.0, 4.1, 2.8 Hz, 1H), 4.00 (m, 1H), 3.47 (app. d, J=11.9 Hz, 1H), 3.21 (app. d, J=12.3 Hz, 1H), 2.93-2.79 (m, 2H), 2.00 (m, 1H), 1.89 (m, 1H), 1.80-1.63 (m, 1H), 1.57 (m, 1H). $^{19}$F NMR (376 MHz, DMSO) δ −74.92, −127.48, −150.57, −156.96.

Example 446: (R)—N-(3-chloro-4-fluorophenyl)-4,5-difluoro-N'-hydroxy-2-(piperidin-3-ylamino)-1H-benzo[d]imidazole-7-carboximidamide

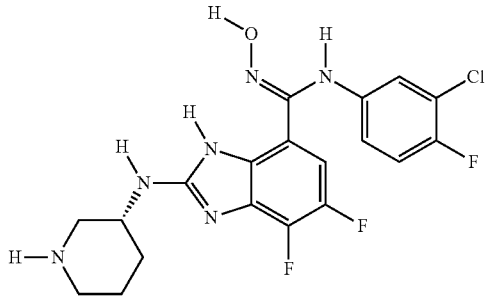 [SMILES: O/N=C(\Nc1ccc(F)c(Cl)c1)c1cc(F)c(F)c2nc(N[C@@H]3CCCNC3)[nH]c12]

Example 446 was made analogously to Example 333 using tert-butyl (R)-3-aminopiperidine-1-carboxylate in place of tert-butyl (2-aminoethyl)carbamate. The TFA salt of (R)—N-(3-chloro-4-fluorophenyl)-4,5-difluoro-N'-hydroxy-2-(piperidin-3-ylamino)-1H-benzo[d]imidazole-7-carboximidamide was isolated as an off-white solid. $C_{19}H_{18}ClF_3N_6O$. 439.2/441.1 (M+1). $^1$H NMR (400 MHz, DMSO-d6) δ 10.79 (s, 1H), 8.78-8.51 (m, 3H), 7.10 (t, J=9.1 Hz, 1H), 6.91 (dd, J=6.5, 2.7 Hz, 1H), 6.86 (d, J=6.6 Hz, 1H), 6.81 (dd, J=12.1, 6.8 Hz, 1H), 6.54 (ddd, J=9.0, 4.0, 2.8 Hz, 1H), 4.02 (m, 1H), 3.47 (app. d, J=12.2 Hz, 1H), 3.21 (app. d, J=12.4 Hz, 1H), 2.93-2.80 (m, 2H), 2.00 (app. d, J=12.2 Hz, 1H), 1.89 (m, 1H), 1.71 (m, 1H), 1.56 (m, 1H). $^{19}$F NMR (377 MHz, DMSO-d6) δ −74.88 (9F), −127.50 (1F), −150.58 (1F), −156.99 (1F).

Example 447: (S)—N-(3-chloro-4-fluorophenyl)-4,5-difluoro-N'-hydroxy-2-((1-methylpyrrolidin-3-yl)amino)-1H-benzo[d]imidazole-7-carboximidamide

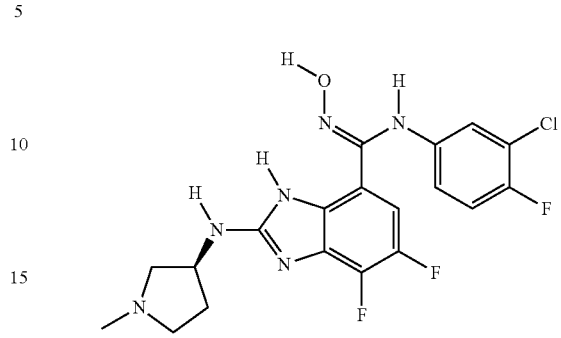

Example 447 was made analogously to Example 333 using (S)-1-methylpyrrolidin-3-amine in place of tert-butyl (2-aminoethyl)carbamate. The TFA salt of (S)—N-(3-chloro-4-fluorophenyl)-4,5-difluoro-N'-hydroxy-2-((1-methylpyrrolidin-3-yl)amino)-1H-benzo[d]imidazole-7-carboximidamide was isolated as an off-white solid. $C_{19}H_{18}ClF_3N_6O$. 439.2/441.1 (M+1). $^1$H NMR (400 MHz, DMSO-d6) δ 10.76 (br. s, 1H), 9.75 (br. s, 1H), 8.67 (d, J=3.5 Hz, 1H), 7.09 (td, J=9.1, 3.4 Hz, 1H), 6.98 (m, 1H), 6.92 (dt, J=6.5, 2.4 Hz, 1H), 6.85 (m, 1H), 6.53 (dt, J=8.9, 3.5 Hz, 1H), 4.49 (m, 1H), 3.94 (m, 1H), 3.36 (m, 1H), 3.23 (m, 1H), 3.06 (m, 1H), 2.89 (app. dd, J=9.0, 4.8 Hz, 3H), 2.06 (m, 1H), 1.90 (m, 1H). $^{19}$F NMR (376 MHz, DMSO-d6) δ −74.77, −127.47, −150.47, −156.78.

Example 448: N-(3-chloro-4-fluorophenyl)-2-((3-(dimethylamino)-2-hydroxypropyl)amino)-4,5-difluoro-N'-hydroxy-1H-benzo[d]imidazole-7-carboximidamide

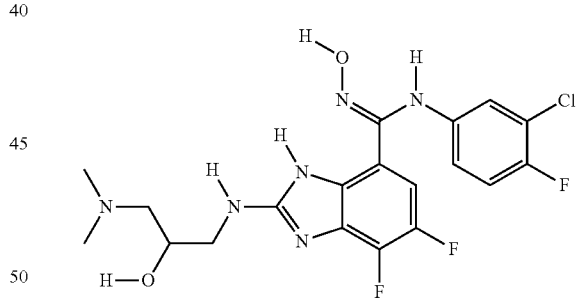

Example 448 was made analogously to Example 333 using 1-amino-3-(dimethylamino)propan-2-ol in place of tert-butyl (2-aminoethyl)carbamate. The TFA salt of N-(3-chloro-4-fluorophenyl)-2-((3-(dimethylamino)-2-hydroxypropyl)amino)-4,5-difluoro-N'-hydroxy-1H-benzo[d]imidazole-7-carboximidamide was isolated as an off-white solid. $C_{19}H_{20}ClF_3N_6O_2$. 457.2/459.1 (M+1). $^1$H NMR (400 MHz, DMSO-d6) δ 10.86 (br. s, 1H), 9.38 (br. s, 1H), 8.73 (s, 1H), 7.30 (m, 1H), 7.10 (t, J=9.1 Hz, 1H), 6.94 (dd, J=6.5, 2.7 Hz, 1H), 6.88 (dd, J=12.2, 6.9 Hz, 1H), 6.54 (ddd, J=9.0, 4.0, 2.7 Hz, 1H), 4.11 (dq, J=9.7, 5.0 Hz, 1H), 3.47 (dt, J=13.9, 5.5 Hz, 1H), 3.39 (m, 1H), 3.16 (app. d, J=12.8 Hz, 1H), 3.06 (dd, J=12.9, 10.1 Hz, 1H), 2.81 (s, 6H). $^{19}$F NMR (377 MHz, DMSO-d6) δ −75.02, −127.32, −149.66, −156.59.

Example 449: N-(3-chloro-4-fluorophenyl)-4,5-difluoro-N'-hydroxy-2-((2-(4-methyl-3-oxopiperazin-1-yl)ethyl)amino)-1H-benzo[d]imidazole-7-carboximidamide

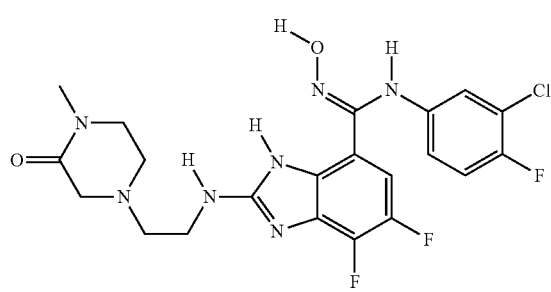 [SMILES: CN1CCN(CCNc2nc3c(F)c(F)cc(/C(=N/O)Nc4ccc(F)c(Cl)c4)c3[nH]2)CC1=O]

Example 449 was made analogously to Example 333 using 4-(2-aminoethyl)-1-methylpiperazin-2-one in place of tert-butyl (2-aminoethyl)carbamate. The TFA salt of N-(3-chloro-4-fluorophenyl)-4,5-difluoro-N'-hydroxy-2-((2-(4-methyl-3-oxopiperazin-1-yl)ethyl)amino)-1H-benzo[d]imidazole-7-carboximidamide was isolated as an off-white solid. $C_{21}H_{21}ClF_3N_7O_2O$. 496.2/498.1 (M+1). $^1$H NMR (400 MHz, DMSO-d6) δ 10.81 (br. s, 1H), 8.71 (s, 1H), 7.14 (br. s, 1H), 7.10 (t, J=9.1 Hz, 1H), 6.94 (dd, J=6.5, 2.7 Hz, 1H), 6.87 (dd, J=12.2, 6.9 Hz, 1H), 6.53 (ddd, J=8.9, 4.0, 2.7 Hz, 1H), 3.90 (s, 2H), 3.71 (m, 2H), 3.65-3.50 (m, 4H), 3.35 (m, 2H), 2.89 (s, 3H). $^{19}$F NMR (376 MHz, DMSO-d6) δ −75.14, −127.23, −149.86, −156.94.

Example 450: N-(3-chloro-4-fluorophenyl)-2-(((1-(dimethylamino)cyclohexyl)methyl)amino)-4,5-difluoro-N'-hydroxy-1H-benzo[d]imidazole-7-carboximidamide

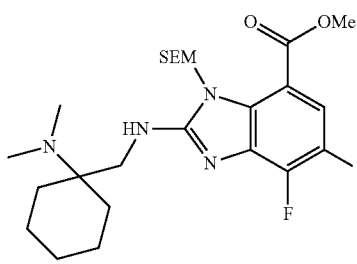

Methyl 4,5-difluoro-2-((1-methylpiperidin-3-yl)amino)-1-((2-(trimethylsilyl)ethoxy)methyl)-1H-benzo[d]imidazole-7-carboxylate was made analogously to Example 39 using 1-(aminomethyl)-N,N-dimethylcyclohexan-1-amine in place of N,N-dimethylpropane-1,3-diamine. The TFA salt of methyl 2-(((1-(dimethylamino)cyclohexyl)methyl)amino)-4,5-difluoro-1-((2-(trimethylsilyl)ethoxy)methyl)-1H-benzo[d]imidazole-7-carboxylate was isolated as a yellow oil. $C_{21}H_{32}F_2N_4O_3Si$. 497.3 (M+1).

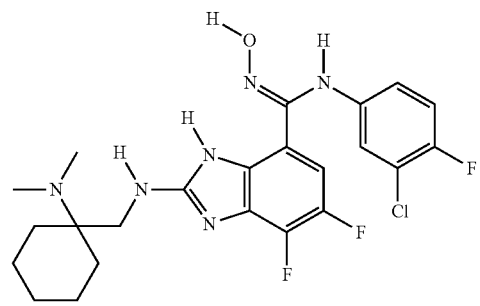 [SMILES: CN(C)C1(CNc2nc3c(F)c(F)cc(/C(=N/O)Nc4ccc(F)c(Cl)c4)c3[nH]2)CCCCC1]

N-(3-chloro-4-fluorophenyl)-2-(((1-(dimethylamino)cyclohexyl)methyl)amino)-4,5-difluoro-1H-benzo[d]imidazole-7-carboxamide was made analogously to Example 39 using methyl 4,5-difluoro-2-((1-methylpiperidin-3-yl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate. N-(3-chloro-4-fluorophenyl)-2-(((1-(dimethylamino)cyclohexyl)methyl)amino)-4,5-difluoro-1H-benzo[d]imidazole-7-carboxamide was isolated as a white solid. $C_{23}H_{25}ClF_3N_5O$. 480.2/482.1 (M+1).

The TFA salt of N-(3-chloro-4-fluorophenyl)-2-(((1-(dimethylamino)cyclohexyl)methyl)amino)-4,5-difluoro-1H-benzo[d]imidazole-7-carboxamide (103 mg, 0.15 mmol, 1 equiv) was dissolved in EtOAc, saturated aqueous NaHCO$_3$ was added and the mixture was extracted twice with EtOAc. The combined organics were dried over MgSO$_4$, filtered and concentrated in vacuo. The resulting residue was dissolved in CH$_2$Cl$_2$ (1 mL) and potassium carbonate (148 mg, 01.05 mmol, 7 equiv) and PCl$_5$ (95 mg, 0.46 mmol, 3 equiv) were added. The reaction was stirred at room temperature for 3 hours before being concentrated in vacuo. A solution of TMSONH$_2$ (0.185 mL, 1.5 mmol, 10 equiv) in trifluoroethanol (1.5 mL) was added at 0° C. The reaction was slowly warmed to room temperature and stirred for 1 hour before being concentrated in vacuo. A solution of 2N HCl was added and the resulting mixture was stirred for 30 minutes before diluting with DMF/H$_2$O and purification by reverse phase HPLC. The TFA salt of N-(3-chloro-4-fluorophenyl)-2-(41-(dimethylamino)cyclohexyl)methyl)amino)-4,5-difluoro-N'-hydroxy-1H-benzo[d]imidazole-7-carboximidamide was isolated as an off-white solid. $C_{23}H_{26}ClF_3N_6O$. 495.2/497.1 (M+1). $^1$H NMR (400 MHz, DMSO-d6) δ 10.80 (s, 1H), 9.49 (br. s, 1H), 8.68 (s, 1H), 7.10 (t, J=9.1 Hz, 1H), 7.03 (br. s, 1H), 6.92 (dd, J=6.5, 2.7 Hz, 1H), 6.85 (dd, J=12.2, 6.9 Hz, 1H), 6.53 (dt, J=8.9, 3.5 Hz, 1H), 4.31 (m, 1H), 3.86 (d, J=6.5 Hz, 1H), 2.81 (s, 3H), 2.80 (s, 3H), 1.83-1.93 (m, 2H), 1.74-1.43 (m, 7H), 1.20 (m, 1H). $^{19}$F NMR (376 MHz, DMSO) δ −75.00, −127.52, −150.3, −156.97.

Example 451: N-(3-chloro-4-fluorophenyl)-4,5-difluoro-N'-hydroxy-2-((1-methylazepan-3-yl)amino)-1H-benzo[d]imidazole-7-carboximidamide

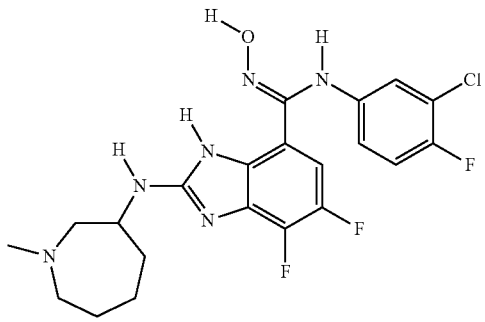 [SMILES: CN1CCCCC(Nc2nc3c(F)c(F)cc(/C(=N/O)Nc4ccc(F)c(Cl)c4)c3[nH]2)C1]

Example 451 was made analogously to Example 333 using 1-methylazepan-3-amine in place of tert-butyl (2-aminoethyl)carbamate. The TFA salt of N-(3-chloro-4-fluorophenyl)-4,5-difluoro-N'-hydroxy-2-((1-methylazepan-3-yl)amino)-1H-benzo[d]imidazole-7-carboximidamide was isolated as an off-white solid. $C_{21}H_{22}ClF_3N_6O$. 467.2/469.1 (M+1). $^1$H NMR (400 MHz, DMSO-d6) δ 10.77 (s, 1H), 9.68 (br. s, 1H), 8.66 (s, 1H), 7.10 (t, J=9.1 Hz, 1H), 6.91 (dd, J=6.5, 2.7 Hz, 1H), 6.83 (m, 1H), 6.54 (m, 1H), 4.19 (m, 1H), 3.37 (m, 2H), 3.20 (m, 2H), 2.87 (s, 3H), 2.03 (m, 1H), 1.97-1.54 (m, 5H). $^{19}$F NMR (376 MHz, DMSO-d6) δ −74.83, −127.52, −150.54, −156.65.

Example 452: (S)—N-(3-chloro-4-fluorophenyl)-4,5-difluoro-N'-hydroxy-2-((2-(3-hydroxypyrrolidin-1-yl)ethyl)amino)-1H-benzo[d]imidazole-7-carboximidamide

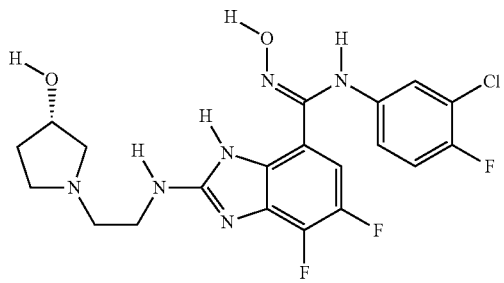 [SMILES: O/N=C(\Nc1ccc(F)c(Cl)c1)c1cc(F)c(F)c2nc(NCCN3CC[C@H](O)C3)[nH]c12]

Example 452 was made analogously to Example 333 using (S)-1-(2-aminoethyl)pyrrolidin-3-ol in place of tert-butyl (2-aminoethyl)carbamate. The TFA salt of (S)—N-(3-chloro-4-fluorophenyl)-4,5-difluoro-N'-hydroxy-2-((2-(3-hydroxypyrrolidin-1-yl)ethyl)amino)-1H-benzo[d]imidazole-7-carboximidamide was isolated as an off-white solid. $C_{20}H_{20}ClF_3N_6O_2$. 469.2/471.1 (M+1). $^1$H NMR (400 MHz, DMSO-d6) δ 10.76 (s, 1H), 10.04 (br. s, 1H), 8.68 (s, 1H), 7.09 (t, J=9.1 Hz, 1H), 6.97-6.90 (m, 2H), 6.83 (dd, J=12.2, 6.9 Hz, 1H), 6.53 (ddd, J=9.0, 4.1, 2.8 Hz, 1H), 4.43 (m, 1H), 3.68 (m, 6H), 3.41 (m, 2H), 2.15 (m, 1H), 1.88 (m, 1H). $^{19}$F NMR (376 MHz, DMSO) δ −74.97, −127.34, −150.40, −156.84.

Example 453: N-(3-chloro-4-fluorophenyl)-4,5-difluoro-N'-hydroxy-2-((1-(2-methoxyethyl)piperidin-3-yl)amino)-1H-benzo[d]imidazole-7-carboximidamide

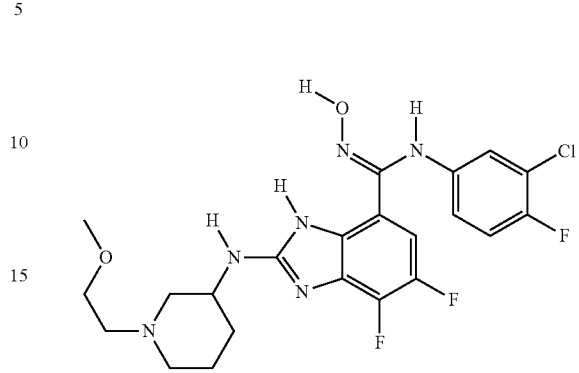

Example 453 was made analogously to Example 333 using 1-(2-methoxyethyl)piperidin-3-amine in place of tert-butyl (2-aminoethyl)carbamate. The TFA salt of N-(3-chloro-4-fluorophenyl)-4,5-difluoro-N'-hydroxy-2-((1-(2-methoxyethyl)piperidin-3-yl)amino)-1H-benzo[d]imidazole-7-carboximidamide was isolated as an off-white solid. $C_{22}H_{24}ClF_3N_6O_2O$. 497.2/499.1 (M+1). $^1$H NMR (400 MHz, DMSO-d6) δ 10.81 (s, 1H), 9.63 (br. s, 1H), 8.68 (s, 1H), 7.10 (t, J=9.1 Hz, 1H), 6.96-6.88 (m, 2H), 6.81 (dd, J=12.2, 6.9 Hz, 1H), 6.55 (ddd, J=9.0, 4.0, 2.8 Hz, 1H), 3.72 (m, 1H), 3.67 (app. t, J=4.9 Hz, 2H), 3.50 (m, 1H), 3.35 (m, 2H), 3.32 (s, 3H), 3.25 (m, 1H), 2.95-2.70 (m, 2H), 2.05-1.75 (m, 3H), 1.48 (m, 1H). $^{19}$F NMR (377 MHz, DMSO-d6) δ −75.0 (9F), −127.5 (1F), −150.6 (1F), −157.0 (1F).

Example 454: N-(3-chloro-4-fluorophenyl)-4,5-difluoro-N'-hydroxy-2-((1-(2-methoxyethyl)pyrrolidin-3-yl)amino)-1H-benzo[d]imidazole-7-carboximidamide

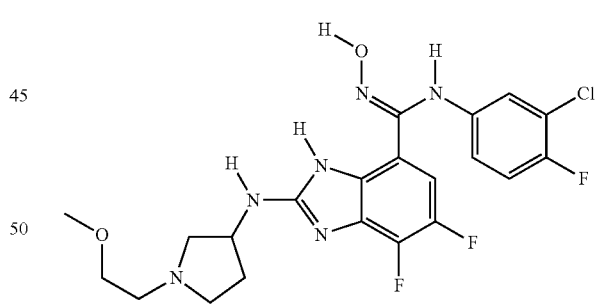

Example 454 was made analogously to Example 333 using 1-(2-methoxyethyl)pyrrolidin-3-amine in place of tert-butyl (2-aminoethyl)carbamate. The TFA salt of N-(3-chloro-4-fluorophenyl)-4,5-difluoro-N'-hydroxy-2-((1-(2-methoxyethyl)pyrrolidin-3-yl)amino)-1H-benzo[d]imidazole-7-carboximidamide was isolated as an off-white solid. $C_{21}H_{22}ClF_3N_6O_2O$. 483.3/485.1 (M+1). $^1$H NMR (400 MHz, DMSO-d6) δ 10.80 (s, 1H), 10.19 (br. s, 1H), 8.72 (s, 1H), 7.26 (d, J=10.0 Hz, 1H), 7.13-7.05 (m, 2H), 6.93 (dd, J=6.5, 2.6 Hz, 1H), 6.87 (dt, J=12.0, 4.8 Hz, 1H), 6.53 (ddd, J=9.0, 4.0, 2.8 Hz, 1H), 4.65-4.45 (m, 1H), 3.98-3.70 (m, 1H), 3.67-3.56 (m, 3H), 3.50-3.37 (m, 3H), 3.32 (d, J=7.0 Hz, 3H), 3.11 (m, 1H), 2.37-2.25 (m, 1H), 2.07-1.84 (m, 1H). $^{19}$F NMR (377 MHz, DMSO-d6) δ −75.04 (9F), −127.36 (1F), −150.26 (1F), −156.63 (1F).

Example 455: N-(3-chloro-4-fluorophenyl)-4,5-difluoro-N'-hydroxy-2-((1-isopropylpiperidin-3-yl)amino)-1H-benzo[d]imidazole-7-carboximidamide

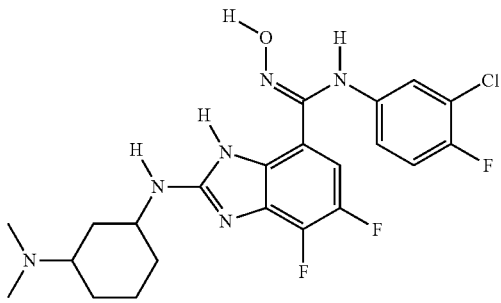 [SMILES: CN(C)C1CCCC(Nc2nc3c(F)c(F)cc(/C(=N/O)Nc4ccc(F)c(Cl)c4)c3[nH]2)C1]

Example 455 was made analogously to Example 333 using 1-isopropylpiperidin-3-amine in place of tert-butyl (2-aminoethyl)carbamate. The TFA salt of N-(3-chloro-4-fluorophenyl)-4,5-difluoro-N'-hydroxy-2-((1-isopropylpiperidin-3-yl)amino)-1H-benzo[d]imidazole-7-carboximidamide was isolated as an off-white solid. $C_{22}H_{24}ClF_3N_6O$. 481.3/483.1 (M+1). $^1$H NMR (400 MHz, DMSO-d6) δ 10.79 (s, 1H), 9.26 (s, 1H), 8.67 (s, 1H), 7.10 (t, J=9.1 Hz, 1H), 6.92 (dd, J=6.5, 2.7 Hz, 1H), 6.85-6.75 (m, 2H), 6.54 (m, 1H), 4.16 (m, 1H), 3.59-3.51 (m, 2H), 3.36 (m, 1H), 2.94-2.77 (m, 2H), 2.00 (m, 2H), 1.77 (m, 1H), 1.54 (m, 1H), 1.26 (t, J=6.2 Hz, 6H). $^{19}$F NMR (377 MHz, DMSO-d6) δ −74.90 (9F), −127.52 (1F), −150.59 (1F), −157.02 (1F).

Example 456: N-(3-chloro-4-fluorophenyl)-4,5-difluoro-N'-hydroxy-2-((2-(3-methoxyazetidin-1-yl)ethyl)amino)-1H-benzo[d]imidazole-7-carboximidamide

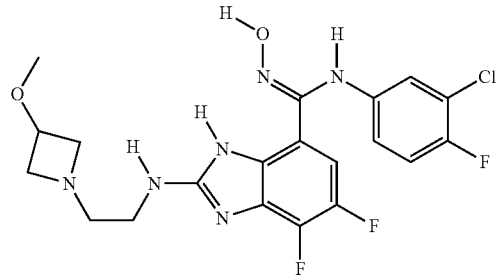 [SMILES: COC1CN(CCNc2nc3c(F)c(F)cc(/C(=N/O)Nc4ccc(F)c(Cl)c4)c3[nH]2)C1]

Example 456 was made analogously to Example 333 using 2-(3-methoxyazetidin-1-yl)ethan-1-amine in place of tert-butyl (2-aminoethyl)carbamate. The TFA salt of N-(3-chloro-4-fluorophenyl)-4,5-difluoro-N'-hydroxy-2-((2-(3-methoxyazetidin-1-yl)ethyl)amino)-1H-benzo[d]imidazole-7-carboximidamide was isolated as an off-white solid. $C_{20}H_{20}ClF_3N_6O_2O$. 469.2/471.1 (M+1). $^1$H NMR (400 MHz, DMSO-d6) δ 10.79 (s, 1H), 9.94 (br. s), 8.72 (s, 1H), 7.09 (t, J=9.1 Hz, 1H), 6.97-6.90 (m, 2H), 6.85 (dd, J=12.2, 6.9 Hz, 1H), 6.53 (ddd, J=8.9, 4.0, 2.8 Hz, 1H), 4.30-4.15 (m, 3H), 4.03 (m, 2H), 3.55 (m, 2H), 3.41 (m, 2H), 3.25 (s, 3H). $^{19}$F NMR (377 MHz, DMSO-d6) δ −75.03 (9F), −127.30 (1F), −150.32 (1F), −157.00 (1F).

Example 457: (R)—N-(3-chloro-4-fluorophenyl)-4,5-difluoro-N'-hydroxy-2-((1-methylpyrrolidin-3-yl)amino)-1H-benzo[d]imidazole-7-carboximidamide

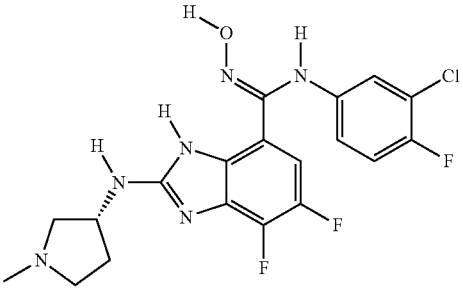 [SMILES: CN1CC[C@@H](Nc2nc3c(F)c(F)cc(/C(=N/O)Nc4ccc(F)c(Cl)c4)c3[nH]2)C1]

Example 457 was made analogously to Example 333 using (R)-1-methylpyrrolidin-3-amine in place of tert-butyl (2-aminoethyl)carbamate. The TFA salt of (R)—N-(3-chloro-4-fluorophenyl)-4,5-difluoro-N'-hydroxy-2-((1-methylpyrrolidin-3-yl)amino)-1H-benzo[d]imidazole-7-carboximidamide was isolated as an off-white solid. $C_{19}H_{18}ClF_3N_6O$. 439.2/441.1 (M+1). $^1$H NMR (400 MHz, DMSO-d6) δ 10.80 (s, 1H), 10.11 (br. s, 0.5H), 9.85 (br. s, 0.5H), 8.71 (s, 1H), 7.28 (d, J=9.3 Hz, 0.5H), 7.15-7.01 (m, 1.5H), 6.93 (dt, J=6.3, 2.8 Hz, 1H), 6.87 (dd, J=12.2, 6.9 Hz, 1H), 6.53 (m, 1H), 4.53 (m, 0.5H), 4.45 (m, 0.5H), 3.71 (m, 0.5H), 3.62 (m, 0.5H), 3.35 (m, 1H), 3.23 (m, 0.5H), 3.16-2.97 (m, 1.5H), 2.90 (d, J=5.0 Hz, 1.5H), 2.88 (d, J=4.6 Hz, 1.5H), 2.56 (m, 0.5H), 2.31 (m, 0.5H), 2.06 (m, 0.5H), 1.91 (m, 0.5H). $^{19}$F NMR (377 MHz, DMSO-d6) δ −75.00, −127.38, −150.33, −156.70.

Example 458: N-(3-chloro-4-fluorophenyl)-4,5-difluoro-N'-hydroxy-2-(((3R,4R)-4-methoxy-1-methylpyrrolidin-3-yl)amino)-1H-benzo[d]imidazole-7-carboximidamide

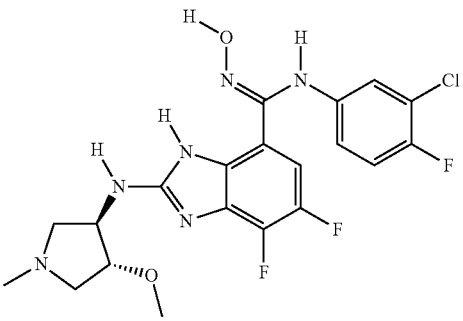 [SMILES: CO[C@@H]1CN(C)C[C@H]1Nc1nc2c(F)c(F)cc(/C(=N/O)Nc3ccc(F)c(Cl)c3)c2[nH]1]

Example 458 was made analogously to Example 333 using (3R,4R)-4-methoxy-1-methylpyrrolidin-3-amine in place of tert-butyl (2-aminoethyl)carbamate. The TFA salt of N-(3-chloro-4-fluorophenyl)-4,5-difluoro-N'-hydroxy-2-(((3R,4R)-4-methoxy-1-methylpyrrolidin-3-yl)amino)-1H-benzo[d]imidazole-7-carboximidamide was isolated as an off-white solid. $C_{20}H_{20}ClF_3N_6O_2O$. 469.2/471.1 (M+1). $^1$H NMR (400 MHz, DMSO-d6) δ 10.76 (s, 1H), 10.13 (br. s, 1H), 8.70 (s, 1H), 7.20 (m, 1H), 7.09 (td, J=9.1, 3.0 Hz, 1H), 6.92 (dd, J=6.5, 2.7 Hz, 1H), 6.86 (m, 1H), 6.53 (dt, J=8.9, 3.4 Hz, 1H), 4.41 (m, 1H), 4.09 (m, 1H), 3.95 (m, 1H), 3.71

(m, 1H), 3.37 (m, 3H), 3.21 (m, 1H), 3.10 (m, 1H), 2.90 (m, 3H). $^{19}$F NMR (377 MHz, DMSO-d6) δ −74.80, −127.49, −150.49, −157.01.

Example 459: (S)—N-(3-chlorophenyl)-4,5-difluoro-N'-hydroxy-2-((1-methylpiperidin-3-yl)amino)-1H-benzo[d]imidazole-7-carboximidamide

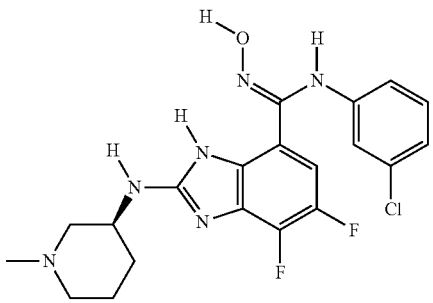 [SMILES: CN1CCC[C@H](Nc2nc3c(F)c(F)cc(/C(=N/O)Nc4cccc(Cl)c4)c3[nH]2)C1]

Example 459 was made analogously to Example 460 using (S)—N-(3-chlorophenyl)-4,5-difluoro-2-((1-methylpiperidin-3-yl)amino)-1-((2-(trimethylsilyl)ethoxy)methyl)-1H-benzo[d]imidazole-7-carboxylate. The TFA salt of (S*)—N-(3-chlorophenyl)-4,5-difluoro-N'-hydroxy-2-((1-methylpiperidin-3-yl)amino)-1H-benzo[d]imidazole-7-carboximidamide was isolated as an off-white solid. $C_{20}H_{21}ClF_2N_6O$. 435.2/437.1 (M+1); 435.2/437.1 (M+1). $^1$H NMR (400 MHz, DMSO-d6) δ 10.90 (s, 1H), 9.66 (br. s, 1H), 8.67 (s, 1H), 7.06 (t, J=8.1 Hz, 1H), 6.95 (m, 1H), 6.82 (dd, J=8.0, 2.2 Hz, 1H), 6.79 (t, J=2.2 Hz, 1H), 6.53 (dd, J=8.2, 2.1 Hz, 1H), 4.06 (m, 1H), 3.67 (m, 1H), 3.42 (m, 1H), 2.83 (d, J=4.4 Hz, 3H), 2.82-2.73 (m, 2H), 2.00 (m, 2H), 1.75 (m, 1H), 1.45 (m, 1H).; 1H NMR (400 MHz, DMSO-d6) δ 10.88 (s, 1H), 9.63 (br. s, 1H), 8.69 (s, 1H), 7.06 (t, J=8.0 Hz, 1H), 6.92 (m, 1H), 6.83 (m, 2H), 6.79 (t, J=2.2 Hz, 1H), 6.52 (dd, J=8.1, 2.2 Hz, 1H), 4.06 (m, 1H), 3.65 (m, 1H), 3.42 (m, 1H), 2.83 (d, J=4.6 Hz, 3H), 2.81-2.75 (m, 2H), 1.99 (m, 2H), 1.72 (m, 1H), 1.45 (m, 1H). $^{19}$F NMR (376 MHz, DMSO-d6) δ −74.95, −150.50, −156.86.

Example 460: (R)—N-(3-chlorophenyl)-4,5-difluoro-N'-hydroxy-2-((1-methylpiperidin-3-yl)amino)-1H-benzo[d]imidazole-7-carboximidamide

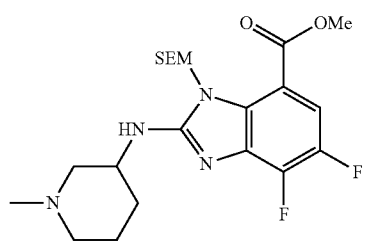 [SMILES: COC(=O)c1cc(F)c(F)c2nc(NC3CCCN(C)C3)n(COCC[Si](C)(C)C)c12]

Methyl 4,5-difluoro-2-((1-methylpiperidin-3-yl)amino)-1-((2-(trimethylsilyl)ethoxy)methyl)-1H-benzo[d]imidazole-7-carboxylate was made analogously to Example 39 using 1-methylpiperidin-3-amine in place of N,N-dimethylpropane-1,3-diamine. The TFA salt of methyl 4,5-difluoro-2-((1-methylpiperidin-3-yl)amino)-1-((2-(trimethylsilyl)ethoxy)methyl)-1H-benzo[d]imidazole-7-carboxylate was isolated as an amorphous yellow oil. $C_{21}H_{32}F_2N_4O_3Si$. 455.2 (M+1).

N-(3-chlorophenyl)-4,5-difluoro-2-((1-methylpiperidin-3-yl)amino)-1-((2-(trimethylsilyl)ethoxy)methyl)-1H-benzo[d]imidazole-7-carboxamide was made analogously to Example 39 using methyl 4,5-difluoro-2-((1-methylpiperidin-3-yl)amino)-1-((2-(trimethylsilyl)ethoxy)methyl)-1H-benzo[d]imidazole-7-carboxylate in place of methyl 2-((3-(dimethylamino)propyl)amino)-4,5-difluoro-1-((2-(trimethylsilyl)ethoxy)methyl)-1H-benzo[d]imidazole-7-carboxylate and 3-chloroaniline in place of 3-chloro-4-fluoroaniline. N-(3-chlorophenyl)-4,5-difluoro-2-((1-methylpiperidin-3-yl)amino)-1-((2-(trimethylsilyl)ethoxy)methyl)-1H-benzo[d]imidazole-7-carboxamide was purified by silica gel chromatography (0-16% MeOH/CH$_2$Cl$_2$ w/0.5% NEt$_3$) isolated as a white solid. $C_{21}H_{32}F_2N_4O_3Si$. 455.2 (M+1). Each enantiomer was isolated using chiral SFC (AD-H, 15% iPrOH, 60 mL/min, 100 bar). $C_{26}H_{34}ClF_2N_5O_2Si$. 550.3/552.1 (M+1).

(R)—N-(3-chlorophenyl)-4,5-difluoro-2-((1-methylpiperidin-3-yl)amino)-1-((2-(trimethylsilyl)ethoxy)methyl)-1H-benzo[d]imidazole-7-carboxamide (60 mg, 0.11 mmol, 1 equiv) was dissolved in CH$_2$Cl$_2$ (2 mL) and TFA (2 mL) was added. The SEM-deprotection was stirred overnight before being concentrated in vacuo. The crude product was dissolved in EtOAc, saturated aqueous NaHCO$_3$ was added and the mixture was extracted twice with EtOAc. The combined organics were dried over MgSO$_4$, filtered and concentrated in vacuo. The resulting residue was dissolved in CH$_2$Cl$_2$ (1 mL) and potassium carbonate (106 mg, 0.76 mmol, 7 equiv) and PC15 (68 mg, 0.33 mmol, 3 equiv) were added. The reaction was stirred at room temperature for 3 hours before being concentrated in vacuo. A solution of TMSONH$_2$ (0.132 mL, 1.1 mmol, 10 equiv) in trifluoroethanol (1.5 mL) was added at 0° C. The reaction was slowly warmed to room temperature and stirred for 1 hour before being concentrated in vacuo. A solution of 2N HCl was added and the resulting mixture was stirred for 30 minutes before diluting with DMF/H₂O and purification by reverse phase HPLC. The TFA salt of (R)—N-(3-chlorophenyl)-4,5-difluoro-N'-hydroxy-2-((1-methylpiperidin-3-yl)amino)-1H-benzo[d]imidazole-7-carboximidamide was isolated as an off-white solid. $C_{20}H_{21}ClF_2N_6O$. 435.2/437.1 (M+1); 435.2/437.1 (M+1). ¹H NMR (400 MHz, DMSO-d6) δ 10.90 (s, 1H), 9.66 (br. s, 1H), 8.67 (s, 1H), 7.06 (t, J=8.1 Hz, 1H), 6.95 (m, 1H), 6.82 (dd, J=8.0, 2.2 Hz, 1H), 6.79 (t, J=2.2 Hz, 1H), 6.53 (dd, J=8.2, 2.1 Hz, 1H), 4.06 (m, 1H), 3.67 (m, 1H), 3.42 (m, 1H), 2.83 (d, J=4.4 Hz, 3H), 2.82-2.73 (m, 2H), 2.00 (m, 2H), 1.75 (m, 1H), 1.45 (m, 1H); 1H NMR (400 MHz, DMSO-d6) δ 10.88 (s, 1H), 9.63 (br. s, 1H), 8.69 (s, 1H), 7.06 (t, J=8.0 Hz, 1H), 6.92 (m, 1H), 6.83 (m, 2H), 6.79 (t, J=2.2 Hz, 1H), 6.52 (dd, J=8.1, 2.2 Hz, 1H), 4.06 (m, 1H), 3.65 (m, 1H), 3.42 (m, 1H), 2.83 (d, J=4.6 Hz, 3H), 2.81-2.75 (m, 2H), 1.99 (m, 2H), 1.72 (m, 1H), 1.45 (m, 1H). ¹⁹F NMR (376 MHz, DMSO-d6) δ −74.95, −150.50, −156.86.

Example 461: N-(3-chloro-4-fluorophenyl)-2-((2-(dimethylamino)cyclopentyl)amino)-4,5-difluoro-N'-hydroxy-1H-benzo[d]imidazole-7-carboximidamide

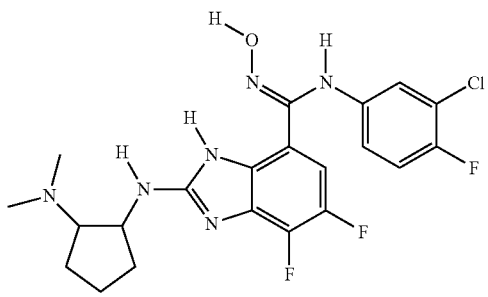 [SMILES: CN(C)C1CCCC1Nc1nc2c(F)c(F)cc(/C(=N/O)Nc3ccc(F)c(Cl)c3)c2[nH]1]

Example 461 was made analogously to Example 333 using N¹,N¹-dimethylcyclopentane-1,2-diamine in place of tert-butyl (2-aminoethyl)carbamate. The TFA salt of N-(3-chloro-4-fluorophenyl)-2-((2-(dimethylamino)cyclopentyl)amino)-4,5-difluoro-N'-hydroxy-1H-benzo[d]imidazole-7-carboximidamide was isolated as an off-white solid. $C_{21}H_{22}ClF_3N_6O$. 467.3/469.1 (M+1). ¹H NMR (400 MHz, DMSO-d6) δ 10.74 (s, 1H), 8.69 (s, 1H), 7.09 (t, J=9.0 Hz, 1H), 6.91 (dd, J=6.5, 2.7 Hz, 1H), 6.83 (m, 1H), 6.52 (m, 1H), 4.34 (m, 1H), 3.63 (m, 1H), 2.85 (s, 6H), 2.15-2.00 (m, 2H), 1.87 (m, 1H), 1.79-1.63 (m, 3H).

Example 462: (S)-2-(azepan-3-ylamino)-N-(3-chloro-4-fluorophenyl)-4,5-difluoro-N'-hydroxy-1H-benzo[d]imidazole-7-carboximidamide

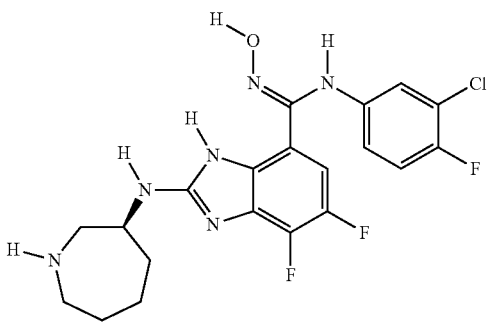 [SMILES: O/N=C(\Nc1ccc(F)c(Cl)c1)c1cc(F)c(F)c2nc(N[C@H]3CCCCNC3)[nH]c12]

Example 462 was made analogously to Example 333 using tert-butyl (S)-3-aminoazepane-1-carboxylate in place of tert-butyl (2-aminoethyl)carbamate. The TFA salt of (S)-2-(azepan-3-ylamino)-N-(3-chloro-4-fluorophenyl)-4,5-difluoro-N'-hydroxy-1H-benzo[d]imidazole-7-carboximidamide was isolated as an off-white solid. $C_{20}H_{20}ClF_3N_6O$. 453.3 (M+1). ¹H NMR (400 MHz, DMSO-d6) δ 10.79 (s, 1H), 8.77 (br. s, 2H), 8.66 (s, 1H), 7.10 (t, J=9.1 Hz, 1H), 6.91 (dd, J=6.5, 2.7 Hz, 1H), 6.86 (d, J=6.9 Hz, 1H), 6.82 (dd, J=12.3, 6.9 Hz, 1H), 6.58-6.51 (m, 1H), 4.15 (m, 1H), 3.42 (m, 1H), 3.26 (m, 1H), 3.21-3.11 (m, 2H), 2.04 (m, 1H), 1.92-1.54 (m, 5H). ¹⁹F NMR (376 MHz, DMSO-d6) δ −74.9, −127.5, −150.5, −156.8.

Example 463: (R)-2-(azepan-3-ylamino)-N-(3-chloro-4-fluorophenyl)-4,5-difluoro-N'-hydroxy-1H-benzo[d]imidazole-7-carboximidamide

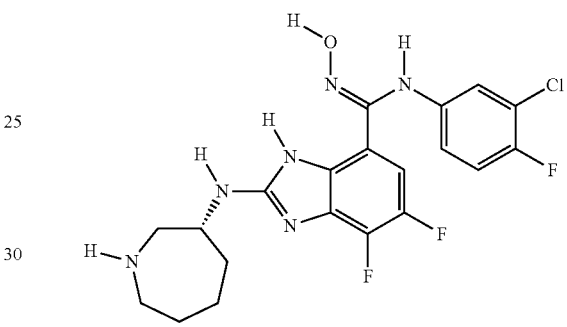

Example 463 was made analogously to Example 333 using tert-butyl (R)-3-aminoazepane-1-carboxylate in place of tert-butyl (2-aminoethyl)carbamate. The TFA salt of (R)-2-(azepan-3-ylamino)-N-(3-chloro-4-fluorophenyl)-4,5-difluoro-N'-hydroxy-1H-benzo[d]imidazole-7-carboximidamide was isolated as an off-white solid. $C_{20}H_{20}ClF_3N_6O$. 453.2/455.1 (M+1). ¹H NMR (400 MHz, DMSO-d6) δ 10.78 (s, 1H), 8.76 (br. s, 2H), 8.66 (s, 1H), 7.10 (t, J=9.1 Hz, 1H), 6.91 (dd, J=6.5, 2.7 Hz, 1H), 6.83 (d, J=6.8 Hz, 1H), 6.80 (d, J=6.7 Hz, 1H), 6.54 (ddd, J=9.0, 4.1, 2.8 Hz, 1H), 4.15 (m, 1H), 3.42 (m, 1H), 3.26 (m, 1H), 3.20-3.07 (m, 2H), 2.05 (m, 1H), 1.91-1.54 (m, 5H). ¹⁹F NMR (376 MHz, DMSO-d6) δ −74.8, −127.5, −150.5, −156.8.

Example 464: N-(3-chloro-4-fluorophenyl)-4,5-difluoro-N'-hydroxy-2-(pyrrolidin-3-ylamino)-1H-benzo[d]imidazole-7-carboximidamide

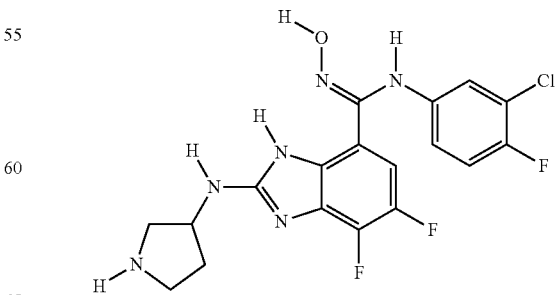

Example 464 was made analogously to Example 333 using tert-butyl 3-aminopyrrolidine-1-carboxylate in place of tert-butyl (2-aminoethyl)carbamate. The TFA salt of N-(3-chloro-4-fluorophenyl)-4,5-difluoro-N'-hydroxy-2-(pyrrolidin-3-ylamino)-1H-benzo[d]imidazole-7-carboximidamide was isolated as an off-white solid. $C_{18}H_{16}ClF_3N_6O$. 425.2/427.1 (M+1). $^1H$ NMR (400 MHz, DMSO-d6) δ 10.78 (s, 1H), 8.89 (br. s, 1H), 8.79 (br. s, 1H), 8.70 (s, 1H), 7.12-7.05 (m, 2H), 6.92 (dd, J=6.5, 2.7 Hz, 1H), 6.85 (dd, J=12.3, 6.9 Hz, 1H), 6.53 (ddd, J=8.9, 4.0, 2.7 Hz, 1H), 4.44 (m, 1H), 3.47 (m, 1H), 3.27 (m, 2H), 2.27 (m, 1H), 1.94 (m, 1H). $^{19}F$ NMR (377 MHz, DMSO-d6) δ −74.9 (9F), −127.4 (1F), −150.44 (1F), −156.81 (1F).

Example 465: (R)—N-(3-chloro-4-fluorophenyl)-4,5-difluoro-N'-hydroxy-2-((1-(oxetan-3-yl)piperidin-3-yl)amino)-1H-benzo[d]imidazole-7-carboximidamide

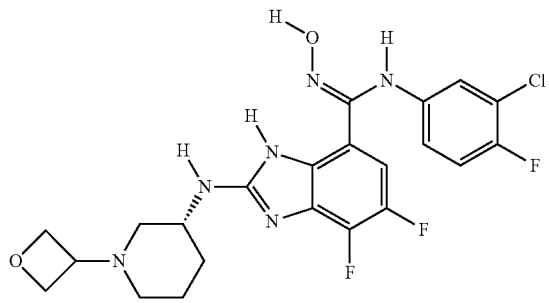 [SMILES: O/N=C(\Nc1ccc(F)c(Cl)c1)c1cc(F)c(F)c2nc(N[C@@H]3CCCN(C4COC4)C3)[nH]c12]

Example 465 was made analogously to Example 333 using (R)-1-(oxetan-3-yl)piperidin-3-amine in place of tert-butyl (2-aminoethyl)carbamate. The TFA salt of (R)—N-(3-chloro-4-fluorophenyl)-4,5-difluoro-N'-hydroxy-2-((1-(oxetan-3-yl)piperidin-3-yl)amino)-1H-benzo[d]imidazole-7-carboximidamide was isolated as an off-white solid. $C_{22}H_{22}ClF_3N_6O_2$. 495.3/497.1 (M+1). $^1H$ NMR (400 MHz, DMSO-d6) δ 10.82 (s, 1H), 10.61 br. (s, 1H), 8.70 (s, 1H), 7.10 (t, J=9.1 Hz, 1H), 7.04 (m, 1H), 6.92 (dd, J=6.6, 2.7 Hz, 1H), 6.84 (dd, J=12.3, 6.9 Hz, 1H), 6.54 (dt, J=8.9, 3.4 Hz, 1H), 4.80-4.65 (m, 4H), 4.40 (m, 1H), 4.14 (m, 1H), 3.53 (m, 1H), 3.38 (m, 1H), 2.84-2.65 (m, 2H), 2.1-1.90 (m, 2H), 1.77 (m, 1H), 1.53 (m, 1H). $^{19}F$ NMR (377 MHz, DMSO-d6) δ −74.8 (9F), −127.3 (1F), −150.3 (1F), −156.7 (1F).

Example 466: N-(3-chloro-4-fluorophenyl)-2-(((1,4-dimethylpiperidin-2-yl)methyl)amino)-4,5-difluoro-N'-hydroxy-1H-benzo[d]imidazole-7-carboximidamide

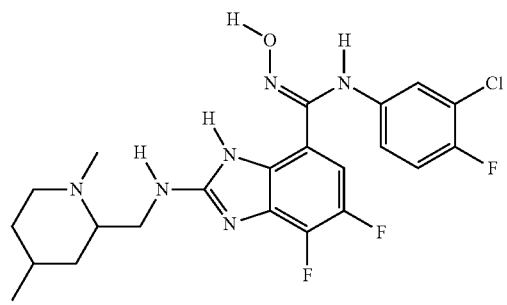 [SMILES: CC1CCN(C)C(CNc2nc3c(F)c(F)cc(/C(=N/O)Nc4ccc(F)c(Cl)c4)c3[nH]2)C1]

Example 466 was made analogously to Example 333 using (1,4-dimethylpiperidin-2-yl)methanamine in place of tert-butyl (2-aminoethyl)carbamate. The TFA salt of N-(3-chloro-4-fluorophenyl)-2-(((1,4-dimethylpiperidin-2-yl)methyl)amino)-4,5-difluoro-N'-hydroxy-1H-benzo[d]imidazole-7-carboximidamide was isolated as an off-white solid. $C_{22}H_{24}ClF_3N_6O$. 481.3/483.2 (M+1). $^1H$ NMR (400 MHz, DMSO-d6) δ 10.79 (s, 1H), 9.20 (br. s, 1H), 8.69 (s, 1H), 7.10 (t, J=9.1 Hz, 1H), 7.02 (m, 1H), 6.92 (dd, J=6.5, 2.7 Hz, 1H), 6.84 (dd, J=12.2, 6.9 Hz, 1H), 6.54 (ddd, J=9.0, 4.1, 2.7 Hz, 1H), 3.81 (m, 1H), 3.66 (m, 1H), 3.40 (m, 1H), 3.27 (m, 1H), 3.08 (m, 1H), 2.99 (s, 3H), 1.93 (m, 1H), 1.84-1.60 (m, 2H), 1.25 (m, 1H), 0.93 (d, J=6.4 Hz, 3H). $^{19}F$ NMR (376 MHz, DMSO-d6) δ −75.1, −127.4, −150.4, −157.0.

Example 467: N-(3-chloro-4-fluorophenyl)-4,5-difluoro-N'-hydroxy-2-((morpholin-3-ylmethyl)amino)-1H-benzo[d]imidazole-7-carboximidamide

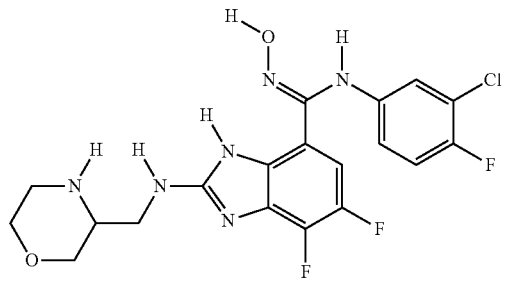 [SMILES: O/N=C(\Nc1ccc(F)c(Cl)c1)c1cc(F)c(F)c2nc(NCC3COCCN3)[nH]c12]

Example 467 was made analogously to Example 333 using tert-butyl 3-(aminomethyl)morpholine-4-carboxylate in place of tert-butyl (2-aminoethyl)carbamate. The TFA salt of N-(3-chloro-4-fluorophenyl)-4,5-difluoro-N'-hydroxy-2-((morpholin-3-ylmethyl)amino)-1H-benzo[d]imidazole-7-carboximidamide was isolated as an off-white solid. $C_{19}H_{18}ClF_3N_6O_2$. 455.2/457.1 (M+1). $^1H$ NMR (400 MHz, DMSO-d6) δ 10.80 (s, 1H), 9.06 (br. s, 2H), 8.71 (s, 1H), 7.10 (t, J=9.1 Hz, 1H), 7.02 (m, 1H), 6.92 (dd, J=6.6, 2.7 Hz, 1H), 6.83 (dd, J=12.3, 6.9 Hz, 1H), 6.53 (dt, J=9.0, 3.4 Hz, 1H), 3.95 (m, 1H), 3.88 (m, 1H), 3.67 (m, 1H), 3.62-3.50 (m, 4H), 3.30 (m, 1H), 3.09 (m, 1H). $^{19}F$ NMR (377 MHz, DMSO-d6) δ −74.9 (9F), −127.2 (1F), −150.2 (1F), −156.4 (1F).

Example 468: N-(3-chloro-4-fluorophenyl)-4,5-difluoro-N'-hydroxy-2-(((3R,4S)-4-hydroxypyrrolidin-3-yl)amino)-1H-benzo[d]imidazole-7-carboximidamide

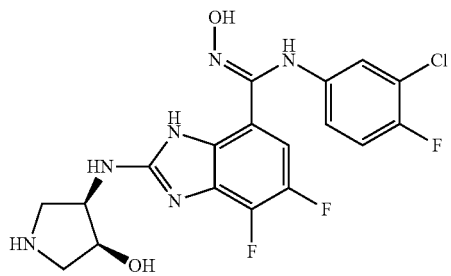 [SMILES: O/N=C(\Nc1ccc(F)c(Cl)c1)c1cc(F)c(F)c2nc(N[C@@H]3CNC[C@@H]3O)[nH]c12]

Example 468 was made analogously to Example 333 using tert-butyl (3R,4S)-3-amino-4-hydroxypyrrolidine-1-carboxylate in place of tert-butyl (2-aminoethyl)carbamate. The TFA salt of N-(3-chloro-4-fluorophenyl)-4,5-difluoro-N'-hydroxy-2-(((3R,4S)-4-hydroxypyrrolidin-3-yl)amino)-1H-benzo[d]imidazole-7-carboximidamide was isolated as an off-white solid. $C_{18}H_{16}ClF_3N_6O_2$. 441.2/443.1 (M+1). $^1$H NMR (400 MHz, DMSO-d6) δ 10.83 (s, 1H), 9.18 (br. s, 1H), 8.81 (br. s, 1H), 8.69 (s, 1H), 7.11 (t, J=9.1 Hz, 1H), 6.95-6.90 (m, 2H), 6.82 (dd, J=12.3, 6.8 Hz, 1H), 6.53 (dt, J=8.8, 3.4 Hz, 1H), 6.13 (br. s, 1H), 4.49 (m, 1H), 4.36 (m, 1H), 3.56 (m, 1H), 3.42 (m, 1H), 3.17 (m, 1H), 3.01 (m, 1H). $^{19}$F NMR (377 MHz, DMSO-d6) δ −74.7 (9F), −127.4 (1F), −150.3 (1F), −156.8 (1F).

Example 469: N-(3-chloro-4-fluorophenyl)-4,5-difluoro-N'-hydroxy-2-(((1R,5R)-8-methyl-8-azabicyclo[3.2.1]octan-2-yl)amino)-1H-benzo[d]imidazole-7-carboximidamide

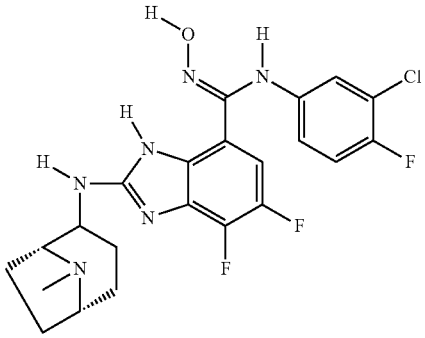 [SMILES: CN1[C@@H]2CCC(Nc3nc4c(F)c(F)cc(/C(=N/O)Nc5ccc(F)c(Cl)c5)c4[nH]3)[C@H]1CC2]

Example 469 was made analogously to Example 333 using (1R,5R)-8-methyl-8-azabicyclo[3.2.1]octan-2-amine in place of tert-butyl (2-aminoethyl)carbamate. The TFA salt of N-(3-chloro-4-fluorophenyl)-4,5-difluoro-N'-hydroxy-2-(41R,5R)-8-methyl-8-azabicyclo[3.2.1]octan-2-yl)amino)-1H-benzo[d]imidazole-7-carboximidamide was isolated as an off-white solid. $C_{22}H_{22}ClF_3N_6O$. 479.3/481.1 (M+1). $^1$H NMR (400 MHz, DMSO-d6, 2:1 mixture of diastereomers) δ 10.82 (br. s, 1H), 9.72 (s, 1H), 8.69 (d, J=7.8 Hz, 1H), 7.17-7.03 (m, 2H), 6.90 (td, J=6.5, 2.8 Hz, 1H), 6.81 (dd, J=12.3, 7.0 Hz, 1H), 6.55 (ddd, J=8.9, 4.6, 3.1 Hz, 1H), 4.29 (m, 1H), 4.05-3.70 (m, 2H), 2.75 (d, J=4.9 Hz, '2'), 2.63 (d, J=4.8 Hz, '1H'), 2.23 (m, 1H), 2.14-1.80 (m, 5H), 1.73 (m, 1H), 1.54 (m, 1H). $^{19}$F NMR (377 MHz, DMSO) δ −75.02, Major: −127.83, −150.68, −156.90, Minor: −127.66, −150.46, −156.51

Example 470: (S)—N-(3-chloro-4-fluorophenyl)-4,5-difluoro-N'-hydroxy-2-((2-(2-(trifluoromethyl)pyrrolidin-1-yl)ethyl)amino)-1H-benzo[d]imidazole-7-carboximidamide

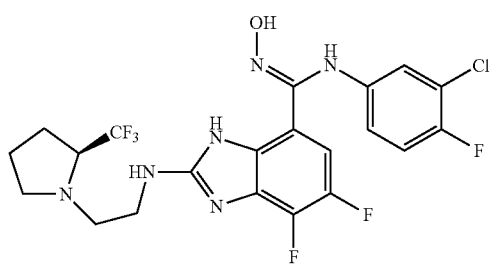 [SMILES: O/N=C(\Nc1ccc(F)c(Cl)c1)c1cc(F)c(F)c2nc(NCCN3CCC[C@H]3C(F)(F)F)[nH]c12]

Example 470 was made analogously to Example 333 using (S)-2-(2-(trifluoromethyl)pyrrolidin-1-yl)ethan-1-amine in place of tert-butyl (2-aminoethyl)carbamate. The TFA salt of (S)—N-(3-chloro-4-fluorophenyl)-4,5-difluoro-N'-hydroxy-2-((2-(2-(trifluoromethyl)pyrrolidin-1-yl)ethyl)amino)-1H-benzo[d]imidazole-7-carboximidamide was isolated as an off-white solid. $C_{21}H_{19}ClF_6N_6O$. 521.3/523.1 (M+1). $^1$H NMR (400 MHz, DMSO-d6) δ 10.99 (br. s, 1H), 8.82 (s, 1H), 7.95 (br. s, 1H), 7.13-7.03 (m, 2H), 6.97 (dd, J=6.5, 2.7 Hz, 1H), 6.54 (ddd, J=9.0, 4.1, 2.8 Hz, 1H), 3.59-3.40 (m, 3H), 3.19 (m, 1H), 3.03 (dt, J=13.6, 7.1 Hz, 1H), 2.82 (dt, J=12.7, 5.2 Hz, 1H), 2.46 (m, 1H), 2.04 (m, 1H), 1.87-1.64 (m, 3H). $^{19}$F NMR (377 MHz, DMSO-d6) δ −75.31 (9F), −75.43 (d, J=8.2 Hz, 3F), −126.82 (1F), −147.12 (1F), −155.04 (1F).

Example 471: N-(3-chloro-4-fluorophenyl)-4,5-difluoro-2-(((hexahydro-1H-pyrrolizin-7a-yl)methyl)amino),N'-hydroxy-1H-benzo[d]imidazole-7-carboximidamide

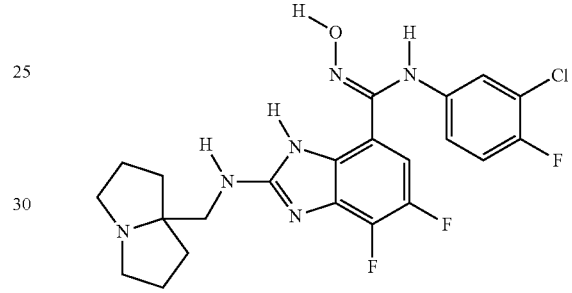

Example 471 was made analogously to Example 333 using (tetrahydro-1H-pyrrolizin-7a(5H)-yl)methanamine in place of tert-butyl (2-aminoethyl)carbamate. The TFA salt of N-(3-chloro-4-fluorophenyl)-4,5-difluoro-2-(((hexahydro-1H-pyrrolizin-7a-yl)methyl)amino)-N'-hydroxy-1H-benzo[d]imidazole-7-carboximidamide was isolated as an off-white solid. $C_{22}H_{22}ClF_3N_6O$. 479.4/481.1 (M+1). $^1$H NMR (400 MHz, DMSO-d6) δ 10.75 (br. s, 1H), 8.74 (s, 1H), 7.08 (t, J=9.1 Hz, 1H), 6.93 (dd, J=6.5, 2.7 Hz, 1H), 6.87 (dd, J=12.2, 7.1 Hz, 1H), 6.50 (dq, J=9.0, 3.0 Hz, 1H), 3.69 (app. d, J=5.9 Hz, 2H), 3.46 (dq, J=12.0, 6.1 Hz, 2H), 3.20 (m, 2H), 2.14-1.96 (m, 4H), 1.95-1.80 (m, 4H). $^{19}$F NMR (377 MHz, DMSO-d6) δ −75.1 (9F), −127.3 (1F), −149.9 (dd, J=22.6, 12.3 Hz, 1F), −156.8 (1F).

Example 472: N-(3-chloro-4-fluorophenyl)-2-(((3,3-dimethylazetidin-2-yl)methyl)amino)-4,5-difluoro-N'-hydroxy-1H-benzo[d]imidazole-7-carboximidamide

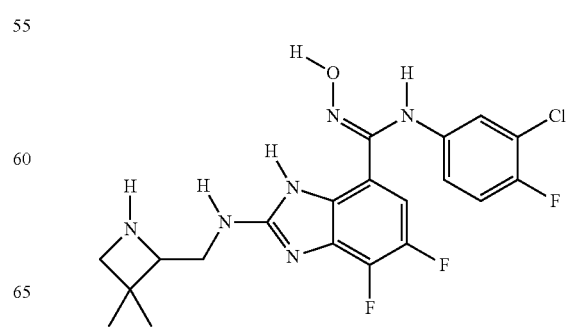

Example 472 was made analogously to Example 333 using tert-butyl 2-(aminomethyl)-3,3-dimethylazetidine-1-carboxylate in place of tert-butyl (2-aminoethyl)carbamate. The TFA salt of N-(3-chloro-4-fluorophenyl)-2-(((3,3-dimethylazetidin-2-yl)methyl)amino)-4,5-difluoro-N'-hydroxy-1H-benzo[d]imidazole-7-carboximidamide was isolated as an off-white solid. $C_{20}H_{20}ClF_3N_6O$. 453.2/455.1 (M+1). $^1$H NMR (400 MHz, DMSO-d6) δ 10.80 (s, 1H), 8.97 (br. s, 1H), 8.75-8.65 (m, 2H), 7.09 (t, J=9.1 Hz, 1H), 6.97-6.78 (m, 3H), 6.53 (ddd, J=9.0, 4.1, 2.8 Hz, 1H), 4.24 (m, 1H), 3.80-3.59 (m, 3H), 3.49 (m, 1H), 1.27 (s, 3H), 1.22 (s, 3H). $^{19}$F NMR (377 MHz, DMSO-d6) δ −75.0 (9F), −127.3 (1F), −150.3 (1F), −156.7 (d, J=23.0 Hz, 1F).

Example 473: N-(3-chloro-4-fluorophenyl)-4,5-difluoro-N'-hydroxy-2-((4-(pyrrolidin-1-yl)tetrahydro-2H-pyran-3-yl)amino)-1H-benzo[d]imidazole-7-carboximidamide

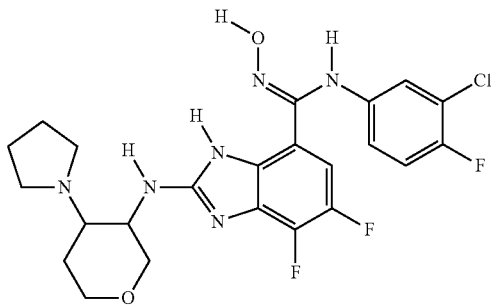 [SMILES: O/N=C(\Nc1ccc(F)c(Cl)c1)c1cc(F)c(F)c2nc(NC3COCCC3N3CCCC3)[nH]c12]

Example 473 was made analogously to Example 333 using 4-(pyrrolidin-1-yl)tetrahydro-2H-pyran-3-amine in place of tert-butyl (2-aminoethyl)carbamate. The TFA salt of N-(3-chloro-4-fluorophenyl)-4,5-difluoro-N'-hydroxy-2-((4-(pyrrolidin-1-yl)tetrahydro-2H-pyran-3-yl)amino)-1H-benzo[d]imidazole-7-carboximidamide was isolated as an off-white solid. $C_{23}H_{24}ClF_3N_6O_2$. 509.3/511.1 (M+1). $^1$H NMR (400 MHz, DMSO-d6) δ 10.79 (s, 1H), 9.65 (br. s, 1H), 8.68 (s, 1H), 7.20 (d, J=8.0 Hz, 1H), 7.11 (t, J=9.1 Hz, 1H), 6.91 (dd, J=6.5, 2.7 Hz, 1H), 6.84 (dd, J=12.3, 6.8 Hz, 1H), 6.54 (ddd, J=9.0, 4.0, 2.8 Hz, 1H), 4.35 (s, 1H), 4.04 (dd, J=12.5, 3.2 Hz, 1H), 3.83-3.73 (m, 2H), 3.66 (m, 1H), 3.55-3.40 (m, 5H), 2.13 (m, 1H), 2.00-1.85 (m, 4H), 1.71 (m, 1H). $^{19}$F NMR (377 MHz, DMSO-d6) δ −74.93 (9F), −127.54 (1F), −150.41 (1F), −156.80 (1F).

Example 474: 2-(((1S,2R)-2-aminocyclohexyl)amino)-N-(3-chloro-4-fluorophenyl)-4,5-difluoro-N'-hydroxy-1H-benzo[d]imidazole-7-carboximidamide

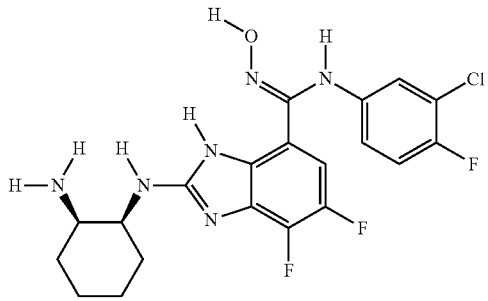 [SMILES: N[C@@H]1CCCC[C@@H]1Nc1nc2c(F)c(F)cc(/C(=N/O)Nc3ccc(F)c(Cl)c3)c2[nH]1]

Example 474 was made analogously to Example 333. The TFA salt of 2-(((1S,2R)-2-aminocyclohexyl)amino)-N-(3-chloro-4-fluorophenyl)-4,5-difluoro-N'-hydroxy-1H-benzo[d]imidazole-7-carboximidamide was isolated as an off-white solid. $C_{20}H_{20}ClF_3N_6O$. 453.2/455.1 (M+1). $^1$H NMR (400 MHz, DMSO-d6) δ 10.79 (s, 1H), 8.64 (s, 1H), 7.78 (br. s, 3H), 7.12 (t, J=9.1 Hz, 1H), 6.95 (d, J=8.5 Hz, 1H), 6.88 (dd, J=6.5, 2.7 Hz, 1H), 6.76 (dd, J=12.3, 6.8 Hz, 1H), 6.53 (ddd, J=9.0, 3.9, 2.6 Hz, 1H), 4.27 (m, 1H), 3.45 (m, 1H), 1.81-1.60 (m, 4H), 1.58-1.31 (m, 4H). $^{19}$F NMR (376 MHz, DMSO-d6) δ −74.8, −127.66, −150.5, −156.8.

Example 475: N-(3-chloro-4-fluorophenyl)-4,5-difluoro-N'-hydroxy-2-((2-methyl-1,2,3,4-tetrahydroisoquinolin-4-yl)amino)-1H-benzo[d]imidazole-7-carboximidamide

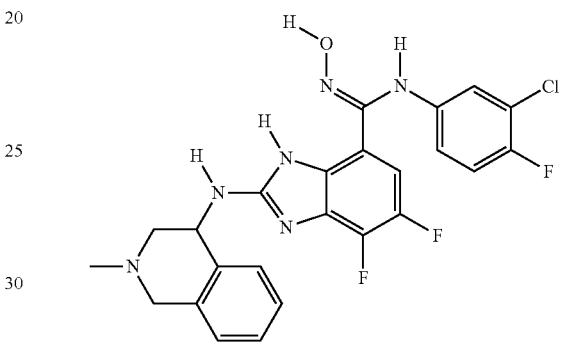

Example 475 was made analogously to Example 333 using 2-methyl-1,2,3,4-tetrahydroisoquinolin-4-amine in place of tert-butyl (2-aminoethyl)carbamate. The TFA salt of N-(3-chloro-4-fluorophenyl)-4,5-difluoro-N'-hydroxy-2-((2-methyl-1,2,3,4-tetrahydroisoquinolin-4-yl)amino)-1H-benzo[d]imidazole-7-carboximidamide was isolated as an off-white solid. $C_{24}H_{20}ClF_3N_6O$. 501.3/503.1 (M+1). $^1$H NMR (400 MHz, DMSO-d6) δ 10.78 (s, 1H), 10.32 (br. s, 1H), 8.69 (s, 1H), 7.49 (m, 1H), 7.45-7.34 (m, 2H), 7.30-7.20 (m, 2H), 7.07 (m, 1H), 6.95-6.80 (m, 2H), 6.51 (m, 1H), 5.62 (m, 1H), 5.16 (m, 1H), 4.61 (m, 1H), 4.37 (m, 1H), 3.40 (m, 1H), 3.03 (s, 3H). $^{19}$F NMR (376 MHz, DMSO-d6) δ −74.8, −127.4, −150.0 −156.9.

Example 476: N-(3-chloro-4-fluorophenyl)-2-(((3S,4S)-4-(diethylamino)tetrahydrofuran-3-yl)amino)-4,5-difluoro-N'-hydroxy-1H-benzo[d]imidazole-7-carboximidamide

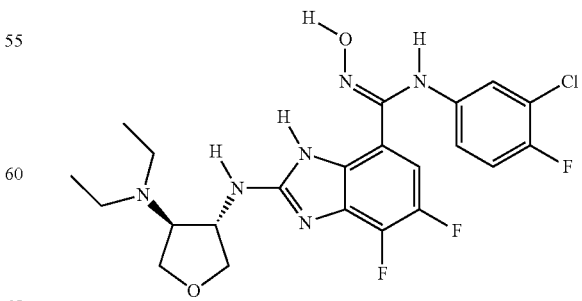

Example 476 was made analogously to Example 333 using (3S,4S)—$N^3,N^3$-diethyltetrahydrofuran-3,4-diamine.

The TFA salt of N-(3-chloro-4-fluorophenyl)-2-(((3S*,4S*)-4-(diethylamino)tetrahydrofuran-3-yl)amino)-4,5-difluoro-N'-hydroxy-1H-benzo[d]imidazole-7-carboximidamide was isolated as an off-white solid. $C_{22}H_{24}ClF_3N_6O_2$. 497.3/499.1 (M+1). $^1$H NMR (400 MHz, DMSO-d6) δ 10.77 (s, 1H), 10.18 (br. s, 1H), 8.69 (s, 1H), 7.38 (s, 1H), 7.08 (t, J=9.1 Hz, 1H), 6.97-6.81 (m, 2H), 6.53 (dt, J=9.0, 3.4 Hz, 1H), 4.63 (m, 1H), 4.21 (m, 1H), 4.15-4.03 (m, 2H), 3.59 (m, 2H), 3.40-3.20 (m, 4H), 1.23 (t, J=7.2 Hz, 6H). $^{19}$F NMR (376 MHz, DMSO-d6) δ −74.9, −127.4, −150.1, −157.2.

Example 477: 2-((1,4-oxazepan-6-yl)amino)-N-(3-chloro-4-fluorophenyl)-4,5-difluoro-N'-hydroxy-1H-benzo[d]imidazole-7-carboximidamide

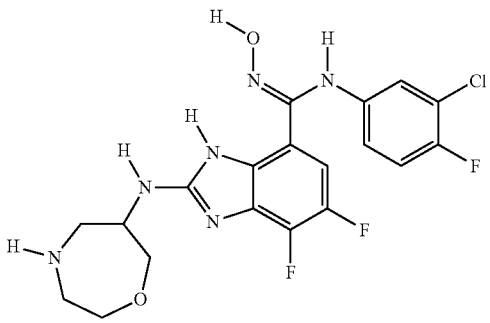 [SMILES: O/N=C(\Nc1ccc(F)c(Cl)c1)c1cc(F)c(F)c2nc(NC3CNCCOC3)[nH]c12]

Example 477 was made analogously to Example 333 using tert-butyl 6-amino-1,4-oxazepane-4-carboxylate in place of tert-butyl (2-aminoethyl)carbamate. The TFA salt of 2-((1,4-oxazepan-6-yl)amino)-N-(3-chloro-4-fluorophenyl)-4,5-difluoro-N'-hydroxy-1H-benzo[d]imidazole-7-carboximidamide was isolated as an off-white solid. $C_{19}H_{18}ClF_3N_6O_2$. 455.2/457.1 (M+1). $^1$H NMR (400 MHz, DMSO-d6) δ 10.81 (s, 1H), 9.01 (br. s, 2H), 8.69 (s, 1H), 7.11 (t, J=9.1 Hz, 1H), 6.97 (d, J=7.3 Hz, 1H), 6.91 (dd, J=6.5, 2.7 Hz, 1H), 6.82 (dd, J=12.3, 6.9 Hz, 1H), 6.53 (ddd, J=9.0, 4.1, 2.8 Hz, 1H), 4.33 (m, 1H), 3.99-3.74 (m, 4H), 3.54 (m, 1H), 3.46 (m, 1H), 3.32 (m, 1H). $^{19}$F NMR (377 MHz, DMSO-d6) δ −74.9 (9F), −127.5 (1F), −150.5 (1F), −156.8 (1F).

Example 478: N-(3-chloro-4-fluorophenyl)-2-((2-((2S,6R)-2,6-dimethylmorpholino)ethyl)amino)-N'-hydroxy-1H-imidazo[4,5-b]pyridine-7-carboximidamide

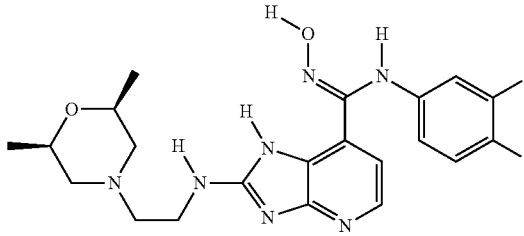

Example 478 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-((2S,6R)-2,6-dimethylmorpholino)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((2-((2S,6R)-2,6-dimethylmorpholino)ethyl)amino)-N'-hydroxy-1H-imidazo[4,5-b]pyridine-7-carboximidamide was isolated as an off-white solid. $C_{21}H_{25}ClFN_7O_2$. 462.3/464.2 (M+1). $^1$H NMR (400 MHz, DMSO-d6) δ 11.40 (br. s, 1H), 8.98 (s, 1H), 8.20 (br. s, 1H), 8.00 (d, J=6.2 Hz, 1H), 7.10 (t, J=9.0 Hz, 1H), 7.02 (dd, J=6.5, 2.7 Hz, 1H), 6.95 (d, J=6.2 Hz, 1H), 6.57 (ddd, J=8.9, 4.0, 2.7 Hz, 1H), 3.88-3.78 (m, 4H), 3.63-3.53 (m, 2H), 3.40-3.31 (m, 2H), 2.77-2.61 (m, 2H), 1.15 (d, J=6.3 Hz, 6H). $^{19}$F NMR (377 MHz, DMSO-d6) δ −74.60 (9F), −126.59 (1F).

Example 479: N-(3-chloro-4-fluorophenyl)-N'-hydroxy-2-(((3R,4R)-4-methoxy-1-methylpyrrolidin-3-yl)amino)-1H-imidazo[4,5-b]pyridine-7-carboximidamide

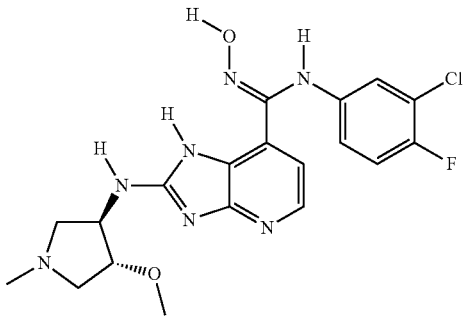 [SMILES: CO[C@@H]1CN(C)C[C@H]1Nc1nc2nccc(/C(=N/O)Nc3ccc(F)c(Cl)c3)c2[nH]1]

Example 479 was made analogously to Example 333 using (3R,4R)-4-methoxy-1-methylpyrrolidin-3-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-(((3R,4R)-4-methoxy-1-methylpyrrolidin-3-yl)amino)-1H-imidazo[4,5-b]pyridine-7-carboximidamide was isolated as an off-white solid. $C_{19}H_{21}ClFN_7O_2$. 434.2/436.1 (M+1). $^1$H NMR (400 MHz, DMSO-d6) δ 11.25 (br. s, 1H), 10.23 (br. s, 1H), 8.92 (s, 1H), 7.98 (s, 1H), 7.09 (t, J=9.0 Hz, 1H), 7.03-6.90 (m, 2H), 6.67 (m, 1H), 4.49 (m, 1H), 4.11 (m, 1H), 3.97 (m, 1H), 3.72 (m, 1H), 3.36 (s, 3H), 3.30-3.04 (m, 2H), 2.90 (s, 3H). $^{19}$F NMR (377 MHz, DMSO-d6) δ −74.4, −126.7.

Example 480: N-(3-chloro-4-fluorophenyl)-2-(((3R,4R)-4-(diethylamino)tetrahydrofuran-3-yl)amino)-N'-hydroxy-1H-imidazo[4,5-b]pyridine-7-carboximidamide

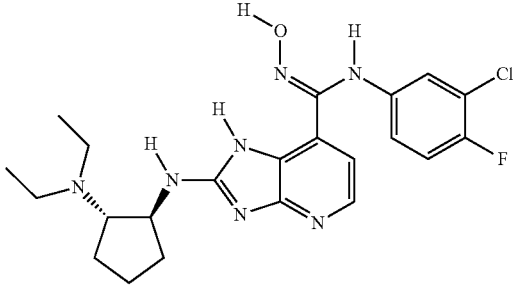 [SMILES: CCN(CC)[C@H]1CCC[C@@H]1Nc1nc2nccc(/C(=N/O)Nc3ccc(F)c(Cl)c3)c2[nH]1]

Example 480 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (3R,4R)—N3,N3-diethyltetrahydrofuran-3,4-diamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-(((3R,4R)-4-(diethylamino)tetrahydrofuran-3-yl)amino)-N'-hydroxy-1H-imidazo[4,5-b]pyridine-7-carboximidamide was isolated as an off-white solid. $C_{21}H_{25}ClFN_7O_2$. 462.2/464.2 (M+1). $^1$H NMR (400 MHz, DMSO-d6) δ 11.20 (br. s, 1H), 8.86 (s, 1H), 7.96 (s, 2H), 7.07 (s, 1H), 7.00-6.85 (m, 1H), 6.53 (s, 1H), 4.65 (m, 1H), 4.21 (m, 1H), 4.16-4.05 (m, 2H), 3.36-3.22 (m, 4H), 1.24 (t, J=7.2 Hz, 6H).

Example 481: (S)—N-(3-chloro-4-fluorophenyl)-N'-hydroxy-2-((2-(2-(trifluoromethyl)pyrrolidin-1-yl)ethyl)amino)-1H-imidazo[4,5-b]pyridine-7-carboximidamide

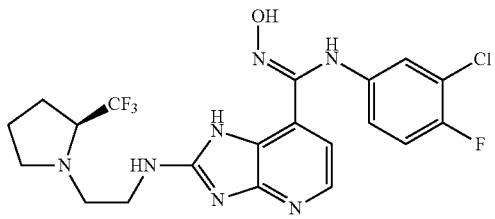 [SMILES: O/N=C(\Nc1ccc(F)c(Cl)c1)c1ccnc2nc(NCCN3CCC[C@H]3C(F)(F)F)[nH]c12]

Example 481 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (S)-2-(2-(trifluoromethyl)pyrrolidin-1-yl)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of (S)—N-(3-chloro-4-fluorophenyl)-N'-hydroxy-2-((2-(2-(trifluoromethyl)pyrrolidin-1-yl)ethyl)amino)-1H-imidazo[4,5-b]pyridine-7-carboximidamide was isolated as an off-white solid. $C_{20}H_{20}ClF_4N_7O$. 486.3/488.1 (M+1). $^1$H NMR (400 MHz, DMSO-d6) δ 11.41 (br. s, 1H), 8.95 (s, 1H), 7.97 (d, J=6.4 Hz, 1H), 7.10 (t, J=9.0 Hz, 1H), 7.02 (dd, J=6.5, 2.7 Hz, 1H), 6.94 (d, J=6.3 Hz, 1H), 6.59 (dt, J=9.0, 3.5 Hz, 1H), 3.60-3.50 (m, 2H), 3.18 (m, 1H), 3.06 (m, 1H), 2.81 (dt, J=11.6, 5.4 Hz, 1H), 2.45 (m, 1H), 2.02 (m, 1H), 1.87-1.64 (m, 4H). $^{19}$F NMR (376 MHz, DMSO-d6) δ −74.5, −75.5, −126.5.

Example 482: (R)—N-(3-chloro-4-fluorophenyl)-N'-hydroxy-2-(((4-methylmorpholin-3-yl)methyl)amino)-1H-imidazo[4,5-b]pyridine-7-carboximidamide

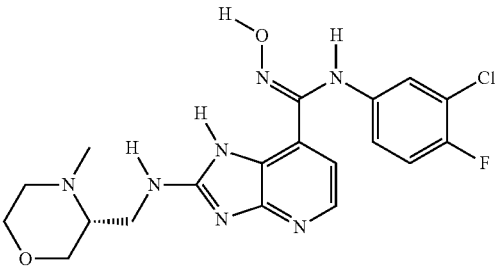 [SMILES: CN1CCOC[C@H]1CNc1nc2nccc(/C(=N/O)Nc3ccc(F)c(Cl)c3)c2[nH]1]

Example 482 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (R)-(4-methylmorpholin-3-yl)methanamine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of (R)—N-(3-chloro-4-fluorophenyl)-N'-hydroxy-2-((4-methylmorpholin-3-yl)methyl)amino)-1H-imidazo[4,5-b]pyridine-7-carboximidamide was isolated as an off-white solid. $C_{19}H_{21}ClFN_7O_2$. 434.2/436.1 (M+1). $^1$H NMR (400 MHz, DMSO-d6) δ 8.87 (br. s, 1H), 7.95 (s, 1H), 7.09 (t, J=8.9 Hz, 1H), 7.05-6.8 (m, 2H), 6.57 (dt, J=9.0, 3.4 Hz, 1H), 4.09-3.88 (m, 2H), 3.69-3.40 (m, 7H), 2.98 (s, 3H).

Example 483: N-(3-chloro-4-fluorophenyl)-2-((2-(2,6-dimethylmorpholino)propyl)amino)-N'-hydroxy-1H-imidazo[4,5-b]pyridine-7-carboximidamide

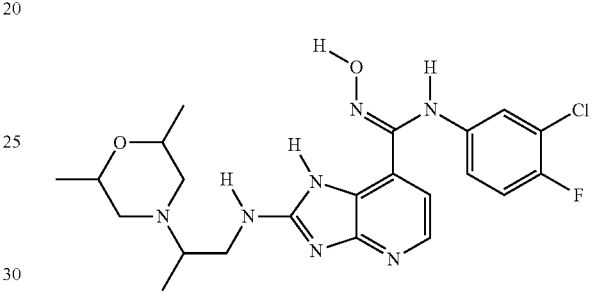

Example 483 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(2,6-dimethylmorpholino)propan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((2-(2,6-dimethylmorpholino)propyl)amino)-N'-hydroxy-1H-imidazo[4,5-b]pyridine-7-carboximidamide was isolated as an off-white solid. $C_{22}H_{27}ClFN_7O_2$. 476.3/478.2 (M+1). $^1$H NMR (400 MHz, DMSO-d6) δ 11.80 (br. s, 1H), 11.31 (br. s, 1H), 8.95 (s, 1H), 7.99 (d, J=6.0 Hz, 1H), 7.10 (t, J=9.0 Hz, 1H), 7.00 (dd, J=6.6, 2.7 Hz, 1H), 6.93 (d, J=6.0 Hz, 1H), 6.57 (ddd, J=9.0, 4.0, 2.7 Hz, 1H), 3.98-3.66 (m, 7H), 2.83-2.65 (m, 2H), 1.28 (d, J=6.6 Hz, 3H), 1.17 (d, J=4.3 Hz, 3H), 1.15 (d, J=4.2 Hz, 3H). $^{19}$F NMR (377 MHz, DMSO-d6) δ −74.5 (9H), −126.8 (1H).

Example 484: N-(3-chloro-4-fluorophenyl)-2-((2-(2,6-dimethylmorpholino)-2-methylpropyl)amino)-N'-hydroxy-1H-imidazo[4,5-b]pyridine-7-carboximidamide

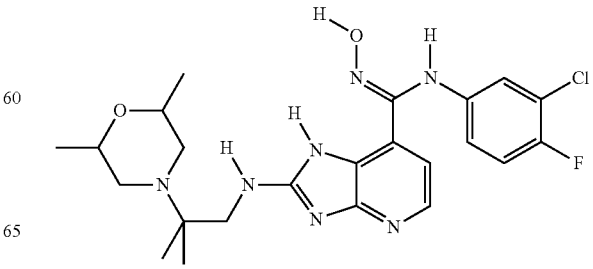

Example 484 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(2,6-dimethylmorpholino)-2-methylpropan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((2-(2,6-dimethylmorpholino)-2-methylpropyl)amino)-N'-hydroxy-1H-imidazo[4,5-b]pyridine-7-carboximidamide was isolated as an off-white solid. $C_{23}H_{29}ClFN_7O_2$. 490.2/492.1 (M+1). $^1$H NMR (400 MHz, DMSO-d6) δ 11.60 (br. s, 1H), 11.27 (br. s, 1H), 8.89 (s, 1H), 7.99 (d, J=6.0 Hz, 1H), 7.10 (t, J=9.0 Hz, 1H), 7.00 (dd, J=6.5, 2.7 Hz, 1H), 6.92 (d, J=6.0 Hz, 1H), 6.57 (ddd, J=8.9, 3.9, 2.7 Hz, 1H), 4.00-3.85 (m, 2H), 3.78-3.50 (m, 4H), 2.70 (m, 2H), 1.32 (s, 6H), 1.19 (s, 3H), 1.17 (s, 3H). $^{19}$F NMR (376 MHz, DMSO-d6) δ −74.51 (9F), −126.81 (1F).

Example 485: N-(3-chloro-4-fluorophenyl)-2-((2-(2,5-dimethylmorpholino)ethyl)amino)-N'-hydroxy-1H-imidazo[4,5-b]pyridine-7-carboximidamide

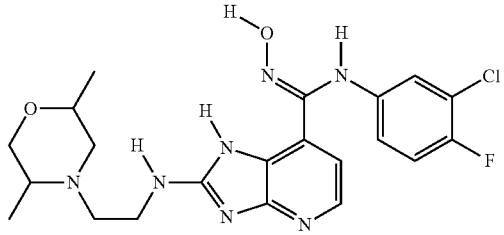 [SMILES: CC1CN(CCNc2nc3nccc(/C(=N/O)Nc4ccc(F)c(Cl)c4)c3[nH]2)C(C)CO1]

Example 485 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(2,5-dimethylmorpholino)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((2-(2,5-dimethylmorpholino)ethyl)amino)-N'-hydroxy-1H-imidazo[4,5-b]pyridine-7-carboximidamide was isolated as an off-white solid. $C_{21}H_{25}ClFN_7O_2$. 462.3/464.2 (M+1). $^1$H NMR (400 MHz, DMSO-d6) δ 11.28 (br. s, 1H), 8.92 (m, 1H), 7.99 (d, J=6.0 Hz, 1H), 7.10 (t, J=9.0 Hz, 1H), 6.99 (d, J=6.3 Hz, 1H), 6.93 (t, J=6.8 Hz, 1H), 6.58 (ddd, J=9.3, 4.4, 2.9 Hz, 1H), 4.00-3.75 (m, 6H), 3.37-3.17 (m, 2H), 2.93 (m, 2H), 1.33 (d, J=6.8 Hz, 2H), 1.16 (d, J=6.2 Hz, 4H). $^{19}$F NMR (376 MHz, DMSO-d6) δ −74.5, −126.6.

Example 486: N-(3-chloro-4-fluorophenyl)-2-(((1R,2R)-2-(dimethylamino)cyclopentyl)amino)-4,5-difluoro-N'-hydroxy-1H-benzo[d]imidazole-7-carboximidamide

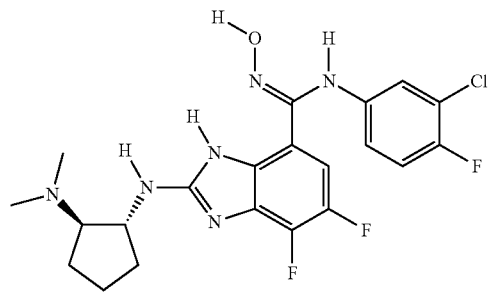 [SMILES: CN(C)[C@@H]1CCC[C@H]1Nc1nc2c(F)c(F)cc(/C(=N/O)Nc3ccc(F)c(Cl)c3)c2[nH]1]

Example 486 was made analogously to Example 333 using (1R,2R)—N1,N1-dimethylcyclopentane-1,2-diamine in place of tert-butyl (2-aminoethyl)carbamate. The TFA salt of N-(3-chloro-4-fluorophenyl)-2-((41R,2R)-2-(dimethylamino)cyclopentyl)amino)-4,5-difluoro-N'-hydroxy-1H-benzo[d]imidazole-7-carboximidamide was isolated as an off-white solid. $C_{21}H_{22}ClF_3N_6O$. 467.3/469.1 (M+1). $^1$H NMR (400 MHz, DMSO-d6) δ 10.74 (br. s, 1H), 8.69 (s, 1H), 7.09 (t, J=9.0 Hz, 1H), 6.91 (dd, J=6.5, 2.7 Hz, 1H), 6.84 (m, 1H), 6.52 (m, 1H), 4.34 (m, 1H), 3.61 (m, 1H), 2.85 (s, 6H), 2.17-1.96 (m, 2H), 1.89 (m, 1H), 1.80-1.59 (m, 3H). $^{19}$F NMR (376 MHz, DMSO-d6) δ −74.8, −127.4, −150.3, −157.2.

Example 487: N-(3-chloro-4-fluorophenyl)-2-((2-(dimethylamino)ethyl)thio)-N'-hydroxy-1H-imidazo[4,5-b]pyridine-7-carboximidamide

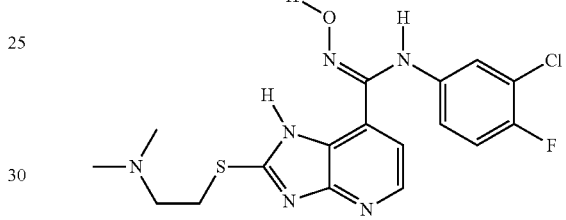

To a solution of 2-(dimethylamino)ethane-1-thiol (0.01 mL, 0.096 mmol, 1.9 equiv) in 0.5 mL THF at −78° C. was added 0.04 mL of n-BuLi (0.06 mmol, 1.6 equiv). The mixture was stirred for 10 minutes before the addition of 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one (25 mg, 0.05 mmol, 1 equiv) in 0.5 mL of THF. The reaction was slowly warmed to room temperature and stirred for 3 hours before being quenched with saturated aqueous $NH_4Cl$. The reaction mixture was extracted twice with EtOAc, the combined organic layers were dried over $MgSO_4$, filtered and concentrated in vacuo. The crude product was dissolved in 0.75 mL $CH_2Cl_2$ and 0.75 mL of TFA was added. The reaction was stirred at room temperature for 3 hours before being concentrated in vacuo. The crude product was then dissolved in 0.4 mL THF, 0.4 mL MeOH and 0.9 mL of 2N aqueous NaOH was added. The reaction was stirred at room temperature for 30 minutes before being neutralized with 0.9 mL of 2N aqueous HCl, diluted with DMF and purified by reverse phase HPLC. The TFA salt of N-(3-chloro-4-fluorophenyl)-2-((2-(dimethylamino)ethyl)thio)-N'-hydroxy-1H-imidazo[4,5-b]pyridine-7-carboximidamide was isolated as an off-white solid. $C_{17}H_{18}ClFN_6OS$. 409.3/411.0 (M+1). $^1$H NMR (400 MHz, DMSO-d6) δ 10.99 (br. s, 1H), 8.87 (s, 1H), 8.21 (d, J=5.2 Hz, 1H), 7.15-7.00 (m, 2H), 6.93 (dd, J=6.6, 2.7 Hz, 1H), 6.50 (ddd, J=8.9, 4.0, 2.7 Hz, 1H), 3.70-3.55 (m, 2H), 3.55-3.45 (m, 2H), 2.89 (s, 6H). $^{19}$F NMR (376 MHz, DMSO-d6) δ −74.69 (9F), −127.08 (1F).

Example 488: N-(3-chloro-4-fluorophenyl)-2-((2-(dimethylamino)ethyl)thio)-4,5-difluoro-N'-hydroxy-1H-benzo[d]imidazole-7-carboximidamide

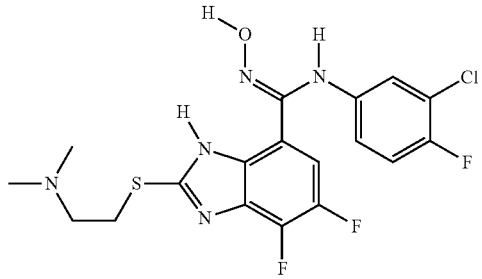 [SMILES: CN(C)CCSc1nc2c(F)c(F)cc(/C(=N/O)Nc3ccc(F)c(Cl)c3)c2[nH]1]

Example 488 was made analogously to Example 212 using 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one. The TFA salt of N-(3-chloro-4-fluorophenyl)-2-((2-(dimethylamino)ethyl)thio)-4,5-difluoro-N'-hydroxy-1H-benzo[d]imidazole-7-carboximidamide was isolated as an off-white solid. $C_{18}H_{17}ClF_3N_5OS$. 444.3/446.0 (M+1). $^1$H NMR (400 MHz, DMSO-d6) δ 12.91 (br. s, 1H), 10.83 (br. s, 1H), 9.65 (s, 1H), 8.76 (s, 1H), 7.18-7.00 (m, 2H), 6.96 (dd, J=6.6, 2.7 Hz, 1H), 6.49 (ddd, J=9.0, 4.1, 2.7 Hz, 1H), 3.61-3.44 (m, 4H), 2.87 (d, J=3.0 Hz, 6H). $^{19}$F NMR (377 MHz, DMSO-d6) δ −74.5 (6F), −127.0 (1F), −149.5 (1F), −154.15 (1F).

Example 489: N-(3-chloro-4-fluorophenyl)-4,5-difluoro-N'-hydroxy-2-((2-(2-(hydroxymethyl)piperidin-1-yl)ethyl)amino)-1H-benzo[d]imidazole-7-carboximidamide

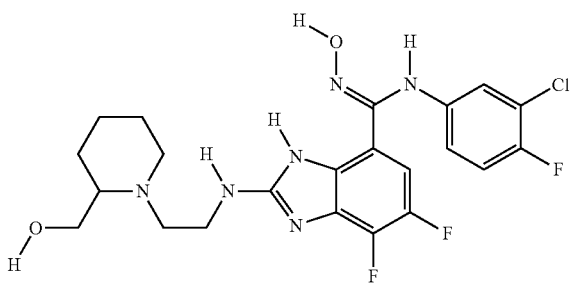 [SMILES: OCC1CCCCN1CCNc1nc2c(F)c(F)cc(/C(=N/O)Nc3ccc(F)c(Cl)c3)c2[nH]1]

Example 489 was made analogously to Example 333 using (1-(2-aminoethyl)piperidin-2-yl)methanol in place of tert-butyl (2-aminoethyl)carbamate. The TFA salt of N-(3-chloro-4-fluorophenyl)-4,5-difluoro-N'-hydroxy-2-((2-(2-(hydroxymethyl)piperidin-1-yl)ethyl)amino)-1H-benzo[d]imidazole-7-carboximidamide was isolated as an off-white solid. $C_{22}H_{24}ClF_3N_6O_2$. 497.3/499.1 (M+1). $^1$H NMR (400 MHz, DMSO-d6) δ 10.80 (s, 1H), 9.56 (br. s, 1H), 8.72 (s, 1H), 7.09 (t, J=9.1 Hz, 1H), 6.98 (s, 1H), 6.94 (dd, J=6.5, 2.7 Hz, 1H), 6.85 (dd, J=12.2, 6.9 Hz, 1H), 6.52 (ddd, J=9.0, 4.1, 2.7 Hz, 1H), 3.88 (m, 1H), 3.80-3.65 (m, 2H), 3.60-3.40 (m, 3H), 3.35-3.20 (m, 2H), 3.13 (m, 1H), 1.90-1.65 (m, 5H), 1.50 (m, 1H). $^{19}$F NMR (377 MHz, DMSO-d6) δ −75.1 (9F), −127.3 (1F), −150.2 (1F), −156.9 (1F).

Example 490: N-(3-chloro-4-fluorophenyl)-4,5-difluoro-N'-hydroxy-2-((2-(2-(hydroxymethyl)pyrrolidin-1-yl)ethyl)amino)-1H-benzo[d]imidazole-7-carboximidamide

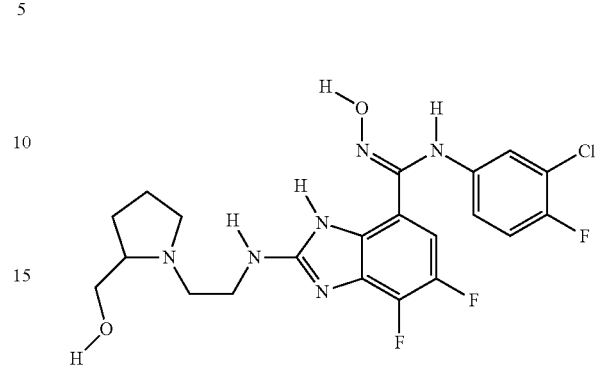

Example 490 was made analogously to Example 333 using (1-(2-aminoethyl)pyrrolidin-2-yl)methanol in place of tert-butyl (2-aminoethyl)carbamate. The TFA salt of N-(3-chloro-4-fluorophenyl)-4,5-difluoro-N'-hydroxy-2-((2-(2-(hydroxymethyl)pyrrolidin-1-yl)ethyl)amino)-1H-benzo[d]imidazole-7-carboximidamide was isolated as an off-white solid. $C_{21}H_{22}ClF_3N_6O_2$. 483.3/485.1 (M+1). $^1$H NMR (400 MHz, DMSO-d6) δ 10.79 (br. s, 1H), 9.82 (br. s, 1H), 8.70 (s, 1H), 7.09 (t, J=9.1 Hz, 1H), 7.02 (s, 1H), 6.94 (dd, J=6.6, 2.7 Hz, 1H), 6.85 (dd, J=12.2, 6.9 Hz, 1H), 6.53 (ddd, J=9.0, 4.1, 2.7 Hz, 1H), 3.78-3.64 (m, 4H), 3.63-3.50 (m, 3H), 3.35 (m, 1H), 3.19 (m, 1H), 2.14-1.95 (m, 2H), 1.90 (m, 1H), 1.75 (m, 1H). $^{19}$F NMR (376 MHz, DMSO-d6) δ −75.1, −127.3, −150.2, −156.9.

Example 491: N-(3-chloro-4-fluorophenyl)-2-((2-(3,3-difluoropyrrolidin-1-yl)ethyl)amino)-N'-hydroxy-1H-imidazo[4,5-b]pyridine-7-carboximidamide

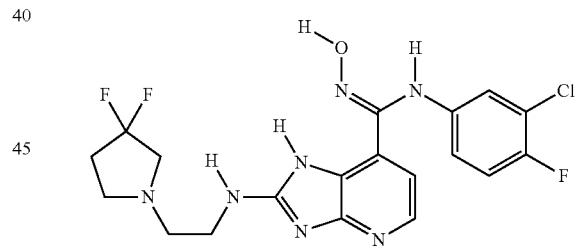

Example 491 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(3,3-difluoropyrrolidin-1-yl)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((2-(3,3-difluoropyrrolidin-1-yl)ethyl)amino)-N'-hydroxy-1H-imidazo[4,5-b]pyridine-7-carboximidamide was isolated as an off-white solid. $C_{19}H_{19}ClF_3N_7O$. 454.3/456.2 (M+1). $^1$H NMR (400 MHz, DMSO-d6) δ 11.40 (br. s, 1H), 8.97 (s, 1H), 7.98 (d, J=6.2 Hz, 1H), 7.11 (t, J=9.0 Hz, 1H), 7.03 (dd, J=6.5, 2.7 Hz, 1H), 6.94 (d, J=6.2 Hz, 1H), 6.59 (ddd, J=8.9, 4.0, 2.7 Hz, 1H), 3.62 (m, 2H), 3.34 (m, 2H), 3.18-2.89 (m, 4H), 2.45-2.28 (m, 2H). $^{19}$F NMR (377 MHz, DMSO-d6) δ −74.7 (9F), −92.1 (2F), −126.6 (1F).

Example 492: N-(3-chloro-4-fluorophenyl)-N'-hydroxy-2-((2-sulfamoylethyl)amino)-1H-imidazo[4,5-b]pyridine-7-carboximidamide

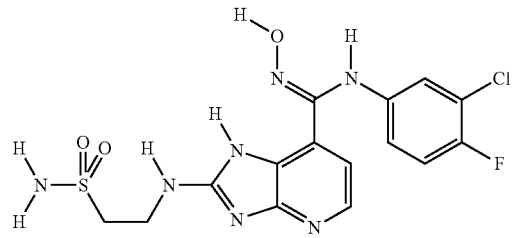 [SMILES: NS(=O)(=O)CCNc1nc2nccc(/C(=N/O)Nc3ccc(F)c(Cl)c3)c2[nH]1]

Example 492 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-aminoethane-1-sulfonamide in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-((2-sulfamoylethyl)amino)-1H-imidazo[4,5-b]pyridine-7-carboximidamide was isolated as an off-white solid. $C_{15}H_{15}ClFN_7O_3S$. 428.1/430.1 (M+1). $^1$H NMR (400 MHz, DMSO-d6) δ 12.00 (br. s, 1H), 11.47 (br. s, 1H), 8.99 (s, 1H), 7.97 (d, J=6.4 Hz, 1H), 7.11 (t, J=9.0 Hz, 1H), 7.06 (s, 2H), 7.04 (dd, J=6.8, 3.0 Hz, 1H), 6.92 (d, J=6.4 Hz, 1H), 6.59 (ddd, J=8.9, 4.0, 2.8 Hz, 1H), 3.87 (q, J=6.5 Hz, 2H), 3.35 (t, J=6.6 Hz, 2H). $^{19}$F NMR (377 MHz, DMSO-d6) δ −74.6 (6F), −126.5 (1F).

Example 493: N-(3-chloro-4-fluorophenyl)-N'-hydroxy-2-((2-(methylsulfonyl)ethyl)amino)-1H-imidazo[4,5-b]pyridine-7-carboximidamide

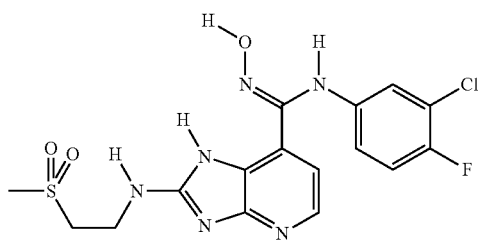 [SMILES: CS(=O)(=O)CCNc1nc2nccc(/C(=N/O)Nc3ccc(F)c(Cl)c3)c2[nH]1]

Example 493 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(methylsulfonyl)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-42-(methylsulfonyl)ethyl)amino)-1H-imidazo[4,5-b]pyridine-7-carboximidamide was isolated as an off-white solid. $C_{16}H_{16}ClFN_6O_3S$. 427.1/429.0 (M+1). $^1$H NMR (400 MHz, DMSO-d6) δ 11.46 (br. s, 1H), 8.97 (s, 1H), 7.99 (d, J=6.3 Hz, 1H), 7.11 (t, J=9.0 Hz, 1H), 7.04 (dd, J=6.5, 2.7 Hz, 1H), 6.95 (d, J=6.3 Hz, 1H), 6.59 (dq, J=8.8, 3.0 Hz, 1H), 3.91 (q, J=6.4 Hz, 2H), 3.51 (d, J=6.4 Hz, 2H), 3.07 (s, 3H). $^{19}$F NMR (376 MHz, DMSO-d6) δ −74.6 (6F), −126.5 (1F).

Example 494: N-(3-chloro-4-fluorophenyl)-N'-hydroxy-2-((pyrimidin-2-ylmethyl)amino)-1H-imidazo[4,5-b]pyridine-7-carboximidamide

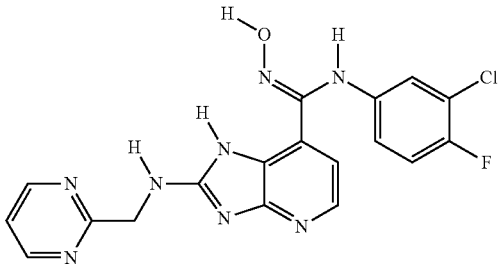 [SMILES: O/N=C(\Nc1ccc(F)c(Cl)c1)c1ccnc2nc(NCc3ncccn3)[nH]c12]

Example 494 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and pyrimidin-2-ylmethanamine in place of 3-(2-chloro-4,5-difluoro-1-((2-(trimethyl silyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-((pyrimidin-2-ylmethyl)amino)-1H-imidazo[4,5-b]pyridine-7-carboximidamide was isolated as an off-white solid. $C_{18}H_{14}ClFN_8O$. 413.2/415.1 (M+1). $^1$H NMR (400 MHz, DMSO-d6) δ 11.49 (br. s, 1H), 9.00 (s, 1H), 8.83 (d, J=4.9 Hz, 2H), 7.99 (d, J=6.3 Hz, 1H), 7.48 (t, J=4.9 Hz, 1H), 7.11 (t, J=9.0 Hz, 1H), 7.05 (dd, J=6.5, 2.7 Hz, 1H), 6.95 (d, J=6.3 Hz, 1H), 6.60 (dt, J=8.9, 3.3 Hz, 1H), 4.91 (d, J=5.9 Hz, 2H). $^{19}$F NMR (377 MHz, DMSO-d6) δ −74.7 (6F), −126.6 (1F).

Example 495: (R)—N-(3-chlorophenyl)-4,5-difluoro-N'-hydroxy-2-((1-(2-methoxyethyl)pyrrolidin-3-yl)amino)-1H-benzo[d]imidazole-7-carboximidamide

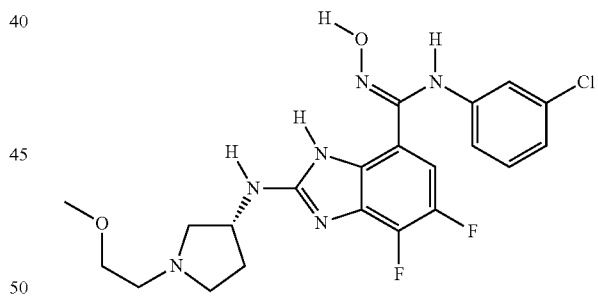

Example 495 was made analogously to Example 333 using (R)-1-(2-methoxyethyl)pyrrolidin-3-amine dihydrochloride and N-ethyl-N-isopropylpropan-2-amine in place of tert-butyl (2-aminoethyl)carbamate and 3-(2-chloro-4,5-difluoro-1-((2-(trimethylsilyl)ethoxy)methyl)-1H-benzo[d]imidazol-7-yl)-4-(3-chlorophenyl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one. The TFA salt of (R)—N-(3-chlor°phenyl)-4,5-difluoro-N'-hydroxy-2-((1-(2-methoxyethyl)pyrrolidin-3-yl)amino)-1H-benzo[d]imidazole-7-carboximidamide was isolated as an off-white solid. $C_{21}H_{23}ClF_2N_6O_2$. 465.2/467.1 (M+1). $^1$H NMR (400 MHz, DMSO-d6) δ 10.87 (s, 1H), 10.20 (br. s, 1H), 8.74 (s, 1H), 7.26 (m, 1H), 7.04 (m, 1H), 6.82 (m, 2H), 6.50 (m, 1H), 4.65-4.40 (m, 1H), 3.98-3.70 (m, 1H), 3.68-3.55 (m, 3H), 3.51-3.36 (m, 2H), 3.33 (m, 3H), 3.13 (m, 2H), 2.10-1.85 (m, 2H). $^{19}$F NMR (377 MHz, DMSO-d6) δ −75.0 (9F), −150.3 (1F), −156.7 (1F).

Example 496: (R)—N-(3-bromophenyl)-4,5-difluoro-N'-hydroxy-2-((1-(2-methoxyethyl)pyrrolidin-3-yl)amino)-1H-benzo[d]imidazole-7-carboximidamide

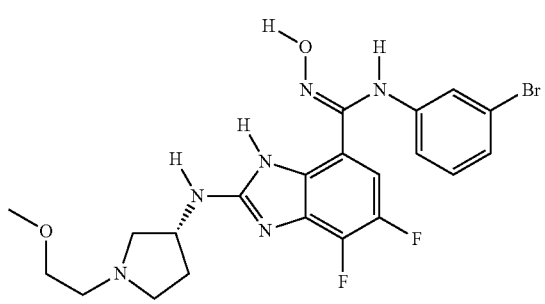 [SMILES: COCCN1CC[C@@H](Nc2nc3c(F)c(F)cc(/C(=N/O)Nc4cccc(Br)c4)c3[nH]2)C1]

Example 496 was made analogously to Example 333 using (R)-1-(2-methoxyethyl)pyrrolidin-3-amine dihydrochloride and N-ethyl-N-isopropylpropan-2-amine in place of tert-butyl (2-aminoethyl)carbamate and 4-(3-bromophenyl)-3-(2-chloro-4,5-difluoro-1-((2-(trimethylsilyl)ethoxy)methyl)-1H-benzo[d]imidazol-7-yl)-1,2,4-oxadiazol-5(4H)-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one. The TFA salt of (R)—N-(3-bromophenyl)-4,5-difluoro-N'-hydroxy-2-((1-(2-methoxyethyl)pyrrolidin-3-yl)amino)-1H-benzo[d]imidazole-7-carboximidamide was isolated as an off-white solid. $C_{21}H_{23}BrF_2N_6O_2$. 509.2/511.1 (M+1). $^1$H NMR (400 MHz, DMSO-d6) δ 10.84 (s, 1H), 10.18 (br. s, 1H), 8.69 (d, J=2.6 Hz, 1H), 7.17 (m, 1H), 7.05 (m, 1H), 7.00-6.91 (m, 3H), 6.84 (dd, J=12.3, 6.9 Hz, 1H), 6.55 (dt, J=7.7, 1.7 Hz, 1H), 4.65-4.35 (m, 1H), 4.00-3.70 (m, 1H), 3.65-3.55 (m, 3H), 3.51-3.36 (m, 2H), 3.32 (m, 3H), 3.12 (m, 2H), 2.11-1.85 (m, 2H). $^{19}$F NMR (376 MHz, DMSO-d6) δ −75.0 (9F), −150.4 (9F), −156.7 (9F).

Example 497: (S)—N-(3-chloro-4-fluorophenyl)-N'-hydroxy-2-((1-(oxetan-3-yl)piperidin-3-yl)amino)-1H-imidazo[4,5-b]pyridine-7-carboximidamide

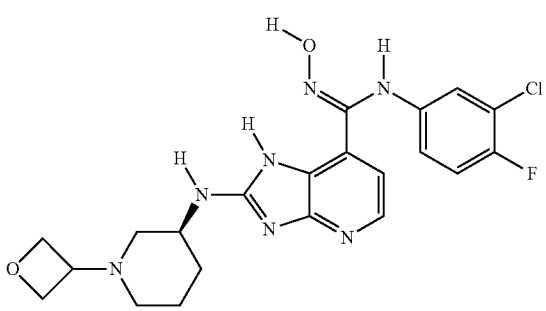 [SMILES: O/N=C(\Nc1ccc(F)c(Cl)c1)c1ccnc2nc(N[C@H]3CCCN(C4COC4)C3)[nH]c12]

Example 497 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (S)-1-(oxetan-3-yl)piperidin-3-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of (S)—N-(3-chloro-4-fluorophenyl)-N'-hydroxy-2-((1-(oxetan-3-yl)piperidin-3-yl)amino)-1H-imidazo[4,5-b]pyridine-7-carboximidamide was isolated as an off-white solid. $C_{21}H_{23}ClFN_7O_2$. 460.2/462.2 (M+1). $^1$H NMR (400 MHz, DMSO-d6) δ 11.39 (br. s, 1H), 8.95 (s, 1H), 8.16 (br. s, 1H), 7.98 (d, J=6.2 Hz, 1H), 7.11 (t, J=9.0 Hz, 1H), 7.02 (dd, J=6.5, 2.7 Hz, 1H), 6.94 (d, J=6.2 Hz, 1H), 6.59 (dt, J=8.9, 3.5 Hz, 1H), 4.75-4.65 (m, 4H), 4.20-4.05 (m, 2H), 3.80-3.55 (m, 2H), 2.85-2.60 (m, 2H), 2.05-1.85 (m, 2H), 1.81-1.45 (m, 2H). $^{19}$F NMR (376 MHz, DMSO-d6) δ −74.6, −126.7.

Example 498: N-(3-chloro-4-fluorophenyl)-N'-hydroxy-2-((1-(2-methoxyethyl)piperidin-3-yl)amino)-1H-imidazo[4,5-b]pyridine-7-carboximidamide

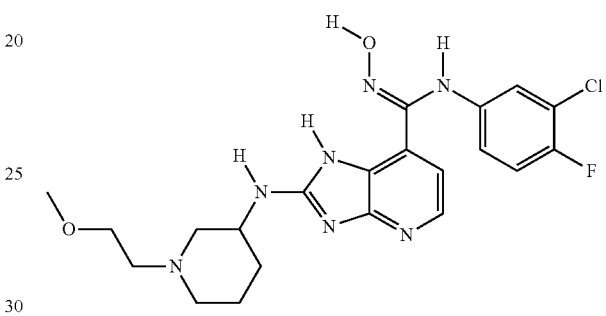

Example 498 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 1-(2-methoxyethyl)piperidin-3-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-((1-(2-methoxyethyl)piperidin-3-yl)amino)-1H-imidazo[4,5-b]pyridine-7-carboximidamide was isolated as an off-white solid. $C_{21}H_{25}ClFN_7O_2$. 462.1/464.1 (M+1). $^1$H NMR (400 MHz, DMSO-d6) δ 9.70 (br. s, 1H), 8.89 (br. s, 1H), 7.96 (s, 1H), 7.10 (t, J=9.0 Hz, 1H), 6.98 (m, 1H), 6.90 (m, 1H), 6.58 (dt, J=8.9, 3.5 Hz, 1H), 4.20 (m, 1H), 3.75-3.60 (m, 2H), 3.50-3.25 (m, 4H), 3.32 (s, 3H), 2.95-2.80 (m, 2H), 2.09-1.73 (m, 3H), 1.51 (m, 1H). $^{19}$F NMR (376 MHz, DMSO-d6) δ −74.31, −126.85.

Example 499: N-(3-chloro-4-fluorophenyl)-2-((1-cyclopropylpyrrolidin-3-yl)amino)-N'-hydroxy-1H-imidazo[4,5-b]pyridine-7-carboximidamide

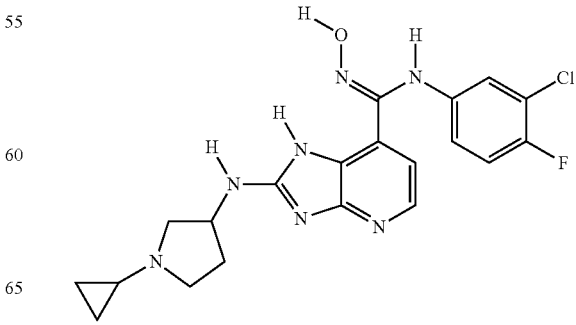

Example 499 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 1-cyclopropylpyrrolidin-3-amine trifluoroacetic acid salt (1:2) and N-ethyl-N-isopropylpropan-2-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((1-cyclopropylpyrrolidin-3-yl)amino)-N'-hydroxy-1H-imidazo[4,5-b]pyridine-7-carboximidamide was isolated as an off-white solid. $C_{20}H_{21}ClFN_7O$. 430.1/432.1 (M+1). $^1$H NMR (400 MHz, DMSO-d6) δ 11.21 (br. s, 1H), 8.89 (s, 1H), 7.96 (m, 1H), 7.08 (t, J=9.1 Hz, 1H), 7.05-6.80 (m, 2H), 6.57 (dt, J=8.9, 3.5 Hz, 1H), 4.60-4.45 (m, 2H), 3.95-3.45 (m, 4H), 3.05-2.90 (m, 2H), 1.00-0.75 (m, 4H).

Example 500: (R)—N-(3-chloro-4-fluorophenyl)-N'-hydroxy-2-((1-(oxetan-3-yl)piperidin-3-yl)amino)-1H-imidazo[4,5-b]pyridine-7-carboximidamide

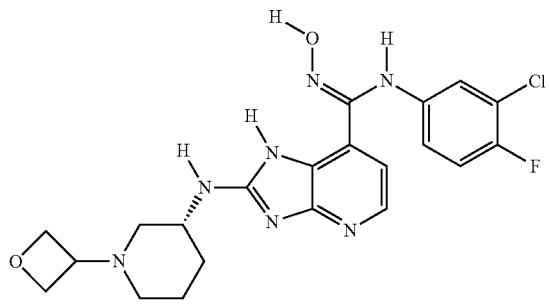 [SMILES: O/N=C(\Nc1ccc(F)c(Cl)c1)c1ccnc2nc(N[C@@H]3CCCN(C4COC4)C3)[nH]c12]

Example 500 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (R)-1-(oxetan-3-yl)piperidin-3-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of (R)—N-(3-chloro-4-fluorophenyl)-N'-hydroxy-2-((1-(oxetan-3-yl)piperidin-3-yl)amino)-1H-imidazo[4,5-b]pyridine-7-carboximidamide was isolated as an off-white solid. $C_{21}H_{23}ClFN_7O_2$. 460.2/462.2 (M+1). $^1$H NMR (400 MHz, DMSO-d6) δ 11.39 (br. s, 1H), 8.95 (s, 1H), 8.17 (br. s, 1H), 7.98 (d, J=6.2 Hz, 1H), 7.11 (t, J=9.0 Hz, 1H), 7.02 (dd, J=6.5, 2.7 Hz, 1H), 6.93 (d, J=6.2 Hz, 1H), 6.59 (dt, J=8.9, 3.5 Hz, 1H), 4.75-4.55 (m, 4H), 4.20-4.05 (m, 2H), 3.80-3.60 (m, 2H), 2.84-2.59 (m, 2H), 2.10-1.80 (m, 2H), 1.80-1.51 (m, 2H). $^{19}$F NMR (377 MHz, DMSO-d6) δ −74.6 (9F), −126.8 (1F).

Example 501: N-(3-chloro-4-fluorophenyl)-N'-hydroxy-2-((2-(4-methyl-3-oxopiperazin-1-yl)ethyl)amino)-1H-imidazo[4,5-b]pyridine-7-carboximidamide

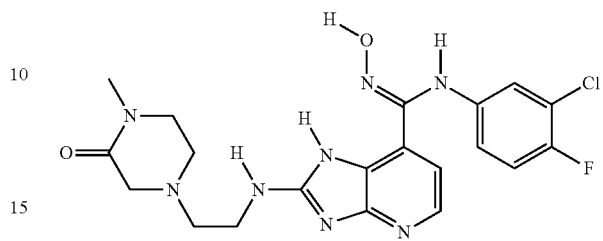

Example 501 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 4-(2-aminoethyl)-1-methyl-piperazin-2-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-((2-(4-methyl-3-oxopiperazin-1-yl)ethyl)amino)-1H-imidazo[4,5-b]pyridine-7-carboximidamide was isolated as an off-white solid. $C_{20}H_{22}ClFN_8O_2$. 461.2/463.2 (M+1). $^1$H NMR (400 MHz, DMSO-d6) δ 11.36 (br. s, 1H), 8.95 (s, 1H), 7.97 (d, J=6.2 Hz, 1H), 7.11 (t, J=9.0 Hz, 1H), 7.02 (dd, J=6.5, 2.7 Hz, 1H), 6.92 (d, J=6.2 Hz, 1H), 6.59 (m, 1H), 3.80-3.60 (m, 3H), 3.45-3.35 (m, 3H), 3.25-3.05 (m, 2H), 3.05-2.90 (m, 2H), 2.85 (s, 3H). $^{19}$F NMR (377 MHz, DMSO-d6) δ −74.7 (9F), −126.7 (1F).

Example 502: N-(3-chloro-4-fluorophenyl)-2-((2-(3,3-difluoropiperidin-1-yl)ethyl)amino)-N'-hydroxy-1H-imidazo[4,5-b]pyridine-7-carboximidamide

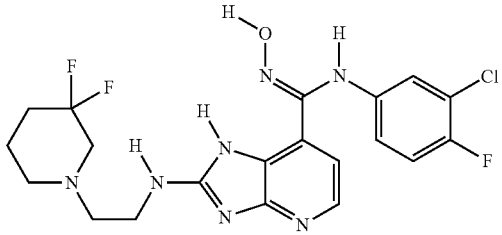 [SMILES: O/N=C(\Nc1ccc(F)c(Cl)c1)c1ccnc2nc(NCCN3CCCC(F)(F)C3)[nH]c12]

Example 502 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 2-(3,3-difluoropiperidin-1-yl)ethan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((2-(3,3-difluoropiperidin-1-yl)ethyl)amino)-N'-hydroxy-1H-imidazo[4,5-b]pyridine-7-carboximidamide was isolated as an off-white solid. $C_{20}H_{21}ClF_3N_7O$. 468.3/470.2 (M+1). $^1$H NMR (400 MHz, DMSO-d6) δ 11.38 (s, 1H), 8.95 (s, 1H), 7.98 (d, J=6.2 Hz, 1H), 7.11 (t, J=9.0 Hz, 1H), 7.02 (dd, J=6.5, 2.7

Hz, 1H), 6.93 (d, J=6.2 Hz, 1H), 6.59 (ddd, J=9.0, 4.1, 2.8 Hz, 1H), 3.66 (m, 2H), 3.10 (m, 2H), 2.90 (m, 2H), 2.75 (m, 2H), 1.97 (m, 2H), 1.77 (m, 2H). $^{19}$F NMR (377 MHz, DMSO-d6) δ −84.9 (9F), −108.4 (2F), −136.8 (1F).

Example 503: 2-((1-acetylpyrrolidin-3-yl)amino)-N-(3-chloro-4-fluorophenyl)-N'-hydroxy-1H-imidazo[4,5-b]pyridine-7-carboximidamide

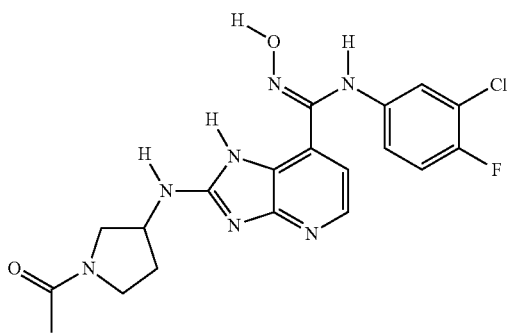 [SMILES: CC(=O)N1CCC(Nc2nc3nccc(/C(=N/O)Nc4ccc(F)c(Cl)c4)c3[nH]2)C1]

Example 503 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 1-(3-aminopyrrolidin-1-yl)ethan-1-one in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of 2-((1-acetylpyrrolidin-3-yl)amino)-N-(3-chloro-4-fluorophenyl)-N'-hydroxy-1H-imidazo[4,5-b]pyridine-7-carboximidamide was isolated as an off-white solid. $C_{19}H_{19}ClFN_7O_2$. 432.4/434.1 (M+1). $^1$H NMR (400 MHz, DMSO-d6) δ 11.40 (s, 1H), 8.96 (s, 1H), 7.98 (dd, J=6.3, 4.2 Hz, 1H), 7.11 (t, J=9.0 Hz, 1H), 7.04 (dd, J=6.3, 2.6 Hz, 1H), 6.94 (dd, J=7.9, 6.3 Hz, 1H), 6.60 (dt, J=9.3, 3.3 Hz, 1H), 4.54-4.36 (m, 2H), 3.77 (m, 1H), 3.59 (m, 1H), 2.34-2.11 (m, 2H), 2.07 (m, 1H), 1.96 (d, J=11.3 Hz, 3H). $^{19}$F NMR (376 MHz, DMSO-d6) δ −74.5, −126.5.

Example 504: N-(3-chloro-4-fluorophenyl)-N'-hydroxy-2-((1-(methylsulfonyl)pyrrolidin-3-yl)amino)-1H-imidazo[4,5-b]pyridine-7-carboximidamide

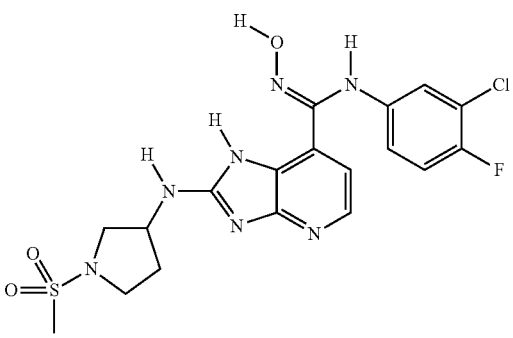 [SMILES: CS(=O)(=O)N1CCC(Nc2nc3nccc(/C(=N/O)Nc4ccc(F)c(Cl)c4)c3[nH]2)C1]

Example 504 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 1-(methylsulfonyl)pyrrolidin-3-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-((1-(methylsulfonyl)pyrrolidin-3-yl)amino)-1H-imidazo[4,5-b]pyridine-7-carboximidamide was isolated as an off-white solid. $C_{18}H_{19}ClFN_7O_3S$. 468.4/470.2 (M+1). $^1$H NMR (400 MHz, DMSO-d6) δ 11.41 (s, 1H), 8.96 (s, 1H), 7.99 (d, J=6.3 Hz, 1H), 7.10 (t, J=9.0 Hz, 1H), 7.03 (dd, J=6.5, 2.7 Hz, 1H), 6.95 (d, J=6.3 Hz, 1H), 6.60 (ddd, J=9.0, 4.1, 2.8 Hz, 1H), 4.55-4.42 (m, 2H), 3.59 (m, 1H), 3.27 (m, 1H), 2.95 (s, 3H), 2.37-2.21 (m, 2H), 2.05 (m, 1H). $^{19}$F NMR (376 MHz, DMSO-d6) δ −74.5, −126.5.

Example 505: N-(3-chloro-4-fluorophenyl)-N'-hydroxy-2-((3-(methylsulfonyl)propyl)amino)-1H-imidazo[4,5-b]pyridine-7-carboximidamide

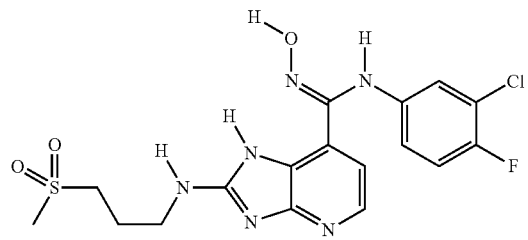 [SMILES: CS(=O)(=O)CCCNc1nc2nccc(/C(=N/O)Nc3ccc(F)c(Cl)c3)c2[nH]1]

Example 505 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 3-(methylsulfonyl)propan-1-amine hydrochloride and N-ethyl-N-isopropylpropan-2-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-N'-hydroxy-2-((3-(methylsulfonyl)propyl)amino)-1H-imidazo[4,5-b]pyridine-7-carboximidamide was isolated as an off-white solid. $C_{17}H_{18}ClFN_6O_3S$. 441.3/443.1 (M+1). $^1$H NMR (400 MHz, DMSO-d6) δ 11.39 (br. s, 1H), 8.95 (s, 1H), 7.97 (d, J=6.3 Hz, 1H), 7.10 (t, J=9.0 Hz, 1H), 7.04 (dd, J=6.5, 2.7 Hz, 1H), 6.92 (d, J=6.2 Hz, 1H), 6.59 (ddd, J=9.0, 4.0, 2.7 Hz, 1H), 3.56 (m, 2H), 3.20 (m, 2H), 3.00 (s, 3H), 2.04 (p, J=7.1 Hz, 2H). $^{19}$F NMR (377 MHz, DMSO-d6) δ −74.2 (6F), −126.3 (1F).

Example 506: N-(3-chloro-4-fluorophenyl)-2-(((1,1-dioxidotetrahydrothiophen-3-yl)methyl)amino)-N'-hydroxy-1H-imidazo[4,5-b]pyridine-7-carboximidamide

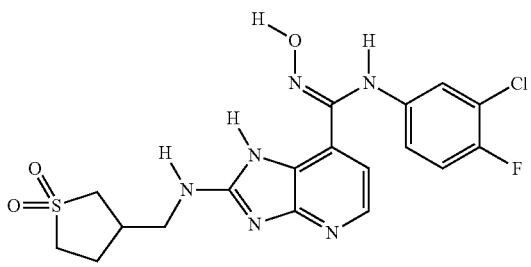 [SMILES: O=S1(=O)CCC(CNc2nc3nccc(/C(=N/O)Nc4ccc(F)c(Cl)c4)c3[nH]2)C1]

Example 506 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 3-(aminomethyl)tetrahydrothiophene 1,1-dioxide hydrochloride and N-ethyl-N-isopropylpropan-2-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-(((1,1-dioxidotetrahydrothiophen-3-yl)methyl)amino)-N'-hydroxy-1H-imidazo[4,5-b]pyridine-7-carboximidamide was isolated as an off-white solid. $C_{18}H_{18}ClFN_6O_3S$. 453.3/455.1 (M+1). $^1$H NMR (400 MHz, DMSO-d6) δ 8.95 (br. s, 1H), 7.97 (d, J=6.3 Hz, 1H), 7.10 (t, J=9.0 Hz, 1H), 7.03 (dd, J=6.4, 2.7 Hz, 1H), 6.93 (d, J=6.2 Hz, 1H), 6.59 (m, 1H), 3.56 (m, 2H), 3.24 (m, 2H), 3.08 (m, 1H), 2.91 (dd, J=13.2, 9.5 Hz, 1H), 2.74 (d, J=11.6 Hz, 1H), 2.25 (m, 1H), 1.86 (dq, J=13.1, 9.3 Hz, 1H). $^{19}$F NMR (376 MHz, DMSO-d6) δ −74.4, −126.5.

Example 507: N-(3-chloro-4-fluorophenyl)-2-((3-((4-fluorophenyl)sulfonyl)propyl)amino)-N'-hydroxy-1H-imidazo[4,5-b]pyridine-7-carboximidamide

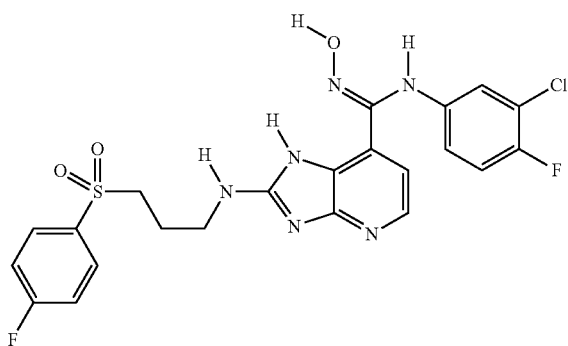 [SMILES: O=S(=O)(CCCNc1nc2nccc(/C(=N/O)Nc3ccc(F)c(Cl)c3)c2[nH]1)c1ccc(F)cc1]

Example 507 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and 3-((4-fluorophenyl)sulfonyl)propan-1-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of N-(3-chloro-4-fluorophenyl)-2-((3-((4-fluorophenyl)sulfonyl)propyl)amino)-N'-hydroxy-1H-imidazo[4,5-b]pyridine-7-carboximidamide was isolated as an off-white solid. $C_{22}H_{19}ClF_2N_6O_3S$. 521.4/523.1 (M+1). $^1$H NMR (400 MHz, DMSO-d6) δ 11.38 (br. s, 1H), 8.94 (s, 1H), 7.97 (m, 3H), 7.51 (m, 2H), 7.10 (t, J=9.0 Hz, 1H), 7.03 (dd, J=6.5, 2.7 Hz, 1H), 6.92 (d, J=6.3 Hz, 1H), 6.59 (dt, J=9.0, 3.5 Hz, 1H), 3.50 (m, 2H), 3.43 (m, 2H), 1.89 (p, J=7.1 Hz, 2H). $^{19}$F NMR (376 MHz, DMSO-d6) δ −74.4, −105.2, −126.5.

Example 508: (R)—N-(3-chloro-4-fluorophenyl)-N'-hydroxy-2-((1-(oxetan-3-yl)pyrrolidin-3-yl)amino)-1H-imidazo[4,5-b]pyridine-7-carboximidamide

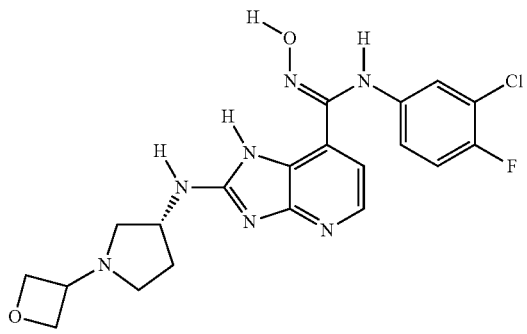 [SMILES: O/N=C(\Nc1ccc(F)c(Cl)c1)c1ccnc2nc(N[C@@H]3CCN(C4COC4)C3)[nH]c12]

Example 508 was made analogously to Example 229 using 3-(2-chloro-1-((2-(trimethylsilyl)ethoxy)methyl)-1H-imidazo[4,5-b]pyridin-7-yl)-4-(3-chloro-4-fluorophenyl)-1,2,4-oxadiazol-5(4H)-one and (R)-1-(oxetan-3-yl)pyrrolidin-3-amine in place of 3-(2-chloro-4,5-difluoro-1-((2-(trimethylsilyl)ethoxy)methyl)-1H-benzo[d]imidazol-7-yl)-4-(3-chloro-4-fluorophenyl)-1,2,4-oxadiazol-5(4H)-one and 3-aminopropanamide hydrochloride, respectively. The TFA salt of (R)—N-(3-chloro-4-fluorophenyl)-N'-hydroxy-2-((1-(oxetan-3-yl)pyrrolidin-3-yl)amino)-1H-imidazo[4,5-b]pyridine-7-carboximidamide was isolated as an off-white solid. $C_{20}H_{21}ClFN_7O_2$. 446.4/448.2 (M+1). $^1$H NMR (400 MHz, DMSO-d6) δ 11.30 (br. s, 1H), 8.93 (s, 1H), 7.99 (d, J=6.1 Hz, 1H), 7.09 (t, J=9.0 Hz, 1H), 7.03-6.92 (m, 2H), 6.58 (ddd, J=8.9, 4.0, 2.7 Hz, 1H), 4.78 (t, J=7.4 Hz, 2H), 4.69-4.55 (m, 3H), 4.47 (m, 1H), 3.8-3.3 (m, 5H), 2.09 (d, J=11.6 Hz, 1H). $^{19}$F NMR (376 MHz, DMSO-d6) δ −74.6, −126.7.

BIOLOGICAL EXAMPLES

Activity testing was conducted in the Examples below using methods described herein and those well known in the art.

Example 509. Cell-Based (HeLa) Assay for Measurement of IDOL Inhibition

To measure IDO1 inhibition in tissue culture, HeLa cells were treated with a test compound in the presence of IFNγ, which induces IDO1 expression. Following incubation, cell supernatants were assayed for kynurenine levels, an indicator of IDO1 activity.

H1-HeLa cells (ATCC #CRL-1958) were seeded in 384-well plates (Greiner #82051-282) at a volume of 50 μL/well in DMEM (Corning #15-018-CM) supplemented with 10% FBS (Corning #35-011-CV) and 1% P/S/G (Corning #30-009-CL) at a density of 1,250 cells/well and incubated overnight at 37° C., 5% $CO_2$/100% humidity. The following day, the test compounds were added in DMSO (0.5% final) at various concentrations, and IDO1 was inducibly expressed by the addition of 50 uL/well of 50/mL of INFγ (Peprotech #300-02) in cell plating media. As a positive control, 50 uL of the cell plating media without IFNγ was added to several wells. Following a 48 hour incubation, the plates were spun down at 1,200 RPM for 5 min at 10° C. 65

µL/well of the supernatant was then transferred to new 384-well plates (Thermo #262160) that contained 10 uL/well of 30% TCA (Sigma #TO699), and the plates were sealed and incubated at 60° C. for 30 min. The plates were then centrifuged for 15 min at 2,000 RPM at 10° C. 40 µL/well of the supernatant was transferred to new 384-well plates (Thermo #262160) and was reacted with 40 µL/well of 2% (w/v) p-dimethlyaminobenzaldehyde (Sigma #156417) in glacial acetic acid (Sigma #A6283). The reaction was incubated at room temperature for 10 min and absorbance at 480 nm was read using a PerkinElmer Envision plate reader.

Data in Table 1 were normalized based on positive (−IFNγ) and negative (+IFNγ) controls and EC50 values were calculated from the fit of the dose response curves to a four-parameter equation. All EC50 values represent geometric mean values of a minimum of four determinations. These assays generally produced results within 2-fold of the reported mean.

TABLE 1

| Example No. | Name | $EC_{50}$ (nM) |
|---|---|---|
| 1 | N-(3-chloro-4-fluorophenyl)-N'-hydroxy-7-methyl-3H-benzimidazole-4-carboximidamide | 1222 |
| 2 | N-(3-chloro-4-fluorophenyl)-N'-hydroxy-7-(trifluoromethoxy)-3H-benzimidazole-4-carboximidamide | 2455 |
| 3 | N-(3-chloro-4-fluorophenyl)-5-fluoro-N'-hydroxy-3H-benzimidazole-4-carboximidamide | 4801 |
| 4 | N-(3-chloro-4-fluorophenyl)-6-fluoro-N'-hydroxy-1H-benzimidazole-4-carboximidamide | 527 |
| 5 | N-(3-chloro-4-fluorophenyl)-7-fluoro-N'-hydroxy-3H-benzimidazole-4-carboximidamide | 542 |
| 6 | 7-chloro-N-(3-chloro-4-fluorophenyl)-N'-hydroxy-3H-benzimidazole-4-carboximidamide | 793 |
| 7 | N-(3-chloro-4-fluorophenyl)-N'-hydroxy-7-(trifluoromethyl)-1H-benzimidazole-4-carboximidamide | 926 |
| 8 | N-(3-chloro-4-fluorophenyl)-N'-hydroxy-3H-benzimidazole-4-carboximidamide | 1792 |
| 9 | N-(3-chloro-4-fluorophenyl)-6-fluoro-N'-hydroxy-7-methyl-3H-benzimidazole-4-carboximidamide | 634 |
| 10 | N-(3-chloro-4-fluorophenyl)-6,7-difluoro-N'-hydroxy-3H-benzimidazole-4-carboximidamide | 438 |
| 11 | 6-chloro-N-(3-chloro-4-fluorophenyl)-N'-hydroxy-3H-benzimidazole-4-carboximidamide | 7604 |
| 12 | 7-bromo-N-(3-chloro-4-fluorophenyl)-N'-hydroxy-3H-benzimidazole-4-carboximidamide | 660 |
| 13 | 2-amino-N-(3-chloro-4-fluorophenyl)-6,7-difluoro-N'-hydroxy-3H-benzimidazole-4-carboximidamide | 2739 |
| 14 | 2-amino-N-(3-bromo-4-fluorophenyl)-6,7-difluoro-N'-hydroxy-3H-benzimidazole-4-carboximidamide | 494 |
| 15 | 2-amino-N-(3-bromophenyl)-6,7-difluoro-N'-hydroxy-3H-benzimidazole-4-carboximidamide | 570 |
| 16 | 2-amino-N-(3-chlorophenyl)-6,7-difluoro-N'-hydroxy-3H-benzimidazole-4-carboximidamide | 607 |
| 17 | 2-amino-6,7-difluoro-N-[4-fluoro-3-(trifluoromethyl)phenyl]-N'-hydroxy-3H-benzimidazole-4-carboximidamide | 1092 |
| 18 | 2-amino-N-(3-bromophenyl)-7-fluoro-N'-hydroxy-3H-benzimidazole-4-carboximidamide | 312 |
| 19 | 2-amino-N-(3-bromo-4-fluorophenyl)-7-fluoro-N'-hydroxy-3H-benzimidazole-4-carboximidamide | 456 |
| 20 | 2-amino-N-(3-chlorophenyl)-7-fluoro-N'-hydroxy-3H-benzimidazole-4-carboximidamide | 404 |
| 21 | 2-amino-7-fluoro-N-[4-fluoro-3-(trifluoromethyl)phenyl]-N'-hydroxy-3H-benzimidazole-4-carboximidamide | 725 |
| 22 | 2-amino-N-(3-chloro-4-fluorophenyl)-7-fluoro-N'-hydroxy-3H-benzimidazole-4-carboximidamide | 382 |
| 23 | N-(3-chloro-4-fluorophenyl)-6,7-difluoro-N'-hydroxy-2-(2-morpholin-4-ylethylamino)-3H-benzimidazole-4-carboximidamide | 346 |
| 24 | N-(3-chlorophenyl)-4,5-difluoro-N'-hydroxy-2-(((3-methoxypropyl)amino)methyl)-1H-benzo[d]imidazole-7-carboximidamide | 1923 |
| 25 | N-(3-chlorophenyl)-2-(((cyclopropylmethyl)amino)methyl)-4,5-difluoro-N'-hydroxy-1H-benzo[d]imidazole-7-carboximidamide | 1457 |
| 26 | N-(3-chlorophenyl)-2-((dimethylamino)methyl)-4,5-difluoro-N'-hydroxy-1H-benzo[d]imidazole-7-carboximidamide | 1212 |
| 27 | N-(3-chlorophenyl)-4,5-difluoro-N'-hydroxy-2-((isopropylamino)methyl)-1H-benzo[d]imidazole-7-carboximidamide | 839 |
| 28 | N-(3-chlorophenyl)-2-((ethylamino)methyl)-4,5-difluoro-N'-hydroxy-1H-benzo[d]imidazole-7-carboximidamide | 801 |
| 29 | N-(3-chlorophenyl)-4,5-difluoro-N'-hydroxy-2-(hydroxymethyl)-1H-benzo[d]imidazole-7-carboximidamide | 1541 |
| 30 | N-(3-chlorophenyl)-4,5-difluoro-N'-hydroxy-2-((methylamino)methyl)-1H-benzo[d]imidazole-7-carboximidamide | 1106 |
| 31 | 2-(aminomethyl)-N-(3-chlorophenyl)-4,5-difluoro-N'-hydroxy-1H-benzo[d]imidazole-7-carboximidamide | 1680 |
| 32 | N-(3-chloro-4-fluorophenyl)-6,7-difluoro-N'-hydroxy-2-morpholin-4-yl-3H-benzimidazole-4-carboximidamide | 9276 |
| 33 | N-(3-chloro-4-fluorophenyl)-7-fluoro-N'-hydroxy-2-(2-methylsulfonylethylamino)-3H-benzimidazole-4-carboximidamide | 1833 |
| 34 | N-(3-Chloro-4-fluorophenyl)-4-fluoro-N'-hydroxy-2-((2-morpholinoethyl)amino)-1H-benzo[d]imidazole-7-carboximidamide | 6739 |
| 35 | N-(3-chloro-4-fluorophenyl)-6,7-difluoro-N'-hydroxy-2-(2-methylsulfonylethylamino)-3H-benzimidazole-4-carboximidamide | 2153 |
| 36 | N-(3-chloro-4-fluorophenyl)-2-[2-(4,4-difluoropiperidin-1-yl)ethylamino]-6,7-difluoro-N'-hydroxy-3H-benzimidazole-4-carboximidamide | 712 |
| 37 | N-(3-chloro-4-fluorophenyl)-6,7-difluoro-N'-hydroxy-2-(1-morpholin-4-ylpropan-2-ylamino)-3H-benzimidazole-4-carboximidamide | 514 |
| 38 | N-(3-chloro-4-fluorophenyl)-6,7-difluoro-N'-hydroxy-2-(methylamino)-3H-benzimidazole-4-carboximidamide | 607 |
| 39 | N-(3-chloro-4-fluorophenyl)-2-[3-(dimethylamino)propylamino]-6,7-difluoro-N'-hydroxy-3H-benzimidazole-4-carboximidamide | 473 |
| 40 | N-(3-chloro-4-fluorophenyl)-6,7-difluoro-N'-hydroxy-2-(2-methoxyethylamino)-3H-benzimidazole-4-carboximidamide | 1523 |
| 41 | N-(3-chloro-4-fluorophenyl)-6,7-difluoro-N'-hydroxy-2-(2-pyrrolidin-1-ylethylamino)-3H-benzimidazole-4-carboximidamide | 240 |
| 42 | N-(3-chloro-4-fluorophenyl)-2-[2-(diethylamino)ethylamino]-6,7-difluoro-N'-hydroxy-3H-benzimidazole-4-carboximidamide | 247 |
| 43 | N-(3-chloro-4-fluorophenyl)-2-[2-(dimethylamino)ethylamino]-6,7-difluoro-N'-hydroxy-3H-benzimidazole-4-carboximidamide | 136 |
| 44 | N-(3-chlorophenyl)-6,7-difluoro-N'-hydroxy-2-(1-methylpiperidin-3-yl)-3H-benzimidazole-4-carboximidamide | 1645 |
| 45 | N-(3-chloro-4-fluorophenyl)-6,7-difluoro-N'-hydroxy-2-[(3-methoxypropylamino)methyl]-1H-benzimidazole-4-carboximidamide | 1324 |
| 46 | N-(3-chloro-4-fluorophenyl)-6,7-difluoro-N'-hydroxy-2-(hydroxymethyl)-3H-benzimidazole-4-carboximidamide | 835 |

TABLE 1-continued

| Example No. | Name | EC$_{50}$ (nM) |
|---|---|---|
| 47 | 2-(aminomethyl)-N-(3-chloro-4-fluorophenyl)-6,7-difluoro-N'-hydroxy-1H-benzimidazole-4-carboximidamide | 1075 |
| 48 | N-(3-chloro-4-fluorophenyl)-6,7-difluoro-N'-hydroxy-2-(methylaminomethyl)-1H-benzimidazole-4-carboximidamide | 434 |
| 49 | N-(3-chloro-4-fluorophenyl)-2-[(cyclopropylmethylamino)methyl]-6,7-difluoro-N'-hydroxy-1H-benzimidazole-4-carboximidamide | 1057 |
| 50 | N-(3-chloro-4-fluorophenyl)-2-(ethylaminomethyl)-6,7-difluoro-N'-hydroxy-1H-benzimidazole-4-carboximidamide | 457 |
| 51 | N-(3-chloro-4-fluorophenyl)-6,7-difluoro-N'-hydroxy-2-[(propan-2-ylamino)methyl]-1H-benzimidazole-4-carboximidamide | 566 |
| 52 | N-(3-chloro-4-fluorophenyl)-2-[(dimethylamino)methyl]-6,7-difluoro-N'-hydroxy-1H-benzimidazole-4-carboximidamide | 526 |
| 53 | N-(3-chloro-4-fluorophenyl)-2-[2-(dimethylamino)ethyl]-6,7-difluoro-N'-hydroxy-1H-benzimidazole-4-carboximidamide | 916 |
| 54 | N-(3-bromo-4-fluorophenyl)-2-[2-(dimethylamino)ethyl]-6,7-difluoro-N'-hydroxy-1H-benzimidazole-4-carboximidamide | 461 |
| 55 | N-(3-bromophenyl)-2-[2-(dimethylamino)ethyl]-6,7-difluoro-N'-hydroxy-1H-benzimidazole-4-carboximidamide | 379 |
| 56 | N-(3-chlorophenyl)-2-[2-(dimethylamino)ethyl]-6,7-difluoro-N'-hydroxy-1H-benzimidazole-4-carboximidamide | 562 |
| 57 | N-(3-chloro-4-fluorophenyl)-6,7-difluoro-N'-hydroxy-2-[2-(methylamino)ethyl]-1H-benzimidazole-4-carboximidamide | 1093 |
| 58 | N-(3-chloro-4-fluorophenyl)-2-[2-(diethylamino)ethyl]-6,7-difluoro-N'-hydroxy-1H-benzimidazole-4-carboximidamide | 786 |
| 59 | N-(3-chloro-4-fluorophenyl)-N'-hydroxy-1H-imidazo[4,5-b]pyridine-7-carboximidamide | 208 |
| 60 | N-(5-chloro-2-fluorophenyl)-N'-hydroxy-1H-imidazo[4,5-b]pyridine-7-carboximidamide | 322 |
| 61 | N-(5-bromo-2,4-difluorophenyl)-N'-hydroxy-1H-imidazo[4,5-b]pyridine-7-carboximidamide | 371 |
| 62 | N-(5-chloro-2,4-difluorophenyl)-N'-hydroxy-1H-imidazo[4,5-b]pyridine-7-carboximidamide | 385 |
| 63 | N-(3,5-dichloro-4-fluorophenyl)-N'-hydroxy-1H-imidazo[4,5-b]pyridine-7-carboximidamide | 774 |
| 64 | N-(3-chloro-2,4-difluorophenyl)-N'-hydroxy-1H-imidazo[4,5-b]pyridine-7-carboximidamide | 813 |
| 65 | N-(3-cyclopropyl-4-fluorophenyl)-N'-hydroxy-1H-imidazo[4,5-b]pyridine-7-carboximidamide | 1809 |
| 66 | N'-hydroxy-N-[4-(trifluoromethoxy)phenyl]-1H-imidazo[4,5-b]pyridine-7-carboximidamide | 4871 |
| 67 | N-(1-benzofuran-4-yl)-N'-hydroxy-1H-imidazo[4,5-b]pyridine-7-carboximidamide | 583 |
| 68 | N-(1-benzofuran-6-yl)-N'-hydroxy-1H-imidazo[4,5-b]pyridine-7-carboximidamide | 890 |
| 69 | N-(1-benzofuran-7-yl)-N'-hydroxy-1H-imidazo[4,5-b]pyridine-7-carboximidamide | 1339 |
| 70 | N-(1-benzofuran-5-yl)-N'-hydroxy-1H-imidazo[4,5-b]pyridine-7-carboximidamide | 1479 |
| 71 | N-(5-bromo-2-fluorophenyl)-N'-hydroxy-3H-imidazo[4,5-b]pyridine-7-carboximidamide | 207 |
| 72 | N-(3-bromo-5-fluorophenyl)-N'-hydroxy-1H-imidazo[4,5-b]pyridine-7-carboximidamide | 280 |
| 73 | N'-hydroxy-N-[3-(trifluoromethyl)phenyl]-1H-imidazo[4,5-b]pyridine-7-carboximidamide | 373 |
| 74 | N-(2,2-difluoro-1,3-benzodioxol-5-yl)-N'-hydroxy-3H-imidazo[4,5-b]pyridine-7-carboximidamide | 923 |
| 75 | N-[3-fluoro-5-(trifluoromethyl)phenyl]-N'-hydroxy-1H-imidazo[4,5-b]pyridine-7-carboximidamide | 2109 |
| 76 | N-(2,5-dichlorophenyl)-N'-hydroxy-1H-imidazo[4,5-b]pyridine-7-carboximidamide | 769 |
| 77 | N-(4-fluoro-3-phenylphenyl)-N'-hydroxy-1H-imidazo[4,5-b]pyridine-7-carboximidamide | 2289 |
| 78 | N-(3-but-1-ynyl-4-fluorophenyl)-N'-hydroxy-1H-imidazo[4,5-b]pyridine-7-carboximidamide | 2641 |
| 79 | N-[3-(2-cyclopropylethynyl)-4-fluorophenyl]-N'-hydroxy-1H-imidazo[4,5-b]pyridine-7-carboximidamide | 3223 |
| 80 | N-(3-bromophenyl)-N'-hydroxy-3H-imidazo[4,5-b]pyridine-7-carboximidamide | 111 |
| 81 | N-(3-bromo-4-fluorophenyl)-N'-hydroxy-3H-imidazo[4,5-b]pyridine-7-carboximidamide | 140 |
| 82 | N-(3-chlorophenyl)-N'-hydroxy-3H-imidazo[4,5-b]pyridine-7-carboximidamide | 160 |
| 83 | N-[4-fluoro-3-(trifluoromethyl)phenyl]-N'-hydroxy-3H-imidazo[4,5-b]pyridine-7-carboximidamide | 315 |
| 84 | N-(4-fluoro-3-prop-1-ynylphenyl)-N'-hydroxy-3H-imidazo[4,5-b]pyridine-7-carboximidamide | 445 |
| 85 | N-(3-bromo-4-chlorophenyl)-N'-hydroxy-3H-imidazo[4,5-b]pyridine-7-carboximidamide | 462 |
| 86 | N-(3,4-dichlorophenyl)-N'-hydroxy-3H-imidazo[4,5-b]pyridine-7-carboximidamide | 639 |
| 87 | N-(4-chlorophenyl)-N'-hydroxy-3H-imidazo[4,5-b]pyridine-7-carboximidamide | 846 |
| 88 | N-(4-bromophenyl)-N'-hydroxy-3H-imidazo[4,5-b]pyridine-7-carboximidamide | 916 |
| 89 | N-(4-fluorophenyl)-N'-hydroxy-3H-imidazo[4,5-b]pyridine-7-carboximidamide | 943 |
| 90 | N-(3-cyano-4-fluorophenyl)-N'-hydroxy-1H-imidazo[4,5-b]pyridine-7-carboximidamide | 1047 |
| 91 | N'-hydroxy-N-[4-(trifluoromethyl)phenyl]-3H-imidazo[4,5-b]pyridine-7-carboximidamide | 2240 |
| 92 | N'-hydroxy-N-(3-methoxyphenyl)-3H-imidazo[4,5-b]pyridine-7-carboximidamide | 3892 |
| 93 | N-(4-fluoro-3-propan-2-ylphenyl)-N'-hydroxy-1H-imidazo[4,5-b]pyridine-7-carboximidamide | 5096 |
| 94 | N'-hydroxy-N-(4-methylphenyl)-3H-imidazo[4,5-b]pyridine-7-carboximidamide | 6350 |
| 95 | N-(3-ethynylphenyl)-N'-hydroxy-1H-imidazo[4,5-b]pyridine-7-carboximidamide | 302 |
| 96 | N-(3-ethylphenyl)-N'-hydroxy-1H-imidazo[4,5-b]pyridine-7-carboximidamide | 803 |
| 97 | N-(3-ethynyl-4-fluorophenyl)-N'-hydroxy-1H-imidazo[4,5-b]pyridine-7-carboximidamide | 380 |
| 98 | N-[3-(difluoromethyl)phenyl]-N'-hydroxy-1H-imidazo[4,5-b]pyridine-7-carboximidamide | 550 |
| 99 | N'-hydroxy-N-[3-(trifluoromethoxy)phenyl]-1H-imidazo[4,5-b]pyridine-7-carboximidamide | 602 |
| 100 | N'-hydroxy-N-phenyl-1H-imidazo[4,5-b]pyridine-7-carboximidamide | 770 |
| 101 | N-[4-fluoro-3-(trifluoromethoxy)phenyl]-N'-hydroxy-1H-imidazo[4,5-b]pyridine-7-carboximidamide | 845 |
| 102 | N'-hydroxy-N-naphthalen-2-yl-1H-imidazo[4,5-b]pyridine-7-carboximidamide | 1928 |
| 103 | N-(3-chloronaphthalen-2-yl)-N'-hydroxy-1H-imidazo[4,5-b]pyridine-7-carboximidamide | 8075 |
| 104 | N'-hydroxy-N-naphthalen-1-yl-1H-imidazo[4,5-b]pyridine-7-carboximidamide | 1966 |
| 105 | N-(4-chloronaphthalen-1-yl)-N'-hydroxy-1H-imidazo[4,5-b]pyridine-7-carboximidamide | 3032 |
| 106 | N-(4-fluoro-3-methoxyphenyl)-N'-hydroxy-1H-imidazo[4,5-b]pyridine-7-carboximidamide | 5536 |
| 107 | N-(3-chloro-4-fluorophenyl)-N'-hydroxy-2-methyl-1H-imidazo[4,5-b]pyridine-7-carboximidamide | 1925 |
| 108 | N-(3-chloro-4-fluorophenyl)-2-ethyl-N'-hydroxy-1H-imidazo[4,5-b]pyridine-7-carboximidamide | 3192 |
| 109 | N-(3-chloro-4-fluorophenyl)-2-cyclopropyl-N'-hydroxy-1H-imidazo[4,5-b]pyridine-7-carboximidamide | 1386 |
| 110 | N-(3-chloro-4-fluorophenyl)-N'-hydroxy-2-(methoxymethyl)-1H-imidazo[4,5-b]pyridine-7-carboximidamide | 2320 |
| 111 | 4-(3-chloro-4-fluorophenyl)-3-[2-(hydroxymethyl)-1H-imidazo[4,5-b]pyridin-7-yl]-1,2,4-oxadiazol-5-one | 4452 |

TABLE 1-continued

| Example No. | Name | EC$_{50}$ (nM) |
|---|---|---|
| 112 | N-(3-chloro-4-fluorophenyl)-N'-hydroxy-2-(morpholin-4-ylmethyl)-3H-imidazo[4,5-b]pyridine-7-carboximidamide | 9531 |
| 113 | N-(3-chloro-4-fluorophenyl)-2-[(dimethylamino)methyl]-N'-hydroxy-3H-imidazo[4,5-b]pyridine-7-carboximidamide | 1837 |
| 114 | N-(3-chloro-4-fluorophenyl)-2-(ethylaminomethyl)-N'-hydroxy-3H-imidazo[4,5-b]pyridine-7-carboximidamide | 927 |
| 115 | 2-[(benzylamino)methyl]-N-(3-chloro-4-fluorophenyl)-N'-hydroxy-3H-imidazo[4,5-b]pyridine-7-carboximidamide | 1761 |
| 116 | N-(3-chloro-4-fluorophenyl)-N'-hydroxy-2-[(propan-2-ylamino)methyl]-3H-imidazo[4,5-b]pyridine-7-carboximidamide | 740 |
| 117 | N-(3-chloro-4-fluorophenyl)-2-[(cyclopropylmethylamino)methyl]-N'-hydroxy-3H-imidazo[4,5-b]pyridine-7-carboximidamide | 765 |
| 118 | N-(3-chloro-4-fluorophenyl)-N'-hydroxy-2-[(2,2,2-trifluoroethylamino)methyl]-3H-imidazo[4,5-b]pyridine-7-carboximidamide | 4644 |
| 119 | N-(3-chloro-4-fluorophenyl)-2-[(cyclopropylamino)methyl]-N'-hydroxy-3H-imidazo[4,5-b]pyridine-7-carboximidamide | 2150 |
| 120 | N-(3-chloro-4-fluorophenyl)-N'-hydroxy-2-[(3-methoxypropylamino)methyl]-3H-imidazo[4,5-b]pyridine-7-carboximidamide | 1334 |
| 121 | N-(3-chloro-4-fluorophenyl)-N'-hydroxy-2-[(pyridin-2-ylmethylamino)methyl]-3H-imidazo[4,5-b]pyridine-7-carboximidamide | 1373 |
| 122 | N-(3-chloro-4-fluorophenyl)-N'-hydroxy-2-[[3-methoxypropyl(methyl)amino]methyl]-1H-imidazo[4,5-b]pyridine-7-carboximidamide | 1883 |
| 123 | N-(3-chloro-4-fluorophenyl)-N'-hydroxy-2-[[(2-methoxyphenyl)methylamino]methyl]-1H-imidazo[4,5-b]pyridine-7-carboximidamide | 1909 |
| 124 | N-(3-chloro-4-fluorophenyl)-N'-hydroxy-2-[(2-methoxyethylamino)methyl]-3H-imidazo[4,5-b]pyridine-7-carboximidamide | 2059 |
| 125 | N-(3-chloro-4-fluorophenyl)-N'-hydroxy-2-[(2-pyridin-2-ylethylamino)methyl]-3H-imidazo[4,5-b]pyridine-7-carboximidamide | 2083 |
| 126 | N-(3-chloro-4-fluorophenyl)-N'-hydroxy-2-[(pyridin-3-ylmethylamino)methyl]-3H-imidazo[4,5-b]pyridine-7-carboximidamide | 2280 |
| 127 | N-(3-chloro-4-fluorophenyl)-N'-hydroxy-2-[(oxan-2-ylmethylamino)methyl]-1H-imidazo[4,5-b]pyridine-7-carboximidamide | 2364 |
| 128 | 2-(anilinomethyl)-N-(3-chloro-4-fluorophenyl)-N'-hydroxy-3H-imidazo[4,5-b]pyridine-7-carboximidamide | 2399 |
| 129 | N-(3-chloro-4-fluorophenyl)-N'-hydroxy-2-[(oxan-3-ylmethylamino)methyl]-1H-imidazo[4,5-b]pyridine-7-carboximidamide | 2575 |
| 130 | N-(3-chloro-4-fluorophenyl)-N'-hydroxy-2-[(pyrimidin-2-ylmethylamino)methyl]-3H-imidazo[4,5-b]pyridine-7-carboximidamide | 2815 |
| 131 | N-(3-chloro-4-fluorophenyl)-N'-hydroxy-2-[(3-morpholin-4-ylpropylamino)methyl]-3H-imidazo[4,5-b]pyridine-7-carboximidamide | 3016 |
| 132 | N-(3-chloro-4-fluorophenyl)-N'-hydroxy-2-[(oxan-4-ylamino)methyl]-1H-imidazo[4,5-b]pyridine-7-carboximidamide | 3433 |
| 133 | N-(3-chloro-4-fluorophenyl)-N'-hydroxy-2-[(pyridin-4-ylmethylamino)methyl]-3H-imidazo[4,5-b]pyridine-7-carboximidamide | 3711 |
| 134 | N-(3-chloro-4-fluorophenyl)-N'-hydroxy-2-[(pyrazin-2-ylmethylamino)methyl]-1H-imidazo[4,5-b]pyridine-7-carboximidamide | 3988 |
| 135 | N-(3-chloro-4-fluorophenyl)-N'-hydroxy-2-[(oxolan-3-ylmethylamino)methyl]-1H-imidazo[4,5-b]pyridine-7-carboximidamide | 5105 |
| 136 | N-(3-chloro-4-fluorophenyl)-2-[[2-(dimethylamino)ethylamino]methyl]-N'-hydroxy-3H-imidazo[4,5-b]pyridine-7-carboximidamide | 6274 |
| 137 | N-(3-chloro-4-fluorophenyl)-N'-hydroxy-2-[(2-pyrimidin-2-ylethylamino)methyl]-3H-imidazo[4,5-b]pyridine-7-carboximidamide | 7492 |
| 138 | N-(3-chloro-4-fluorophenyl)-N'-hydroxy-2-[(3-hydroxypropylamino)methyl]-1H-imidazo[4,5-b]pyridine-7-carboximidamide | 8239 |
| 139 | N-(3-chloro-4-fluorophenyl)-N'-hydroxy-2-(pyrrolidin-1-ylmethyl)-3H-imidazo[4,5-b]pyridine-7-carboximidamide | 1400 |
| 140 | N-(3-chloro-4-fluorophenyl)-N'-hydroxy-2-(piperidin-1-ylmethyl)-3H-imidazo[4,5-b]pyridine-7-carboximidamide | 1609 |
| 141 | N-(3-chloro-4-fluorophenyl)-2-[(2,2-dimethylpropylamino)methyl]-N'-hydroxy-1H-imidazo[4,5-b]pyridine-7-carboximidamide | 1677 |
| 142 | N-(3-chloro-4-fluorophenyl)-2-[(2,2-difluoroethylamino)methyl]-N'-hydroxy-1H-imidazo[4,5-b]pyridine-7-carboximidamide | 5155 |
| 143 | N-(3-chloro-4-fluorophenyl)-N'-hydroxy-2-[[(3-hydroxy-2,2-dimethylpropyl)amino]methyl]-1H-imidazo[4,5-b]pyridine-7-carboximidamide | 7346 |
| 144 | N-(3-chloro-4-fluorophenyl)-N'-hydroxy-2-[(1,3-thiazol-2-ylmethylamino)methyl]-1H-imidazo[4,5-b]pyridine-7-carboximidamide | 8228 |
| 145 | N-[[7-[(Z)-N-(3-chloro-4-fluorophenyl)-N'-hydroxycarbamimidoyl]-3H-imidazo[4,5-b]pyridin-2-yl]methyl]acetamide | 9760 |
| 146 | N-(3-chloro-4-fluorophenyl)-N'-hydroxy-2-thiophen-2-yl-3H-imidazo[4,5-b]pyridine-7-carboximidamide | 4215 |
| 147 | N-(3-chloro-4-fluorophenyl)-N'-hydroxy-2-pyridin-3-yl-1H-imidazo[4,5-b]pyridine-7-carboximidamide | 1935 |
| 148 | N-(3-chloro-4-fluorophenyl)-N'-hydroxy-2-(1H-pyrrol-2-yl)-1H-imidazo[4,5-b]pyridine-7-carboximidamide | 2229 |
| 149 | N-(3-chloro-4-fluorophenyl)-N'-hydroxy-2-(1H-imidazol-2-yl)-1H-imidazo[4,5-b]pyridine-7-carboximidamide | 529 |
| 150 | N-(3-chloro-4-fluorophenyl)-N'-hydroxy-2-(1H-pyrazol-5-yl)-1H-imidazo[4,5-b]pyridine-7-carboximidamide | 8480 |
| 151 | N-(3-chloro-4-fluorophenyl)-N'-hydroxy-2-(5-methyl-1H-imidazol-2-yl)-1H-imidazo[4,5-b]pyridine-7-carboximidamide | 463 |
| 152 | N-(3-chloro-4-fluorophenyl)-N'-hydroxy-2-[(2S)-pyrrolidin-2-yl]-1H-imidazo[4,5-b]pyridine-7-carboximidamide | 4036 |
| 153 | 2-amino-N-(3-chloro-4-fluorophenyl)-N'-hydroxy-1H-imidazo[4,5-b]pyridine-7-carboximidamide | 897 |
| 154 | N-(3-chloro-4-fluorophenyl)-2-(cyclopropylamino)-N'-hydroxy-1H-imidazo[4,5-b]pyridine-7-carboximidamide | 529 |
| 155 | 2-anilino-N-(3-chloro-4-fluorophenyl)-N'-hydroxy-1H-imidazo[4,5-b]pyridine-7-carboximidamide | 2146 |
| 156 | N-(3-chloro-4-fluorophenyl)-N'-hydroxy-2-(2-phenylethylamino)-1H-imidazo[4,5-b]pyridine-7-carboximidamide | 769 |
| 157 | N-(3-chloro-4-fluorophenyl)-N'-hydroxy-2-(2,2,2-trifluoroethylamino)-1H-imidazo[4,5-b]pyridine-7-carboximidamide | 1088 |
| 158 | N-(3-chloro-4-fluorophenyl)-N'-hydroxy-2-(methylamino)-1H-imidazo[4,5-b]pyridine-7-carboximidamide | 460 |
| 159 | propan-2-yl N-[7-[(Z)-N-(3-chloro-4-fluorophenyl)-N'-hydroxycarbamimidoyl]-1H-imidazo[4,5-b]pyridin-2-yl]carbamate | 453 |
| 160 | ethyl N-[7-[(Z)-N-(3-chloro-4-fluorophenyl)-N'-hydroxycarbamimidoyl]-1H-imidazo[4,5-b]pyridin-2-yl]carbamate | 423 |
| 161 | N-(3-chloro-4-fluorophenyl)-2-(cyclopropylmethylamino)-N'-hydroxy-1H-imidazo[4,5-b]pyridine-7-carboximidamide | 655 |

TABLE 1-continued

| Example No. | Name | EC$_{50}$ (nM) |
|---|---|---|
| 162 | N-(3-chloro-4-fluorophenyl)-2-[(3,3-difluorocyclobutyl)amino]-N'-hydroxy-1H-imidazo[4,5-b]pyridine-7-carboximidamide | 4017 |
| 163 | N-(3-chloro-4-fluorophenyl)-2-(ethylamino)-N'-hydroxy-1H-imidazo[4,5-b]pyridine-7-carboximidamide | 1084 |
| 164 | N-(3-chloro-4-fluorophenyl)-2-(cyclobutylamino)-N'-hydroxy-1H-imidazo[4,5-b]pyridine-7-carboximidamide | 798 |
| 165 | N-(3-chloro-4-fluorophenyl)-N'-hydroxy-2-(propan-2-ylamino)-1H-imidazo[4,5-b]pyridine-7-carboximidamide | 705 |
| 166 | N-(3-chlorophenyl)-N'-hydroxy-2-(methylamino)-1H-imidazo[4,5-b]pyridine-7-carboximidamide | 383 |
| 167 | N-(3-chloro-4-fluorophenyl)-2-[2-(diethylamino)ethylamino]-N'-hydroxy-1H-imidazo[4,5-b]pyridine-7-carboximidamide | 2912 |
| 168 | N-(3-chloro-4-fluorophenyl)-N'-hydroxy-2-(2-morpholin-4-ylethylamino)-1H-imidazo[4,5-b]pyridine-7-carboximidamide | 1158 |
| 169 | N-(3-chloro-4-fluorophenyl)-2-(dimethylamino)-N'-hydroxy-1H-imidazo[4,5-b]pyridine-7-carboximidamide | 6269 |
| 170 | 2-(chloromethyl)-N-[4-fluoro-3-(trifluoromethyl)phenyl]-N'-hydroxy-1H-imidazo[4,5-b]pyridine-7-carboximidamide | 1936 |
| 171 | N-[4-fluoro-3-(trifluoromethyl)phenyl]-N'-hydroxy-2-(hydroxymethyl)-1H-imidazo[4,5-b]pyridine-7-carboximidamide | 4000 |
| 172 | N-(3-chloro-4-fluorophenyl)-N'-hydroxy-2-(1-hydroxyethyl)-1H-imidazo[4,5-b]pyridine-7-carboximidamide | 3858 |
| 173 | N-(3-chloro-4-fluorophenyl)-N'-hydroxy-2-[hydroxy(phenyl)methyl]-1H-imidazo[4,5-b]pyridine-7-carboximidamide | 9700 |
| 174 | N-(3-chloro-4-fluorophenyl)-2-[cyclopropyl(hydroxy)methyl]-N'-hydroxy-1H-imidazo[4,5-b]pyridine-7-carboximidamide | 7086 |
| 175 | N-(3-chloro-4-fluorophenyl)-N'-hydroxy-2-(2-hydroxypropan-2-yl)-1H-imidazo[4,5-b]pyridine-7-carboximidamide | 6417 |
| 176 | N-(3-chloro-4-fluorophenyl)-N'-hydroxy-2-(2,2,2-trifluoro-1-hydroxyethyl)-1H-imidazo[4,5-b]pyridine-7-carboximidamide | 4201 |
| 177 | N-(3-chloro-4-fluorophenyl)-N'-hydroxy-2-(hydroxymethyl)-1H-imidazo[4,5-b]pyridine-7-carboximidamide | 1674 |
| 178 | N-(3-chloro-4-fluorophenyl)-N'-hydroxy-2-(methylaminomethyl)-1H-imidazo[4,5-b]pyridine-7-carboximidamide | 1477 |
| 179 | 2-(aminomethyl)-N-(3-chloro-4-fluorophenyl)-N'-hydroxy-1H-imidazo[4,5-b]pyridine-7-carboximidamide | 7664 |
| 180 | 2-(benzenesulfonamidomethyl)-N-(3-chloro-4-fluorophenyl)-N'-hydroxy-1H-imidazo[4,5-b]pyridine-7-carboximidamide | 1406 |
| 181 | N-(3-chloro-4-fluorophenyl)-N'-hydroxy-2-(methanesulfonamidomethyl)-3H-imidazo[4,5-b]pyridine-7-carboximidamide | 8969 |
| 182 | N-(3-chloro-4-fluorophenyl)-N'-hydroxy-2-[(pyrimidin-2-ylamino)methyl]-3H-imidazo[4,5-b]pyridine-7-carboximidamide | 6401 |
| 183 | N-(3-chloro-4-fluorophenyl)-N'-hydroxy-2-(2-hydroxyethyl)-1H-imidazo[4,5-b]pyridine-7-carboximidamide | 2401 |
| 184 | N-(3-chloro-4-fluorophenyl)-2-[2-(dimethylamino)ethyl]-N'-hydroxy-3H-imidazo[4,5-b]pyridine-7-carboximidamide | 593 |
| 185 | N-(3-chloro-4-fluorophenyl)-2-[2-(diethylamino)ethyl]-N'-hydroxy-1H-imidazo[4,5-b]pyridine-7-carboximidamide | 531 |
| 186 | N-(3-chloro-4-fluorophenyl)-2-[2-[cyclopropylmethyl(methyl)amino]ethyl]-N'-hydroxy-1H-imidazo[4,5-b]pyridine-7-carboximidamide | 565 |
| 187 | N-(3-chloro-4-fluorophenyl)-2-[2-[2,2-difluoroethyl(methyl)amino]ethyl]-N'-hydroxy-1H-imidazo[4,5-b]pyridine-7-carboximidamide | 3405 |
| 188 | N-(3-chloro-4-fluorophenyl)-N'-hydroxy-2-[2-(methylamino)ethyl]-3H-imidazo[4,5-b]pyridine-7-carboximidamide | 1513 |
| 189 | 2-(2-aminoethyl)-N-(3-chloro-4-fluorophenyl)-N'-hydroxy-3H-imidazo[4,5-b]pyridine-7-carboximidamide | 1777 |
| 190 | N-(3-Chloro-4-fluorophenyl)-N'-hydroxy-2-(2-((2-methoxyethyl)amino)ethyl)-1H-imidazo[4,5-b]pyridine-7-carboximidamide | 1513 |
| 191 | N-(3-chloro-4-fluorophenyl)-N'-hydroxy-2-(2-morpholin-4-ylethyl)-3H-imidazo[4,5-b]pyridine-7-carboximidamide | 2824 |
| 192 | N-(3-chloro-4-fluorophenyl)-N'-hydroxy-2-(2-piperidin-1-ylethyl)-1H-imidazo[4,5-b]pyridine-7-carboximidamide | 241 |
| 193 | N-(3-chloro-4-fluorophenyl)-N'-hydroxy-2-(2-pyrrolidin-1-ylethyl)-1H-imidazo[4,5-b]pyridine-7-carboximidamide | 358 |
| 194 | N-(3-chloro-4-fluorophenyl)-N'-hydroxy-2-[2-[2-methoxyethyl(methyl)amino]ethyl]-1H-imidazo[4,5-b]pyridine-7-carboximidamide | 504 |
| 195 | N-(3-chloro-4-fluorophenyl)-2-[2-(dimethylamino)-1-hydroxyethyl]-N'-hydroxy-1H-imidazo[4,5-b]pyridine-7-carboximidamide | 1158 |
| 196 | N-(3-chloro-4-fluorophenyl)-N'-hydroxy-2-[(2-methylpropylamino)methyl]-1H-imidazo[4,5-b]pyridine-7-carboximidamide | 1330 |
| 197 | N-(3-chloro-4-fluorophenyl)-N'-hydroxy-3-methylimidazo[4,5-b]pyridine-7-carboximidamide | 5456 |
| 198 | N-(3-chloro-4-fluorophenyl)-N'-hydroxy-2-[2-(2-methoxyethylamino)ethyl]-3H-imidazo[4,5-b]pyridine-7-carboximidamide | 2339 |
| 199 | N-(3-chloro-4-fluorophenyl)-2-[3-(dimethylamino)propyl]-6,7-difluoro-N'-hydroxy-3H-benzimidazole-4-carboximidamide | 4488 |
| 200 | N-(3-chloro-4-fluorophenyl)-7-fluoro-N'-hydroxy-2-(3-morpholin-4-ylpropylamino)-3H-benzimidazole-4-carboximidamide | 564 |
| 201 | N-(3-chloro-4-fluorophenyl)-2-[2-(dimethylamino)ethylamino]-7-fluoro-N'-hydroxy-3H-benzimidazole-4-carboximidamide | 428 |
| 202 | N-(3-chloro-4-fluorophenyl)-N'-hydroxy-2-[(1-methylpiperidin-2-yl)methylamino]-1H-imidazo[4,5-b]pyridine-7-carboximidamide | 2090 |
| 203 | N-(3-chloro-4-fluorophenyl)-N'-hydroxy-2-[(1-methylpyrrolidin-3-yl)amino]-1H-imidazo[4,5-b]pyridine-7-carboximidamide | 1344 |
| 204 | N-(3-chloro-4-fluorophenyl)-2-(2-(ethylamino)ethyl)-N'-hydroxy-3H-imidazo[4,5-b]pyridine-7-carboximidamide | 2195 |
| 205 | N-(3-chloro-4-fluorophenyl)-N'-hydroxy-2-(2-(isopropylamino)ethyl)-3H-imidazo[4,5-b]pyridine-7-carboximidamide | 2823 |
| 206 | N-(3-chloro-4-fluorophenyl)-N'-hydroxy-2-(2-(isobutylamino)ethyl)-3H-imidazo[4,5-b]pyridine-7-carboximidamide | 2295 |
| 207 | N-(3-chloro-4-fluorophenyl)-2-(2-(cyclopropylamino)ethyl)-N'-hydroxy-3H-imidazo[4,5-b]pyridine-7-carboximidamide | 1257 |
| 209 | 2-(2-(2-amino-4,5-dihydro-1H-imidazol-1-yl)ethyl)-N-(3-chloro-4-fluorophenyl)-N'-hydroxy-1H-imidazo[4,5-b]pyridine-7-carboximidamide | 5000 |
| 210 | N-(3-chloro-4-fluorophenyl)-4,5-difluoro-N'-hydroxy-2-(2-(methylsulfonamido)ethyl)-1H-benzo[d]imidazole-7-carboximidamide | >10000 |
| 211 | 2-(2-aminoethyl)-N-(3-chloro-4-fluorophenyl)-4,5-difluoro-N'-hydroxy-1H-benzo[d]imidazole-7-carboximidamide | >10000 |
| 212 | N-(3-chloro-4-fluorophenyl)-N'-hydroxy-2-((2-methoxyethyl)amino)-1H-imidazo[4,5-b]pyridine-7-carboximidamide | 876 |

TABLE 1-continued

| Example No. | Name | EC$_{50}$ (nM) |
|---|---|---|
| 213 | tert-butyl(2-(7-(N-(3-chloro-4-fluorophenyl)-N'-hydroxycarbamimidoyl)-4,5-difluoro-1H-benzo[d]imidazol-2-yl)ethyl)carbamate | 3623 |
| 214 | N-(3-chloro-4-fluorophenyl)-2-((2-(4,4-difluoropiperidin-1-yl)ethyl)amino)-N'-hydroxy-1H-imidazo[4,5-b]pyridine-7-carboximidamide | 1908 |
| 215 | N-(3-chloro-4-fluorophenyl)-2-((2-(dimethylamino)ethyl)amino)-N'-hydroxy-1H-imidazo[4,5-b]pyridine-7-carboximidamide | 1195 |
| 216 | N-(3-chloro-4-fluorophenyl)-N'-hydroxy-2-((2-(methylamino)ethyl)amino)-1H-imidazo[4,5-b]pyridine-7-carboximidamide | 2009 |
| 217 | N-(3-chloro-4-fluorophenyl)-N'-hydroxy-2-((1-methylazepan-3-yl)amino)-1H-imidazo[4,5-b]pyridine-7-carboximidamide | 2870 |
| 218 | N-(3-chloro-4-fluorophenyl)-2-((2-(1,1-dioxidothiomorpholino)ethyl)amino)-N'-hydroxy-1H-imidazo[4,5-b]pyridine-7-carboximidamide | >10000 |
| 219 | N-(3-chloro-4-fluorophenyl)-N'-hydroxy-2-((2-((2-methoxyethyl)(methyl)amino)ethyl)amino)-1H-imidazo[4,5-b]pyridine-7-carboximidamide | 3829 |
| 220 | N-(3-chloro-4-fluorophenyl)-2-((2-((2,2-difluoroethyl)(methyl)amino)ethyl)amino)-N'-hydroxy-1H-imidazo[4,5-b]pyridine-7-carboximidamide | 2383 |
| 221 | N-(3-chloro-4-fluorophenyl)-N'-hydroxy-2-((3-morpholinopropyl)amino)-1H-imidazo[4,5-b]pyridine-7-carboximidamide | 899 |
| 222 | N-(3-chloro-4-fluorophenyl)-N'-hydroxy-2-((2-(piperidin-1-yl)ethyl)amino)-1H-imidazo[4,5-b]pyridine-7-carboximidamide | 1521 |
| 223 | N-(3-chloro-4-fluorophenyl)-2-((2-cyclohexylethyl)amino)-N'-hydroxy-1H-imidazo[4,5-b]pyridine-7-carboximidamide | 2182 |
| 224 | N-(3-chloro-4-fluorophenyl)-N'-hydroxy-2-((2-(tetrahydro-2H-pyran-4-yl)ethyl)amino)-1H-imidazo[4,5-b]pyridine-7-carboximidamide | 3735 |
| 225 | N-(3-chloro-4-fluorophenyl)-2-((2,2-difluoroethyl)amino)-N'-hydroxy-1H-imidazo[4,5-b]pyridine-7-carboximidamide | 2190 |
| 226 | N-(3-chloro-4-fluorophenyl)-N'-hydroxy-2-(oxetan-3-ylamino)-1H-imidazo[4,5-b]pyridine-7-carboximidamide | >10000 |
| 227 | N-(3-chloro-4-fluorophenyl)-N'-hydroxy-2-((tetrahydrofuran-3-yl)amino)-1H-imidazo[4,5-b]pyridine-7-carboximidamide | 2195 |
| 228 | N-(3-chloro-4-fluorophenyl)-N'-hydroxy-2-((tetrahydro-2H-pyran-4-yl)amino)-1H-imidazo[4,5-b]pyridine-7-carboximidamide | 2135 |
| 229 | 3-((7-(N-(3-chloro-4-fluorophenyl)-N'-hydroxycarbamimidoyl)-4,5-difluoro-1H-benzo[d]imidazol-2-yl)amino)propanamide | >10000 |
| 230 | N-(3-chloro-4-fluorophenyl)-2-((2-((2,2-difluoroethyl)amino)ethyl)amino)-N'-hydroxy-1H-imidazo[4,5-b]pyridine-7-carboximidamide | 3836 |
| 231 | N-(3-chloro-4-fluorophenyl)-2-((2-(cyclopropyl(methyl)amino)ethyl)amino)-N'-hydroxy-1H-imidazo[4,5-b]pyridine-7-carboximidamide | 291 |
| 232 | N-(3-chloro-4-fluorophenyl)-2-((2-(cyclopropyl(2-methoxyethyl)amino)ethyl)amino)-N'-hydroxy-1H-imidazo[4,5-b]pyridine-7-carboximidamide | 460 |
| 233 | 2-((2-(azetidin-1-yl)amino)-N-(3-chloro-4-fluorophenyl)-N'-hydroxy-1H-imidazo[4,5-b]pyridine-7-carboximidamide | 1122 |
| 234 | N-(3-chloro-4-fluorophenyl)-N'-hydroxy-2-((3-methoxypropyl)amino)-1H-imidazo[4,5-b]pyridine-7-carboximidamide | 698 |
| 235 | N-(3-chloro-4-fluorophenyl)-N'-hydroxy-2-((2-(2-oxopyrrolidin-1-yl)ethyl)amino)-1H-imidazo[4,5-b]pyridine-7-carboximidamide | 4818 |
| 236 | N-(3-chloro-4-fluorophenyl)-N'-hydroxy-2-((2-(morpholinosulfonyl)ethyl)amino)-1H-imidazo[4,5-b]pyridine-7-carboximidamide | 4765 |
| 237 | N-(3-chloro-4-fluorophenyl)-2-((2-(3-fluoropiperidin-1-yl)ethyl)amino)-N'-hydroxy-1H-imidazo[4,5-b]pyridine-7-carboximidamide | 442 |
| 238 | N-(3-bromo-4-fluorophenyl)-N'-hydroxy-2-((2-morpholinoethyl)amino)-1H-imidazo[4,5-b]pyridine-7-carboximidamide | 853 |
| 239 | N-(3-chloro-4-fluorophenyl)-N'-hydroxy-2-((2-(methyl(tetrahydro-2H-pyran-4-yl)amino)ethyl)amino)-1H-imidazo[4,5-b]pyridine-7-carboximidamide | 1212 |
| 240 | N-(3-chloro-4-fluorophenyl)-N'-hydroxy-2-((2-(isopropyl(methyl)amino)ethyl)amino)-1H-imidazo[4,5-b]pyridine-7-carboximidamide | 590 |
| 241 | 2-(((1-aminocyclopropyl)methyl)amino)-N-(3-chloro-4-fluorophenyl)-N'-hydroxy-1H-imidazo[4,5-b]pyridine-7-carboximidamide | 1374 |
| 257 | N-(3-bromo-4-fluorophenyl)-N'-hydroxy-2-(methylamino)-1H-imidazo[4,5-b]pyridine-7-carboximidamide | 241 |
| 242 | 2-((2-(1-aminocyclopropyl)ethyl)amino)-N-(3-chloro-4-fluorophenyl)-N'-hydroxy-1H-imidazo[4,5-b]pyridine-7-carboximidamide | 1626 |
| 258 | 2-(2-(azepan-1-yl)ethyl)-N-(3-chloro-4-fluorophenyl)-N'-hydroxy-1H-imidazo[4,5-b]pyridine-7-carboximidamide | 844 |
| 259 | 2-(2-(azetidin-1-yl)ethyl)-N-(3-chloro-4-fluorophenyl)-N'-hydroxy-1H-imidazo[4,5-b]pyridine-7-carboximidamide | 1299 |
| 260 | (R)-N-(3-chloro-4-fluorophenyl)-N'-hydroxy-2-(2-(3-hydroxypyrrolidin-1-yl)ethyl)-1H-imidazo[4,5-b]pyridine-7-carboximidamide | 3205 |
| 261 | (S)-N-(3-chloro-4-fluorophenyl)-N'-hydroxy-2-(2-(3-hydroxypyrrolidin-1-yl)ethyl)-1H-imidazo[4,5-b]pyridine-7-carboximidamide | 3453 |
| 262 | N-(3-chloro-4-fluorophenyl)-N'-hydroxy-2-(2-(4-hydroxypiperidin-1-yl)ethyl)-1H-imidazo[4,5-b]pyridine-7-carboximidamide | 3238 |
| 263 | N-(3-bromo-4-fluorophenyl)-2-(2-(dimethylamino)ethyl)-N'-hydroxy-1H-imidazo[4,5-b]pyridine-7-carboximidamide | 559 |
| 264 | N-(3-chlorophenyl)-2-(2-(dimethylamino)ethyl)-N'-hydroxy-1H-imidazo[4,5-b]pyridine-7-carboximidamide | 722 |
| 265 | N-(3-bromophenyl)-2-(2-(dimethylamino)ethyl)-N'-hydroxy-1H-imidazo[4,5-b]pyridine-7-carboximidamide | 501 |
| 266 | N-(3-chloro-4-fluorophenyl)-N'-hydroxy-2-(2-(methylsulfonamido)ethyl)-1H-imidazo[4,5-b]pyridine-7-carboximidamide | >10000 |
| 267 | N-(3-chloro-4-fluorophenyl)-N'-hydroxy-2-(2-(sulfamoylamino)ethyl)-1H-imidazo[4,5-b]pyridine-7-carboximidamide | >10000 |
| 268 | N-(3-chlorophenyl)-N'-hydroxy-2-(2-(pyrrolidin-1-yl)ethyl)-1H-imidazo[4,5-b]pyridine-7-carboximidamide | 952 |
| 269 | N-(3-bromophenyl)-N'-hydroxy-2-(2-(pyrrolidin-1-yl)ethyl)-1H-imidazo[4,5-b]pyridine-7-carboximidamide | 979 |
| 270 | N-(2-(7-(N-(3-chloro-4-fluorophenyl)-N'-hydroxycarbamimidoyl)-1H-imidazo[4,5-b]pyridin-2-yl)ethyl)acetamide | >10000 |
| 271 | N-(3-chlorophenyl)-N'-hydroxy-2-(2-(piperidin-1-yl)ethyl)-1H-imidazo[4,5-b]pyridine-7-carboximidamide | 602 |
| 272 | N-(3-bromophenyl)-N'-hydroxy-2-(2-(piperidin-1-yl)ethyl)-1H-imidazo[4,5-b]pyridine-7-carboximidamide | 477 |
| 273 | Methyl (2-(7-(N-(3-chloro-4-fluorophenyl)-N'-hydroxycarbamimidoyl)-1H-imidazo[4,5-b]pyridin-2-yl)ethyl)carbamate | >10000 |
| 274 | N-(3-chloro-4-fluorophenyl)-2-(2-((2,4-dimethoxybenzyl)amino)ethyl)-N'-hydroxy-1H-imidazo[4,5-b]pyridine-7-carboximidamide | 1966 |
| 275 | 2-(2-(4-benzylpiperidin-1-yl)ethyl)-N-(3-chloro-4-fluorophenyl)-N'-hydroxy-1H-imidazo[4,5-b]pyridine-7-carboximidamide | 675 |

TABLE 1-continued

| Example No. | Name | EC$_{50}$ (nM) |
|---|---|---|
| 276 | 2-(2-(3-azabicyclo[3.3.1]nonan-3-yl)ethyl)-N-(3-chloro-4-fluorophenyl)-N'-hydroxy-1H-imidazo[4,5-b]pyridine-7-carboximidamide | 618 |
| 277 | 2-(2-(3-azabicyclo[3.2.1]octan-3-yl)ethyl)-N-(3-chloro-4-fluorophenyl)-N'-hydroxy-1H-imidazo[4,5-b]pyridine-7-carboximidamide | 576 |
| 278 | N-(3-chloro-4-fluorophenyl)-N'-hydroxy-2-((1-methylpiperidin-3-yl)amino)-1H-imidazo[4,5-b]pyridine-7-carboximidamide | 1073 |
| 279 | (S)-N-(3-chloro-4-fluorophenyl)-N'-hydroxy-2-((2-(3-hydroxypyrrolidin-1-yl)ethyl)amino)-1H-imidazo[4,5-b]pyridine-7-carboximidamide | 5279 |
| 280 | (S)-N-(3-chloro-4-fluorophenyl)-N'-hydroxy-2-(3-hydroxypyrrolidin-1-yl)-1H-imidazo[4,5-b]pyridine-7-carboximidamide | >10000 |
| 281 | N-(3-chloro-4-fluorophenyl)-N'-hydroxy-2-((1-(2-methoxyethyl)pyrrolidin-3-yl)amino)-1H-imidazo[4,5-b]pyridine-7-carboximidamide | 1257 |
| 282 | N-(3-chloro-4-fluorophenyl)-N'-hydroxy-2-(((4-methylmorpholin-3-yl)methyl)amino)-1H-imidazo[4,5-b]pyridine-7-carboximidamide | >10000 |
| 283 | N-(3-chloro-4-fluorophenyl)-N'-hydroxy-2-((2-(pyrrolidin-1-yl)ethyl)amino)-1H-imidazo[4,5-b]pyridine-7-carboximidamide | 2719 |
| 287 | N-(3-chloro-4-fluorophenyl)-2-((ethylamino)methyl)-4-fluoro-N'-hydroxy-1H-benzo[d]imidazole-7-carboximidamide | 1669 |
| 288 | N-(3-chloro-4-fluorophenyl)-2-((dimethylamino)methyl)-4-fluoro-N'-hydroxy-1H-benzo[d]imidazole-7-carboximidamide | 1816 |
| 289 | -(3-chloro-4-fluorophenyl)-4-fluoro-N'-hydroxy-2-((isopropylamino)methyl)-1H-benzo[d]imidazole-7-carboximidamide | 2232 |
| 290 | N-(3-chloro-4-fluorophenyl)-4-fluoro-N'-hydroxy-2-((methylamino)methyl)-1H-benzo[d]imidazole-7-carboximidamide | 1292 |
| 291 | 2-(aminomethyl)-N-(3-chloro-4-fluorophenyl)-4-fluoro-N'-hydroxy-1H-benzo[d]imidazole-7-carboximidamide | 2647 |
| 292 | N-(3-chloro-4-fluorophenyl)-4,5-difluoro-N'-hydroxy-2-((2-hydroxy-2-methylpropyl)amino)-1H-benzo[d]imidazole-7-carboximidamide | 3317 |
| 293 | N-(3-chloro-4-fluorophenyl)-4,5-difluoro-N'-hydroxy-2-((2-hydroxypropyl)amino)-1H-benzo[d]imidazole-7-carboximidamide | 3003 |
| 294 | 2-((7-(N-(3-chloro-4-fluorophenyl)-N'-hydroxycarbamimidoyl)-4,5-difluoro-1H-benzo[d]imidazol-2-yl)amino)acetamide | 9954 |
| 295 | N-(3-chloro-4-fluorophenyl)-4,5-difluoro-N'-hydroxy-2-((2-hydroxyethyl)amino)-1H-benzo[d]imidazole-7-carboximidamide | 3264 |
| 296 | N-(3-chloro-4-fluorophenyl)-4,5-difluoro-N'-hydroxy-2-((3-hydroxycyclobutyl)amino)-1H-benzo[d]imidazole-7-carboximidamide | >10000 |
| 297 | N-(3-chloro-4-fluorophenyl)-4,5-difluoro-N'-hydroxy-2-((3-(pyridin-2-ylamino)propyl)amino)-1H-benzo[d]imidazole-7-carboximidamide | 1153 |
| 298 | N-(3-chloro-4-fluorophenyl)-4,5-difluoro-N'-hydroxy-2-((2-sulfamoylethyl)amino)-1H-benzo[d]imidazole-7-carboximidamide | 9558 |
| 299 | N-(3-chloro-4-fluorophenyl)-4,5-difluoro-N'-hydroxy-2-(((1-methyl-1H-pyrazol-5-yl)methyl)amino)-1H-benzo[d]imidazole-7-carboximidamide | 3443 |
| 300 | 2-((2-(1H-pyrazol-1-yl)ethyl)amino)-N-(3-chloro-4-fluorophenyl)-4,5-difluoro-N'-hydroxy-1H-benzo[d]imidazole-7-carboximidamide | 3572 |
| 301 | 2-((7-(N-(3-chloro-4-fluorophenyl)-N'-hydroxycarbamimidoyl)-4,5-difluoro-1H-benzo[d]imidazol-2-yl)amino)-N,N-dimethylacetamide | 3960 |
| 302 | N-(3-chloro-4-fluorophenyl)-4,5-difluoro-N'-hydroxy-2-(2-hydroxy-2-methylpropyl)-1H-benzo[d]imidazole-7-carboximidamide | >10000 |
| 303 | N-(3-chloro-4-fluorophenyl)-2-((4-(dimethylamino)butyl)amino)-4,5-difluoro-N'-hydroxy-1H-benzo[d]imidazole-7-carboximidamide | 2935 |
| 304 | N-(3-chloro-4-fluorophenyl)-4,5-difluoro-N'-hydroxy-2-((piperidin-3-ylmethyl)amino)-1H-benzo[d]imidazole-7-carboximidamide | >10000 |
| 305 | N-(3-chloro-4-fluorophenyl)-N'-hydroxy-2-((1-methylpiperidin-2-yl)amino)-1H-imidazo[4,5-b]pyridine-7-carboximidamide | 3494 |
| 306 | N-(3-bromophenyl)-N'-hydroxy-2-((2-morpholinoethyl)amino)-1H-imidazo[4,5-b]pyridine-7-carboximidamide | 681 |
| 307 | N-(3-chloro-4-fluorophenyl)-5-fluoro-N'-hydroxy-4-methoxy-1H-benzo[d]imidazole-7-carboximidamide | 209 |
| 325 | N-(3-chloro-4-fluorophenyl)-N'-hydroxy-2-(piperidin-2-ylmethyl)-1H-imidazo[4,5-b]pyridine-7-carboximidamide | >10000 |
| 326 | N-(3-chloro-4-fluorophenyl)-2-(1-(dimethylamino)propan-2-yl)-N'-hydroxy-1H-imidazo[4,5-b]pyridine-7-carboximidamide | 4054 |
| 327 | N-(3-chloro-4-fluorophenyl)-N'-hydroxy-2-(2-(methylamino)propyl)-1H-imidazo[4,5-b]pyridine-7-carboximidamide | 7619 |
| 328 | N-(3-chloro-4-fluorophenyl)-2-(2-(dimethylamino)propyl)-N'-hydroxy-1H-imidazo[4,5-b]pyridine-7-carboximidamide | 3242 |
| 329 | N-(3-chloro-4-fluorophenyl)-N'-hydroxy-2-(pyrrolidin-2-ylmethyl)-1H-imidazo[4,5-b]pyridine-7-carboximidamide | 5000 |
| 330 | N-(3-chlorophenyl)-4,5-difluoro-N'-hydroxy-2-((2-(pyrrolidin-1-yl)ethyl)amino)-1H-benzo[d]imidazole-7-carboximidamide | 414 |
| 331 | N-(3-bromophenyl)-4,5-difluoro-N'-hydroxy-2-((2-(pyrrolidin-1-yl)ethyl)amino)-1H-benzo[d]imidazole-7-carboximidamide | 692 |
| 333 | 2-((2-aminoethyl)amino)-N-(3-chloro-4-fluorophenyl)-4,5-difluoro-N'-hydroxy-1H-benzo[d]imidazole-7-carboximidamide | 1386 |
| 334 | N-(2-((7-(N-(3-chloro-4-fluorophenyl)-N'-hydroxycarbamimidoyl)-4,5-difluoro-1H-benzo[d]imidazol-2-yl)amino)ethyl)acetamide | 6119 |
| 335 | N-(3-chloro-4-fluorophenyl)-4,5-difluoro-N'-hydroxy-2-((2-(methylsulfonamido)ethyl)amino)-1H-benzo[d]imidazole-7-carboximidamide | >10000 |
| 336 | N-(3-chloro-4-fluorophenyl)-2-((2-(cyclopropanesulfonamido)ethyl)amino)-4,5-difluoro-N'-hydroxy-1H-benzo[d]imidazole-7-carboximidamide | >10000 |
| 337 | Methyl (2-((7-(N-(3-chloro-4-fluorophenyl)-N'-hydroxycarbamimidoyl)-4,5-difluoro-1H-benzo[d]imidazol-2-yl)amino)ethyl)carbamate | 4405 |
| 338 | N-(3-chloro-4-fluorophenyl)-4,5-difluoro-N'-hydroxy-2-((2-(sulfamoylamino)ethyl)amino)-1H-benzo[d]imidazole-7-carboximidamide | >10000 |
| 339 | N-(3-chloro-4-fluorophenyl)-4,5-difluoro-N'-hydroxy-2-((2-(phenylsulfonamido)ethyl)amino)-1H-benzo[d]imidazole-7-carboximidamide | >10000 |
| 340 | N-(3-chloro-4-fluorophenyl)-2-((2-cyanoethyl)amino)-4,5-difluoro-N'-hydroxy-1H-benzo[d]imidazole-7-carboximidamide | 1781 |
| 341 | N-(3-chloro-4-fluorophenyl)-2-((2-(3-ethylureido)ethyl)amino)-4,5-difluoro-N'-hydroxy-1H-benzo[d]imidazole-7-carboximidamide | >10000 |
| 342 | N-(3-chloro-4-fluorophenyl)-4,5-difluoro-N'-hydroxy-2-((pyridin-2-ylmethyl)amino)-1H-benzo[d]imidazole-7-carboximidamide | 8493 |
| 343 | N-(3-chloro-4-fluorophenyl)-4,5-difluoro-N'-hydroxy-2-((pyridin-3-ylmethyl)amino)-1H-benzo[d]imidazole-7-carboximidamide | 3857 |
| 344 | N-(3-chloro-4-fluorophenyl)-4,5-difluoro-N'-hydroxy-2-((pyridin-3-ylmethyl)amino)-1H-benzo[d]imidazole-7-carboximidamide | 3058 |

TABLE 1-continued

| Example No. | Name | EC$_{50}$ (nM) |
|---|---|---|
| 345 | 2-(((1H-imidazol-2-yl)methyl)amino)-N-(3-chloro-4-fluorophenyl)-4,5-difluoro-N'-hydroxy-1H-benzo[d]imidazole-7-carboximidamide | 3843 |
| 346 | 2-chloro-N-(3-chloro-4-fluorophenyl)-4,5-difluoro-N'-hydroxy-1H-benzo[d]imidazole-7-carboximidamide | 8468 |
| 347 | 2-((2-aminobenzyl)amino)-N-(3-chloro-4-fluorophenyl)-4,5-difluoro-N'-hydroxy-1H-benzo[d]imidazole-7-carboximidamide | 3269 |
| 348 | N-(3-chloro-4-fluorophenyl)-2-((2-(dimethylamino)benzyl)amino)-4,5-difluoro-N'-hydroxy-1H-benzo[d]imidazole-7-carboximidamide | 3431 |
| 349 | N-(3-chloro-4-fluorophenyl)-4,5-difluoro-N'-hydroxy-2-(((1-methyl-1H-imidazol-2-yl)methyl)amino)-1H-benzo[d]imidazole-7-carboximidamide | 2544 |
| 350 | N-(3-chloro-4-fluorophenyl)-4,5-difluoro-N'-hydroxy-2-((pyrimidin-2-ylmethyl)amino)-1H-benzo[d]imidazole-7-carboximidamide | 7031 |
| 351 | N-(3-chloro-4-fluorophenyl)-2-((3-(dimethylamino)-2,2-dimethylpropyl)amino)-4,5-difluoro-N'-hydroxy-1H-benzo[d]imidazole-7-carboximidamide | 432 |
| 352 | N-(3-chloro-4-fluorophenyl)-2-((3-(dimethylamino)-2-methylpropyl)amino)-4,5-difluoro-N'-hydroxy-1H-benzo[d]imidazole-7-carboximidamide | 437 |
| 353 | N-(3-chloro-4-fluorophenyl)-2-((3-(dimethylamino)butyl)amino)-4,5-difluoro-N'-hydroxy-1H-benzo[d]imidazole-7-carboximidamide | 1295 |
| 354 | N-(3-chloro-4-fluorophenyl)-4,5-difluoro-N'-hydroxy-2-((2-(1-methylpyrrolidin-2-yl)ethyl)amino)-1H-benzo[d]imidazole-7-carboximidamide | 1207 |
| 355 | N-(3-chloro-4-fluorophenyl)-4,5-difluoro-N'-hydroxy-2-((2-(1-methylpiperidin-2-yl)ethyl)amino)-1H-benzo[d]imidazole-7-carboximidamide | 2021 |
| 356 | N-(3-chloro-4-fluorophenyl)-4,5-difluoro-N'-hydroxy-2-(((4-methylmorpholin-2-yl)methyl)amino)-1H-benzo[d]imidazole-7-carboximidamide | 3264 |
| 357 | N-(3-chloro-4-fluorophenyl)-N'-hydroxy-2-(((4-methylmorpholin-2-yl)methyl)amino)-1H-imidazo[4,5-b]pyridine-7-carboximidamide | 3239 |
| 358 | N-(3-chloro-4-fluorophenyl)-N'-hydroxy-2-(((1-methyl-1H-pyrazol-5-yl)methyl)amino)-1H-imidazo[4,5-b]pyridine-7-carboximidamide | 8791 |
| 368 | N-(3-chloro-4-fluorophenyl)-4-fluoro-N'-hydroxy-2-((2-morpholinoethyl)amino)-1H-benzo[d]imidazole-7-carboximidamide | 4004 |
| 369 | N-(3-chloro-4-fluorophenyl)-N'-hydroxy-N-methyl-1H-imidazo[4,5-b]pyridine-7-carboximidamide | >10000 |
| 370 | 2-amino-N-(3-chloro-4-fluorophenyl)-5-fluoro-N'-hydroxy-1H-benzo[d]imidazole-7-carboximidamide | 1078 |
| 371 | 2-amino-N-(3-chlorophenyl)-5-fluoro-N'-hydroxy-1H-benzo[d]imidazole-7-carboximidamide | 644 |
| 372 | 2-amino-N-(3-bromophenyl)-5-fluoro-N'-hydroxy-1H-benzo[d]imidazole-7-carboximidamide | 483 |
| 373 | 2-amino-N-(3-bromo-4-fluorophenyl)-5-fluoro-N'-hydroxy-1H-benzo[d]imidazole-7-carboximidamide | 736 |
| 374 | N-(3-chloro-4-fluorophenyl)-2-((2-(1,1-dioxidothiomorpholino)ethyl)amino)-4,5-difluoro-N'-hydroxy-1H-benzo[d]imidazole-7-carboximidamide | 2399 |
| 375 | N-(3-chloro-4-fluorophenyl)-2-((2-(diethylamino)ethyl)amino)-4-fluoro-N'-hydroxy-1H-benzo[d]imidazole-7-carboximidamide | 1190 |
| 376 | N-(3-chloro-4-fluorophenyl)-4-fluoro-N'-hydroxy-2-((2-(pyrrolidin-1-yl)ethyl)amino)-1H-benzo[d]imidazole-7-carboximidamide | 1258 |
| 377 | N-(3-chloro-4-fluorophenyl)-4,5-difluoro-N'-hydroxy-2-((2-morpholinopropyl)amino)-1H-benzo[d]imidazole-7-carboximidamide | 838 |
| 378 | N-(3-chloro-4-fluorophenyl)-2-((1-(dimethylamino)propan-2-yl)amino)-4,5-difluoro-N'-hydroxy-1H-benzo[d]imidazole-7-carboximidamide | 1396 |
| 379 | N-(3-chloro-4-fluorophenyl)-2-((2-(dimethylamino)ethyl)amino)-5-fluoro-N'-hydroxy-1H-benzo[d]imidazole-7-carboximidamide | 435 |
| 380 | N-(3-chloro-4-fluorophenyl)-5-fluoro-N'-hydroxy-2-((2-(pyrrolidin-1-yl)ethyl)amino)-1H-benzo[d]imidazole-7-carboximidamide | 1388 |
| 381 | N-(3-chloro-4-fluorophenyl)-2-((3-(dimethylamino)-2,2-dimethylpropyl)amino)-4-fluoro-N'-hydroxy-1H-benzo[d]imidazole-7-carboximidamide | 3025 |
| 382 | N-(3-bromo-4-fluorophenyl)-2-((2-(dimethylamino)ethyl)amino)-4-fluoro-N'-hydroxy-1H-benzo[d]imidazole-7-carboximidamide | 608 |
| 383 | N-(3-bromophenyl)-2-((2-(dimethylamino)ethyl)amino)-4-fluoro-N'-hydroxy-1H-benzo[d]imidazole-7-carboximidamide | 319 |
| 384 | N-(3-chlorophenyl)-2-((2-(dimethylamino)ethyl)amino)-4-fluoro-N'-hydroxy-1H-benzo[d]imidazole-7-carboximidamide | 290 |
| 385 | N-(3-chlorophenyl)-2-((3-(dimethylamino)propyl)amino)-4,5-difluoro-N'-hydroxy-1H-benzo[d]imidazole-7-carboximidamide | 580 |
| 386 | N-(3-bromophenyl)-2-((3-(dimethylamino)propyl)amino)-4,5-difluoro-N'-hydroxy-1H-benzo[d]imidazole-7-carboximidamide | 559 |
| 387 | N-(3-bromo-4-fluorophenyl)-2-((3-(dimethylamino)propyl)amino)-4,5-difluoro-N'-hydroxy-1H-benzo[d]imidazole-7-carboximidamide | 692 |
| 388 | N-(3-chloro-4-fluorophenyl)-2-((3-(dimethylamino)propyl)amino)-4-fluoro-N'-hydroxy-1H-benzo[d]imidazole-7-carboximidamide | 939 |
| 389 | N-(3-chloro-4-fluorophenyl)-2-((3-(dimethylamino)propyl)amino)-5-fluoro-N'-hydroxy-1H-benzo[d]imidazole-7-carboximidamide | 1157 |
| 390 | 2-((2-(benzyl(methyl)amino)ethyl)amino)-N-(3-chloro-4-fluorophenyl)-4,5-difluoro-N'-hydroxy-1H-benzo[d]imidazole-7-carboximidamide | 1017 |
| 391 | N-(3-chloro-4-fluorophenyl)-2-(2-((cyclohexylmethyl)(methyl)amino)ethyl)-N'-hydroxy-1H-imidazo[4,5-b]pyridine-7-carboximidamide | 1480 |
| 392 | N-(3-chloro-4-fluorophenyl)-N'-hydroxy-2-(2-(methyl(neopentyl)amino)ethyl)-1H-imidazo[4,5-b]pyridine-7-carboximidamide | 1226 |
| 393 | N-(3-chloro-4-fluorophenyl)-2-(2-(cyclohexyl(methyl)amino)ethyl)-N'-hydroxy-1H-imidazo[4,5-b]pyridine-7-carboximidamide | 1794 |
| 394 | N-(3-chloro-4-fluorophenyl)-4,5-difluoro-N'-hydroxy-2-((2-(methyl((tetrahydro-2H-pyran-4-yl)methyl)amino)ethyl)amino)-1H-benzo[d]imidazole-7-carboximidamide | 332 |
| 395 | N-(3-chloro-4-fluorophenyl)-4,5-difluoro-N'-hydroxy-2-((2-(methylamino)ethyl)amino)-1H-benzo[d]imidazole-7-carboximidamide | 757 |
| 396 | 2-(2-(benzyl(methyl)amino)ethyl)-N-(3-chloro-4-fluorophenyl)-N'-hydroxy-1H-imidazo[4,5-b]pyridine-7-carboximidamide | 790 |

TABLE 1-continued

| Example No. | Name | EC$_{50}$ (nM) |
|---|---|---|
| 397 | N-(3-chloro-4-fluorophenyl)-2-((2-((2-ethylbutyl)(methyl)amino)ethyl)amino)-4,5-difluoro-N'-hydroxy-1H-benzo[d]imidazole-7-carboximidamide | 1317 |
| 398 | N-(3-chloro-4-fluorophenyl)-2-((2-((cyclopropylmethyl)(methyl)amino)ethyl)amino)-4,5-difluoro-N'-hydroxy-1H-benzo[d]imidazole-7-carboximidamide | 555 |
| 399 | N-(3-chloro-4-fluorophenyl)-N'-hydroxy-2-(2-(methyl((tetrahydro-2H-pyran-4-yl)methyl)amino)ethyl)-1H-imidazo[4,5-b]pyridine-7-carboximidamide | 1329 |
| 400 | 2-(2-(((1,4-dioxan-2-yl)methyl)(methyl)amino)ethyl)-N-(3-chloro-4-fluorophenyl)-N'-hydroxy-1H-imidazo[4,5-b]pyridine-7-carboximidamide | 2814 |
| 401 | N-(3-chloro-4-fluorophenyl)-N'-hydroxy-2-(2-(methyl(2-(tetrahydro-2H-pyran-4-yl)ethyl)amino)ethyl)-1H-imidazo[4,5-b]pyridine-7-carboximidamide | 581 |
| 402 | N-(3-chloro-4-fluorophenyl)-2-((2-(cyclopropylamino)ethyl)amino)-N'-hydroxy-1H-imidazo[4,5-b]pyridine-7-carboximidamide | 561 |
| 403 | N-(3-chloro-4-fluorophenyl)-2-((2-(cyclopropyl(ethyl)amino)ethyl)amino)-N'-hydroxy-1H-imidazo[4,5-b]pyridine-7-carboximidamide | 192 |
| 404 | N-(2-((7-(N-(3-chloro-4-fluorophenyl)-N'-hydroxycarbamimidoyl)-1H-imidazo[4,5-b]pyridin-2-yl)amino)ethyl)acetamide | >10000 |
| 405 | N-(3-chloro-4-fluorophenyl)-N'-hydroxy-2-((2-(methylsulfonamido)ethyl)amino)-1H-imidazo[4,5-b]pyridine-7-carboximidamide | 7112 |
| 406 | N-(3-chloro-4-fluorophenyl)-2-((2-(cyclopropyl(isopropyl)amino)ethyl)amino)-N'-hydroxy-1H-imidazo[4,5-b]pyridine-7-carboximidamide | 185 |
| 407 | N-(3-chloro-4-fluorophenyl)-2-((2-(cyclopropyl(2-hydroxyethyl)amino)ethyl)amino)-N'-hydroxy-1H-imidazo[4,5-b]pyridine-7-carboximidamide | 2122 |
| 427 | N-(3-chloro-4-fluorophenyl)-N'-hydroxy-2-(((5-methyl-1,3,4-oxadiazol-2-yl)methyl)amino)-1H-imidazo[4,5-b]pyridine-7-carboximidamide | 1071 |
| 429 | N-(3-chloro-4-fluorophenyl)-4,5-difluoro-N'-hydroxy-2-(((4-methylmorpholin-3-yl)methyl)amino)-1H-benzo[d]imidazole-7-carboximidamide | 1346 |
| 430 | N-(3-bromophenyl)-2-((2-(dimethylamino)ethyl)amino)-4,5-difluoro-N'-hydroxy-1H-benzo[d]imidazole-7-carboximidamide | 180 |
| 431 | N-(3-chlorophenyl)-2-((2-(dimethylamino)ethyl)amino)-4,5-difluoro-N'-hydroxy-1H-benzo[d]imidazole-7-carboximidamide | 139 |
| 432 | N-(3-bromo-4-fluorophenyl)-2-((2-(dimethylamino)ethyl)amino)-4,5-difluoro-N'-hydroxy-1H-benzo[d]imidazole-7-carboximidamide | 253 |
| 433 | N-(3-chloro-4-fluorophenyl)-4,5-difluoro-2-((3-morpholinopropyl)amino)-1H-benzo[d]imidazole-7-carboxamide | 882 |
| 434 | N-(3-chloro-4-fluorophenyl)-4,5-difluoro-N'-hydroxy-2-((3-(pyrrolidin-1-yl)propyl)amino)-1H-benzo[d]imidazole-7-carboximidamide | 1240 |
| 435 | 2-(((3R)-4-amino-1-methylpyrrolidin-3-yl)amino)-N-(3-chloro-4-fluorophenyl)-4,5-difluoro-N'-hydroxy-1H-benzo[d]imidazole-7-carboximidamide | 1814 |
| 436 | N-(3-chloro-4-fluorophenyl)-2-((2-(dimethylamino)-2-phenylethyl)amino)-4,5-difluoro-N'-hydroxy-1H-benzo[d]imidazole-7-carboximidamide | 2015 |
| 437 | N-(3-chloro-4-fluorophenyl)-2-(((1R,2R)-2-(dimethylamino)cyclohexyl)amino)-4,5-difluoro-N'-hydroxy-1H-benzo[d]imidazole-7-carboximidamide | 998 |
| 438 | N-(3-chloro-4-fluorophenyl)-2-(((1-(dimethylamino)cyclopentyl)methyl)amino)-4,5-difluoro-N'-hydroxy-1H-benzo[d]imidazole-7-carboximidamide | 838 |
| 439 | N-(3-chloro-4-fluorophenyl)-2-((((1S*,3S*)-3-(dimethylamino)cyclohexyl)amino)-4,5-difluoro-N'-hydroxy-1H-benzo[d]imidazole-7-carboximidamide | 6799 |
| 440 | N-(3-chloro-4-fluorophenyl)-2-((((1S,3R)-3-(dimethylamino)cyclohexyl)amino)-4,5-difluoro-N'-hydroxy-1H-benzo[d]imidazole-7-carboximidamide | 6660 |
| 441 | N-(3-chloro-4-fluorophenyl)-2-(((1-(dimethylamino)cyclobutyl)methyl)amino)-4,5-difluoro-N'-hydroxy-1H-benzo[d]imidazole-7-carboximidamide | >10000 |
| 442 | N-(3-chloro-4-fluorophenyl)-4,5-difluoro-N'-hydroxy-2-((1-methylpiperidin-4-yl)amino)-1H-benzo[d]imidazole-7-carboximidamide | 2881 |
| 443 | N-(3-chloro-4-fluorophenyl)-4,5-difluoro-N'-hydroxy-2-((1-methylpiperidin-3-yl)amino)-1H-benzo[d]imidazole-7-carboximidamide | 389 |
| 444 | N-(3-chloro-4-fluorophenyl)-2-((((1S,2S)-2-(dimethylamino)cyclohexyl)amino)-4,5-difluoro-N'-hydroxy-1H-benzo[d]imidazole-7-carboximidamide | 3144 |
| 445 | (S)-N-(3-chloro-4-fluorophenyl)-4,5-difluoro-N'-hydroxy-2-(piperidin-3-ylamino)-1H-benzo[d]imidazole-7-carboximidamide | 1946 |
| 446 | (R)-N-(3-chloro-4-fluorophenyl)-4,5-difluoro-N'-hydroxy-2-(piperidin-3-ylamino)-1H-benzo[d]imidazole-7-carboximidamide | 1490 |
| 447 | (S)-N-(3-chloro-4-fluorophenyl)-4,5-difluoro-N'-hydroxy-2-((1-methylpyrrolidin-3-yl)amino)-1H-benzo[d]imidazole-7-carboximidamide | 325 |
| 448 | N-(3-chloro-4-fluorophenyl)-2-((3-(dimethylamino)-2-hydroxypropyl)amino)-4,5-difluoro-N'-hydroxy-1H-benzo[d]imidazole-7-carboximidamide | 1118 |
| 449 | N-(3-chloro-4-fluorophenyl)-4,5-difluoro-N'-hydroxy-2-((2-(4-methyl-3-oxopiperazin-1-yl)ethyl)amino)-1H-benzo[d]imidazole-7-carboximidamide | 6249 |
| 450 | N-(3-chloro-4-fluorophenyl)-2-(((1-(dimethylamino)cyclohexyl)methyl)amino)-4,5-difluoro-N'-hydroxy-1H-benzo[d]imidazole-7-carboximidamide | 1586 |
| 451 | N-(3-chloro-4-fluorophenyl)-4,5-difluoro-N'-hydroxy-2-((1-methylazepan-3-yl)amino)-1H-benzo[d]imidazole-7-carboximidamide | 205 |
| 452 | (S)-N-(3-chloro-4-fluorophenyl)-4,5-difluoro-N'-hydroxy-2-((2-(3-hydroxypyrrolidin-1-yl)ethyl)amino)-1H-benzo[d]imidazole-7-carboximidamide | 568 |
| 453 | N-(3-chloro-4-fluorophenyl)-4,5-difluoro-N'-hydroxy-2-((1-(2-methoxyethyl)piperidin-3-yl)amino)-1H-benzo[d]imidazole-7-carboximidamide | 651 |
| 454 | N-(3-chloro-4-fluorophenyl)-4,5-difluoro-N'-hydroxy-2-((1-(2-methoxyethyl)pyrrolidin-3-yl)amino)-1H-benzo[d]imidazole-7-carboximidamide | 247 |
| 455 | N-(3-chloro-4-fluorophenyl)-4,5-difluoro-N'-hydroxy-2-((1-isopropylpiperidin-3-yl)amino)-1H-benzo[d]imidazole-7-carboximidamide | 376 |
| 456 | N-(3-chloro-4-fluorophenyl)-4,5-difluoro-N'-hydroxy-2-((2-(3-methoxyazetidin-1-yl)ethyl)amino)-1H-benzo[d]imidazole-7-carboximidamide | 274 |
| 457 | (R)-N-(3-chloro-4-fluorophenyl)-4,5-difluoro-N'-hydroxy-2-((1-methylpyrrolidin-3-yl)amino)-1H-benzo[d]imidazole-7-carboximidamide | 271 |

TABLE 1-continued

| Example No. | Name | EC$_{50}$ (nM) |
|---|---|---|
| 458 | N-(3-chloro-4-fluorophenyl)-4,5-difluoro-N'-hydroxy-2-(((3R,4R)-4-methoxy-1-methylpyrrolidin-3-yl)amino)-1H-benzo[d]imidazole-7-carboximidamide | 261 |
| 459 | (S)-N-(3-chlorophenyl)-4,5-difluoro-N'-hydroxy-2-((1-methylpiperidin-3-yl)amino)-1H-benzo[d]imidazole-7-carboximidamide | 337 |
| 460 | (R)-N-(3-chlorophenyl)-4,5-difluoro-N'-hydroxy-2-((1-methylpiperidin-3-yl)amino)-1H-benzo[d]imidazole-7-carboximidamide | 193 |
| 461 | N-(3-chloro-4-fluorophenyl)-2-((2-(dimethylamino)cyclopentyl)amino)-4,5-difluoro-N'-hydroxy-1H-benzo[d]imidazole-7-carboximidamide | 472 |
| 462 | (S)-2-(azepan-3-ylamino)-N-(3-chloro-4-fluorophenyl)-4,5-difluoro-N'-hydroxy-1H-benzo[d]imidazole-7-carboximidamide | 1429 |
| 463 | (R)-2-(azepan-3-ylamino)-N-(3-chloro-4-fluorophenyl)-4,5-difluoro-N'-hydroxy-1H-benzo[d]imidazole-7-carboximidamide | 1020 |
| 464 | N-(3-chloro-4-fluorophenyl)-4,5-difluoro-N'-hydroxy-2-(pyrrolidin-3-ylamino)-1H-benzo[d]imidazole-7-carboximidamide | 2346 |
| 465 | (R)-N-(3-chloro-4-fluorophenyl)-4,5-difluoro-N'-hydroxy-2-((1-(oxetan-3-yl)piperidin-3-yl)amino)-1H-benzo[d]imidazole-7-carboximidamide | 957 |
| 466 | N-(3-chloro-4-fluorophenyl)-2-(((1,4-dimethylpiperidin-2-yl)methyl)amino)-4,5-difluoro-N'-hydroxy-1H-benzo[d]imidazole-7-carboximidamide | 685 |
| 467 | N-(3-chloro-4-fluorophenyl)-4,5-difluoro-N'-hydroxy-2-((morpholin-3-ylmethyl)amino)-1H-benzo[d]imidazole-7-carboximidamide | 2116 |
| 468 | N-(3-chloro-4-fluorophenyl)-4,5-difluoro-N'-hydroxy-2-(((3R,4S)-4-hydroxypyrrolidin-3-yl)amino)-1H-benzo[d]imidazole-7-carboximidamide | >10000 |
| 469 | N-(3-chloro-4-fluorophenyl)-4,5-difluoro-N'-hydroxy-2-(((1R,5R)-8-methyl-8-azabicyclo[3.2.1]octan-2-yl)amino)-1H-benzo[d]imidazole-7-carboximidamide | 959 |
| 470 | (S)-N-(3-chloro-4-fluorophenyl)-4,5-difluoro-N'-hydroxy-2-((2-(2-(trifluoromethyl)pyrrolidin-1-yl)ethyl)amino)-1H-benzo[d]imidazole-7-carboximidamide | 4200 |
| 471 | N-(3-chloro-4-fluorophenyl)-4,5-difluoro-2-(((hexahydro-1H-pyrrolizin-7a-yl)methyl)amino)-N'-hydroxy-1H-benzo[d]imidazole-7-carboximidamide | 852 |
| 472 | N-(3-chloro-4-fluorophenyl)-2-(((3,3-dimethylazetidin-2-yl)methyl)amino)-4,5-difluoro-N'-hydroxy-1H-benzo[d]imidazole-7-carboximidamide | 2452 |
| 473 | N-(3-chloro-4-fluorophenyl)-4,5-difluoro-N'-hydroxy-2-((4-(pyrrolidin-1-yl)tetrahydro-2H-pyran-3-yl)amino)-1H-benzo[d]imidazole-7-carboximidamide | 1034 |
| 474 | 2-(((1S,2R)-2-aminocyclohexyl)amino)-N-(3-chloro-4-fluorophenyl)-4,5-difluoro-N'-hydroxy-1H-benzo[d]imidazole-7-carboximidamide | 7584 |
| 475 | N-(3-chloro-4-fluorophenyl)-4,5-difluoro-N'-hydroxy-2-((2-methyl-1,2,3,4-tetrahydroisoquinolin-4-yl)amino)-1H-benzo[d]imidazole-7-carboximidamide | 1993 |
| 476 | N-(3-chloro-4-fluorophenyl)-2-(((3S,4S)-4-(diethylamino)tetrahydrofuran-3-yl)amino)-4,5-difluoro-N'-hydroxy-1H-benzo[d]imidazole-7-carboximidamide | 468 |
| 477 | 2-((1,4-oxazepan-6-yl)amino)-N-(3-chloro-4-fluorophenyl)-4,5-difluoro-N'-hydroxy-1H-benzo[d]imidazole-7-carboximidamide | 1525 |
| 478 | N-(3-chloro-4-fluorophenyl)-2-((2-((2S,6R)-2,6-dimethylmorpholino)ethyl)amino)-N'-hydroxy-1H-imidazo[4,5-b]pyridine-7-carboximidamide | 1011 |
| 479 | N-(3-chloro-4-fluorophenyl)-N'-hydroxy-2-(((3R,4R)-4-methoxy-1-methylpyrrolidin-3-yl)amino)-1H-imidazo[4,5-b]pyridine-7-carboximidamide | 1069 |
| 480 | N-(3-chloro-4-fluorophenyl)-2-(((3R,4R)-4-(diethylamino)tetrahydrofuran-3-yl)amino)-N'-hydroxy-1H-imidazo[4,5-b]pyridine-7-carboximidamide | 1194 |
| 481 | (S)-N-(3-chloro-4-fluorophenyl)-N'-hydroxy-2-((2-(2-(trifluoromethyl)pyrrolidin-1-yl)ethyl)amino)-1H-imidazo[4,5-b]pyridine-7-carboximidamide | 760 |
| 482 | (R)-N-(3-chloro-4-fluorophenyl)-N'-hydroxy-2-(((4-methylmorpholin-3-yl)methyl)amino)-1H-imidazo[4,5-b]pyridine-7-carboximidamide | 2653 |
| 483 | N-(3-chloro-4-fluorophenyl)-2-((2-(2,6-dimethylmorpholino)propyl)amino)-N'-hydroxy-1H-imidazo[4,5-b]pyridine-7-carboximidamide | 668 |
| 484 | N-(3-chloro-4-fluorophenyl)-2-((2-(2,6-dimethylmorpholino)-2-methylpropyl)amino)-N'-hydroxy-1H-imidazo[4,5-b]pyridine-7-carboximidamide | 566 |
| 485 | N-(3-chloro-4-fluorophenyl)-2-((2-(2,5-dimethylmorpholino)ethyl)amino)-N'-hydroxy-1H-imidazo[4,5-b]pyridine-7-carboximidamide | 639 |
| 486 | N-(3-chloro-4-fluorophenyl)-2-(((1R,2R)-2-(dimethylamino)cyclopentyl)amino)-4,5-difluoro-N'-hydroxy-1H-benzo[d]imidazole-7-carboximidamide | 284 |
| 487 | N-(3-chloro-4-fluorophenyl)-2-((2-(dimethylamino)ethyl)thio)-N'-hydroxy-1H-imidazo[4,5-b]pyridine-7-carboximidamide | 1361 |
| 488 | N-(3-chloro-4-fluorophenyl)-2-((2-(dimethylamino)ethyl)thio)-4,5-difluoro-N'-hydroxy-1H-benzo[d]imidazole-7-carboximidamide | 3012 |
| 489 | N-(3-chloro-4-fluorophenyl)-4,5-difluoro-N'-hydroxy-2-((2-(2-(hydroxymethyl)piperidin-1-yl)ethyl)amino)-1H-benzo[d]imidazole-7-carboximidamide | 289 |
| 490 | N-(3-chloro-4-fluorophenyl)-4,5-difluoro-N'-hydroxy-2-((2-(2-(hydroxymethyl)pyrrolidin-1-yl)ethyl)amino)-1H-benzo[d]imidazole-7-carboximidamide | 186 |
| 491 | N-(3-chloro-4-fluorophenyl)-2-((2-(3,3-difluoropyrrolidin-1-yl)ethyl)amino)-N'-hydroxy-1H-imidazo[4,5-b]pyridine-7-carboximidamide | 917 |
| 492 | N-(3-chloro-4-fluorophenyl)-N'-hydroxy-2-((2-sulfamoylethyl)amino)-1H-imidazo[4,5-b]pyridine-7-carboximidamide | 5660 |
| 493 | N-(3-chloro-4-fluorophenyl)-N'-hydroxy-2-((2-(methylsulfonyl)ethyl)amino)-1H-imidazo[4,5-b]pyridine-7-carboximidamide | 7215 |
| 494 | N-(3-chloro-4-fluorophenyl)-N'-hydroxy-2-((pyrimidin-2-ylmethyl)amino)-1H-imidazo[4,5-b]pyridine-7-carboximidamide | >10000 |

What is claimed is:
1. A compound of Formula I:

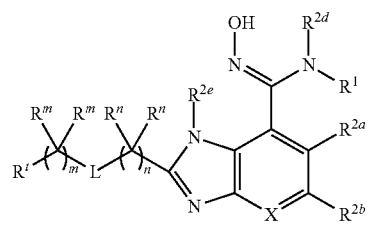

wherein
$R^1$ is mono or bicyclic aryl or heteroaryl, wherein each mono or bicyclic aryl or heteroaryl is optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl, wherein two of the optional substituents can join to form an additional partially saturated heterocyclic ring; and wherein each $C_{1-6}$ alkoxy, $C_{1-6}$ alkyl, $C_{2-6}$ alkenyl, $C_{2-6}$ alkynyl, and $C_{3-6}$ cycloalkyl is optionally substituted with one, two, or three substituents independently selected from hydroxyl, halo, —CN, —N($R^{20}$)($R^{22}$) and $C_{3-6}$ cycloalkyl;

X is N or $CR^{2c}$;

$R^{2a}$, $R^{2b}$, and $R^{2c}$ are independently hydrogen, hydroxyl, halo, CN, $C_{1-6}$ haloalkyl, $C_{1-6}$ haloalkoxy, $C_{1-6}$ alkoxy, or $C_{1-6}$ alkyl;

$R^{2d}$ and $R^{2e}$ are independently hydrogen, $C_{1-6}$ haloalkyl, $C_{1-6}$ haloalkoxy, or $C_{1-6}$ alkyl;

n and m are independently 0, 1, 2, or 3;

each $R''$ and $R'''$ are independently hydrogen, hydroxyl, halo, $C_{1-6}$ alkoxy, $C_{1-6}$ alkyl, $C_{3-6}$ cycloalkyl, aryl, heterocyclyl, or heteroaryl; or two $R''$ or $R'''$ join to form a $C_{3-6}$ cycloalkyl; and wherein each $C_{1-6}$ alkoxy, $C_{1-6}$ alkyl, $C_{3-6}$ cycloalkyl aryl, heterocyclyl, or heteroaryl is optionally substituted with one, two, or three substituents independently selected from hydroxyl, halo, —CN, —N($R^{20}$)($R^{22}$), $C_{2-6}$ alkenyl, $C_{2-6}$ alkynyl, $C_{1-6}$ haloalkyl, $C_{1-6}$ haloalkoxy, $C_{1-6}$ alkoxy, $C_{1-6}$ alkyl, and $C_{3-6}$ cycloalkyl;

L is a bond, —$NR^3$—, —C(O)—$NR^3$—, —$NR^3$—C(O)—, —$NR^3SO_2$—, —$NR^3SO_2$—$NR^3$—, —$SO_2NR^3$—, —O—, —S—, or S(O)$_t$—, where t is 0, 1 or 2;

each $R^3$ is independently hydrogen, $C_{1-6}$ alkyl, $C_{3-6}$ cycloalkyl, aryl, heterocyclyl, or heteroaryl; and $R^t$ is hydrogen, $C_{1-6}$ alkyl, $C_{1-6}$ alkoxy, —C(O)$R^{20}$, —C(O)O$R^{20}$, —NC(O)O$R^{20}$, —N($R^{20}$)($R^{22}$), —C(O)N($R^{20}$)($R^{22}$), —SO$_2R^{20}$, —N($R^{20}$)SO$_2$($R^{21}$), —N($R^{20}$)SO$_2$—N($R^{21}$)($R^{22}$), —SO$_2$N($R^{20}$)($R^{22}$), $C_{3-15}$ cycloalkyl, aryl, heteroaryl, or heterocyclyl, provided that when $R^t$ is $C_{1-6}$ alkoxy, —NC(O)O$R^{20}$, —N($R^{20}$)($R^{22}$), —N($R^{20}$)SO$_2$($R^{21}$), —N($R^{20}$)SO$_2$—N($R^{21}$)($R^{22}$), or —SO$_2$N($R^{20}$)($R^{22}$), and m is 0, then L is a bond;

wherein said $C_{1-6}$ alkyl, $C_{1-6}$ alkoxy, $C_{3-15}$ cycloalkyl, aryl, heterocyclyl, or heteroaryl is optionally substituted with one, two, or three substituents independently selected from hydroxyl, halo, —NO$_2$, $C_{1-6}$ haloalkyl, $C_{1-6}$ haloalkoxy, —C(O)$R^{20}$, —N($R^{20}$)($R^{22}$), SO$_2R^{20}$, —N($R^{20}$)SO$_2$($R^{21}$), —N($R^{20}$)SO$_2$—N($R^{21}$)($R^{22}$), SO$_2$N($R^{20}$)($R^{22}$), $C_{3-6}$ cycloalkyl, —CN, $C_{1-6}$ alkoxy, $C_{1-6}$ alkyl, and heterocyclyl; and wherein said heterocyclyl is optionally substituted with one or two oxo;

wherein said $C_{3-6}$ cycloalkyl, $C_{1-6}$ alkyl or $C_{1-6}$ alkoxy is optionally substituted with one, two, or three substituents independently selected from hydroxyl, halo, —NO$_2$, $C_{1-6}$ haloalkyl, $C_{1-6}$ haloalkoxy, $C_{1-6}$ alkoxy, —N($R^{20}$)($R^{22}$), —SO$_2R^{20}$, —N($R^{20}$)SO$_2$($R^{22}$), —N($R^{20}$)SO$_2$—N($R^{21}$)($R^{22}$)—, and —SO$_2$N($R^{20}$)($R^{22}$); and said $C_{1-6}$ alkyl is optionally substituted with aryl;

$R^{20}$, $R^{21}$, and $R^{22}$ are independently selected from hydrogen, $C_{1-6}$ alkyl, $C_{1-6}$ haloalkyl, $C_{3-6}$ cycloalkyl, aryl, heterocyclyl, and heteroaryl;

wherein said aryl, heterocyclyl, or heteroaryl is optionally substituted with one, two, or three halogen;

or a pharmaceutically acceptable salt, tautomer, optical isomer, stereoisomer, or mixture thereof.

2. The compound of claim 1, wherein the compound is represented by Formula IV:

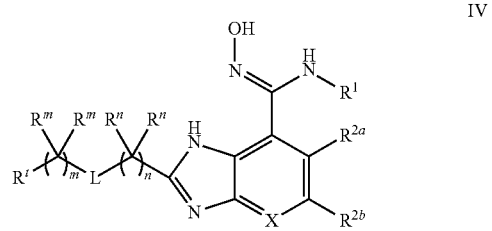

or a pharmaceutically acceptable salt, tautomer, optical isomer, stereoisomer, or mixture thereof.

3. The compound of claim 1 wherein $R^1$ is bicyclic aryl or heteroaryl optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl; or a pharmaceutically acceptable salt, tautomer, optical isomer, stereoisomer, or mixture thereof.

4. The compound of claim 1 wherein $R^1$ is phenyl optionally substituted with one, two, or three substituents independently selected from hydroxyl, halo, —CN, $C_{1-6}$ haloalkyl, $C_{1-6}$ haloalkoxy, $C_{1-6}$ alkoxy, $C_{1-6}$ alkyl, $C_{2-6}$ alkenyl, $C_{2-6}$ alkynyl, and $C_{3-6}$ cycloalkyl, and wherein two of the optional substituents can join to form an additional partially saturated heterocyclic ring;

or a pharmaceutically acceptable salt, tautomer, optical isomer, stereoisomer, or mixture thereof.

5. The compound of claim 1 wherein $R^1$ is selected from the group consisting of

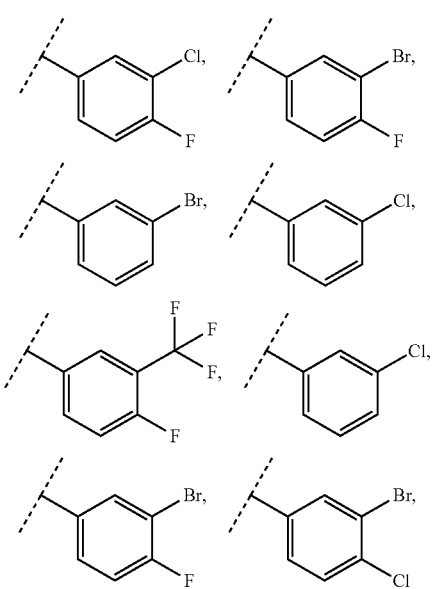

411
-continued
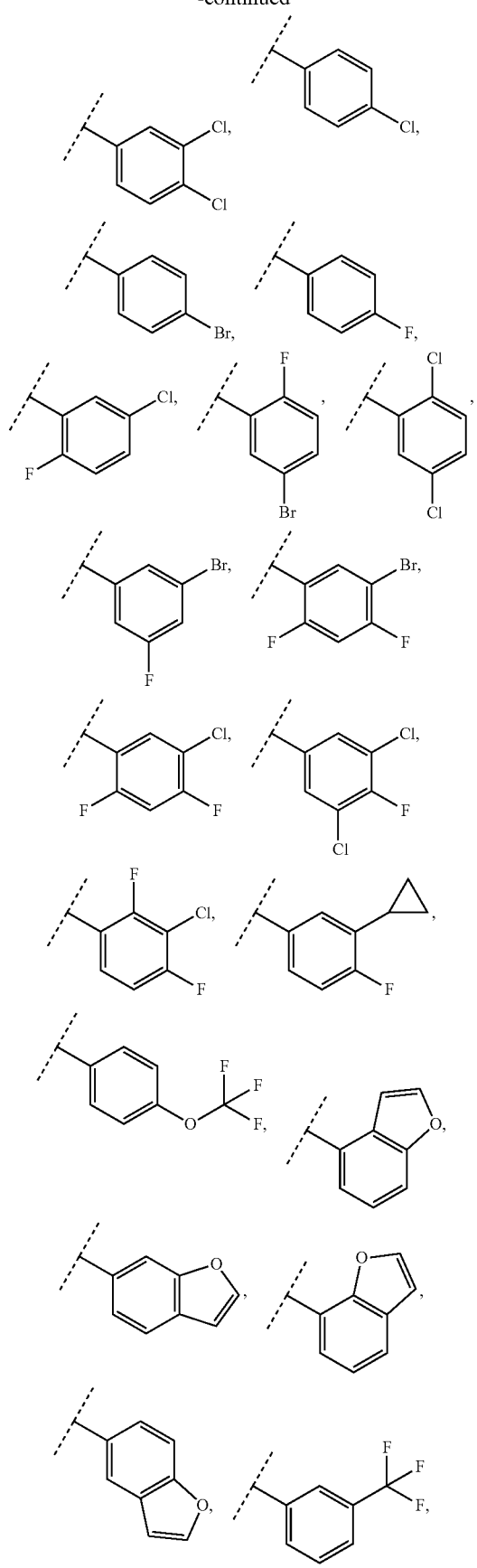
412
-continued
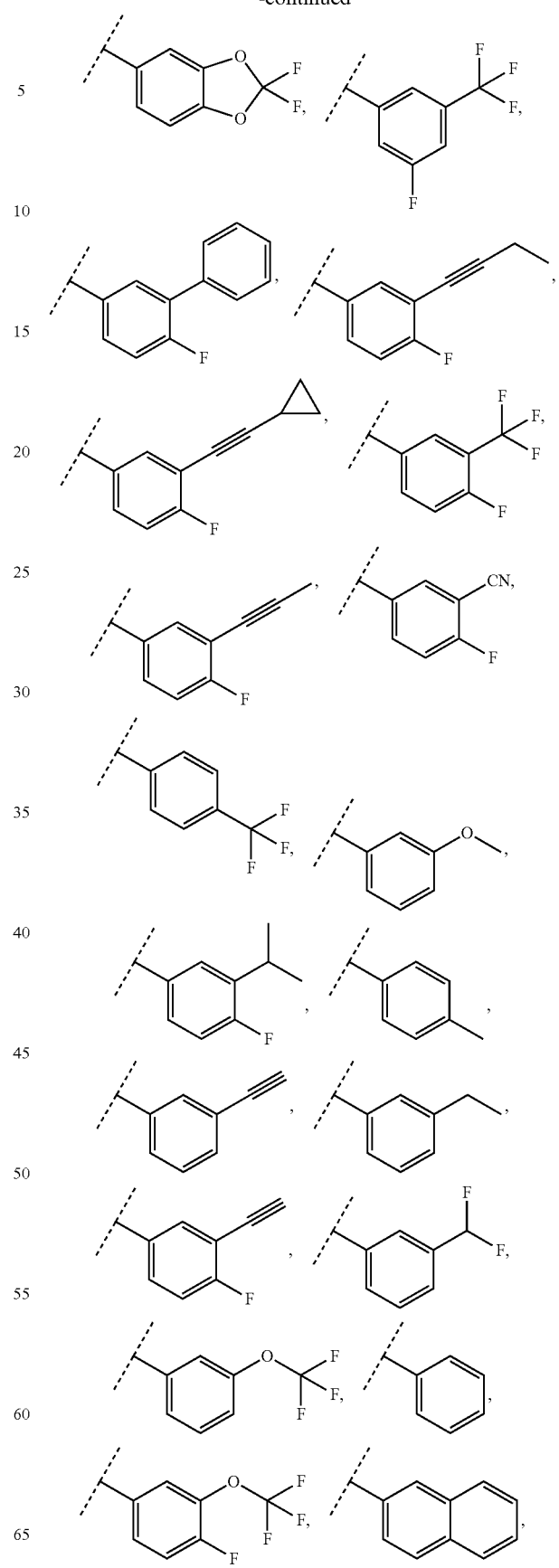

-continued

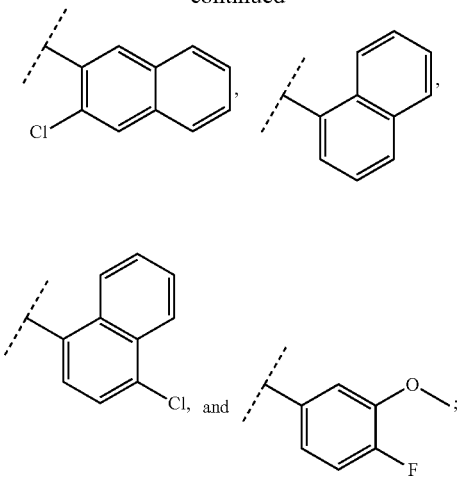

or a pharmaceutically acceptable salt, tautomer, optical isomer, stereoisomer, or mixture thereof.

6. The compound of claim 1 wherein X is N; or a pharmaceutically acceptable salt, tautomer, optical isomer, stereoisomer, or mixture thereof.

7. The compound of claim 1 wherein X is $CR^{2c}$; or a pharmaceutically acceptable salt, tautomer, optical isomer, stereoisomer, or mixture thereof.

8. The compound of claim 1 wherein L is a bond; or a pharmaceutically acceptable salt, tautomer, optical isomer, stereoisomer, or mixture thereof.

9. The compound of claim 1 wherein L is —$NR^3$; or a pharmaceutically acceptable salt, tautomer, optical isomer, stereoisomer, or mixture thereof.

10. The compound of claim 1 wherein $R^t$ is hydrogen; or a pharmaceutically acceptable salt, tautomer, optical isomer, stereoisomer, or mixture thereof.

11. The compound of claim 1 wherein $R^t$ is $C_{1-6}$ alkyl optionally substituted with one, two, or three substituents independently selected from hydroxyl, halo, —$NO_2$, $C_{1-6}$ haloalkyl, $C_{1-6}$ haloalkoxy, $C_{3-6}$ cycloalkyl, —CN, and $C_{1-6}$ alkoxy; or a pharmaceutically acceptable salt, tautomer, optical isomer, stereoisomer, or mixture thereof.

12. The compound of claim 1 wherein $R^t$ is $C_{3-15}$ cycloalkyl, aryl, heteroaryl, or heterocyclyl, wherein said cycloalkyl, aryl, heterocyclyl, or heteroaryl is optionally substituted with one, two, or three substituents independently selected from hydroxyl, halo, —$NO_2$, $C_{1-6}$ haloalkyl, $C_{1-6}$ haloalkoxy, $C_{3-6}$ cycloalkyl, —CN, $C_{1-6}$ alkoxy and $C_{1-6}$ alkyl; or a pharmaceutically acceptable salt, tautomer, optical isomer, stereoisomer, or mixture thereof.

13. The compound of claim 1 wherein L is —$NR^3$ and $R^t$ is $C_{3-15}$ cycloalkyl, aryl, heteroaryl, or heterocyclyl, wherein said cycloalkyl, aryl, heterocyclyl, or heteroaryl is optionally substituted with one, two, or three substituents independently selected from hydroxyl, halo, —$NO_2$, $C_{1-6}$ haloalkyl, $C_{1-6}$ haloalkoxy, $C_{3-6}$ cycloalkyl, —CN, and $C_{1-6}$ alkoxy; or a pharmaceutically acceptable salt, tautomer, optical isomer, stereoisomer, or mixture thereof.

14. The compound of claim 1 wherein the group

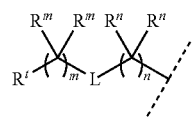

is selected from the group consisting of:

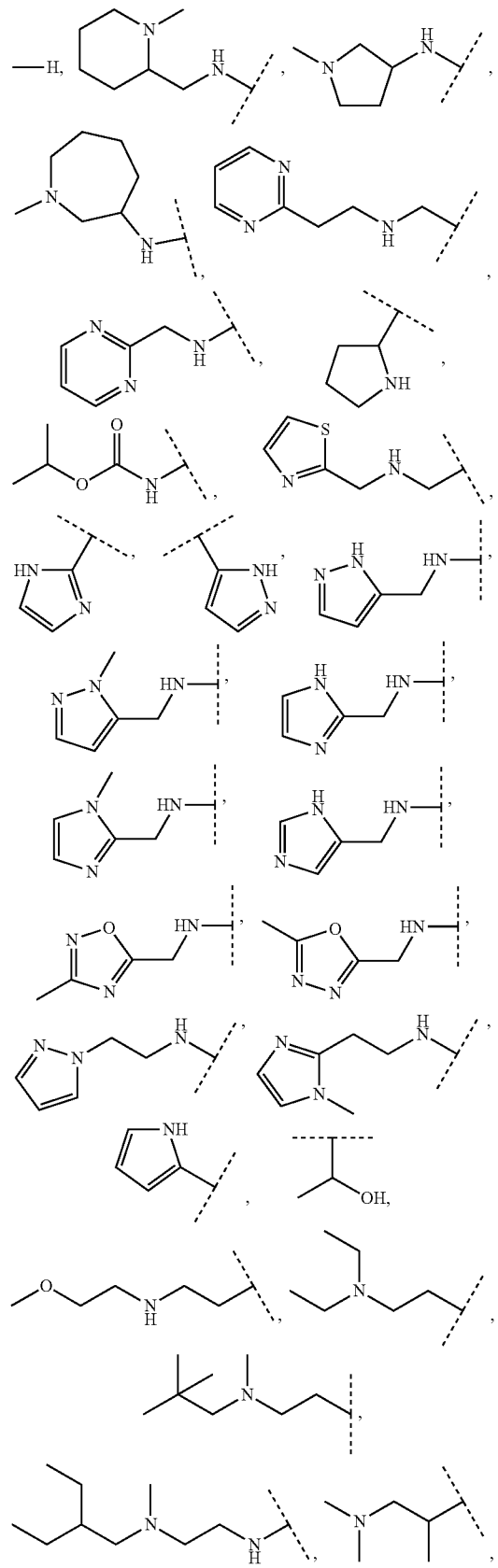

415
-continued
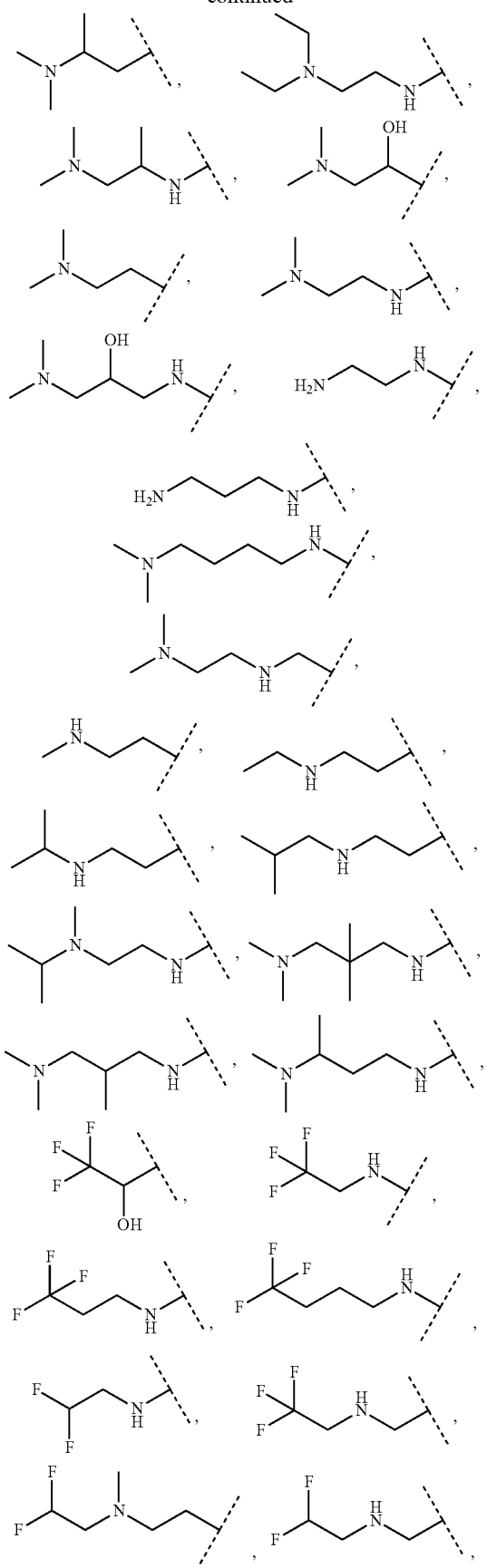
416
-continued
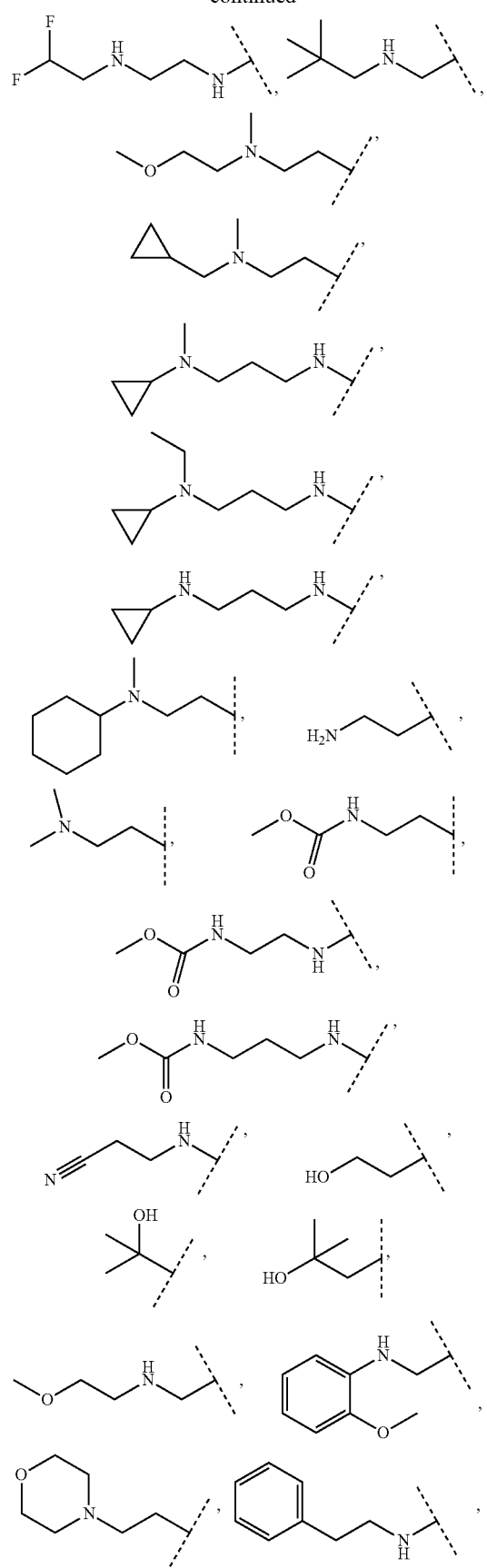

417
-continued
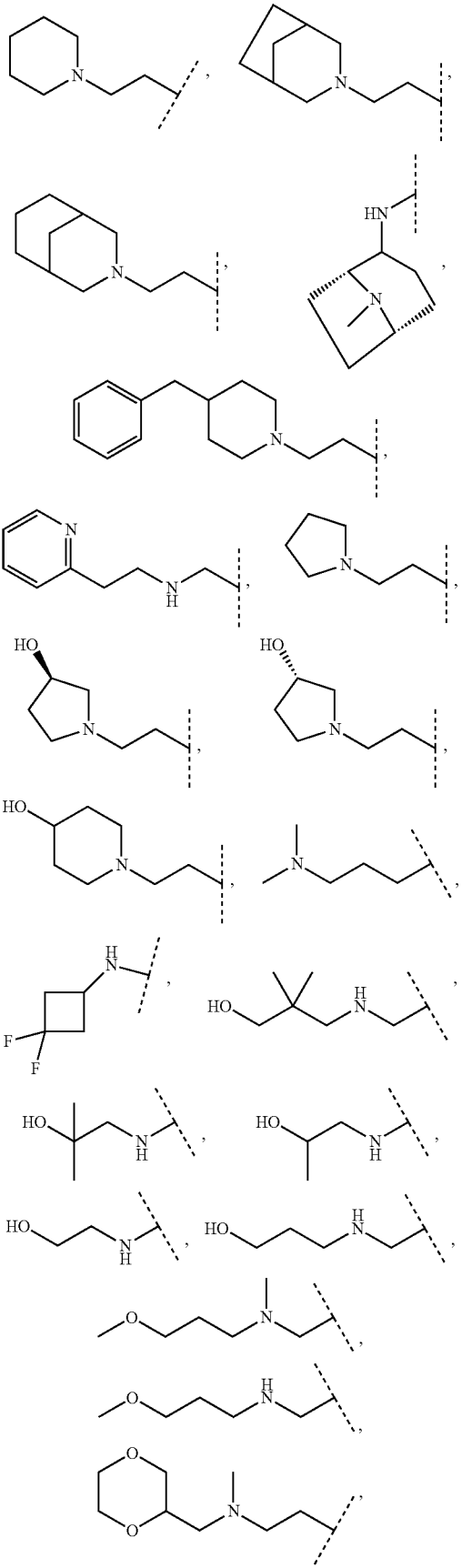
418
-continued
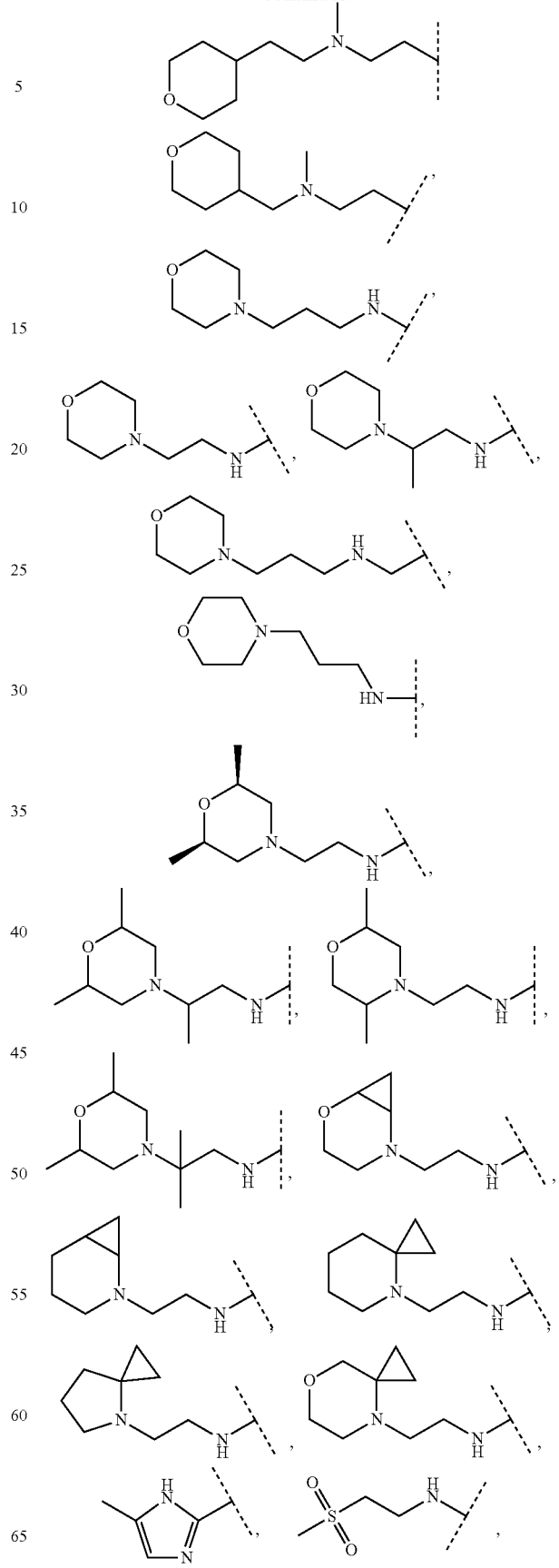

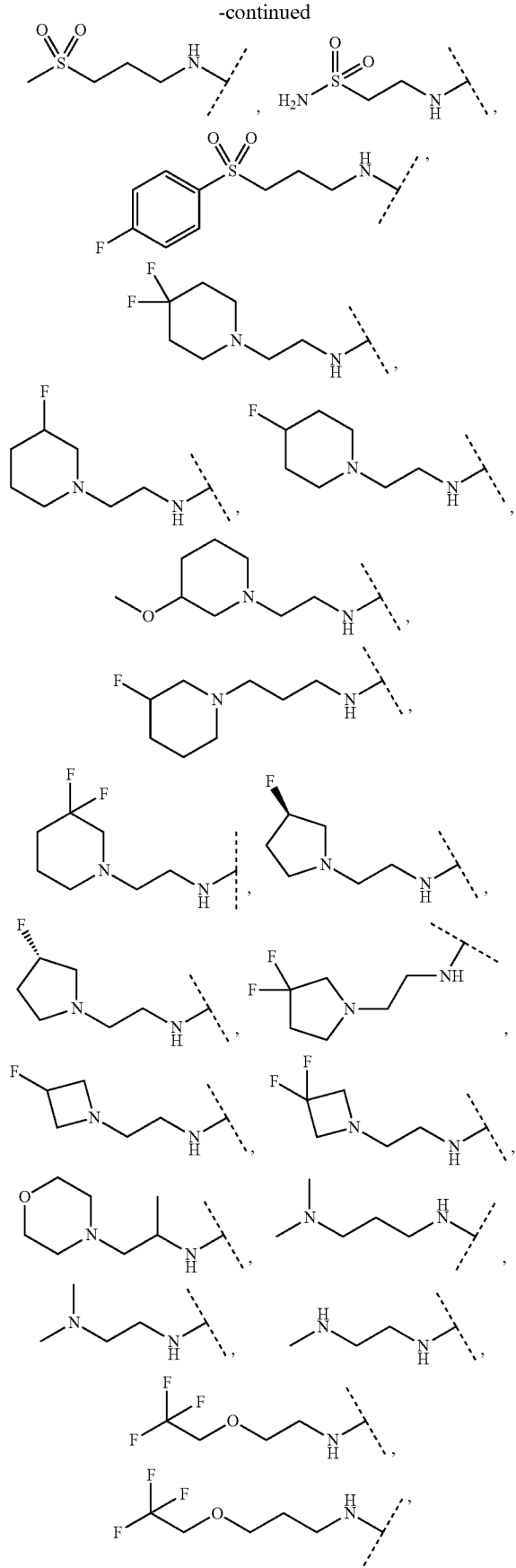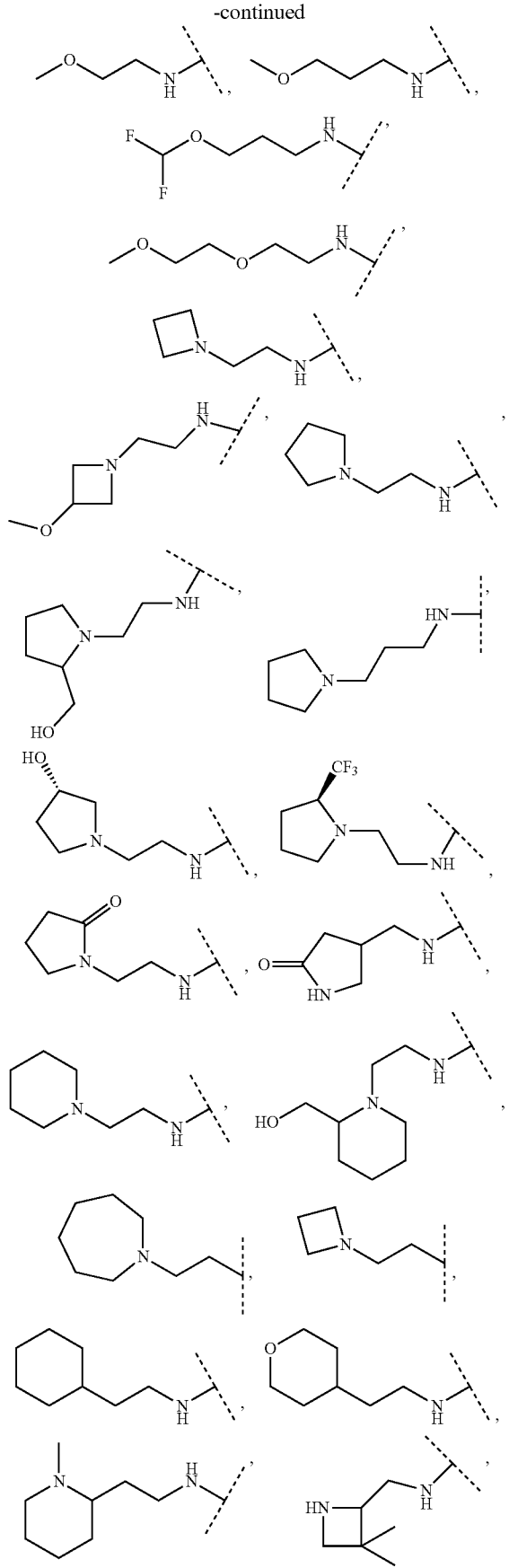

421
-continued
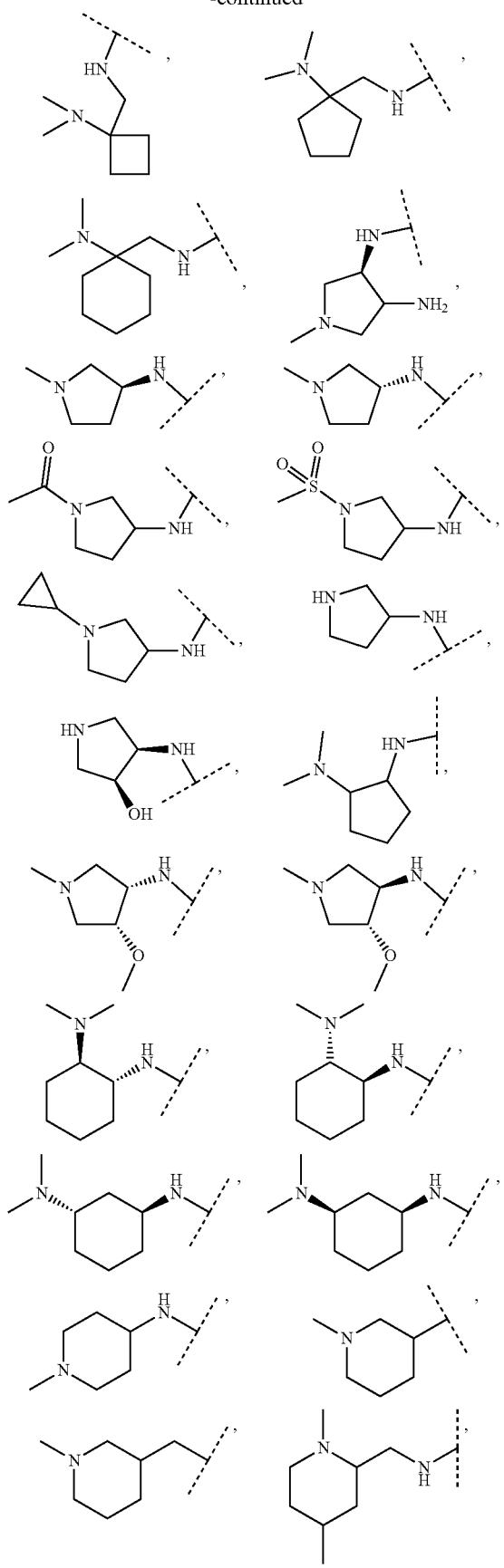
422
-continued
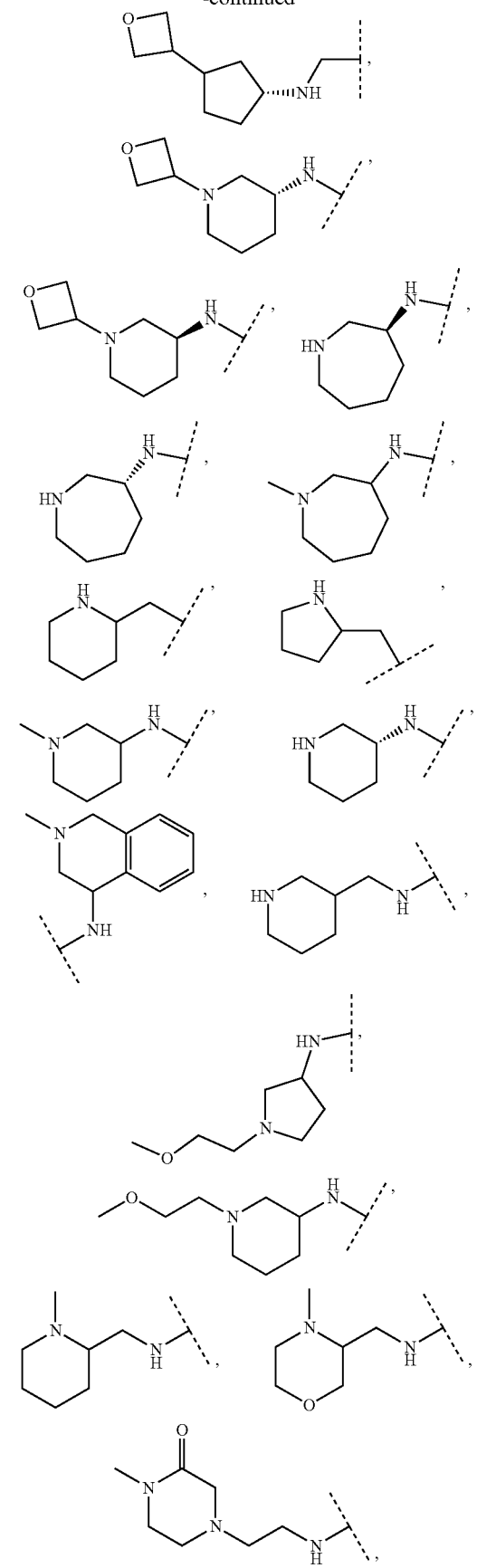

423
-continued
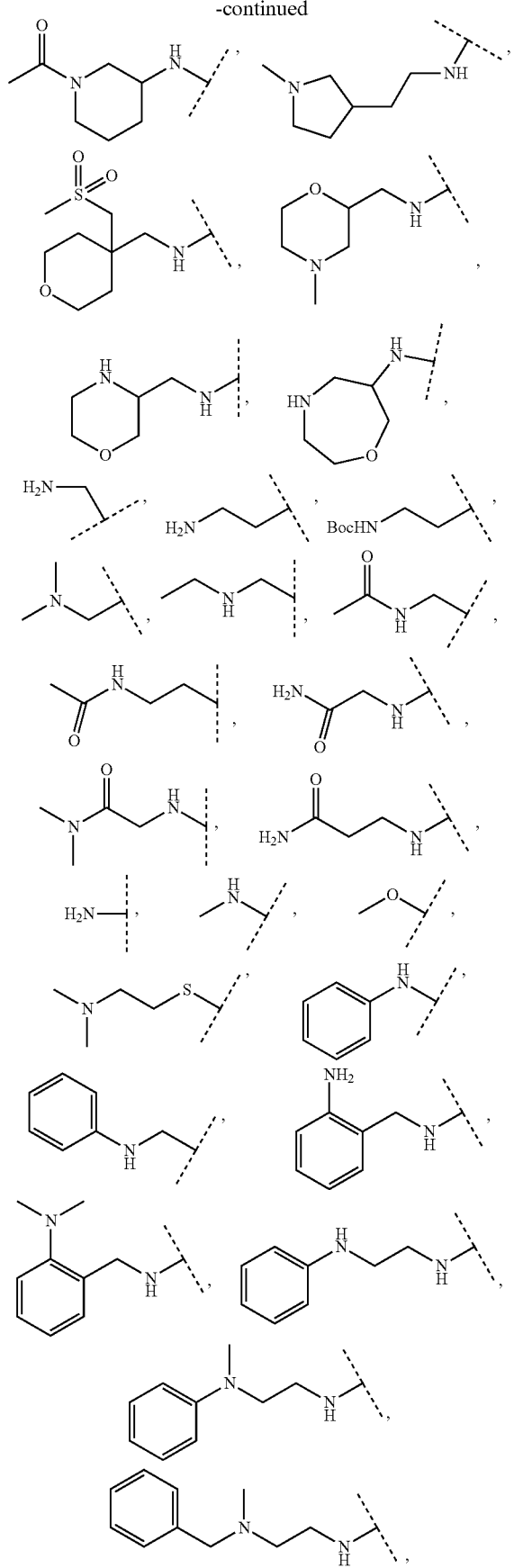
424
-continued
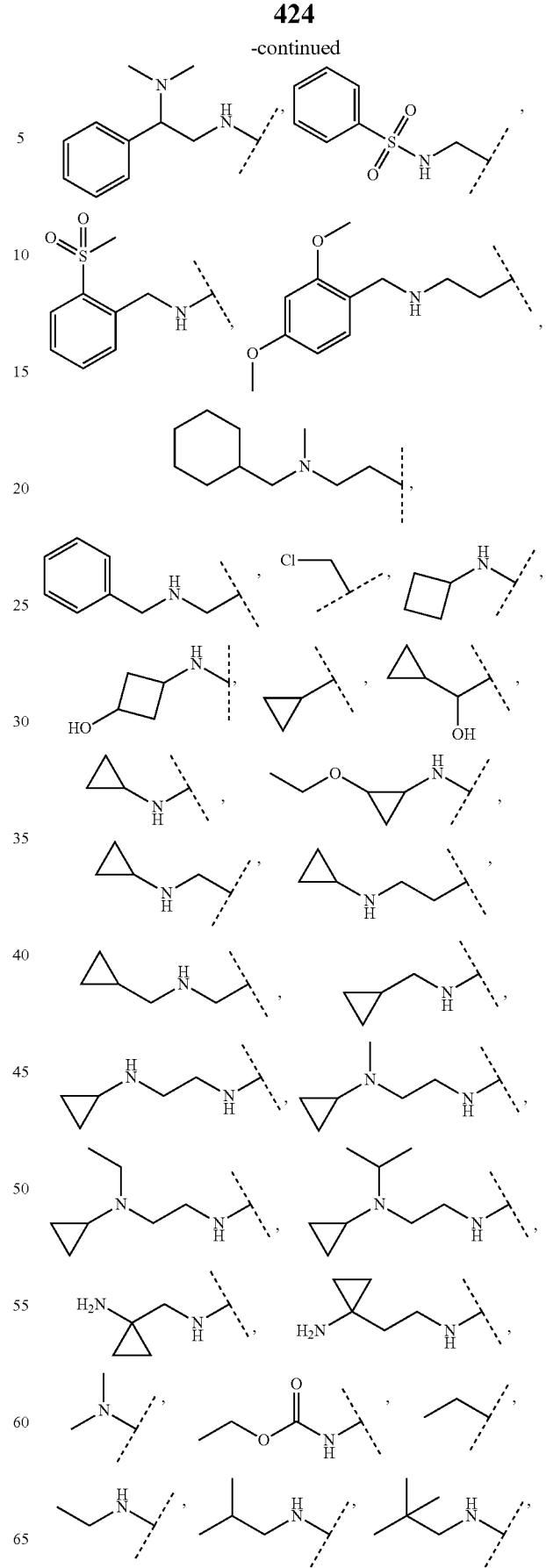

425
-continued
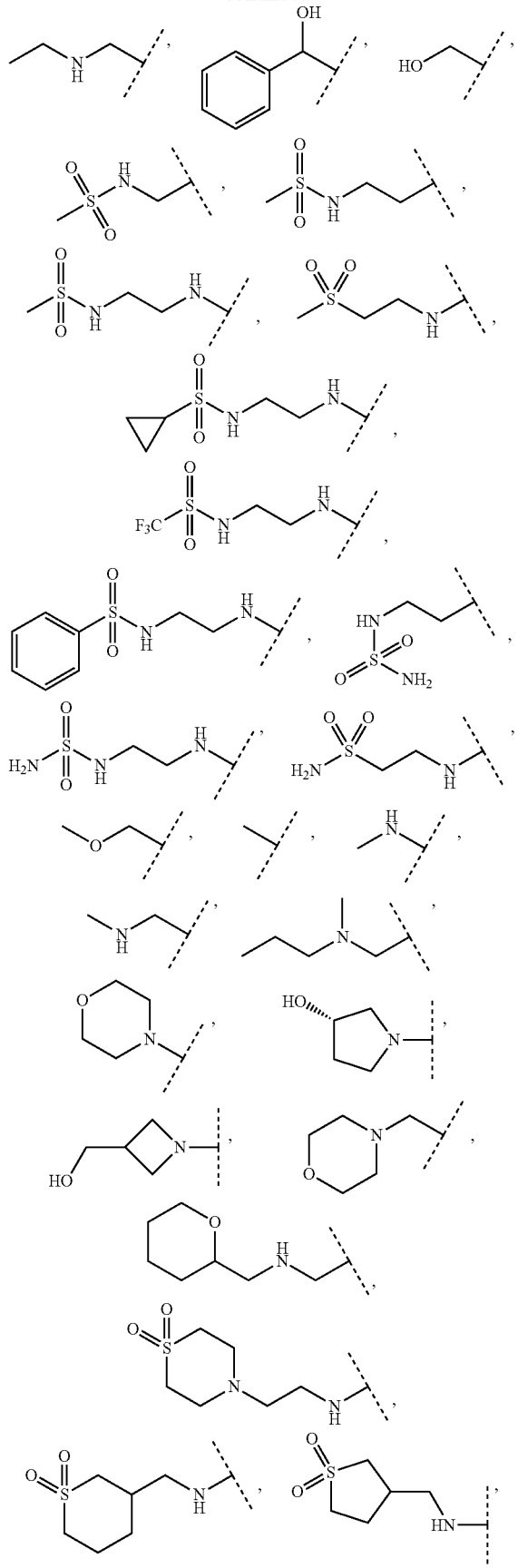
426
-continued
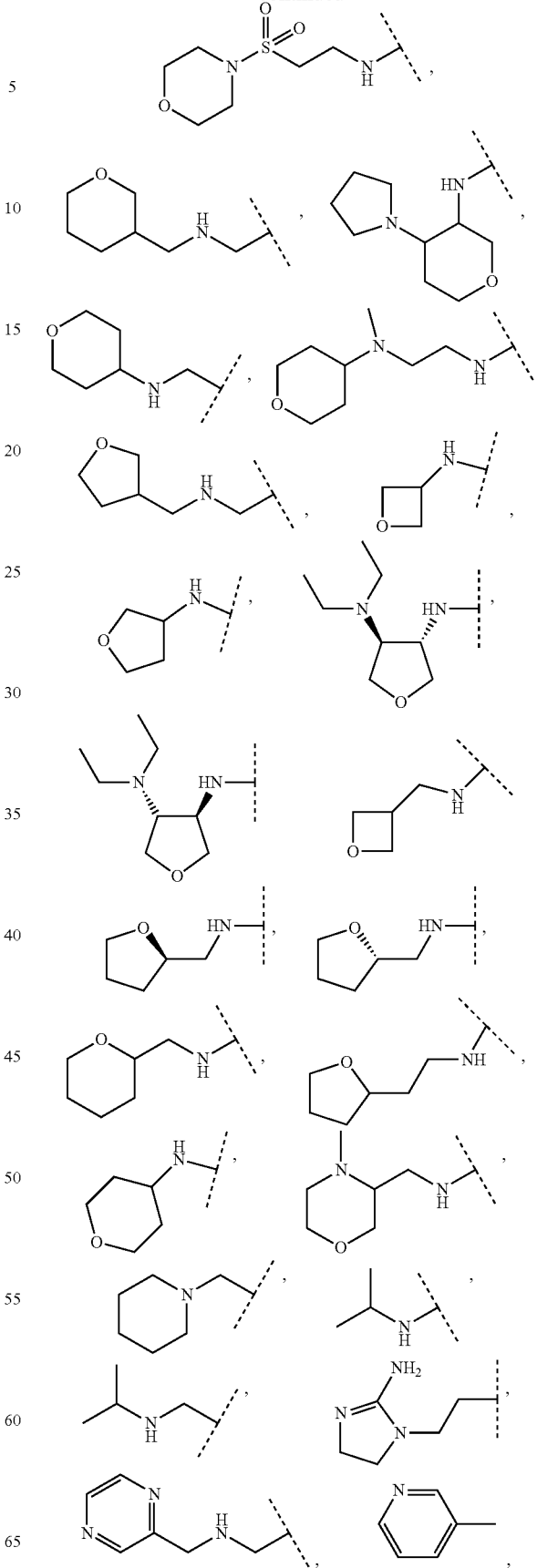

-continued

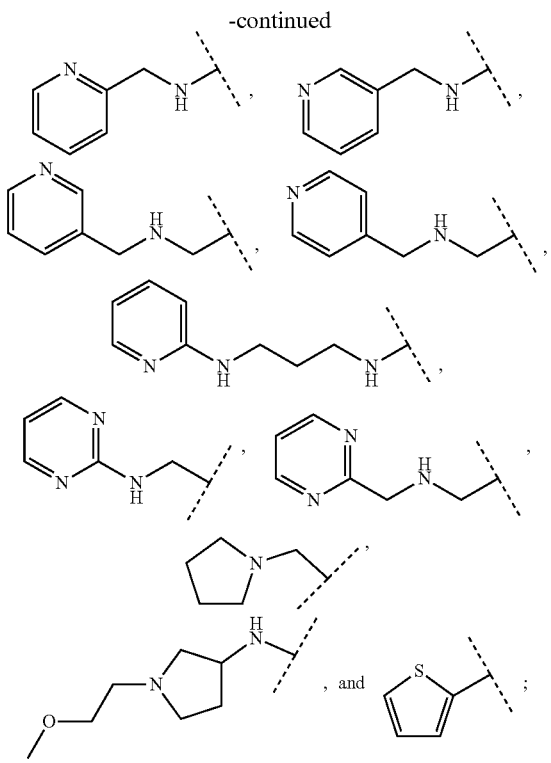

or a pharmaceutically acceptable salt, tautomer, optical isomer, stereoisomer, or mixture thereof.

15. A compound selected from the group consisting of:
N-(3-Chloro-4-fluorophenyl)-N'-hydroxy-4-methyl-1H-benzo[d]imidazole-7-carboximidamide,
N-(3-Chloro-4-fluorophenyl)-N'-hydroxy-4-(trifluoromethoxy)-1H-benzo[d]imidazole-7-carboximidamide,
N-(3-Chloro-4-fluorophenyl)-6-fluoro-N'-hydroxy-1H-benzo[d]imidazole-7-carboximidamide,
N-(3-Chloro-4-fluorophenyl)-5-fluoro-N'-hydroxy-1H-benzo[d]imidazole-7-carboximidamide,
N-(3-Chloro-4-fluorophenyl)-4-fluoro-N'-hydroxy-1H-benzo[d]imidazole-7-carboximidamide,
4-Chloro-N-(3-chloro-4-fluorophenyl)-N'-hydroxy-1H-benzo[d]imidazole-7-carboximidamide,
N-(3-Chloro-4-fluorophenyl)-N'-hydroxy-4-(trifluoromethyl)-1H-benzo[d]imidazole-7-carboximidamide,
N-(3-Chloro-4-fluorophenyl)-N'-hydroxy-1H-benzo[d]imidazole-7-carboximidamide,
N-(3-Chloro-4-fluorophenyl)-6-fluoro-N'-hydroxy-7-methyl-3H-benzimidazole-4-carboximidamide,
N-(3-Chloro-4-fluorophenyl)-4,5-difluoro-N'-hydroxy-1H-benzo[d]imidazole-7-carboximidamide,
6-Chloro-N-(3-chloro-4-fluorophenyl)-N'-hydroxy-1H-benzo[d]imidazole-4-carboximidamide,
4-Bromo-N-(3-chloro-4-fluorophenyl)-N'-hydroxy-1H-benzo[d]imidazole-7-carboximidamide,
2-Amino-N-(3-chloro-4-fluorophenyl)-4,5-difluoro-N'-hydroxy-1H-benzo[d]imidazole-7-carboximidamide,
2-Amino-N-(3-bromo-4-fluorophenyl)-4,5-difluoro-N'-hydroxy-1H-benzo[d]imidazole-7-carboximidamide,
2-Amino-N-(3-bromophenyl)-4,5-difluoro-N'-hydroxy-1H-benzo[d]imidazole-7-carboximidamide,
2-Amino-N-(3-chlorophenyl)-4,5-difluoro-N'-hydroxy-1H-benzo[d]imidazole-7-carboximidamide,
2-Amino-4,5-difluoro-N-(4-fluoro-3-(trifluoromethyl)phenyl)-N'-hydroxy-1H-benzo[d]imidazole-7-carboximidamide,
2-Amino-N-(3-bromophenyl)-4-fluoro-N'-hydroxy-1H-benzo[d]imidazole-7-carboximidamide,
2-Amino-N-(3-bromo-4-fluorophenyl)-4-fluoro-N'-hydroxy-1H-benzo[d]imidazole-7-carboximidamide,
2-Amino-N-(3-chlorophenyl)-4-fluoro-N'-hydroxy-1H-benzo[d]imidazole-7-carboximidamide,
2-Amino-4-fluoro-N-(4-fluoro-3-(trifluoromethyl)phenyl)-N'-hydroxy-1H-benzo[d]imidazole-7-carboximidamide,
2-Amino-N-(3-chloro-4-fluorophenyl)-4-fluoro-N'-hydroxy-1H-benzo[d]imidazole-7-carboximidamide,
2-Amino-N-(3-chloro-4-fluorophenyl)-4-fluoro-N'-hydroxy-1H-benzo[d]imidazole-7-carboximidamide,
N-(3-Chloro-4-fluorophenyl)-4,5-difluoro-N'-hydroxy-2-((2-morpholinoethyl)amino)-1H-benzo[d]imidazole-7-carboximidamide,
N-(3-Chlorophenyl)-4,5-difluoro-N'-hydroxy-2-(((3-methoxypropyl)amino)methyl)-1H-benzo[d]imidazole-7-carboximidamide,
N-(3-Chlorophenyl)-2-(((cyclopropylmethyl)amino)methyl)-4,5-difluoro-N'-hydroxy-1H-benzo[d]imidazole-7-carboximidamide,
N-(3-Chlorophenyl)-2-((dimethylamino)methyl)-4,5-difluoro-N'-hydroxy-1H-benzo[d]imidazole-7-carboximidamide
N-(3-Chlorophenyl)-4,5-difluoro-N'-hydroxy-2-((isopropylamino)methyl)-1H-benzo[d]imidazole-7-carboximidamide,
N-(3-Chlorophenyl)-2-((ethylamino)methyl)-4,5-difluoro-N'-hydroxy-1H-benzo[d]imidazole-7-carboximidamide,
N-(3-Chlorophenyl)-4,5-difluoro-N'-hydroxy-2-(hydroxymethyl)-1H-benzo[d]imidazole-7-carboximidamide,
N-(3-Chlorophenyl)-4,5-difluoro-N'-hydroxy-2-((methylamino)methyl)-1H-benzo[d]imidazole-7-carboximidamide,
2-(Aminomethyl)-N-(3-chlorophenyl)-4,5-difluoro-N'-hydroxy-1H-benzo[d]imidazole-7-carboximidamide,
N-(3-Chloro-4-fluorophenyl)-4,5-difluoro-N'-hydroxy-2-morpholino-1H-benzo-[d]imidazole-7-carboximidamide,
N-(3-Chloro-4-fluorophenyl)-4-fluoro-N'-hydroxy-2-((2-(methylsulfonyl)ethyl)amino)-1H-benzo[d]imidazole-7-carboximidamide,
N-(3-Chloro-4-fluorophenyl)-4-fluoro-N'-hydroxy-2-((2-morpholinoethyl)amino)-1H-benzo[d]imidazole-7-carboximidamide,
N-(3-Chloro-4-fluorophenyl)-4,5-difluoro-N'-hydroxy-2-((2-(methylsulfonyl)ethyl)amino)-1H-benzo[d]imidazole-7-carboximidamide,
N-(3-Chloro-4-fluorophenyl)-2-((2-(4,4-difluoropiperidin-1-yl)ethyl)amino)-4,5-difluoro-N'-hydroxy-1H-benzo[d]imidazole-7-carboximidamide,
N-(3-Chloro-4-fluorophenyl)-4,5-difluoro-N'-hydroxy-2-((1-morpholinopropan-2-yl)amino)-1H-benzo[d]imidazole-7-carboximidamide,
N-(3-Chloro-4-fluorophenyl)-4,5-difluoro-N'-hydroxy-2-(methylamino)-1H-benzo[d]imidazole-7-carboximidamide,
N-(3-Chloro-4-fluorophenyl)-2-((3-(dimethylamino)propyl)amino)-4,5-difluoro-N'-hydroxy-1H-benzo[d]imidazole-7-carboximidamide, N-(3-Chloro-4-fluorophenyl)-4,5-difluoro-N'-hydroxy-2-((2-methoxyethyl)amino)-1H-benzo[d]imidazole-7-carboximidamide,
N-(3-Chloro-4-fluorophenyl)-4,5-difluoro-N'-hydroxy-2-((2-(pyrrolidin-1-yl)ethyl)amino)-1H-benzo[d]imidazole-7-carboximidamide,
N-(3-Chloro-4-fluorophenyl)-2-((2-(diethylamino)ethyl)amino)-4,5-difluoro-N'-hydroxy-1H-benzo[d]imidazole-7-carboximidamide,
N-(3-Chloro-4-fluorophenyl)-2-((2-(dimethylamino)ethyl)amino)-4,5-difluoro-N'-hydroxy-1H-benzo[d]imidazole-7-carboximidamide,
N-(3-Chlorophenyl)-4,5-difluoro-N'-hydroxy-2-(1-methylpiperidin-3-yl)-1H-benzo[d]imidazole-7-carboximidamide,
N-(3-Chloro-4-fluorophenyl)-6,7-difluoro-N'-hydroxy-2-(((3-methoxypropyl)amino)methyl)-1H-benzo[d]imidazole-4-carboximidamide,
N-(3-Chloro-4-fluorophenyl)-4,5-difluoro-N'-hydroxy-2-(hydroxymethyl)-1H-benzo[d]imidazole-7-carboximidamide,
2-(Aminomethyl)-N-(3-chloro-4-fluorophenyl)-4,5-difluoro-N'-hydroxy-1H-benzo[d]imidazole-7-carboximidamide,
N-(3-Chloro-4-fluorophenyl)-4,5-difluoro-N'-hydroxy-2-((methylamino)methyl)-1H-benzo[d]imidazole-7-carboximidamide,
N-(3-Chloro-4-fluorophenyl)-2-(((cyclopropylmethyl)amino)methyl)-4,5-difluoro-N-hydroxy-1H-benzo[d]imidazole-7-carboximidamide,
N-(3-Chloro-4-fluorophenyl)-2-((ethylamino)methyl)-6,7-difluoro-N'-hydroxy-1H-benzo[d]imidazole-4-carboximidamide,
N-(3-Chloro-4-fluorophenyl)-6,7-difluoro-N'-hydroxy-2-((isopropylamino)methyl)-1H-benzo[d]imidazole-4-carboximidamide,
N-(3-Chloro-4-fluorophenyl)-2-((dimethylamino)methyl)-6,7-difluoro-N'-hydroxy-1H-benzo[d]imidazole-4-carboximidamide,
N-(3-Chloro-4-fluorophenyl)-2-(2-(dimethylamino)ethyl)-6,7-difluoro-N'-hydroxy-1H-benzo[d]imidazole-4-carboximidamide,
N-(3-Bromo-4-fluorophenyl)-2-(2-(dimethylamino)ethyl)-6,7-difluoro-N'-hydroxy-1H-benzo[d]imidazole-4-carboximidamide,
N-(3-Bromophenyl)-2-(2-(dimethylamino)ethyl)-6,7-difluoro-N'-hydroxy-1H-benzo[d]imidazole-4-carboximidamide,
N-(3-Chlorophenyl)-2-(2-(dimethylamino)ethyl)-6,7-difluoro-N'-hydroxy-1H-benzo[d]imidazole-4-carboximidamide,
N-(3-Chloro-4-fluorophenyl)-6,7-difluoro-N'-hydroxy-2-(2-(methylamino)ethyl)-1H-benzo[d]imidazole-4-carboximidamide,
N-(3-Chloro-4-fluorophenyl)-2-(2-(diethylamino)ethyl)-4,5-difluoro-N'-hydroxy-1H-benzo[d]imidazole-7-carboximidamide,
N-(3-Chloro-4-fluorophenyl)-N'-hydroxy-1H-imidazo[4,5-b]pyridine-7-carboximidamide,
N-(5-Chloro-2-fluorophenyl)-N'-hydroxy-1H-imidazo[4,5-b]pyridine-7-carboximidamide,
N-(5-Bromo-2,4-difluorophenyl)-N'-hydroxy-1H-imidazo[4,5-b]pyridine-7-carboximidamide,
N-(5-Chloro-2,4-difluorophenyl)-N'-hydroxy-1H-imidazo[4,5-b]pyridine-7-carboximidamide,
N-(3,5-Dichloro-4-fluorophenyl)-N'-hydroxy-1H-imidazo[4,5-b]pyridine-7-carboximidamide,
N-(3-Chloro-2,4-difluorophenyl)-N'-hydroxy-1H-imidazo[4,5-b]pyridine-7-carboximidamide,
N-(3-Cyclopropyl-4-fluorophenyl)-N'-hydroxy-1H-imidazo[4,5-b]pyridine-7-carboximidamide,
N'-Hydroxy-N-(4-(trifluoromethoxy)phenyl)-1H-imidazo[4,5-b]pyridine-7-carboximidamide,
N-(Benzofuran-4-yl)-N'-hydroxy-1H-imidazo[4,5-b]pyridine-7-carboximidamide,
N-(Benzofuran-6-yl)-N'-hydroxy-1H-imidazo[4,5-b]pyridine-7-carboximidamide,
N-(Benzofuran-7-yl)-N'-hydroxy-1H-imidazo[4,5-b]pyridine-7-carboximidamide,
N-(benzofuran-5-yl)-N'-hydroxy-1H-imidazo[4,5-b]pyridine-7-carboximidamide,
N-(5-Bromo-2-fluorophenyl)-N'-hydroxy-1H-imidazo[4,5-b]pyridine-7-carboximidamide,
N-(3-Bromo-5-fluorophenyl)-N'-hydroxy-1H-imidazo[4,5-b]pyridine-7-carboximidamide,
N'-Hydroxy-N-(3-(trifluoromethyl)phenyl)-1H-imidazo[4,5-b]pyridine-7-carboximidamide,
N-(2,2-Difluorobenzo[d][1,3]dioxol-5-yl)-N'-hydroxy-1H-imidazo[4,5-b]pyridine-7-carboximidamide,
N-(3-Fluoro-5-(trifluoromethyl)phenyl)-N'-hydroxy-1H-imidazo[4,5-b]pyridine-7-carboximidamide,
N-(2,5-Dichlorophenyl)-N'-hydroxy-1H-imidazo[4,5-b]pyridine-7-carboximidamide,
N-(6-Fluoro-[1,1'-biphenyl]-3-yl)-N'-hydroxy-1H-imidazo[4,5-b]pyridine-7-carboximidamide,
N-(3-(But-1-yn-1-yl)-4-fluorophenyl)-N'-hydroxy-1H-imidazo[4,5-b]pyridine-7-carboximidamide,
N-(3-(Cyclopropylethynyl)-4-fluorophenyl)-N'-hydroxy-1H-imidazo[4,5-b]pyridine-7-carboximidamide,
N-(3-Bromophenyl)-N'-hydroxy-1H-imidazo[4,5-b]pyridine-7-carboximidamide,
N-(3-Bromo-4-fluorophenyl)-N'-hydroxy-1H-imidazo[4,5-b]pyridine-7-carboximidamide,
N-(3-Chlorophenyl)-N'-hydroxy-1H-imidazo[4,5-b]pyridine-7-carboximidamide,
N-(4-Fluoro-3-(trifluoromethyl)phenyl)-N'-hydroxy-1H-imidazo[4,5-b]pyridine-7-carboximidamide,
N-(4-Fluoro-3-(prop-1-yn-1-yl)phenyl)-N'-hydroxy-1H-imidazo[4,5-b]pyridine-7-carboximidamide,
N-(3-Bromo-4-chlorophenyl)-N'-hydroxy-1H-imidazo[4,5-b]pyridine-7-carboximidamide,
N-(3,4-Dichlorophenyl)-N'-hydroxy-1H-imidazo[4,5-b]pyridine-7-carboximidamide,
N-(4-Chlorophenyl)-N'-hydroxy-1H-imidazo[4,5-b]pyridine-7-carboximidamide,
N-(4-Bromophenyl)-N'-hydroxy-1H-imidazo[4,5-b]pyridine-7-carboximidamide,
N-(4-Fluorophenyl)-N'-hydroxy-1H-imidazo[4,5-b]pyridine-7-carboximidamide,
N-(3-Cyano-4-fluorophenyl)-N'-hydroxy-1H-imidazo[4,5-b]pyridine-7-carboximidamide,
N'-Hydroxy-N-(4-(trifluoromethyl)phenyl)-1H-imidazo[4,5-b]pyridine-7-carboximidamide,
N'-Hydroxy-N-(3-methoxyphenyl)-1H-imidazo[4,5-b]pyridine-7-carboximidamide,
N-(4-Fluoro-3-isopropylphenyl)-N'-hydroxy-1H-imidazo[4,5-b]pyridine-7-carboximidamide,
N'-Hydroxy-N-(p-tolyl)-1H-imidazo[4,5-b]pyridine-7-carboximidamide,
N-(3-Ethynylphenyl)-N'-hydroxy-1H-imidazo[4,5-b]pyridine-7-carboximidamide,
N-(3-Ethylphenyl)-N'-hydroxy-1H-imidazo[4,5-b]pyridine-7-carboximidamide, N-(3-Ethynyl-4-fluorophenyl)-N'-hydroxy-1H-imidazo[4,5-b]pyridine-7-carboximidamide,
N-(3-(Difluoromethyl)phenyl)-N'-hydroxy-1H-imidazo[4,5-b]pyridine-7-carboximidamide,
N-Hydroxy-N-(3-(trifluoromethoxy)phenyl)-1H-imidazo[4,5-b]pyridine-7-carboximidamide,
N-Hydroxy-N-phenyl-1H-imidazo[4,5-b]pyridine-7-carboximidamide,
N-(4-Fluoro-3-(trifluoromethoxy)phenyl)-N'-hydroxy-1H-imidazo[4,5-b]pyridine-7-carboximidamide,
N-Hydroxy-N-(naphthalen-2-yl)-1H-imidazo[4,5-b]pyridine-7-carboximidamide,
N-(3-Chloronaphthalen-2-yl)-N'-hydroxy-1H-imidazo[4,5-b]pyridine-7-carboximidamide,
N'-hydroxy-N-(naphthalen-1-yl)-1H-imidazo[4,5-b]pyridine-7-carboximidamide,
N-(4-Chloronaphthalen-1-yl)-N'-hydroxy-1H-imidazo[4,5-b]pyridine-7-carboximidamide,
N-(4-Fluoro-3-methoxyphenyl)-N'-hydroxy-1H-imidazo[4,5-b]pyridine-7-carboximidamide,
N-(3-Chloro-4-fluorophenyl)-N'-hydroxy-2-methyl-1H-imidazo[4,5-b]pyridine-7-carboximidamide,
N-(3-Chloro-4-fluorophenyl)-2-ethyl-N-hydroxy-1H-imidazo[4,5-b]pyridine-7-carboximidamide,
N-(3-Chloro-4-fluorophenyl)-2-cyclopropyl-N-hydroxy-1H-imidazo[4,5-b]pyridine-7-carboximidamide,
N-(3-Chloro-4-fluorophenyl)-N'-hydroxy-2-(methoxymethyl)-1H-imidazo[4,5-b]pyridine-7-carboximidamide,
4-(3-Chloro-4-fluorophenyl)-3-(2-(hydroxymethyl)-1H-imidazo[4,5-b]pyridin-7-yl)-1,2,4-oxadiazol-5(4H)-one,
N-(3-Chloro-4-fluorophenyl)-N'-hydroxy-2-(morpholinomethyl)-1H-imidazo[4,5-b]pyridine-7-carboximidamide,
N-(3-Chloro-4-fluorophenyl)-2-((dimethylamino)methyl)-N'-hydroxy-1H-imidazo[4,5-b]pyridine-7-carboximidamide,
N-(3-Chloro-4-fluorophenyl)-2-((ethyl amino)methyl)-N'-hydroxy-1H-imidazo[4,5-b]pyridine-7-carboximidamide,
2-((Benzyl amino)methyl)-N-(3-chloro-4-fluorophenyl)-N'-hydroxy-1H-imidazo[4,5-b]pyridine-7-carboximidamide,
N-(3-Chloro-4-fluorophenyl)-N'-hydroxy-2-((isopropylamino)methyl)-1H-imidazo[4,5-b]pyridine-7-carboximidamide,
N-(3-Chloro-4-fluorophenyl)-2-(((cyclopropylmethyl)amino)methyl)-N'-hydroxy-1H-imidazo[4,5-b]pyridine-7-carboximidamide,
N-(3-Chloro-4-fluorophenyl)-N'-hydroxy-2-(((2,2,2-trifluoroethyl)amino)methyl)-1H-imidazo[4,5-b]pyridine-7-carboximidamide,
N-(3-Chloro-4-fluorophenyl)-2-((cyclopropylamino)methyl)-N'-hydroxy-1H-imidazo[4,5-b]pyridine-7-carboximidamide,
N-(3-Chloro-4-fluorophenyl)-N'-hydroxy-2-(((3-methoxypropyl)amino)methyl)-1H-imidazo[4,5-b]pyridine-7-carboximidamide,
N-(3-Chloro-4-fluorophenyl)-N'-hydroxy-2-(((pyridin-2-ylmethyl)amino)methyl)-1H-imidazo[4,5-b]pyridine-7-carboximidamide,
N-(3-Chloro-4-fluorophenyl)-N'-hydroxy-2-(((3-methoxypropyl)(methyl)amino)methyl)-1H-imidazo[4,5-b]pyridine-7-carboximidamide,
N-(3-Chloro-4-fluorophenyl)-N'-hydroxy-2-(((2-methoxybenzyl)amino)methyl)-1H-imidazo[4,5-b]pyridine-7-carboximidamide,
N-(3-Chloro-4-fluorophenyl)-N'-hydroxy-2-(((2-methoxyethyl)amino)methyl)-1H-imidazo[4,5-b]pyridine-7-carboximidamide,
N-(3-Chloro-4-fluorophenyl)-N'-hydroxy-2-(((2-(pyridin-2-yl)ethyl)amino)methyl)-1H-imidazo[4,5-b]pyridine-7-carboximidamide,
N-(3-Chloro-4-fluorophenyl)-N'-hydroxy-2-(((pyridin-3-ylmethyl)amino)methyl)-1H-imidazo[4,5-b]pyridine-7-carboximidamide,
N-(3-Chloro-4-fluorophenyl)-N'-hydroxy-2-(((((tetrahydro-2H-pyran-2-yl)methyl)amino)methyl)-1H-imidazo[4,5-b]pyridine-7-carboximidamide,
N-(3-Chloro-4-fluorophenyl)-N'-hydroxy-2-((phenylamino)methyl)-1H-imidazo[4,5-b]pyridine-7-carboximidamide,
N-(3-Chloro-4-fluorophenyl)-N'-hydroxy-2-(((((tetrahydro-2H-pyran-3-yl)methyl)amino)methyl)-1H-imidazo[4,5-b]pyridine-7-carboximidamide,
N-(3-Chloro-4-fluorophenyl)-N'-hydroxy-2-(((pyrimidin-2-ylmethyl)amino)methyl)-1H-imidazo[4,5-b]pyridine-7-carboximidamide,
N-(3-Chloro-4-fluorophenyl)-N'-hydroxy-2-(((3-morpholinopropyl)amino)methyl)-1H-imidazo[4,5-b]pyridine-7-carboximidamide,
N-(3-Chloro-4-fluorophenyl)-N'-hydroxy-2-(((tetrahydro-2H-pyran-4-yl)amino)methyl)-1H-imidazo[4,5-b]pyridine-7-carboximidamide,
N-(3-Chloro-4-fluorophenyl)-N'-hydroxy-2-(((pyridin-4-ylmethyl)amino)methyl)-1H-imidazo[4,5-b]pyridine-7-carboximidamide,
N-(3-Chloro-4-fluorophenyl)-N'-hydroxy-2-(((pyrazin-2-ylmethyl)amino)methyl)-1H-imidazo[4,5-b]pyridine-7-carboximidamide,
N-(3-Chloro-4-fluorophenyl)-N'-hydroxy-2-(((((tetrahydrofuran-3-yl)methyl)amino)methyl)-1H-imidazo[4,5-b]pyridine-7-carboximidamide,
N-(3-Chloro-4-fluorophenyl)-2-(((2-(dimethylamino)ethyl)amino)methyl)-N'-hydroxy-1H-imidazo[4,5-b]pyridine-7-carboximidamide,
N-(3-Chloro-4-fluorophenyl)-N'-hydroxy-2-(((2-(pyrimidin-2-yl)ethyl)amino)methyl)-1H-imidazo[4,5-b]pyridine-7-carboximidamide,
N-(3-Chloro-4-fluorophenyl)-N'-hydroxy-2-(((3-hydroxypropyl)amino)methyl)-1H-imidazo[4,5-b]pyridine-7-carboximidamide,
N-(3-Chloro-4-fluorophenyl)-N'-hydroxy-2-(pyrrolidin-1-ylmethyl)-1H-imidazo[4,5-b]pyridine-7-carboximidamide,
N-(3-Chloro-4-fluorophenyl)-N'-hydroxy-2-(piperidin-1-ylmethyl)-1H-imidazo[4,5-b]pyridine-7-carboximidamide,
N-(3-Chloro-4-fluorophenyl)-N'-hydroxy-2-((neopentylamino)methyl)-1H-imidazo[4,5-b]pyridine-7-carboximidamide,
N-(3-Chloro-4-fluorophenyl)-2-(((2,2-difluoroethyl)amino)methyl)-N'-hydroxy-1H-imidazo[4,5-b]pyridine-7-carboximidamide,
N-(3-Chloro-4-fluorophenyl)-N'-hydroxy-2-(((3-hydroxy-2,2-dimethylpropyl)amino)methyl)-1H-imidazo[4,5-b]pyridine-7-carboximidamide,
N-(3-Chloro-4-fluorophenyl)-N'-hydroxy-2-(((thiazol-2-ylmethyl)amino)methyl)-1H-imidazo[4,5-b]pyridine-7-carboximidamide,
N-((7-(N-(3-Chloro-4-fluorophenyl)-N'-hydroxycarbamimidoyl)-1H-imidazo[4,5-b]pyridin-2-yl)methyl)acetamide, N-(3-Chloro-4-fluorophenyl)-N'-hydroxy-2-(thiophen-2-yl)-1H-imidazo[4,5-b]pyridine-7-carboximidamide,
N-(3-Chloro-4-fluorophenyl)-N'-hydroxy-2-(pyridin-3-yl)-1H-imidazo[4,5-b]pyridine-7-carboximidamide,
N-(3-Chloro-4-fluorophenyl)-N'-hydroxy-2-(1H-pyrrol-2-yl)-1H-imidazo[4,5-b]pyridine-7-carboximidamide,
N-(3-Chloro-4-fluorophenyl)-N'-hydroxy-2-(1H-imidazol-2-yl)-1H-imidazo[4,5-b]pyridine-7-carboximidamide,
N-(3-Chloro-4-fluorophenyl)-N'-hydroxy-2-(1H-pyrazol-5-yl)-1H-imidazo[4,5-b]pyridine-7-carboximidamide,
N-(3-Chloro-4-fluorophenyl)-N'-hydroxy-2-(4-methyl-1H-imidazol-2-yl)-1H-imidazo[4,5-b]pyridine-7-carboximidamide,
N-(3-Chloro-4-fluorophenyl)-N'-hydroxy-2-(pyrrolidin-2-yl)-1H-imidazo[4,5-b]pyridine-7-carboximidamide,
2-Amino-N-(3-chloro-4-fluorophenyl)-N'-hydroxy-1H-imidazo[4,5-b]pyridine-7-carboximidamide,
N-(3-Chloro-4-fluorophenyl)-2-(cyclopropylamino)-N'-hydroxy-1H-imidazo[4,5-b]pyridine-7-carboximidamide,
N-(3-Chloro-4-fluorophenyl)-N'-hydroxy-2-(phenylamino)-1H-imidazo[4,5-b]pyridine-7-carboximidamide,
N-(3-Chloro-4-fluorophenyl)-N'-hydroxy-2-(phenethylamino)-1H-imidazo[4,5-b]pyridine-7-carboximidamide,
N-(3-Chloro-4-fluorophenyl)-N'-hydroxy-2-((2,2,2-trifluoroethyl)amino)-1H-imidazo[4,5-b]pyridine-7-carboximidamide,
N-(3-Chloro-4-fluorophenyl)-N'-hydroxy-2-(methylamino)-1H-imidazo[4,5-b]pyridine-7-carboximidamide,
Isopropyl (7-(N-(3-chloro-4-fluorophenyl)-N'-hydroxycarbamimidoyl)-1H-imidazo[4,5-b]pyridin-2-yl)carbamate,
Ethyl (7-(N-(3-chloro-4-fluorophenyl)-N'-hydroxycarbamimidoyl)-1H-imidazo[4,5-b]pyridin-2-yl)carbamate,
N-(3-Chloro-4-fluorophenyl)-2-((cyclopropylmethyl)amino)-N'-hydroxy-1H-imidazo[4,5-b]pyridine-7-carboximidamide,
N-(3-Chloro-4-fluorophenyl)-2-((3,3-difluorocyclobutyl)amino)-N'-hydroxy-1H-imidazo[4,5-b]pyridine-7-carboximidamide,
N-(3-Chloro-4-fluorophenyl)-2-(ethylamino)-N'-hydroxy-1H-imidazo[4,5-b]pyridine-7-carboximidamide,
N-(3-Chloro-4-fluorophenyl)-2-(cyclobutylamino)-N'-hydroxy-1H-imidazo[4,5-b]pyridine-7-carboximidamide,
N-(3-Chloro-4-fluorophenyl)-N'-hydroxy-2-(isopropylamino)-1H-imidazo[4,5-b]pyridine-7-carboximidamide,
N-(3-Chlorophenyl)-N'-hydroxy-2-(methylamino)-1H-imidazo[4,5-b]pyridine-7-carboximidamide,
N-(3-Chloro-4-fluorophenyl)-2-((2-(diethylamino)ethyl)amino)-N'-hydroxy-1H-imidazo[4,5-b]pyridine-7-carboximidamide,
N-(3-Chloro-4-fluorophenyl)-N'-hydroxy-2-((2-morpholinoethyl)amino)-1H-imidazo[4,5-b]pyridine-7-carboximidamide,
N-(3-Chloro-4-fluorophenyl)-2-(dimethylamino)-N'-hydroxy-1H-imidazo[4,5-b]pyridine-7-carboximidamide,
2-(Chloromethyl)-N-(4-fluoro-3-(trifluoromethyl)phenyl)-N'-hydroxy-3H-imidazo[4,5-b]pyridine-7-carboximidamide,
N-(4-Fluoro-3-(trifluoromethyl)phenyl)-N'-hydroxy-2-(hydroxymethyl)-3H-imidazo[4,5-b]pyridine-7-carboximidamide,
N-(3-Chloro-4-fluorophenyl)-N'-hydroxy-2-(1-hydroxyethyl)-1H-imidazo[4,5-b]pyridine-7-carboximidamide,
N-(3-Chloro-4-fluorophenyl)-N'-hydroxy-2-(hydroxy(phenyl)methyl)-1H-imidazo[4,5-b]pyridine-7-carboximidamide,
N-(3-Chloro-4-fluorophenyl)-2-(cyclopropyl(hydroxy)methyl)-N'-hydroxy-1H-imidazo[4,5-b]pyridine-7-carboximidamide,
N-(3-Chloro-4-fluorophenyl)-N'-hydroxy-2-(2-hydroxypropan-2-yl)-1H-imidazo[4,5-b]pyridine-7-carboximidamide,
N-(3-Chloro-4-fluorophenyl)-N'-hydroxy-2-(2,2,2-trifluoro-1-hydroxyethyl)-1H-imidazo[4,5-b]pyridine-7-carboximidamide,
N-(3-Chloro-4-fluorophenyl)-N'-hydroxy-2-(hydroxymethyl)-1H-imidazo[4,5-b]pyridine-7-carboximidamide,
N-(3-Chloro-4-fluorophenyl)-N'-hydroxy-2-((methylamino)methyl)-1H-imidazo[4,5-b]pyridine-7-carboximidamide,
2-(Aminomethyl)-N-(3-chloro-4-fluorophenyl)-N'-hydroxy-1H-imidazo[4,5-b]pyridine-7-carboximidamide,
N-(3-Chloro-4-fluorophenyl)-N'-hydroxy-2-(phenylsulfonamidomethyl)-1H-imidazo[4,5-b]pyridine-7-carboximidamide,
N-(3-Chloro-4-fluorophenyl)-N'-hydroxy-2-(methylsulfonamidomethyl)-1H-imidazo[4,5-b]pyridine-7-carboximidamide,
N-(3-Chloro-4-fluorophenyl)-N'-hydroxy-2-((pyrimidin-2-ylamino)methyl)-1H-imidazo[4,5-b]pyridine-7-carboximidamide,
N-(3-Chloro-4-fluorophenyl)-N'-hydroxy-2-(2-hydroxyethyl)-1H-imidazo[4,5-b]pyridine-7-carboximidamide,
N-(3-Chloro-4-fluorophenyl)-2-(2-(dimethylamino)ethyl)-N'-hydroxy-1H-imidazo[4,5-b]pyridine-7-carboximidamide,
N-(3-Chloro-4-fluorophenyl)-2-(2-(diethylamino)ethyl)-N'-hydroxy-1H-imidazo[4,5-b]pyridine-7-carboximidamide,
N-(3-Chloro-4-fluorophenyl)-2-(2-((cyclopropylmethyl)(methyl)amino)ethyl)-N'-hydroxy-1H-imidazo[4,5-b]pyridine-7-carboximidamide,
N-(3-Chloro-4-fluorophenyl)-2-(2-((2,2-difluoroethyl)(methyl)amino)ethyl)-N'-hydroxy-1H-imidazo[4,5-b]pyridine-7-carboximidamide,
N-(3-Chloro-4-fluorophenyl)-N'-hydroxy-2-(2-(methylamino)ethyl)-1H-imidazo[4,5-b]pyridine-7-carboximidamide,
2-(2-Aminoethyl)-N-(3-chloro-4-fluorophenyl)-N'-hydroxy-1H-imidazo[4,5-b]pyridine-7-carboximidamide,
N-(3-Chloro-4-fluorophenyl)-N'-hydroxy-2-(2-((2-methoxyethyl)amino)ethyl)-1H-imidazo[4,5-b]pyridine-7-carboximidamide,
N-(3-Chloro-4-fluorophenyl)-N'-hydroxy-2-(2-morpholinoethyl)-1H-imidazo[4,5-b]pyridine-7-carboximidamide,
N-(3-Chloro-4-fluorophenyl)-N'-hydroxy-2-(2-(piperidin-1-yl)ethyl)-1H-imidazo[4,5-b]pyridine-7-carboximidamide,
N-(3-Chloro-4-fluorophenyl)-N'-hydroxy-2-(2-(pyrrolidin-1-yl)ethyl)-1H-imidazo[4,5-b]pyridine-7-carboximidamide,
N-(3-Chloro-4-fluorophenyl)-N'-hydroxy-2-(2-((2-methoxyethyl)(methyl)amino)ethyl)-1H-imidazo[4,5-b]pyridine-7-carboximidamide, N-(3-Chloro-4-fluorophenyl)-2-(2-(dimethylamino)-1-hydroxyethyl)-N'-hydroxy-1H-imidazo[4,5-b]pyridine-7-carboximidamide,
N-(3-Chloro-4-fluorophenyl)-N'-hydroxy-2-((isobutylamino)methyl)-1H-imidazo[4,5-b]pyridine-7-carboximidamide,
N-(3-Chloro-4-fluorophenyl)-N'-hydroxy-3-methyl-3H-imidazo[4,5-b]pyridine-7-carboximidamide,
N-(3-Chloro-4-fluorophenyl)-N'-hydroxy-2-[2-(2-methoxyethylamino)ethyl]-3H-imidazo[4,5-b]pyridine-7-carboximidamide,
N-(3-Chloro-4-fluorophenyl)-2-[3-(dimethylamino)propyl]-6,7-difluoro-N'-hydroxy-3H-benzimidazole-4-carboxamide,
N-(3-Chloro-4-fluorophenyl)-7-fluoro-N'-hydroxy-2-(3-morpholin-4-ylpropylamino)-3H-benzimidazole-4-carboxamide,
N-(3-Chloro-4-fluorophenyl)-2-((2-(dimethylamino)ethylamino]-7-fluoro-N'-hydroxy-3H-benzimidazole-4-carboxamide,
N-(3-Chloro-4-fluorophenyl)-N'-hydroxy-2-[(1-methylpiperidin-2-yl)methylamino]-1H-imidazo[4,5-b]pyridine-7-carboximidamide,
N-(3-Chloro-4-fluorophenyl)-N'-hydroxy-2-[(1-methylpyrrolidin-3-yl)amino]-1H-imidazo[4,5-b]pyridine-7-carboximidamide,
N-(3-chloro-4-fluorophenyl)-2-(2-(ethylamino)ethyl)-N'-hydroxy-3H-imidazo[4, 5-b]pyridine-7-carboximidamide,
N-(3-chloro-4-fluorophenyl)-N'-hydroxy-2-(2-(isopropylamino)ethyl)-3H-imidazo[4,5-b]pyridine-7-carboximidamide,
N-(3-chloro-4-fluorophenyl)-N'-hydroxy-2-(2-(isobutylamino)ethyl)-3H-imidazo[4,5-b]pyridine-7-carboximidamide,
N-(3-chloro-4-fluorophenyl)-2-(2-(cyclopropylamino)ethyl)-N'-hydroxy-3H-imidazo[4,5-b]pyridine-7-carboximidamide,
N-(3-chloro-4-fluorophenyl)-2-(2-((cyclopropylmethyl)amino)ethyl)-N'-hydroxy-3H-imidazo[4,5-b]pyridine-7-carboximidamide,
2-(2-(2-amino-4,5-dihydro-1H-imidazol-1-yl)ethyl)-N-(3-chloro-4-fluorophenyl)-N'-hydroxy-1H-imidazo[4, 5-b]pyridine-7-carboximidamide,
N-(3-chloro-4-fluorophenyl)-4,5-difluoro-N'-hydroxy-2-(2-(methylsulfonamido)ethyl)-1H-benzo[d]imidazole-7-carboximidamide,
2-(2-aminoethyl)-N-(3-chloro-4-fluorophenyl)-4,5-difluoro-N'-hydroxy-1H-benzo[d]imidazole-7-carboximidamide,
N-(3-chloro-4-fluorophenyl)-N'-hydroxy-2-((2-methoxyethyl)amino)-1H-imidazo[4,5-b]pyridine-7-carboximidamide,
tert-butyl (2-(7-(N-(3-chloro-4-fluorophenyl)-N'-hydroxycarbamimidoyl)-4,5-difluoro-1H-benzo[d]imidazol-2-yl)ethyl)carbamate,
N-(3-chloro-4-fluorophenyl)-2-((2-(4,4-difluoropiperidin-1-yl)ethyl)amino)-N'-hydroxy-1H-imidazo[4,5-b]pyridine-7-carboximidamide,
N-(3-chloro-4-fluorophenyl)-2-((2-(dimethylamino)ethyl)amino)-N'-hydroxy-1H-imidazo[4,5-b]pyridine-7-carboximidamide,
N-(3-chloro-4-fluorophenyl)-N'-hydroxy-2-((2-(methylamino)ethyl)amino)-1H-imidazo[4,5-b]pyridine-7-carboximidamide,
N-(3-chloro-4-fluorophenyl)-N'-hydroxy-2-((1-methylazepan-3-yl)amino)-1H-imidazo[4,5-b]pyridine-7-carboximidamide,
N-(3-chloro-4-fluorophenyl)-2-((2-(1,1-dioxidothiomorpholino)ethyl)amino)-N'-hydroxy-1H-imidazo[4,5-b]pyridine-7-carboximidamide,
N-(3-chloro-4-fluorophenyl)-N'-hydroxy-2-((2-(2-methoxyethyl)(methyl)amino)ethyl)amino)-1H-imidazo[4,5-b]pyridine-7-carboximidamide,
N-(3-chloro-4-fluorophenyl)-2-((2-(2,2-difluoroethyl)(methyl)amino)ethyl)amino)-N'-hydroxy-1H-imidazo[4,5-b]pyridine-7-carboximidamide,
N-(3-chloro-4-fluorophenyl)-N'-hydroxy-2-((3-morpholinopropyl)amino)-1H-imidazo[4,5-b]pyridine-7-carboximidamide,
N-(3-chloro-4-fluorophenyl)-N'-hydroxy-2-((2-(piperidin-1-yl)ethyl)amino)-1H-imidazo[4,5-b]pyridine-7-carboximidamide,
N-(3-chloro-4-fluorophenyl)-2-((2-cyclohexylethyl)amino)-N'-hydroxy-1H-imidazo[4,5-b]pyridine-7-carboximidamide,
N-(3-chloro-4-fluorophenyl)-N'-hydroxy-2-((2-(tetrahydro-2H-pyran-4-yl)ethyl)amino)-1H-imidazo[4,5-b]pyridine-7-carboximidamide,
N-(3-chloro-4-fluorophenyl)-2-((2,2-difluoroethyl)amino)-N'-hydroxy-1H-imidazo[4,5-b]pyridine-7-carboximidamide,
N-(3-chloro-4-fluorophenyl)-N'-hydroxy-2-(oxetan-3-ylamino)-1H-imidazo[4,5-b]pyridine-7-carboximidamide,
N-(3-chloro-4-fluorophenyl)-N'-hydroxy-2-((tetrahydrofuran-3-yl)amino)-1H-imidazo[4,5-b]pyridine-7-carboximidamide,
N-(3-chloro-4-fluorophenyl)-N'-hydroxy-2-((tetrahydro-2H-pyran-4-yl)amino)-1H-imidazo[4,5-b]pyridine-7-carboximidamide,
3-((7-(N-(3-chloro-4-fluorophenyl)-N'-hydroxycarbamimidoyl)-4,5-difluoro-1H-benzo[d]imidazol-2-yl)amino)propanamide),
N-(3-chloro-4-fluorophenyl)-2-((2-((2,2-difluoroethyl)amino)ethyl)amino)-N'-hydroxy-1H-imidazo[4,5-b]pyridine-7-carboximidamide,
N-(3-chloro-4-fluorophenyl)-2-((2-(cyclopropyl(methyl)amino)ethyl)amino)-N'-hydroxy-1H-imidazo[4,5-b]pyridine-7-carboximidamide,
N-(3-chloro-4-fluorophenyl)-2-((2-(cyclopropyl(2-methoxyethyl)amino)ethyl)amino)-N'-hydroxy-1H-imidazo[4,5-b]pyridine-7-carboximidamide,
2-((2-(azetidin-1-yl)ethyl)amino)-N-(3-chloro-4-fluorophenyl)-N'-hydroxy-1H-imidazo[4,5-b]pyridine-7-carboximidamide,
N-(3-chloro-4-fluorophenyl)-N'-hydroxy-2-((3-methoxypropyl)amino)-1H-imidazo[4,5-b]pyridine-7-carboximidamide,
N-(3-chloro-4-fluorophenyl)-N'-hydroxy-2-((2-(2-oxopyrrolidin-1-yl)ethyl)amino)-1H-imidazo[4,5-b]pyridine-7-carboximidamide,
N-(3-chloro-4-fluorophenyl)-N'-hydroxy-2-((2-(morpholinosulfonyl)ethyl)amino)-1H-imidazo[4,5-b]pyridine-7-carboximidamide,
N-(3-chloro-4-fluorophenyl)-2-((2-(3-fluoropiperidin-1-yl)ethyl)amino)-N'-hydroxy-1H-imidazo[4,5-b]pyridine-7-carboximidamide,
N-(3-bromo-4-fluorophenyl)-N'-hydroxy-2-((2-morpholinoethyl)amino)-1H-imidazo[4,5-b]pyridine-7-carboximidamide, N-(3-chloro-4-fluorophenyl)-N'-hydroxy-2-((2-(methyl(tetrahydro-2H-pyran-4-yl)amino)ethyl)amino)-1H-imidazo[4,5-b]pyridine-7-carboximidamide, N-(3-chloro-4-fluorophenyl)-N'-hydroxy-2-((2-(isopropyl(methyl)amino)ethyl)amino)-1H-imidazo[4,5-b]pyridine-7-carboximidamide, 2-(((1-aminocyclopropyl)methyl)amino)-N-(3-chloro-4-fluorophenyl)-N'-hydroxy-1H-imidazo[4,5-b]pyridine-7-carboximidamide, 2-((2-(1-aminocyclopropyl)ethyl)amino)-N-(3-chloro-4-fluorophenyl)-N'-hydroxy-1H-imidazo[4,5-b]pyridine-7-carboximidamide, 2-((2-(2-oxa-5-azabicyclo[4.1.0]heptan-5-yl)ethyl)amino)-N-(3-chloro-4-fluorophenyl)-N'-hydroxy-1H-imidazo[4,5-b]pyridine-7-carboximidamide, 2-((2-(7-oxa-4-azaspiro[2.5]octan-4-yl)ethyl)amino)-N-(3-chloro-4-fluorophenyl)-N'-hydroxy-1H-imidazo[4,5-b]pyridine-7-carboximidamide, (R)-(3-chloro-4-fluorophenyl)-2-((2-(3-fluoropyrrolidin-1-yl)ethyl)amino)-N'-hydroxy-1H-imidazo[4,5-b]pyridine-7-carboximidamide, (S)-(3-chloro-4-fluorophenyl)-2-((2-(3-fluoropyrrolidin-1-yl)ethyl)amino)-N'-hydroxy-1H-imidazo[4,5-b]pyridine-7-carboximidamide, 2-((2-(2-azabicyclo[4.1.0]heptan-2-yl)ethyl)amino)-N-(3-chloro-4-fluorophenyl)-N'-hydroxy-1H-imidazo[4,5-b]pyridine-7-carboximidamide, 2-((2-(4-azaspiro[2.5]octan-4-yl)ethyl)amino)-N-(3-chloro-4-fluorophenyl)-N'-hydroxy-1H-imidazo[4,5-b]pyridine-7-carboximidamide, N-(3-chloro-4-fluorophenyl)-2-((2-(3-fluoroazetidin-1-yl)ethyl)amino)-N'-hydroxy-1H-imidazo[4,5-b]pyridine-7-carboximidamide, N-(3-chloro-4-fluorophenyl)-2-((2-(3,3-difluoroazetidin-1-yl)ethyl)amino)-N'-hydroxy-1H-imidazo[4,5-b]pyridine-7-carboximidamide, 2-((2-(4-azaspiro[2.4]heptan-4-yl)ethyl)amino)-N-(3-chloro-4-fluorophenyl)-N'-hydroxy-1H-imidazo[4,5-b]pyridine-7-carboximidamide, N-(3-chloro-4-fluorophenyl)-2-((3-(3-fluoropiperidin-1-yl)propyl)amino)-N'-hydroxy-1H-imidazo[4,5-b]pyridine-7-carboximidamide, N-(3-chloro-4-fluorophenyl)-N'-hydroxy-2-((2-(phenylamino)ethyl)amino)-1H-imidazo[4,5-b]pyridine-7-carboximidamide, N-(3-chloro-4-fluorophenyl)-N'-hydroxy-2-((2-(methyl(phenyl)amino)ethyl)amino)-1H-imidazo[4,5-b]pyridine-7-carboximidamide, N-(3-chloro-4-fluorophenyl)-2-(((1,1-dioxidotetrahydro-2H-thiopyran-3-yl)methyl)amino)-N-hydroxy-1H-imidazo[4,5-b]pyridine-7-carboximidamide, N-(3-chloro-4-fluorophenyl)-2-((2-ethoxycyclopropyl)amino)-N'-hydroxy-1H-imidazo[4,5-b]pyridine-7-carboximidamide, N-(3-bromo-4-fluorophenyl)-N'-hydroxy-2-(methylamino)-1H-imidazo[4,5-b]pyridine-7-carboximidamide, 2-(2-(azepan-1-yl)ethyl)-N-(3-chloro-4-fluorophenyl)-N'-hydroxy-1H-imidazo[4,5-b]pyridine-7-carboximidamide, 2-(2-(azetidin-1-yl)ethyl)-N-(3-chloro-4-fluorophenyl)-N'-hydroxy-1H-imidazo[4,5-b]pyridine-7-carboximidamide, (R)—N-(3-chloro-4-fluorophenyl)-N'-hydroxy-2-(2-(3-hydroxypyrrolidin-1-yl)ethyl)-1H-imidazo[4,5-b]pyridine-7-carboximidamide, (S)—N-(3-chloro-4-fluorophenyl)-N'-hydroxy-2-(2-(3-hydroxypyrrolidin-1-yl)ethyl)-1H-imidazo[4,5-b]pyridine-7-carboximidamide, N-(3-chloro-4-fluorophenyl)-N'-hydroxy-2-(2-(4-hydroxypiperidin-1-yl)ethyl)-1H-imidazo[4,5-b]pyridine-7-carboximidamide, N-(3-bromo-4-fluorophenyl)-2-(2-(dimethylamino)ethyl)-N'-hydroxy-1H-imidazo[4,5-b]pyridine-7-carboximidamide, N-(3-chlorophenyl)-2-(2-(dimethylamino)ethyl)-N'-hydroxy-1H-imidazo[4,5-b]pyridine-7-carboximidamide, N-(3-bromophenyl)-2-(2-(dimethylamino)ethyl)-N'-hydroxy-1H-imidazo[4,5-b]pyridine-7-carboximidamide, N-(3-chloro-4-fluorophenyl)-N'-hydroxy-2-(2-(methylsulfonamido)ethyl)-1H-imidazo[4,5-b]pyridine-7-carboximidamide, N-(3-chloro-4-fluorophenyl)-N'-hydroxy-2-(2-(sulfamoylamino)ethyl)-1H-imidazo[4,5-b]pyridine-7-carboximidamide, N-(3-chlorophenyl)-N'-hydroxy-2-(2-(pyrrolidin-1-yl)ethyl)-1H-imidazo[4,5-b]pyridine-7-carboximidamide, N-(3-bromophenyl)-N'-hydroxy-2-(2-(pyrrolidin-1-yl)ethyl)-1H-imidazo[4,5-b]pyridine-7-carboximidamide, N-(2-(7-(N-(3-chloro-4-fluorophenyl)-N'-hydroxycarbamimidoyl)-1H-imidazo[4,5-b]pyridin-2-yl)ethyl)acetamide, N-(3-chlorophenyl)-N'-hydroxy-2-(2-(piperidin-1-yl)ethyl)-1H-imidazo[4,5-b]pyridine-7-carboximidamide, N-(3-bromophenyl)-N'-hydroxy-2-(2-(piperidin-1-yl)ethyl)-1H-imidazo[4,5-b]pyridine-7-carboximidamide, Methyl (2-(7-(N-(3-chloro-4-fluorophenyl)-N'-hydroxycarbamimidoyl)-1H-imidazo[4,5-b]pyridin-2-yl)ethyl)carbamate, N-(3-chloro-4-fluorophenyl)-2-(2-((2,4-dimethoxybenzyl)amino)ethyl)-N'-hydroxy-1H-imidazo[4,5-b]pyridine-7-carboximidamide, 2-(2-(4-benzylpiperidin-1-yl)ethyl)-N-(3-chloro-4-fluorophenyl)-N'-hydroxy-1H-imidazo[4,5-b]pyridine-7-carboximidamide, 2-(2-(3-azabicyclo[3.3.1]nonan-3-yl)ethyl)-N-(3-chloro-4-fluorophenyl)-N'-hydroxy-1H-imidazo[4,5-b]pyridine-7-carboximidamide, 2-(2-(3-azabicyclo[3.2.1]octan-3-yl)ethyl)-N-(3-chloro-4-fluorophenyl)-N'-hydroxy-1H-imidazo[4,5-b]pyridine-7-carboximidamide, N-(3-chloro-4-fluorophenyl)-N'-hydroxy-2-((1-methylpiperidin-3-yl)amino)-1H-imidazo[4,5-b]pyridine-7-carboximidamide, (S)—N-(3-chloro-4-fluorophenyl)-N'-hydroxy-2-((2-(3-hydroxypyrrolidin-1-yl)ethyl)amino)-1H-imidazo[4,5-b]pyridine-7-carboximidamide, (S)—N-(3-chloro-4-fluorophenyl)-N'-hydroxy-2-(3-hydroxypyrrolidin-1-yl)-1H-imidazo[4,5-b]pyridine-7-carboximidamide, N-(3-chloro-4-fluorophenyl)-N'-hydroxy-2-((1-(2-methoxyethyl)pyrrolidin-3-yl)amino)-1H-imidazo[4,5-b]pyridine-7-carboximidamide, N-(3-chloro-4-fluorophenyl)-N'-hydroxy-2-(((4-methylmorpholin-3-yl)methyl)amino)-1H-imidazo[4,5-b]pyridine-7-carboximidamide, N-(3-chloro-4-fluorophenyl)-N'-hydroxy-2-((2-(pyrrolidin-1-yl)ethyl)amino)-1H-imidazo[4,5-b]pyridine-7-carboximidamide, N-(3-chloro-4-fluorophenyl)-N'-hydroxy-2-(((4-((methylsulfonyl)methyl)tetrahydro-2H-pyran-4-yl)methyl)amino)-1H-imidazo[4,5-b]pyridine-7-carboximidamide, N-(3-chloro-4-fluorophenyl)-N'-hydroxy-2-((2-(methylsulfonyl)benzyl)amino)-1H-imidazo[4,5-b]pyridine-7-carboximidamide,
2-((1-acetylpiperidin-3-yl)amino)-N-(3-chloro-4-fluorophenyl)-N'-hydroxy-1H-imidazo[4,5-b]pyridine-7-carboximidamide,
N-(3-chloro-4-fluorophenyl)-2-((ethylamino)methyl)-4-fluoro-N'-hydroxy-1H-benzo[d]imidazole-7-carboximidamide,
N-(3-chloro-4-fluorophenyl)-2-((dimethylamino)methyl)-4-fluoro-N'-hydroxy-1H-benzo[d]imidazole-7-carboximidamide,
N-(3-chloro-4-fluorophenyl)-4-fluoro-N'-hydroxy-2-((isopropylamino)methyl)-1H-benzo[d]imidazole-7-carboximidamide,
N-(3-chloro-4-fluorophenyl)-4-fluoro-N'-hydroxy-2-((methylamino)methyl)-1H-benzo[d]imidazole-7-carboximidamide,
2-(aminomethyl)-N-(3-chloro-4-fluorophenyl)-4-fluoro-N'-hydroxy-1H-benzo[d]imidazole-7-carboximidamide,
N-(3-chloro-4-fluorophenyl)-4,5-difluoro-N'-hydroxy-2-((2-hydroxy-2-methylpropyl)amino)-1H-benzo[d]imidazole-7-carboximidamide,
N-(3-chloro-4-fluorophenyl)-4,5-difluoro-N'-hydroxy-2-((2-hydroxypropyl)amino)-1H-benzo[d]imidazole-7-carboximidamide,
2-((7-(N-(3-chloro-4-fluorophenyl)-N'-hydroxycarbamimidoyl)-4,5-difluoro-1H-benzo[d]imidazol-2-yl)amino)acetamide,
N-(3-chloro-4-fluorophenyl)-4,5-difluoro-N'-hydroxy-2-((2-hydroxyethyl)amino)-1H-benzo[d]imidazole-7-carboximidamide,
N-(3-chloro-4-fluorophenyl)-4,5-difluoro-N'-hydroxy-2-((3-hydroxycyclobutyl)amino)-1H-benzo[d]imidazole-7-carboximidamide,
N-(3-chloro-4-fluorophenyl)-4,5-difluoro-N'-hydroxy-2-((3-(pyridin-2-yl amino)propyl)amino)-1H-benzo[d]imidazole-7-carboximidamide,
N-(3-chloro-4-fluorophenyl)-4,5-difluoro-N'-hydroxy-2-((2-sulfamoylethyl)amino)-1H-benzo[d]imidazole-7-carboximidamide,
N-(3-chloro-4-fluorophenyl)-4,5-difluoro-N'-hydroxy-2-(((1-methyl-1H-pyrazol-5-yl)methyl)amino)-1H-benzo[d]imidazole-7-carboximidamide,
2-((2-(1H-pyrazol-1-yl)ethyl)amino)-N-(3-chloro-4-fluorophenyl)-4,5-difluoro-N'-hydroxy-1H-benzo[d]imidazole-7-carboximidamide,
2-((7-(N-(3-chloro-4-fluorophenyl)-N'-hydroxycarbamimidoyl)-4,5-difluoro-1H-benzo[d]imidazol-2-yl)amino)-N,N-dimethylacetamide,
N-(3-chloro-4-fluorophenyl)-4,5-difluoro-N'-hydroxy-2-(2-hydroxy-2-methylpropyl)-1H-benzo[d]imidazole-7-carboximidamide,
N-(3-chloro-4-fluorophenyl)-2-((4-(dimethylamino)butyl)amino)-4,5-difluoro-N'-hydroxy-1H-benzo[d]imidazole-7-carboximidamide,
N-(3-chloro-4-fluorophenyl)-4,5-difluoro-N'-hydroxy-2-((piperidin-3-ylmethyl)amino)-1H-benzo[d]imidazole-7-carboximidamide,
N-(3-chloro-4-fluorophenyl)-N'-hydroxy-2-((1-methylpiperidin-2-yl)methyl)-1H-imidazo[4,5-b]pyridine-7-carboximidamide,
N-(3-bromophenyl)-N'-hydroxy-2-((2-morpholinoethyl)amino)-1H-imidazo[4,5-b]pyridine-7-carboximidamide,
N-(3-chloro-4-fluorophenyl)-5-fluoro-N'-hydroxy-4-methoxy-1H-benzo[d]imidazole-7-carboximidamide,
N-(3-chloro-4-fluorophenyl)-N'-hydroxy-2-((pyridin-2-ylmethyl)amino)-1H-imidazo[4,5-b]pyridine-7-carboximidamide,
2-((2-(1H-pyrazol-1-yl)ethyl)amino)-N-(3-chloro-4-fluorophenyl)-N'-hydroxy-1H-imidazo[4,5-b]pyridine-7-carboximidamide,
N-(3-chloro-4-fluorophenyl)-N'-hydroxy-2-(((1-methyl-1H-pyrazol-3-yl)methyl)amino)-1H-imidazo[4,5-b]pyridine-7-carboximidamide,
N-(3-chloro-4-fluorophenyl)-N'-hydroxy-2-((4,4,4-trifluorobutyl)amino)-1H-imidazo[4,5-b]pyridine-7-carboximidamide,
N-(3-chloro-4-fluorophenyl)-N'-hydroxy-2-((3,3,3-trifluoropropyl)amino)-1H-imidazo[4,5-b]pyridine-7-carboximidamide,
N-(3-chloro-4-fluorophenyl)-N'-hydroxy-2-((2-(2-methoxyethoxy)ethyl)amino)-1H-imidazo[4,5-b]pyridine-7-carboximidamide,
N-(3-chloro-4-fluorophenyl)-2-((3-(cyclopropyl(methyl)amino)propyl)amino)-N'-hydroxy-1H-imidazo[4,5-b]pyridine-7-carboximidamide,
N-(3-chloro-4-fluorophenyl)-2-((3-(cyclopropylamino)propyl)amino)-N'-hydroxy-1H-imidazo[4,5-b]pyridine-7-carboximidamide,
N-(3-chloro-4-fluorophenyl)-2-((3-(cyclopropyl(ethyl)amino)propyl)amino)-N'-hydroxy-1H-imidazo[4,5-b]pyridine-7-carboximidamide,
N-(3-chloro-4-fluorophenyl)-2-((2-(4-fluoropiperidin-1-yl)ethyl)amino)-N'-hydroxy-1H-imidazo[4,5-b]pyridine-7-carboximidamide,
N-(3-chloro-4-fluorophenyl)-N'-hydroxy-2-((2-(2,2,2-trifluoroethoxy)ethyl)amino)-1H-imidazo[4,5-b]pyridine-7-carboximidamide,
N-(3-chloro-4-fluorophenyl)-N'-hydroxy-2-((3-(2,2,2-trifluoroethoxy)propyl)amino)-1H-imidazo[4,5-b]pyridine-7-carboximidamide,
N-(3-chloro-4-fluorophenyl)-N'-hydroxy-2-((2-(3-methoxypiperidin-1-yl)ethyl)amino)-1H-imidazo[4,5-b]pyridine-7-carboximidamide,
N-(3-chloro-4-fluorophenyl)-2-((3-(difluoromethoxy)propyl)amino)-N'-hydroxy-1H-imidazo[4,5-b]pyridine-7-carboximidamide,
(R)—N-(3-chloro-4-fluorophenyl)-N'-hydroxy-2-(((tetrahydrofuran-2-yl)methyl)amino)-1H-imidazo[4,5-b]pyridine-7-carboximidamide,
(S)—N-(3-chloro-4-fluorophenyl)-N'-hydroxy-2-(((tetrahydrofuran-2-yl)methyl)amino)-1H-imidazo[4,5-b]pyridine-7-carboximidamide,
N-(3-chloro-4-fluorophenyl)-N'-hydroxy-2-((2-(tetrahydrofuran-2-yl)ethyl)amino)-1H-imidazo[4,5-b]pyridine-7-carboximidamide,
N-(3-chloro-4-fluorophenyl)-N'-hydroxy-2-(piperidin-2-ylmethyl)-1H-imidazo[4,5-b]pyridine-7-carboximidamide,
N-(3-chloro-4-fluorophenyl)-2-(1-(dimethylamino)propan-2-yl)-N'-hydroxy-1H-imidazo[4,5-b]pyridine-7-carboximidamide,
N-(3-chloro-4-fluorophenyl)-N'-hydroxy-2-(2-(methylamino)propyl)-1H-imidazo[4,5-b]pyridine-7-carboximidamide,
N-(3-chloro-4-fluorophenyl)-2-(2-(dimethylamino)propyl)-N'-hydroxy-1H-imidazo[4,5-b]pyridine-7-carboximidamide, N-(3-chloro-4-fluorophenyl)-N'-hydroxy-2-(pyrrolidin-2-ylmethyl)-1H-imidazo[4,5-b]pyridine-7-carboximidamide, N-(3-chlorophenyl)-4,5-difluoro-N'-hydroxy-2-((2-(pyrrolidin-1-yl)ethyl)amino)-1H-benzo[d]imidazole-7-carboximidamide, N-(3-bromophenyl)-4,5-difluoro-N'-hydroxy-2-((2-(pyrrolidin-1-yl)ethyl)amino)-1H-benzo[d]imidazole-7-carboximidamide, N-(3-bromo-4-fluorophenyl)-4,5-difluoro-N'-hydroxy-2-((2-(pyrrolidin-1-yl)ethyl)amino)-1H-benzo[d]imidazole-7-carboximidamide, 2-((2-aminoethyl)amino)-N-(3-chloro-4-fluorophenyl)-4,5-difluoro-N'-hydroxy-1H-benzo[d]imidazole-7-carboximidamide, N-(2-((7-(N-(3-chloro-4-fluorophenyl)-N'-hydroxycarbamimidoyl)-4,5-difluoro-1H-benzo[d]imidazol-2-yl)amino)ethyl)acetamide, N-(3-chloro-4-fluorophenyl)-4,5-difluoro-N'-hydroxy-2-((2-(methylsulfonamido)ethyl)amino)-1H-benzo[d]imidazole-7-carboximidamide, N-(3-chloro-4-fluorophenyl)-2-((2-(cyclopropanesulfonamido)ethyl)amino)-4,5-difluoro-N-hydroxy-1H-benzo[d]imidazole-7-carboximidamide, Methyl (2-((7-(N-(3-chloro-4-fluorophenyl)-N'-hydroxycarbamimidoyl)-4,5-difluoro-1H-benzo[d]imidazol-2-yl)amino)ethyl)carbamate, N-(3-chloro-4-fluorophenyl)-4,5-difluoro-N'-hydroxy-2-((2-(sulfamoylamino)ethyl)amino)-1H-benzo[d]imidazole-7-carboximidamide, N-(3-chloro-4-fluorophenyl)-4,5-difluoro-N'-hydroxy-2-((2-(phenylsulfonamido)ethyl)amino)-1H-benzo[d]imidazole-7-carboximidamide, N-(3-chloro-4-fluorophenyl)-2-((2-cyanoethyl)amino)-4,5-difluoro-N'-hydroxy-1H-benzo[d]imidazole-7-carboximidamide, N-(3-chloro-4-fluorophenyl)-2-((2-(3-ethylureido)ethyl)amino)-4,5-difluoro-N'-hydroxy-1H-benzo[d]imidazole-7-carboximidamide, N-(3-chloro-4-fluorophenyl)-4,5-difluoro-N'-hydroxy-2-((pyridin-2-ylmethyl)amino)-1H-benzo[d]imidazole-7-carboximidamide, N-(3-chloro-4-fluorophenyl)-4,5-difluoro-N'-hydroxy-2-((pyridin-3-ylmethyl)amino)-1H-benzo[d]imidazole-7-carboximidamide, N-(3-chloro-4-fluorophenyl)-4,5-difluoro-N'-hydroxy-2-((pyridin-3-ylmethyl)amino)-1H-benzo[d]imidazole-7-carboximidamide, 2-(((1H-imidazol-2-yl)methyl)amino)-N-(3-chloro-4-fluorophenyl)-4,5-difluoro-N'-hydroxy-1H-benzo[d]imidazole-7-carboximidamide, 2-chloro-N-(3-chloro-4-fluorophenyl)-4,5-difluoro-N'-hydroxy-1H-benzo[d]imidazole-7-carboximidamide, 2-((2-aminobenzyl)amino)-N-(3-chloro-4-fluorophenyl)-4,5-difluoro-N'-hydroxy-1H-benzo[d]imidazole-7-carboximidamide, N-(3-chloro-4-fluorophenyl)-2-((2-(dimethylamino)benzyl)amino)-4,5-difluoro-N'-hydroxy-1H-benzo[d]imidazole-7-carboximidamide, N-(3-chloro-4-fluorophenyl)-4,5-difluoro-N'-hydroxy-2-(((1-methyl-1H-imidazol-2-yl)methyl)amino)-1H-benzo[d]imidazole-7-carboximidamide, N-(3-chloro-4-fluorophenyl)-4,5-difluoro-N'-hydroxy-2-((pyrimidin-2-ylmethyl)amino)-1H-benzo[d]imidazole-7-carboximidamide, N-(3-chloro-4-fluorophenyl)-2-((3-(dimethylamino)-2,2-dimethylpropyl)amino)-4,5-difluoro-N'-hydroxy-1H-benzo[d]imidazole-7-carboximidamide, N-(3-chloro-4-fluorophenyl)-2-((3-(dimethylamino)-2-methylpropyl)amino)-4,5-difluoro-N-hydroxy-1H-benzo[d]imidazole-7-carboximidamide, N-(3-chloro-4-fluorophenyl)-2-((3-(dimethylamino)butyl)amino)-4,5-difluoro-N'-hydroxy-1H-benzo[d]imidazole-7-carboximidamide, N-(3-chloro-4-fluorophenyl)-4,5-difluoro-N'-hydroxy-2-((2-(1-methylpyrrolidin-2-yl)ethyl)amino)-1H-benzo[d]imidazole-7-carboximidamide, N-(3-chloro-4-fluorophenyl)-4,5-difluoro-N'-hydroxy-2-((2-(1-methylpiperidin-2-yl)ethyl)amino)-1H-benzo[d]imidazole-7-carboximidamide, N-(3-chloro-4-fluorophenyl)-4,5-difluoro-N'-hydroxy-2-(((4-methylmorpholin-2-yl)methyl)amino)-1H-benzo[d]imidazole-7-carboximidamide, N-(3-chloro-4-fluorophenyl)-N'-hydroxy-2-(((4-methylmorpholin-2-yl)methyl)amino)-1H-imidazo[4,5-b]pyridine-7-carboximidamide, N-(3-chloro-4-fluorophenyl)-N'-hydroxy-2-(((1-methyl-1H-pyrazol-5-yl)methyl)amino)-1H-imidazo[4,5-b]pyridine-7-carboximidamide, 2-((7-(N-(3-chloro-4-fluorophenyl)-N'-hydroxycarbamimidoyl)-1H-imidazo[4,5-b]pyridin-2-yl)amino)-N,N-dimethylacetamide, N-(3-chloro-4-fluorophenyl)-N'-hydroxy-2-(3-(hydroxymethyl)azetidin-1-yl)-1H-imidazo[4,5-b]pyridine-7-carboximidamide, N-(3-chloro-4-fluorophenyl)-N'-hydroxy-2-((oxetan-3-ylmethyl)amino)-1H-imidazo[4,5-b]pyridine-7-carboximidamide, N-(3-chloro-4-fluorophenyl)-N'-hydroxy-2-((2-(1-methyl-1H-imidazol-2-yl)ethyl)amino)-1H-imidazo[4,5-b]pyridine-7-carboximidamide, N-(3-chloro-4-fluorophenyl)-N'-hydroxy-2-((3-(pyridin-2-ylamino)propyl)amino)-1H-imidazo[4,5-b]pyridine-7-carboximidamide, N-(3-chloro-4-fluorophenyl)-N'-hydroxy-2-(neopentylamino)-1H-imidazo[4,5-b]pyridine-7-carboximidamide, N-(3-chloro-4-fluorophenyl)-N'-hydroxy-2-(isobutylamino)-1H-imidazo[4,5-b]pyridine-7-carboximidamide, N-(3-chloro-4-fluorophenyl)-N'-hydroxy-2-(((tetrahydro-2H-pyran-2-yl)methyl)amino)-1H-imidazo[4,5-b]pyridine-7-carboximidamide, N-(3-chloro-4-fluorophenyl)-N'-hydroxy-2-(((tetrahydrofuran-3-yl)methyl)amino)-1H-imidazo[4,5-b]pyridine-7-carboximidamide, N-(3-chloro-4-fluorophenyl)-4-fluoro-N'-hydroxy-2-((2-morpholinoethyl)amino)-1H-benzo[d]imidazole-7-carboximidamide, N-(3-chloro-4-fluorophenyl)-N'-hydroxy-N-methyl-1H-imidazo[4,5-b]pyridine-7-carboximidamide, 2-amino-N-(3-chloro-4-fluorophenyl)-5-fluoro-N'-hydroxy-1H-benzo[d]imidazole-7-carboximidamide, 2-amino-N-(3-chlorophenyl)-5-fluoro-N'-hydroxy-1H-benzo[d]imidazole-7-carboximidamide, 2-amino-N-(3-bromophenyl)-5-fluoro-N'-hydroxy-1H-benzo[d]imidazole-7-carboximidamide, 2-amino-N-(3-bromo-4-fluorophenyl)-5-fluoro-N'-hydroxy-1H-benzo[d]imidazole-7-carboximidamide, N-(3-chloro-4-fluorophenyl)-2-((2-(1,1-dioxidothiomorpholino)ethyl)amino)-4,5-difluoro-N-hydroxy-1H-benzo[d]imidazole-7-carboximidamide, N-(3-chloro-4-fluorophenyl)-2-((2-(diethylamino)ethyl)amino)-4-fluoro-N'-hydroxy-1H-benzo[d]imidazole-7-carboximidamide,
N-(3-chloro-4-fluorophenyl)-4-fluoro-N'-hydroxy-2-((2-(pyrrolidin-1-yl)ethyl)amino)-1H-benzo[d]imidazole-7-carboximidamide,
N-(3-chloro-4-fluorophenyl)-4,5-difluoro-N'-hydroxy-2-((2-morpholinopropyl)amino)-1H-benzo[d]imidazole-7-carboximidamide,
N-(3-chloro-4-fluorophenyl)-2-((1-(dimethylamino)propan-2-yl)amino)-4,5-difluoro-N-hydroxy-1H-benzo[d]imidazole-7-carboximidamide,
N-(3-chloro-4-fluorophenyl)-2-((2-(dimethylamino)ethyl)amino)-5-fluoro-N'-hydroxy-1H-benzo[d]imidazole-7-carboximidamide,
N-(3-chloro-4-fluorophenyl)-5-fluoro-N'-hydroxy-2-((2-(pyrrolidin-1-yl)ethyl)amino)-1H-benzo[d]imidazole-7-carboximidamide,
N-(3-chloro-4-fluorophenyl)-2-((3-(dimethylamino)-2,2-dimethylpropyl)amino)-4-fluoro-N-hydroxy-1H-benzo[d]imidazole-7-carboximidamide,
N-(3-bromo-4-fluorophenyl)-2-((2-(dimethylamino)ethyl)amino)-4-fluoro-N'-hydroxy-1H-benzo[d]imidazole-7-carboximidamide,
N-(3-bromophenyl)-2-((2-(dimethylamino)ethyl)amino)-4-fluoro-N'-hydroxy-1H-benzo[d]imidazole-7-carboximidamide,
N-(3-chlorophenyl)-2-((2-(dimethylamino)ethyl)amino)-4-fluoro-N'-hydroxy-1H-benzo[d]imidazole-7-carboximidamide,
N-(3-chlorophenyl)-2-((3-(dimethylamino)propyl)amino)-4,5-difluoro-N'-hydroxy-1H-benzo[d]imidazole-7-carboximidamide,
N-(3-bromophenyl)-2-((3-(dimethylamino)propyl)amino)-4,5-difluoro-N'-hydroxy-1H-benzo[d]imidazole-7-carboximidamide,
N-(3-bromo-4-fluorophenyl)-2-((3-(dimethylamino)propyl)amino)-4,5-difluoro-N'-hydroxy-1H-benzo[d]imidazole-7-carboximidamide,
N-(3-chloro-4-fluorophenyl)-2-((3-(dimethylamino)propyl)amino)-4-fluoro-N'-hydroxy-1H-benzo[d]imidazole-7-carboximidamide,
N-(3-chloro-4-fluorophenyl)-2-((3-(dimethylamino)propyl)amino)-5-fluoro-N'-hydroxy-1H-benzo[d]imidazole-7-carboximidamide,
2-((2-(benzyl(methyl)amino)ethyl)amino)-N-(3-chloro-4-fluorophenyl)-4,5-difluoro-N-hydroxy-1H-benzo[d]imidazole-7-carboximidamide,
N-(3-chloro-4-fluorophenyl)-2-(2-((cyclohexylmethyl)(methyl)amino)ethyl)-N'-hydroxy-1H-imidazo[4,5-b]pyridine-7-carboximidamide,
N-(3-chloro-4-fluorophenyl)-N'-hydroxy-2-(2-(methyl(neopentyl)amino)ethyl)-1H-imidazo[4,5-b]pyridine-7-carboximidamide,
N-(3-chloro-4-fluorophenyl)-2-(2-(cyclohexyl(methyl)amino)ethyl)-N'-hydroxy-1H-imidazo[4,5-b]pyridine-7-carboximidamide,
N-(3-chloro-4-fluorophenyl)-4,5-difluoro-N'-hydroxy-2-((2-(methyl((tetrahydro-2H-pyran-4-yl)methyl)amino)ethyl)amino)-1H-benzo[d]imidazole-7-carboximidamide,
N-(3-chloro-4-fluorophenyl)-4,5-difluoro-N'-hydroxy-2-((2-(methylamino)ethyl)amino)-1H-benzo[d]imidazole-7-carboximidamide,
2-(2-(benzyl(methyl)amino)ethyl)-N-(3-chloro-4-fluorophenyl)-N'-hydroxy-1H-imidazo[4,5-b]pyridine-7-carboximidamide,
N-(3-chloro-4-fluorophenyl)-2-((2-(2-ethylbutyl)(methyl)amino)ethyl)amino)-4,5-difluoro-N-hydroxy-1H-benzo[d]imidazole-7-carboximidamide,
N-(3-chloro-4-fluorophenyl)-2-((2-((cyclopropylmethyl)(methyl)amino)ethyl)amino)-4,5-difluoro-N'-hydroxy-1H-benzo[d]imidazole-7-carboximidamide,
N-(3-chloro-4-fluorophenyl)-N'-hydroxy-2-(2-(methyl((tetrahydro-2H-pyran-4-yl)methyl)amino)ethyl)-1H-imidazo[4,5-b]pyridine-7-carboximidamide,
2-(2-(((1,4-dioxan-2-yl)methyl)(methyl)amino)ethyl)-N-(3-chloro-4-fluorophenyl)-N'-hydroxy-1H-imidazo[4,5-b]pyridine-7-carboximidamide,
N-(3-chloro-4-fluorophenyl)-N'-hydroxy-2-(2-(methyl(2-(tetrahydro-2H-pyran-4-yl)ethyl)amino)ethyl)-1H-imidazo[4,5-b]pyridine-7-carboximidamide,
N-(3-chloro-4-fluorophenyl)-2-((2-(cyclopropylamino)ethyl)amino)-N'-hydroxy-1H-imidazo[4,5-b]pyridine-7-carboximidamide,
N-(3-chloro-4-fluorophenyl)-2-((2-(cyclopropyl(ethyl)amino)ethyl)amino)-N'-hydroxy-1H-imidazo[4,5-b]pyridine-7-carboximidamide,
N-(2-((7-(N-(3-chloro-4-fluorophenyl)-N'-hydroxycarbamimidoyl)-1H-imidazo[4,5-b]pyridin-2-yl)amino)ethyl)acetamide,
N-(3-chloro-4-fluorophenyl)-N'-hydroxy-2-((2-(methylsulfonamido)ethyl)amino)-1H-imidazo[4,5-b]pyridine-7-carboximidamide,
N-(3-chloro-4-fluorophenyl)-2-((2-(cyclopropyl(isopropyl)amino)ethyl)amino)-N'-hydroxy-1H-imidazo[4,5-b]pyridine-7-carboximidamide,
N-(3-chloro-4-fluorophenyl)-2-((2-(cyclopropyl(2-hydroxyethyl)amino)ethyl)amino)-N'-hydroxy-1H-imidazo[4,5-b]pyridine-7-carboximidamide,
2-((2-aminoethyl)amino)-N-(3-chloro-4-fluorophenyl)-N'-hydroxy-1H-imidazo[4,5-b]pyridine-7-carboximidamide,
N-(3-chloro-4-fluorophenyl)-N'-hydroxy-2-(((5-oxopyrrolidin-3-yl)methyl)amino)-1H-imidazo[4,5-b]pyridine-7-carboximidamide,
2-(((1H-pyrazol-5-yl)methyl)amino)-N-(3-chloro-4-fluorophenyl)-N'-hydroxy-1H-imidazo[4,5-b]pyridine-7-carboximidamide,
N-(3-((7-(N-(3-chloro-4-fluorophenyl)-N'-hydroxycarbamimidoyl)-1H-imidazo[4,5-b]pyridin-2-yl)amino)propyl)acetamide,
2-((3-aminopropyl)amino)-N-(3-chloro-4-fluorophenyl)-N'-hydroxy-1H-imidazo[4,5-b]pyridine-7-carboximidamide,
N-(3-chloro-4-fluorophenyl)-N'-hydroxy-2-((2-(sulfamoylamino)ethyl)amino)-1H-imidazo[4,5-b]pyridine-7-carboximidamide,
N-(3-chloro-4-fluorophenyl)-N'-hydroxy-2-((2-(phenylsulfonamido)ethyl)amino)-1H-imidazo[4,5-b]pyridine-7-carboximidamide,
Methyl (2-((7-(N-(3-chloro-4-fluorophenyl)-N'-hydroxycarbamimidoyl)-1H-imidazo[4,5-b]pyridin-2-yl)amino)ethyl)carbamate,
N-(3-chloro-4-fluorophenyl)-2-((2-(cyclopropanesulfonamido)ethyl)amino)-N'-hydroxy-1H-imidazo[4,5-b]pyridine-7-carboximidamide,
N-(3-chloro-4-fluorophenyl)-N'-hydroxy-2-((2-((trifluoromethyl)sulfonamido)ethyl)amino)-1H-imidazo[4,5-b]pyridine-7-carboximidamide,
2-(((1H-imidazol-2-yl)methyl)amino)-N-(3-chloro-4-fluorophenyl)-N'-hydroxy-1H-imidazo[4,5-b]pyridine-7-carboximidamide, 2-(((1H-imidazol-5-yl)methyl)amino)-N-(3-chloro-4-fluorophenyl)-N'-hydroxy-1H-imidazo[4,5-b]pyridine-7-carboximidamide, N-(3-chloro-4-fluorophenyl)-N'-hydroxy-2-(((3-methyl-1,2,4-oxadiazol-5-yl)methyl)amino)-1H-imidazo[4,5-b]pyridine-7-carboximidamide, N-(3-bromophenyl)-N'-hydroxy-2-(methylamino)-1H-imidazo[4,5-b]pyridine-7-carboximidamide, Methyl (3-((7-(N-(3-chloro-4-fluorophenyl)-N'-hydroxycarbamimidoyl)-1H-imidazo[4,5-b]pyridin-2-yl)amino)propyl)carbamate, N-(3-bromophenyl)-N'-hydroxy-2-methoxy-1H-imidazo[4,5-b]pyridine-7-carboximidamide, N-(3-bromophenyl)-N'-hydroxy-2-(((2-(methylsulfonyl)ethyl)amino)-1H-imidazo[4,5-b]pyridine-7-carboximidamide, N-(3-bromophenyl)-N'-hydroxy-2-(((2-(methylsulfonamido)ethyl)amino)-1H-imidazo[4,5-b]pyridine-7-carboximidamide, N-(3-bromophenyl)-N'-hydroxy-2-(((2-sulfamoylethyl)amino)-1H-imidazo[4,5-b]pyridine-7-carboximidamide, N-(3-chloro-4-fluorophenyl)-N'-hydroxy-2-(((5-methyl-1,3,4-oxadiazol-2-yl)methyl)amino)-1H-imidazo[4,5-b]pyridine-7-carboximidamide, N-(3-chloro-4-fluorophenyl)-4,5-difluoro-N'-hydroxy-2-(((1-methylpiperidin-2-yl)methyl)amino)-1H-benzo[d]imidazole-7-carboximidamide, N-(3-chloro-4-fluorophenyl)-4,5-difluoro-N'-hydroxy-2-(((4-methylmorpholin-3-yl)methyl)amino)-1H-benzo[d]imidazole-7-carboximidamide, N-(3-bromophenyl)-2-((2-(dimethylamino)ethyl)amino)-4,5-difluoro-N'-hydroxy-1H-benzo[d]imidazole-7-carboximidamide, N-(3-chlorophenyl)-2-((2-(dimethylamino)ethyl)amino)-4,5-difluoro-N'-hydroxy-1H-benzo[d]imidazole-7-carboximidamide, N-(3-bromo-4-fluorophenyl)-2-((2-(dimethylamino)ethyl)amino)-4,5-difluoro-N'-hydroxy-1H-benzo[d]imidazole-7-carboximidamide, N-(3-chloro-4-fluorophenyl)-4,5-difluoro-2-((3-morpholinopropyl)amino)-1H-benzo[d]imidazole-7-carboxamide, N-(3-chloro-4-fluorophenyl)-4,5-difluoro-N'-hydroxy-2-((3-(pyrrolidin-1-yl)propyl)amino)-1H-benzo[d]imidazole-7-carboximidamide, 2-(((3R)-4-amino-1-methylpyrrolidin-3-yl)amino)-N-(3-chloro-4-fluorophenyl)-4,5-difluoro-N-hydroxy-1H-benzo[d]imidazole-7-carboximidamide, N-(3-chloro-4-fluorophenyl)-2-((2-(dimethylamino)-2-phenylethyl)amino)-4,5-difluoro-N-hydroxy-1H-benzo[d]imidazole-7-carboximidamide, N-(3-chloro-4-fluorophenyl)-2-(((1R,2R)-2-(dimethylamino)cyclohexyl)amino)-4,5-difluoro-N'-hydroxy-1H-benzo[d]imidazole-7-carboximidamide, N-(3-chloro-4-fluorophenyl)-2-(((1-(dimethylamino)cyclopentyl)methyl)amino)-4,5-difluoro-N'-hydroxy-1H-benzo[d]imidazole-7-carboximidamide, N-(3-chloro-4-fluorophenyl)-2-(((1S,3S)-3-(dimethylamino)cyclohexyl)amino)-4,5-difluoro-N-hydroxy-1H-benzo[d]imidazole-7-carboximidamide, N-(3-chloro-4-fluorophenyl)-2-(((1S,3R)-3-(dimethylamino)cyclohexyl)amino)-4,5-difluoro-N'-hydroxy-1H-benzo[d]imidazole-7-carboximidamide, N-(3-chloro-4-fluorophenyl)-2-(((1-(dimethylamino)cyclobutyl)methyl)amino)-4,5-difluoro-N-hydroxy-1H-benzo[d]imidazole-7-carboximidamide, N-(3-chloro-4-fluorophenyl)-4,5-difluoro-N'-hydroxy-2-((1-methylpiperidin-4-yl)amino)-1H-benzo[d]imidazole-7-carboximidamide, N-(3-chloro-4-fluorophenyl)-4,5-difluoro-N'-hydroxy-2-((1-methylpiperidin-3-yl)amino)-1H-benzo[d]imidazole-7-carboximidamide, N-(3-chloro-4-fluorophenyl)-2-(((1S,2S)-2-(dimethylamino)cyclohexyl)amino)-4,5-difluoro-N-hydroxy-1H-benzo[d]imidazole-7-carboximidamide, (S)—N-(3-chloro-4-fluorophenyl)-4,5-difluoro-N'-hydroxy-2-(piperidin-3-ylamino)-1H-benzo[d]imidazole-7-carboximidamide, (R)—N-(3-chloro-4-fluorophenyl)-4,5-difluoro-N'-hydroxy-2-(piperidin-3-ylamino)-1H-benzo[d]imidazole-7-carboximidamide, (S)—N-(3-chloro-4-fluorophenyl)-4,5-difluoro-N'-hydroxy-2-(((1-methylpyrrolidin-3-yl)amino)-1H-benzo[d]imidazole-7-carboximidamide, N-(3-chloro-4-fluorophenyl)-2-((3-(dimethylamino)-2-hydroxypropyl)amino)-4,5-difluoro-N'-hydroxy-1H-benzo[d]imidazole-7-carboximidamide, N-(3-chloro-4-fluorophenyl)-4,5-difluoro-N'-hydroxy-2-((2-(4-methyl-3-oxopiperazin-l-yl)ethyl)amino)-1H-benzo[d]imidazole-7-carboximidamide, N-(3-chloro-4-fluorophenyl)-2-(((1-(dimethylamino)cyclohexyl)methyl)amino)-4,5-difluoro-N'-hydroxy-1H-benzo[d]imidazole-7-carboximidamide, N-(3-chloro-4-fluorophenyl)-4,5-difluoro-N'-hydroxy-2-((1-methylazepan-3-yl)amino)-1H-benzo[d]imidazole-7-carboximidamide, (S)—N-(3-chloro-4-fluorophenyl)-4,5-difluoro-N'-hydroxy-2-(((2-(3-hydroxypyrrolidin-l-yl)ethyl)amino)-1H-benzo[d]imidazole-7-carboximidamide, N-(3-chloro-4-fluorophenyl)-4,5-difluoro-N'-hydroxy-2-((1-(2-methoxyethyl)piperidin-3-yl)amino)-1H-benzo[d]imidazole-7-carboximidamide, N-(3-chloro-4-fluorophenyl)-4,5-difluoro-N'-hydroxy-2-((1-(2-methoxyethyl)pyrrolidin-3-yl)amino)-1H-benzo[d]imidazole-7-carboximidamide, N-(3-chloro-4-fluorophenyl)-4,5-difluoro-N'-hydroxy-2-((1-isopropylpiperidin-3-yl)amino)-1H-benzo[d]imidazole-7-carboximidamide, N-(3-chloro-4-fluorophenyl)-4,5-difluoro-N'-hydroxy-2-((2-(3-methoxyazetidin-l-yl)ethyl)amino)-1H-benzo[d]imidazole-7-carboximidamide, (R)—N-(3-chloro-4-fluorophenyl)-4,5-difluoro-N'-hydroxy-2-((1-methylpyrrolidin-3-yl)amino)-1H-benzo[d]imidazole-7-carboximidamide, N-(3-chloro-4-fluorophenyl)-4,5-difluoro-N'-hydroxy-2-(((3R,4R)-4-methoxy-1-methylpyrrolidin-3-yl)amino)-1H-benzo[d]imidazole-7-carboximidamide, (S)—N-(3-chlorophenyl)-4,5-difluoro-N'-hydroxy-2-((1-methylpiperidin-3-yl)amino)-1H-benzo[d]imidazole-7-carboximidamide, (R)—N-(3-chlorophenyl)-4,5-difluoro-N'-hydroxy-2-((1-methylpiperidin-3-yl)amino)-1H-benzo[d]imidazole-7-carboximidamide, N-(3-chloro-4-fluorophenyl)-2-((2-(dimethylamino)cyclopentyl)amino)-4,5-difluoro-N'-hydroxy-1H-benzo[d]imidazole-7-carboximidamide, (S)-2-(azepan-3-ylamino)-N-(3-chloro-4-fluorophenyl)-4,5-difluoro-N'-hydroxy-1H-benzo[d]imidazole-7-carboximidamide, (R)-2-(azepan-3-ylamino)-N-(3-chloro-4-fluorophenyl)-4,5-difluoro-N'-hydroxy-1H-benzo[d]imidazole-7-carboximidamide, N-(3-chloro-4-fluorophenyl)-4,5-difluoro-N'-hydroxy-2-(pyrrolidin-3-ylamino)-1H-benzo[d]imidazole-7-carboximidamide, (R)—N-(3-chloro-4-fluorophenyl)-4,5-difluoro-N'-hydroxy-2-((1-(oxetan-3-yl)piperidin-3-yl)amino)-1H-benzo[d]imidazole-7-carboximidamide, N-(3-chloro-4-fluorophenyl)-2-(((1,4-dimethylpiperidin-2-yl)methyl)amino)-4,5-difluoro-N'-hydroxy-1H-benzo[d]imidazole-7-carboximidamide, N-(3-chloro-4-fluorophenyl)-4,5-difluoro-N'-hydroxy-2-((morpholin-3-ylmethyl)amino)-1H-benzo[d]imidazole-7-carboximidamide, N-(3-chloro-4-fluorophenyl)-4,5-difluoro-N'-hydroxy-2-(((3R,4S)-4-hydroxypyrrolidin-3-yl)amino)-1H-benzo[d]imidazole-7-carboximidamide, N-(3-chloro-4-fluorophenyl)-4,5-difluoro-N'-hydroxy-2-(((1R,5R)-8-methyl-8-azabicyclo[3.2.1]octan-2-yl)amino)-1H-benzo[d]imidazole-7-carboximidamide, (S)—N-(3-chloro-4-fluorophenyl)-4,5-difluoro-N'-hydroxy-2-(((2-(2-(trifluoromethyl)pyrrolidin-1-yl)ethyl)amino)-1H-benzo[d]imidazole-7-carboximidamide, N-(3-chloro-4-fluorophenyl)-4,5-difluoro-2-(((hexahydro-1H-pyrrolizin-7a-yl)methyl)amino)-N'-hydroxy-1H-benzo[d]imidazole-7-carboximidamide, N-(3-chloro-4-fluorophenyl)-2-(((3,3-dimethylazetidin-2-yl)methyl)amino)-4,5-difluoro-N'-hydroxy-1H-benzo[d]imidazole-7-carboximidamide, N-(3-chloro-4-fluorophenyl)-4,5-difluoro-N'-hydroxy-2-((4-(pyrrolidin-1-yl)tetrahydro-2H-pyran-3-yl)amino)-1H-benzo[d]imidazole-7-carboximidamide, 2-(((1S,2R)-2-aminocyclohexyl)amino)-N-(3-chloro-4-fluorophenyl)-4,5-difluoro-N'-hydroxy-1H-benzo[d]imidazole-7-carboximidamide, N-(3-chloro-4-fluorophenyl)-4,5-difluoro-N'-hydroxy-2-((2-methyl-1,2,3,4-tetrahydroisoquinolin-4-yl)amino)-1H-benzo[d]imidazole-7-carboximidamide, N-(3-chloro-4-fluorophenyl)-2-(((3S,4S)-4-(diethylamino)tetrahydrofuran-3-yl)amino)-4,5-difluoro-N'-hydroxy-1H-benzo[d]imidazole-7-carboximidamide, 2-(((1,4-oxazepan-6-yl)amino)-N-(3-chloro-4-fluorophenyl)-4,5-difluoro-N'-hydroxy-1H-benzo[d]imidazole-7-carboximidamide, N-(3-chloro-4-fluorophenyl)-2-((2-((2S,6R)-2,6-dimethylmorpholino)ethyl)amino)-N'-hydroxy-1H-imidazo[4,5-b]pyridine-7-carboximidamide, N-(3-chloro-4-fluorophenyl)-N'-hydroxy-2-(((3R,4R)-4-methoxy-1-methylpyrrolidin-3-yl)amino)-1H-imidazo[4,5-b]pyridine-7-carboximidamide, N-(3-chloro-4-fluorophenyl)-2-(((3R,4R)-4-(diethylamino)tetrahydrofuran-3-yl)amino)-N'-hydroxy-1H-imidazo[4,5-b]pyridine-7-carboximidamide, (S)—N-(3-chloro-4-fluorophenyl)-N'-hydroxy-2-(((2-(2-(trifluoromethyl)pyrrolidin-1-yl)ethyl)amino)-1H-imidazo[4,5-b]pyridine-7-carboximidamide, (R)—N-(3-chloro-4-fluorophenyl)-N'-hydroxy-2-(((4-methylmorpholin-3-yl)methyl)amino)-1H-imidazo[4,5-b]pyridine-7-carboximidamide, N-(3-chloro-4-fluorophenyl)-2-((2-(2,6-dimethylmorpholino)propyl)amino)-N'-hydroxy-1H-imidazo[4,5-b]pyridine-7-carboximidamide, N-(3-chloro-4-fluorophenyl)-2-((2-(2,6-dimethylmorpholino)-2-methylpropyl)amino)-N'-hydroxy-1H-imidazo[4,5-b]pyridine-7-carboximidamide, N-(3-chloro-4-fluorophenyl)-2-((2-(2,5-dimethylmorpholino)ethyl)amino)-N'-hydroxy-1H-imidazo[4,5-b]pyridine-7-carboximidamide, N-(3-chloro-4-fluorophenyl)-2-(((1R,2R)-2-(dimethylamino)cyclopentyl)amino)-4,5-difluoro-N'-hydroxy-1H-benzo[d]imidazole-7-carboximidamide, N-(3-chloro-4-fluorophenyl)-2-((2-(dimethylamino)ethyl)thio)-N'-hydroxy-1H-imidazo[4,5-b]pyridine-7-carboximidamide, N-(3-chloro-4-fluorophenyl)-2-((2-(dimethylamino)ethyl)thio)-4,5-difluoro-N'-hydroxy-1H-benzo[d]imidazole-7-carboximidamide, N-(3-chloro-4-fluorophenyl)-4,5-difluoro-N'-hydroxy-2-((2-(2-(hydroxymethyl)piperidin-1-yl)ethyl)amino)-1H-benzo[d]imidazole-7-carboximidamide, N-(3-chloro-4-fluorophenyl)-4,5-difluoro-N'-hydroxy-2-((2-(2-(hydroxymethyl)pyrrolidin-1-yl)ethyl)amino)-1H-benzo[d]imidazole-7-carboximidamide, N-(3-chloro-4-fluorophenyl)-2-((2-(3,3-difluoropyrrolidin-1-yl)ethyl)amino)-N'-hydroxy-1H-imidazo[4,5-b]pyridine-7-carboximidamide, N-(3-chloro-4-fluorophenyl)-N'-hydroxy-2-((2-sulfamoylethyl)amino)-1H-imidazo[4,5-b]pyridine-7-carboximidamide, N-(3-chloro-4-fluorophenyl)-N'-hydroxy-2-((2-(methylsulfonyl)ethyl)amino)-1H-imidazo[4,5-b]pyridine-7-carboximidamide, N-(3-chloro-4-fluorophenyl)-N'-hydroxy-2-((pyrimidin-2-ylmethyl)amino)-1H-imidazo[4,5-b]pyridine-7-carboximidamide, (R)—N-(3-chlorophenyl)-4,5-difluoro-N'-hydroxy-2-((1-(2-methoxyethyl)pyrrolidin-3-yl)amino)-1H-benzo[d]imidazole-7-carboximidamide, (R)—N-(3-bromophenyl)-4,5-difluoro-N'-hydroxy-2-((1-(2-methoxyethyl)pyrrolidin-3-yl)amino)-1H-benzo[d]imidazole-7-carboximidamide, (S)—N-(3-chloro-4-fluorophenyl)-N'-hydroxy-2-((1-(oxetan-3-yl)piperidin-3-yl)amino)-1H-imidazo[4,5-b]pyridine-7-carboximidamide, N-(3-chloro-4-fluorophenyl)-N'-hydroxy-2-((1-(2-methoxyethyl)piperidin-3-yl)amino)-1H-imidazo[4,5-b]pyridine-7-carboximidamide, N-(3-chloro-4-fluorophenyl)-2-((1-cyclopropylpyrrolidin-3-yl)amino)-N'-hydroxy-1H-imidazo[4,5-b]pyridine-7-carboximidamide, (R)—N-(3-chloro-4-fluorophenyl)-N'-hydroxy-2-((1-(oxetan-3-yl)piperidin-3-yl)amino)-1H-imidazo[4,5-b]pyridine-7-carboximidamide, N-(3-chloro-4-fluorophenyl)-N'-hydroxy-2-((2-(4-methyl-3-oxopiperazin-1-yl)ethyl)amino)-1H-imidazo[4,5-b]pyridine-7-carboximidamide, N-(3-chloro-4-fluorophenyl)-2-((2-(3,3-difluoropiperidin-1-yl)ethyl)amino)-N'-hydroxy-1H-imidazo[4,5-b]pyridine-7-carboximidamide, 2-((1-acetylpyrrolidin-3-yl)amino)-N-(3-chloro-4-fluorophenyl)-N'-hydroxy-1H-imidazo[4,5-b]pyridine-7-carboximidamide, N-(3-chloro-4-fluorophenyl)-N'-hydroxy-2-((1-(methylsulfonyl)pyrrolidin-3-yl)amino)-1H-imidazo[4,5-b]pyridine-7-carboximidamide, N-(3-chloro-4-fluorophenyl)-N'-hydroxy-2-((3-(methylsulfonyl)propyl)amino)-1H-imidazo[4,5-b]pyridine-7-carboximidamide, N-(3-chloro-4-fluorophenyl)-2-(((1,1-dioxidotetrahydrothiophen-3-yl)methyl)amino)-N'-hydroxy-1H-imidazo[4,5-b]pyridine-7-carboximidamide, N-(3-chloro-4-fluorophenyl)-2-((3-((4-fluorophenyl)sulfonyl)propyl)amino)-N'-hydroxy-1H-imidazo[4,5-b]pyridine-7-carboximidamide, and (R)—N-(3-chloro-4-fluorophenyl)-N'-hydroxy-2-((1-(ox-etan-3-yl)pyrrolidin-3-yl)amino)-1H-imidazo[4,5-b]pyridine-7-carboximidamide;

or a pharmaceutically acceptable salt, tautomer, optical isomer, stereoisomer, or mixture thereof.

16. A pharmaceutical composition comprising a compound of claim 1 or a pharmaceutically acceptable salt, tautomer, optical isomer, stereoisomer, or mixture thereof, and at least one pharmaceutically acceptable vehicle.

17. The compound of claim 1, selected from the group consisting of:
- N-(3-chloro-4-fluorophenyl)-2-[2-(dimethylamino)ethylamino]-6,7-difluoro-N'-hydroxy-3H-benzimidazole-4-carboximidamide;
- N-(3-bromophenyl)-N'-hydroxy-3H-imidazo[4,5-b]pyridine-7-carboximidamide;
- N-(3-bromo-4-fluorophenyl)-N'-hydroxy-3H-imidazo[4,5-b]pyridine-7-carboximidamide;
- N-(3-chlorophenyl)-N'-hydroxy-3H-imidazo[4,5-b]pyridine-7-carboximidamide; and
- N-(3-chloro-4-fluorophenyl)-4,5-difluoro-N'-hydroxy-2-((2-(2-(hydroxymethyl)pyrrolidin-1-yl)ethyl)amino)-1H-benzo[d]imidazole-7-carboximidamide;

or a pharmaceutically acceptable salt, tautomer, optical isomer, stereoisomer, or mixture thereof.

18. A method of inhibiting an IDO1 protein in a patient having a disease, wherein the disease is responsive to IDO1 protein inhibition, comprising administering a compound of claim 1, or a pharmaceutically acceptable salt thereof.

19. A method of inhibiting an IDO1 protein in a patient afflicted with a disease, wherein the disease is responsive to IDO1 protein inhibition, comprising administering a compound selected from the group consisting of:
- N-(3-chloro-4-fluorophenyl)-2-[2-(dimethylamino)ethylamino]-6,7-difluoro-N'-hydroxy-3H-benzimidazole-4-carboximidamide;
- N-(3-bromophenyl)-N'-hydroxy-3H-imidazo[4,5-b]pyridine-7-carboximidamide;
- N-(3-bromo-4-fluorophenyl)-N'-hydroxy-3H-imidazo[4,5-b]pyridine-7-carboximidamide;
- N-(3-chlorophenyl)-N'-hydroxy-3H-imidazo[4,5-b]pyridine-7-carboximidamide; and
- N-(3-chloro-4-fluorophenyl)-4,5-difluoro-N'-hydroxy-2-((2-(2-(hydroxymethyl)pyrrolidin-1-yl)ethyl)amino)-1H-benzo[d]imidazole-7-carboximidamide;

or a pharmaceutically acceptable salt, tautomer, optical isomer, stereoisomer, or mixture thereof.

20. The method of claim 18, wherein the disease is cancer.

21. The method of claim 19, wherein the disease is cancer.

22. The method of claim 18, further comprising administering to the subject at least one additional therapeutic agent selected from the group consisting of PD1 inhibitors and/or PD-L1 inhibitors.

23. The method of claim 19, further comprising administering to the subject at least one additional therapeutic agent selected from the group consisting of PD1 inhibitors and/or PD-L1 inhibitors.

\* \* \* \* \*